(12) United States Patent
Li et al.

(10) Patent No.: US 8,022,206 B2
(45) Date of Patent: Sep. 20, 2011

(54) FURO[3,2-C]PYRIDINES

(75) Inventors: An-Hu Li, Commack, NY (US); Arno G. Steinig, East Northport, NY (US); Andrew Kleinberg, East Meadow, NY (US); Qinghua Weng, West Islip, NY (US); Mark J. Mulvihill, East Northport, NY (US); Jing Wang, Syosset, NY (US); Xin Chen, Commack, NY (US); Ti Wang, Evanston, IL (US); Hanqing Dong, Syosset, NY (US); Meizhong Jin, Dix Hills, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 251 days.

(21) Appl. No.: 12/366,743

(22) Filed: Feb. 6, 2009

(65) Prior Publication Data

US 2009/0197864 A1 Aug. 6, 2009

Related U.S. Application Data

(60) Provisional application No. 61/063,800, filed on Feb. 6, 2008, provisional application No. 61/119,553, filed on Dec. 3, 2008.

(51) Int. Cl.
  *C07D 413/00* (2006.01)
  *C07D 403/00* (2006.01)
  *C07D 471/02* (2006.01)
(52) U.S. Cl. .................... 544/127; 544/362; 546/116
(58) Field of Classification Search .................. 546/116; 544/362, 127, 295
See application file for complete search history.

(56) References Cited

U.S. PATENT DOCUMENTS

| | | | |
|---|---|---|---|
| 7,230,098 B2 | 6/2007 | Cui | |
| 7,259,154 B2 | 8/2007 | Cox | |
| 7,592,352 B2 * | 9/2009 | Miyazaki | 514/301 |
| 7,704,995 B2 | 4/2010 | Buhr | |
| 2006/0046991 A1 | 3/2006 | Cui | |
| 2006/0128724 A1 | 6/2006 | Cui | |
| 2006/0178374 A1 | 8/2006 | Cui | |
| 2007/0072874 A1 | 3/2007 | Cui | |
| 2008/0032972 A1 | 2/2008 | Dorsey | |
| 2008/0167338 A1 | 7/2008 | Spevak | |
| 2008/0221148 A1 | 9/2008 | Ibrahim | |
| 2008/0293769 A1 | 11/2008 | Cui | |
| 2009/0005356 A1 | 1/2009 | Blaney | |
| 2009/0005378 A1 | 1/2009 | Arnold | |
| 2009/0118305 A1 | 5/2009 | Barlaam | |

FOREIGN PATENT DOCUMENTS

| | | |
|---|---|---|
| WO | 03059913 A1 | 7/2003 |
| WO | 2004069160 A2 | 8/2004 |
| WO | 2004076412 A2 | 9/2004 |
| WO | 2006021881 A2 | 3/2006 |
| WO | 2007027855 A2 | 3/2007 |
| WO | 2007111904 A2 | 10/2007 |
| WO | 2007124181 A2 | 11/2007 |
| WO | 2008074997 A1 | 6/2008 |
| WO | 2008124849 A2 | 10/2008 |
| WO | 2009053737 A2 | 4/2009 |
| WO | 2009070294 A2 | 6/2009 |
| WO | 2009139576 A2 | 11/2009 |
| WO | 2009140549 A1 | 11/2009 |

OTHER PUBLICATIONS

International Preliminary Report on Patentability in PCT/US2009/033311.
Arteaga, C.L. (2007) Nature Medicine 13(6): 675-677.
Brabletz, T. et al. Nature Reviews Cancer 5:745-749.
Camp, E.R. et al. (2007) American Cancer Society pp. 1030-1039 Published online Feb. 20, 2007 in Wiley Interscience (www.interscience.wiley.com).
Christofori, G. (2006) Nature 441:444-450.
Duyster, J. et al. (2001) Oncogene 20: 5623-5637.
Engelman, J.A. et al. (2007) Science 316: 1039-1043.
Grotegut,S. et al. (2006) The EMBO Journal 25: 3534-3545.
Gupta, G.P. et al. (2006) Cell 127:679-695.
International Search Report in PCT/US2009/033311.
Jarvis, L.M. (2007) Chemical and Engineering News 85 (34): 15-23.
Kutok, J.L. et al. (2002) Journal of Clinical Oncology 20(17): 3691-3702.
Maggiora, P. et al. (1997) Journal of Cellular Physiology 173:183-186.
Maulik, G. et al. (2002) Cytokine and Growth Factor Reviews 13:41-59.
Oft, M. et al. (1996) Genes and Development 10:2462-2477.
Perl, A. et al. (1998) Nature 392:190-193. Powers, C. et al. (2002) The Journal of Biological Chemistry 277(16): 14153-14158.
Schlessinger, J. and Ullrich, A. (1992) Neuron 9: 383-391.
Thiery, J.P. (2002) Nature 2:442-454.
Turturro, F. et al. (2002) Clinical Cancer Research 8: 240-245.
Ullrich, A and Schlessinger, J. (1990) Cell 61: 203-212.
Wang, D. (2004) Oncogene 23: 1668-1680.
Yarden, Y. et al. (1988) Ann. Rev. Biochem. 57:443-478.
Zou, H.Y. et at (2007) Cancer Res 67(9):4408-4417.

* cited by examiner

Primary Examiner — Nizal Chandrakumar

(57) ABSTRACT

Furo[3,2-c]Pyridine and Thieno[3,2-c]pyridine compounds of Formula I, and pharmaceutically acceptable salts thereof, preparation, intermediates, pharmaceutical compositions, and use, such as in disease treatment, including cancers, including conditions in which EMT is involved, including conditions mediated by protein kinase activity such as RON and/or MET.

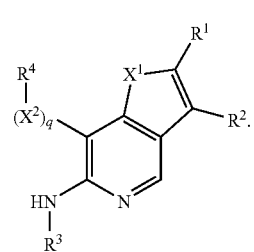

19 Claims, No Drawings

FURO[3,2-C]PYRIDINES

BACKGROUND

The present invention is directed to Furo[3,2-c]Pyridine and Thieno[3,2-c]Pyridine compounds, their salts, compositions, and therapeutic uses, in particular, compounds that inhibit the activity of tyrosine kinase enzymes in animals, including humans, for the treatment and/or prevention of various diseases and conditions such as cancer.

RON (recepteur d'origine nantais) is a receptor tyrosine kinase that is part of the MET proto-oncogene family. It is activated by binding to its natural ligand MSP and signals via the PI3K and MAPK pathways. RON can be deregulated in cancer by mechanisms such as over-expression of the receptor and/or the presence of constitutively active splice variants. Inhibition of RON has been shown to lead to a decrease in proliferation, induction of apoptosis and affects cell metastasis. RON overexpression is observed in a variety of human cancers and exhibit increased expression with progression of the disease.

MET is a receptor tyrosine kinase that is a heterodimeric protein comprising of a 50 kDa α-subunit and a 145 kDa β-subunit (Maggiora et al, *J. Cell Physiol.*, 173:183-186, 1997). It is activated by binding to its natural ligand HGF (hepatocyte growth factor, also known as scatter factor) and signals via the PI3K and MAPK pathways. MET can be deregulated in cancer by mechanisms such as autocrine/paracrine HGF activation, over-expression of the receptor, and/or the presence of activating mutations. Significant expression of MET has been observed in a variety of human tumors, such as colon, lung, prostate (including bone metastases), gastric, renal, HCC, ovarian, breast, ESCC, and melanoma (Maulik et al, *Cytokine & Growth Factor Reviews* 13:41-59, 2002). MET is also implicated in atherosclerosis and lung fibrosis. Inhibition of MET can cause a decrease in cell motility, proliferation and metastasis, as reviewed in, e.g., *Chemical & Engineering News* 2007, 85 (34), 15-23.

As human cancers progress to a more invasive, metastatic state, multiple signaling programs regulating cell survival and migration programs are observed depending on cell and tissue contexts (Gupta and Massague, 2006). Recent data highlight the transdifferentiation of epithelial cancer cells to a more mesenchymal-like state, a process resembling epithelial-mesenchymal transition (EMT); (Oft et al., 1996; Perl et al., 1998), to facilitate cell invasion and metastasis (Brabletz et al., 2005; Christofori, 2006). Through EMT-like transitions mesenchymal-like tumor cells are thought to gain migratory capacity at the expense of proliferative potential. A mesenchymal-epithelial transition (MET) has been postulated to regenerate a more proliferative state and allow macrometastases resembling the primary tumor to form at distant sites (Thiery, 2002). MET and RON kinases have been shown to play a role in the EMT process (Camp et al., 2007; Grotegut et al., 2006; Wang et al., 2004).

Thus, it is desirable to identify compounds that inhibit RON and/or its related family MET for use in proliferative diseases, such as, but not limited to, cancer.

It has been documented in vitro that RON and MET can form heterodimers and signal via such RON-MET dimers. Since co-expression of RON and MET in cancer has been observed, such "cross-talk" may contribute to tumor growth. It is therefore especially desirable to identify compounds that inhibit both RON and MET.

There is a continuing need to improve anticancer pharmaceuticals with better selectivity or potency, reduced toxicity, or fewer side effects.

SUMMARY

In some aspects, the present invention is directed to Furo [3,2-c]Pyridine and Thieno[3,2-c]Pyridine compounds having the structure of Formula I, and pharmaceutically acceptable salts thereof:

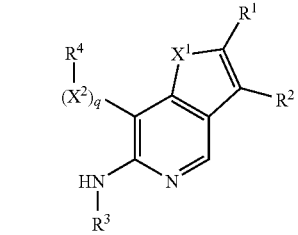

I wherein $R^1$-$R^4$ are optional substituents; $X^1$ is O or S; $(X^2)_q$ is absent or is O, S, S(O), S(O)$_2$, or optionally substituted N.

In some embodiments, $R^1$ and $R^3$ are both H; $X^1$ and $X^2$ are both O; q is 1; $R^2$ is optionally substituted aryl, heterocyclyl, or heteroaryl; and $R^4$ is optionally substituted aryl-alkyl.

Compounds of the invention are inhibitors of kinases such as RON and/or MET, including dual inhibition.

In some aspects, the invention includes the preparation of the compounds, and associated intermediates.

In some aspects, the invention includes pharmaceutical compositions containing the compounds.

In some aspects, the invention includes treating disease with the compounds and compositions, including hyperproliferative disorders, cancers, mesenchymal cancers, cancers mediated at least in part by MET and/or RON, and cancers in which inhibiting EMT is desirable.

DETAILED DESCRIPTION

Compounds

In some aspects, the present invention includes a compound or a pharmaceutically acceptable salt thereof, of Formula I:

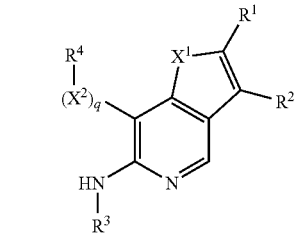

I wherein:
$X^1$ is O or S;
$X^2$ is O, S(O)$_m$, or —NR$^5$;
$R^1$ is H, halo, —CN, —CF$_3$, —NO$_2$, C$_{0-12}$alkyl, C$_{2-12}$alkenyl, C$_{2-12}$alkynyl, C$_{3-12}$cycloalkylC$_{0-12}$alkyl, C$_{3-12}$heterocycloalkylC$_{0-12}$alkyl, arylC$_{0-12}$alkyl or heteroarylC$_{0-12}$alkyl, any of which is optionally substituted with one or more independent G$^1$ substituents;
$R^2$ is H, halo, —CN, —CF$_3$, —NO$_2$, C$_{0-12}$alkyl, C$_{2-12}$alkenyl, C$_{2-12}$alkynyl, C$_{3-12}$cycloalkylC$_{0-12}$alkyl, C$_{3-12}$heterocycloalkylC$_{0-12}$alkyl, arylC$_{0-12}$alkyl or heteroarylC$_{0-12}$alkyl, any of which is optionally substituted with one or more independent G$^2$ substituents;

or R$^2$ is tetrahydropyridinyl, which is a structure of Formula II:

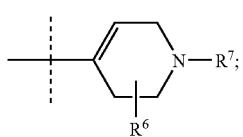

R$^3$ is H or C$_{1-12}$alkyl;

R$^4$ is H, C$_{0-12}$alkyl, C$_{3-12}$cycloalkylC$_{0-12}$alkyl, C$_{3-12}$heterocycloalkylC$_{0-12}$alkyl, arylC$_{0-12}$alkyl, arylC$_{3-12}$cycloalkyl, arylC$_{3-12}$heterocycloalkyl, heteroarylC$_{0-12}$alkyl, heteroarylC$_{3-12}$cycloalkyl or heteroarylC$_{3-12}$heterocycloalkyl, any of which is optionally substituted with one or more independent G$^3$ substituents;

or R$^4$ is —(CR$^{10}$R$^{11}$)$_n$A$^1$;

A$^1$ is aryl or heteroaryl optionally substituted by one or more independent G$^4$;

R$^5$ is H, C$_{0-12}$alkyl, C$_{3-12}$cycloalkylC$_{0-12}$alkyl, C$_{3-12}$heterocycloalkylC$_{0-12}$alkyl, arylC$_{0-12}$alkyl, heteroarylC$_{0-12}$alkyl, C$_{1-12}$alkyl-O—C$_{2-12}$alkyl, C$_{1-12}$alkyl-S(O)$_m$—C$_{2-12}$alkyl, (C$_{0-12}$alkyl)(C$_{0-12}$alkyl)N—C$_{2-12}$alkyl, C$_{2-12}$alkenylC$_{1-12}$alkyl or C$_{2-12}$alkynylC$_{1-12}$alkyl, any of which is optionally substituted with one or more independent G$^5$ substituents;

R$^{10}$ and R$^{11}$ are each independently H, C$_{0-12}$alkyl, C$_{1-12}$alkyl-O—C$_{1-12}$alkyl, (C$_{1-12}$alkyl)(C$_{0-12}$alkyl)N—C$_{1-12}$alkyl, C$_{1-12}$alkyl-S(O)$_m$—C$_{1-12}$alkyl, C$_{3-12}$cycloalkylC$_{0-12}$alkyl, C$_{3-12}$cycloalkenylC$_{1-12}$alkyl or C$_{3-12}$heterocycloalkylC$_{0-10}$alkyl, any of which is optionally substituted by one or more independent G$^6$ substituents; or R$^{10}$ and R$^{11}$ are taken together with the carbon atom to which they are attached to form a 3-12 membered saturated or unsaturated ring, wherein said ring is optionally substituted by one or more independent G$^7$ substituents and said ring optionally includes one or more heteroatoms selected from O, N, or S(O)$_m$;

R$^6$ is selected from H, C$_{0-12}$alkyl, C$_{1-12}$alkyl-O—C$_{1-12}$alkyl, (C$_{1-12}$alkyl)(C$_{0-12}$alkyl)N—C$_{1-12}$alkyl or C$_{1-12}$alkyl-S(O)$_m$—C$_{1-12}$alkyl, any of which is optionally substituted by one or more independent G$^8$ substituents;

R$^7$ is H, C$_{0-12}$alkyl, R$^8$O—C$_{2-12}$alkyl, R$^8$R$^9$N—C$_{2-12}$alkyl, R$^8$S(O)$_m$—C$_{2-12}$alkyl, C$_{3-12}$cycloalkylC$_{0-12}$alkyl, C$_{3-12}$cycloalkenylC$_{1-12}$alkyl, C$_{3-12}$heterocycloalkylC$_{0-12}$alkyl, arylC$_{0-12}$alkyl, heteroarylC$_{0-12}$alkyl, C$_{1-12}$alkylC$_{3-12}$cycloalkyl, C$_{3-12}$cycloalkylC$_{3-12}$cycloalkyl, C$_{3-12}$cycloalkenylC$_{3-12}$cycloalkyl, C$_{3-12}$heterocycloalkylC$_{3-12}$cycloalkyl, arylC$_{3-12}$cycloalkyl, heteroarylC$_{3-12}$cycloalkyl, C$_{1-12}$alkylC$_{3-12}$heterocycloalkyl, C$_{3-12}$cycloalkylC$_{3-12}$heterocycloalkyl, C$_{3-12}$cycloalkenylC$_{3-12}$heterocycloalkyl, C$_{3-12}$heterocycloalkylC$_{3-12}$heterocycloalkyl, arylC$_{3-12}$heterocycloalkyl, heteroarylC$_{3-12}$heterocycloalkyl, —C(O)R$^a$, R$^8$O—C$_{0-12}$alkylC(O)—, R$^8$R$^9$N—C$_{0-12}$alkylC(O)—, R$^8$S(O)$_m$C$_{0-12}$alkylC(O)—, —CO$_2$R$^8$, —C(O)NR$^8$R$^9$, —S(O)$_m$R$^8$, —SO$_2$NR$^8$R$^9$ or —C(S)OR$^8$, any of which is optionally substituted with one or more independent G$^9$ substituents;

G$^1$, G$^2$, G$^3$, G$^4$, G$^5$, G$^6$, G$^7$, G$^8$, and G$^9$ are each independently selected from H, halo, —CN, —CF$_3$, —OCF$_3$, —NO$_2$, C$_{0-12}$alkyl, C$_{2-12}$ alkenyl, C$_{2-12}$ alkynyl, C$_{3-12}$cycloalkylC$_{0-12}$alkyl, C$_{3-12}$heterocycloalkylC$_{0-12}$alkyl, arylC$_{0-12}$alkyl, heteroarylC$_{0-12}$alkyl, —OR$^{12}$, —S(O)$_m$R$^{12}$, —NR$^{12}$R$^{13}$, —SO$_2$NR$^{12}$R$^{13}$, —C(O)R$^b$, —C(O)NR$^{12}$R$^{13}$, —C(O)—C(O)NR$^{12}$R$^{13}$, —C(O)OR$^{12}$, —C(O)—C(O)OR$^{12}$, —OC(O)R$^b$, —NR$^{12}$C(O)R$^b$, —NR$^{12}$S(O)$_2$R$^{13}$, —(CR$^{14}$R$^{15}$)$_n$C(O)R$^b$, —(CR$^{14}$R$^{15}$)$_n$C(O)OR$^{12}$, —(CR$^{14}$R$^{15}$)$_n$C(O)NR$^{12}$R$^{13}$, —(CR$^{14}$R$^{15}$)$_n$S(O)$_2$NR$^{12}$R$^{13}$, —(CR$^{14}$R$^{15}$)$_n$NR$^{12}$R$^{13}$, —(CR$^{14}$R$^{15}$)$_n$OR$^{12}$, —(CR$^{14}$R$^{15}$)$_n$S(O)$_m$R$^{12}$, —NR$^{16}$C(O)NR$^{12}$R$^{13}$, —NR$^{16}$S(O)$_2$NR$^{12}$R$^{13}$ or —NR$^{16}$S(O)NR$^{12}$R$^{13}$, any of which is optionally substituted with one or more independent Q$^1$ substituents;

Q$^1$ is selected from H, halo, —CN, —NO$_2$, oxo, —CF$_3$, —OCF$_3$, C$_{0-12}$alkyl, arylC$_{0-12}$alkyl, heteroarylC$_{0-12}$alkyl, C$_{3-12}$cycloalkylC$_{0-12}$alkyl, C$_{3-12}$heterocycloalkylC$_{0-12}$alkyl, arylC$_{3-12}$cycloalkyl, heteroarylC$_{3-12}$cycloalkyl, C$_{3-12}$heterocycloalkylC$_{3-12}$cycloalkyl, C$_{3-12}$cycloalkylC$_{3-12}$cycloalkyl, C$_{1-12}$alkylC$_{3-12}$heterocycloalkyl, C$_{3-12}$heterocycloalkylC$_{3-12}$ heterocycloalkyl, arylC$_{3-12}$heterocycloalkyl, heteroarylC$_{3-12}$ heterocycloalkyl, —C(O)—C(O)NR$^{17}$R$^{18}$, —C(O)—C(O)OR$^{17}$, —OC(O)R$^c$, —NR$^{17}$C(O)R$^c$, —NR$^{17}$S(O)$_2$R$^{18}$, —(CR$^{19}$R$^{20}$)$_n$C(O)R$^c$, —(CR$^{19}$R$^{20}$)$_n$C(O)OR$^{17}$, —(CR$^{19}$R$^{20}$)$_n$C(O)NR$^{17}$R$^{18}$, —(CR$^{19}$R$^{20}$)$_n$S(O)$_2$NR$^{17}$R$^{18}$, —(CR$^{19}$R$^{20}$)$_n$NR$^{17}$R$^{18}$, —(CR$^{19}$R$^{20}$)$_n$OR$^{17}$, —(CR$^{19}$R$^{20}$)$_n$S(O)$_m$R$^{17}$, —NR$^{21}$C(O)NR$^{17}$R$^{18}$, —NR$^{21}$S(O)$_2$NR$^{17}$R$^{18}$ or —NR$^{21}$S(O)NR$^{17}$R$^{18}$, any of which is optionally substituted with one or more independent Q$^2$ substituents;

Q$^2$ is selected from H, halo, —CN, —OH, —NH$_2$, —NO$_2$, oxo, —CF$_3$, —OCF$_3$, —CO$_2$H, —S(O)$_m$H, C$_{0-12}$alkyl, arylC$_{0-12}$alkyl, heteroarylC$_{0-12}$alkyl, C$_{3-12}$cycloalkylC$_{0-12}$alkyl, C$_{3-12}$heterocycloalkylC$_{0-12}$alkyl, arylC$_{3-12}$cycloalkyl, heteroarylC$_{3-12}$cycloalkyl, C$_{3-12}$heterocycloalkylC$_{3-12}$cycloalkyl, C$_{3-12}$cycloalkylC$_{3-12}$cycloalkyl, C$_{1-12}$alkylC$_{3-12}$heterocycloalkyl, C$_{3-12}$heterocycloalkylC$_{3-12}$ heterocycloalkyl, arylC$_{3-12}$heterocycloalkyl or heteroarylC$_{3-12}$ heterocycloalkyl, any of which is optionally substituted with one or more independent halo, —CN, —OH, —NH$_2$ or C$_{1-10}$alkyl which may be partially or fully halogenated, or —O—C$_{1-10}$ alkyl which may be partially or fully halogenated;

R$^8$, R$^9$, R$^{12}$, R$^{13}$, R$^{14}$, R$^{15}$, R$^{16}$, R$^{17}$, R$^{18}$, R$^{19}$, R$^{20}$, R$^{21}$, R$^a$, R$^b$, and R$^c$ are each independently selected from H, C$_{0-12}$alkyl, arylC$_{0-12}$alkyl, heteroarylC$_{0-12}$alkyl, C$_{3-12}$cycloalkylC$_{0-12}$alkyl, C$_{3-12}$heterocycloalkylC$_{0-12}$alkyl, aryl C$_{3-12}$ cycloalkyl, heteroarylC$_{3-12}$cycloalkyl, C$_{3-12}$heterocycloalkylC$_{3-12}$cycloalkyl, C$_{3-12}$cycloalkylC$_{3-12}$cycloalkyl, C$_{1-12}$alkylC$_{3-12}$heterocycloalkyl, C$_{3-12}$heterocycloalkylC$_{3-12}$ heterocycloalkyl, arylC$_{3-12}$heterocycloalkyl, or heteroarylC$_{3-12}$heterocycloalkyl substituents;

—NR$^8$R$^9$, —NR$^{12}$R$^{13}$ and —NR$^{17}$R$^{18}$ is each independently linear structure; or R$^8$ and R$^9$, or R$^{12}$ and R$^{13}$, or R$^{17}$ and R$^{18}$, respectively, is taken together with the nitrogen atom to which they are attached to form a 3-12 membered saturated or unsaturated ring, wherein said ring optionally includes one or more heteroatoms selected from O, N, or S(O)$_m$;

—CR$^{14}$R$^{15}$ or —CR$^{19}$R$^{20}$ is each independently linear structure; or R$^{14}$ and R$^{15}$, or R$^{19}$ and R$^{20}$, respectively, is taken together with the carbon atom to which they are attached to form a 3-12 membered saturated or unsaturated ring, wherein said ring optionally includes one or more heteroatoms selected from O, N, or S(O)$_m$;

each q is independently 0 or 1; each n is independently 0-7; each m is independently 0-2.

In some aspects of the invention, there is provided a compound or salt of Formula I as defined above, wherein X$^1$ is O.

In some aspects of the invention, there is provided a compound or salt of Formula I as defined above, wherein R$^3$ is hydrogen.

In some aspects of the invention, there is provided a compound or salt of Formula I as defined above, wherein $(X^2)_q$ is O.

In some aspects of the invention, there is provided a compound or salt of Formula I as defined above, wherein $R^1$ is hydrogen.

In some aspects of the invention, there is provided a compound or salt of Formula I as defined above, wherein $R^4$ is $-(CR^{10}R^{11})_nA^1$.

In some aspects of the invention, there is provided a compound or salt of Formula I as defined above, wherein $X^1$ is O, $(X^2)_q$ is O and $R^4$ is $-(CR^{10}R^{11})_nA^1$. More specifically, $R^3$ can be hydrogen. More specifically, $R^1$ can be hydrogen.

In some aspects of the invention, there is provided a compound or salt of Formula I as defined above, wherein the compound has the Formula Ia:

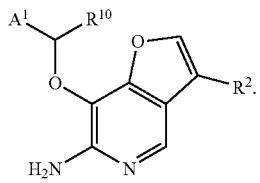

Ia

In some aspects of the invention, there is provided a compound or salt of Formula I as defined above, wherein the compound has the Formula Ib:

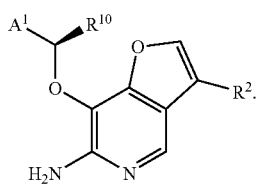

Ib

In some aspects of the invention, there is provided a compound or salt of Formula I as defined above, wherein $A^1$ is aryl which is optionally further substituted by one or more independent $G^4$ substituents.

In some aspects of the invention, there is provided a compound or salt of Formula I as defined above, wherein $R^{10}$ is H, $C_{0-12}$alkyl, $C_{0-12}$alkyl-O—$C_{1-12}$alkyl, $(C_{0-12}$alkyl)$(C_{0-12}$alkyl)N—$C_{1-12}$alkyl, $C_{0-12}$alkyl-S(O)$_m$—$C_{1-12}$alkyl, $C_{3-12}$cycloalkyl$C_{0-12}$alkyl, $C_{3-12}$cycloalkenyl$C_{1-12}$alkyl, or $C_{3-12}$heterocycloalkyl$C_{0-10}$alkyl, any of which is optionally substituted by one or more independent $G^6$ substituents.

In some aspects of the invention, there is provided a compound or salt of Formula I as defined above, wherein $R^2$ is aryl$C_{0-12}$alkyl or heteroaryl$C_{0-12}$alkyl, any of which is optionally substituted with one or more independent $G^2$ substituents;

In some aspects of the invention, there is provided a compound or salt of Formula I as defined above, wherein $R^2$ is a structure of Formula II

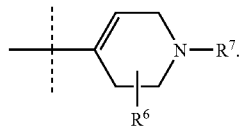

II

In some aspects of the invention, there is provided a compound or salt of Formula I as defined above, wherein $A^1$ is aryl which is optionally further substituted by one or more independent $G^4$ substituents; $R^{10}$ is H or $C_{0-12}$alkyl which is optionally substituted by one or more independent $G^6$ substituents; and $R^2$ is aryl or heteroaryl which is optionally substituted with one or more independent $G^2$ substituents, or $R^2$ is a structure of Formula II

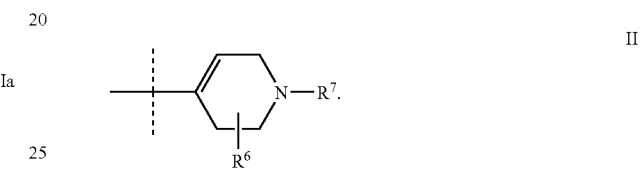

II

In some aspects of the invention, there is provided a compound having the Formula:

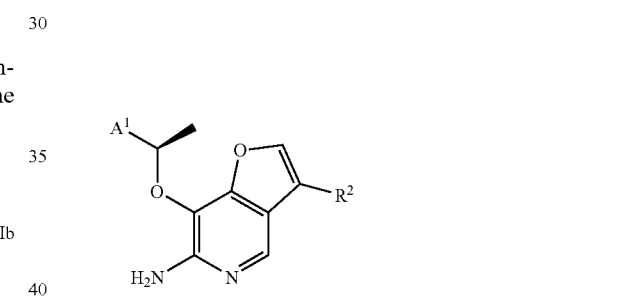

wherein:
$R^2$ is

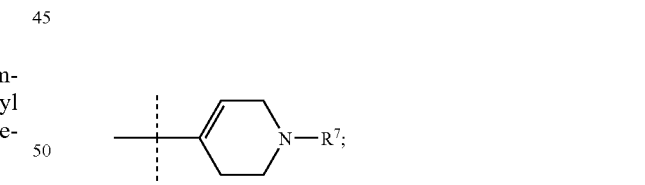

$R^7$ is $C_{0-6}$alkyl, $-C(O)R^a$, $-C(O)NR^8R^9$, any of which is optionally substituted with 1-2 independent $G^9$ substituents;

$G^9$ is selected from $C_{0-6}$alkyl, $C_{2-6}$alkenyl, $C_{2-6}$alkynyl, $-OR^{12}$, $-S(O)_mR^{12}$, $-NR^{12}R^{13}$, $-SO_2NR^{12}R^{13}$, $-C(O)R^b$, $-C(O)(CR^{14}R^{15})_nNR^{12}R^{13}$, $-C(O)-C(O)NR^{12}R^{13}$, $-C(O)OR^{12}$, $-C(O)-C(O)OR^{12}$, $-OC(O)R^b$, $-NR^{12}C(O)R^b$, $-NR^{12}S(O)_2R^{13}$, $-(CR^{14}R^{15})_nC(O)R^b$, $-(CR^{14}R^{15})_nC(O)OR^{12}$, $-(CR^{14}R^{15})_nC(O)NR^{12}R^{13}$, $-(CR^{14}R^{15})_nS(O)_2NR^{12}R^{13}$, $-(CR^{14}R^{15})_nNR^{12}R^{13}$, $-(CR^{14}R^{15})_nOR^{12}$, $-(CR^{14}R^{15})_nS(O)_mR^{12}$, $-NR^{16}C(O)NR^{12}R^{13}$, $-NR^{16}S(O)_2NR^{12}R^{13}$, or $-NR^{16}S(O)NR^{12}R^{13}$, any of which is optionally substituted by 1-2 $Q^1$;

each $Q^1$ is independently selected from $C_{0-6}$alkyl, aryl$C_{0-6}$alkyl, heteroaryl$C_{0-6}$alkyl, $C_{3-6}$cycloalkyl$C_{0-6}$alkyl, $C_{3-6}$heterocycloalkyl$C_{0-6}$alkyl, or $-(CR^{14}R^{15})_nNR^{12}R^{13}$;

each $R^{12}$, $R^{13}$, $R^{14}$, $R^{15}$, $R^{16}$, and $R^b$ is independently $C_{0-6}$alkyl; —$NR^{12}R^{13}$ is independently linear structure; or $R^{12}$ and $R^{13}$ can be taken together with the nitrogen atom to which they are attached to form a 3-6 membered saturated or unsaturated ring, wherein said ring optionally includes one or more heteroatoms selected from O, N, or $S(O)_m$; —$CR^{14}R^{15}$ is linear structure; or $R^{14}$ and $R^{15}$ can be taken together with the carbon atom to which they are attached to form a 3-6 membered saturated or unsaturated ring, wherein said ring optionally includes one or more heteroatoms selected from O, N, or $S(O)_m$;

each n is independently 0-6; each m is independently 0-2; and $A^1$ is phenyl which is optionally substituted with 3-4 ortho or meta substituents each independently selected from Br, Cl, F, or methoxy.

In some aspects of the invention, there is provided a compound having the Formula:

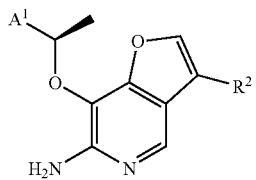

wherein:

$R^2$ is phenyl or pyridyl each optionally substituted by $G^2$;

$G^2$ is selected from $C_{0-6}$alkyl, $C_{2-6}$alkenyl, $C_{2-6}$alkynyl, —$OR^{12}$, —$S(O)_mR^{12}$, —$NR^{12}R^{13}$, —$SO_2NR^{12}R^{13}$, —$C(O)R^b$, —$C(O)(CR^{14}R^{15})_nNR^{12}R^{13}$, —$C(O)$—$C(O)NR^{12}R^{13}$, —$C(O)OR^{12}$, —$C(O)$—$C(O)OR^{12}$, $OC(O)R^b$, —$NR^{12}C(O)R^b$, —$NR^{12}S(O)_2R^{13}$, —$(CR^{14}R^{15})_nC(O)R^b$, —$(CR^{14}R^{15})_nC(O)OR^{12}$, —$(CR^{14}R^{15})_nC(O)NR^{12}R^{13}$, —$(CR^{14}R^{15})_nS(O)_2NR^{12}R^{13}$, —$(CR^{14}R^{15})_nNR^{12}R^{13}$, —$(CR^{14}R^{15})_nOR^{12}$, —$(CR^{14}R^{15})_nS(O)_mR^{12}$, —$NR^{16}C(O)NR^{12}R^{13}$, —$NR^{16}S(O)_2NR^{12}R^{13}$, or —$NR^{16}S(O)NR^{12}R^{13}$, any of which is optionally substituted by 1-2 $Q^1$;

each $Q^1$ is independently selected from $C_{0-6}$alkyl, aryl$C_{0-6}$alkyl, heteroaryl$C_{0-6}$alkyl, $C_{3-6}$cycloalkyl$C_{0-6}$alkyl, $C_{3-6}$heterocycloalkyl$C_{0-6}$alkyl, or —$(CR^{14}R^{15})_nNR^{12}R^{13}$;

each $R^{12}$, $R^{13}$, $R^{14}$, $R^{15}$, $R^{16}$, and $R^b$ is independently $C_{0-6}$alkyl; —$NR^{12}R^{13}$ is independently linear structure; or $R^{12}$ and $R^{13}$ can be taken together with the nitrogen atom to which they are attached to form a 3-6 membered saturated or unsaturated ring, wherein said ring optionally includes one or more heteroatoms selected from O, N, or $S(O)_m$; —$CR^{14}R^{15}$ is linear structure; or $R^{14}$ and $R^{15}$ can be taken together with the carbon atom to which they are attached to form a 3-6 membered saturated or unsaturated ring, wherein said ring optionally includes one or more heteroatoms selected from O, N, or $S(O)_m$;

each n is independently 0-6; each m is independently 0-2; and $A^1$ is phenyl which is optionally substituted with 3-4 ortho or meta substituents each independently selected from Br, Cl, F, or methoxy.

In some aspects of the invention, there is provided a compound having the Formula:

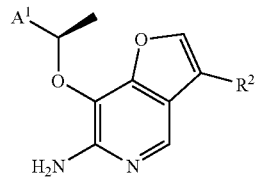

wherein:

$R^2$ is pyrazolyl, imidazolyl, or thiazolyl, each optionally substituted by $G^2$;

$G^2$ is selected from $C_{0-6}$alkyl, $C_{2-6}$alkenyl, $C_{2-6}$alkynyl, —$OR^{12}$, —$S(O)_mR^{12}$, —$NR^{12}R^{13}$, —$SO_2NR^{12}R^{13}$, —$C(O)R^b$, —$C(O)(CR^{14}R^{15})_nNR^{12}R^{13}$, —$C(O)$—$C(O)NR^{12}R^{13}$, —$C(O)OR^{12}$, —$C(O)$—$C(O)OR^{12}$, —$OC(O)R^b$, —$NR^{12}C(O)R^b$, —$NR^{12}S(O)_2R^{13}$, —$(CR^{14}R^{15})_nC(O)R^b$, —$(CR^{14}R^{15})_nC(O)OR^{12}$, —$(CR^{14}R^{15})_nC(O)NR^{12}R^{13}$, —$(CR^{14}R^{15})_nS(O)_2NR^{12}R^{13}$, —$(CR^{14}R^{15})_nNR^{12}R^{13}$, —$(CR^{14}R^{15})_nOR^{12}$, —$(CR^{14}R^{15})_nS(O)_mR^{12}$, —$NR^{16}C(O)NR^{12}R^{13}$, —$NR^{16}S(O)_2NR^{12}R^{13}$, or —$NR^{16}S(O)NR^{12}R^{13}$, any of which is optionally substituted by 1-2 $Q^1$;

each $Q^1$ is independently selected from $C_{0-6}$alkyl, aryl$C_{0-6}$alkyl, heteroaryl$C_{0-6}$alkyl, $C_{3-6}$cycloalkyl$C_{0-6}$alkyl, $C_{3-6}$heterocycloalkyl$C_{0-6}$alkyl, or —$(CR^{14}R^{15})_nNR^{12}R^{13}$;

each $R^{12}$, $R^{13}$, $R^{14}$, $R^{15}$, $R^{16}$, and $R^b$ is independently $C_{0-6}$alkyl; —$NR^{12}R^{13}$ is independently linear structure; or $R^{12}$ and $R^{13}$ can be taken together with the nitrogen atom to which they are attached to form a 3-6 membered saturated or unsaturated ring, wherein said ring optionally includes one or more heteroatoms selected from O, N, or $S(O)_m$; —$CR^{14}R^{15}$ is linear structure; or $R^{14}$ and $R^{15}$ can be taken together with the carbon atom to which they are attached to form a 3-6 membered saturated or unsaturated ring, wherein said ring optionally includes one or more heteroatoms selected from O, N, or $S(O)_m$;

each n is independently 0-6; each m is independently 0-2; and $A^1$ is phenyl which is optionally substituted with 3-4 ortho or meta substituents each independently selected from Br, Cl, F, or methoxy.

In some aspects of the invention, there is provided a compound or salt of Formula I as defined above, wherein $A^1$ is:

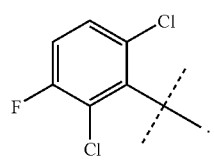

In some aspects of the invention, the compound or salt thereof which is selected from any of the examples herein.

In some aspects, the compound is selected from:

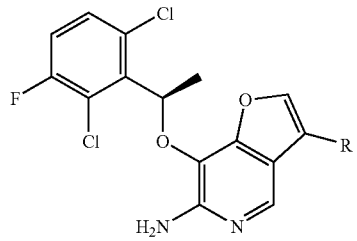

| R | Name |
|---|---|
| *pyrazole with N-methyl* | 7-[(R)-1-(2,6-Dichloro-3-fluorophenyl)-ethoxy]-3-(1-methyl-1H-pyrazol-4-yl)-furo[3,2-c]pyridin-6-ylamine |
| *pyrazole with N-piperidin-4-yl* | 7-[(R)-1-(2,6-Dichloro-3-fluorophenyl)ethoxy]-3-(1-piperidin-4-yl-1H-pyrazol-4-yl)-furo[3,2-c]pyridin-6-ylamine |
| *1H-pyrazole* | 7-[(R)-1-(2,6-Dichloro-3-fluorophenyl)ethoxy]-3-(1H-pyrazol-4-yl)-furo[3,2-c]pyridin-6-ylamine |
| *tetrahydropyridine* | 7-[(R)-1-(2,6-Dichloro-3-fluorophenyl)-ethoxy]-3-(1,2,3,6-tetrahydropyridin-4-yl)-furo[3,2-c]pyridin-6-ylamine |
| *N-(dimethylaminoacetyl)tetrahydropyridine* | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2-dimethylaminoethanone |
| *N-formyl tetrahydropyridine* | 4-{6-Amino-7-[(R)-1-(2,6-dichloro-3-fluorophenyl)-ethoxy]-furo[3,2-c]pyridin-3-yl}-3,6-dihydro-2H-pyridine-1-carbaldehyde |
| *N-acetyl tetrahydropyridine* | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-ethanone |
| *N-(pyrrolidinylacetyl)tetrahydropyridine* | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2-pyrrolidin-1-ylethanone |
| *N-(1-methylpiperidine-4-carbonyl)tetrahydropyridine* | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(1-methylpiperidin-4-yl)-methanone |

-continued

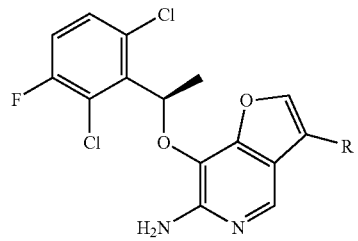

| R | Name |
|---|---|
| (pyrrolidinyl-methylpiperidine) | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-((S)-1-methylpyrrolidin-2-yl)-methanone |
| (dimethylaminobutanoyl-piperidine) | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-4-dimethylaminobutan-1-one |
| (piperidinyl-carbonyl-piperidine) | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperidin-4-ylmethanone |
| (pyrrolidinyl-carbonyl-piperidine) | (4-{6-Amino-7-[(R)-1-(2,6-dichloro-3-fluorophenyl)ethoxy]furo[3,2-c]pyridin-3-yl}-3,6-dihydro-2H-pyridin-1-yl)-(S)-pyrrolidin-2-ylmethanone |
| (aminocyclopropyl-carbonyl-piperidine) | (1-Aminocyclopropyl)-(4-{6-amino-7-[(R)-1-(2,6-dichloro-3-fluorophenyl)-ethoxy]-furo[3,2-c]pyridin-3-yl}-3,6-dihydro-2H-pyridin-1-yl)-methanone |
| (aminomethylpropanoyl-piperidine) | 2-Amino-1-(4-{6-amino-7-[(R)-1-(2,6-dichloro-3-fluorophenyl)-ethoxy]-furo[3,2-c]pyridin-3-yl}-3,6-dihydro-2H-pyridin-1-yl)-2-methylpropan-1-one |
| (ethylpiperazinyl-carbonyl-piperidine) | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-ethylpiperazin-1-yl)-methanone |

-continued

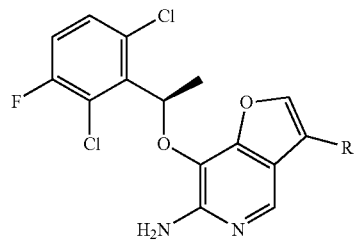

| R | Name |
|---|---|
| ![piperazine-tBu] | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-tert-butylpiperazin-1-yl)-methanone |
| ![piperazine-H] | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperazin-1-ylmethanone |
| ![carboxamide] | 4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid amide |
| ![methylamide] | 4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid methylamide |
| ![N-methyl] | 7-[(R)-1-(2,6-Dichloro-3-fluorophenyl)-ethoxy]-3-(1-methyl-1,2,3,6-tetrahydropyridin-4-yl)-furo[3,2-c]pyridin-6-ylamine |
| ![N-ethyl] | 7-[(R)-1-(2,6-Dichloro-3-fluorophenyl)-ethoxy]-3-(1-ethyl-1,2,3,6-tetrahydropyridin-4-yl)-furo[3,2-c]pyridin-6-ylamine |
| ![N-aminoethyl] | 3-[1-(2-Aminoethyl)-1,2,3,6-tetrahydropyridin-4-yl]-7-[(R)-1-(2,6-dichloro-3-fluorophenyl)-ethoxy]-furo[3,2-c]pyridin-6-ylamine |
| ![N-mesyl] | 7-[(R)-1-(2,6-Dichloro-3-fluorophenyl)-ethoxy]-3-(1-methanesulfonyl-1,2,3,6-tetrahydropyridin-4-yl)-furo[3,2-c]pyridin-6-ylamine |

-continued

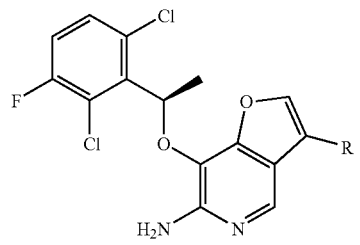

| R | Name |
|---|---|
| 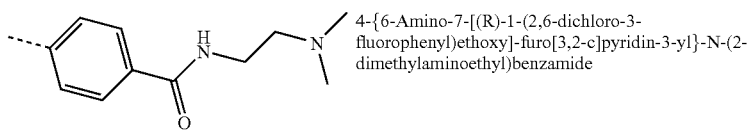 | 4-{6-Amino-7-[(R)-1-(2,6-dichloro-3-fluorophenyl)ethoxy]-furo[3,2-c]pyridin-3-yl}-N-(2-dimethylaminoethyl)benzamide |
| 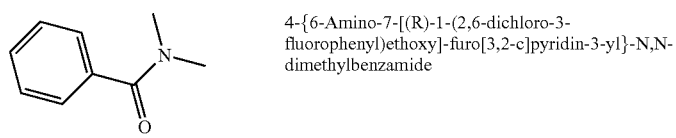 | 4-{6-Amino-7-[(R)-1-(2,6-dichloro-3-fluorophenyl)ethoxy]-furo[3,2-c]pyridin-3-yl}-N,N-dimethylbenzamide |
| 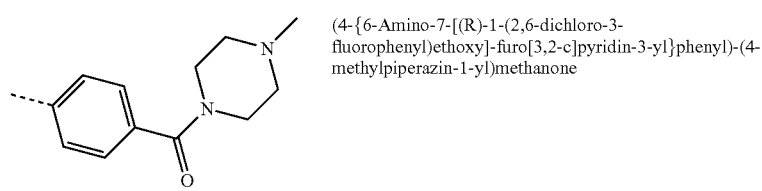 | (4-{6-Amino-7-[(R)-1-(2,6-dichloro-3-fluorophenyl)ethoxy]-furo[3,2-c]pyridin-3-yl}phenyl)-(4-methylpiperazin-1-yl)methanone |
| 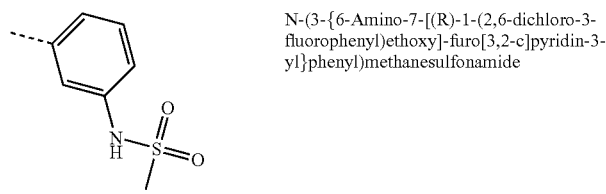 | N-(3-{6-Amino-7-[(R)-1-(2,6-dichloro-3-fluorophenyl)ethoxy]-furo[3,2-c]pyridin-3-yl}phenyl)methanesulfonamide |
| 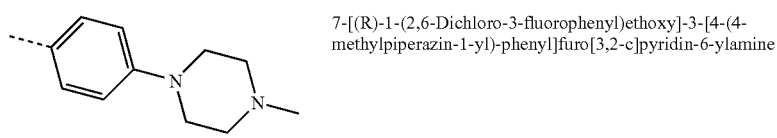 | 7-[(R)-1-(2,6-Dichloro-3-fluorophenyl)ethoxy]-3-[4-(4-methylpiperazin-1-yl)-phenyl]furo[3,2-c]pyridin-6-ylamine |
| 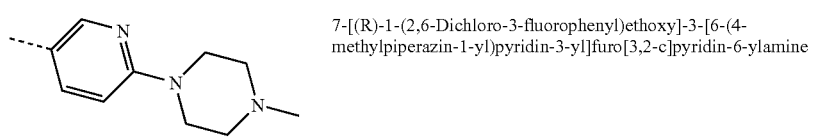 | 7-[(R)-1-(2,6-Dichloro-3-fluorophenyl)ethoxy]-3-[6-(4-methylpiperazin-1-yl)pyridin-3-yl]furo[3,2-c]pyridin-6-ylamine |

-continued

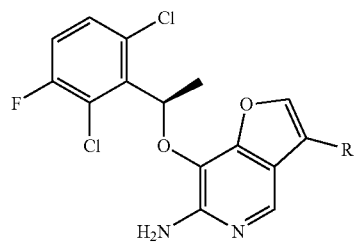

| R | Name |
|---|---|
| 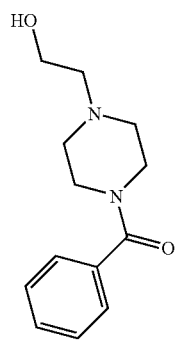 | (3-{6-Amino-7-[(R)-1-(2,6-dichloro-3-fluorophenyl)ethoxy]-furo[3,2-c]pyridin-3-yl}phenyl)-[4-(2-hydroxyethyl)piperazin-1-yl]methanone |
| 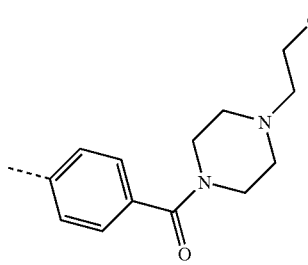 | (4-{6-Amino-7-[(R)-1-(2,6-dichloro-3-fluorophenyl)ethoxy]-furo[3,2-c]pyridin-3-yl}phenyl)-[4-(2-hydroxyethyl)piperazin-1-yl]methanone |
| 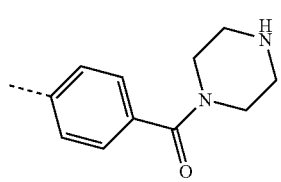 | (4-{6-Amino-7-[(R)-1-(2,6-dichloro-3-fluorophenyl)ethoxy]furo[3,2-c]pyridin-3-yl}phenyl)piperazin-1-ylmethanone |
| 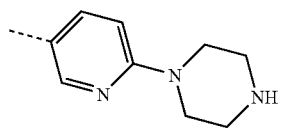 | 7-[(R)-(2,6-Dichloro-3-fluorophenyl)ethoxy]-3-(6-piperazin-1-yl-pyridin-3-yl)furo[3,2-c]pyridin-6-ylamine, or |
| 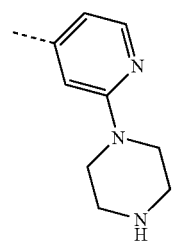 | 7-[(R)-(2,6-Dichloro-3-fluorophenyl)ethoxy]-3-(2-piperazin-1-yl-pyridin-4-yl)furo[3,2-c]pyridin-6-ylamine. |

In some aspects, the compound is selected from:

| R | Name |
|---|---|
| 1-methyl-1H-pyrazol-4-yl | 7-[(R)-1-(2-Chloro-3,6-difluorophenyl)-ethoxy]-3-(1-methyl-1H-pyrazol-4-yl)-furo[3,2-c]pyridin-6-ylamine |
| 1-(piperidin-4-yl)-1H-pyrazol-4-yl | 7-[(R)-1-(2-Chloro-3,6-difluorophenyl)ethoxy]-3-(1-piperidin-4-yl-1H-pyrazol-4-yl)-furo[3,2-c]pyridin-6-ylamine |
| 1H-pyrazol-4-yl | 7-[(R)-1-(2-Chloro-3,6-difluorophenyl)ethoxy]-3-(1H-pyrazol-4-yl)-furo[3,2-c]pyridin-6-ylamine |
| 1,2,3,6-tetrahydropyridin-4-yl | 7-[(R)-1-(2-Chloro-3,6-difluorophenyl)-ethoxy]-3-(1,2,3,6-tetrahydropyridin-4-yl)-furo[3,2-c]pyridin-6-ylamine |
| 1-(dimethylaminoacetyl)-1,2,3,6-tetrahydropyridin-4-yl | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-2-dimethylaminoethanone |
| 1-formyl-1,2,3,6-tetrahydropyridin-4-yl | 4-{6-Amino-7-[(R)-1-(2-chloro-3,6-difluorophenyl)-ethoxy]-furo[3,2-c]pyridin-3-yl}-3,6-dihydro-2H-pyridine-1-carbaldehyde |
| 1-acetyl-1,2,3,6-tetrahydropyridin-4-yl | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-ethanone |
| 1-(pyrrolidin-1-ylacetyl)-1,2,3,6-tetrahydropyridin-4-yl | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-2-pyrrolidin-1-ylethanone |
| 1-(1-methylpiperidine-4-carbonyl)-1,2,3,6-tetrahydropyridin-4-yl | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-(1-methylpiperidin-4-yl)-methanone |

-continued

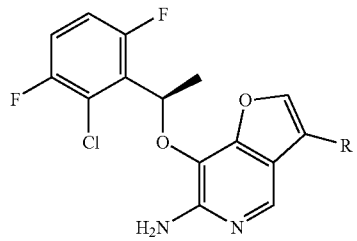

| R | Name |
|---|---|
| ![structure] tetrahydropyridine-N-C(O)-pyrrolidine-N-methyl | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-((S)-1-methylpyrrolidin-2-yl)-methanone |
| ![structure] tetrahydropyridine-N-C(O)-(CH2)3-N(CH3)2 | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-4-dimethylaminobutan-1-one |
| ![structure] tetrahydropyridine-N-C(O)-piperidine-NH | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-piperidin-4-ylmethanone |
| ![structure] tetrahydropyridine-N-C(O)-pyrrolidine-NH | (4-{6-Amino-7-[(R)-1-(2-chloro-3,6-difluorophenyl)ethoxy]furo[3,2-c]pyridin-3-yl}-3,6-dihydro-2H-pyridin-1-yl)-(S)-pyrrolidin-2-ylmethanone |
| ![structure] tetrahydropyridine-N-C(O)-cyclopropyl-NH2 | (1-Aminocyclopropyl)-(4-{6-amino-7-[(R)-1-(2-chloro-3,6-difluorophenyl)-ethoxy]-furo[3,2-c]pyridin-3-yl}-3,6-dihydro-2H-pyridin-1-yl)-methanone |
| ![structure] tetrahydropyridine-N-C(O)-C(CH3)2-NH2 | 2-Amino-1-(4-{6-amino-7-[(R)-1-(2-chloro-3,6-difluorophenyl)-ethoxy]-furo[3,2-c]pyridin-3-yl}-3,6-dihydro-2H-pyridin-1-yl)-2-methylpropan-1-one |
| ![structure] tetrahydropyridine-N-C(O)-piperazine-N-CH2-(4-ethylpiperazine) | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-(4-ethylpiperazin-1-yl)-methanone |
| ![structure] tetrahydropyridine-N-C(O)-piperazine-N-tBu | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-(4-tert-butylpiperazin-1-yl)-methanone |

-continued

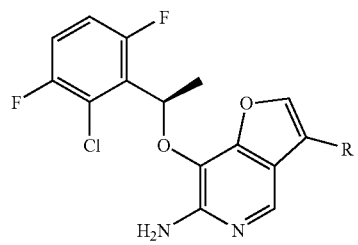

| R | Name |
|---|------|
| ![piperazine-carbonyl-tetrahydropyridine] | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-piperazin-1-ylmethanone |
| ![carboxamide-tetrahydropyridine] | 4-{6-Amino-7-[(R)-1-(2-chloro-3,6-difluorophenyl)-ethoxy]-furo[3,2-c]pyridin-3-yl}-3,6-dihydro-2H-pyridine-1-carboxylic acid amide |
| ![N-methyl-carboxamide-tetrahydropyridine] | 4-{6-Amino-7-[(R)-1-(2-chloro-3,6-difluorophenyl)-ethoxy]-furo[3,2-c]pyridin-3-yl}-3,6-dihydro-2H-pyridine-1-carboxylic acid methylamide |
| ![N-methyl-tetrahydropyridine] | 7-[(R)-1-(2-chloro-3,6-difluorophenyl)-ethoxy]-3-(1-methyl-1,2,3,6-tetrahydropyridin-4-yl)-furo[3,2-c]pyridin-6-ylamine |
| ![N-ethyl-tetrahydropyridine] | 7-[(R)-1-(2-chloro-3,6-difluorophenyl)-ethoxy]-3-(1-ethyl-1,2,3,6-tetrahydropyridin-4-yl)-furo[3,2-c]pyridin-6-ylamine |
| ![N-aminoethyl-tetrahydropyridine] | 3-[1-(2-Aminoethyl)-1,2,3,6-tetrahydropyridin-4-yl]-7-[(R)-1-(2-chloro-3,6-difluorophenyl)-ethoxy]-furo[3,2-c]pyridin-6-ylamine |
| ![N-methanesulfonyl-tetrahydropyridine] | 7-[(R)-1-(2-chloro-3,6-difluorophenyl)-ethoxy]-3-(1-methanesulfonyl-1,2,3,6-tetrahydropyridin-4-yl)-furo[3,2-c]pyridin-6-ylamine |
| ![benzamide-dimethylaminoethyl] | 4-{6-Amino-7-[(R)-1-(2-chloro-3,6-difluorophenyl)ethoxy]-furo[3,2-c]pyridin-3-yl}-N-(2-dimethylaminoethyl)benzamide |
| ![N,N-dimethylbenzamide] | 4-{6-Amino-7-[(R)-1-(2-chloro-3,6-difluorophenyl)ethoxy]-furo[3,2-c]pyridin-3-yl}-N,N-dimethylbenzamide |

-continued

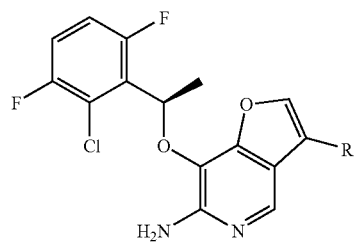

| R | Name |
|---|---|
| (piperazine-methylpiperazin-carbonyl-phenyl) | (4-{6-Amino-7-[(R)-1-(2-chloro-3,6-difluorophenyl)ethoxy]-furo[3,2-c]pyridin-3-yl}phenyl)-(4-methylpiperazin-1-yl)methanone |
| (methanesulfonamido-phenyl) | N-(3-{6-Amino-7-[(R)-1-(2-chloro-3,6-difluorophenyl)ethoxy]-furo[3,2-c]pyridin-3-yl}phenyl)methanesulfonamide |
| (4-methylpiperazinyl-phenyl) | 7-[(R)-1-(2-Chloro-3,6-difluorophenyl)ethoxy]-3-[4-(4-methylpiperazin-1-yl)-phenyl]furo[3,2-c]pyridin-6-ylamine |
| (4-methylpiperazinyl-pyridyl) | 7-[(R)-1-(2-Chloro-3,6-difluorophenyl)ethoxy]-3-[6-(4-methylpiperazin-1-yl)pyridin-3-yl]furo[3,2-c]pyridin-6-ylamine |
| (3-hydroxyethylpiperazinyl-carbonyl-phenyl) | (3-{6-Amino-7-[(R)-1-(2-chloro-3,6-difluorophenyl)ethoxy]-furo[3,2-c]pyridin-3-yl}phenyl)-[4-(2-hydroxyethyl)piperazin-1-yl]methanone |
| (4-hydroxyethylpiperazinyl-carbonyl-phenyl) | (4-{6-Amino-7-[(R)-1-(2-chloro-3,6-difluorophenyl)ethoxy]-furo[3,2-c]pyridin-3-yl}phenyl)-[4-(2-hydroxyethyl)piperazin-1-yl]methanone |

-continued

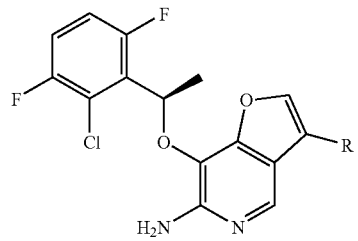

| R | Name |
|---|---|
| (piperazine-carbonyl-pyridinyl group) | (4-{6-Amino-7-[(R)-1-(2-chloro-3,6-difluorophenyl)ethoxy]furo[3,2-c]pyridin-3-yl}phenyl)piperazin-1-ylmethanone |
| (piperazin-1-yl-pyridin-3-yl group) | 7-[(R)-(2-Chloro-3,6-difluorophenyl)ethoxy]-3-(6-piperazin-1-yl-pyridin-3-yl)furo[3,2-c]pyridin-6-ylamine, or |
| (piperazin-1-yl-pyridin-4-yl group) | 7-[(R)-(2-Chloro-3,6-difluorophenyl)ethoxy]-3-(2-piperazin-1-yl-pyridin-4-yl)furo[3,2-c]pyridin-6-ylamine. |

In some aspects, the compound is selected from:

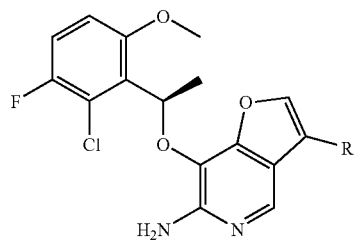

| R | Name |
|---|---|
| (1-methyl-1H-pyrazol-4-yl) | 7-[(R)-1-(2-Chloro-3-fluoro-6-methoxyphenyl)-ethoxy]-3-(1-methyl-1H-pyrazol-4-yl)-furo[3,2-c]pyridin-6-ylamine |
| (1-piperidin-4-yl-1H-pyrazol-4-yl) | 7-[(R)-1-(2-Chloro-3-fluoro-6-methoxyphenyl)ethoxy]-3-(1-piperidin-4-yl-1H-pyrazol-4-yl)-furo[3,2-c]pyridin-6-ylamine |

-continued

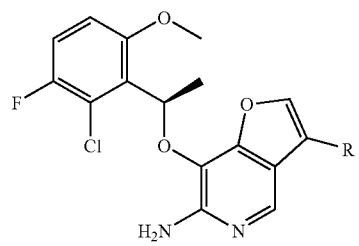

| R | Name |
|---|---|
| pyrazol-4-yl (NH) | 7-[(R)-1-(2-Chloro-3-fluoro-6-methoxyphenyl)ethoxy]-3-(1H-pyrazol-4-yl)-furo[3,2-c]pyridin-6-ylamine |
| 1,2,3,6-tetrahydropyridin-4-yl (NH) | 7-[(R)-1-(2-Chloro-3-fluoro-6-methoxyphenyl)-ethoxy]-3-(1,2,3,6-tetrahydropyridin-4-yl)-furo[3,2-c]pyridin-6-ylamine |
| tetrahydropyridinyl-N-C(O)CH₂N(CH₃)₂ | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-2-dimethylaminoethanone |
| tetrahydropyridinyl-N-CHO | 4-{6-Amino-7-[(R)-1-(2-chloro-3-fluoro-6-methoxyphenyl)-ethoxy]-furo[3,2-c]pyridin-3-yl}-3,6-dihydro-2H-pyridine-1-carbaldehyde |
| tetrahydropyridinyl-N-C(O)CH₃ | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-ethanone |
| tetrahydropyridinyl-N-C(O)CH₂-pyrrolidinyl | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-2-pyrrolidin-1-ylethanone |
| tetrahydropyridinyl-N-C(O)-(1-methylpiperidin-4-yl) | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-(1-methylpiperidin-4-yl)-methanone |
| tetrahydropyridinyl-N-C(O)-((S)-1-methylpyrrolidin-2-yl) | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-((S)-1-methylpyrrolidin-2-yl)-methanone |
| tetrahydropyridinyl-N-C(O)(CH₂)₃N(CH₃)₂ | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-4-dimethylaminobutan-1-one |

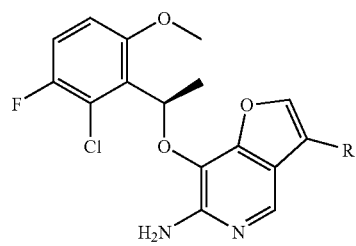

| R | Name |
|---|---|
| ![piperidine-carbonyl-tetrahydropyridine] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-piperidin-4-ylmethanone |
| ![pyrrolidine-carbonyl-tetrahydropyridine] | (4-{6-Amino-7-[(R)-1-(2-chloro-3-fluoro-6-methoxyphenyl)ethoxy]furo[3,2-c]pyridin-3-yl}-3,6-dihydro-2H-pyridin-1-yl)-(S)-pyrrolidin-2-ylmethanone |
| ![aminocyclopropyl-carbonyl] | (1-Aminocyclopropyl)-(4-{6-amino-7-[(R)-1-(2-chloro-3-fluoro-6-methoxyphenyl)-ethoxy]-furo[3,2-c]pyridin-3-yl}-3,6-dihydro-2H-pyridin-1-yl)-methanone |
| ![2-amino-2-methylpropanoyl] | 2-Amino-1-(4-{6-amino-7-[(R)-1-(2-chloro-3-fluoro-6-methoxyphenyl)-ethoxy]-furo[3,2-c]pyridin-3-yl}-3,6-dihydro-2H-pyridin-1-yl)-2-methylpropan-1-one |
| ![ethylpiperazine-carbonyl] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-(4-ethylpiperazin-1-yl)-methanone |
| ![tert-butylpiperazine-carbonyl] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-(4-tert-butylpiperazin-1-yl)-methanone |
| ![piperazine-carbonyl] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-piperazin-1-ylmethanone |

-continued

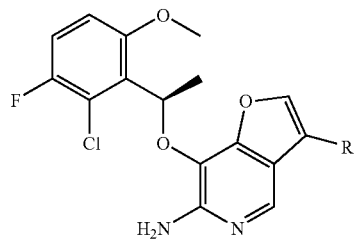

| R | Name |
|---|---|
| piperidine-N-C(O)NH2 (3,6-dihydro-2H-pyridine-1-carboxamide) | 4-{6-Amino-7-[(R)-1-(2-chloro-3-fluoro-6-methoxyphenyl)-ethoxy]-furo[3,2-c]pyridin-3-yl}-3,6-dihydro-2H-pyridine-1-carboxylic acid amide |
| piperidine-N-C(O)NHMe | 4-{6-Amino-7-[(R)-1-(2-chloro-3-fluoro-6-methoxyphenyl)-ethoxy]-furo[3,2-c]pyridin-3-yl}-3,6-dihydro-2H-pyridine-1-carboxylic acid methylamide |
| N-methyl-tetrahydropyridinyl | 7-[(R)-1-(2-chloro-3-fluoro-6-methoxyphenyl)-ethoxy]-3-(1-methyl-1,2,3,6-tetrahydropyridin-4-yl)-furo[3,2-c]pyridin-6-ylamine |
| N-ethyl-tetrahydropyridinyl | 7-[(R)-1-(2-chloro-3-fluoro-6-methoxyphenyl)-ethoxy]-3-(1-ethyl-1,2,3,6-tetrahydropyridin-4-yl)-furo[3,2-c]pyridin-6-ylamine |
| N-(2-aminoethyl)-tetrahydropyridinyl | 3-[1-(2-Aminoethyl)-1,2,3,6-tetrahydropyridin-4-yl]-7-[(R)-1-(2-chloro-3-fluoro-6-methoxyphenyl)-ethoxy]-furo[3,2-c]pyridin-6-ylamine |
| N-methanesulfonyl-tetrahydropyridinyl | 7-[(R)-1-(2-chloro-3-fluoro-6-methoxyphenyl)-ethoxy]-3-(1-methanesulfonyl-1,2,3,6-tetrahydropyridin-4-yl)-furo[3,2-c]pyridin-6-ylamine |
| 4-C(O)NH-CH2CH2-N(Me)2 phenyl | 4-{6-Amino-7-[(R)-1-(2-chloro-3-fluoro-6-methoxyphenyl)ethoxy]-furo[3,2-c]pyridin-3-yl}-N-(2-dimethylaminoethyl)benzamide |
| 4-C(O)N(Me)2 phenyl | 4-{6-Amino-7-[(R)-1-(2-chloro-3-fluoro-6-ethoxyphenyl)ethoxy]-furo[3,2-c]pyridin-3-yl}-N,N-dimethylbenzamide |
| 4-(4-methylpiperazin-1-yl-C(O))-phenyl | (4-{6-Amino-7-[(R)-1-(2-chloro-3-fluoro-6-methoxyphenyl)ethoxy]-furo[3,2-c]pyridin-3-yl}phenyl)-(4-methylpiperazin-1-yl)methanone |

-continued

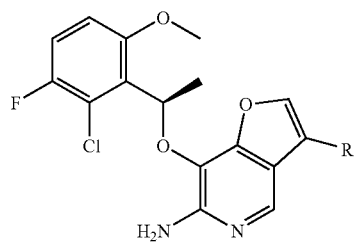

| R | Name |
|---|------|
| (3-methanesulfonamidophenyl) | N-(3-{6-Amino-7-[(R)-1-(2-chloro-3-fluoro-6-methoxyphenyl)ethoxy]-furo[3,2-c]pyridin-3-yl}phenyl)methanesulfonamide |
| [4-(4-methylpiperazin-1-yl)phenyl] | 7-[(R)-1-(2-Chloro-3-fluoro-6-methoxyphenyl)ethoxy]-3-[4-(4-methylpiperazin-1-yl)-phenyl]furo[3,2-c]pyridin-6-ylamine |
| [6-(4-methylpiperazin-1-yl)pyridin-3-yl] | 7-[(R)-1-(2-Chloro-3-fluoro-6-methoxyphenyl)ethoxy]-3-[6-(4-methylpiperazin-1-yl)pyridin-3-yl]furo[3,2-c]pyridin-6-ylamine |
| {3-[4-(2-hydroxyethyl)piperazine-1-carbonyl]phenyl} | (3-{6-Amino-7-[(R)-1-(2-chloro-3-fluoro-6-methoxyphenyl)ethoxy]-furo[3,2-c]pyridin-3-yl}phenyl)-[4-(2-hydroxyethyl)piperazin-1-yl]methanone |
| {4-[4-(2-hydroxyethyl)piperazine-1-carbonyl]phenyl} | (4-{6-Amino-7-[(R)-1-(2-chloro-3-fluoro-6-methoxyphenyl)ethoxy]-furo[3,2-c]pyridin-3-yl}phenyl)-[4-(2-hydroxyethyl)piperazin-1-yl]methanone |
| [4-(piperazine-1-carbonyl)phenyl] | (4-{6-Amino-7-[(R)-1-(2-chloro-3-fluoro-6-methoxyphenyl)ethoxy]furo[3,2-c]pyridin-3-yl}phenyl)piperazin-1-ylmethanone |

-continued

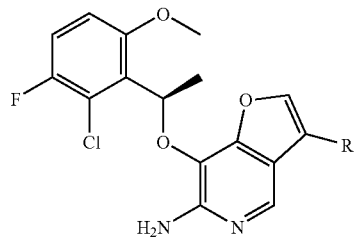

| R | Name |
|---|---|
| 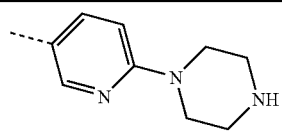 | 7-[(R)-(2-chloro-3-fluoro-6-methoxyphenyl)ethoxy]-3-(6-piperazin-1-yl-pyridin-3-yl)furo[3,2-c]pyridin-6-ylamine, or |
| 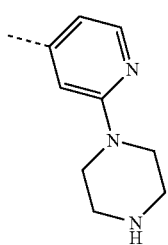 | 7-[(R)-(2-chloro-3-fluoro-6-methoxyphenyl)ethoxy]-3-(2-piperazin-1-yl-pyridin-4-yl)furo[3,2-c]pyridin-6-ylamine. |

In some aspects, the compound is selected from:

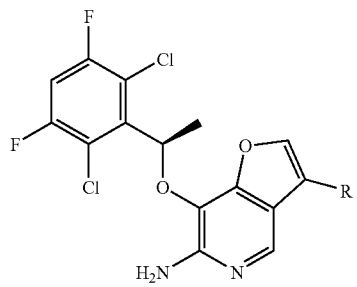

| R | Name |
|---|---|
| 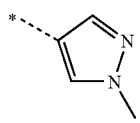 | 7-[(R)-1-(2,6-Dichloro-3,5-difluorophenyl)-ethoxy]-3-(1-methyl-1H-pyrazol-4-yl)-furo[3,2-c]pyridin-6-ylamine |
| 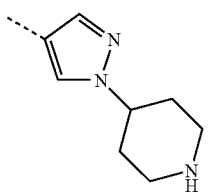 | 7-[(R)-1-(2,6-Dichloro-3,5-difluorophenyl)ethoxy]-3-(1-piperidin-4-yl-1H-pyrazol-4-yl)-furo[3,2-c]pyridin-6-ylamine |
| 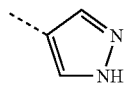 | 7-[(R)-1-(2,6-Dichloro-3,5-difluorophenyl)ethoxy]-3-(1H-pyrazol-4-yl)-furo[3,2-c]pyridin-6-ylamine |

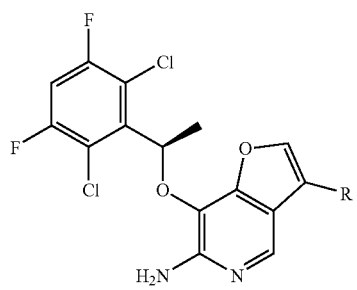

| R | Name |
|---|---|
| (4-tetrahydropyridinyl-NH) | 7-[(R)-1-(2,6-Dichloro-3,5-difluorophenyl)-ethoxy]-3-(1,2,3,6-tetrahydropyridin-4-yl)-furo[3,2-c]pyridin-6-ylamine |
| (tetrahydropyridinyl-N-C(O)CH2N(CH3)2) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-2-dimethylaminoethanone |
| (tetrahydropyridinyl-N-CHO) | 4-{6-Amino-7-[(R)-1-(2,6-dichloro-3,5-difluorophenyl)-ethoxy]-furo[3,2-c]pyridin-3-yl}-3,6-dihydro-2H-pyridine-1-carbaldehyde |
| (tetrahydropyridinyl-N-C(O)CH3) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-ethanone |
| (tetrahydropyridinyl-N-C(O)CH2-pyrrolidinyl) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-2-pyrrolidin-1-ylethanone |
| (tetrahydropyridinyl-N-C(O)-(1-methylpiperidin-4-yl)) | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-(1-methylpiperidin-4-yl)-methanone |
| (tetrahydropyridinyl-N-C(O)-((S)-1-methylpyrrolidin-2-yl)) | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-((S)-1-methylpyrrolidin-2-yl)-methanone |
| (tetrahydropyridinyl-N-C(O)(CH2)3N(CH3)2) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-4-dimethylaminobutan-1-one |

-continued

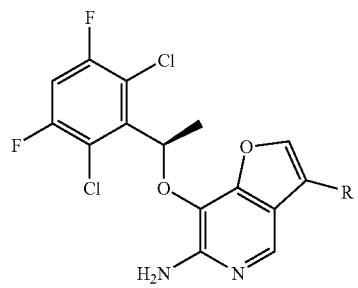

| R | Name |
|---|---|
| ![piperidine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-piperidin-4-ylmethanone |
| ![pyrrolidine-carbonyl-tetrahydropyridine] | (4-{6-Amino-7-[(R)-1-(2,6-dichloro-3,5-difluorophenyl)ethoxy]furo[3,2-c]pyridin-3-yl}-3,6-dihydro-2H-pyridin-1-yl)-(S)-pyrrolidin-2-ylmethanone |
| ![aminocyclopropyl-carbonyl-tetrahydropyridine] | (1-Aminocyclopropyl)-(4-{6-amino-7-[(R)-1-(2,6-dichloro-3,5-difluorophenyl)-ethoxy]-furo[3,2-c]pyridin-3-yl}-3,6-dihydro-2H-pyridin-1-yl)-methanone |
| ![amino-methylpropanone-tetrahydropyridine] | 2-Amino-1-(4-{6-amino-7-[(R)-1-(2,6-dichloro-3,5-difluorophenyl)-ethoxy]-furo[3,2-c]pyridin-3-yl}-3,6-dihydro-2H-pyridin-1-yl)-2-methylpropan-1-one |
| ![N-methylpiperidine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-(4-ethylpiperazin-1-yl)-methanone |
| ![N-tertbutylpiperidine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-(4-tert-butylpiperazin-1-yl)-methanone |
| ![piperazine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-piperazin-1-ylmethanone |

-continued

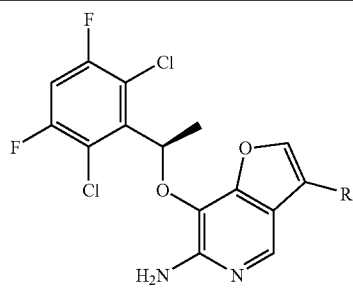

| R | Name |
|---|---|
| (4-piperidinyl-carboxamide, dihydro) | 4-{6-Amino-7-[(R)-1-(2,6-dichloro-3,5-difluorophenyl)-ethoxy]-furo[3,2-c]pyridin-3-yl}-3,6-dihydro-2H-pyridine-1-carboxylic acid amide |
| (4-piperidinyl-N-methylcarboxamide, dihydro) | 4-{6-Amino-7-[(R)-1-(2,6-dichloro-3,5-difluorophenyl)-ethoxy]-furo[3,2-c]pyridin-3-yl}-3,6-dihydro-2H-pyridine-1-carboxylic acid methylamide |
| (1-methyl-tetrahydropyridin-4-yl) | 7-[(R)-1-(2,6-Dichloro-3,5-difluorophenyl)-ethoxy]-3-(1-methyl-1,2,3,6-tetrahydropyridin-4-yl)-furo[3,2-c]pyridin-6-ylamine |
| (1-ethyl-tetrahydropyridin-4-yl) | 7-[(R)-1-(2,6-Dichloro-3,5-difluorophenyl)-ethoxy]-3-(1-ethyl-1,2,3,6-tetrahydropyridin-4-yl)-furo[3,2-c]pyridin-6-ylamine |
| (1-(2-aminoethyl)-tetrahydropyridin-4-yl) | 3-[1-(2-Aminoethyl)-1,2,3,6-tetrahydropyridin-4-yl]-7-[(R)-1-(2,6-dichloro-3,5-difluorophenyl)-ethoxy]-furo[3,2-c]pyridin-6-ylamine |
| (1-methanesulfonyl-tetrahydropyridin-4-yl) | 7-[(R)-1-(2,6-Dichloro-3,5-difluorophenyl)-ethoxy]-3-(1-methanesulfonyl-1,2,3,6-tetrahydropyridin-4-yl)-furo[3,2-c]pyridin-6-ylamine |
| (4-(N-(2-dimethylaminoethyl)carbamoyl)phenyl) | 4-{6-Amino-7-[(R)-1-(2,6-dichloro-3,5-difluorophenyl)ethoxy]-furo[3,2-c]pyridin-3-yl}-N-(2-dimethylaminoethyl)benzamide |
| (4-(N,N-dimethylcarbamoyl)phenyl) | 4-{6-Amino-7-[(R)-1-(2,6-dichloro-3,5-difluorophenyl)ethoxy]-furo[3,2-c]pyridin-3-yl}-N,N-dimethylbenzamide |
| (4-(4-methylpiperazin-1-ylcarbonyl)phenyl) | (4-{6-Amino-7-[(R)-1-(2,6-dichloro-3,5-difluorophenyl)ethoxy]-furo[3,2-c]pyridin-3-yl}phenyl)-(4-methylpiperazin-1-yl)methanone |

-continued

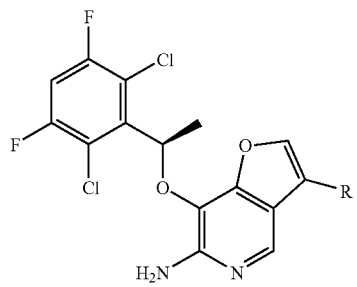

| R | Name |
|---|---|
| ![meta-phenyl-NHSO2Me] | N-(3-{6-Amino-7-[(R)-1-(2,6-dichloro-3,5-difluorophenyl)ethoxy]-furo[3,2-c]pyridin-3-yl}phenyl)methanesulfonamide |
| ![para-phenyl-(4-methylpiperazin-1-yl)] | 7-[(R)-1-(2,6-Dichloro-3,5-difluorophenyl)ethoxy]-3-[4-(4-methylpiperazin-1-yl)-phenyl]furo[3,2-c]pyridin-6-ylamine |
| ![pyridin-2-yl-(4-methylpiperazin-1-yl)] | 7-[(R)-1-(2,6-Dichloro-3,5-difluorophenyl)ethoxy]-3-[6-(4-methylpiperazin-1-yl)pyridin-3-yl]furo[3,2-c]pyridin-6-ylamine |
| ![meta-benzoyl-4-(2-hydroxyethyl)piperazine] | (3-{6-Amino-7-[(R)-1-(2,6-dichloro-3,5-difluorophenyl)ethoxy]-furo[3,2-c]pyridin-3-yl}phenyl)-[4-(2-hydroxyethyl)piperazin-1-yl]methanone |
| ![para-benzoyl-4-(2-hydroxyethyl)piperazine] | (4-{6-Amino-7-[(R)-1-(2,6-dichloro-3,5-difluorophenyl)ethoxy]-furo[3,2-c]pyridin-3-yl}phenyl)-[4-(2-hydroxyethyl)piperazin-1-yl]methanone |
| ![para-benzoyl-piperazine] | (4-{6-Amino-7-[(R)-1-(2,6-dichloro-3,5-difluorophenyl)ethoxy]furo[3,2-c]pyridin-3-yl}phenyl)piperazin-1-ylmethanone |

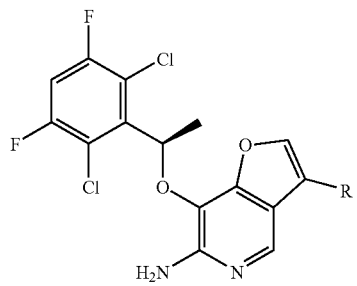

| R | Name |
|---|---|
| 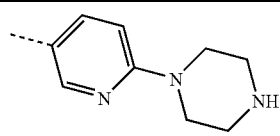 | 7-[(R)-(2,6-Dichloro-3,5-difluorophenyl)ethoxy]-3-(6-piperazin-1-yl-pyridin-3-yl)furo[3,2-c]pyridin-6-ylamine, or |
| 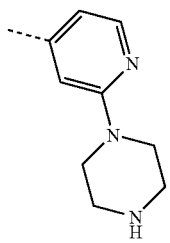 | 7-[(R)-(2,6-Dichloro-3,5-difluorophenyl)ethoxy]-3-(2-piperazin-1-yl-pyridin-4-yl)furo[3,2-c]pyridin-6-ylamine. |

Compounds described can contain one or more asymmetric centers and may thus give rise to diastereomers and optical isomers. Compound of Formula (I) of the present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The compound of formula (I) of the present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the compound of formula (I) of the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the compound of formula (I) of the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

Since the compounds of Formula (I) are intended for pharmaceutical use they are preferably provided in substantially pure form, for example at least 60% pure, more suitably at least 75% pure especially at least 98% pure (% are on a weight for weight basis).

Preparation and Intermediates

The compounds of the formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)) or Larock, R. C. *Comprehensive Organic Transformations*, 2$^{nd}$ ed.; Wiley and Sons: New York, 1999. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed hereinbelow. Unless otherwise indicated, the substituents in the Schemes are defined as above. Isolation and purification of the products is accomplished by standard procedures, which are known to a chemist of ordinary skill.

Scheme 1 illustrates a method for the preparation of Intermediate 7.

Scheme 1

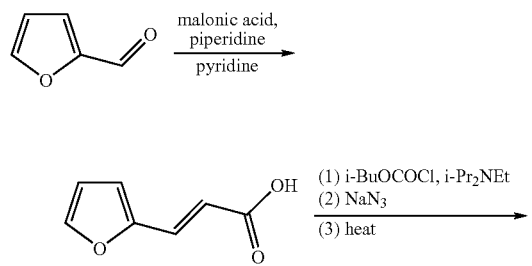

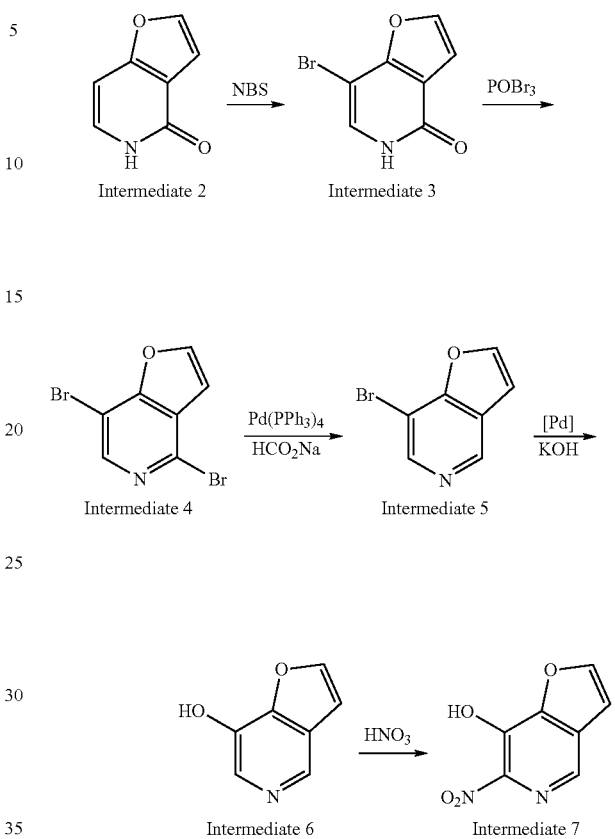

Intermediate 2 can be prepared from 2-furylaldehyde in a known four-step sequence consisting of Knoevenagel condensation with malonic acid and subsequent decarboxylation, conversion of the resulting acid to its acyl azide, thermal rearrangement of said azide to give an isocyanate, and thermal cyclization of this isocyanate. This type of sequence has been described in the literature for furo[3,2-c]pyridines and thieno[3,2-c]pyridines, e.g., Ger. Offen. DE2059386 (1971), Ger. Offen. DE1965710 (1970), U.S. Pat. No. 3,663,559 (1971), WO2004/000828A1. Bromination with a brominating agent such as, but not limited to, NBS, occurs at the position shown to give Intermediate 3, which can be further brominated with, e.g., POBr$_3$, yielding Intermediate 4. The corresponding thieno[3,2-c]pyridine can be prepared in the same manner, e.g., US2005043347. Palladium-mediated reduction of the 4-Br followed by conversion of the 7-Br to 7-OH and nitration with HNO$_3$ gives Intermediate 7. Someone skilled in the art will realize that other reagents can also be used for these transformation; for example, Intermediate 5 may first be converted to a pinacolboronate using a palladium catalyst and bis(pinacolato)diboron followed by oxidation of said pinacolboronate to give Intermediate 6.

Scheme 2 illustrates a method for the preparation of compounds of formula Ia in which R$^2$ is introduced at the last or second last step.

Scheme 2

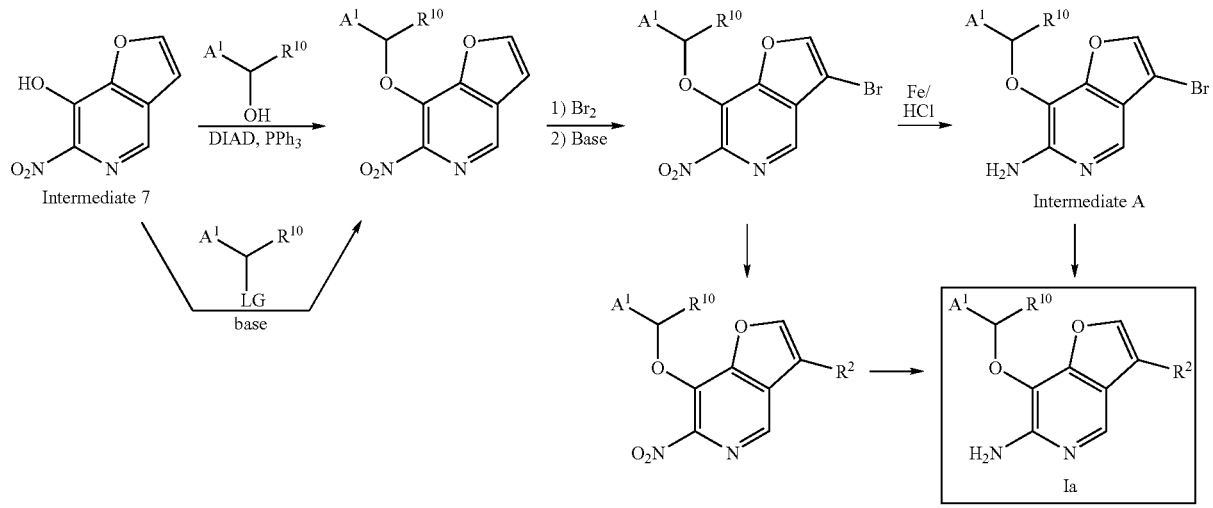

Intermediate 7 can be reacted with $R^4$—OH wherein $R^4$=$A^1CH(R^{10})$—OH under typical Mitsunobu conditions. Alternatively, Intermediate 7 can be reacted with $R^4$-LG wherein $R^4$=$A^1CH(R^{10})$-L and LG=Leaving Group such as, but not limited to, mesylate, tosylate, triflate, iodide, bromide, or chloride under typical alkylation conditions such as, but not limited to, $K_2CO_3$ or $Cs_2CO_3$ as base in a polar aprotic solvent such as DMF. Addition of $Br_2$ followed by elimination of HBr, reduction of the nitro group to an amine, and conversion of the 3-Br group in Intermediate A to $R^2$ gives compounds of formula Ia. The order of the last two steps may be switched if deemed advantageous. The general methods to convert the 3-Br group to $R^2$ as defined herein are well known to the skilled artisan and include, but are not limited to, Suzuki coupling with (het)arylboronic acids or boronates, with vinylboronates, alkylboronates, or 9-BBN-derived alkylboranes; Stille coupling with (het)arylstannanes or vinylstannanes; Negishi coupling with dialkylzinc reagents, alkylzinc halides, or (het)arylzinc halides; Sonogashira coupling with terminal alkynes; Cu- or Pd-mediated cyanations; Cu-mediated trifluoromethylations; and Pd-mediated carbonylations.

Scheme 3 illustrates a method for the preparation of compounds of formula Ia in which $R^4$—OH wherein $R^4$=$A^1CH(R^{10})$—OH is introduced near the end of the synthesis, after $R^2$ has been introduced.

Scheme 3

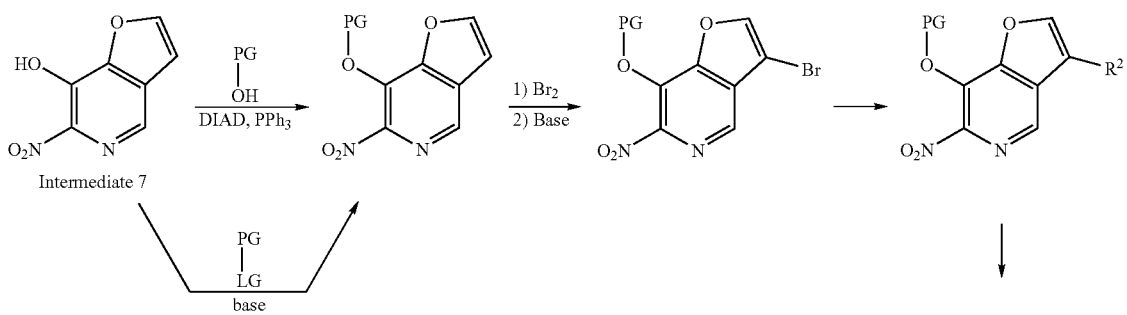

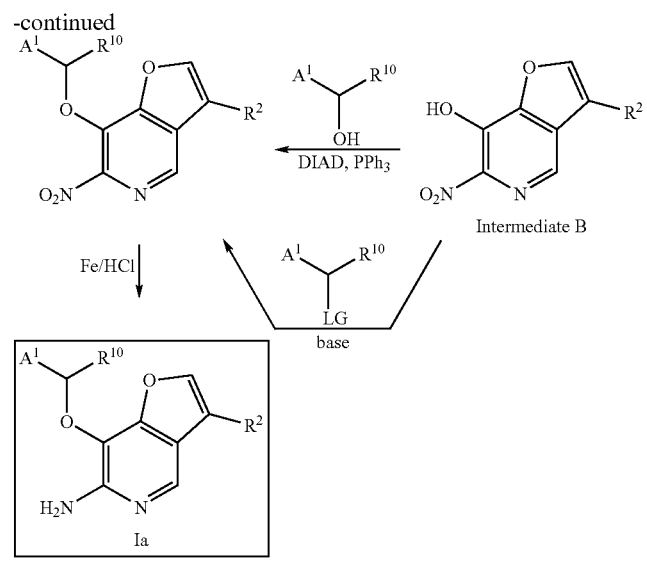

Following the route outlined in Scheme 2, a protecting group PG is installed initially that is removed after $R^2$ has been introduced, giving Intermediate B. Suitable protecting groups PG-OH include, but are not limited to, substituted benzyl groups such as 1-(2,6-dichloro-3-fluorophenyl)-ethanol, which is removed by heating with 48% aq. HBr. Mitsunobu reaction of Intermediate B with $R^4$—OH wherein $R^4 = A^1CH(R^{10})$—OH or alkylation with $R^4$-LG wherein $R^4 = A^1CH(R^{10})$-L and LG=Leaving Group as described above, followed by reduction of the nitro group to an amine gives the compounds of formula Ia.

The route in Schemes 2 and 3 are applicable not only to $R^4$—OH wherein $R^4 = A^1CH(R^{10})$—OH but to other $R^4$—OH moieties wherein the alcohol is primary or secondary.

Scheme 4 illustrates methods to introduce the substituents R1 and R3.

substituent $R^3$ may be introduced by reductive amination under conditions well known to someone skilled in the art.

Compound of formula Ia.1 is compound of formula I, when $X^1=O$; $X^2=O$; q=1; $R^3=H$; $R^4=$—$(CR^{10}R^{11})_n A^1$, wherein $R^{11}=H$ and n=1; Compound of formula Ia.2 is compound of formula I, when $X^1=O$; $X^2=O$; q=1; $R^1=H$; $R^4=$—$(CR^{10}R^{11})_n A^1$, wherein $R^{11}=H$ and n=1; Compound of formula Ia.1 is compound of formula Ia when $R^1=H$.

Scheme 5 illustrates a synthetic method to functionalize the N of the piperidinyl when $R^2$ of Formula Ia is -$L^1$-piperidinyl.

Scheme 4

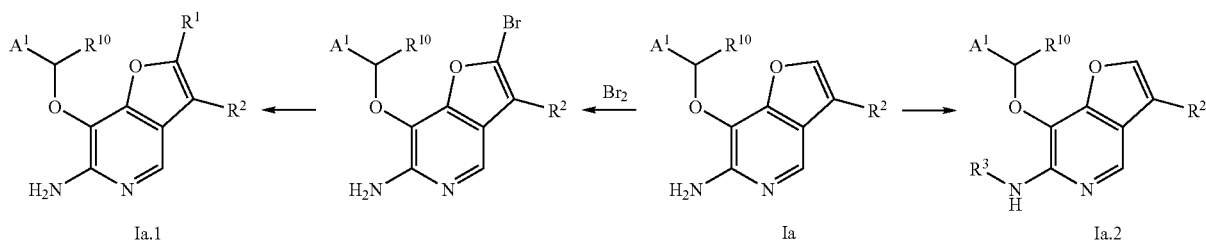

Electrophilic bromination of compounds of formula Ia is followed by conversion of the 2-Br to $R^1$, giving compounds of formula Ia.1. The general methods to convert the 3-Br group to $R^1$ as defined herein are well known to the skilled artisan and include, but are not limited to, Suzuki coupling with (het)arylboronic acids or boronates, with vinylboronates, alkylboronates, or 9-BBN-derived alkylboranes; Stille coupling with (het)arylstannanes or vinylstannanes; Negishi coupling with dialkylzinc, alkylzinc halide, or (het) arylzinc halides; Sonogashira coupling with terminal alkynes; Cu- or Pd-mediated cyanations; Cu-mediated trifluoromethylations; and Pd-mediated carbonylations. The Scheme 5

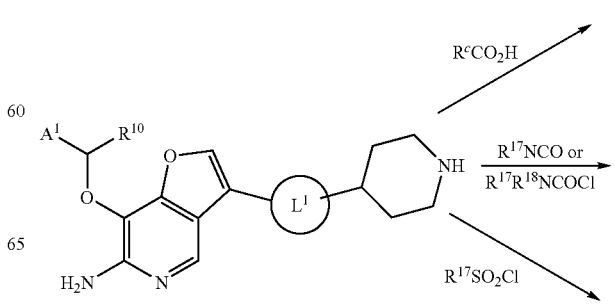

-continued

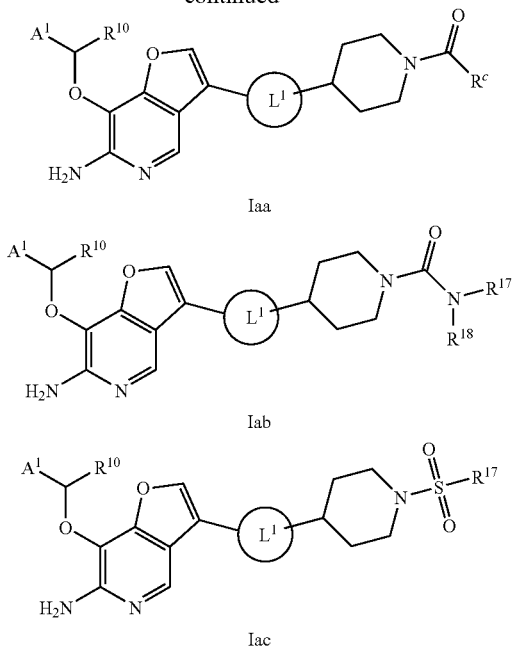

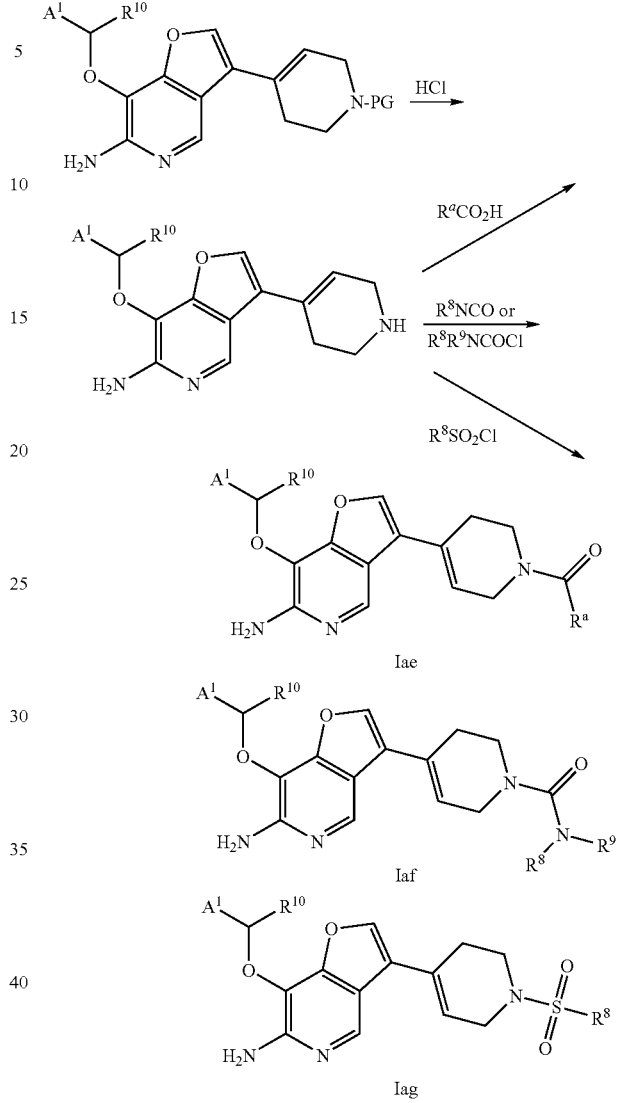

In compound of formula Iaa, Iab, or Iac, $L^1=C_{0-12}$alkyl, $C_{2-12}$ alkenyl, $C_{2-12}$ alkynyl, $C_{3-12}$cycloalkyl$C_{0-12}$alkyl, $C_{3-12}$heterocycloalkyl$C_{0-12}$alkyl, aryl$C_{0-12}$alkyl or heteroaryl$C_{0-12}$alkyl.

Scheme 6 illustrates a synthetic method to convert a carboxylic acid into the corresponding amide when $R^2$ of Formula Ia is -$L^2$-$CO_2H$.

Scheme 6

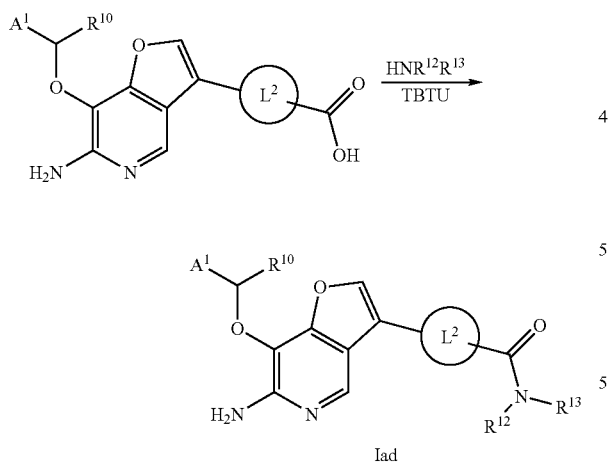

In compound of formula Iad, $L^2=C_{0-12}$alkyl, $C_{3-12}$cycloalkyl$C_{0-12}$alkyl, $C_{3-12}$heterocycloalkyl$C_{0-12}$alkyl, aryl $C_{0-12}$alkyl or heteroaryl$C_{0-12}$alkyl.

Scheme 7 illustrates a synthetic method to further elaborate the tetrahydropyridinyl moiety when $R^2$ of Formula Ia is tetrahydropyridinyl-PG.

PG=suitable protecting groups, such as t-butoxycarbonyl (Boc), benzyloxycarbonyl (CBZ), and the like; tetrahydropyridinyl, which is a structure of formula II:

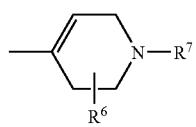

(II)

wherein: $R^6$=H; $R^7$=—C(O)$R^a$, —C(O)N$R^8R^9$ or —S(O)$_m$ $R^8$; m=2.

In the compounds shown in the foregoing schemes, $R^4$=$A^1$CH($R^{10}$)—. The carbon atom in the group $R^4$=$A^1$CH ($R^{10}$)— that is connected to $A^1$ and $R^{10}$ is an asymmetric center. If the compounds do not contain additional asymmetric centers, then two enantiomers of these compounds exist. A skilled artisan appreciates that various methods can be used to separate mixtures of the enantiomers, such as, but not limited to, chromatography on a chiral column, crystallization with an enantiopure acid or base, formation of diastereomeric adducts with an enantiopure auxiliary, or enzymatic resolutions. As an example, the racemic mixture of the alcohol $R^4$—OH=$A^1$CH($R^{10}$)—OH may be esterified and then reacted with hydrolases that hydrolyze preferentially one of the enantiomers, thus enabling a separation (as demonstrated, e.g., in WO 2006/021885). Instead of separating a mixture of enantiomers, one of the enantiomers may be prepared selectively. For example, achiral ketones of formula $A^1$C(=O)$R^{10}$ may be reduced to give selectively one enantiomer of the alcohol $R^4$—OH=$A^1$CH($R^{10}$)—OH with chiral reducing agents. Such methods are known in the literature. As an example, the highly enantioselective reduction of 2,6-dichloro-3-fluoroacetophenone with $NaBH_4$/$Me_3SiCl$ catalyzed by (S)-α,α-diphenylpyrrolidinemethanol to give (R)-1-(2,6-dichloro-3-fluorophenyl)ethanol has been reported in *Tetrahedron Let.* 2000, 41 (52), 10281-10283. Someone skilled in the art will realize that the (S) enantiomer of 1-(2,6-dichloro-3-fluorophenyl)ethanol is accessible by the same method but using the other enantiomer of the chiral ligand, namely (R)-α,α-diphenylpyrrolidinemethanol.

EXAMPLES

The following illustrate the synthesis of various compounds of the present invention. Additional compounds within the scope of this invention may be prepared using the methods illustrated in these Examples, either alone or in combination with techniques generally known in the art.

The following abbreviations are used:
NMR Nuclear magnetic resonance
MDPS Mass-directed HPLC purification system
MDP Mass-directed HPLC purification
LC/MS Liquid chromatography mass spectrometry
LDA Lithium diisopropylamide
DCM Dichloromethane
THF Tetrahydrofuran
EtOAc Ethyl acetate
MeCN Acetonitrile
DMSO Dimethylsulfoxide
Boc t-Butyloxycarbonyl
DMF N,N-Dimethylformamide
PS-DIEA Polymer-supported diisopropylethylamine
PS-PPh$_3$-Pd Polymer-supported Pd(PPh$_3$)$_4$
EDCI or EDC 1-(3-Dimethylaminopropyl)-3-ethylcarbodiimide
HOBt 1-Hydroxybenzotriazole
DMAP 4-Dimethylaminopyridine
TFA Trifluoroacetic acid
DIPEA N,N-diisopropylethylamine
TBTU O-Benzotriazol-1-yl-N,N,N',N'-tetramethyluronium tetrafluoroborate
CDCl$_3$ Deuterated chloroform
CD$_3$OD Deuterated methanol
DMSO-d$_6$ Deuterated dimethylsulfoxide
TLC Thin layer chromatography
HPLC High performance liquid chromatography
Min Minute(s)
h Hour(s)
d Day(s)
RT or rt Room temperature
$t_R$ Retention time
L Liter
mL Milliliter
mmol Millimole Unless otherwise noted, all materials/reagents were obtained from commercial suppliers and used without further purification. $^1$H NMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), m$_c$ (centered multiplet), br or broad (broadened), AA'BB'. The signal multiplicities in $^{13}$C NMR spectra were determined using the DEPT135 pulse sequence and are abbreviated as follows: + (CH or CH$_3$), − (CH$_2$), C$_{quart}$(C). Reactions were monitored by thin layer chromatography (TLC) on silica gel 60 F$_{254}$ (0.2 mm) precoated aluminum foil and visualized using UV light. Flash chromatography was performed with silica gel (400-230 mesh). Preparatory TLC was performed on Whatman LK6F Silica Gel 60 Å size 20×20 cm plates with a thickness of 1000 μm. Hydromatrix (=diatomaceous earth) was purchased from Varian. Mass-directed HPLC purification of compounds was performed on a Waters system composed of the following: 2767 Sample Manager, 2525 Binary Gradient Module, 600 Controller, 2487 Dual λ Absorbance Detector, Micromass ZQ2000 for ionization, Phenomenex Luna 5μ C18(2) 100 Å 150×21.2 mm 5μ column with mobile phases of 0.01% Formic Acid Acetonitrile (A) and 0.01% Formic Acid in HPLC water (B), a flow rate of 20 mL/min, and a run time of 13 min. LC-MS data was collected on ZQ2, ZQ3, or HPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5μ particle size, 4.6×50 mm with a mobile phase of Acetonitrile (A) and 0.01% Formic Acid in HPLC water (B). The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min and 0.00 min 25% A, 3.00 min 99% A, 3.50 min 99% A, 4.00 min 25% A, 5.00 min 25% A for nonpolar_5 min. All Waters Micromass ZQ2000 instruments utilized electrospray ionization in positive (ES+) or negative (ES−) mode. The Waters Micromass ZQ2000 instruments from ZQ2 and ZQ3 can also utilize atmospheric pressure chemical ionization in positive (AP+) or negative (AP−) mode. The Waters HPLC-ACQUITY system consists of an ACQUITY sample manager attached to ACQUITY SQ MS and ACQUITY PDA detectors. It uses an ACQUITY HPLC BEH® C18 2.1×50 mm 1.7 μm column with a mobile phase of 0.1% formic acid in water (A) and 0.1% formic acid in acetonitrile (B). The flow rate is 1.0 mL/min, run time is 2 min, and the gradient profile is 0.00 min 95% A, 1.50 min 1% A, 1.85 min 1% A, 2.0 min 95% A for analytical. UV detection is at 254 nm, and the MS utilizes electrospray ionization in positive mode (ES+). HPLC purification of compounds was performed on a Gilson system consisting of a 215 Liquid Handler, 819 Injection Module, a 322 Pump, and a 155 UV/VIS dual wavelength detector set to 254 and 210 nm. This system uses Phenomenex Luna C18(2), 5μ particle size, 50×21.2 mm or 60×21.2 mm columns with a mobile phase of Acetonitrile and 0.1% Formic Acid in HPLC water. The flow rate is 15 mL/min and the run time is 25 min. All melting points were determined with a MeI-Temp II appa- (d, J=7.2 Hz, 1H), 7.00 (d, J=2.1 Hz, 1H), 7.28 (d, J=6.9 Hz, 1H), 7.53 (d, J=2.1 Hz, 1H), 12.21 (br s, 1H).

Intermediate 3: 7-Bromo-5H-furo[3,2-c]pyridin-4-one

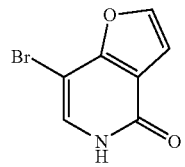

To a suspension of 5H-furo[3,2-c]pyridin-4-one (11.1 g, 0.082 mol) in anhydrous acetonitrile (200 mL) was added a solution of NBS (19.0 g, 0.107 mol) in anhydrous acetonitrile (100 ml) at 0° C. over 1 h. The resulting suspension was stirred at 0° C. for 1 h and then warmed to rt for 10 min. Water (500 mL) and saturated sodium bicarbonate aqueous solution (4 ml) were added to the mixture. Off-white solids were collected by filtration and dried under vacuum to afford 7.33 g of desired product (yield: 42%). $^1$H NMR (DMSO-$d_6$, 400 MHz): δ=7.06 (d, J=2.3 Hz, 1H), 7.60 (s, 1H), 8.00 (d, J=2.0 Hz, 1H). MS (ES+): 214.04/216.04 (1/1) [MH$^+$].

Intermediate 4: 4,7-Dibromofuro[3,2-c]pyridine

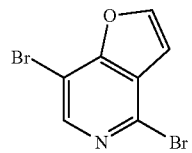

A mixture of 7-bromo-5H-furo[3,2-c]pyridin-4-one (21.2 g, 99 mmol) and POBr$_3$ (31.2 g, 109 mmol) was heated at 70° C. for 5 min, then heated to 120° C. for 2 h. After cooled to rt, the solid was crashed and quenched with aqueous Na$_2$CO$_3$ (200 mL), then diluted with EtOAc (300 mL). The insoluble material was filtered off through a pad of Celite. The organic phase was collected and dried over Na$_2$SO$_4$. The crude material was purified by silica gel chromatography eluting with Hexanes-EtOAc (90:10→85:15) to give the title compound as a white solid (20.75 g, 68%). $^1$H NMR (CDCl$_3$, 400 MHz): δ=6.91 (d, J=2.3 Hz, 1H), 7.79 (d, J=2.3 Hz, 1H), 8.37 (s, 1H).

Intermediate 5: 7-Bromofuro[3,2-c]pyridine

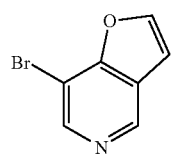

A suspension of 4,7-dibromofuro[3,2-c]pyridine (3.50 g, 12.6 mmol), HCO$_2$Na (2.59 g, 38.1 mmol) and Pd(PPh$_3$)$_4$ (360 mg, 0.32 mmol) in dry DMF (35 mL) was heated at 100° C. (bath temperature) under Ar for 9 h. LC-MS showed the reaction was almost complete. The mixture was diluted with Intermediate 1: (E)-3-Furan-2-yl-acryloyl azide

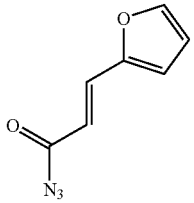

In an oven dried three-necked round-bottom flask (3 L) fitted with a mechanical stirrer, a nitrogen inlet, a thermometer and addition funnel was placed a mixture of β-(2-furyl) acrylic acid (60.0 g, 434 mmol) and dry triethylamine (51.6 g, 510 mmol) in acetone (600 mL, dried over anhydrous MgSO$_4$). The mixture was cooled to −2 to 0° C. To the cold mixture, isobutyl chloroformate (79.2 g, 580 mmol) was added at 0° C. gradually over a period of time. After completion of addition, the reaction mixture was stirred at 0~2° C. for 1 h. Then a solution of sodium azide (42.0 g, 646 mmol) in water (180 mL) was added slowly at 0~5° C. The resulting mixture was stirred at the same temperature for 1 h. The reaction mixture was then quenched with ice-cold water (1.7 L). The desired product was extracted with toluene (4×500 mL), dried over anhydrous sodium sulfate and filtered. The filtrate was used in next reaction as such.

Intermediate 2: 5H-Furo[3,2-c]pyridin-4-one

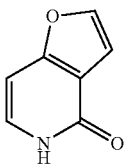

In an oven dried three-necked round-bottom flask (3 L) were placed tributylamine (65.3 g, 352 mmol) and diphenylmethane (480 mL). The mixture was heated to 210-215° C. while being stirred mechanically. To the hot reaction mixture was added the above azide in toluene slowly drop-wise through an addition funnel while the toluene was removed continuously by a Dean-stark assemble. The reaction mixture was maintained at the same temperature for another hour. The diphenylmethane was distilled off from the reaction mixture under reduced pressure. The residue was washed with diisopropylether (3×100 mL) and triturated with hexane. The resulting dark brown solid was collected by filtration, washed with diethylether (100 mL) and dried to give 35.0 g of the product (yield: 60%). $^1$H NMR (CDCl$_3$, 300 MHz): δ=6.63 water (50 mL) and EtOAc (200 mL). Layers were separated and the organic phase was washed with water (3×40 mL), brine (40 mL), and dried over Na₂SO₄. The solvent was removed and residue was purified by silica gel chromatography eluting with Hexanes-EtOAc (80:20→70:30) to provide the title compound as an off-white solid (1.92 g, 77%). ¹H NMR (CDCl₃, 400 MHz): δ=6.98 (d, J=2.3 Hz, 1H), 7.79 (d, J=2.3 Hz, 1H), 8.62 (s, 1H), 8.89 (s, 1H).

Intermediate 6: Furo[3,2-c]pyridin-7-ol

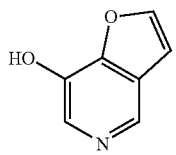

A mixture of 7-bromofuro[3,2-c]pyridine (9.15 g, 46.2 mmol), potassium hydroxide (7.78 g, 139 mmol), Pd₂(dba)₃ (0.02 eq) and 2-di-tert-butylphosphino-3,4,5,6-tetramethyl-2',4',6'-triisopropyl-1,1'-biphenyl (0.08 eq) in H₂O (22.5 mL) and 1,4-dioxane (22.5 mL) was vigorously stirred at 100° C. overnight. LC-MS showed completion of the reaction. The reaction mixture was washed with DCM (3×30 mL). The aqueous layer was neutralized and concentrated by freeze dryer. The resulting solid was washed with massive amount of acetone to give the title compound as a white solid (6.2 g, 81% yield). ¹H NMR (DMSO-d₆, 400 MHz): δ=7.05 (d, J=2.0 Hz, 1H), 8.04 (s, 1H), 8.06 (d, J=2.2 Hz, 1H), 8.44 (s, 1H). MS (ES+): m/z=136.15 [MH⁺].

Intermediate 7: 6-Nitrofuro[3,2-c]pyridin-7-ol

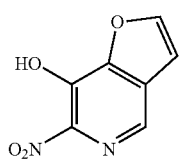

The reaction was conducted with 1 g starting material/10 mL 90% aq. nitric acid ratio. Reactions were run at 2×200 mg, 500 mg, 4×1.05 g scales. The nitric acid was cooled down to 0° C. and furo[3,2-c]pyridin-7-ol was added in portions slowly. The color of the reaction mixture turned to deep orange/red. The reaction mixture was stirred at 0° C. for 30 min. LC-MS showed complete consumption of the starting material. The mixture was poured into crashed ice to quench reaction, then extracted with DCM (3×10 mL for 200 mg scale). The combined organic layers were washed with brine (10 mL), dried over Na₂SO₄, and concentrated under vacuum. The resulting yellow solid (1.83 g, 26% yield) was directly used in the next step. ¹H NMR (CD₃OD, 400 MHz): δ=7.16 (d, J=2.0 Hz, 1H), 8.18 (d, J=2.0 Hz, 1H), 8.39 (s, 1H). MS (ES+): 181.01 [MH⁺].

Intermediate 8: 7-[(R)-1-(2,6-Dichloro-3-fluorophenyl)ethoxy]-6-nitrofuro[3,2-c]pyridine

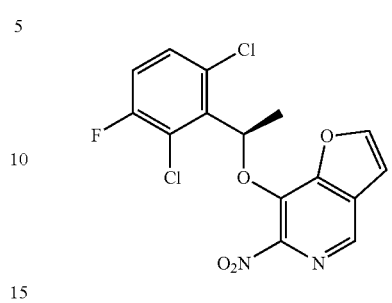

To a solution of 6-nitrofuro[3,2-c]pyridin-7-ol (Intermediate 7) (2.10 g, 11.6 mmol) and (S)-1-(2,6-dichloro-3-fluorophenyl)-ethanol (2.68 g, 12.8 mmol, prepared according to literature procedures: WO2006/021881A2) in THF (30 mL) were added PPh₃ (4.31 g, 16.4 mmol) and diisopropyl azodicarboxylate (3.32 g, 16.4 mmol) at 0° C. After 10 min, the cold-bath was removed and the resulting mixture was stirred at rt overnight. LC-MS showed completion of the reaction. The reaction mixture was evaporated under vacuum to give an oil, which was purified by silica gel flash chromatography (DCM:Hexanes=2:1) to afford 4.2 g of the desired product as a light-yellow oil (yield: 97%). ¹H NMR (CDCl₃, 400 MHz): δ=1.94 (d, J=6.8 Hz, 3H), 6.69 (q, J=6.8 Hz, 1H), 6.93 (d, J=2.3 Hz, 1H), 7.05 (t, J=8.3 Hz, 1H), 7.27 (dd, J=8.8, 4.8 Hz, 1H), 7.78 (d, J=2.3 Hz, 1H), 8.42 (s, 1H).

Alternate synthesis: To a solution of Methanesulfonic acid (S)-1-(2,6-dichloro-3-fluorophenyl)-ethyl ester (109 mg, 0.380 mmol) and 6-nitrofuro[3,2-c]pyridin-7-ol (68.4 mg, 0.380 mmol) in DMF (1.0 mL) was added potassium carbonate (57.2 mg, 0.414 mmol), and the resulting suspension was stirred at ambient temperature for 1 h and at 60° C. overnight. Methanesulfonic acid (S)-1-(2,6-dichloro-3-fluorophenyl) ethyl ester (32.7 mg, 0.114 mmol) and potassium carbonate (16 mg, 0.12 mmol) were added to the reaction mixture, and the mixture was heated at 70° C. for 3 days. Water and EtOAc were added to the reaction mixture, the layers were separated, and the aqueous layer was extracted with EtOAc (3×15 mL). The combined EtOAc extracts were washed with 1N NaOH (2×), water (2×), and brine, dried over MgSO₄, filtered and concentrated in vacuo. The residue was purified by chromatography on silica gel to afford the title compound.

Methanesulfonic Acid (S)-1-(2,6-dichloro-3-fluorophenyl)ethyl ester

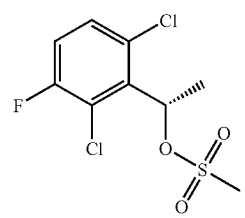

To a cooled (ice bath) solution of (S)-1-(2,6-Dichloro-3-fluorophenyl)ethanol (4.00 g, 16.3 mmol) and triethylamine (3.4 mL, 24 mmol) in toluene (20 mL) was added dropwise methanesulfonyl chloride (1.64 mL, 21.1 mmol). A white suspension formed that was stirred at 0-5° C. for 35 min. The reaction mixture was diluted with H$_2$O (20 mL), the layers were separated, and the aqueous layer was extracted with toluene (10 mL). The combined organic layers were washed with water (2×10 mL) and concentrated under vacuum at 40-45° C. to give the title compound as colorless oil containing ≈0.2 eq. of toluene according to $^1$H NMR. This material was used directly in the next step. $^1$H NMR (CDCl$_3$, 400 MHz): δ=7.33 (dd, J=9.0, 4.9 Hz, 1H), 7.12 (dd, J=9.0, 8.0 Hz, 1H), 6.45 (q, J=6.8 Hz, 1H), 2.91 (s, 3H), 1.84 (d, J=6.8 Hz).

Intermediate 8a: 7-[1-(2,6-Dichloro-3-fluorophenyl)ethoxy]-6-nitrofuro[3,2-c]pyridine

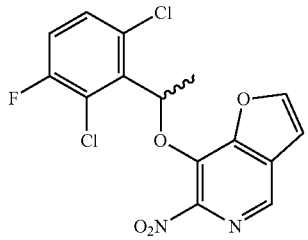

A solution of 6-nitrofuro[3,2-c]pyridin-7-ol (8.0 g, 44.44 mmol) and 1-(2,6-dichloro-3-fluorophenyl)ethanol (10.20 g, 49.04 mmol) in THF (150 mL) was placed in a three necked RB flask (IL) and was cooled with ice bath. To the cold solution were added PPh$_3$ (15.78 g, 16.41 mmol) and diisopropyl azodicarboxylate (12.65 g, 62.48 mmol) at 0° C. After 10 min, the ice bath was removed and the resulting mixture was stirred at RT overnight. TLC (20% ethyl acetate in hexane) indicated the completion of the reaction. The reaction mixture was evaporated under vacuum below 50° C. to give an oil (58.8 g), which was purified by silica gel flash chromatography (DCM:Hexanes: 2:1) to afford the desired product as a light-yellow oil (13.7 g, 84% yield). The $^1$H NMR spectrum matches that of Intermediate 8.

Intermediate 9: 3-Bromo-7-[(R)-1-(2,6-dichloro-3-fluorophenyl)ethoxy]-6-nitrofuro[3,2-c]pyridine

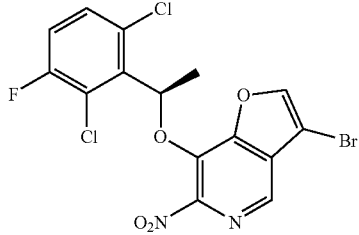

A mixture of 7-[(1R)-1-(2,6-dichloro-3-fluorophenyl)ethoxy]-6-nitrofuro[3,2-c]pyridine (4.20 g, 11.3 mmol) and bromine (7.23 g, 45.3 mmol) in carbon tetrachloride (50 mL) was stirred at 50° C. overnight. LC-MS showed the reaction reached ca. 92% conversion. After cooled to rt, sat. aq. Na$_2$S$_2$O$_3$ solution (30 mL) was added to quench the reaction and the mixture was diluted with DCM (100 mL). The organic layer was washed with sat. aq. Na$_2$S$_2$O$_3$ (30 mL), brine (30 mL), and dried over anhydrous Na$_2$SO$_4$. Evaporation of solvents under reduced pressure gave a yellow oil, which was directly used in the next step.

The above crude material was dissolved in THF (50 mL) and treated with 1,8-diazabicyclo[5.4.0]undec-7-ene (2.0 mL, 14.0 mmol) at 0° C. for 1 h. The mixture was diluted with EtOAc (100 mL), washed with water (30 mL), brine (30 mL), dried over anhydrous sodium sulfate, filtered, and concentrated to give a residue, which was purified by silica gel chromatography (Hexane:EtOAc=80:20) to give 4.31 g of the title compound as a light-yellow oil (85% yield over two steps). $^1$H NMR (CDCl$_3$, 400 MHz): δ=1.93 (d, J=6.6 Hz, 3H), 6.69 (q, J=6.6 Hz, 1H), 7.06 (dd, J=8.8, 7.8 Hz, 1H), 7.27 (dd, J=8.8, 4.8 Hz, 1H), 7.78 (s, 1H), 8.36 (s, 1H).

Intermediate 9a: 3-Bromo-7-[1-(2,6-dichloro-3-fluorophenyl)ethoxy]-6-nitrofuro[3,2-c]-pyridine

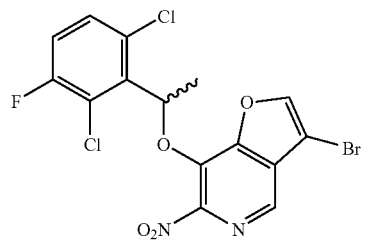

A mixture of 7-(1-(2,6-dichloro-3-fluorophenyl)ethoxy]-6-nitrofuro[3,2-c]pyridine (Intermediate 8a, 13.7 g, 37.0 mmol) and bromine (35.54 gm, 222.1 mmol) in carbon tetrachloride (150 mL) was stirred at 55-60° C. overnight. At this point the TLC (10% in hexane) showed the reaction was almost complete. It was cooled to RT and saturated aqueous Na$_2$S$_2$O$_3$ solution (50 mL) was added to quench the reaction and the mixture was diluted with DCM (200 mL). The organic layer was washed with saturated aqueous Na$_2$S$_2$O$_3$ (100 mL) followed by brine (100 mL), and dried over anhydrous Na$_2$SO$_4$. Evaporation of solvents under reduced pressure gave a yellow oil (62 g) that was directly used in the next step.

The above crude material was dissolved in THF (250 mL) and treated with 1,8-diaza-bicyclo[5.4.0]undec-7-ene (7.21 mL, 50.5 mmol) at 0° C. for 2 h. The mixture was diluted with EtOAc (500 mL) and the organic layer washed with water (100 mL), brine (100 mL), dried over anhydrous sodium sulfate, filtered, and concentrated to give a residue (19 g) that was purified by silica gel chromatography (Hexane:EtOAc: 80:20) to give the title compound as a light-yellow oil (14 g, 84% yield). The $^1$H NMR spectrum matches that of Intermediate 9.

Example 1

7-[(R)-1-(2,6-dichloro-3-fluorophenyl)-ethoxy]-furo[3,2-c]pyridin-6-ylamine

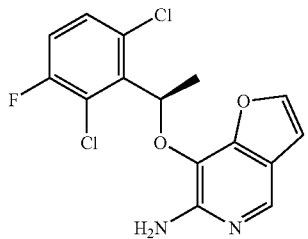

To a solution of 7-[(1R)-1-(2,6-dichloro-3-fluorophenyl)ethoxy]-6-nitrofuro[3,2-c]pyridine (40 mg, 0.11 mmol) in EtOH (1 mL) was added Fe powder (24 mg, 0.43 mmol) and 1M HCl (aq.) (0.05 mL, 0.05 mmol). The reaction mixture was stirred at 95° C. for 20 min. After cooled down to room temperature, the reaction mixture was passed through a pad of Celite. The filtrate was concentrated in vacuo and residue was purified by preparative TLC (5% MeOH in DCM) to afford the title compound as a brown oil (25 mg, 68% yield). $^1$H NMR (CDCl$_3$, 400 MHz): δ=1.86 (d, J=6.60 Hz, 3H), 4.75 (br, s, 2H), 6.55 (q, J=6.97 Hz, 1H), 6.65 (d, J=2.20 Hz, 1H), 7.04 (t, J=8.43 Hz, 1H), 7.27 (dd, J=8.80, 4.77 Hz, 1H), 7.39 (d, J=2.20 Hz, 1H), 8.05 (s, 1H). MS (ES$^+$): m/z 341.03, 343.01 (100) [MH$^+$]. HPLC: t$_R$=2.77 min (ZQ3: polar_5 min).

Example 2

3-Bromo-7-[(R)-1-(2,6-dichloro-3-fluorophenyl)-ethoxy]-furo[3,2-c]pyridin-6-ylamine

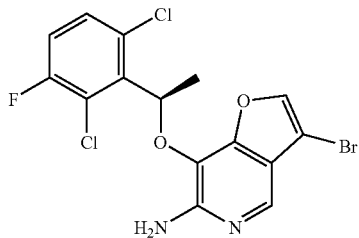

To a solution of 3-bromo-7-[(1R)-1-(2,6-dichloro-3-fluorophenyl)ethoxy]-6-nitrofuro[3,2-c]pyridine (1.00 g, 2.22 mmol) in EtOH (10 mL) was added iron (0.62 g, 11.1 mmol), followed by 0.1 N aq. HCl (1.1 mL, 0.11 mmol) at 95° C. (bath temp). The resulting mixture was stirred at this temperature for 30 min. Additional 0.1 N aq. HCl (1.1 mL, 0.11 mmol) was added and the mixture was refluxed for another 30 min. TLC and LC-MS showed the reaction was complete. The mixture was diluted with EtOAc (100 mL) and the solid was filtered off through a pad of Celite. The mother liquor was washed with brine (3×25 mL) and dried over anhydrous sodium sulfate. Evaporation of solvents under reduced pressure afforded the title compound as a light-yellow semi-solid (930 mg, 100% yield). $^1$H NMR (CDCl$_3$, 400 MHz): δ=1.87 (d, J=6.6 Hz, 3H), 5.15 (br s, 2H), 6.55 (q, J=6.6 Hz, 1H), 7.06 (dd, J=9.1, 8.1 Hz, 1H), 7.27 (dd, J=9.1, 5.1 Hz, 1H), 7.44 (s, 1H), 7.96 (s, 1H). MS (ES$^+$): 418.91/420.86/422.89 [MH$^+$].

Example 3

7-[(R)-1-(2,6-dichloro-3-fluorophenyl)-ethoxy]-3-phenyl-furo[3,2-c]pyridin-6-ylamine

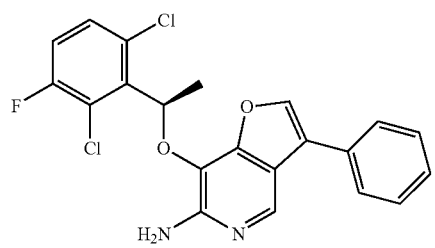

A mixture of 3-bromo-7-[(R)-1-(2,6-dichloro-3-fluorophenyl)-ethoxy]-furo[3,2-c]pyridin-6-ylamine (25 mg, 0.0595 mmol), phenylboronic acid (8.7 mg, 0.071 mmol), Cs$_2$CO$_3$ (58 mg, 0.18 mmol), and Pd(PPh$_3$)$_4$ (6.9 mg, 0.006 mmol) in DME (1.5 mL) and H$_2$O (0.5 mL) was degassed and refilled with nitrogen (3×). This mixture was then heated at 100° C. using microwave for 30 min. LC-MS showed completion of the reaction. The reaction mixture was diluted with EtOAc (30 mL), washed with brine (10 mL), and dried over anhydrous sodium sulfate. The residue was purified by silica gel chromatography (Hexane:EtOAc=70:30) to give a brown oil, which was further purified by mass-directed purification to afford the title compound as a brown oil (10.3 mg). $^1$H NMR (CDCl$_3$, 400 MHz): δ=1.93 (d, J=6.8 Hz, 3H), 6.70 (q, J=6.8 Hz, 1H), 7.10 (dd, J=9.1, 7.8 Hz, 1H), 7.33 (dd, J=9.1, 4.8 Hz, 1H), 7.42-7.55 (m, 5H), 7.67 (s, 1H), 8.12 (s, 1H), 8.18 (s, 1H). MS (ES$^+$): 417.01/418.99 [MH$^+$].

Example 4

7-[(R)-1-(2,6-Dichloro-3-fluorophenyl)-ethoxy]-3-(1-methyl-1H-pyrazol-4-yl)-furo[3,2-c]pyridin-6-ylamine

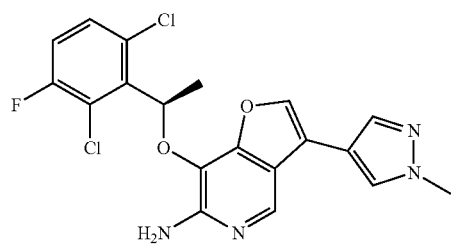

A mixture of 3-bromo-7-[(R)-1-(2,6-dichloro-3-fluorophenyl)-ethoxy]-furo[3,2-c]pyridin-6-ylamine (40 mg, 0.095 mmol), 1-methyl-4-(4,4,5,5-tetramethyl-1,3,2-dioxaborolan-2-yl)-1H-pyrazole (30 mg, 0.14 mmol), and potassium carbonate (39 mg, 0.28 mmol) in 1,4-dioxane (1.5 mL) and H$_2$O (0.5 mL) was degassed and refilled with argon (3×) prior to addition of (1,1'-bis(diphenylphosphino)-ferrocene)

palladium dichloride (7.0 mg, 0.0095 mmol). The reaction mixture was degassed and refilled with argon (2×) and stirred at 100° C. for 30 min in a CEM microwave. LC-MS showed completion of the reaction. The mixture was diluted with EtOAc (30 mL), washed with brine (10 mL), and dried over anhydrous sodium sulfate. The residue was purified by mass-directed purification to give the title compound as a brown oil (15.9 mg). $^1$H NMR (CDCl$_3$, 400 MHz): δ=1.91 (d, J=6.8 Hz, 3H), 4.00 (s, 3H), 5.93 (br s, 2H), 6.65 (q, J=6.8 Hz, 1H), 7.09 (dd, J=9.1, 7.8 Hz, 1H), 7.31 (dd, J=9.1, 4.8 Hz, 1H), 7.58 (s, 1H), 7.64 (s, 1H), 7.71 (s, 1H), 8.03 (s, 1H). MS (ES$^+$): 421.00/423.02 [MH$^+$].

Example 5

7-[(R)-1-(2,6-Dichloro-3-fluorophenyl)ethoxy]-3-(1-piperidin-4-yl-1H-pyrazol-4-yl)-furo[3,2-c]pyridin-6-ylamine

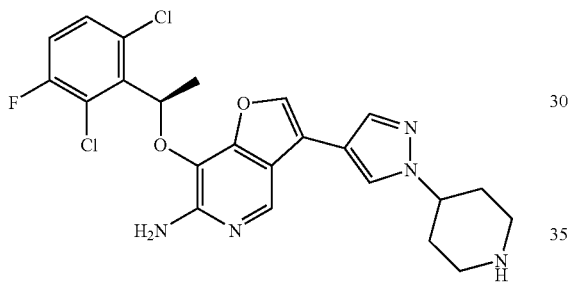

General procedure A: A mixture of 3-bromo-7-[(1R)-1-(2,6-dichloro-3-fluorophenyl)ethoxy]-6-nitrofuro[3,2-c]pyridine (10 mg, 0.022 mmol), 4-[4-(4,4,5,5-tetramethyl-[1,3,2]dioxaborolan-2-yl)-pyrazol-1-yl]-piperidine-1-carboxylic acid tert-butyl ester (12.5 mg, 0.033 mmol), Pd(PPh$_3$)$_4$ (2.6 mg, 0.0022 mmol), and potassium carbonate (9.2 mg, 0.0667 mmol) in DME (0.15 mL) and H$_2$O (0.05 mL) was stirred at 100° C. under microwave condition for 1 h. LC-MS showed completion of the reaction. The reaction mixture was purified by preparatory TLC (DCM). The resulting material was reduced by Fe powder (12.3 mg, 0.22 mmol), 0.1 N aq. HCl (5%) in EtOH at 95° C. for 30 min. The resulting material was directly loaded onto preparatory TLC for purification (1%→2% MeOH in DCM). The obtained material was deprotected by 2 M HCl in ether at 40° C. for 2-3 h to afford 3.1 mg of the desired product as bis-HCl salt (28% yield for 3 steps). $^1$H-NMR (CD$_3$OD, 400 MHz): δ=1.89 (d, J=6.8 Hz, 2H), 2.00 (dd, J=12.3, 3.9 Hz, 1H), 2.13 (d, J=2.3 Hz, 1H), 2.75-2.85 (m, 1H), 3.22 (d, J=12.9 Hz, 1H), 4.36 (m, 1H), 6.54 (m, 1H), 7.23 (t, J=8.8 Hz, 1H), 7.40 (dd, J=9.0, 4.9 Hz, 1H), 7.62 (dd, J=5.7, 3.4 Hz, 1H), 7.69-7.74 (m, 1H), 7.78 (s, 1H), 7.83 (s, 1H), 8.09 (s, 1H), 8.15 (s, 1H). MS (ES$^+$): m/z 490.04 (MH$^+$, $^{35}$Cl, $^{37}$Cl), 492.00 (MH$^+$, $^{37}$Cl, $^{37}$Cl). HPLC: t$_R$=2.26 min (polar_5 min, ZQ3).

Example 6

7-[(R)-1-(2,6-Dichloro-3-fluorophenyl)ethoxy]-3-(1H-pyrazol-4-yl)-furo[3,2-c]pyridin-6-ylamine

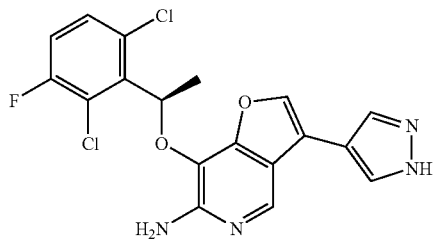

Prepared according to General procedure A. Yield: 36%. MS (ES$^+$): m/z 407.02 (MH$^+$, $^{35}$Cl, $^{37}$Cl), 408.97 (MH$^+$, $^{37}$Cl, $^{37}$Cl). HPLC: t$_R$=2.26 min (polar_5 min, ZQ3).

Example 7

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid tert-butyl ester

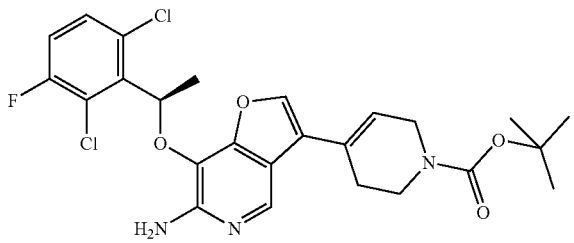

A mixture of 3-bromo-7-[(R)-1-(2,6-dichloro-3-fluorophenyl)-ethoxy]-furo[3,2-c]pyridin-6-ylamine (100.0 mg, 0.2381 mmol), 4-(4,4,5,5-tetramethyl-[1,3,2]dioxaborolan-2-yl)-3,6-dihydro-2H-pyridine-1-carboxylic acid tert-butyl ester (88.3 mg, 0.286 mmol), Pd(PPh$_3$)$_4$ (10 mg, 0.01 mmol), potassium carbonate (98.7 mg, 0.714 mmol) and 4:1 dioxane:water (4 mL) was microwaved at 100° C. for 2 h. The solution was concentrated in vacuo, and dry-loaded onto silica gel for column chromatography, eluted with 2-5% MeOH in DCM. Fractions containing the product were concentrated in vacuo to afford the title compound as an off-white solid. $^1$H NMR (CD$_3$OD, 400 MHz): δ=1.49 (s, 9H), 1.88 (d, J=6.8 Hz, 3H), 2.48 (d, J=1.5 Hz, 2H), 3.59-3.69 (m, 2H), 4.11 (br, s, 2H), 6.26 (br, s, 1H), 6.50 (q, J=6.9 Hz, 1H), 7.19-7.25 (m, 1H), 7.40 (dd, J=9.0, 4.9 Hz, 1H), 7.64 (s, 1H), 8.20 (s, 1H). MS (ES$^+$): m/z 522.14 [MH$^+$]. HPLC: t$_R$=3.51 min (ZQ3, polar_5 min).

Example 8

7-[(R)-1-(2,6-Dichloro-3-fluorophenyl)ethoxy]-3-(1,2,3,6-tetrahydropyridin-4-yl)-furo[3,2-c]pyridin-6-ylamine

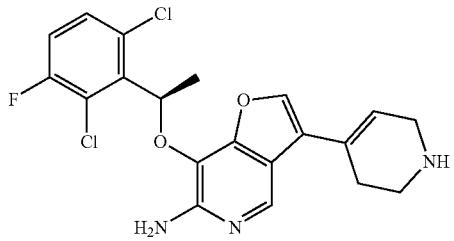

A solution of 4-{6-amino-7-[(R)-1-(2,6-dichloro-3-fluorophenyl)ethoxy]furo[3,2-c]pyridin-3-yl}-3,6-dihydro-2H-pyridine-1-carboxylic acid tert-butyl ester (98.0 mg, 0.188 mmol) in 4 M HCl in 1,4-dioxane (8 mL) was cooled to 0° C., then stirred at 50° C. for 2 h. The material was concentrated in vacuo and then extracted with DCM and sat. aq. NaHCO₃. The organic layer was concentrated in vacuo to afford the title compound as a brown solid. $^1$H NMR (CDCl₃, 400 MHz): δ=1.86 (d, J=6.8 Hz, 3H), 2.37-2.47 (m, 2H), 3.15 (t, J=5.8 Hz, 2H), 3.60 (d, J=2.8 Hz, 2H), 4.74 (s, 2H), 6.28 (br, s, 1H), 6.52 (q, J=6.7 Hz, 1H), 7.02-7.08 (m, 1H), 7.27-7.32 (m, 1H), 7.37 (s, 1H), 8.25 (s, 1H). MS (ES⁺): m/z 422.06 [MH⁺]. HPLC: $t_R$=2.23 min (ZQ3, polar_5 min).

Example 9

1-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-2-dimethylaminoethanone

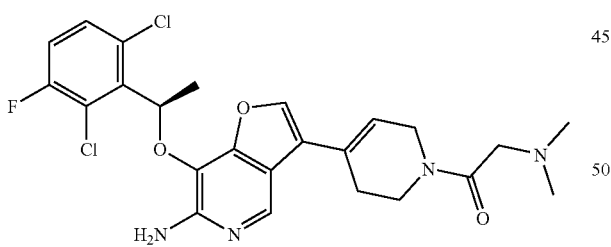

General procedure B: A mixture of 7-[(R)-1-(2,6-dichloro-3-fluorophenyl)ethoxy]-3-(1,2,3,6-tetrahydropyridin-4-yl)-furo[3,2-c]pyridin-6-ylamine (10.0 mg, 0.0237 mmol), dimethylaminoacetic acid (2.44 mg, 0.0237 mmol), TBTU (15.2 mg, 0.0474 mmol), DIPEA (0.02 mL, 0.1 mmol) and DMF (0.5 mL) was stirred at rt for 10 min. The solution was passed through a syringe filter pad and submitted for HPLC purification. The fractions containing the pure product were concentrated in vacuo to afford the title compound as a white solid. $^1$H NMR (CD₃OD, 400 MHz): δ=1.87 (d, J=6.6 Hz, 3H), 2.53 (d, J=1.5 Hz, 1H), 2.60 (br, s, 1H), 2.88 (s, 6H), 3.61-3.68 (m, 1H), 3.85 (t, J=5.9 Hz, 1H), 4.15 (s, 2H), 4.19 (s, 1H), 4.28 (d, J=2.5 Hz, 1H), 6.27 (d, J=14.9 Hz, 1H), 6.48 (q, J=6.8 Hz, 1H), 7.21 (t, J=8.6 Hz, 1H), 7.39 (dd, J=9.0, 4.9 Hz, 1H), 7.66 (d, J=10.4 Hz, 1H), 8.18 (s, 1H). MS (ES⁺): m/z 507.04 [MH⁺]. HPLC: $t_R$=2.09 min (ZQ2, polar_5 min).

Example 10

4-{6-Amino-7-[(R)-1-(2,6-dichloro-3-fluorophenyl)-ethoxy]-furo[3,2-c]pyridin-3-yl}-3,6-dihydro-2H-pyridine-1-carbaldehyde

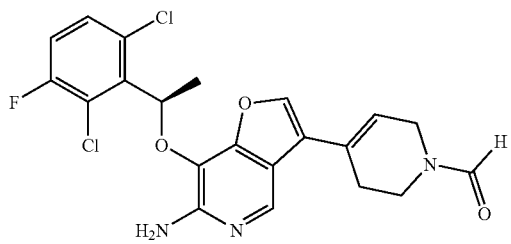

The title compound was prepared according to General procedure B. $^1$H NMR (CD₃OD, 400 MHz): δ=1.88 (d, J=6.8 Hz, 3H), 2.48-2.61 (m, 2H), 3.68-3.81 (m, 2H), 4.19 (d, J=2.3 Hz, 2H), 6.24-6.32 (m, 1H), 6.49 (q, J=6.7 Hz, 1H), 7.22 (t, J=8.7 Hz, 1H), 7.40 (dd, J=9.0, 4.9 Hz, 1H), 7.62-7.68 (m, 1H), 8.13 (s, 1H), 8.16-8.23 (m, 1H). MS (ES⁺): m/z 450.07 [MH⁺]. HPLC: $t_R$=2.89 min (ZQ2, polar_5 min).

Example 11

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-phenylmethanone

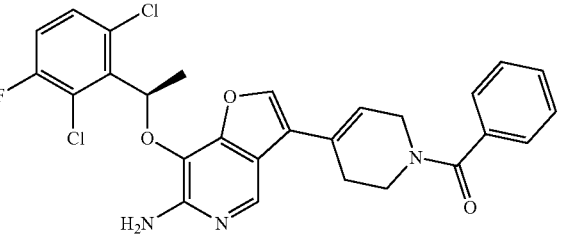

The title compound was prepared according to General procedure B. $^1$H NMR (CD₃OD, 400 MHz): δ=1.88 (d, J=6.8 Hz, 3H), 2.56 (br, s, 1H), 2.61 (br, s, 1H), 3.66 (br, s, 1H), 4.00 (br, s, 1H), 4.19 (br, s, 1H), 4.42 (br, s, 1H), 6.37 (br, s, 1H), 6.50 (q, J=6.7 Hz, 1H), 7.19-7.25 (m, 1H), 7.40 (dd, J=9.1, 4.8 Hz, 1H), 7.45-7.53 (m, 5H), 7.64-7.70 (m, 1H), 8.25 (br, s, 1H). MS (ES⁺): m/z 526.05 [MH⁺]. HPLC: $t_R$=3.20 min (ZQ2, polar_5 min).

Example 12

1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-ethanone

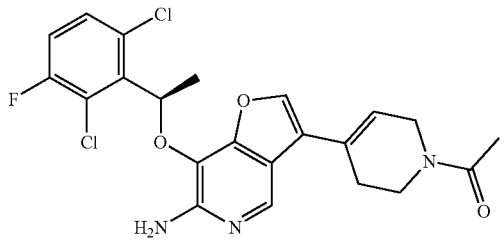

The title compound was prepared according to General procedure B. $^1$H NMR (CD$_3$OD, 400 MHz): δ=1.83-1.96 (m, 3H), 2.12-2.24 (m, 3H), 2.50 (d, J=13.4 Hz, 1H), 2.59 (d, J=14.4 Hz, 1H), 3.70-3.85 (m, 2H), 4.26 (d, J=9.3 Hz, 2H), 6.27 (br, s, 1H), 6.52 (dd, J=18.7, 6.8 Hz, 1H), 7.17-7.29 (m, 1H), 7.36-7.48 (m, 1H), 7.62-7.72 (m, 1H), 8.10-8.20 (m, 1H). MS (ES$^+$): m/z 464.01 [MH$^+$]. HPLC: $t_R$=2.66 min (ZQ2, polar_5 min).

Example 13

1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2-pyrrolidin-1-ylethanone

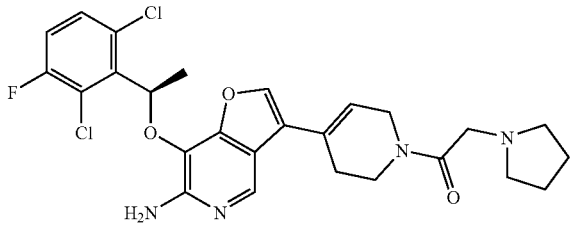

The title compound was prepared according to General procedure B. $^1$H NMR (CD$_3$OD, 400 MHz): δ=1.89 (d, J=6.8 Hz, 3H), 2.08-2.15 (m, 4H), 2.55 (d, J=1.0 Hz, 1H), 2.62 (br, s, 1H), 3.45 (br, s, 4H), 3.61-3.67 (m, 1H), 3.86 (t, J=5.9 Hz, 1H), 4.15 (d, J=2.5 Hz, 1H), 4.29 (d, J=2.5 Hz, 1H), 4.36 (s, 1H), 4.42 (s, 1H), 6.29 (d, J=15.9 Hz, 1H), 6.50 (q, J=6.8 Hz, 1H), 7.22 (t, J=8.7 Hz, 1H), 7.40 (dd, J=9.0, 4.9 Hz, 1H), 7.68 (d, J=10.6 Hz, 1H), 8.20 (d, J=1.8 Hz, 1H). MS (ES$^+$): m/z 533.07 [MH$^+$]. HPLC: $t_R$=2.17 min (ZQ2, polar_5 min).

Example 14

1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-propan-1-one

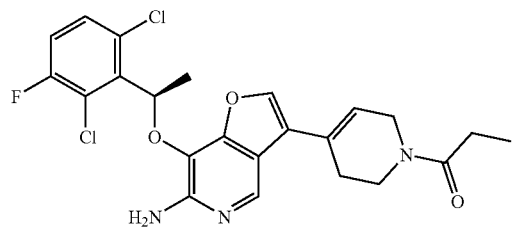

The title compound was prepared according to General procedure B. $^1$H NMR (CD$_3$OD, 400 MHz): δ=1.15 (q, J=7.4 Hz, 3H), 1.88 (d, J=6.8 Hz, 3H), 2.41-2.53 (m, 3H), 2.56 (d, J=1.0 Hz, 1H), 3.72-3.84 (m, 2H), 4.25 (br, s, 2H), 6.24-6.31 (m, 1H), 6.50 (q, J=6.8 Hz, 1H), 7.22 (t, J=8.6 Hz, 1H), 7.40 (dd, J=9.0, 4.9 Hz, 1H), 7.65 (d, J=8.6 Hz, 1H), 8.20 (s, 1H). MS (ES$^+$): m/z 478.02 [MH$^+$]. HPLC: $t_R$=2.83 min (ZQ2, polar_5 min).

Example 15

1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2-methylpropan-1-one

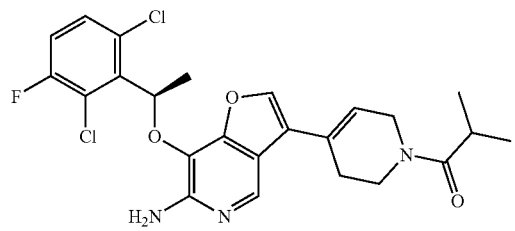

The title compound was prepared according to General procedure B. $^1$H NMR (CD$_3$OD, 400 MHz): δ=1.09-1.16 (m, 6H), 1.87 (d, J=6.8 Hz, 3H), 2.48 (br, s, 1H), 2.57 (br, s, 1H), 2.92-3.09 (m, 1H), 3.81 (t, J=5.4 Hz, 2H), 4.24 (br, s, 1H), 4.32 (br, s, 1H), 6.29 (br, s, 1H), 6.49 (q, J=6.7 Hz, 1H), 7.21 (t, J=8.6 Hz, 1H), 7.39 (dd, J=9.0, 4.9 Hz, 1H), 7.65 (d, J=7.3 Hz, 1H), 8.20 (s, 1H). MS (ES$^+$): m/z 492.01 [MH$^+$]. HPLC: $t_R$=2.99 min (ZQ2, polar_5 min).

Example 16

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-cyclohexylmethanone

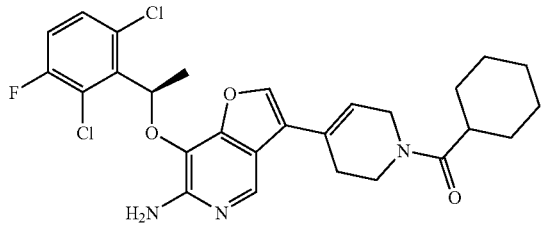

The title compound was prepared according to General procedure B. $^1$H NMR (CD$_3$OD, 400 MHz): δ=1.28 (d, J=3.0 Hz, 1H), 1.32-1.47 (m, 3H), 1.50 (br, s, 1H), 1.70-1.76 (m, 2H), 1.76-1.83 (m, 3H), 1.86-1.91 (m, 3H), 2.47 (br, s, 1H), 2.56 (br, s, 1H), 2.64-2.77 (m, 1H), 3.79 (t, J=5.7 Hz, 2H), 4.22 (d, J=2.3 Hz, 1H), 4.31 (d, J=2.3 Hz, 1H), 6.28 (br, s, 1H), 6.50 (q, J=6.8 Hz, 1H), 7.21 (t, J=8.6 Hz, 1H), 7.39 (dd, J=9.1, 4.8 Hz, 1H), 7.65 (d, J=6.1 Hz, 1H), 8.20 (d, J=2.3 Hz, 1H). MS (ES$^+$): m/z 532.06 [MH$^+$]. HPLC: t$_R$=3.43 min (ZQ2, polar__5 min).

Example 17

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(1-methylpiperidin-4-yl)-methanone

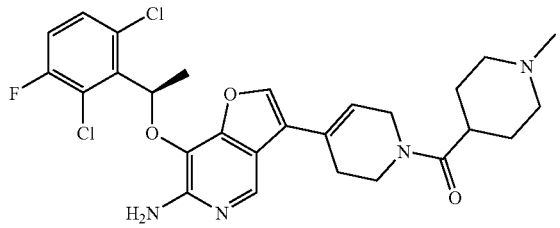

The title compound was prepared according to General procedure B. $^1$H NMR (CD$_3$OD, 400 MHz): δ=1.87 (d, J=6.8 Hz, 3H), 2.01 (d, J=3.5 Hz, 4H), 2.49 (br, s, 1H), 2.60 (br, s, 1H), 2.86 (d, J=3.8 Hz, 3H), 3.05 (br, s, 1H), 3.11 (d, J=4.3 Hz, 2H), 3.52 (br, s, 2H), 3.78-3.86 (m, 2H), 4.24 (br, s, 1H), 4.34 (br, s, 1H), 6.28 (d, J=3.3 Hz, 1H), 6.49 (q, J=6.8 Hz, 1H), 7.21 (t, J=8.7 Hz, 1H), 7.39 (dd, J=8.8, 4.8 Hz, 1H), 7.66 (d, J=9.6 Hz, 1H), 8.19 (s, 1H). MS (ES$^+$): m/z 547.11 [MH$^+$]. HPLC: t$_R$=2.48 min (ZQ3, polar__5 min).

General Procedure for forming HCl/bis-HCl salts from the free base: To a solution of the free base (0.083 mmol) in MeOH/DCM 1:1 (2.0 mL) was added HCl Et$_2$O (2.0M solution; 0.21 mL, 0.42 mmol, 5.1 eq.) at ambient temperature. The mixture was stirred at ambient temperature for 30 min. The solvents were evaporated in vacuo to give the salt; alternatively, the solid material formed was filtered off, rinsed with Et$_2$O, and dried in vacuo to give the salt.

Example 18

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-((S)-1-methylpyrrolidin-2-yl)-methanone

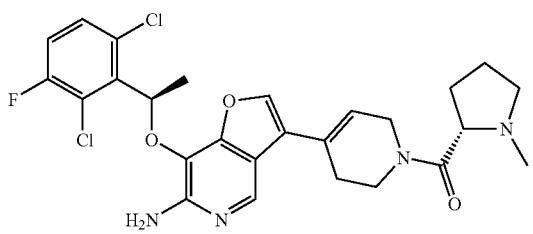

The title compound was prepared according to General procedure B. $^1$H NMR (CD$_3$OD, 400 MHz): δ=1.88 (d, J=6.8 Hz, 3H), 1.96-2.11 (m, 2H), 2.17-2.32 (m, 1H), 2.54-2.75 (m, 3H), 2.93 (d, J=4.8 Hz, 3H), 3.16-3.26 (m, 1H), 3.65-3.76 (m, 2H), 3.81 (ddd, J=12.9, 6.3, 6.1 Hz, 1H), 4.10-4.29 (m, 1H), 4.31 (d, J=2.3 Hz, 1H), 4.51-4.63 (m, 1H), 6.29 (d, J=14.1 Hz, 1H), 6.49 (q, J=6.8 Hz, 1H), 7.22 (t, J=8.6 Hz, 1H), 7.36-7.42 (m, 1H), 7.65-7.71 (m, 1H), 8.19 (d, J=2.8 Hz, 1H). MS (ES$^+$): m/z 533.06 [MH$^+$]. HPLC: t$_R$=2.42 min (ZQ3, polar__5 min).

The compound was converted to its bis-HCl salt following the General Procedure for forming HCl/bis-HCl salts from the free base.

Example 19

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(1-hydroxycyclopropyl)-methanone

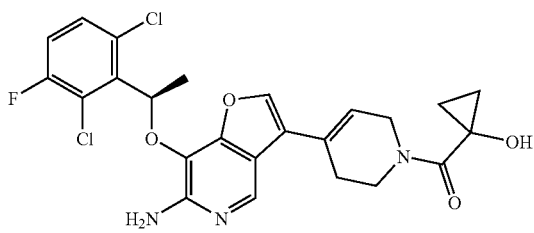

The title compound was prepared according to General procedure B. $^1$H NMR (CD$_3$OD, 400 MHz): δ=0.89-0.95 (m, 2H), 1.05-1.10 (m, 2H), 1.88 (d, J=6.8 Hz, 3H), 2.58 (br, s, 2H), 4.06 (br, s, 2H), 4.21 (br, s, 1H), 4.61 (br, s, 1H), 6.30 (br, s, 1H), 6.51 (q, J=6.7 Hz, 1H), 7.22 (t, J=8.6 Hz, 1H), 7.40 (dd, J=9.1, 4.8 Hz, 1H), 7.67 (s, 1H), 8.14 (s, 1H). MS (ES$^+$): m/z 506.07 [MH$^+$]. HPLC: t$_R$=2.89 min (ZQ3, polar__5 min).

Example 20

1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-4-dimethylaminobutan-1-one

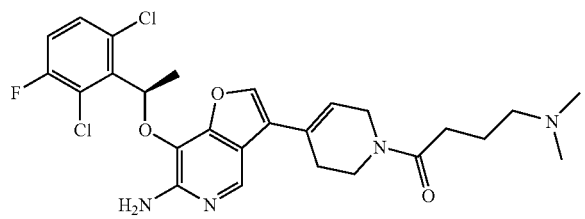

The title compound was prepared according to General procedure B. $^1$H NMR (CD$_3$OD, 400 MHz): δ=1.88 (d, J=6.6 Hz, 3H), 1.97-2.09 (m, 2H), 2.50 (d, J=1.3 Hz, 1H), 2.56-2.68 (m, 3H), 2.88-2.92 (m, 6H), 3.12-3.19 (m, 2H), 3.75 (t, J=5.8 Hz, 1H), 3.83 (t, J=5.8 Hz, 1H), 4.25 (dd, J=7.6, 2.8 Hz, 2H), 6.24-6.31 (m, 1H), 6.49 (q, J=6.8 Hz, 1H), 7.22 (t, J=8.7 Hz, 1H), 7.40 (dd, J=9.0, 4.9 Hz, 1H), 7.66 (d, J=9.3 Hz, 1H), 8.19 (s, 1H). MS (ES$^+$): m/z 535.11 [MH$^+$]. HPLC: t$_R$=2.40 min (ZQ3, polar_5 min).

The compound was converted to its bis-HCl salt following the General Procedure for forming HCl/bis-HCl salts from the free base.

Example 21

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperidin-4-ylmethanone

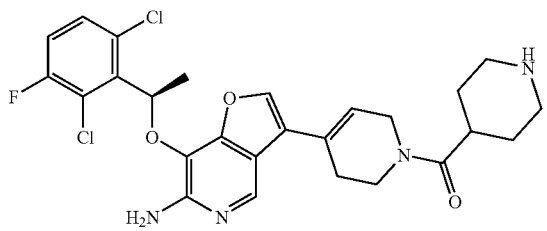

General procedure C: A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), 1-(tert-butoxycarbonyl)isonipecotic acid (10.8 mg, 0.0474 mmol), TBTU (11.4 mg, 0.0355 mmol), DIPEA (0.02 mL, 0.1 mmol) and DCM (2 mL, 0.03 mol) was stirred at rt for 10 min. The material was transferred to a separatory funnel and washed with sat. aq. NaHCO$_3$. The organic layer was concentrated in vacuo, redissolved in dioxane, and transferred to a sealed tube. 4 M HCl in 1,4-dioxane (0.2 mL) was added, and the solution was heated to 50° C. for 3 h. The material was concentrated in vacuo and redissolved in DMF (0.5 mL). The solution was purified by HPLC. The fractions containing the pure product were concentrated in vacuo to afford the title compound as a white solid. $^1$H NMR (CD$_3$OD, 400 MHz): δ=1.88 (d, J=6.8 Hz, 3H), 1.89-2.07 (m, 4H), 2.50 (br, s, 1H), 2.60 (br, s, 1H), 3.03-3.19 (m, 3H), 3.45 (dd, J=13.0, 3.9 Hz, 2H), 3.78-3.86 (m, 2H), 4.24 (d, J=2.3 Hz, 1H), 4.34 (d, J=2.5 Hz, 1H), 6.29 (d, J=3.3 Hz, 1H), 6.49 (q, J=6.7 Hz, 1H), 7.21 (t, J=8.7 Hz, 1H), 7.39 (dd, J=9.0, 4.9 Hz, 1H), 7.66 (d, J=10.6 Hz, 1H), 8.19 (d, J=2.3 Hz, 1H). MS (ES$^+$): m/z 533.10 [MH$^+$]. HPLC: t$_R$=2.16 min (ZQ2, polar_5 min).

The compound was converted to its bis-HCl salt following the General Procedure for forming HCl/bis-HCl salts from the free base.

Example 22

(4-{6-Amino-7-[(R)-1-(2,6-dichloro-3-fluorophenyl)ethoxy]furo[3,2-c]pyridin-3-yl}-3,6-dihydro-2H-pyridin-1-yl)-(S)-pyrrolidin-2-ylmethanone

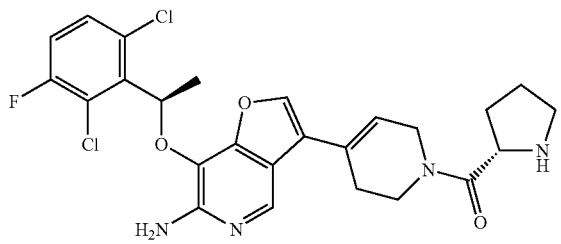

The title compound was prepared according to General procedure C. $^1$H NMR (CD$_3$OD, 400 MHz): δ=1.88 (d, J=6.8 Hz, 3H), 1.94-2.14 (m, 3H), 2.48-0.65 (m, 3H), 3.33-0.49 (m, 2H), 3.70-3.88 (m, 1H), 3.99 (ddd, J=13.0, 5.7, 5.6 Hz, 1H), 4.15-4.39 (m, 2H), 4.64-4.77 (m, 1H), 6.25-6.33 (m, 1H), 6.49 (q, J=6.7 Hz, 1H), 7.22 (t, J=8.7 Hz, 1H), 7.40 (dd, J=9.0, 4.9 Hz, 1H), 7.68 (d, J=9.1 Hz, 1H), 8.20 (d, J=2.3 Hz, 1H). MS (ES$^+$): m/z 519.07 [MH$^+$]. HPLC: t$_R$=2.19 min (ZQ2, polar_5 min).

The compound was converted to its bis-HCl salt following the General Procedure for forming HCl/bis-HCl salts from the free base.

Example 23

(1-Aminocyclopropyl)-(4-{6-amino-7-[(R)-1-(2,6-dichloro-3-fluorophenyl)-ethoxy]-furo[3,2-c]pyridin-3-yl}-3,6-dihydro-2H-pyridin-1-yl)-methanone

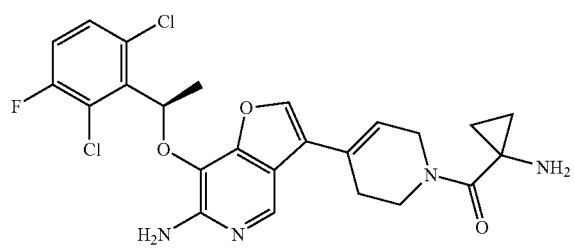

The title compound was prepared according to General procedure C. $^1$H NMR (CD$_3$OD, 400 MHz): δ=0.82-0.93 (m, 4H), 1.88 (d, J=6.8 Hz, 3H), 2.58 (br, s, 2H), 3.92 (br, s, 2H), 4.34 (br, s, 2H), 6.31 (t, J=3.3 Hz, 1H), 6.50 (q, J=6.7 Hz, 1H), 7.18-7.25 (m, 1H), 7.40 (dd, J=9.0, 4.9 Hz, 1H), 7.66 (s, 1H), 8.21 (s, 1H). MS (ES+): m/z 505.08 [MH+]. HPLC: $t_R$=2.21 min (ZQ2, polar_5 min).

Example 24

2-Amino-1-(4-{6-amino-7-[(R)-1-(2,6-dichloro-3-fluorophenyl)-ethoxy]-furo[3,2-c]pyridin-3-yl}-3,6-dihydro-2H-pyridin-1-yl)-2-methylpropan-1-one

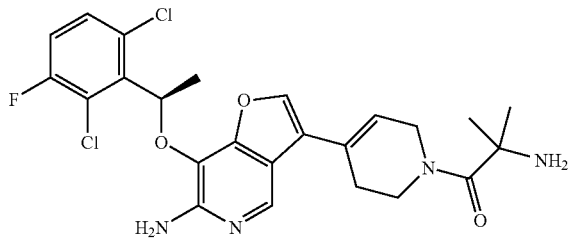

The title compound was prepared according to General procedure C. ¹H NMR (CD₃OD, 400 MHz): δ=1.72 (s, 6H), 1.89 (d, J=6.8 Hz, 3H), 2.58 (br, s, 2H), 3.89 (t, J=5.8 Hz, 2H), 4.34 (br, s, 2H), 6.31 (br, s, 1H), 6.50 (q, J=6.7 Hz, 1H), 7.22 (t, J=8.6 Hz, 1H), 7.40 (dd, J=9.0, 4.9 Hz, 1H), 7.68 (s, 1H), 8.20 (s, 1H). MS (ES+): m/z 507.09 [MH+]. HPLC: $t_R$=2.14 min (ZQ2, polar_5 min).

The compound was converted to its bis-HCl salt following the General Procedure for forming HCl/bis-HCl salts from the free base.

Example 25

7-[(R)-1-(2,6-Dichloro-3-fluorophenyl)-ethoxy]-3-piperidin-4-yl-furo[3,2-c]pyridin-6-ylamine

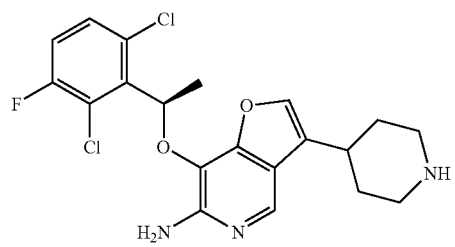

A solution of 7-[(R)-1-(2,6-dichloro-3-fluorophenyl)-ethoxy]-3-(1,2,3,6-tetrahydropyridin-4-yl)-furo[3,2-c]pyridin-6-ylamine (5.00 mg, 0.0118 mmol) in EtOAc (2 mL) with palladium (0.53 mg, 0.0050 mmol) on carbon was sealed and flushed with a nitrogen balloon at rt. The nitrogen balloon was replaced with a hydrogen balloon, and the mixture was allowed to stir for 1 h. The hydrogen balloon was removed and replaced with the nitrogen balloon to flush out all hydrogen gas. The palladium was filtered off, and the product was loaded onto a preparatory TLC plate, eluting with 10% (7 N NH₃ in MeOH) in DCM to afford the title compound as a yellow solid. ¹H NMR (CD₃OD, 400 MHz): δ=1.62 (br, s, 2H), 1.83 (d, J=6.8 Hz, 3H), 2.09-2.22 (m, 2H), 2.70-2.85 (m, 3H), 3.11 (br, s, 2H), 6.50-6.57 (m, 1H), 7.10 (t, J=8.5 Hz, 1H), 7.24 (s, 1H), 7.31 (dd, J=9.1, 4.8 Hz, 1H), 7.95 (s, 1H).

Example 26

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid Dimethylamide

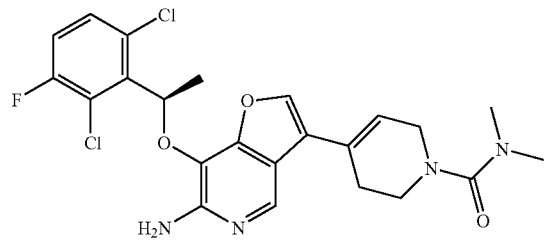

General procedure D: A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), N,N-dimethylcarbamoyl chloride (2.39 μL, 0.0260 mmol) and DMF (1 mL, 0.01 mol) at rt was charged with DIPEA (0.02 mL, 0.1 mmol) and allowed to stir for 10 min. The mixture was used directly for HPLC purification. The fractions containing the pure product were concentrated in vacuo to afford the title compound as a white solid. ¹H NMR (CD₃OD, 400 MHz): δ=1.88 (d, J=6.8 Hz, 3H), 2.50-2.57 (m, 2H), 2.88 (s, 6H), 3.48 (t, J=5.7 Hz, 2H), 3.98 (d, J=2.8 Hz, 2H), 6.26 (t, J=3.4 Hz, 1H), 6.50 (q, J=6.7 Hz, 1H), 7.17-7.25 (m, 1H), 7.39 (dd, J=9.0, 4.9 Hz, 1H), 7.64 (s, 1H), 8.19 (s, 1H). MS (ES+): m/z 493.02 [MH+]. HPLC: $t_R$=2.82 min (ZQ2, polar_5 min).

Example 27

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-ethylpiperazin-1-yl)-methanone

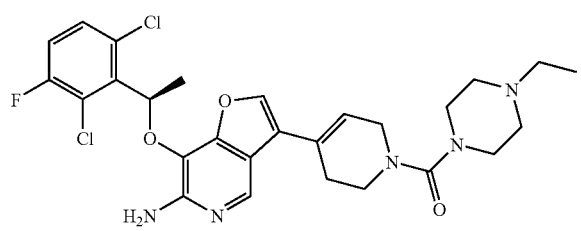

The title compound was prepared according to General procedure D. ¹H NMR (CD₃OD, 400 MHz): δ=1.32 (t, J=7.3 Hz, 3H), 1.88 (d, J=6.8 Hz, 3H), 2.55 (br, s, 2H), 3.09 (q, J=7.2 Hz, 2H), 3.17 (br, s, 4H), 3.50 (br, s, 4H), 3.55 (t, J=5.7 Hz, 2H), 4.06 (d, J=2.3 Hz, 2H), 6.25 (br, s, 1H), 6.49 (q, J=6.7 Hz, 1H), 7.21 (t, J=8.7 Hz, 1H), 7.39 (dd, J=9.0, 4.9 Hz, 1H), 7.65 (s, 1H), 8.18 (br, s, 1H). MS (ES+): m/z 562.14 [MH+]. HPLC: $t_R$=2.12 min (ZQ2, polar_5 min).

Example 28

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-[4-(2,2,2-trifluoroethyl)-piperazin-1-yl]-methanone

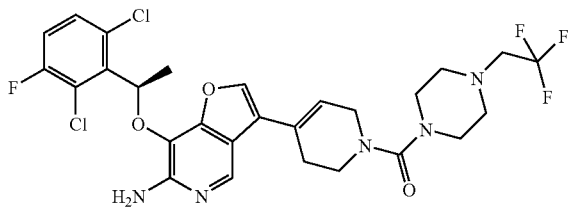

The title compound was prepared according to General procedure D. $^1$H NMR (CD$_3$OD, 400 MHz): δ=1.30 (d, J=16.7 Hz, 4H), 1.85-1.96 (m, 3H), 2.56 (d, J=16.7 Hz, 2H), 2.72 (d, J=7.6 Hz, 4H), 3.04-3.19 (m, 2H), 3.50 (br, s, 2H), 4.04 (d, J=18.9 Hz, 2H), 6.21-6.33 (m, 1H), 6.45-6.59 (m, 1H), 7.17-7.30 (m, 1H), 7.36-7.49 (m, 1H), 7.63 (br, s, 1H), 7.69 (br, s, 1H), 8.17-8.28 (m, 1H). MS (ES+): m/z 616.05 [MH+]. HPLC: $t_R$=3.30 min (ZQ2, polar_5 min).

Example 29

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-tert-butylpiperazin-1-yl)-methanone

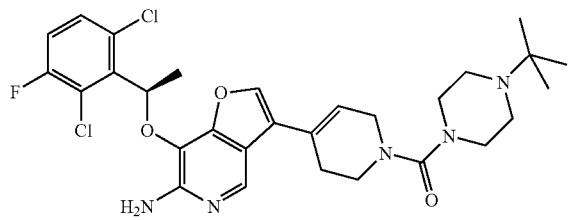

General procedure E: A solution of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol) and triphosgene (14.0 mg, 0.0474 mmol) in DCM (1 mL) was stirred at 0° C. and allowed to warm to rt. The mixture was charged with a solution of tert-butylpiperazine dihydrochloride (30.0 mg, 0.139 mmol) in DCM and DIPEA (0.1 mL, 0.7 mmol), and stirred at rt for 10 min. The solution was transferred to a separatory funnel and extracted with sat. aq. NaHCO$_3$. The organic layer was concentrated in vacuo, redissolved in DMF (0.5 mL), and purified by HPLC. The fractions containing the pure product were concentrated in vacuo to afford the title compound as a yellow solid. $^1$H NMR (CD$_3$OD, 400 MHz): δ=1.42 (s, 9H), 1.88 (d, J=6.8 Hz, 3H), 2.55 (d, J=1.3 Hz, 2H), 3.31-3.38 (m, 4H), 3.57 (t, J=5.7 Hz, 6H), 4.08 (d, J=2.5 Hz, 2H), 6.25 (br, s, 1H), 6.49 (q, J=6.8 Hz, 1H), 7.21 (t, J=8.6 Hz, 1H), 7.39 (dd, J=8.8, 4.8 Hz, 1H), 7.65 (s, 1H), 8.18 (s, 1H). MS (ES+): m/z 590.14 [MH+]. HPLC: $t_R$=2.26 min (ZQ2, polar_5 min).

Example 30

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-((2R,6S)-2,6-dimethylmorpholin-4-yl)-methanone

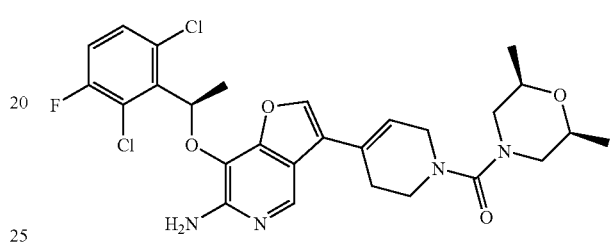

The title compound was prepared according to General procedure E. $^1$H NMR (CD$_3$OD, 400 MHz): δ=1.16 (d, J=6.1 Hz, 6H), 1.88 (d, J=6.8 Hz, 3H), 2.54 (d, J=1.5 Hz, 2H), 2.60 (dd, J=13.1, 10.6 Hz, 2H), 3.47-3.59 (m, 4H), 3.65 (ddd, J=10.4, 6.3, 2.3 Hz, 2H), 4.02 (d, J=2.5 Hz, 2H), 6.26 (br, s, 1H), 6.50 (q, J=6.8 Hz, 1H), 7.19-7.25 (m, 1H), 7.40 (dd, J=9.0, 4.9 Hz, 1H), 7.65 (s, 1H), 8.20 (br, s, 1H). MS (ES+): m/z 563.09 [MH+]. HPLC: $t_R$=3.08 min (ZQ2, polar_5 min).

Example 31

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-morpholin-4-ylmethanone

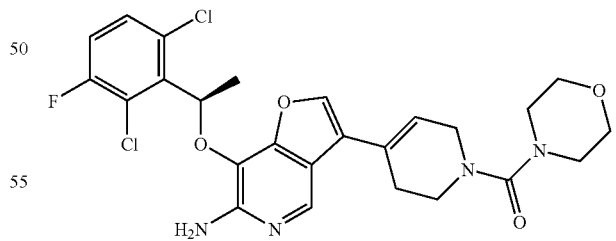

The title compound was prepared according to General procedure E. $^1$H NMR (CD$_3$OD, 400 MHz): δ=1.88 (d, J=6.8 Hz, 3H), 2.53 (d, J=1.3 Hz, 2H), 3.27-3.30 (m, 4H), 3.51 (t, J=5.7 Hz, 2H), 3.67-3.71 (m, 4H), 4.02 (d, J=2.5 Hz, 2H), 6.25 (br, s, 1H), 6.50 (q, J=6.8 Hz, 1H), 7.21 (t, J=8.6 Hz, 1H), 7.39 (dd, J=9.0, 4.9 Hz, 1H), 7.65 (s, 1H), 8.19 (s, 1H). MS (ES+): m/z 535.06 [MH+]. HPLC: $t_R$=2.76 min (ZQ2, polar_5 min).

Example 32

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperidin-1-ylmethanone

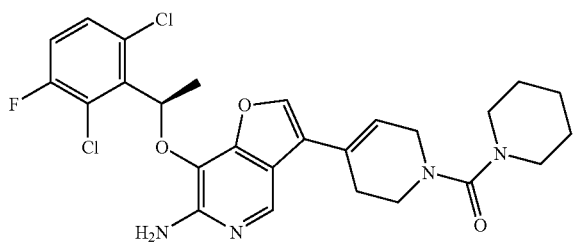

The title compound was prepared according to General procedure E. $^1$H NMR (CD$_3$OD, 400 MHz): δ=1.57-1.66 (m, 6H), 1.88 (d, J=6.8 Hz, 3H), 2.49-2.57 (m, 2H), 3.22-3.28 (m, 4H), 3.48 (t, J=5.7 Hz, 2H), 3.99 (d, J=2.5 Hz, 2H), 6.26 (br, s, 1H), 6.50 (d, J=6.8 Hz, 1H), 7.19-7.25 (m, 1H), 7.40 (dd, J=9.0, 4.9 Hz, 1H), 7.64 (s, 1H), 8.20 (s, 1H). MS (ES$^+$): m/z 533.07 [MH$^+$]. HPLC: t$_R$=3.27 min (ZQ2, polar_5 min).

Example 33

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperazin-1-ylmethanone

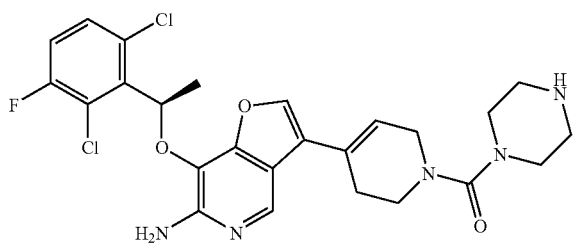

A solution of triphosgene (4 mg, 0.01 mmol) in DCM (0.8 mL) was cooled to 0° C. A solution of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), DIPEA (0.04 mL, 0.2 mmol) and DCM was added, and the mixture was allowed to warm to rt. A solution of tert-butyl 1-piperazinecarboxylate (8.82 mg, 0.0474 mmol) in DCM was then added, and the mixture was stirred at rt for 30 min. The material was transferred to a separatory funnel and washed with sat. aq. NaHCO$_3$. The organic layer was concentrated in vacuo, redissolved in dioxane and transferred to a sealed tube. 4 M HCl in 1,4-dioxane (0.2 mL) was added, and the solution was heated to 50° C. for 3 h. The material was concentrated in vacuo and redissolved in DMF (0.5 mL). The solution was purified by HPLC. The fractions containing the pure product were concentrated in vacuo to afford the title compound as a brown solid. $^1$H NMR (CD$_3$OD, 400 MHz): δ=1.89 (d, J=6.8 Hz, 3H), 2.56 (br, s, 2H), 3.21-3.29 (m, 4H), 3.44-3.52 (m, 4H), 3.56 (t, J=5.8 Hz, 2H), 4.08 (d, J=2.5 Hz, 2H), 6.26 (br, s, 1H), 6.50 (q, J=6.7 Hz, 1H), 7.22 (t, J=8.7 Hz, 1H), 7.40 (dd, J=9.0, 4.9 Hz, 1H), 7.66 (s, 1H), 8.19 (s, 1H). MS (ES$^+$): m/z 534.14 [MH$^+$]. HPLC: t$_R$=2.16 min (ZQ2, polar_5 min).

Example 34

4-{6-Amino-7-[(R)-1-(2,6-dichloro-3-fluorophenyl)ethoxy]-furo[3,2-c]pyridin-3-yl}-3,6-dihydro-2H-pyridine-1-carboxamide

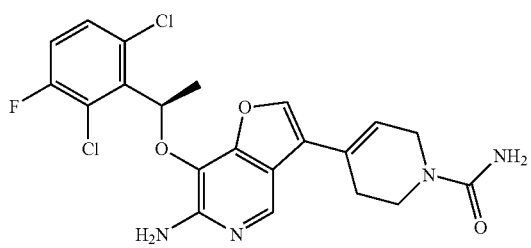

A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (9.00 mg, 0.0213 mmol), trimethylsilyl isocyanate (5.31 µL, 0.0392 mmol), DMF (0.5 mL, 0.005 mol), and DIPEA (0.03 mL, 0.2 mmol) was stirred at rt for 3 h. The solution was taken directly for HPLC purification. The fractions containing the pure product were concentrated in vacuo to afford the title compound as a yellow solid. $^1$H NMR (CD$_3$OD, 400 MHz): δ=1.85-1.92 (m, 3H), 2.51 (br, s, 2H), 3.60-3.68 (m, 2H), 4.10 (br, s, 2H), 6.27 (d, J=3.5 Hz, 1H), 6.52 (q, J=6.8 Hz, 1H), 7.18-7.27 (m, 1H), 7.36-7.44 (m, 1H), 7.63-7.70 (m, 1H), 8.13-8.17 (m, 1H). MS (ES$^+$): m/z 465.02 [MH$^+$]. HPLC: t$_R$=2.49 min (ZQ2, polar_5 min). The title compound was also converted to its mesylate and maleic acid salts by precipitation from ethanol.

Example 35

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid methylamide

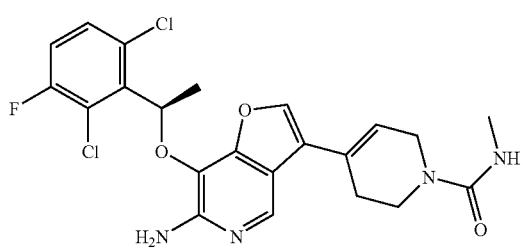

The title compound was prepared according to the procedures described for 4-{6-amino-7-[(R)-1-(2,6-dichloro-3-fluorophenyl)-ethoxy]-furo[3,2-c]pyridin-3-yl}-3,6-dihydro-2H-pyridine-1-carboxamide. $^1$H NMR (CD$_3$OD, 400 MHz): δ=1.88 (d, J=6.8 Hz, 3H), 2.49 (br, s, 2H), 2.76 (s, 3H), 3.63 (t, J=5.7 Hz, 2H), 4.06 (d, J=2.3 Hz, 2H), 6.26 (br, s, 1H), 6.50 (d, J=6.8 Hz, 1H), 7.19-7.25 (m, 1H), 7.40 (dd, J=9.0, 4.9

Hz, 1H), 7.65 (s, 1H), 8.19 (s, 1H). MS (ES$^+$): m/z 478.98 [MH$^+$]. HPLC: $t_R$=2.59 min (ZQ2, polar_5 min).

Example 36

[7-[(R)-1-(2,6-Dichloro-3-fluorophenyl)-ethoxy]-3-(1-methyl-1,2,3,6-tetrahydropyridin-4-yl)-furo[3,2-c]pyridin-6-yl]-methylamine

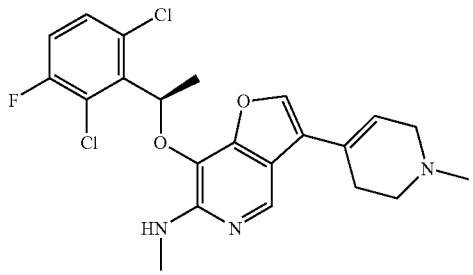

A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), methyl iodide (6.72 mg, 0.0474 mmol), DIPEA (0.02 mL, 0.1 mmol), and DMF (0.5 mL) was stirred at rt for 20 min. The solution was used directly for HPLC purification. The fractions containing the pure product were concentrated in vacuo to afford the title compound as a brown solid. $^1$H NMR (CDCl$_3$, 400 MHz): δ=1.88 (d, J=6.6 Hz, 3H), 2.90 (d, J=6.3 Hz, 2H), 3.50 (br, s, 6H), 3.99 (br, s, 2H), 4.31 (br, s, 2H), 4.87 (br, s, 1H), 6.17 (br, s, 1H), 6.51 (d, J=6.8 Hz, 1H), 7.06 (t, J=8.5 Hz, 1H), 7.28-7.34 (m, 1H), 7.51 (s, 1H), 8.19 (br, s, 1H). MS (ES$^+$): m/z 450.05 [MH$^+$]. HPLC: $t_R$=2.55 min (ZQ3, polar_5 min).

Example 37

7-[(R)-1-(2,6-Dichloro-3-fluorophenyl)-ethoxy]-3-(1-methyl-1,2,3,6-tetrahydropyridin-4-yl)-furo[3,2-c]pyridin-6-ylamine

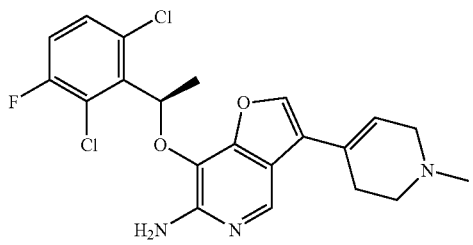

General procedure F: A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), sodium triacetoxyborohydride (7.53 mg, 0.0355 mmol) and DMF (0.5 mL) at rt was added 37% formaldehyde solution (0.00353 mL), and allowed to warm to rt. The material was filtered through a syringe filter pad, and used directly for HPLC purification. The fractions containing the pure product were concentrated in vacuo to afford the title compound as a yellow solid. $^1$H NMR (CDCl$_3$, 400 MHz): δ=1.87 (d, J=6.6 Hz, 3H), 2.70-2.77 (m, 5H), 3.17 (t, J=5.8 Hz, 2H), 3.61 (br, s, 2H), 5.69 (br, s, 2H), 6.16 (br, s, 1H), 6.55 (q, J=6.8 Hz, 1H), 7.07 (t, J=8.5 Hz, 1H), 7.28-7.33 (m, 1H), 7.44 (s, 1H), 8.13 (s, 1H). MS (ES$^+$): m/z 436.03 [MH$^+$]. HPLC: $t_R$=2.23 min (ZQ2, polar_5 min).

Alternate synthesis: A mixture of 1-Methyl-4-piperidinone (31.1 mg, 0.275 mmol), lithium tert-butoxide (46.0 mg, 0.575 mmol), p-Toluenesulfonylhydrazide (54.0 mg, 0.290 mmol), 2-Dicyclo-hexylphosphino-2',4',6'-triisopropylbiphenyl (9.5 mg, 0.020 mmol), and Tris(dibenzylideneacetone)-dipalladium(0) (4.6 mg, 0.0050 mmol) in 1,4-dioxane (2.5 mL, 32 mmol) in a microwave reactor vial was evacuated and refilled with nitrogen (3×). 3-Bromo-7-[(R)-1-(2,6-dichloro-3-fluorophenyl)-ethoxy]furo[3,2-c]pyridin-6-ylamine (105 mg, 0.250 mmol) was added, and the reaction mixture was heated to 110° C. for 5 h. The reaction mixture was diluted with DCM and washed with water. The DCM solution was washed with brine, dried over Na$_2$SO$_4$, filtered, and concentrated in vacuo. The residue was chromatographed first on an SCX column and then on silica gel to afford the title compound.

Example 38

3-(1-Cyclohexylmethyl-1,2,3,6-tetrahydropyridin-4-yl)-7-[(R)-1-(2,6-dichloro-3-fluorophenyl)-ethoxy]-furo[3,2-c]pyridin-6-ylamine

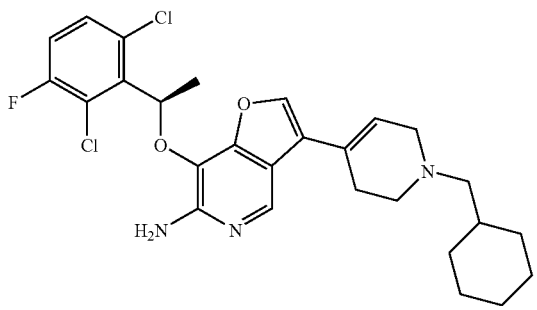

The title compound was prepared according to General procedure F. $^1$H NMR (CD$_3$OD, 400 MHz): δ=1.04 (d, J=12.4 Hz, 2H), 1.19-1.42 (m, 3H), 1.71-1.90 (m, 9H), 2.74 (d, J=1.3 Hz, 2H), 2.83 (d, J=6.6 Hz, 2H), 3.25 (t, J=5.8 Hz, 2H), 3.70 (r, s, 2H), 6.27 (br, 1H), 6.49 (q, J=6.8 Hz, 1H), 7.22 (t, J=8.6 Hz, 1H), 7.40 (dd, J=8.8, 4.8 Hz, 1H), 7.71 (s, 1H), 8.20 (s, 1H). MS (ES$^+$): m/z 518.10 [MH$^+$]. HPLC: $t_R$=2.81 min (ZQ2, polar_5 min).

Example 39

3-(1-Benzyl-1,2,3,6-tetrahydropyridin-4-yl)-7-[(R)-1-(2,6-dichloro-3-fluorophenyl)-ethoxy]-furo[3,2-c]pyridin-6-ylamine

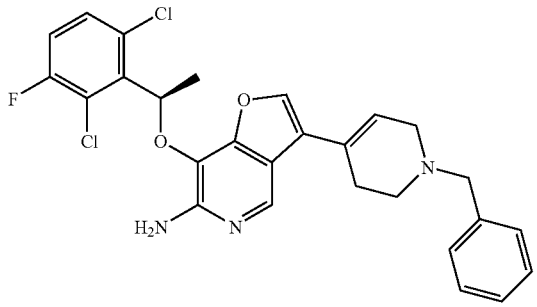

The title compound was prepared according to General procedure F. $^1$H NMR (CD$_3$OD, 400 MHz): δ=1.88 (d, J=6.6 Hz, 3H), 2.60-2.69 (m, 2H), 3.08 (t, J=5.9 Hz, 2H), 3.50 (d, J=2.5 Hz, 2H), 3.99 (s, 2H), 6.26 (br, s, 1H), 6.49 (q, J=6.8 Hz, 1H), 7.17-7.24 (m, 1H), 7.36-7.47 (m, 6H), 7.66 (s, 1H), 8.17 (s, 1H). MS (ES+): m/z 512.05 [MH+]. HPLC: $t_R$=2.35 min (ZQ2, polar_5 min).

Example 40

7-[(R)-1-(2,6-Dichloro-3-fluorophenyl)-ethoxy]-3-(1-ethyl-1,2,3,6-tetrahydropyridin-4-yl)-furo[3,2-c]pyridin-6-ylamine

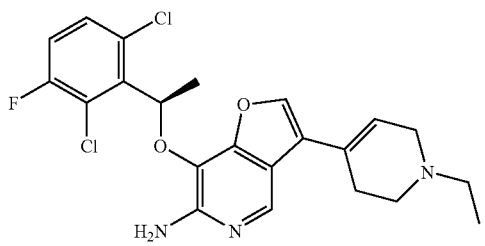

The title compound was prepared according to General procedure F. $^1$H NMR (CD$_3$OD, 400 MHz): δ=1.34-1.49 (m, 3H), 1.86-1.97 (m, 3H), 2.78-2.91 (m, 2H), 3.20-3.30 (m, 2H), 3.50 (d, J=8.3 Hz, 2H), 3.92 (d, J=11.9 Hz, 2H), 6.27-6.38 (m, 1H), 6.51 (d, J=10.6 Hz, 1H), 7.25 (d, J=8.8 Hz, 1H), 7.41 (t, J=12.8 Hz, 1H), 7.76 (br, s, 1H), 7.81 (br, s, 1H), 8.21 (d, J=13.6 Hz, 1H). MS (ES+): m/z 450.06 [MH+]. HPLC: $t_R$=2.20 min (ZQ2, polar_5 min).

Example 41

7-[(R)-1-(2,6-Dichloro-3-fluorophenyl)-ethoxy]-3-(1-isobutyl-1,2,3,6-tetrahydropyridin-4-yl)-furo[3,2-c]pyridin-6-ylamine

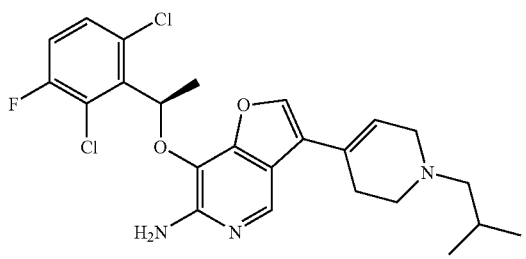

The title compound was prepared according to General procedure F. $^1$H NMR (CD$_3$OD, 400 MHz): δ=1.08 (d, J=6.8 Hz, 6H), 1.89 (d, J=6.8 Hz, 3H), 2.21 (ddd, J=13.5, 6.9, 6.8 Hz, 1H), 2.79-2.87 (m, 2H), 3.04 (d, J=7.3 Hz, 2H), 3.48 (t, J=6.1 Hz, 2H), 3.91 (br, s, 2H), 6.28 (br, s, 1H), 6.49 (q, J=6.7 Hz, 1H), 7.22 (t, J=8.7 Hz, 1H), 7.40 (dd, J=9.0, 4.9 Hz, 1H), 7.76 (s, 1H), 8.21 (s, 1H). MS (ES+): m/z 478.04 [MH+]. HPLC: $t_R$=2.29 min (ZQ2, polar_5 min).

Example 42

7-[(R)-1-(2,6-Dichloro-3-fluorophenyl)-ethoxy]-3-(1-propyl-1,2,3,6-tetrahydropyridin-4-yl)-furo[3,2-c]pyridin-6-ylamine

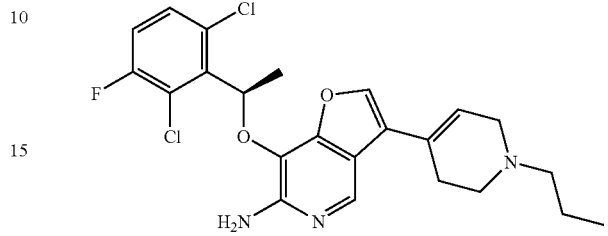

The title compound was prepared according to General procedure F. $^1$H NMR (CD$_3$OD, 400 MHz): δ=1.05 (t, J=7.5 Hz, 3H), 1.82 (ddd, J=11.2, 7.4, 5.2 Hz, 2H), 1.88 (d, J=6.8 Hz, 3H), 2.78-2.85 (m, 2H), 3.12-3.19 (m, 2H), 3.49 (t, J=6.1 Hz, 2H), 3.92 (br, s, 2H), 6.28 (br, s, 1H), 6.48 (q, J=6.8 Hz, 1H), 7.21 (t, J=8.6 Hz, 1H), 7.39 (dd, J=9.0, 4.9 Hz, 1H), 7.75 (s, 1H), 8.19 (s, 1H). MS (ES+): m/z 464.07 [MH+]. HPLC: $t_R$=2.20 min (ZQ2, polar_5 min).

Example 43

3-[1-(2-Aminoethyl)-1,2,3,6-tetrahydropyridin-4-yl]-7-[(R)-1-(2,6-dichloro-3-fluorophenyl)ethoxy]-furo[3,2-c]pyridin-6-ylamine

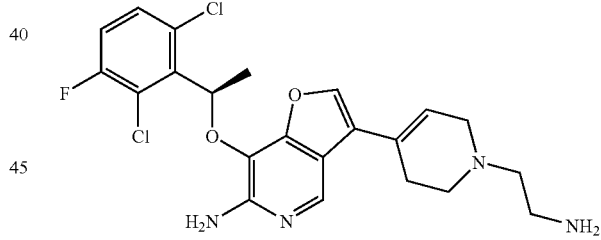

A mixture of 7-[(R)-1-(2,6-Dichloro-3-fluorophenyl)ethoxy]-3-(1,2,3,6-tetrahydropyridin-4-yl)-furo[3,2-c]pyridin-6-ylamine (35.0 mg, 0.0829 mmol), tert-butyl N-(2-oxoethyl)carbamate (26.4 mg, 0.166 mmol), sodium triacetoxyborohydride (19.3 mg, 0.0912 mmol) and DCM (3 mL, 50 mmol) was stirred at rt for 30 min. The solution was transferred to a separatory funnel and extracted with DCM and sat. NaHCO$_3$. The organic layer was concentrated in vacuo, redissolved in 1,4-dioxane and transferred to a sealed tube. 4 M of HCl in 1,4-Dioxane (0.5 mL, 2 mmol) was added, and the mixture was heated to 50° C. for 2 h. The solution was concentrated in vacuo, redissolved in DCM and transferred to a separatory funnel. The organic layer was washed with sat. NaHCO$_3$, concentrated in vacuo, and loaded onto a prep TLC plate, eluting with 7% (7N NH$_3$ in MeOH)/DCM. The band containing the pure product was filtered off using 1:1 MeOH/DCM. To the filtrate was added 2.0 M of HCl in Et$_2$O (0.207 mL, 0.414 mmol) to form the HCl salt, and the mixture was stirred for 30 min at rt. The material was concentrated in vacuo to afford the title compound as bis-HCl salt. ¹H NMR (CD₃OD, 400 MHz): δ=1.88 (d, J=6.8 Hz, 3H), 2.56 (d, J=1.5 Hz, 2H), 2.79 (ddd, J=19.3, 5.8, 5.7 Hz, 4H), 3.12 (t, J=5.9 Hz, 2H), 3.28 (d, J=2.5 Hz, 2H), 6.27 (br, s, 1H), 6.50 (q, J=6.8 Hz, 1H), 7.22 (t, J=8.6 Hz, 1H), 7.40 (dd, J=9.0, 4.9 Hz, 1H), 7.63 (s, 1H), 8.17 (s, 1H). MS (ES⁺): m/z 465.04 [MH⁺]. HPLC: $t_R$=2.43 min (ZQ3, polar_5 min).

Example 44

3-(1-Cyclobutyl-1,2,3,6-tetrahydropyridin-4-yl)-7-[(R)-1-(2,6-dichloro-3-fluorophenyl)-ethoxy]-furo[3,2-c]pyridin-6-ylamine

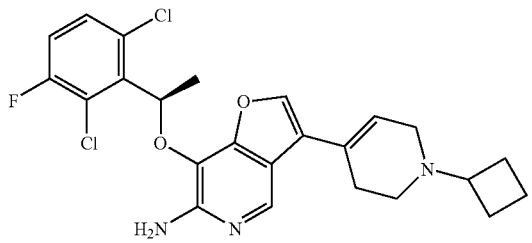

General procedure G: A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), sodium triacetoxyborohydride (7.53 mg, 0.0355 mmol), and 1,2-dichloroethane (1 mL) at 0° C. was added cyclobutanone (0.00312 mL, 0.0474 mmol), and allowed to warm to rt. The material was transferred to a separatory funnel and extracted with DCM and sat. aq. NaHCO₃. The organic layer was concentrated in vacuo and redissolved in DMF (0.5 mL) for HPLC purification. The fractions containing the pure product were concentrated in vacuo to afford the title compound as a white solid. ¹H NMR (CD₃OD, 400 MHz): δ=1.85-1.96 (m, 5H), 2.21-2.32 (m, 2H), 2.34-2.43 (m, 2H), 2.76-2.85 (m, 2H), 3.35 (t, J=6.1 Hz, 2H), 3.72-3.84 (m, 3H), 6.29 (br, s, 1H), 6.49 (q, J=6.8 Hz, 1H), 7.22 (t, J=8.7 Hz, 1H), 7.39 (dd, J=9.1, 4.8 Hz, 1H), 7.76 (s, 1H), 8.19 (s, 1H). MS (ES⁺): m/z 476.08 [MH⁺]. HPLC: $t_R$=2.19 min (ZQ2, polar_5 min).

Example 45

7-[(R)-1-(2,6-Dichloro-3-fluorophenyl)-ethoxy]-3-(1-isopropyl-1,2,3,6-tetrahydropyridin-4-yl)-furo[3,2-c]pyridin-6-ylamine

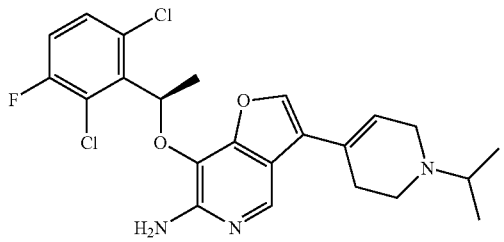

The title compound was prepared according to General procedure G. ¹H NMR (CD₃OD, 400 MHz): δ=1.42 (d, J=6.6 Hz, 6H), 1.84-1.91 (m, 3H), 2.85 (d, J=1.5 Hz, 2H), 3.51 (t, J=5.8 Hz, 2H), 3.64 (quin, J=6.6 Hz, 1H), 3.94 (d, J=2.8 Hz, 2H), 6.31 (br, s, 1H), 6.49 (q, J=6.7 Hz, 1H), 7.22 (t, J=8.7 Hz, 1H), 7.40 (dd, J=9.0, 4.9 Hz, 1H), 7.76 (s, 1H), 8.20 (s, 1H). MS (ES⁺): m/z 464.08 [MH⁺]. HPLC: $t_R$=2.11 min (ZQ2, polar_5 min).

Example 46

7-[(R)-1-(2,6-Dichloro-3-fluorophenyl)-ethoxy]-3-(1-methanesulfonyl-1,2,3,6-tetrahydropyridin-4-yl)-furo[3,2-c]pyridin-6-ylamine

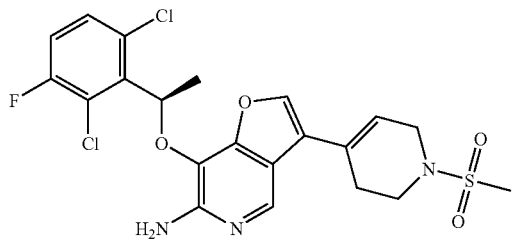

General procedure H: A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (8.00 mg, 0.0189 mmol), DIPEA (0.02 mL, 0.09 mmol), and DMF (1 mL) at rt was charged with methanesulfonyl chloride (4.34 mg, 0.0379 mmol), and then immediately quenched with 1 drop of water. The solution was used directly for HPLC purification. The fractions containing the pure product were concentrated in vacuo to afford the title compound as a white solid. ¹H NMR (CD₃OD, 400 MHz): δ=1.88 (d, J=6.8 Hz, 3H), 2.57-2.64 (m, 2H), 2.90 (s, 3H), 3.49 (t, J=5.8 Hz, 2H), 3.97 (d, J=3.0 Hz, 2H), 6.30 (t, J=3.4 Hz, 1H), 6.49 (q, J=6.8 Hz, 1H), 7.21 (t, J=8.7 Hz, 1H), 7.39 (dd, J=9.0, 4.9 Hz, 1H), 7.66 (s, 1H), 8.20 (s, 1H). MS (ES⁺): m/z 499.95 [MH⁺]. HPLC: $t_R$=2.92 min (ZQ2, polar_5 min).

The compound was prepared on larger scale and converted to an HCl salt as follows: A mixture of 7-[(R)-1-(2,6-Dichloro-3-fluorophenyl)ethoxy]-3-(1,2,3,6-tetrahydropyridin-4-yl)furo[3,2-c]pyridin-6-ylamine (35.0 mg, 0.0829 mmol), DIPEA (70 μL, 0.4 mmol) and DCM (3 mL, 40 mmol) was cooled to −78° C. A solution of Methanesulfonyl chloride (9.97 mg, 0.0870 mmol) in DCM was added dropwise. The mixture was allowed to stir at −78° C. for 1 h. A few drops of water was added to quench, and the solution was transferred to a separatory funnel, washing with sat. NaHCO₃. The organic layer was concentrated in vacuo and loaded onto a prep TLC plate, eluting with 3% (7N NH₃ in MeOH)/DCM. The band containing the pure product was collected, and the product was eluted using 1:1 MeOH/DCM. To the solution of the product was added 2.0 M of HCl in Et₂O (0.207 mL, 0.414 mmol) to form the HCl salt, and the mixture was stirred for 30 min at rt. The material was concentrated in vacuo to afford the HCl salt of the title compound as a light brown solid.

Example 47

7-[(R)-1-(2,6-Dichloro-3-fluorophenyl)-ethoxy]-3-(1-ethanesulfonyl-1,2,3,6-tetrahydropyridin-4-yl)-furo[3,2-c]pyridin-6-ylamine

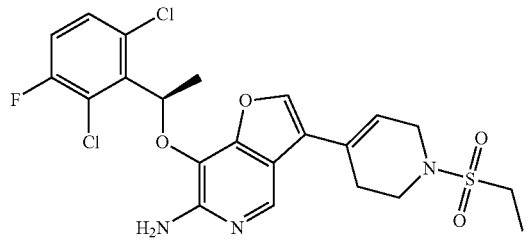

The title compound was prepared according to General procedure H. $^1$H NMR (CD$_3$OD, 400 MHz): δ=1.34 (t, J=7.3 Hz, 3H), 1.88 (d, J=6.8 Hz, 3H), 2.53-2.61 (m, 2H), 3.10 (q, J=7.3 Hz, 2H), 3.55 (t, J=5.8 Hz, 2H), 4.03 (d, J=2.8 Hz, 2H), 6.26-6.33 (m, 1H), 6.50 (q, J=6.7 Hz, 1H), 7.22 (t, J=8.6 Hz, 1H), 7.40 (dd, J=9.0, 4.9 Hz, 1H), 7.66 (s, 1H), 8.20 (s, 1H). MS (ES$^+$): m/z 513.98 [MH$^+$]. HPLC: t$_R$=3.03 min (ZQ2, polar_5 min).

Example 48

3-(1-Cyclopropanesulfonyl-1,2,3,6-tetrahydropyridin-4-yl)-7-[(R)-1-(2,6-dichloro-3-fluorophenyl)-ethoxy]-furo[3,2-c]pyridin-6-ylamine

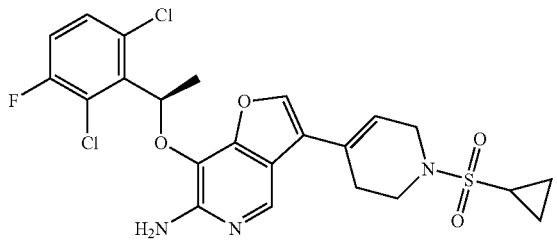

The title compound was prepared according to General procedure H. $^1$H NMR (CD$_3$OD, 400 MHz): δ=0.98-1.05 (m, 2H), 1.06-1.13 (m, 2H), 1.88 (d, J=6.8 Hz, 3H), 2.48-2.56 (m, 1H), 2.58-2.65 (m, 2H), 3.56 (t, J=5.8 Hz, 2H), 4.04 (d, J=3.0 Hz, 2H), 6.30 (t, J=3.4 Hz, 1H), 6.50 (q, J=6.7 Hz, 1H), 7.18-7.25 (m, 1H), 7.39 (dd, J=8.8, 4.8 Hz, 1H), 7.66 (s, 1H), 8.20 (s, 1H). MS (ES$^+$): m/z 526.03 [MH$^+$]. HPLC: t$_R$=3.31 min (ZQ2, polar_5 min).

Example 49

3-(1-Benzenesulfonyl-1,2,3,6-tetrahydropyridin-4-yl)-7-[(R)-1-(2,6-dichloro-3-fluorophenyl)-ethoxy]-furo[3,2-c]pyridin-6-ylamine

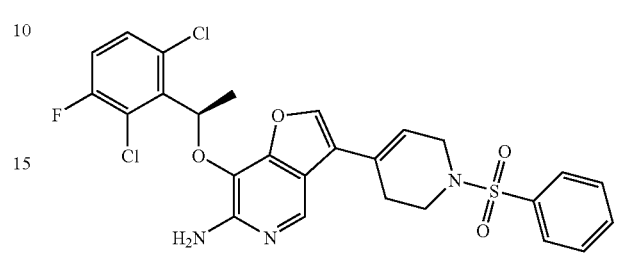

The title compound was prepared according to General procedure H. $^1$H NMR (CD$_3$OD, 400 MHz): δ=1.86 (d, J=6.6 Hz, 3H), 2.48-2.55 (m, 2H), 3.32-3.38 (m, 2H), 3.80 (d, J=2.8 Hz, 2H), 6.20 (t, J=3.4 Hz, 1H), 6.47 (q, J=6.7 Hz, 1H), 7.20 (t, J=8.7 Hz, 1H), 7.38 (dd, J=9.0, 4.9 Hz, 1H), 7.58-7.69 (m, 4H), 7.82-7.87 (m, 2H), 8.12 (s, 1H). MS (ES$^+$): m/z 562.01 [MH$^+$]. HPLC: t$_R$=3.48 min (ZQ2, polar_5 min).

Example 50

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid methyl ester

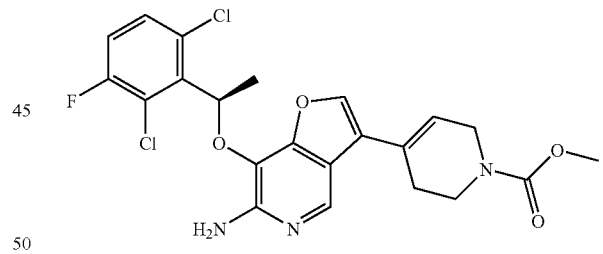

General procedure I: A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (8.00 mg, 0.0189 mmol), DIPEA (0.02 mL, 0.09 mmol), and DMF (0.5 mL) at 0° C. was charged with methyl chloroformate (3.58 mg, 0.0379 mmol) and then immediately quenched with 1 drop of water. The material was passed through a syringe filter pad, and the solution was used directly for HPLC purification. The fractions containing the pure product were concentrated in vacuo to afford the title compound as a while solid. $^1$H NMR (CD$_3$OD, 400 MHz): δ=1.90 (d, J=6.8 Hz, 3H), 2.51 (d, J=1.5 Hz, 2H), 3.68-3.73 (m, 2H), 3.75 (s, 3H), 4.17 (br, s, 2H), 6.28 (br, s, 1H), 6.51 (q, J=6.8 Hz, 1H), 7.20-7.27 (m, 1H), 7.42 (dd, J=9.0, 4.9 Hz, 1H), 7.66 (s, 1H), 8.21 (s, 1H). MS (ES$^+$): m/z 479.99 [MH$^+$]. HPLC: t$_R$=3.08 min (ZQ2, polar_5 min).

Example 51

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid ethyl ester

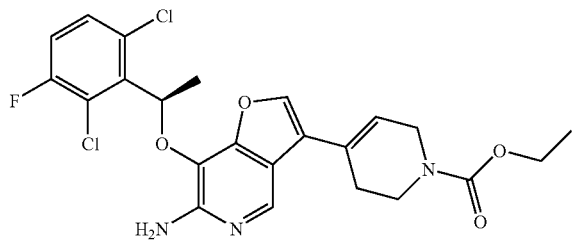

The title compound was prepared according to General procedure I. $^1$H NMR (CD$_3$OD, 400 MHz): δ=1.28 (t, J=7.1 Hz, 3H), 1.88 (d, J=6.6 Hz, 3H), 2.49 (d, J=1.3 Hz, 2H), 3.62-3.72 (m, 2H), 4.16 (q, J=7.1 Hz, 4H), 6.26 (br, s, 1H), 6.49 (q, J=6.7 Hz, 1H), 7.21 (t, J=8.6 Hz, 1H), 7.39 (dd, J=9.1, 4.8 Hz, 1H), 7.64 (s, 1H), 8.19 (s, 1H). MS (ES$^+$): m/z 494.02 [MH$^+$]. HPLC: t$_R$=3.28 min (ZQ2, polar__5 min).

Example 52

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid propyl ester

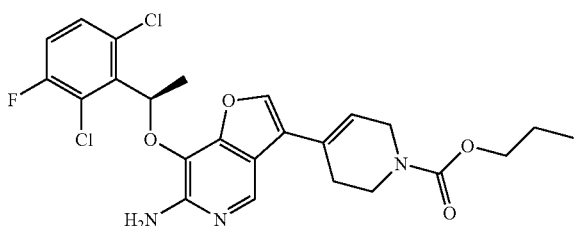

The title compound was prepared according to General procedure I. $^1$H NMR (CD$_3$OD, 400 MHz): δ=0.98 (t, J=7.3 Hz, 3H), 1.64-1.73 (m, 2H), 1.87 (d, J=6.6 Hz, 3H), 2.49 (d, J=1.5 Hz, 2H), 3.63-3.74 (m, 2H), 4.07 (t, J=6.6 Hz, 2H), 6.26 (br, s, 1H), 6.49 (q, J=6.7 Hz, 1H), 7.21 (t, J=8.7 Hz, 1H), 7.39 (dd, J=9.0, 4.9 Hz, 1H), 7.64 (s, 1H), 8.19 (s, 1H). MS (ES$^+$): m/z 508.05 [MH$^+$]. HPLC: t$_R$=3.51 min (ZQ2, polar__5 min).

Example 53

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid isopropyl ester

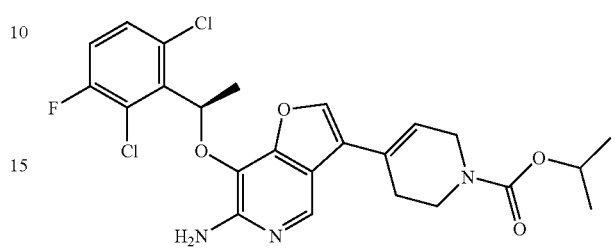

The title compound was prepared according to General procedure I. $^1$H NMR (CD$_3$OD, 400 MHz): δ=1.28 (d, J=6.3 Hz, 6H), 1.88 (d, J=6.8 Hz, 3H), 2.49 (d, J=1.3 Hz, 2H), 3.65-3.71 (m, 2H), 4.14 (br, s, 2H), 4.91-4.95 (m, 1H), 6.26 (br, s, 1H), 6.49 (q, J=6.7 Hz, 1H), 7.22 (t, J=8.7 Hz, 1H), 7.40 (dd, J=9.1, 4.8 Hz, 1H), 7.64 (s, 1H), 8.19 (s, 1H). MS (ES$^+$): m/z 508.10 [MH$^+$]. HPLC: t$_R$=3.67 min (ZQ3, polar__5 min).

Example 54

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid cyclopentyl ester

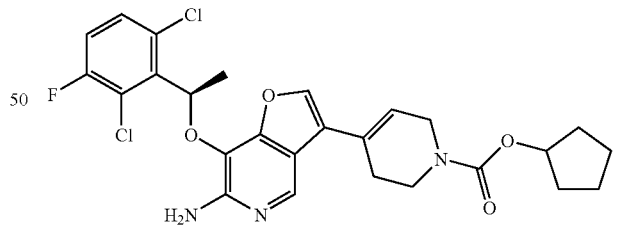

The title compound was prepared according to General procedure I. $^1$H NMR (CD$_3$OD, 400 MHz): δ=1.59-1.68 (m, 2H), 1.70-1.79 (m, 4H), 1.84-1.91 (m, 5H), 2.48 (br, s, 2H), 3.67 (t, J=5.8 Hz, 2H), 4.13 (d, J=2.5 Hz, 2H), 5.07-5.13 (m, 1H), 6.25 (br, s, 1H), 6.49 (q, J=6.8 Hz, 1H), 7.21 (t, J=8.6 Hz, 1H), 7.40 (dd, J=9.1, 4.8 Hz, 1H), 7.64 (s, 1H), 8.19 (s, 1H). MS (ES$^+$): m/z 534.08 [MH$^+$]. HPLC: t$_R$=3.81 min (ZQ2, polar__5 min).

Example 55

4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid phenyl ester

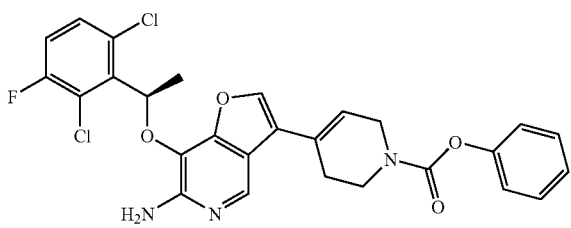

The title compound was prepared according to General procedure I. $^1$H NMR (CD$_3$OD, 400 MHz): δ=1.89 (d, J=6.8 Hz, 3H), 2.58 (br, s, 2H), 3.77 (br, s, 1H), 3.92 (br, s, 1H), 4.23 (br, s, 1H), 4.41 (br, s, 1H), 6.33 (br, s, 1H), 6.51 (q, J=6.8 Hz, 1H), 7.13 (d, J=7.8 Hz, 2H), 7.19-7.26 (m, 2H), 7.36-7.43 (m, 3H), 7.69 (s, 1H), 8.23 (s, 1H). MS (ES$^+$): m/z 542.04 [MH$^+$]. HPLC: $t_R$=3.56 min (ZQ2, polar_5 min).

Example 56

1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2,2,2-trifluoroethanone

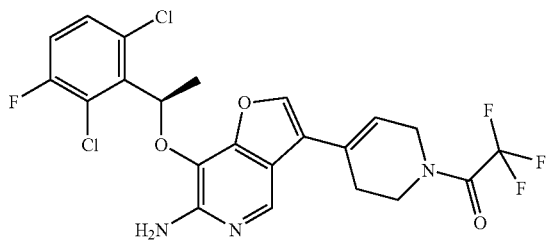

A mixture of 7-[(R)-1-(2,6-dichloro-3-fluorophenyl)-ethoxy]-3-(1,2,3,6-tetrahydropyridin-4-yl)-furo[3,2-c]pyridin-6-ylamine (10.0 mg, 0.0237 mmol), 4-dimethylaminopyridine (0.29 mg, 0.0024 mmol), triethylamine (0.00396 mL, 0.0284 mmol) and DCM (1 mL) at 0° C. was added trifluoroacetic anhydride (5.47 mg, 0.0260 mmol), and the solution was allowed to warm to rt overnight. The material was transferred to a separatory funnel, and extracted with sat. aq. NaHCO$_3$. The organic layer was concentrated in vacuo, then redissolved in minimal DCM/MeOH and loaded onto a preparatory TLC plate, eluting with 5% MeOH in DCM to afford the title compound as a white solid. $^1$H NMR (CD$_3$OD, 400 MHz): δ=1.88 (d, J=6.8 Hz, 3H), 2.53-2.65 (m, 2H), 3.84-3.94 (m, 2H), 4.31-4.40 (m, 2H), 6.24-6.32 (m, 1H), 6.49 (q, J=6.7 Hz, 1H), 7.22 (t, J=8.6 Hz, 1H), 7.40 (dd, J=9.1, 4.8 Hz, 1H), 7.64-7.72 (m, 1H), 8.19-8.22 (m, 1H). MS (ES$^+$): m/z 517.98 [MH$^+$]. HPLC: $t_R$=3.64 min (ZQ3, polar_5 min).

Example 57

(3-{6-Amino-7-[(R)-1-(2,6-dichloro-3-fluorophenyl)ethoxy]-furo[3,2-c]pyridin-3-yl}phenyl)methanol

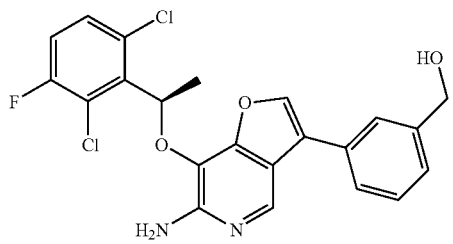

General procedure J: To a solution of 3-bromo-7-[(R)-1-(2,6-dichloro-3-fluorophenyl)-ethoxy]-furo[3,2-c]pyridin-6-ylamine (10.0 mg, 0.0238 mmol, 1 eq), a boronic acid or boronate (0.476 mmol, 2 eq), potassium carbonate (9.9 mg, 0.0714, 3 eq) in dioxane (0.9 mL) and water (0.3 mL) was added 1,1'-bis(diphenylphosphino)ferrocene]dichloropalladium(II), complex with dichloromethane (1:1) (1 mg, 0.001 mmol, 0.05 eq). The mixture was evacuated by vacuum and filled with nitrogen 3 times and subjected to CEM microwave reactor at 100° C. for 30 min with stirring on and cooling off. The crude was passed through 500 mg Thiol-SPE to remove Pd. The clear solution was submitted to mass-directed purification system for purification. $^1$H NMR (DMSO-d$_6$, 400 MHz): δ=1.85 (d, J=6.8 Hz, 3H), 4.56 (s, 2H), 5.64 (s, 2H), 6.28 (q, J=6.7 Hz, 1H), 7.31 (d, J=7.8 Hz, 1H), 7.38-7.48 (m, 2H), 7.50-7.58 (m, 2H), 7.64 (s, 1H), 8.10 (s, 1H), 8.34 (s, 1H). MS (ES$^+$): m/z 447.15, 449.13 (100, 69) [MH$^+$]. HPLC: $t_R$=0.84 min (HPLC-ACQUITY, Analytical).

Example 58

N-(4-{6-Amino-7-[(R)-1-(2,6-dichloro-3-fluorophenyl)ethoxy]-furo[3,2-c]pyridin-3-yl}phenyl)acetamide

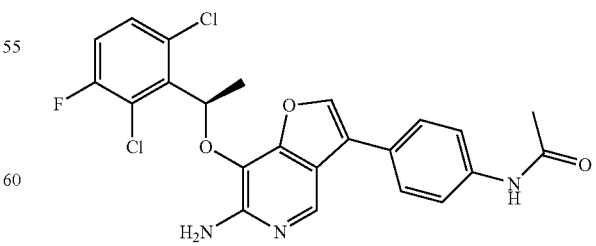

The title compound was prepared according to General procedure J. MS (ES$^+$): m/z 474.17, 476.17 (100, 69) [MH$^+$]. HPLC: $t_R$=0.83 min (HPLC-ACQUITY, Analytical).

Example 59

4-{6-Amino-7-[(R)-1-(2,6-dichloro-3-fluorophenyl)ethoxy]-furo[3,2-c]pyridin-3-yl}phenol

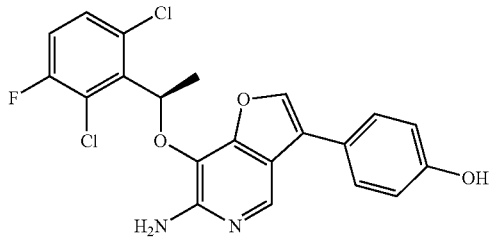

The title compound was prepared according to General procedure J. MS (ES+): m/z 433.14, 435.14 (100, 69) [MH+]. HPLC: $t_R$=0.86 min (HPLC-ACQUITY, Analytical).

Example 60

7-[(R)-1-(2,6-Dichloro-3-fluorophenyl)ethoxy]-3-(3-methoxy-phenyl)furo[3,2-c]pyridin-6-ylamine

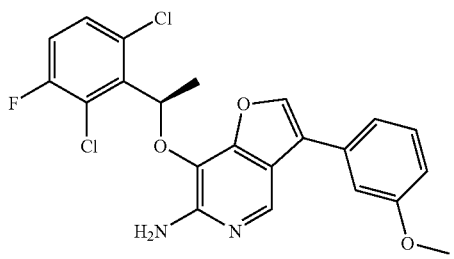

The title compound was prepared according to General procedure J. MS (ES+): m/z 447.16, 449.14 (100, 69) [MH+]. HPLC: $t_R$=1.00 min (HPLC-ACQUITY, Analytical).

Example 61

3-{6-Amino-7-[(R)-1-(2,6-dichloro-3-fluorophenyl)-ethoxy]furo[3,2-c]pyridin-3-yl}phenol

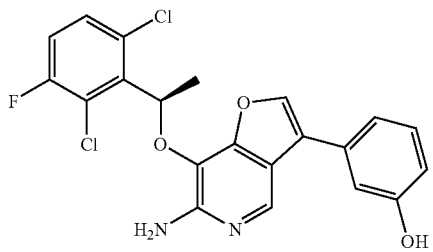

The title compound was prepared according to General procedure J. MS (ES+): m/z 433.14, 435.14 (100, 69) [MH+]. HPLC: $t_R$=0.88 min (HPLC-ACQUITY, Analytical).

Example 62

7-[(R)-1-(2,6-Dichloro-3-fluorophenyl)ethoxy]-3-(4-methane-sulfonylphenyl)furo[3,2-c]pyridin-6-ylamine

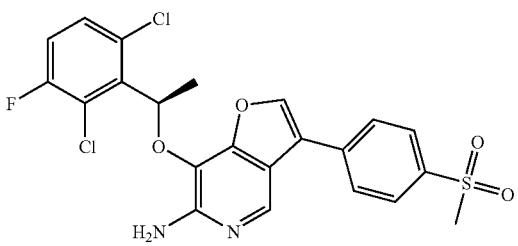

The title compound was prepared according to General procedure J. MS (ES+): m/z 495.13, 497.13 (100, 69) [MH+]. HPLC: $t_R$=0.89 min (HPLC-ACQUITY, Analytical).

Example 63

4-{6-Amino-7-[(R)-1-(2,6-dichloro-3-fluorophenyl)ethoxy]-furo[3,2-c]pyridin-3-yl}benzamide

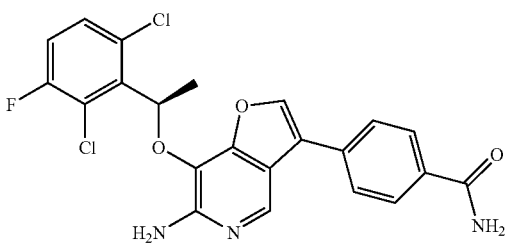

The title compound was prepared according to General procedure J. MS (ES+): m/z 460.14, 462.14 (100, 69) [MH+]. HPLC: $t_R$=0.78 min (HPLC-ACQUITY, Analytical).

Example 64

(4-{6-Amino-7-[(R)-1-(2,6-dichloro-3-fluorophenyl)ethoxy]-furo[3,2-c]pyridin-3-yl}-phenyl)methanol

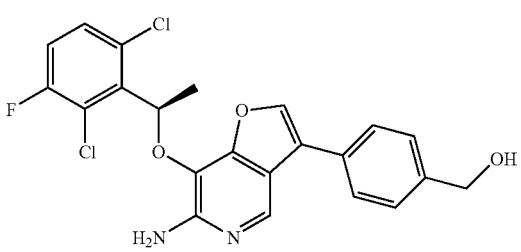

The title compound was prepared according to General procedure J. MS (ES+): m/z 447.17, 449.13 (100, 69) [MH+]. HPLC: $t_R$=0.84 min (HPLC-ACQUITY, Analytical).

Example 65

4-{6-Amino-7-[(R)-1-(2,6-dichloro-3-fluorophenyl)ethoxy]-furo[3,2-c]pyridin-3-yl}benzoic Acid

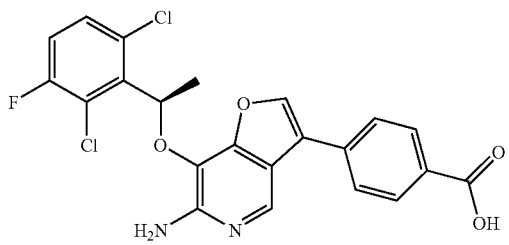

The title compound was prepared according to General procedure J. MS (ES⁺): m/z 461.13, 463.12 (100, 69) [MH⁺]. HPLC: $t_R$=0.87 min (HPLC-ACQUITY, Analytical).

Example 66

3-(3-Aminophenyl)-7-[(R)-1-(2,6-dichloro-3-fluorophenyl)ethoxy]-furo[3,2-c]pyridin-6-ylamine

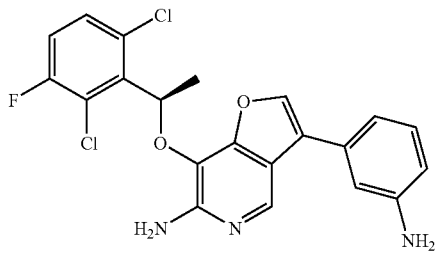

The title compound was prepared according to General procedure J. MS (ES⁺): m/z 432.16, 434.17 (100, 69) [MH⁺]. HPLC: $t_R$=0.81 min (HPLC-ACQUITY, Analytical).

Example 67

7-[(R)-1-(2,6-Dichloro-3-fluor-phenyl)ethoxy]-3-(3-methane-sulfonylphenyl)-furo[3,2-c]pyridin-6-ylamine

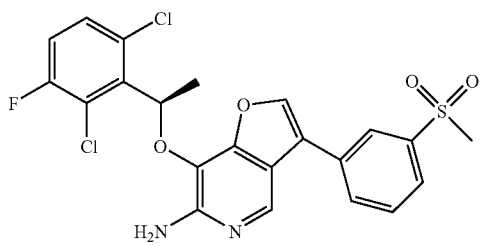

The title compound was prepared according to General procedure J. MS (ES⁺): m/z 495.13, 497.13 (100, 69) [MH⁺]. HPLC: $t_R$=0.88 min (HPLC-ACQUITY, Analytical).

Example 68

3-{6-Amino-7-[(R)-1-(2,6-dichloro-3-fluorophenyl)ethoxy]-furo[3,2-c]pyridin-3-yl}-N-methylbenzamide

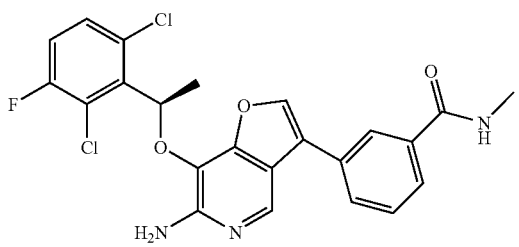

The title compound was prepared according to General procedure J. MS (ES⁺): m/z 474.17, 476.17 (100, 69) [MH⁺]. HPLC: $t_R$=0.82 min (HPLC-ACQUITY, Analytical).

Example 69

7-[(R)-1-(2,6-Dichloro-3-fluorophenyl)ethoxy]-3-(4-methoxyphenyl)-furo[3,2-c]pyridin-6-ylamine

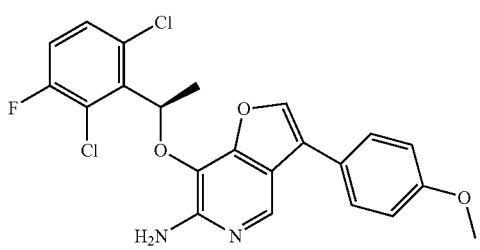

The title compound was prepared according to General procedure J. MS (ES⁺): m/z 447.17, 449.16 (100, 69) [MH⁺]. HPLC: $t_R$=0.99 min (HPLC-ACQUITY, Analytical).

Example 70

3-{6-Amino-7-[(R)-1-(2,6-dichloro-3-fluorophenyl)ethoxy]-furo[3,2-c]pyridin-3-yl}benzamide

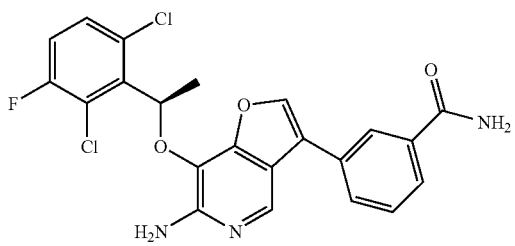

The title compound was prepared according to General procedure J. MS (ES⁺): m/z 460.17, 462.18 (100, 69) [MH⁺]. HPLC: $t_R$=0.78 min (HPLC-ACQUITY, Analytical).

Example 71

4-{6-Amino-7-[(R)-1-(2,6-dichloro-3-fluorophenyl)ethoxy]-furo[3,2-c]pyridin-3-yl}-N-(2-dimethylaminoethyl)benzamide

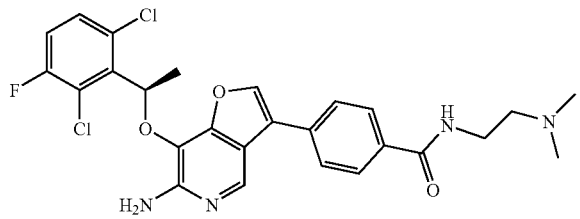

The title compound was prepared according to General procedure J. MS (ES+): m/z 531.26, 533.26 (100, 69) [MH+]. HPLC: $t_R$=0.65 min (HPLC-ACQUITY, Analytical).

Example 72

4-{6-Amino-7-[(R)-1-(2,6-dichloro-3-fluorophenyl)ethoxy]-furo[3,2-c]pyridin-3-yl}-N,N-dimethylbenzamide

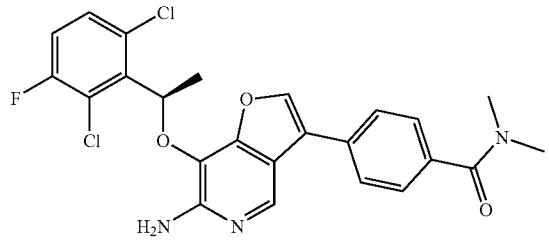

The title compound was prepared according to General procedure J. MS (ES+): m/z 488.20, 490.20 (100, 69) [MH+]. HPLC: $t_R$=0.84 min (HPLC-ACQUITY, Analytical).

Example 73

3-{6-Amino-7-[(R)-1-(2,6-dichloro-3-fluorophenyl)ethoxy]-furo[3,2-c]pyridin-3-yl}-N,N-dimethylbenzamide

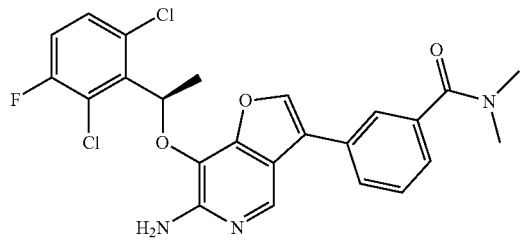

The title compound was prepared according to General procedure J. MS (ES+): m/z 488.21, 490.20 (100, 69) [MH+]. HPLC: $t_R$=0.85 min (HPLC-ACQUITY, Analytical).

Example 74

3-{6-Amino-7-[(R)-1-(2,6-dichloro-3-fluorophenyl)ethoxy]-furo[3,2-c]pyridin-3-yl}-N-(2-dimethylaminoethyl)benzamide

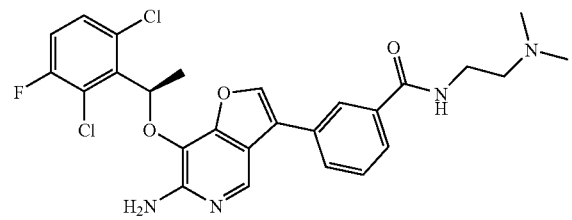

The title compound was prepared according to General procedure J. MS (ES+): m/z 531.24, 533.25 (100, 69) [MH+]. HPLC: $t_R$=0.65 min (HPLC-ACQUITY, Analytical).

Example 75

(4-{6-Amino-7-[(R)-1-(2,6-dichloro-3-fluorophenyl)ethoxy]-furo[3,2-c]pyridin-3-yl}phenyl)-(4-methylpiperazin-1-yl)methanone

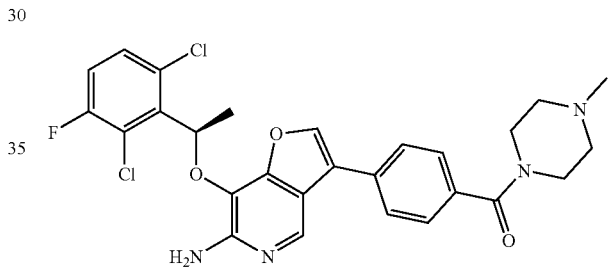

The title compound was prepared according to General procedure J. MS (ES+): m/z 543.25.17, 545.22 (100, 69) [MH+]. HPLC: $t_R$=0.65 min (HPLC-ACQUITY, Analytical).

Example 76

N-(4-{6-Amino-7-[(R)-1-(2,6-dichloro-3-fluorophenyl)ethoxy]-furo[3,2-c]pyridin-3-yl}phenyl)methanesulfonamide

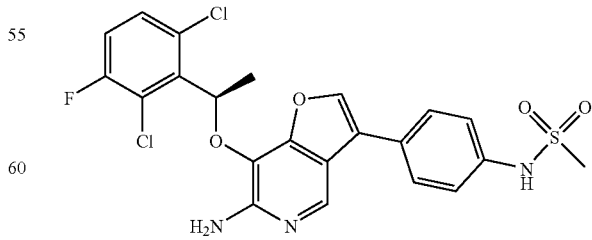

The title compound was prepared according to General procedure J. MS (ES+): m/z 510.16, 512.15 (100, 69) [MH+]. HPLC: $t_R$=0.87 min (HPLC-ACQUITY, Analytical).

Example 77

3-(4-Aminophenyl)-7-[(R)-1-(2,6-dichloro-3-fluorophenyl)-ethoxy]furo[3,2-c]pyridin-6-ylamine

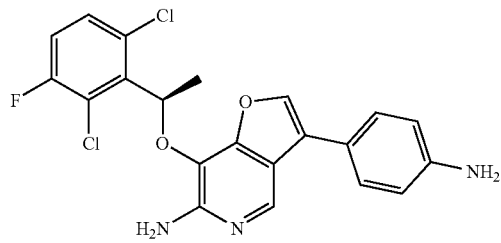

The title compound was prepared according to General procedure J. MS (ES+): m/z 432.17, 434.17 (100, 69) [MH+]. HPLC: $t_R$=0.81 min (HPLC-ACQUITY, Analytical).

Example 78

N-(3-{6-Amino-7-[(R)-1-(2,6-dichloro-3-fluorophenyl)ethoxy]-furo[3,2-c]pyridin-3-yl}phenyl)acetamide

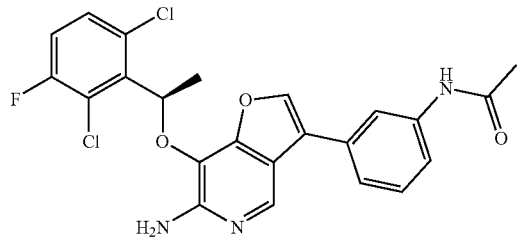

The title compound was prepared according to General procedure J. MS (ES+): m/z 474.20, 476.17 (100, 69) [MH+]. HPLC: $t_R$=0.84 min (HPLC-ACQUITY, Analytical).

Example 79

N-(3-{6-Amino-7-[(R)-1-(2,6-dichloro-3-fluorophenyl)ethoxy]-furo[3,2-c]pyridin-3-yl}phenyl)methanesulfonamide

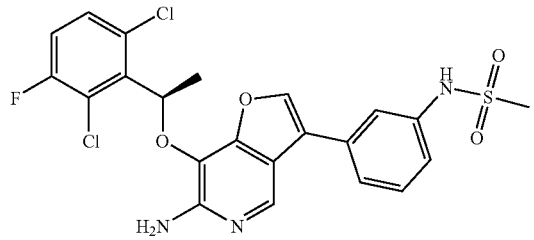

The title compound was prepared according to General procedure J. MS (ES+): m/z 510.18, 512.15 (100, 69) [MH+]. HPLC: $t_R$=0.88 min (HPLC-ACQUITY, Analytical).

Example 80

3-{6-Amino-7-[(R)-1-(2,6-dichloro-3-fluorophenyl)ethoxy]-furo[3,2-c]pyridin-3-yl}benzoic acid

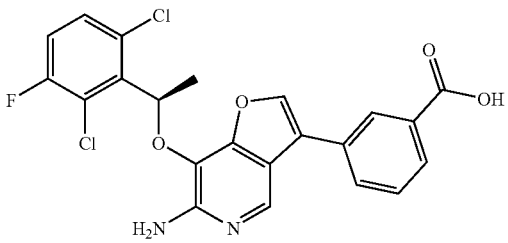

The title compound was prepared according to General procedure J. MS (ES+): m/z 461.16, 463.16 (100, 69) [MH+]. HPLC: $t_R$=0.85 min (HPLC-ACQUITY, Analytical).

Example 81

7-[(R)-1-(2,6-Dichloro-3-fluorophenyl)ethoxy]-3-(3,5-dimethoxyphenyl)furo[3,2-c]pyridin-6-ylamine

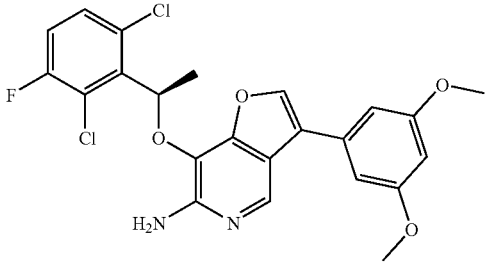

The title compound was prepared according to General procedure J. MS (ES+): m/z 477.20, 479.19 (100, 69) [MH+]. HPLC: $t_R$=1.01 min (HPLC-ACQUITY, Analytical).

Example 82

7-[(R)-1-(2,6-Dichloro-3-fluorophenyl)ethoxy]-3-imidazo[1,2-a]pyridin-7-ylfuro[3,2-c]pyridin-6-ylamine

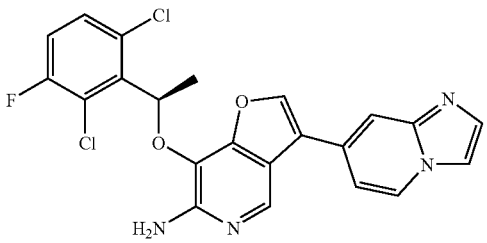

The title compound was prepared according to General procedure J. MS (ES+): m/z 457.16, 459.16 (100, 69) [MH+]. HPLC: $t_R$=0.64 min (HPLC-ACQUITY, Analytical).

Example 83

3-{6-Amino-7-[(R)-1-(2,6-dichloro-3-fluorophenyl)ethoxy]-furo[3,2-c]pyridin-3-yl}-N-methylbenzenesulfonamide

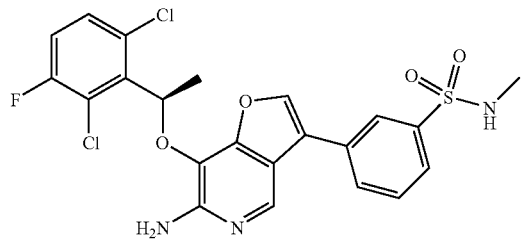

The title compound was prepared according to General procedure J. MS (ES+): m/z 510.13, 512.16 (100, 69) [MH+]. HPLC: $t_R$=0.90 min (HPLC-ACQUITY, Analytical).

Example 84

(4-{6-Amino-7-[(R)-1-(2,6-dichloro-3-fluorophenyl)ethoxy]-furo[3,2-c]pyridin-3-yl}phenyl)pyrrolidin-1-ylmethanone

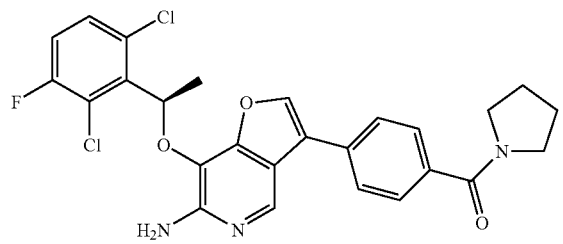

The title compound was prepared according to General procedure J. MS (ES+): m/z 514.23, 516.21 (100, 69) [MH+]. HPLC: $t_R$=0.89 min (HPLC-ACQUITY, Analytical).

Example 85

7-[(R)-1-(2,6-Dichloro-3-fluorophenyl)ethoxy]-3-(4-morpholin-4-ylmethylphenyl)furo[3,2-c]pyridin-6-ylamine

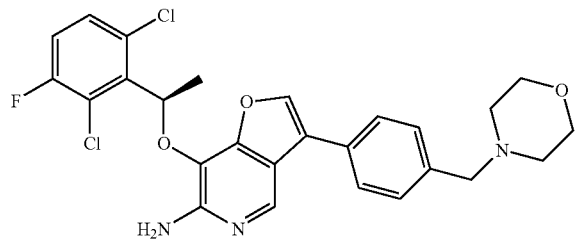

The title compound was prepared according to General procedure J. MS (ES+): m/z 516.25, 518.27 (100, 69) [MH+]. HPLC: $t_R$=0.66 min (HPLC-ACQUITY, Analytical).

Example 86

7-[(R)-1-(2,6-Dichloro-3-fluor-phenyl)ethoxy]-3-[4-(4-methylpiperazin-1-yl)-phenyl]furo[3,2-c]pyridin-6-ylamine

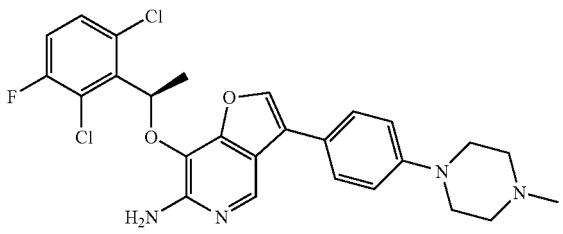

The title compound was prepared according to General procedure J. MS (ES+): m/z 515.28.17, 513.27 (100, 69) [MH+]. HPLC: $t_R$=0.68 min (HPLC-ACQUITY, Analytical).

Example 87

7-[(R)-1-(2,6-Dichloro-3-fluorophenyl)ethoxy]-3-[1-(2-morpholin-4-ylethyl)-1H-pyrazol-4-yl]furo[3,2-c]pyridin-6-ylamine

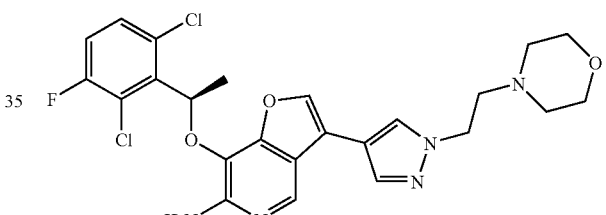

The title compound was prepared according to General procedure J. MS (ES+): m/z 520.27, 522.26 (100, 69) [MH+]. HPLC: $t_R$=0.63 min (HPLC-ACQUITY, Analytical).

Example 88

7-[(R)-1-(2,6-Dichloro-3-fluorophenyl)ethoxy]-3-[6-(4-methylpiperazin-1-yl)pyridin-3-yl]furo[3,2-c]pyridin-6-ylamine

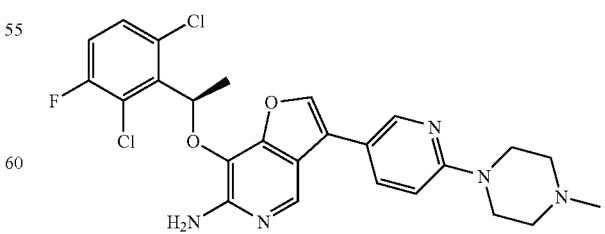

The title compound was prepared according to General procedure J. MS (ES+): m/z 516.27, 518.25 (100, 69) [MH+]. HPLC: $t_R$=0.65 min (HPLC-ACQUITY, Analytical).

Example 89

7-[(R)-1-(2,6-Dichloro-3-fluorophenyl)ethoxy]-3-[2-(4-methylpiperazin-1-yl)pyridin-4-yl]-furo[3,2-c]pyridin-6-ylamine

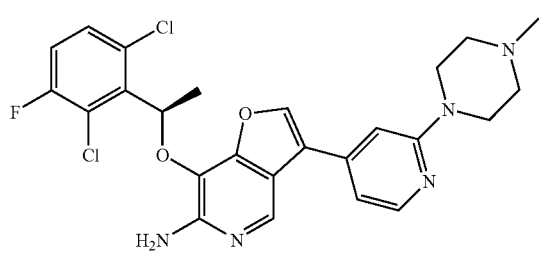

The title compound was prepared according to General procedure J. MS (ES$^+$): m/z 516.25, 518.27 (100, 69) [MH$^+$]. HPLC: $t_R$=0.66 min (HPLC-ACQUITY, Analytical).

Example 90

3-(3-Aminomethylphenyl)-7-[(R)-1-(2,6-dichloro-3-fluorophenyl)-ethoxy]furo[3,2-c]pyridin-6-ylamine

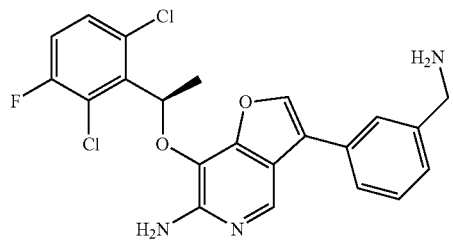

The title compound was prepared according to General procedure J. MS (ES$^+$): m/z 446.20, 448.21 (100, 69) [MH$^+$]. HPLC: $t_R$=0.65 min (HPLC-ACQUITY, Analytical).

Example 91

7-[(R)-1-(2,6-Dichloro-3-fluorophenyl)ethoxy]-3-(3-piperidin-1-ylmethylphenyl)furo[3,2-c]pyridin-6-ylamine

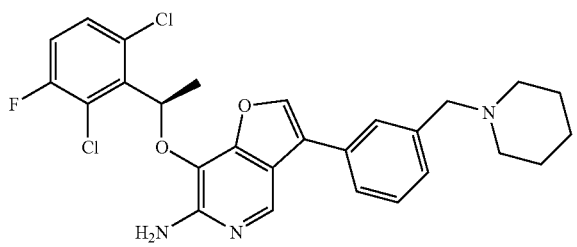

The title compound was prepared according to General procedure J. MS (ES$^+$): m/z 514.30, 516.27 (100, 69) [MH$^+$]. HPLC: $t_R$=0.72 min (HPLC-ACQUITY, Analytical).

Example 92

7-[(R)-1-(2,6-Dichloro-3-fluorophenyl)ethoxy]-3-quinolin-4-ylfuro[3,2-c]pyridin-6-ylamine

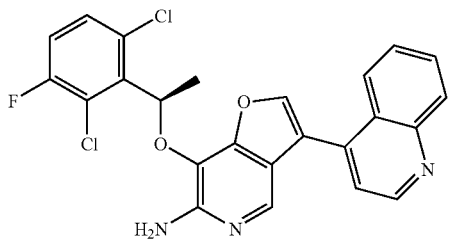

The title compound was prepared according to General procedure J. MS (ES$^+$): m/z 468.18, 470.17 (100, 69) [MH$^+$]. HPLC: $t_R$=0.88 min (HPLC-ACQUITY, Analytical).

Example 93

7-[(R)-1-(2,6-Dichloro-3-fluorophenyl)ethoxy]-3-(2-methoxypyrimidin-5-yl)furo[3,2-c]pyridin-6-ylamine

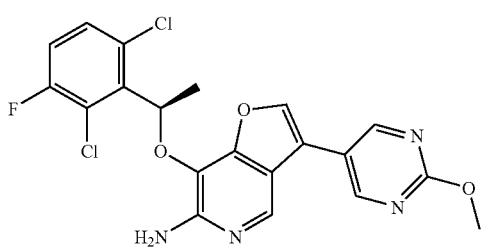

The title compound was prepared according to General procedure J. MS (ES$^+$): m/z 449.17, 451.16 (100, 69) [MH$^+$]. HPLC: $t_R$=0.84 min (HPLC-ACQUITY, Analytical).

Example 94

(3-{6-Amino-7-[(R)-1-(2,6-dichloro-3-fluorophenyl)ethoxy]furo[3,2-c]pyridin-3-yl}phenyl)(4-methylpiperazin-1-yl)methanone

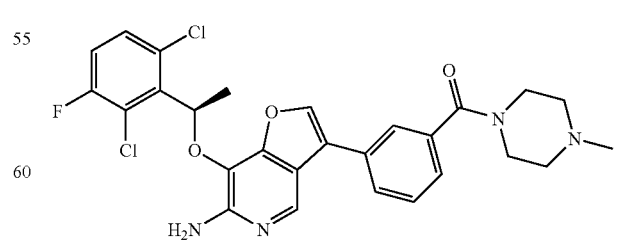

The title compound was prepared according to General procedure J. MS (ES$^+$): m/z 543.25, 545.27 (100, 69) [MH$^+$]. HPLC: $t_R$=0.64 min (HPLC-ACQUITY, Analytical).

Example 95

7-[(R)-1-(2,6-Dichloro-3-fluorophenyl)ethoxy]-3-(5-methylthiophen-2-yl)furo[3,2-c]pyridin-6-ylamine

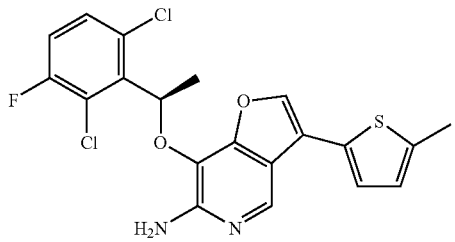

The title compound was prepared according to General procedure J. MS (ES$^+$): m/z 437.14, 439.11 (100, 69) [MH$^+$]. HPLC: $t_R$=1.10 min (HPLC-ACQUITY, Analytical).

Example 96

7-[(R)-1-(2,6-Dichloro-3-fluorophenyl)ethoxy]-3-(3-dimethyl-aminomethylphenyl)furo[3,2-c]pyridin-6-ylamine

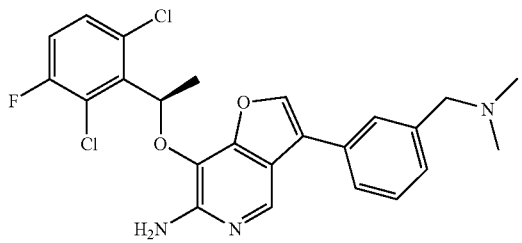

The title compound was prepared according to General procedure J. MS (ES$^+$): m/z 474.21, 476.21 (100, 69) [MH$^+$]. HPLC: $t_R$=0.66 min (HPLC-ACQUITY, Analytical).

Example 97

3-{6-Amino-7-[(R)-1-(2,6-dichloro-3-fluorophenyl)ethoxy]-furo[3,2-c]pyridin-3-yl}-N-(2-morpholin-4-ylethyl)benzamide

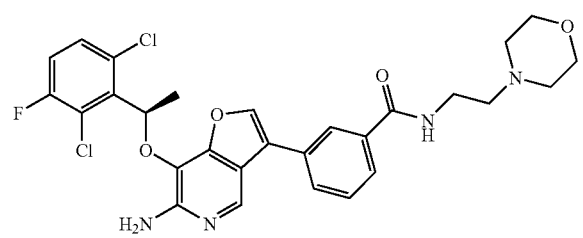

The title compound was prepared according to General procedure J. MS (ES$^+$): m/z 573.21, 575.21 (100, 69) [MH$^+$]. HPLC: $t_R$=0.67 min (HPLC-ACQUITY, Analytical).

Example 98

(3-{6-Amino-7-[(R)-1-(2,6-dichloro-3-fluorophenyl)ethoxy]-furo[3,2-c]pyridin-3-yl}phenyl)-[4-(2-hydroxyethyl)piperazin-1-yl]methanone

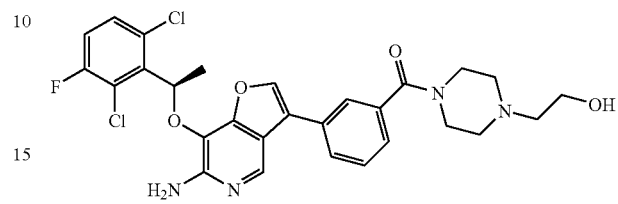

The title compound was prepared according to General procedure J. MS (ES$^+$): m/z 573.21, 575.22 (100, 69) [MH$^+$]. HPLC: $t_R$=0.65 min (HPLC-ACQUITY, Analytical).

Example 99

(4-{6-Amino-7-[(R)-1-(2,6-dichloro-3-fluorophenyl)ethoxy]-furo[3,2-c]pyridin-3-yl}phenyl)-[4-(2-hydroxyethyl)piperazin-1-yl]methanone

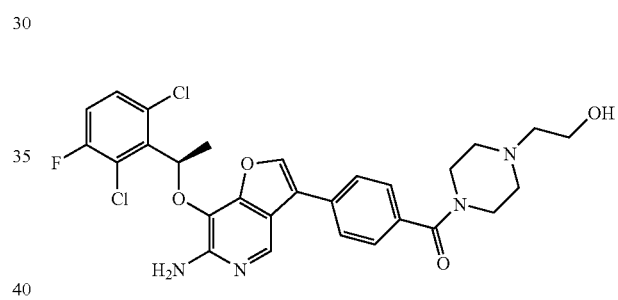

The title compound was prepared according to General procedure J. MS (ES$^+$): m/z 573.21, 575.19 (100, 69) [MH$^+$]. HPLC: $t_R$=0.64 min (HPLC-ACQUITY, Analytical).

Example 100

4-{6-Amino-7-[(R)-1-(2,6-dichloro-3-fluorophenyl)ethoxy]-furo[3,2-c]pyridin-3-yl}-N-(2-morpholin-4-ylethyl)benzamide

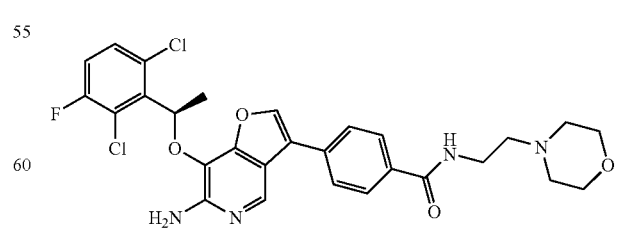

The title compound was prepared according to General procedure J. MS (ES$^+$): m/z 573.21, 575.21 (100, 69) [MH$^+$]. HPLC: $t_R$=0.67 min (HPLC-ACQUITY, Analytical).

Example 101

4-{6-Amino-7-[(R)-1-(2,6-dichloro-3-fluorophenyl)ethoxy]-furo[3,2-c]pyridin-3-yl}-N-(2-pyrrolidin-1-ylethyl)benzamide

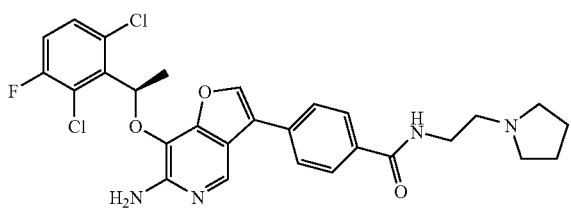

The title compound was prepared according to General procedure J. MS (ES+): m/z 557.23, 559.20 (100, 69) [MH+]. HPLC: $t_R$=0.68 min (HPLC-ACQUITY, Analytical).

Example 102

3-{6-Amino-7-[(R)-1-(2,6-dichloro-3-fluorophenyl)ethoxy]-furo[3,2-c]pyridin-3-yl}-N-(2-pyrrolidin-1-ylethyl)benzamide

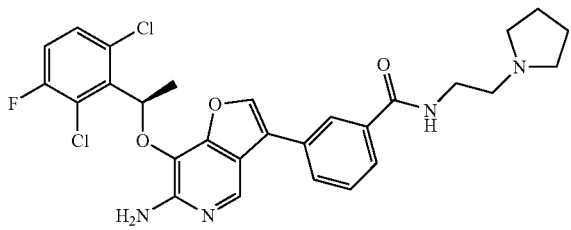

The title compound was prepared according to General procedure J. MS (ES+): m/z 557.21, 559.25 (100, 69) [MH+]. HPLC: $t_R$=0.68 min (HPLC-ACQUITY, Analytical).

Example 103

4-{6-Amino-7-[(R)-1-(2,6-dichloro-3-fluorophenyl)ethoxy]furo[3,2-c]pyridin-3-yl}-N-(2-piperidin-1-ylethyl)benzamide

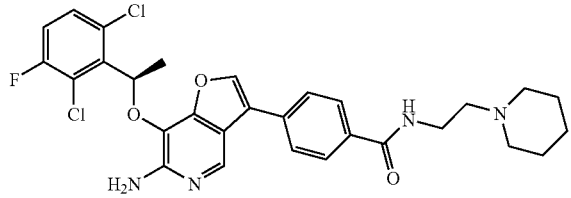

The title compound was prepared according to General procedure J. MS (ES+): m/z 571.26, 573.26 (100, 69) [MH+]. HPLC: $t_R$=0.70 min (HPLC-ACQUITY, Analytical).

Example 104

7-[(R)-1-(2,6-Dichloro-3-fluorophenyl)ethoxy]-3-[6-(2-morpholin-4-yl-ethylamino)pyridin-3-yl]furo[3,2-c]pyridin-6-ylamine

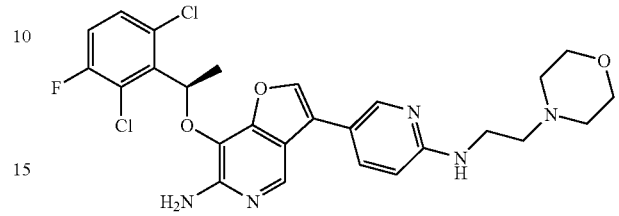

The title compound was prepared according to General procedure J. MS (ES+): m/z 546.22, 548.22 (100, 69) [MH+]. HPLC: $t_R$=0.63 min (HPLC-ACQUITY, Analytical).

Example 105

7-[(R)-1-(2,6-Dichloro-3-fluorophenyl)ethoxy]-3-(4-dimethylaminomethylphenyl)-furo[3,2-c]pyridin-6-ylamine

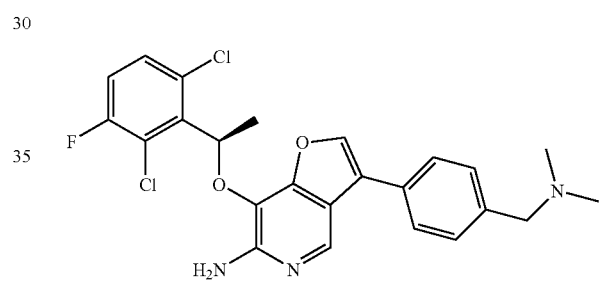

The title compound was prepared according to General procedure J. MS (ES+): m/z 474.17, 476.18 (100, 69) [MH+]. HPLC: $t_R$=0.66 min (HPLC-ACQUITY, Analytical).

Example 106

(4-{6-Amino-7-[(R)-1-(2,6-dichloro-3-fluorophenyl)ethoxy]furo[3,2-c]pyridin-3-yl}phenyl)piperazin-1-ylmethanone

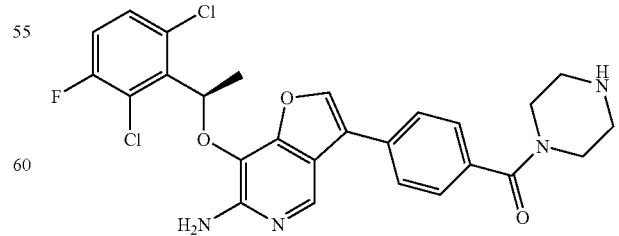

The title compound was prepared according to General procedure J. MS (ES+): m/z 529.18, 531.22 (100, 69) [MH+]. HPLC: $t_R$=0.64 min (HPLC-ACQUITY, Analytical).

The compound was converted to its bis-HCl salt following the General Procedure for forming HCl/bis-HCl salts from the free base.

Example 107

7-[(R)-1-(2,6-Dichloro-3-fluorophenyl)ethoxy]-3-(6-morpholin-4-ylpyridin-3-yl)-furo[3,2-c]pyridin-6-ylamine

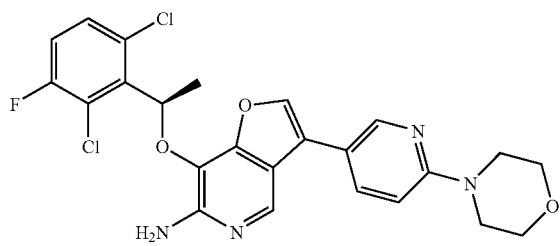

The title compound was prepared according to General procedure J. MS (ES+): m/z 503.16, 505.16 (100, 69) [MH+]. HPLC: $t_R$=0.83 min (HPLC-ACQUITY, Analytical).

Example 108

(4-{6-Amino-7-[(R)-1-(2,6-dichloro-3-fluorophenyl)ethoxy]furo[3,2-c]pyridin-3-yl}phenyl)urea

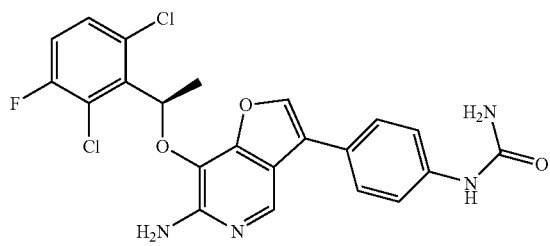

The title compound was prepared according to General procedure J. MS (ES+): m/z 475.15, 477.12 (100, 69) [MH+]. HPLC: $t_R$=0.79 min (HPLC-ACQUITY, Analytical).

Example 109

4-{6-Amino-7-[(R)-1-(2,6-dichloro-3-fluorophenyl)ethoxy]-furo[3,2-c]pyridin-3-yl}-N-thiazol-2-yl-benzamide

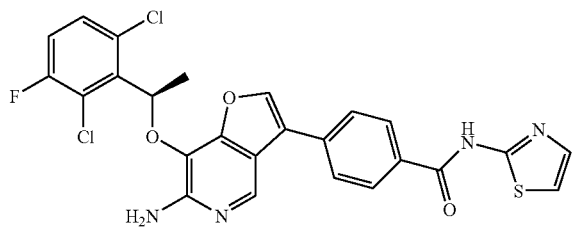

The title compound was prepared according to General procedure J. MS (ES+): m/z 543.16, 545.16 (100, 69) [MH+]. HPLC: $t_R$=0.95 min (HPLC-ACQUITY, Analytical).

Example 110

7-[(R)-1-(2,6-Dichloro-3-fluorophenyl)ethoxy]-3-(4-pyrazol-1-ylmethylphenyl)-furo[3,2-c]pyridin-6-ylamine

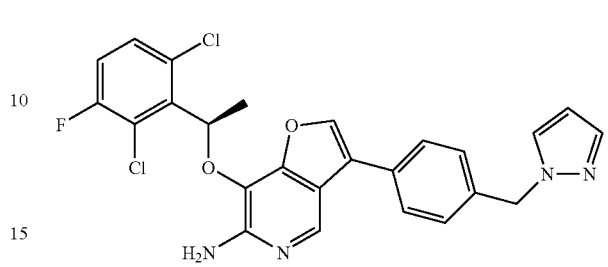

The title compound was prepared according to General procedure J. MS (ES+): m/z 497.21, 499.21 (100, 69) [MH+]. HPLC: $t_R$=0.96 min (HPLC-ACQUITY, Analytical).

Example 111

7-[(R)-1-(2,6-Dichloro-3-fluorophenyl)ethoxy]-3-(4-methylthiophen-3-yl)furo[3,2-c]pyridin-6-ylamine

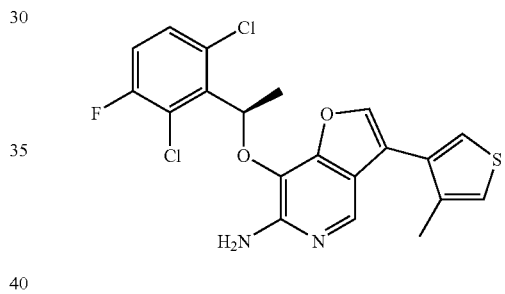

The title compound was prepared according to General procedure J. MS (ES+): m/z 437.09, 439.05 (100, 69) [MH+]. HPLC: $t_R$=1.02 min (HPLC-ACQUITY, Analytical).

Example 112

7-[(R)-1-(2,6-Dichloro-3-fluorophenyl)ethoxy]-3-pyrimidin-5-ylfuro[3,2-c]pyridin-6-ylamine

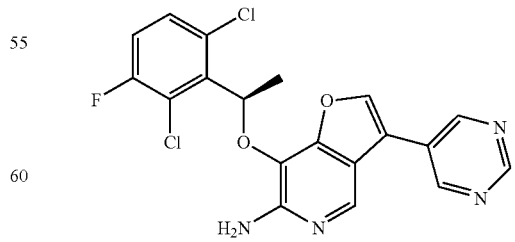

The title compound was prepared according to General procedure J. MS (ES+): m/z 419.09, 421.10 (100, 69) [MH+]. HPLC: $t_R$=0.78 min (HPLC-ACQUITY, Analytical).

Example 113

3-(2-Amino-pyrimidin-5-yl)-7-[(R)-1-(2,6-dichloro-3-fluorophenyl)ethoxy]furo[3,2-c]pyridin-6-ylamine

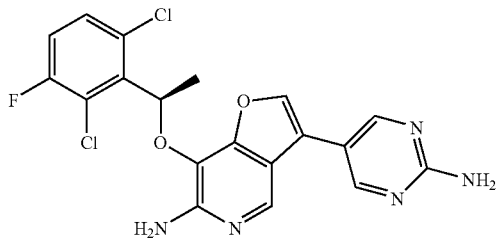

The title compound was prepared according to General procedure J. MS (ES+): m/z 434.08, 436.08 (100, 69) [MH+]. HPLC: $t_R$=0.74 min (HPLC-ACQUITY, Analytical).

Example 114

1-(5-{6-Amino-7-[(R)-1-(2,6-dichloro-3-fluorophenyl)ethoxy]furo[3,2-c]pyridin-3-yl}thiophen-2-yl)ethanone

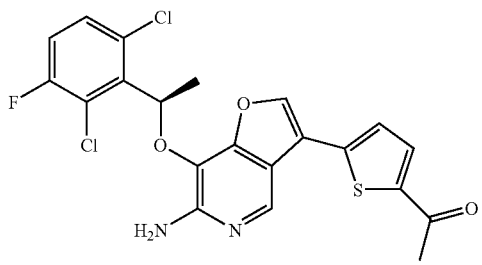

The title compound was prepared according to General procedure J. MS (ES+): m/z 465.07, 467.06 (100, 69) [MH+]. HPLC: $t_R$=1.00 min (HPLC-ACQUITY, Analytical).

Example 115

7-[(R)-1-(2,6-Dichloro-3-fluorophenyl)ethoxy]-3-(4-methylthiophen-2-yl)furo[3,2-c]pyridin-6-ylamine

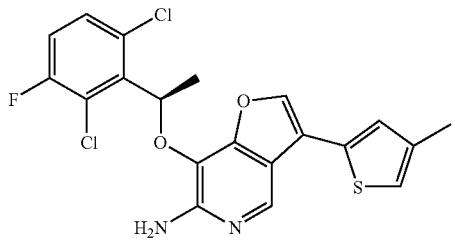

The title compound was prepared according to General procedure J. MS (ES+): m/z 437.07, 439.05 (100, 69) [MH+]. HPLC: $t_R$=1.10 min (HPLC-ACQUITY, Analytical).

Example 116

7-[(R)-1-(2,6-Dichloro-3-fluorophenyl)ethoxy]-3-(3-methylthiophen-2-yl)furo[3,2-c]pyridin-6-ylamine

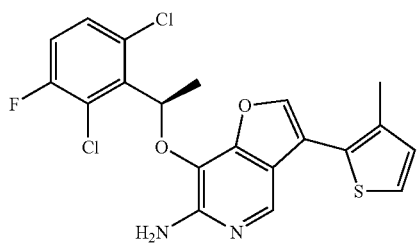

The title compound was prepared according to General procedure J. MS (ES+): m/z 437.06, 439.05 (100, 69) [MH+]. HPLC: $t_R$=1.06 min (HPLC-ACQUITY, Analytical).

Example 117

7-[(R)-1-(2,6-Dichloro-3-fluorophenyl)ethoxy]-3-(5-methylfuran-2-yl)-furo[3,2-c]pyridin-6-ylamine

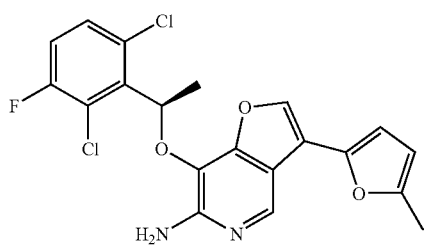

The title compound was prepared according to General procedure J. MS (ES+): m/z 421.10.09, 423.09 (100, 69) [MH+]. HPLC: $t_R$=1.04 min (HPLC-ACQUITY, Analytical).

Example 118

(5-{6-Amino-7-[(R)-1-(2,6-dichloro-3-fluorophenyl)ethoxy]furo[3,2-c]pyridin-3-yl}pyridin-2-yl)methanol

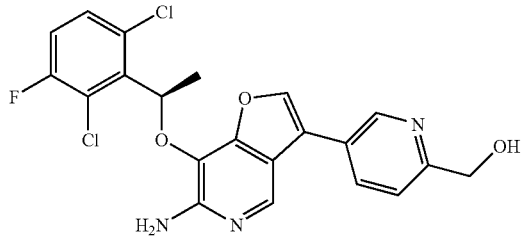

The title compound was prepared according to General procedure J. MS (ES+): m/z 448.11, 450.11 (100, 69) [MH+]. HPLC: $t_R$=0.72 min (HPLC-ACQUITY, Analytical).

Example 119

7-[(R)-1-(2,6-Dichloro-3-fluorophenyl)ethoxy]-3-(6-nitropyridin-3-yl)furo[3,2-c]pyridin-6-ylamine

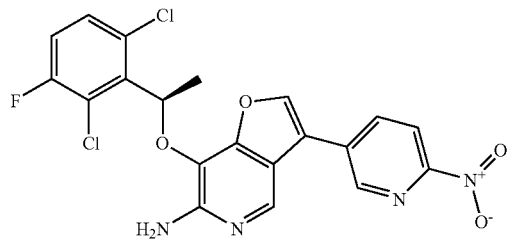

The title compound was prepared according to General procedure J. MS (ES+): m/z 463.07, 465.07 (100, 69) [MH+]. HPLC: $t_R$=0.94 min (HPLC-ACQUITY, Analytical).

Example 120

N-(5-{6-Amino-7-[(R)-1-(2,6-dichloro-3-fluorophenyl)ethoxy]furo[3,2-c]pyridin-3-yl}pyridin-2-yl)acetamide

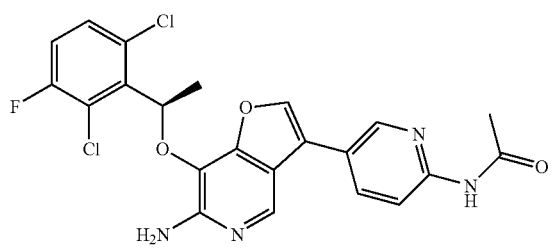

The title compound was prepared according to General procedure J. MS (ES+): m/z 475.10, 477.10 (100, 69) [MH+]. HPLC: $t_R$=0.81 min (HPLC-ACQUITY, Analytical).

Example 121

7-[(R)-1-(2,6-Dichloro-3-fluorophenyl)ethoxy]-3-(1-methyl-1H-pyrrol-2-yl)furo[3,2-c]pyridin-6-ylamine

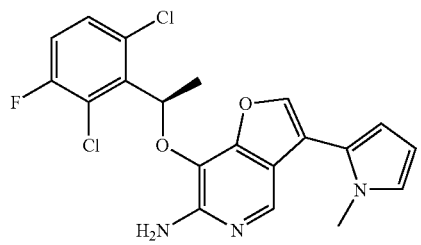

The title compound was prepared according to General procedure J. MS (ES+): m/z 420.09, 422.11 (100, 69) [MH+]. HPLC: $t_R$=0.93 min (HPLC-ACQUITY, Analytical).

Example 122

7-[(R)-1-(2,6-Dichloro-3-fluorophenyl)ethoxy]-3-[6-(3-dimethylaminopropoxy)pyridin-3-yl]furo[3,2-c]pyridin-6-ylamine

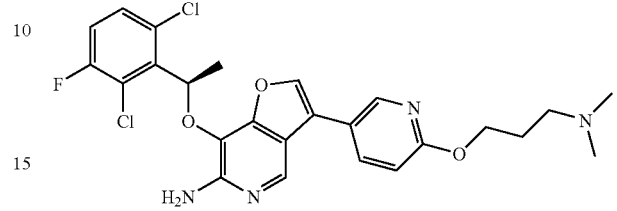

The title compound was prepared according to General procedure J. MS (ES+): m/z 519.20, 521.19 (100, 69) [MH+]. HPLC: $t_R$=0.68 min (HPLC-ACQUITY, Analytical).

Example 123

7-[(R)-1-(2,6-Dichloro-3-fluorophenyl)ethoxy]-3-[2-(4-methylpiperazin-1-yl)pyrimidin-5-yl]furo[3,2-c]pyridin-6-ylamine

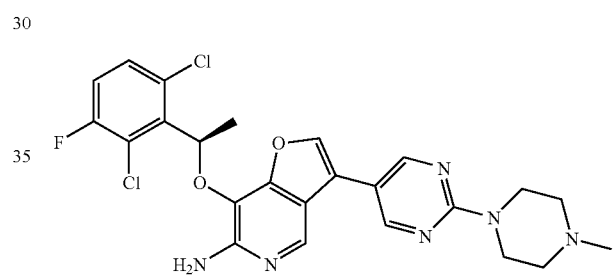

The title compound was prepared according to General procedure J. MS (ES+): m/z 517.16, 519.17 (100, 69) [MH+]. HPLC: $t_R$=0.66 min (HPLC-ACQUITY, Analytical).

Example 124

7-[(R)-1-(2,6-Dichloro-3-fluorophenyl)ethoxy]-3-(2-dimethylaminopyrimidin-5-yl)furo[3,2-c]pyridin-6-ylamine

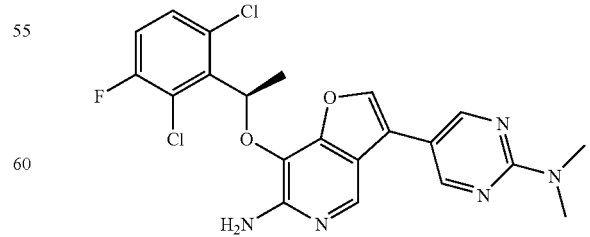

The title compound was prepared according to General procedure J. MS (ES+): m/z 462.14, 464.14 (100, 69) [MH+]. HPLC: $t_R$=0.91 min (HPLC-ACQUITY, Analytical).

Example 125

5-{6-Amino-7-[(R)-1-(2,6-dichloro-3-fluorophenyl)-ethoxy]furo[3,2-c]pyridin-3-yl}pyridine-2-carbonitrile

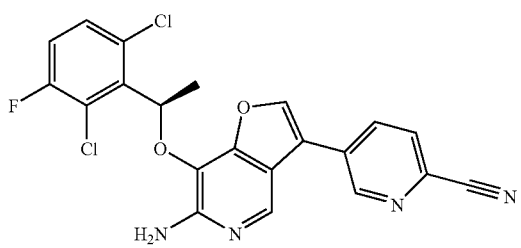

The title compound was prepared according to General procedure J. MS (ES+): m/z 443.07, 445.07 (100, 69) [MH⁺]. HPLC: $t_R$=0.95 min (HPLC-ACQUITY, Analytical).

Example 126

7-[(R)-(2,6-Dichloro-3-fluorophenyl)ethoxy]-3-pyridin-3-ylfuro[3,2-c]pyridin-6-ylamine

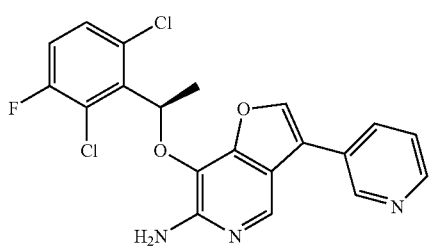

General procedure K: A mixture of 3-bromo-7-[(1R)-(2,6-dichloro-3-fluoro-phenyl)ethoxy]furo[3,2-c]pyridin-6-ylamine (20 mg, 0.05 mmol), 3-pyridylboronic acid (7 mg, 0.06 mmol), and potassium carbonate (20 mg, 0.1 mmol) in 1,4-dioxane (1.2 mL) and H₂O (0.4 mL) was stirred at 100° C. for 30 min in a Biotage microwave. The mixture was then passed through a PL-Thiol MP SPE+ resin and concentrated in vacuo. Purification by mass-directed purification system afforded the title compound as a white solid (3 mg, 14% yield). ¹H NMR (400 MHz, DMSO-d₆): δ=1.85 (d, J=6.6 Hz, 3H), 5.70 (br, s, 2H), 6.27 (q, J=6.8 Hz, 1H), 7.43-7.57 (m, 3H), 8.13 (ddd, J=8.2, 2.0, 1.8 Hz, 1H), 8.25 (s, 1H), 8.28 (s, 1H), 8.36 (s, 1H), 8.56 (dd, J=4.8, 1.8 Hz, 1H), 8.93 (d, J=1.5 Hz, 1H). MS (ES⁺): m/z 418.04/420.02 (100/30) [MH⁺]. HPLC: $t_R$=2.55 min (ZQ3: nonpolar_5 min).

Example 127

7-[(R)-(2,6-Dichloro-3-fluorophenyl)ethoxy]-3-pyridin-4-ylfuro[3,2-c]pyridin-6-ylamine

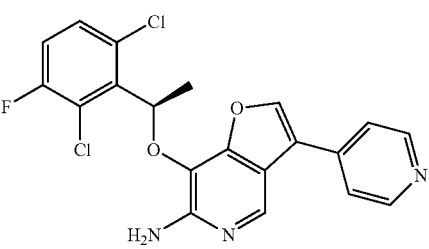

The title compound was prepared according to General procedure K. ¹H NMR (DMSO-d₆, 400 MHz): δ=1.85 (d, J=6.8 Hz, 3H), 5.74 (s, 2H), 6.25 (q, J=6.7 Hz, 1H), 7.46 (t, J=8.7 Hz, 1H), 7.50-7.56 (m, 1H), 7.70-7.76 (m, 2H), 8.41 (s, 1H), 8.44 (s, 1H), 8.59-8.65 (m, 2H). MS (ES⁺): m/z 418.04/420.02 (100/90) [MH⁺]. HPLC: $t_R$=2.30 min (ZQ3: nonpolar_5 min).

Example 128

3-{6-Amino-7-[(R)-(2,6-dichloro-3-fluorophenyl)ethoxy]-furo[3,2-c]pyridin-3-yl}phenol

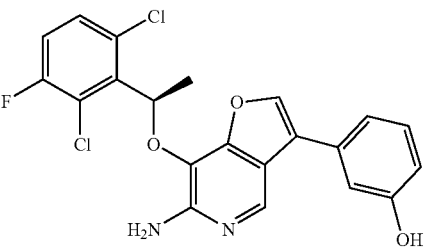

The title compound was prepared according to General procedure K. ¹H NMR (DMSO-d₆, 400 MHz): δ=1.84 (d, J=6.8 Hz, 3H), 5.64 (br, s, 2H), 6.27 (q, J=6.7 Hz, 1H), 6.74-6.78 (m, 1H), 7.07-7.13 (m, 2H), 7.21-7.29 (m, 1H), 7.46 (t, J=8.7 Hz, 1H), 7.51-7.57 (m, 1H), 8.06 (s, 1H), 8.27 (s, 1H), 9.57 (br, s, 1H). MS (ES⁺): m/z 433.05/434.96 (100/35) [MH⁺]. HPLC: $t_R$=2.65 min (ZQ3: nonpolar_5 min).

Example 129

7-[(R)-(2,6-Dichloro-3-fluorophenyl)ethoxy]-3-(1H-indol-6-yl)furo[3,2-c]pyridin-6-ylamine

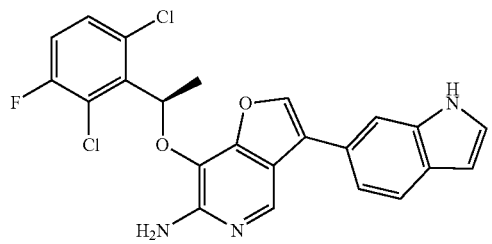

The title compound was prepared according to General procedure K. $^1$H NMR (DMSO-$d_6$, 400 MHz): δ=1.85 (d, J=6.8 Hz, 3H), 5.62 (br, s, 2H), 6.31 (q, J=6.6 Hz, 1H), 6.44-6.47 (m, 1H), 7.31 (dd, J=8.3, 1.5 Hz, 1H), 7.39 (t, J=2.8 Hz, 1H), 7.48 (d, J=8.6 Hz, 1H), 7.52-7.57 (m, 1H), 7.61 (d, J=8.1 Hz, 1H), 7.70 (s, 1H), 8.06 (s, 1H), 8.34 (s, 1H), 11.14 (br, s, 1H). MS (ES$^+$): m/z 456.04/458.02 (100/90) [MH$^+$]. HPLC: $t_R$=2.99 min (ZQ3: nonpolar_5 min).

Example 131

3-(6-Amino-pyridin-3-yl)-7-[(R)-(2,6-dichloro-3-fluorophenyl)ethoxy]furo[3,2-c]pyridin-6-ylamine

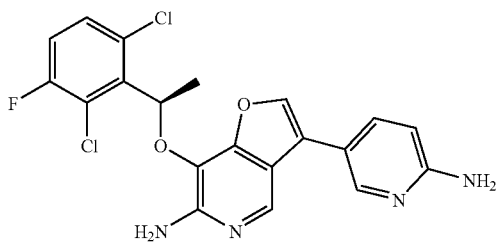

The title compound was prepared according to General procedure K. $^1$H NMR (DMSO-$d_6$, 400 MHz): δ=1.83 (d, J=6.8 Hz, 3H), 5.60 (br, s, 2H), 6.11 (br, s, 2H), 6.26 (q, J=6.6 Hz, 1H), 6.53 (d, J=8.6 Hz, 1H), 7.46 (t, J=8.7 Hz, 1H), 7.51-7.55 (m, 1H), 7.69 (dd, J=8.5, 2.40 Hz, 1H), 7.95 (s, 1H), 8.16 (s, 1H), 8.24 (s, 1H). MS (ES$^+$): m/z 433.05/435.03 (100/98) [MH$^+$]. HPLC: $t_R$=1.70 min (ZQ3: nonpolar_5 min).

Example 130

7-[(R)-(2,6-Dichloro-3-fluorophenyl)ethoxy]-3-(6-piperazin-1-yl-pyridin-3-yl)furo[3,2-c]pyridin-6-ylamine

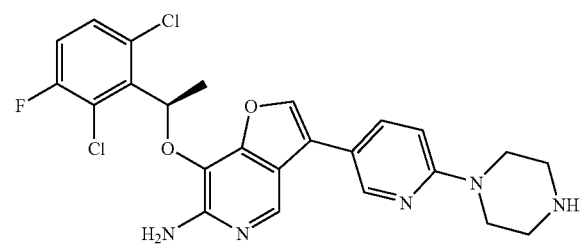

The title compound was prepared according to General procedure K. $^1$H NMR (DMSO-$d_6$, 400 MHz): δ=1.83 (d, J=6.8 Hz, 3H), 2.83-2.89 (m, 4H), 3.49-3.54 (m, 4H), 5.62 (br, s, 2H), 6.27 (q, J=6.6 Hz, 1H), 6.91 (d, J=8.8 Hz, 1H), 7.46 (t, J=8.7 Hz, 1H), 7.51-7.57 (m, 1H), 7.86 (dd, J=8.8, 2.5 Hz, 1H), 8.03 (s, 1H), 8.23 (s, 1H), 8.28 (s, 1H), 8.47 (d, J=2.3 Hz, 1H). MS (ES$^+$): m/z 502.09/504.06 (70/60) [MH$^+$]. HPLC: $t_R$=1.72 min (ZQ3: nonpolar_5 min).

Example 132

7-[(R)-(2,6-Dichloro-3-fluorophenyl)ethoxy]-3-(2-piperazin-1-yl-pyridin-4-yl)furo[3,2-c]pyridin-6-ylamine

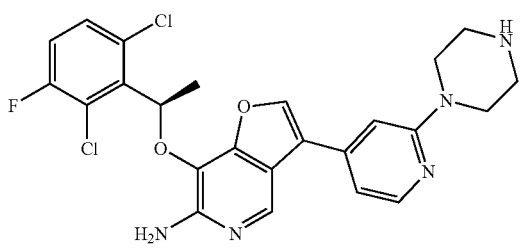

The title compound was prepared according to General procedure K. $^1$H NMR (DMSO-$d_6$, 400 MHz): δ=1.84 (d, J=6.8 Hz, 3H), 2.87-2.94 (m, 4H), 3.52-3.58 (m, 4H), 5.69 (br, s, 2H), 6.25 (q, J=6.7 Hz, 1H), 6.98 (dd, J=5.2, 1.1 Hz, 1H), 7.03 (br, s, 1H), 7.46 (t, J=8.7 Hz, 1H), 7.51-7.56 (m, 1H), 8.17 (d, J=5.3 Hz, 1H), 8.24 (s, 1H), 8.30 (s, 1H), 8.35 (s, 1H). MS (ES$^+$): m/z 502.09/504.06 (70/60) [MH$^+$]. HPLC: $t_R$=1.74 min (ZQ3: nonpolar_5 min).

Example 133

7-[(R)-1-(2,6-Dichloro-3-fluorophenyl)ethoxy]-3-(1H-pyrrol-2-yl)furo[3,2-c]pyridin-6-amine

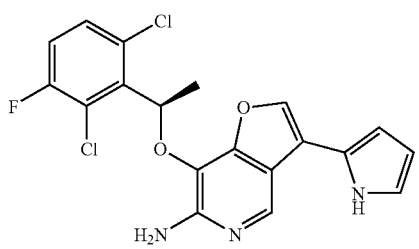

The title compound was prepared according to General procedure K. ¹H NMR (DMSO-d₆, 400 MHz): δ=1.94 (d, J=6.8 Hz, 3H), 6.22 (t, J=3.2 Hz, 1H), 6.52 (dd, J=3.4, 1.4 Hz, 1H), 6.68 (q, J=6.6 Hz, 1H), 6.87 (dd, J=2.7, 1.4 Hz, 1H), 7.18-7.27 (m, 1H), 7.43 (dd, J=9.1, 4.8 Hz, 1H), 7.86 (s, 1H), 8.07 (s, 1H), 8.22 (s, 1H). MS (ES⁺): m/z 406.03/408.01 (100/90) [MH⁺]. HPLC: $t_R$=2.60 min (ZQ3: nonpolar_5 min).

Example 134

7-[(R)-(2,6-Dichloro-3-fluorophenyl)ethoxy]-3-thiophen-3-ylfuro[3,2-c]pyridin-6-ylamine

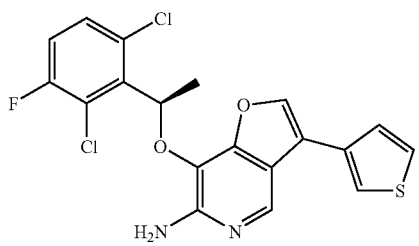

The title compound was prepared according to General procedure K. ¹H NMR (DMSO-d₆, 400 MHz): δ=1.84 (d, J=6.8 Hz, 3H), 5.64 (br, s, 2H), 6.26 (q, J=6.8 Hz, 1H), 7.45 (t, J=8.7 Hz, 1H), 7.50-7.55 (m, 2H), 7.67 (dd, J=5.1, 2.8 Hz, 1H), 7.96 (dd, J=2.7, 1.1 Hz, 1H), 8.15 (s, 1H), 8.42 (s, 1H). MS (ES⁺): m/z 422.95/424.98 (100/90) [MH⁺]. HPLC: $t_R$=3.54 min (ZQ3: polar_5 min).

Example 135

7-[(R)-1-(2,6-Dichloro-3-fluorophenyl)-ethoxy]-3-thiazol-2-ylfuro[3,2-c]pyridin-6-ylamine

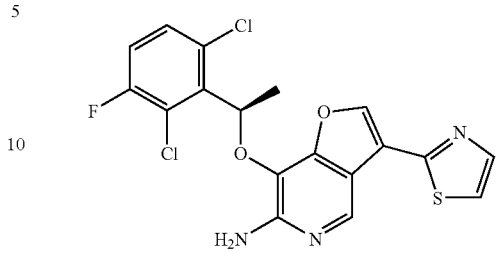

A mixture of 3-bromo-7-[(R)-1-(2,6-dichloro-3-fluorophenyl)-ethoxy]-furo[3,2-c]pyridin-6-ylamine (49.0 mg, 0.117 mmol), KF (44 mg, 0.75 mmol), and Pd(PPh₃)₄ (13 mg, 0.011 mmol) in 1,4-dioxane (1.0 mL, 13 mmol) in a microwave reactor vial was evacuated and refilled with nitrogen (3×). 2-Tributylstannylthiazole (50 μL, 0.16 mmol) was added, and the reaction mixture was heated to 100° C. for 45 min in a microwave reactor. Further 2-tributylstannylthiazole (50 μL, 0.16 mmol) was added, and the reaction mixture was heated to 100° C. for 45 min. The reaction mixture was diluted with DCM and washed with water. The DCM solution was washed with brine, dried over MgSO₄, filtered, and concentrated. The residue was redissolved in MeOH and prepurified by passing through a thiol SPE cartridge (500 mg/6 mL, PL-Thiol MP SPE+). The material from the thiol SPE treatment was chromatographed on silica gel [10 g/70 mL cartridge, eluting with DCM→10% EtOAc in DCM→15% EtOAc in DCM→20% EtOAc in DCM]. Fractions containing product were combined, concentrated in vacuo, chromatographed on a SCX column (1 g/6 mL cartridge), and the fraction that eluted with NH₃/MeOH was concentrated and dried in vacuo to give the title compound as pale yellow film. ¹H NMR (CDCl₃, 400 MHz): δ=8.61 (s, 1H), 8.00 (s, 1H), 7.91 (d, J=3.2 Hz, 1H), 7.37 (d, J=3.2 Hz, 1H), 7.29 (dd, J=4.4, 8.4 Hz, 1H), 7.06 (dd, J=8.4, 9.2 Hz, 1H), 6.56 (q, J=6.8 Hz, 1H), 4.83 (brs, 2H), 1.89 (d, J=6.8 Hz, 3H). MS (ES⁺): m/z=423.96/425.90/427.93 (100/95/27) [MH⁺], 234.03 (30) [MH⁺−3-F-2,6-di-Cl-Ph-CH=CH₂]. HPLC: $t_R$=3.65 min (polar_5 min, ZQ3).

Example 136

7-[(R)-1-(2,6-Dichloro-3-fluorophenyl)-ethoxy]-3-thiazol-4-ylfuro[3,2-c]pyridin-6-ylamine

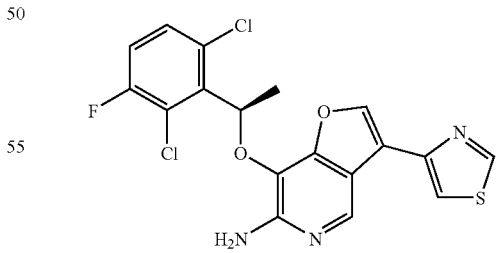

To a solution of 3-bromo-7-[(R)-1-(2,6-dichloro-3-fluorophenyl)-ethoxy]-furo[3,2-c]pyridin-6-ylamine (32.6 mg, 0.0776 mmol) and 4-(4,4,5,5-tetramethyl-[1,3,2]dioxaborolan-2-yl)-thiazole (18.0 mg, 0.0854 mmol) in 1,4-dioxane (1.1 mL, 14 mmol) in a microwave reactor tube were added PS-PPh₃-Pd (0.10 mmol/g loading; 45 mg, 0.0045 mmol; Argonaut) and a solution of Cs₂CO₃ (52.1 mg, 0.160 mmol)

in H₂O (0.33 mL, 18 mmol). The tube was sealed, evacuated and refilled with nitrogen (3×), and heated in the microwave reactor to 105° C. for 30 min. Further 4-(4,4,5,5-tetramethyl-[1,3,2]dioxaborolan-2-yl)-thiazole (21 mg, 0.099 mmol) was added, and the reaction mixture was heated in the microwave reactor to 105° C. for 30 min. A solution of the remaining 4-(4,4,5,5-tetramethyl-[1,3,2]dioxaborolan-2-yl)-thiazole (61 mg, 0.29 mmol) in 1,4-dioxane (0.30 mL, 3.8 mmol) was added to the reaction mixture, which was then heated to 105° C. for 45 min. The resin was filtered off and washed with DCM. The combined filtrate and washings were diluted with DCM to 50 mL, washed with water and brine, dried over MgSO₄, filtered, and concentrated in vacuo. The residue was submitted to MDP for purification. The product fractions were combined and dried in vacuo overnight. The product was chromatographed on an SCX column (500 mg/3 mL), and the fraction eluting with NH₃/MeOH was concentrated and dried in vacuo to give the title compound as an off-white film. ¹H NMR (CDCl₃, 400 MHz): δ=8.91 (d, J=2.4 Hz, 1H), 8.43 (s, 1H), 7.98 (s, 1H), 7.53 (d, J=2.4 Hz, 1H), 7.29 (dd, J=4.8, 8.0 Hz, 1H), 7.06 (dd, J=8.0, 8.8 Hz, 1H), 6.62 (q, J=6.8 Hz, 1H), 5.29 (brs, 2H), 1.91 (d, J=6.8 Hz, 3H). MS (ES⁺): m/z=423.90/425.88/427.86 (98/100/28) [MH⁺], 234.00 (25) [MH⁺−3-F-2,6-di-Cl-Ph-CH=CH₂]. HPLC: t$_R$=3.33 min (polar_5 min, ZQ3).

Example 137

7-[(R)-1-(2,6-Dichloro-3-fluorophenyl)-ethoxy]-3-pyridin-2-ylfuro[3,2-c]pyridin-6-ylamine

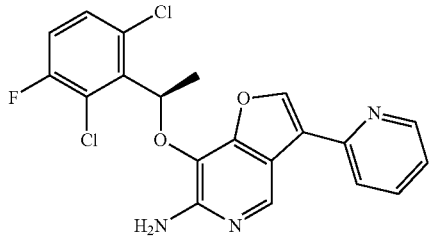

A mixture of 3-bromo-7-[(R)-1-(2,6-dichloro-3-fluorophenyl)-ethoxy]-furo[3,2-c]pyridin-6-ylamine (49.0 mg, 0.117 mmol), KF (44 mg, 0.75 mmol), and Pd(PPh₃)₄ (13 mg, 0.011 mmol) in 1,4-dioxane (1.0 mL, 13 mmol) in a microwave reactor vial was evacuated and refilled with nitrogen (3×). 2-(1,1,1-Tributylstannyl)pyridine (90% pure; 60 µL, 0.17 mmol) was added, and the reaction mixture was heated to 100° C. for 45 min. Further 2-(1,1,1-tributylstannyl)pyridine (90% pure; 30 µL, 0.083 mmol) was added, and the reaction mixture was heated to 100° C. for a total of 2 h. The reaction mixture was diluted with DCM and washed with water. The DCM solution was washed with brine, dried over MgSO₄, filtered, and concentrated. The residue was redissolved in MeOH and pre-purified by passing through a thiol SPE cartridge (500 mg/6 mL, PL-Thiol MP SPE+). The material from the thiol SPE treatment was chromatographed on a SCX column (1 g/6 mL cartridge), and the fraction that eluted with NH₃/MeOH was concentrated and chromatographed on silica gel [10 g/70 mL cartridge, eluting with DCM→10% EtOAc in DCM→15% EtOAc in DCM→20% EtOAc in DCM→30% EtOAc in DCM]. Fractions containing product were combined and concentrated in vacuo to give the title compound as a foam. ¹H NMR (CDCl₃, 400 MHz): δ=8.69 (d, J=5.6 Hz, 1H), 8.68 (s, 1H), 7.94 (s, 1H), 7.75 (dd, J=7.6, 7.6 Hz, 1H), 7.62 (d, J=7.6 Hz, 1H), 7.29 (dd, J=8.4, 4.4, Hz, 1H), 7.23 (dd, J=7.2, 5.6 Hz, 1H), 7.05 (dd, J=8.4, 8.0 Hz, 1H), 6.56 (q, J=6.8 Hz, 1H), 4.78 (brs, 2H), 1.89 (d, J=6.8 Hz, 3H). MS (ES⁺): m/z=417.94/419.91/421.93 (100/80/15) [MH⁺], 228.03 (19) [MH⁺−3-F-2,6-di-Cl-Ph-CH=CH₂]. HPLC: t$_R$=3.27 min (polar_5 min, ZQ3).

Example 138

7-[(R)-1-(2,6-Dichloro-3-fluorophenyl)-ethoxy]-3-(3,6-dihydro-2H-pyran-4-yl)-furo[3,2-c]pyridin-6-ylamine

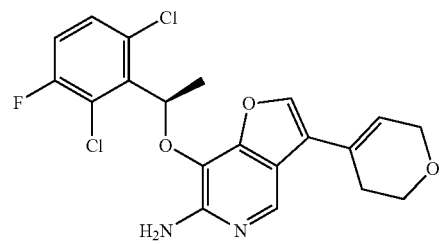

The title compound was prepared according to General procedure A with starting materials 3-Bromo-7-[(R)-1-(2,6-dichloro-3-fluorophenyl)-ethoxy]-furo[3,2-c]pyridin-6-ylamine and 4-(4,4,5,5-Tetramethyl-[1,3,2]dioxaborolan-2-yl)-3,6-dihydro-2H-pyran. ¹H-NMR (CDCl₃, 400 MHz): δ=1.86 (d, 3H), 2.40-2.52 (m, 2H), 3.94 (t, J=5.6 Hz, 2H), 4.36 (q, J=2.5 Hz, 2H), 4.77 (br. s., 2H), 6.24 (br. s., 1H), 6.52 (q, J=6.6 Hz, 1H), 7.01-7.10 (m, 1H), 7.29 (t, 1H), 7.37 (s, 1H), 8.24 (s, 1H). MS (ES⁺): m/z 423.02 (MH⁺, ³⁵Cl, ³⁷Cl), 424.94 (MH⁺, ³⁷Cl, ³⁷Cl). HPLC: t$_R$=3.34 min (polar_5 min, ZQ3).

4-(4,4,5,5-Tetramethyl-[1,3,2]dioxaborolan-2-yl)-3,6-dihydro-2H-pyran

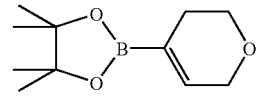

General procedure L: A mixture of Trifluoromethanesulfonic acid 3,6-dihydro-2H-pyran-4-yl ester (0.072 g, 0.31 mmol), bis(pinacolato)diboron (0.118 g, 0.465 mmol), (1,1'Bis-(diphenylphosphino)-ferrocene palladium dichloride (0.034 g, 0.046 mmol) and AcOK (0.0761 g, 0.775 mmol) in 1,4-Dioxane (2 mL) was stirred at 100° C. overnight. The reaction mixture was filtered to remove Pd complex. The resulting mixture was diluted with DCM (20 mg), washed with H₂O (3×15 mL), concentrated under reduced pressure and purified by silica gel (Hexanes:EtOAc 10:1→5:1). The resulting material was used directly in above step.

Trifluoromethanesulfonic Acid 3,6-dihydro-2H-pyran-4-yl Ester

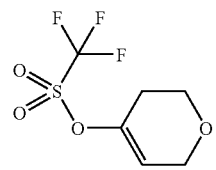

General procedure M: To a freshly prepared LDA solution in THF was added Tetrahydro-4H-pyran-4-one (0.200 g, 2.00 mmol) at −78° C. dropwise. The mixture was warmed up to rt for 30 min and then cooled down to −78° C. again. A solution of N-Phenylbis(trifluoromethanesulfonimide) (0.93 g, 2.60 mmol) in 4 ml THF was dropwise added to the reaction mixture. The resulting mixture was warmed up to rt and stirred for another 3 h. Treated with 30 mL EtOAc, the mixture was washed with H$_2$O (3×20 mL) and brine (10 mL), dried with Na$_2$SO$_4$, concentrated under reduced pressure and purified by chromatography on silica gel (5% EtOAc in Hexanes→20% EtOAc in Hexanes). The product was directly used in next step. $^1$H-NMR (CD$_3$OD, 400 MHz): δ=2.35-2.56 (m, 2H), 3.78-3.93 (m, 2H), 4.23 (q, J=3.0 Hz, 2H), 5.91 (tt, J=2.9, 1.4 Hz, 1H).

Example 139

7-[(R)-1-(2,6-Dichloro-3-fluorophenyl)-ethoxy]-3-(3,6-dihydro-2H-thiopyran-4-yl)-furo[3,2-c]pyridin-6-ylamine

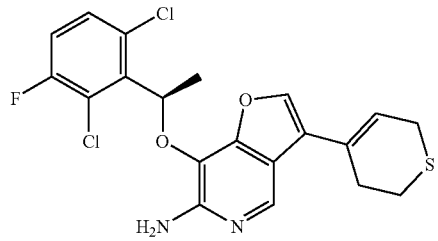

The title compound was prepared according to General procedure A with starting materials 3-Bromo-7-[(R)-1-(2,6-dichloro-3-fluorophenyl)-ethoxy]-furo[3,2-c]pyridin-6-ylamine and 2-(3,6-Dihydro-2H-thiopyran-4-yl)-4,4,5,5-tetramethyl-[1,3,2]dioxaborolane. $^1$H-NMR (CDCl$_3$, 400 MHz): δ=1.79 (d, J=6.8 Hz, 3H), 2.47-2.68 (m, 2H), 2.82 (t, J=5.8 Hz, 2H), 3.20-3.46 (m, 2H), 4.68 (br. s., 2H), 6.31-6.38 (m, 1H), 6.44 (q, J=6.7 Hz, 1H), 6.97 (t, J=8.5 Hz, 1H), 7.30 (s, 1H), 8.14 (s, 1H). MS (ES$^+$): m/z (MH$^+$, $^{35}$Cl, $^{37}$Cl), 440.94 (MH$^+$, $^{37}$Cl, $^{37}$Cl). HPLC: t$_R$=3.69 min (polar_5 min, ZQ3).

2-(3,6-Dihydro-2H-thiopyran-4-yl)-4,4,5,5-tetramethyl-[1,3,2]dioxaborolane

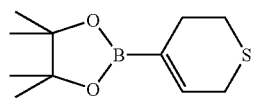

The compound was prepared according to General procedures M and L, using tetrahydrothiopyran-4-one, and directly used in above step.

Example 140

7-[(1R)-1-(2,6-Dichloro-3-fluorophenyl)ethoxy]-3-(1,1-dioxido-3,6-dihydro-2H-thiopyran-4-yl)furo[3,2-c]pyridin-6-amine

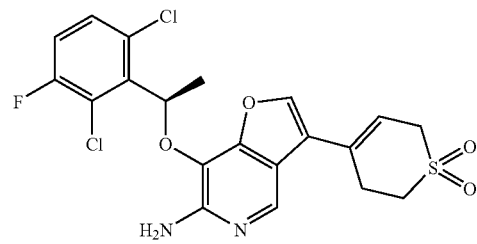

To a solution of 7-[(R)-1-(2,6-Dichloro-3-fluorophenyl)-ethoxy]-3-(3,6-dihydro-2H-thiopyran-4-yl)-furo[3,2-c]pyridin-6-ylamine (0.030 g, 0.068 mmol) in DCM was added m-Chloroperbenzoic acid (0.023 g, 0.13 mmol) at 0° C. The mixture was slowly warmed up to rt and stirred for 3 h. The mixture was diluted with DCM (10 mL), washed with sat. aq. NaHCO$_3$ solution (10 mL), concentrated under reduced pressure and purified by prep TLC (silica gel plates, eluting with 4% MeOH in DCM) to afford the title compound as a yellow solid. $^1$H-NMR (CD$_3$OD, 400 MHz): δ=1.88 (d, J=6.8 Hz, 3H) 3.09 (td, J=6.4, 1.5 Hz, 2H), 3.32-3.37 (m, 2H), 3.90 (d, J=2.0 Hz, 2H), 6.21 (t, J=4.6 Hz, 1H), 6.48 (q, J=6.8 Hz, 1H), 7.15-7.28 (m, 1H), 7.39 (dd, J=9.0, 4.9 Hz, 1H), 7.71 (s, 1H), 8.16 (s, 1H). MS (ES$^+$): m/z 470.94 (MH$^+$, $^{35}$Cl, $^{37}$Cl), 472.92 (MH$^+$, $^{37}$Cl, $^{37}$Cl). HPLC: t$_R$=2.97 min (polar_5 min, ZQ3).

Example 141

4-{6-Amino-7-[(1R)-1-(2,6-dichloro-3-fluorophenyl)ethoxy]furo[3,2-c]pyridin-3-yl}-3,6-dihydropyridine-1(2H)-sulfonamide

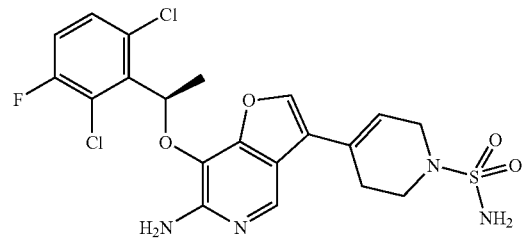

A mixture of 7-[(R)-1-(2,6-Dichloro-3-fluorophenyl)-ethoxy]-3-(1,2,3,6-tetrahydropyridin-4-yl)-furo[3,2-c]pyridin-6-ylamine (0.0300 g, 0.071 mmol) and Sulfamide (0.00819 g, 0.0852 mmol) in 1,4-Dioxane (2 mL) was stirred under reflux for 7 h. The reaction mixture was directly loaded onto prep TLC for purification (silica gel, eluting with 4% MeOH in DCM) to afford the title compound as a yellow solid. $^1$H-NMR (CD$_3$OD, 400 MHz): δ=1.87 (d, J=6.6 Hz, 3H), 2.60 (d, J=1.5 Hz, 2H), 3.36 (t, J=5.7 Hz, 2H), 3.85 (d, J=2.8 Hz, 2H), 6.29 (br. s., 1H), 6.49 (q, 1H), 7.21 (t, J=8.7 Hz, 1H), 7.39 (dd, J=9.0, 4.9 Hz, 1H), 7.64 (s, 1H), 8.19 (s, 1H). MS (ES+): m/z 500.98 (MH+, 35Cl, 37Cl), 502.88 (MH+, 37Cl, 37Cl). HPLC: $t_R$=2.92 min (polar_5 min, ZQ3).

Example 142

1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-2-hydroxyethanone

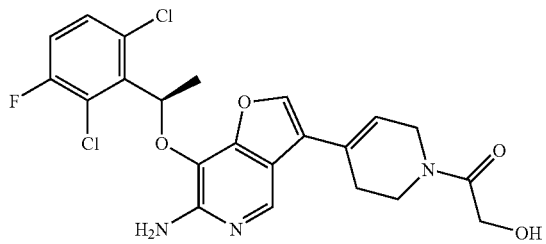

A mixture of 7-[(R)-1-(2,6-Dichloro-3-fluorophenyl)-ethoxy]-3-(1,2,3,6-tetrahydro-pyridin-4-yl)-furo[3,2-c]pyridin-6-ylamine (0.010 g, 0.024 mmol), DIPEA (0.00918 g, 0.071 mmol), TBTU (0.0228 g, 0.071 mmol) in DCM (2 mL) was added Glycolic acid (0.00360 g, 0.0474 mmol) at 0° C. The mixture was stirred for 1 h. The reaction mixture was directly loaded onto Prep TLC for purification (silica gel, eluting with 4% MeOH in DCM) to afford the title compound as a yellow solid. $^1$H-NMR (CD$_3$OD, 400 MHz): δ=1.88 (d, J=6.8 Hz, 3H), 2.53 (d, J=17.2 Hz, 2H), 3.63 (t, J=5.8 Hz, 1H), 3.83 (t, J=5.8 Hz, 1H), 4.12 (d, J=2.0 Hz, 1H), 4.26 (s, 2H), 4.30 (s, 1H), 6.29 (d, 1H), 6.49 (q, J=6.7 Hz, 1H), 7.15-7.25 (m, 1H), 7.39 (dd, J=9.0, 4.9 Hz, 1H), 7.64 (d, J=10.4 Hz, 1H), 8.20 (s, 1H). MS (ES+): m/z 480.01 (MH+, 35Cl, 37Cl), 481.96 (MH+, 37Cl, 37Cl). HPLC: $t_R$=2.76 min (polar_5 min, ZQ3).

Example 143

5-{6-Amino-7-[(R)-1-(2,6-dichloro-3-fluorophenyl)ethoxy]furo[3,2-c]pyridin-3-yl}-3,6-dihydro-2H-pyridine-1-carboxamide

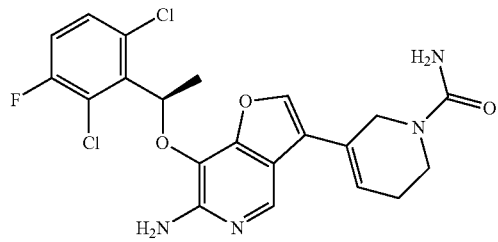

To a solution of 7-[(R)-1-(2,6-Dichloro-3-fluorophenyl)ethoxy]-3-(1,2,5,6-tetrahydropyridin-3-yl)-furo[3,2-c]pyridin-6-ylamine in DCM (5 mL) was added a few drops of Trimethylsilyl isocyanate and stirred at 0° C. for 2 h to afford the title compound as a yellow solid. $^1$H-NMR (CD$_3$OD, 400 MHz): δ=1.88 (d, J=6.8 Hz, 3H), 2.39 (d, J=3.8 Hz, 2H), 3.57 (t, J=5.7 Hz, 2H), 4.18 (d, J=2.0 Hz, 2H), 6.45 (br. s., 1H), 6.50 (q, 1H), 7.21 (t, 1H), 7.39 (dd, J=8.8, 4.8 Hz, 1H), 7.65 (s, 1H), 8.18 (s, 1H). MS (ES+): m/z 465.04 (MH+, 35Cl, 37Cl), 466.96 (MH+, 37Cl, 37Cl). HPLC: $t_R$=2.64 min (polar_5 min, ZQ3).

Example 144

7-[(R)-1-(2,6-Dichloro-3-fluorophenyl)ethoxy]-3-(1,2,5,6-tetrahydropyridin-3-yl)-furo[3,2-c]pyridin-6-ylamine

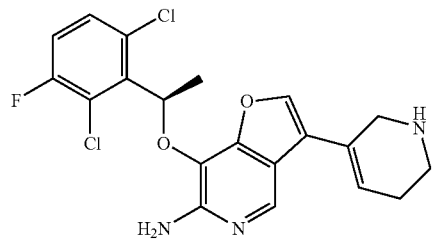

The title compound was prepared according to General procedure A with starting materials 3-Bromo-7-[(R)-1-(2,6-dichloro-3-fluorophenyl)ethoxy]furo[3,2-c]pyridin-6-ylamine and 5-(4,4,5,5-Tetramethyl[1,3,2]dioxaborolan-2-yl)-3,6-dihydro-2H-pyridine-1-carboxylic acid tert-butyl ester. MS (ES+): m/z 422.05 (MH+, 35Cl, 37Cl), 424.06 (MH+, 37Cl, 37Cl).

5-(4,4,5,5-Tetramethyl[1,3,2]dioxaborolan-2-yl)-3,6-dihydro-2H-pyridine-1-carboxylic acid tert-butyl ester

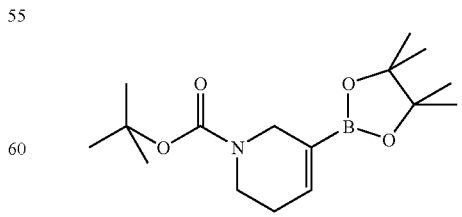

The title compound was prepared according to General procedures M and L, starting from 3-Oxopiperidine-1-carboxylic acid tert-butyl ester. $^1$H-NMR (CDCl$_3$, 400 MHz):

δ=1.38 (s, 9H), 2.01-2.19 (m, 2H), 3.28-3.41 (m, 2H), 3.89 (d, J=2.3 Hz, 2H), 6.55 (br. s., 1H).

Example 145

3-(5-Aminocyclohex-1-enyl)-7-[(R)-1-(2,6-dichloro-3-fluoro-phenyl)ethoxy]furo[3,2-c]pyridin-6-ylamine

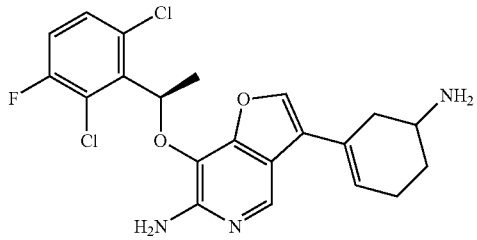

The title compound was prepared according to General procedure A with starting material 3-Bromo-7-[(R)-1-(2,6-dichloro-3-fluorophenyl)ethoxy]furo[3,2-c]pyridin-6-ylamine and the mixture of [3-(4,4,5,5-Tetramethyl[1,3,2]dioxaborolan-2-yl)-cyclohex-3-enyl]-carbamic acid tert-butyl ester and [3-(4,4,5,5-Tetramethyl-[1,3,2]dioxaborolan-2-yl)-cyclohex-2-enyl]-carbamic acid tert-butyl ester. $^1$H-NMR (CD$_3$OD, 400 MHz): δ=1.43-1.59 (m, 1H), 1.86 (d, J=6.8 Hz, 3H), 1.89-1.98 (m, 1H), 2.08-2.22 (m, 1H), 2.28-2.45 (m, 2H), 2.59 (dd, J=16.3, 4.93 Hz, 1H), 2.98-3.14 (m, 1H), 6.25 (br. s., 1H), 6.48 (q, J=6.7 Hz, 1H), 7.15-7.24 (m, 1H), 7.38 (dd, J=9.0, 4.9 Hz, 1H), 7.54 (s, 1H), 8.15 (s, 1H). MS (ES$^+$): m/z 436.03 (MH$^+$, $^{35}$Cl, $^{37}$Cl), 437.97 (MH$^+$, $^{35}$Cl, $^{37}$Cl). HPLC: $t_R$=2.20 min (polar_5 min, ZQ3).

[3-(4,4,5,5-Tetramethyl[1,3,2]dioxaborolan-2-yl)-cyclohex-3-enyl]-carbamic Acid tert-butyl Ester and [3-(4,4,5,5-Tetramethyl-[1,3,2]dioxaborolan-2-yl)-cyclohex-2-enyl]-carbamic acid tert-butyl ester

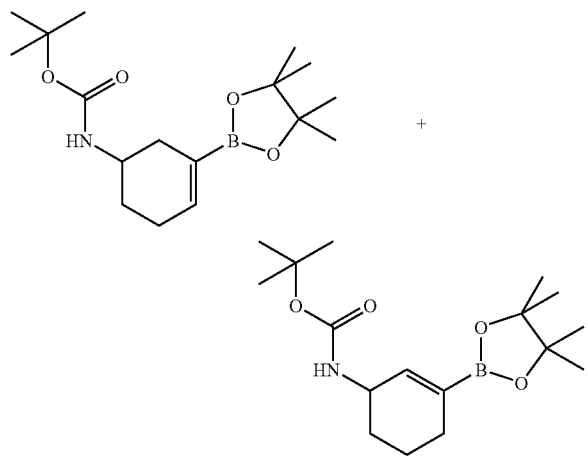

The title compounds were prepared according to General procedures M and L, starting from (3-Oxocyclohexyl)car-bamic acid tert-butyl ester. They were obtained as a mixture that was used directly in the next step Example 146

3-(3-Aminocyclohex-1-enyl)-7-[(R)-1-(2,6-dichloro-3-fluoro-phenyl)ethoxy]furo[3,2-c]pyridin-6-ylamine

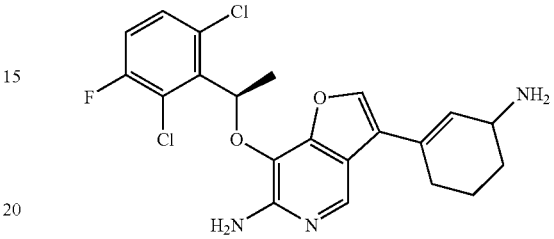

The title compound was prepared according to General procedure A with starting material 3-Bromo-7-[(R)-1-(2,6-dichloro-3-fluorophenyl)ethoxy]furo[3,2-c]pyridin-6-ylamine and the mixture of [3-(4,4,5,5-Tetramethyl[1,3,2]dioxaborolan-2-yl)-cyclohex-3-enyl]-carbamic acid tert-butyl ester and [3-(4,4,5,5-Tetramethyl-[1,3,2]dioxaborolan-2-yl)-cyclohex-2-enyl]-carbamic acid tert-butyl ester. $^1$H-NMR (CD$_3$OD, 400 MHz): δ=1.48-1.82 (m, 2H), 1.88 (d, 3H), 1.91-2.16 (m, 2H), 2.38 (d, J=5.3 Hz, 2H), 3.72 (br. s., 1H), 6.21 (br. s., 1H), 6.48 (qd, J=6.7, 2.5 Hz, 1H), 7.02-7.14 (m, 1H), 7.38 (dd, J=8.8, 4.8 Hz, 1H), 7.63 (s, 1H), 8.22 (s, 1H). MS (ES$^+$): m/z 436.03 (MH$^+$, $^{35}$Cl, $^{37}$Cl), 437.96 (MH$^+$, $^{37}$Cl, $^{37}$Cl). HPLC: $t_R$=2.38 min (polar_5 min, ZQ3).

Example 147

4-{6-Amino-7-[(1R)-1-(2,6-dichloro-3-fluorophenyl)ethoxy]furo[3,2-c]pyridin-3-yl}-N-phenyl-3,6-dihydropyridine-1(2H)-carboxamide

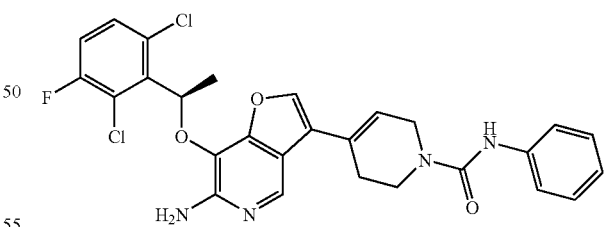

A mixture of 7-[(R)-1-(2,6-Dichloro-3-fluorophenyl)-ethoxy]-3-(1,2,3,6-tetrahydropyridin-4-yl)-furo[3,2-c]pyridin-6-ylamine (10.0 mg, 0.0237 mmol), phenyl isocyanate (0.00519 g, 0.0436 mmol), DIPEA (0.033 mL, 0.19 mmol) in DMF (1 mL) was stirred at rt for 15 min. Purification by HPLC afforded the title compound as a colorless solid. $^1$H NMR (CD$_3$OD, 400 MHz): δ=1.90 (d, J=6.8 Hz, 3H), 2.58 (br. s., 2H), 3.77 (t, J=5.7 Hz, 2H), 4.25 (d, J=2.5 Hz, 2H), 6.32 (br. s., 1H), 6.52 (d, J=6.8 Hz, 1H), 7.04 (t, J=7.3 Hz, 1H), 7.17-7.32 (m, 3H), 7.34-7.46 (m, 3H) 7.69 (s, 1H), 8.23

(s, 1H). MS (ES+): m/z 541.03/543.05 (100/68) [MH+]. HPLC: $t_R$=3.39 min (ZQ3, polar_5 min).

Example 148

4-{6-Amino-7-[(1R)-1-(2,6-dichloro-3-fluorophenyl)ethoxy]furo[3,2-c]pyridin-3-yl}-N-tert-butyl-3,6-dihydropyridine-1(2H)-carboxamide

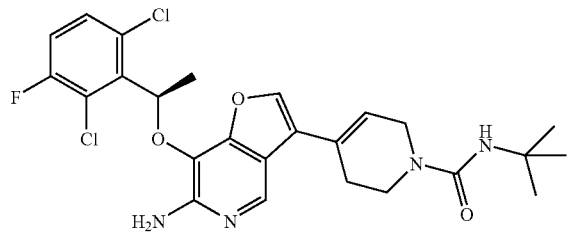

A mixture of 7-[(R)-1-(2,6-Dichloro-3-fluorophenyl)ethoxy]-3-(1,2,3,6-tetrahydropyridin-4-yl)-furo[3,2-c]pyridin-6-ylamine (10.0 mg, 0.0237 mmol), tert-butyl isocyanate (0.0042 g, 0.043 mmol), DIPEA (33 µL, 0.19 mmol) in DMF (1 mL) was stirred at rt for 15 min. Purification by HPLC afforded the title compound as a colorless solid. $^1$H NMR (400 MHz, CD$_3$OD): δ=1.36 (s, 9H), 1.89 (d, J=6.8 Hz, 3H), 2.49 (br. s., 2H), 3.59 (t, J=5.7 Hz, 2H), 4.04 (d, J=2.5 Hz, 2H), 6.25 (br. s., 1H), 6.48-6.53 (m, 1H), 7.22 (t, J=8.7 Hz, 1H), 7.40 (dd, J=9.0, 4.9 Hz, 1H), 7.65 (s, 1H), 8.20 (s, 1H). MS (ES+): m/z 521.07/523.09 (100/72) [MH+]. HPLC: $t_R$=3.37 min (ZQ3, polar_5 min).

Example 149

4-{6-Amino-7-[(1R)-1-(2,6-dichloro-3-fluorophenyl)ethoxy]furo[3,2-c]pyridin-3-yl}-N-(propan-2-yl)-3,6-dihydropyridine-1(2H)-carboxamide

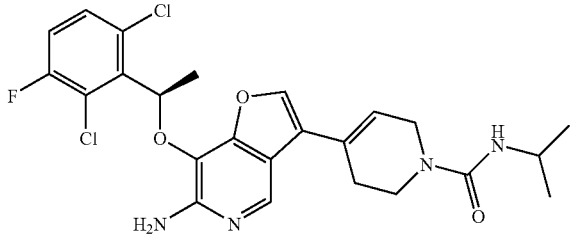

To a flask were added 7-[(R)-1-(2,6-Dichloro-3-fluorophenyl)ethoxy]-3-(1,2,3,6-tetrahydropyridin-4-yl)-furo[3,2-c]pyridin-6-ylamine (10.0 mg, 0.0237 mmol), isopropyl isocyanate (0.00371 g, 0.0436 mmol), DIPEA (33 µL, 0.19 mmol) and DMF (1 mL) and the reaction mixture was stirred at rt for 15 min. Purification by HPLC followed by prep TLC in 5% NH$_3$ in DCM afforded the title compound. $^1$H NMR (400 MHz, CD$_3$OD): δ=1.17 (d, J=6.6 Hz, 6H), 1.88 (d, J=6.8 Hz, 3H), 2.49 (br. s., 2H), 3.63 (t, J=5.7 Hz, 2H), 3.87-3.99 (m, 1H), 4.06 (d, J=2.5 Hz, 2H), 6.13 (d, J=7.6 Hz, 1H), 6.25 (br. s., 1H), 6.49 (d, J=6.8 Hz, 1H), 7.21 (t, J=8.6 Hz, 1H), 7.39 (dd, J=9.0, 4.9 Hz, 1H), 7.63 (s, 1H). MS (ES+): m/z 507.04/509.06 (100/71) [MH+]. HPLC: $t_R$=3.14 min (ZQ3, polar_5 min).

Example 150

4-{6-Amino-7-[(1R)-1-(2,6-dichloro-3-fluorophenyl)ethoxy]furo[3,2-c]pyridin-3-yl}-N-(2-fluorophenyl)-3,6-dihydropyridine-1(2H)-carboxamide

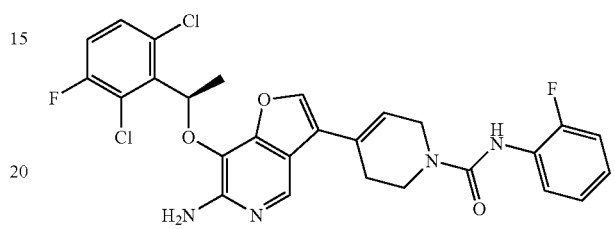

A mixture of 7-[(R)-1-(2,6-dichloro-3-fluorophenyl)ethoxy]-3-(1,2,3,6-tetrahydropyridin-4-yl)-furo[3,2-c]pyridin-6-ylamine (10.0 mg, 0.0237 mmol), 2-fluorophenyl isocyanate (0.00597 g, 0.0436 mmol), DIPEA (0.033 mL, 0.19 mmol) in DMF (1 mL) was stirred at rt for 3 h. Purification by HPLC afforded the title compound. $^1$H NMR (400 MHz, CD$_3$OD): δ=1.89 (d, J=6.8 Hz, 3H), 2.58 (br. s., 2H), 3.69-3.80 (m, 2H), 4.25 (d, J=2.5 Hz, 2H), 6.31 (br. s., 1H), 6.51 (q, J=6.7 Hz, 1H), 7.08-7.16 (m, 3H), 7.22 (t, J=8.7 Hz, 1H), 7.40 (dd, J=9.0, 4.9 Hz, 1H), 7.45-7.52 (m, 1H), 7.68 (s, 1H), 8.22 (s, 1H). MS (ES+): m/z 559.05/561.04 (100/75) [MH+]. HPLC: $t_R$=3.42 min (ZQ3, polar_5 min).

Example 151

4-{6-Amino-7-[(1R)-1-(2,6-dichloro-3-fluorophenyl)ethoxy]furo[3,2-c]pyridin-3-yl}-N-ethyl-3,6-dihydropyridine-1(2H)-carboxamide

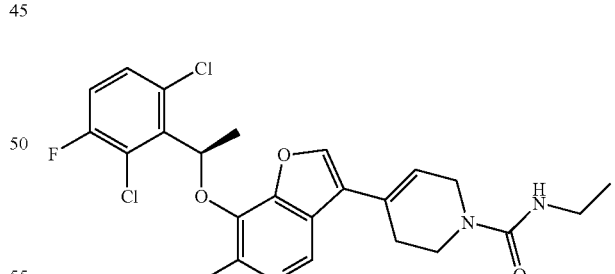

A mixture of 7-[(R)-1-(2,6-dichloro-3-fluorophenyl)ethoxy]-3-(1,2,3,6-tetrahydro-pyridin-4-yl)furo[3,2-c]pyridin-6-ylamine (10.0 mg, 0.0237 mmol), ethyl isocyanate (0.00310 g, 0.0436 mmol), DIPEA (0.033 mL, 0.19 mmol) in DMF (1 mL) was stirred at rt for 15 min. Purification by HPLC afforded the title compound as a colorless solid. $^1$H NMR (400 MHz, CD$_3$OD): δ=1.13 (t, J=7.2 Hz, 3H), 1.87 (d, J=6.8 Hz, 3H), 2.48 (br. s., 2H), 3.22 (q, J=7.1 Hz, 2H), 3.62 (t, J=5.8 Hz, 2H), 4.06 (d, J=2.5 Hz, 2H), 6.25 (br. s., 1H), 6.43-6.56 (m, 1H), 7.21 (t, J=8.7 Hz, 1H), 7.39 (dd, J=9.0, 4.9

Hz, 1H), 7.65 (s, 1H), 8.16 (s, 1H). MS (ES+): m/z 493.02/495.04 (100/68) [MH+]. HPLC: $t_R$=2.95 min (ZQ3, polar_5 min).

Example 152

4-{6-Amino-7-[(1R)-1-(2,6-dichloro-3-fluorophenyl)ethoxy]furo[3,2-c]pyridin-3-yl}-N-(2-chlorophenyl)-3,6-dihydropyridine-1(2H)-carboxamide

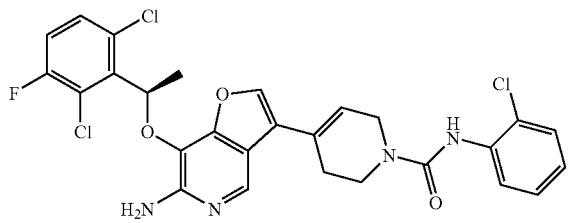

A mixture of 7-[(R)-1-(2,6-Dichloro-3-fluorophenyl)ethoxy]-3-(1,2,3,6-tetrahydropyridin-4-yl)-furo[3,2-c]pyridin-6-ylamine (10.0 mg, 0.0237 mmol), 2-chlorophenylisocyanate (0.00669 g, 0.0436 mmol), DIPEA (0.033 mL, 0.19 mmol) in DMF (1 mL) was stirred at rt for 15 min. Purification by HPLC afforded the title compound as a light yellow solid. $^1$H NMR (400 MHz, CD$_3$OD): δ=1.89 (d, J=6.6 Hz, 3H), 2.59 (br. s., 2H), 3.78 (t, J=5.8 Hz, 2H), 4.28 (d, J=2.5 Hz, 2H), 6.32 (br. s., 1H), 6.45-6.55 (m, 1H), 7.08-7.17 (m, 1H), 7.18-7.32 (m, 2H), 7.36-7.46 (m, 2H), 7.60 (dd, J=8.1, 1.5 Hz, 1H), 7.69 (s, 1H), 8.23 (br. s., 1H). MS (ES+): m/z 575.03/577.01 (98/100) [MH+]. HPLC: $t_R$=3.63 min (ZQ3, polar_5 min).

Example 153

3-(8-Azabicyclo[3.2.1]oct-2-en-3-yl)-7-[(1R)-1-(2,6-dichloro-3-fluorophenyl)ethoxy]furo[3,2-c]pyridin-6-amine

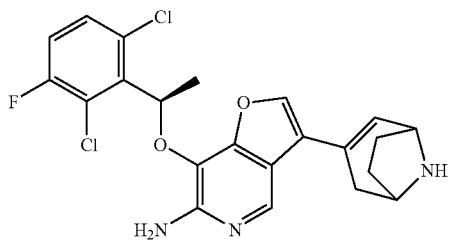

In a microwave vessel were added 3-(4,4,5,5-tetramethyl-[1,3,2]dioxaborolan-2-yl)-8-azabicyclo[3.2.1]oct-2-ene-8-carboxylic acid tert-butyl ester (60 mg, 0.2 mmol), 3-bromo-7-[(R)-1-(2,6-dichloro-3-fluorophenyl)ethoxy]-furo[3,2-c]pyridin-6-ylamine (0.098 g, 0.23 mmol), potassium carbonate (0.074 g, 0.54 mmol), DME/Water (4:1) (5 mL), and the vessel was degassed 3×. Pd(PPh$_3$)$_4$ (0.01 g, 0.009 mmol) was then added and the reaction mixture was heated in a microwave reactor to 100° C. for 30 min. The crude reaction mixture was passed through SPE cartridge. The compound was then dissolved in dioxane and 4 M HCl in 1,4-Dioxane (0.4 mL) was added slowly at 0° C. The reaction mixture was warmed to rt and stirred overnight at rt. Purification by prep TLC using 9% NH$_3$ in MeOH in DCM afforded the title compound. $^1$H NMR (400 MHz, CD$_3$OD): δ=1.64-1.77 (m, 1H), 1.85 (d, 3H), 1.89-1.98 (m, 1H), 2.01-2.12 (m, 2H), 2.18 (d, J=16.9 Hz, 1H), 2.88 (dd, J=16.8, 4.2 Hz, 1H), 3.82 (ddd, J=17.1, 5.8, 5.7 Hz, 2H), 6.46 (q, 1H), 6.52 (d, J=5.6 Hz, 1H), 7.19 (t, J=8.6 Hz, 1H), 7.37 (dd, J=9.0, 4.9 Hz, 1H), 7.54 (s, 1H), 8.16 (s, 1H). MS (ES+): m/z 447.97/450.01 (30/21) [MH+]. HPLC: $t_R$=2.14 min (ZQ3, polar_5 min).

3-(4,4,5,5-Tetramethyl-[1,3,2]dioxaborolan-2-yl)-8-azabicyclo[3.2.1]oct-2-ene-8-carboxylic acid tert-butyl ester

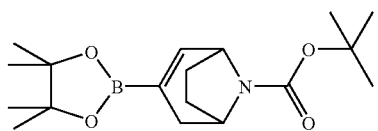

The title compound was prepared from N-Boc-nortropinone according to General procedures M and L.

Example 154

7-[1-(2,6-Dichloro-3,5-difluorophenyl)ethoxy]-3-[1-(piperidin-4-yl)-1H-pyrazol-4-yl]furo[3,2-c]pyridin-6-amine

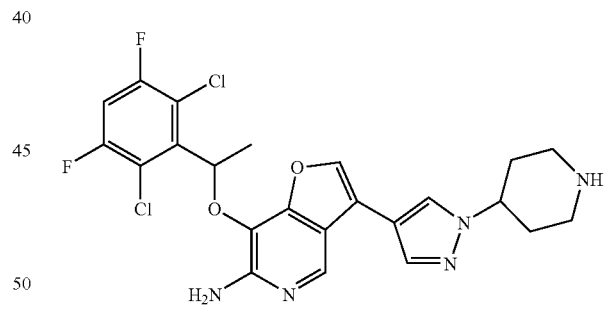

Into a round bottom flask were added tert-Butyl 4-(4-{6-amino-7-[1-(2,6-dichloro-3,5-difluorophenyl)ethoxy]furo[3,2-c]pyridin-3-yl}-1H-pyrazol-1-yl)piperidine-1-carboxylate (12.0 mg, 0.0197 mmol) and 1,4-Dioxane (3.0 mL, 38 mmol). 4 M HCl in 1,4-Dioxane (0.2 mL) was added slowly at 0° C. and the reaction mixture was stirred at rt (1 h), 30° C. (2 h), and 45-50° C. until completion. The reaction mixture was passed through SCX-2 and then purified by HPLC to afford the title compound. $^1$H NMR (400 MHz, CD$_3$OD): δ=1.91 (d, J=6.8 Hz, 3H), 2.15-2.41 (m, 4H), 3.10-3.27 (m, 2H), 3.46-3.63 (m, 2H), 4.50-4.67 (m, 1H), 6.54 (q, J=6.7 Hz, 1H), 7.34 (t, J=8.7 Hz, 1H), 7.78 (s, 1H), 7.87 (s, 1H), 8.12 (s, 2H), 8.16 (s, 1H). MS (ES+): m/z 507.95/509.96 (40/24) [MH+]. HPLC: $t_R$=2.56 min (ZQ3, polar_5 min).

135 tert-Butyl 4-(4-{6-amino-7-[1-(2,6-dichloro-3,5-difluorophenyl)ethoxy]furo[3,2-c]pyridin-3-yl}-1H-pyrazol-1-yl)piperidine-1-carboxylate

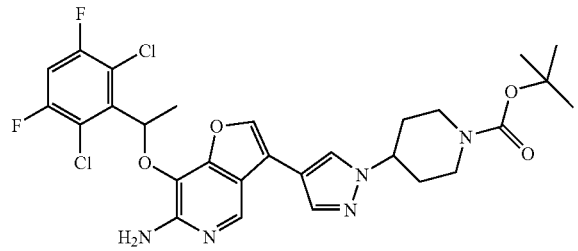

Into a round bottom flask were added tert-Butyl 4-(4-{7-[1-(2,6-dichloro-3,5-difluorophenyl)ethoxy]-6-nitrofuro[3,2-c]pyridin-3-yl}-1H-pyrazol-1-yl)piperidine-1-carboxylate (220 mg, 0.34 mmol), iron (192 mg, 3.44 mmol), 2 drops of 0.1 M HCl and EtOH (7 mL), and the reaction mixture was refluxed for 30 min. 0.1 M HCl was added dropwise and reaction refluxed until consumption of SM was observed. Reaction was stopped and filtered through silica gel washing with 5% MeOH in DCM. Reaction mixture was concentrated in vacuo to obtain the title compound. MS (ES+): m/z 608.06/610.07 (100/70) [MH$^+$]. HPLC: $t_R$=3.74 min (ZQ3, polar_5 min).

tert-Butyl 4-(4-{7-[1-(2,6-dichloro-3,5-difluorophenyl)ethoxy]-6-nitrofuro[3,2-c]pyridin-3-yl}-1H-pyrazol-1-yl)piperidine-1-carboxylate

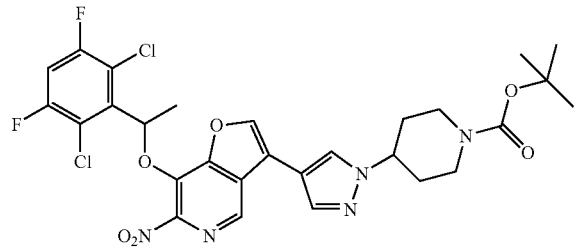

1-(2,6-Dichloro-3,5-difluorophenyl)ethanol (133 mg, 0.586 mmol), 4-[4-(7-Hydroxy-6-nitrofuro[3,2-c]pyridin-3-yl)-pyrazol-1-yl]-piperidine-1-carboxylic acid tert-butyl ester (250 mg, 0.52 mmol), PPh$_3$ (410 mg, 1.60 mmol) and THF (20 mL) was added to a dry round bottom flask. Diisopropyl azodicarboxylate (320 mg, 1.60 mmol) was added and the reaction mixture was heated at 40° C. More DIAD (320 mg, 1.60 mmol) was then added and the reaction mixture was heated at 40° C. for 2 h. Purification by flash column chromatography using 10%→40% EtOAc in hexanes afforded the title compound as a yellow solid. MS (ES+): m/z 581.88/583.80 (100/80) [MH$^+$–isobutene]. HPLC: $t_R$=4.29 min (ZQ3, polar_5 min).

136

Example 155

7-{1-[3-(3-Aminopropoxy)-2,6-dichloro-5-fluorophenyl]ethoxy}-3-[1-(piperidin-4-yl)-1H-pyrazol-4-yl]furo[3,2-c]pyridin-6-amine

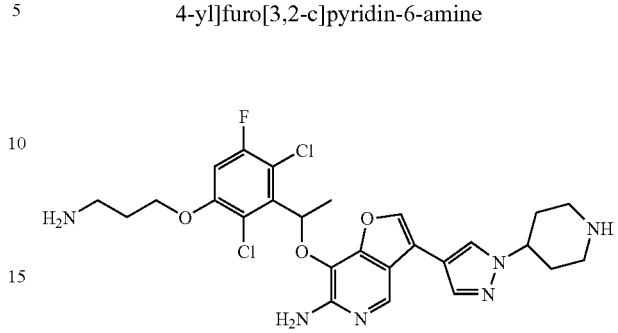

In a round bottom flask were added 3-(Boc-amino)-1-propanol (300 mg, 2.0 mmol), sodium hydride (33 mg, 0.0014 mol) and THF (1.0 mL) and the reaction mixture was stirred until gas evolution stopped. [4-(4-6-Amino-7-[1-(2,6-dichloro-3,5-difluorophenyl)ethoxy]furo[3,2-c]pyridin-3-ylpyrazol-1-yl)-piperidine-1-carboxylic acid tert-butyl ester (24 mg, 0.039 mmol) was added slowly at 0° C. Reaction was stirred for 2 h at rt and at 30° C. for 1.5 h. Additional sodium salt of 3-(boc-amino)-1-propanol (6 eq.) was added to the reaction mixture, the temperature was raised to 40° C., and the reaction mixture was stirred for 1 h. 6 eq more of the sodium salt of 3-(boc-amino)-1-propanol was added and stirring was continued for another hour. The reaction mixture was passed through SPE SCX-2 and concentrated in vacuo. The compound was taken up in 1,4-Dioxane (0.6 mL, 0.008 mol) and 4 M HCl in 1,4-Dioxane (0.4 mL) was added slowly at 0° C. Reaction mixture was stirred at rt for 1 h and for 2.5 h at 35-40° C. Purification by HPLC afforded the title compound as a light yellow solid. $^1$H NMR (400 MHz, CD$_3$OD): δ=1.89 (d, J=6.8 Hz, 3H), 2.19 (dq, J=6.7, 6.4 Hz, 2H), 2.25-2.39 (m, 4H), 3.11-3.20 (m, 2H), 3.20-3.27 (m, 2H), 3.47-3.65 (m, 2H), 4.17 (t, J=5.7 Hz, 2H), 4.51-4.68 (m, 1H), 6.63 (q, J=6.7 Hz, 1H), 7.11 (d, J=10.6 Hz, 1H), 7.81 (s, 1H), 7.87 (s, 1H), 8.13 (d, J=11.4 Hz, 2H). MS (ES+): m/z 563.01/565.03 (20/14) [MH$^+$]. HPLC: $t_R$=2.10 min (ZQ3, polar_5 min).

Example 156

7-(1-{2,6-Dichloro-3-[3-(dimethylamino)propoxy]-5-fluorophenyl}ethoxy)-3-[1-(piperidin-4-yl)-1H-pyrazol-4-yl]furo[3,2-c]pyridin-6-amine

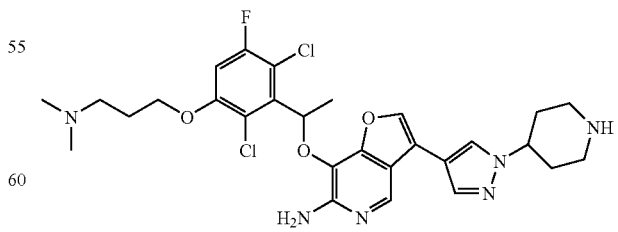

The procedure for example 155 was followed. Purification by HPLC afforded the title compound as a light yellow solid. $^1$H NMR (400 MHz, CD$_3$OD): δ=1.89 (d, J=6.8 Hz, 3H), 2.18-2.42 (m, 6H), 2.90 (s, 6H), 3.10-3.27 (m, 2H), 3.32-3.37

(m, 2H), 3.58 (d, J=13.1 Hz, 2H), 4.16 (t, J=5.6 Hz, 2H), 4.53-4.68 (m, 1H), 6.62 (q, J=6.7 Hz, 1H), 7.11 (d, J=10.4 Hz, 1H), 7.81 (s, 1H), 7.88 (s, 1H), 8.13 (d, J=12.1 Hz, 2H). MS (ES+): m/z 591.04/593.04 (10/7) [MH$^+$]. HPLC: $t_R$=2.09 min (ZQ3, polar_5 min).

Example 157

7-(1-{2,6-Dichloro-3-[2-(dimethylamino)ethoxy]-5-fluorophenyl}ethoxy)-3-[1-(piperidin-4-yl)-1H-pyrazol-4-yl]furo[3,2-c]pyridin-6-amine

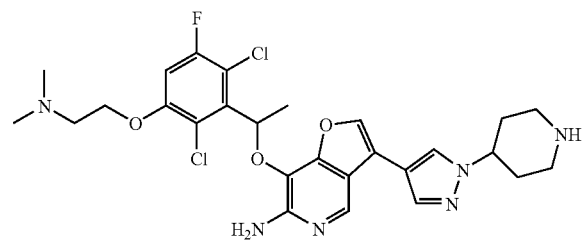

The procedure for example 155 was followed. Purification by HPLC afforded the title compound as a light yellow solid. MS (ES+): m/z 577.02/579.04 (30/21) [MH$^+$]. HPLC: $t_R$=1.93 min (Open Lynx polar_5 min).

Example 158

7-{1-[2,6-Dichloro-3-fluoro-5-(piperidin-4-yloxy)phenyl]ethoxy}-3-[1-(piperidin-4-yl)-1H-pyrazol-4-yl]furo[3,2-c]pyridin-6-amine

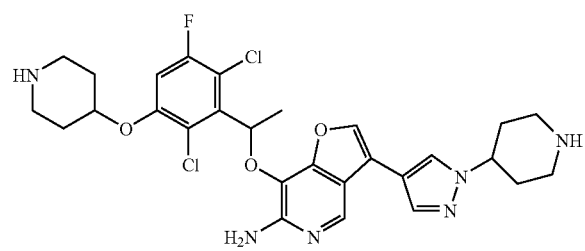

The procedure for example 155 was followed. Purification by HPLC afforded the title compound as a light yellow solid. $^1$H NMR (400 MHz, CD$_3$OD): δ=1.90 (d, J=6.8 Hz, 3H), 1.98-2.21 (m, 4H), 2.27-2.43 (m, 4H), 3.13-3.28 (m, 4H), 3.34-3.43 (m, 2H), 3.51-3.65 (m, 2H), 4.61 (td, J=9.7, 4.9 Hz, 1H), 4.74-4.82 (m, 1H), 6.61 (q, J=6.7 Hz, 1H), 7.23 (d, J=10.6 Hz, 1H), 7.80 (s, 1H), 7.88 (s, 1H), 8.03-8.22 (m, 2H). MS (ES+): m/z 589.00/591.01 (20/15) [MH$^+$]. HPLC: $t_R$=2.12 min (ZQ3, polar_5 min).

Example 159

7-{1-[3-(Azetidin-3-yloxy)-2,6-dichloro-5-fluorophenyl]ethoxy}-3-[1-(piperidin-4-yl)-1H-pyrazol-4-yl]furo[3,2-c]pyridin-6-amine

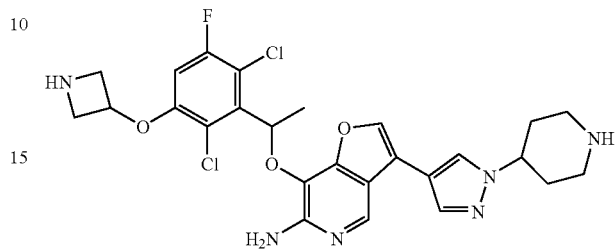

The procedure for example 155 was followed. $^1$H NMR (400 MHz, CD$_3$OD): δ=1.89 (d, J=6.8 Hz, 3H), 2.22-2.39 (m, 4H), 3.08-3.27 (m, 2H), 3.49-3.63 (m, 2H), 4.19 (dd, J=12.4, 4.6 Hz, 2H), 4.49-4.66 (m, 3H), 5.08-5.23 (m, 1H), 6.63 (q, J=6.8 Hz, 1H), 6.93 (d, J=10.1 Hz, 1H), 7.81 (s, 1H), 7.88 (s, 1H), 8.13 (d, J=12.9 Hz, 2H). MS (ES+): m/z 560.98/563.00 (20/14) [MH$^+$]. HPLC: $t_R$=2.08 min (ZQ3, polar_5 min).

Example 160

[4-{6-Amino-7-[(1R)-1-(2,6-dichloro-3-fluorophenyl)ethoxy]furo[3,2-c]pyridin-3-yl}-3,6-dihydropyridin-1(2H)-yl][(2S)-2-methylpyrrolidin-2-yl]methanone

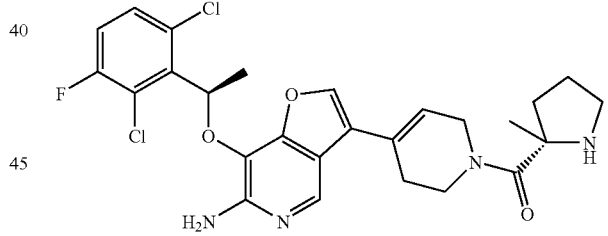

A mixture of 7-[(R)-1-(2,6-Dichloro-3-fluorophenyl)-ethoxy]-3-(1,2,3,6-tetrahydropyridin-4-yl)furo[3,2-c]pyridin-6-ylamine (150 mg, 0.36 mmol), (S)-2-Methylpyrrolidine-1,2-dicarboxylic acid 1-tert-butyl ester (98 mg, 0.43 mmol), TBTU (171 mg, 0.533 mmol), DIPEA (0.30 mL, 2.0 mmol) and DMF (10 mL) was stirred at 50° C. for 3 h. Reaction mixture was concentrated in vacuo, and the residue was taken up with DCM, washed with H$_2$O, dried over sodium sulfate, filtered, and concentrated in vacuo. Purification of the residue by flash column chromatography using 1→4% NH$_3$ in MeOH in DCM afforded an oil that was dissolved in 1,4-dioxane (2.0 mL). 4 M HCl in 1,4-Dioxane (0.9 mL) was added to the solution and the reaction mixture was stirred at 40° C. for 1 h and at 60° C. for 3 h. Purification of the crude material by prep TLC (eluting with NH$_3$/MeOH/DCM) afforded the title compound as a light yellow solid. The compound was dissolved in DCM and 2 M of HCl in Et$_2$O (4 mL) was added to the reaction mixture. The reaction mixture was concentrated in vacuo to afford the title compound as HCl salt. ¹H NMR (400 MHz, CD₃OD): δ=1.46 (s, 3H), 1.66-1.84 (m, 2H), 1.88 (d, J=6.8 Hz, 3H), 2.20 (br. s., 2H), 2.55 (br. s., 2H), 2.73-3.00 (m, 2H), 3.68-3.98 (m, 2H), 4.30 (br. s., 2H), 6.30 (br. s., 1H), 6.49 (q, J=6.7 Hz, 1H), 7.22 (t, J=8.7 Hz, 1H), 7.40 (dd, J=8.8, 4.8 Hz, 1H), 7.65 (s, 1H), 8.20 (s, 1H). MS (ES+): m/z 533.08/535.09 (100/69) [MH⁺]. HPLC: t$_R$=2.45 min.

Example 161

7-[(1R)-1-(2,6-dichloro-3-fluorophenyl)ethoxy]-3-{1-[(3S)-pyrrolidin-3-yl]-1H-pyrazol-4-yl}furo[3,2-c]pyridin-6-amine

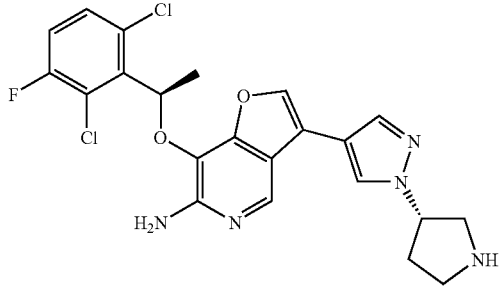

A mixture of 3-bromo-7-[(R)-1-(2,6-dichloro-3-fluorophenyl)ethoxy]furo[3,2-c]pyridin-6-ylamine (20 mg, 0.048 mmol), (S)-3-[4-(4,4,5,5-tetramethyl-1,3,2-dioxaborolan-2-yl)pyrazol-1-yl]pyrrolidine-1-carboxylic acid tert-butyl ester (26 mg, 0.071 mmol) and potassium carbonate (20 mg, 0.10 mmol) in 1,4-dioxane (2 mL) and H₂O (0.5 mL) was stirred at 100° C. for 30 min in the microwave reactor. Then, the mixture was passed through PL-Thiol MP SPE+ resin and concentrated in vacuo. The resulting solid was left to stir in DCM (0.2 mL) and TFA (0.2 mL) at rt for 30 min. Purification via MDP afforded the title compound as a white solid. MS (ES+): m/z: 475.96/477.94 (70/50) [MH⁺]. HPLC: t$_R$=2.35 min (ZQ3, polar_5 min). ¹H NMR (400 MHz, CD₃OD): δ 1.89 (d, J=6.6 Hz, 3H), 2.40 (ddd, J=13.9, 7.6, 3.3 Hz, 1H), 2.50-2.62 (m, 1H), 3.50 (ddd, J=11.5, 8.8, 4.4 Hz, 1H), 3.63-3.73 (m, 2H), 3.75-3.82 (m, 1H), 5.28 (q, J=6.4 Hz, 1H), 6.53 (q, J=6.8 Hz, 1H), 7.21 (t, J=8.6 Hz, 1H), 7.39 (dd, J=8.9, 4.9 Hz, 1H), 7.79 (s, 1H), 7.89 (s, 1H), 8.14 (d, J=4.8 Hz, 2H).

(S)-3-[4-(4,4,5,5-tetramethyl-1,3,2-dioxaborolan-2-yl)-pyrazol-1-yl]-pyrrolidincarboxylic acid tert-butyl ester

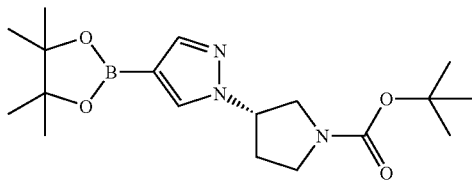

A solution of 4-(4,4,5,5-tetramethyl[1,3,2]dioxaborolan-2-yl)-1H-pyrazole (0.375 g, 1.93 mmol), (R)-3-methanesulfonyloxypyrrolidine-1-carboxylic acid tert-butyl ester (0.513 g, 1.93 mmol), C₂CO₃ (0.943 g, 2.90 mmol) in anhydrous DMF (5.13 mL) was heated to 100° C. for 6 h. The reaction mixture was partitioned between EtOAc and H₂O and separated and the aqueous was re-extracted with EtOAc (3×) and the combined organic fractions were washed with H₂O (3×), brine (2×), dried over Na₂SO₄, filtered and concentrated in vacuo resulting in a crude brown oil. The crude was purified by chromatography on silica gel [eluting with 12% EtOAc in CHCl₃] resulting in the title compound as a viscous oil. ¹H NMR (400 MHz, CDCl₃) δ 1.32 (s, 12H), 1.47 (s, 9H), 2.36 (q, J=7.0 Hz, 2H), 3.46-3.79 (m, 3H), 3.81-3.92 (m, 1H), 4.90 (quint, J=6.1 Hz, 1H), 7.73 (s, 1H), 7.81 (s, 1H).

(R)-3-methanesulfonyloxy-pyrrolidine-1-carboxylic acid tert-butyl ester

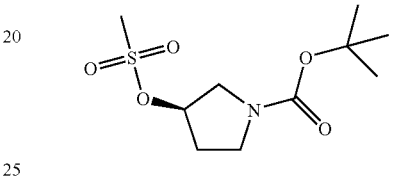

A solution of (R)-3-hydroxypyrrolidine-1-carboxylic acid tert-butyl ester (0.500 g, 2.67 mmol) in DCM (6.7 mL) was cooled to 0° C. and charged with triethylamine (0.45 mL, 3.20 mmol), methanesulfonyl chloride (0.23 mL, 2.90 mmol), and 4-dimethylaminopyridine (3.0 mg, 0.03 mmol) and stirred at rt for 6 h. The reaction mixture was partitioned between CHCl₃ and sat. NaHCO₃ and separated. The aqueous was re-extracted with CHCl₃ (3×) and the combined organic fractions were washed with sat. NaHCO₃ (2×), brine (2×), dried over Na₂SO₄, filtered and concentrated in vacuo resulting in the title compound as a pale yellow oil. This material was taken on to the next step without further purification. ¹H NMR (400 MHz, CDCl₃) δ 1.47 (s, 9H), 2.06-2.39 (m, 2H), 3.05 (s, 3H), 3.38-3.82 (m, 4H), 5.27 (t, J=4.4 Hz, 1H).

Example 162

7-[(1R)-1-(2,6-dichloro-3-fluorophenyl)ethoxy]-3-{1-[(3R)-pyrrolidin-3-yl]-1H-pyrazol-4-yl}furo[3,2-c]pyridin-6-amine

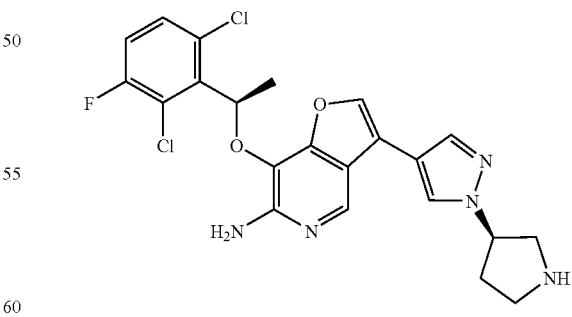

The procedure for example 161 was followed except for replacing (S)-3-[4-(4,4,5,5-tetramethyl-1,3,2-dioxaborolan-2-yl)pyrazol-1-yl]pyrrolidine-1-carboxylic acid tert-butyl ester with (R)-3-[4-(4,4,5,5-tetramethyl-1,3,2-dioxaborolan-2-yl)pyrazol-1-yl]pyrrolidine-1-carboxylic acid tert-butyl ester. Purification via MDP afforded the title compound as a white solid. MS (ES+): m/z 475.96/477.94 (40/30) [MH+]. HPLC: $t_R$=2.53 min (ZQ3, polar_5 min). $^1$H NMR (400 MHz, CD$_3$OD) δ 1.89 (d, J=6.8 Hz, 3H), 2.40 (ddd, J=13.9, 7.6, 3.3 Hz, 1H), 2.49-2.62 (m, 1H), 3.48 (ddd, J=8.9, 7.1, 4.4 Hz, 1H), 3.61-3.71 (m, 2H), 3.73-3.80 (m, 1H), 5.27 (q, J=6.5 Hz, 1H), 6.54 (q, J=6.6 Hz, 1H), 7.21 (t, J=8.6 Hz, 1H), 7.40 (dd, J=8.9, 4.9 Hz, 1H), 7.79 (s, 1H), 7.89 (s, 1H), 8.14 (d, J=4.3 Hz, 2H).

(R)-3-[4-(4,4,5,5-tetramethyl-1,3,2-dioxaborolan-2-yl)-pyrazol-1-yl]-pyrrolidincarboxylic acid tert-butyl ester

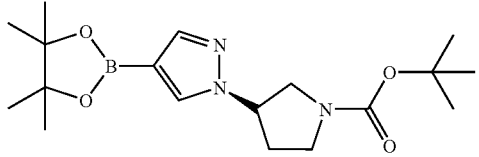

A solution of 4-(4,4,5,5-tetramethyl[1,3,2]dioxaborolan-2-yl)-1H-pyrazole (0.856 g, 4.41 mmol), (S)-3-methanesulfonyloxy-pyrrolidine-1-carboxylic acid tert-butyl ester (1.17 g, 4.41 mmol) and Cs$_2$CO$_3$ (2.16 g, 6.61 mmol) in anhydrous DMF (11.7 mL) was heated to 100° C. for 16 h. The reaction mixture was allowed to cool to rt and was partitioned between EtOAc and H$_2$O and separated. The aqueous was re-extracted with EtOAc (3×) and the combined organic fractions were washed with H$_2$O (3×), brine (2×), dried over Na$_2$SO$_4$, filtered and concentrated in vacuo resulting in a crude brown oil. The reaction mixture was purified by chromatography on silica gel [eluting with 12% EtOAc in CHCl$_3$] resulting in 538 mg, 33% yield of the title compound as a light yellow oil. $^1$H NMR (400 MHz, CDCl$_3$) δ 1.31 (s, 12H), 1.46 (s, 9H), 2.36 (q, J=7.0 Hz, 2H), 3.46-3.78 (m, 3H), 3.80-3.91 (m, 1H), 4.89 (quint, J=6.1 Hz, 1H), 7.73 (s, 1H), 7.80 (s, 1H).

(S)-3-methanesulfonyloxy-pyrrolidine-1-carboxylic acid tert-butyl ester

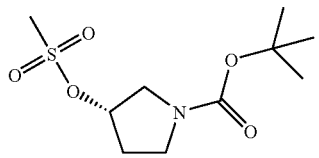

A solution of (S)-3-hydroxypyrrolidine-1-carboxylic acid tert-butyl ester (0.500 g, 2.67 mmol) in DCM (6.7 mL) was cooled to 0° C. and charged with triethylamine (0.45 mL, 3.20 mmol), methanesulfonyl chloride (0.23 mL, 2.90 mmol), and 4-dimethylaminopyridine (3.0 mg, 0.03 mmol) and stirred at rt for 6 h. The reaction mixture was partitioned between CHCl$_3$ and sat. NaHCO$_3$ and separated. The aqueous was re-extracted with CHCl$_3$ (3×) and the combined organic fractions were washed with sat. NaHCO$_3$ (2×), brine (2×), dried over Na$_2$SO$_4$, filtered and concentrated in vacuo resulting in the title compound as a pale yellow oil. This material was taken on to the next step without further purification. $^1$H NMR (400 MHz, CDCl$_3$) δ 1.47 (s, 9H), 2.06-2.39 (m, 2H), 3.05 (s, 3H), 3.38-3.82 (m, 4H), 5.27 (t, J=4.4 Hz, 1H).

Example 163

3-(1-tert-Butyl-1,2,3,6-tetrahydropyridin-4-yl)-7-[(1R)-1-(2,6-dichloro-3-fluorophenyl)ethoxy]furo[3,2-c]pyridin-6-amine

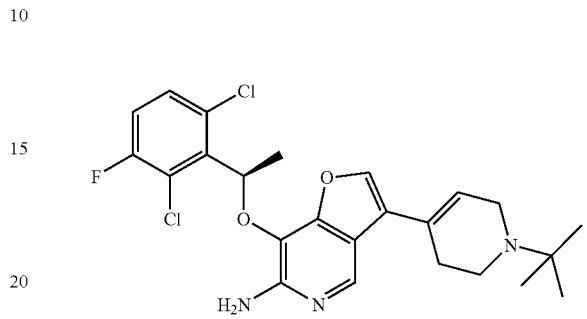

In a two necked RB flask (50 mL), equipped with a N$_2$ inlet, a water condenser, and a magnetic stirrer, were placed 7-((R)-1-(2,6-dichloro-3-fluorophenyl)ethoxy)-3-bromo-furo[3,2-c]pyridine-6-amine (230 mg, 0.55 mmol), 1-tert-Butyl-1,2,3,6-tetrahydro-4-(trimethylstannyl)pyridine (240 mg, 0.79 mmol), tris(dibenzylideneacetone)dipalladium(0) (100 mg), tri-O-tolylphosphine (26 mg), DMF (10 mL) and triethylamine (1.0 mL). This reaction mixture was heated at 114-116° C. for 4 h. The TLC (10% MeOH in DCM) indicated that the starting material was consumed. From the reaction mixture DMF was removed under reduced pressure, water was added to the residue, and the mixture was extracted with DCM. The organic layer was dried over anhydrous sodium sulfate, filtered and concentrated in vacuo. The crude material was purified on silica gel column chromatography eluting with 2-5% methanol in dichloromethane to give the title compound. $^1$H NMR (CDCl$_3$, 300 MHz): δ=1.19 (s, 9H), 1.81 (d, J=6.6 Hz, 3H), 2.42 (br, m, 2H), 2.80 (m, 2H), 3.40 (br, m, 2H), 4.75 (br, 2H), 6.22 (br, 1H), 6.50 (m, 1H), 7.05 (t, J=8.4 Hz, 1H), 7.25 (m, J=8.4 Hz, 1H), 7.34 (s, 1H), 8.23 (s, 1H). EI-MS 478/480 (MH+).

1-tert-Butyl-1,2,3,6-tetrahydro-4-(trimethylstannyl)pyridine

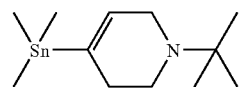

A thick-walled Pyrex bottle containing magnetic stirring bar was charged with a solution of 1-tert-Butyl-1,2,3,6-tetrahydropyridin-4-yl trifluoromethanesulfonate (2.3 g, 8.0 mmol) in dry THF (15 mL), hexamethylditin (2.21 g, 6.75 mmol), and lithium chloride (825 mg, 19.5 mmol). The reaction mixture was degassed with N$_2$ for 15 min, tetrakis(triphenylphosphine)palladium (162 mg, 0.14 mmol) was added, and the reaction mixture was heated at 60° C. overnight. The reaction mixture was cooled to room temperature, poured into diethyl ether, washed with water and dried on MgSO$_4$. It was filtered and evaporated under reduced pressure to give an orange colored residue that was used without further purification. $^1$H NMR (CDCl$_3$, 300 MHz): δ=0.02 (s, 9H), 1.10 (s, 9H), 2.39 (t, 2H), 2.70 (t, 2H), 3.30 (t, 2H), 5.70 (t, 1H).

1-tert-Butyl-1,2,3,6-tetrahydropyridin-4-yltrifluoromethanesulfonate

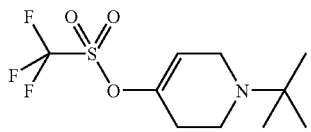

In an oven dried three-necked RB flask (250 mL) was placed 0.5 M solution of potassium hexamethyldisilazide in toluene (31.52 mL, 15.44 mmol) and was cooled to −78° C. To this cold solution was added a solution of N-tert-butyl piperidone (2.00 g, 12.9 mmol) in dry THF (20 mL) over a period of 30 min under nitrogen atmosphere. After stirring the reaction mixture for 3.5 h at −78° C., it was treated with a solution of 2-[N,N-bis(trifluoromethanesulfonyl)]amino-5-chloropyridine (6.11 g, 15.5 mmol) in dry THF (10 mL). The resulting reaction mixture was stirred at −78° C. for 4 h and slowly allowed to warm to room temperature. The reaction mixture was quenched with cold water (10 mL), stirred for 10 min. and then the solvent was removed on rotary evaporator. The residue was dissolved in ethyl acetate, washed with water followed by aqueous saturated NaHCO$_3$ solution, 5% aqueous NaOH solution and water. The organic layer was dried over anhydrous sodium sulfate, filtered and evaporated to give an orange oil that was used as such in the next reaction. $^1$H NMR (CDCl$_3$, 300 MHz): δ=1.10 (s, 9H), 2.40 (m, 2H), 2.79 (t, 2H), 3.30 (t, 2H), 5.79 (t, 1H).

Example 164

7-[(1R)-1-(2,6-Dichloro-3-fluorophenyl)ethoxy]-3-(8-methyl-8-azabicyclo[3.2.1]oct-2-en-3-yl)furo[3,2-c]pyridin-6-amine

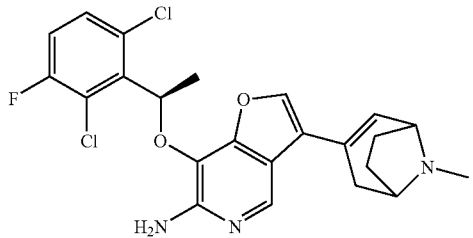

In a two necked RB flask (50 mL), equipped with a N$_2$ inlet, a water condenser and a magnetic stirrer, were placed 7-((R)-1-(2,6-dichloro-3-fluorophenyl)ethoxy)-3-bromofuro[3,2-c]pyridine-6-amine (200 mg, 0.48 mmol), 8-methyl-3-(trimethylstannyl)-8-azabicyclo[3.2.1]oct-2-ene (216 mg, 0.75 mmol), tris(dibenzylideneacetone)dipalladium (100 mg, 0.11 mmol), tri-o-tolylphosphine (26 mg, 0.085 mmol), DMF (10 mL) and triethylamine (1.0 mL). This reaction mixture was heated at 114-116° C. for 4 h. TLC (10% MeOH in DCM) indicated that the starting material was consumed. DMF was removed under reduced pressure; water was added to the residue and extracted with DCM (3×10 mL). The organic layer was dried over anhydrous sodium sulfate, filtered and concentrated in vacuo. The crude material was purified on silica gel column chromatography eluting with 2-5% methanol in dichloromethane to give the title compound. $^1$H NMR (CDCl$_3$, 300 MHz): δ=1.2 (m, 1H), 2.85 (d, J=6.6 Hz, 3H), 2.31 (m, 2H), 2.58 (br, m, 2H), 2.70 (s, 3H), 3.10 (br, d, 1H), 3.90 (d, br, 2H), 4.77 (br, 2H), 6.40 (d, J=6.0 Hz, 1H), 6.55 (m, 1H), 7.01 (t, J=6.6 Hz, 1H), 7.30 (t, J=6.6 Hz, 1H), 7.40 (s, 1H), 8.21 (s, 1H).

8-Methyl-3-(trimethylstannyl)-8-azabicyclo[3.2.1]oct-2-ene

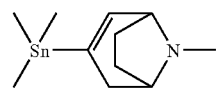

The compound was prepared from 8-methyl-8-azabicyclo[3.2.1]octan-3-one as described above for 1-tert-Butyl-1,2,3,6-tetrahydro-4-(trimethylstannyl)pyridine.

Example 165

4-(4-{6-Amino-7-[(R)-1-(2,6-dichloro-3-fluorophenyl)ethoxy]-furo[3,2-c]pyridin-3-yl}-pyrazol-1-yl)-piperidine-1-carboxylic acid tert-butyl ester

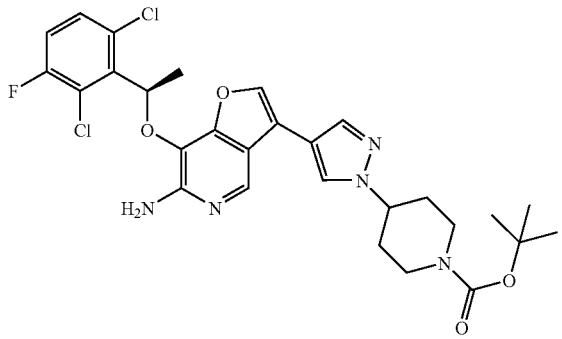

A mixture of 3-bromo-7-[(R)-1-(2,6-dichloro-3-fluorophenyl)ethoxy]-furo[3,2-c]pyridin-6-ylamine (601 mg, 1.43 mmol), 4-[4-(4,4,5,5-tetramethyl-1,3,2-dioxaborolan-2-yl)-pyrazol-1-yl]-piperidine-1-carboxylic acid tert-butyl ester (810 mg, 2.1 mmol) and potassium carbonate (590 mg, 4.3 mmol) in 1,4-dioxane (10 mL) and H$_2$O (3 mL) was degassed and refilled with argon (3×) prior to the addition of PdCl$_2$(dppf) (105 mg, 0.143 mmol). The reaction mixture was degassed and refilled with argon (2×) and heated at 100° C. for 2 h (conventional heating). The mixture was diluted with EtOAc (60 mL), then washed with brine (20 mL), and dried over anhydrous sodium sulfate. The residue was purified by silica gel chromatography (Hex:EtOAc=50:50→20:80→100% EtOAc) to give the title compound as a light-yellow solid. LC-MS (ES+): 590.07/592.09 [MH$^+$]. $^1$H NMR (CDCl$_3$, 400 MHz): δ 1.49 (s, 9H), 1.90 (d, J=6.8 Hz, 3H), 1.91-2.02 (m, 2H), 2.17-2.20 (m, 2H), 2.93 (m, 2H), 4.27-4.36 (m, 3H), 5.24 (br s, 2H), 6.62 (q, J=6.8 Hz, 1H), 7.07 (dd, J=8.8, 7.8 Hz, 1H), 7.30 (dd, J=8.8, 4.8 Hz, 1H), 7.55 (s, 1H), 7.68 (s, 1H), 7.75 (s, 1H), 8.11 (s, 1H).

Example 166

4-(4-{6-Amino-2-bromo-7-[(R)-1-(2,6-dichloro-3-fluorophenyl)ethoxy]furo[3,2-c]pyridin-3-yl}-pyrazol-1-yl)-piperidine-1-carboxylic acid tert-butyl ester

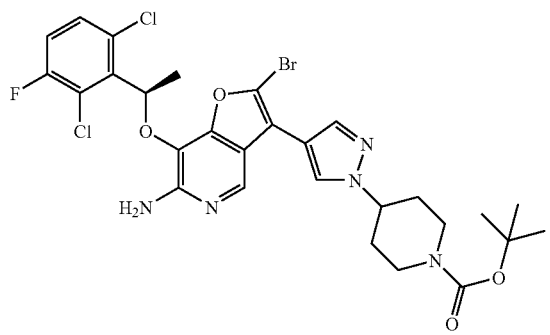

To a solution of 4-(4-{6-amino-7-[(R)-1-(2,6-dichloro-3-fluorophenyl)ethoxy]-furo[3,2-c]pyridin-3-yl}-pyrazol-1-yl)-piperidine-1-carboxylic acid tert-butyl ester (400 mg, 0.68 mmol) in anhydrous DCM (10 mL) was added a solution of bromine (430 mg, 2.7 mmol) in DCM (3 mL). The resulting mixture was stirred at rt for 30 min. The mixture was quenched with sat. aq. Na$_2$S$_2$O$_3$ (15 mL) and diluted with DCM (50 mL), then washed with brine (20 mL), and dried over anhydrous sodium sulfate. Evaporation afforded a yellow residue, which was purified by silica gel chromatography (Hex.-EtOAc=30:70→100% EtOAc) to give the title compound as a light-yellow solid. LC-MS (ES+): 668.01/669.99/671.97 [MH$^+$]. $^1$H NMR (CDCl$_3$, 400 MHz): δ 1.49 (s, 9H), 1.90 (d, J=6.8 Hz, 3H), 1.95-2.04 (m, 2H), 2.18-2.21 (m, 2H), 2.93 (m, 2H), 4.31-4.38 (m, 3H), 5.19 (br s, 2H), 6.54 (q, J=6.6 Hz, 1H), 7.08 (dd, J=8.8, 8.0 Hz, 1H), 7.30 (dd, J=8.8, 4.8 Hz, 1H), 7.85 (s, 1H), 7.94 (s, 1H), 8.05 (s, 1H).

Example 167

2-Bromo-7-[(R)-1-(2,6-dichloro-3-fluorophenyl)ethoxy]-3-(1-piperidin-4-yl-1H-pyrazol-4-yl)-furo[3,2-c]pyridin-6-ylamine

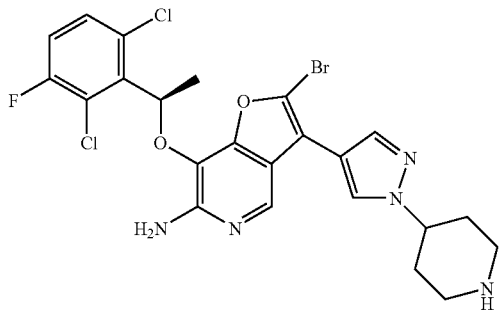

To a solution of 4-(4-{6-amino-2-bromo-7-[(R)-1-(2,6-dichloro-3-fluoro-phenyl)-ethoxy]-furo[3,2-c]pyridin-3-yl}-pyrazol-1-yl)-piperidine-1-carboxylic acid tert-butyl ester (2.0 mg, 0.0030 mmol) in DCM (0.1 mL) was added 1N HCl in diethyl ether (0.2 mL). The resulting mixture was stirred at rt overnight. Evaporation afforded the title compound as a light-yellow gum. LC-MS (ES+): 567.97/569.97/571.99 [MH$^+$].

Example 168

7-[(R)-1-(2,6-Dichloro-3-fluorophenyl)ethoxy]-2-methyl-3-(1-piperidin-4-yl-1H-pyrazol-4-yl)-furo[3,2-c]pyridin-6-ylamine

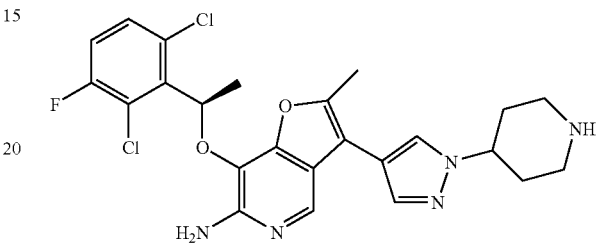

A mixture of 4-(4-{6-amino-2-bromo-7-[(R)-1-(2,6-dichloro-3-fluorophenyl)ethoxy]-furo[3,2-c]pyridin-3-yl}-pyrazol-1-yl)-piperidine-1-carboxylic acid tert-butyl ester (20.0 mg, 0.0299 mmol), 2.0 M Me$_2$Zn in PhMe (0.04 mL, 0.08 mmol), and Pd(PPh$_3$)$_4$ (2.9 mg, 0.0025 mmol) in THF (1 mL) was degassed and refilled with argon (3×), then heated at 100° C. for 30 min using a CEM microwave reactor. The solution was passed through a PL-Thiol SPE cartridge to remove metals. The material was then dissolved in dioxane and EtOH, charged with 4M HCl in Dioxane (0.2 mL) and stirred at rt for 4 h. The solution was concentrated in vacuo, redissolved in DMF (0.5 mL) and purified via HPLC. The fractions containing the pure product were concentrated in vacuo to afford the title compound as a white solid. $^1$H NMR (400 MHz, CD$_3$OD): δ=1.90 (d, J=6.8 Hz, 3H), 2.28-2.39 (m, 4H), 2.43 (s, 3H), 3.16-3.26 (m, 2H), 3.55-3.62 (m, 2H), 4.61 (dt, J=10.0, 5.0 Hz, 1H), 6.50 (q, J=6.7 Hz, 1H), 7.22 (t, J=8.6 Hz, 1H), 7.40 (dd, J=9.1, 4.8 Hz, 1H), 7.79 (s, 1H), 7.89 (s, 1H), 7.99 (s, 1H). MS (ES$^+$): m/z 504.06/506.07 (100/71) [MH$^+$]. HPLC: t$_R$=2.73 min (ZQ3, polar_5 min).

Example 169

6-Amino-7-[(R)-1-(2,6-dichloro-3-fluorophenyl)ethoxy]-3-(1-piperidin-4-yl-1H-pyrazol-4-yl)-furo[3,2-c]pyridine-2-carbonitrile

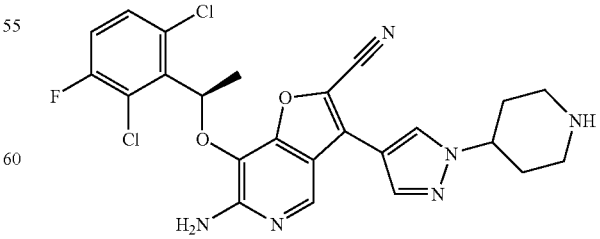

A mixture of [4-(4-{6-amino-2-bromo-7-[(R)-1-(2,6-dichloro-3-fluorophenyl)ethoxy]-furo[3,2-c]pyridin-3-yl}-pyrazol-1-yl)-piperidine-1-carboxylic acid tert-butyl ester (20.0 mg, 0.0299 mmol), zinc cyanide (4.2 mg, 0.036 mmol) and Pd(PPh₃)₄ (3 mg, 0.003 mmol) in DMF (1 mL) was degassed and refilled with nitrogen (3×). The reaction was heated at 150° C. using a microwave reactor for 2 min. The solution was passed through a PL-Thiol SPE cartridge to remove metals. The material was then dissolved in dioxane and EtOH, charged with 4M HCl in Dioxane (0.2 mL) and stirred at rt for 4 h. The solution was concentrated in vacuo, redissolved in DMF (0.5 mL) and purified via HPLC. The fractions containing the pure product were concentrated in vacuo to afford the title compound as a white solid. $^1$H NMR (400 MHz, CD₃OD): δ=1.93 (d, J=6.8 Hz, 3H), 2.30-2.40 (m, 4H), 3.18-3.26 (m, 2H), 3.59 (d, J=13.4 Hz, 2H), 4.64-4.71 (m, 1H), 6.43 (q, J=6.8 Hz, 1H), 7.21-7.27 (m, 1H), 7.42 (dd, J=9.0, 4.9 Hz, 1H), 8.11 (s, 1H), 8.33-8.39 (m, 2H). MS (ES$^+$): m/z 515.06/517.07 (100/68) [MH$^+$]. HPLC: $t_R$=2.78 min (ZQ2, polar_5 min).

resulting mixture was stirred at rt for 1 h. LC-MS indicated completion of reaction. Solvent was then removed under reduced pressure to give a crude product which was then purified by chromatography (7% methanol in DCM, NH₃ added). $^1$H NMR (400 MHz, CD₃OD): δ=1.85-2.03 (m, 5H), 2.08-2.19 (m, 2H), 2.75 (td, J=12.6, 2.5 Hz, 2H), 3.12-3.22 (m, 2H), 4.35 (tt, J=11.6, 4.0 Hz, 1H), 6.46 (q, J=6.8 Hz, 1H), 7.18 (t, J=8.7 Hz, 1H), 7.32-7.42 (m, 4H), 7.55-7.64 (m, 3H), 7.89 (s, 1H), 7.93 (s, 1H). MS (ES+): m/z 566.05/568.04 [MH$^+$]. HPLC: $t_R$=2.98 min (ZQ3, polar_5 min).

Example 170

7-[(R)-1-(2,6-Dichloro-3-fluorophenyl)ethoxy]-2-phenyl-3-(1-piperidin-4-yl-1H-pyrazol-4-yl)-furo[3,2-c]pyridin-6-ylamine Example 171

4-[6-Amino-7-[(R)-1-(2,6-dichloro-3-fluorophenyl)ethoxy]-3-(1-piperidin-4-yl-1H-pyrazol-4-yl)-furo[3,2-c]pyridin-2-yl]-2-methylbut-3-yn-2-ol

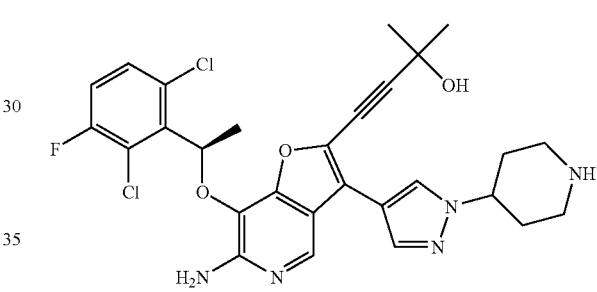

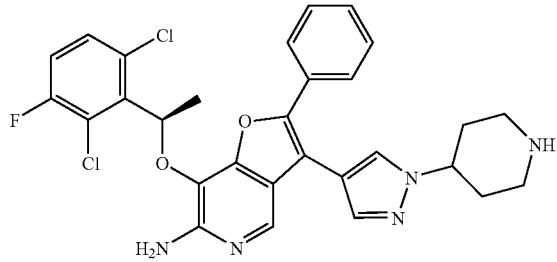

To a solution of 4-(4-6-amino-2-bromo-7-[(R)-1-(2,6-dichloro-3-fluorophenyl)ethoxy]-furo[3,2-c]pyridin-3-yl-pyrazol-1-yl)-piperidine-1-carboxylic acid tert-butyl ester (20.00 mg, 0.029 mmol) and phenylboronic acid (4.73 mg, 0.038 mmol) in DME (2 mL) and H₂O (0.5 mL) was added potassium carbonate (12.4 mg, 0.089 mmol). To the resulting mixture, Nitrogen was bubbled through for 5 min before (1,1′bis-(diphenylphosphino)-ferrocene) palladium dichloride (2.2 mg, 0.0030 mmol) was added. The mixture was stirred at 85° C. for 1 h. LC-MS indicated completion of reaction. Solvent was removed under reduced pressure and the product was purified by flash chromatography (2% methanol in DCM). $^1$H NMR (400 MHz, CD₃OD): δ=1.48 (s, 9H), 1.86-2.03 (m, 5H), 2.07-2.18 (m, 2H), 2.86-3.07 (m, 2H), 4.17-4.28 (m, 2H), 4.37-4.50 (m, 1H), 6.47 (q, J=6.8 Hz, 1H), 7.19 (t, J=8.7 Hz, 1H), 7.32-7.43 (m, 4H), 7.56-7.65 (m, 3H), 7.86-8.01 (m, 2H). MS (ES+): m/z 666.17/668.15 [MH$^+$]. HPLC: $t_R$=4.24 min (ZQ3, polar_5 min). This material was dissolved in 1,4-dioxane (2 mL), and to this solution 4 M of HCl in 1,4-dioxane (0.1 mL) was added at 5° C. The To a suspension of 4-(4-6-amino-2-bromo-7-[(R)-1-(2,6-dichloro-3-fluorophenyl)ethoxy]furo[3,2-c]pyridin-3-yl-pyrazol-1-yl)-piperidine-1-carboxylic acid tert-butyl ester (20.00 mg, 0.029 mmol), 2-methyl-3-butyn-2-ol (12.6 mg, 0.15 mmol), PPh₃ (2.35 mg, 0.0089 mmol) and copper(I) iodide (0.569 mg, 0.0030 mmol) in triethylamine (0.083 mL, 0.59 mmol) and 1,4-dioxane (3.00 mL) was added (1,1′bis-(diphenylphosphino)ferrocene) palladium dichloride (2.19 mg, 0.0029 mmol). The mixture was stirred at 95° C. for 2 h. The solvent was removed under reduced pressure to give a residue which was then purified by flash chromatography (1% MeOH in DCM). MS (ES+): m/z 672.17/674.18 [MH$^+$]. HPLC: $t_R$=3.65 min (ZQ3, polar_5 min). This material was then dissolved in 2 mL dioxane, to this solution was added solution of 4 N HCl in dioxane (1 mL) at r.t., the resulting mixture was stirred at r.t. for 1.5 h. The solvent was removed under reduced pressure to give a residue which was then purified by flash chromatography (5% MeOH in DCM) to give the title compound. $^1$H NMR (400 MHz, CD₃OD): δ=1.65 (s, 6H), 1.90 (d, J=6.8 Hz, 3H), 1.94-2.06 (m, 2H), 2.08-2.18 (m, 2H), 2.77 (td, J=12.57, 2.40 Hz, 2H), 3.15-3.24 (m, 2H), 4.31-4.45 (m, 1H), 6.44 (q, J=6.74 Hz, 1H), 7.21 (t, J=8.59 Hz, 1H), 7.38 (dd, J=8.97, 4.93 Hz, 1H), 8.08 (s, 1H), 8.18 (s, 1H), 8.25 (s, 1H). MS (ES+): m/z 572.14/574.13 [MH$^+$]. HPLC: $t_R$=2.58 min (ZQ3, polar_5 min).

Example 172

4-[6-Amino-7-[(R)-1-(2,6-dichloro-3-fluorophenyl)ethoxy]-3-(1-piperidin-4-yl-1H-pyrazol-4-yl)-furo[3,2-c]pyridin-2-yl]-but-3-yn-1-ol

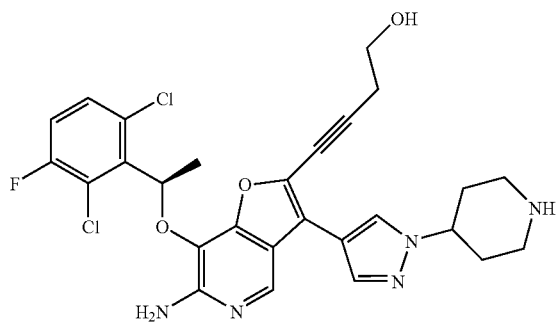

Prepared according to the procedure described above. $^1$H NMR (400 MHz, CD$_3$OD): δ=1.89 (d, J=6.8 Hz, 3H), 1.94-2.18 (m, 4H), 2.72-2.87 (m, 4H), 3.17-3.27 (m, 2H), 3.83 (t, J=6.4 Hz, 2H), 4.33-4.43 (m, 1H), 6.45 (q, J=6.7 Hz, 1H), 7.15-7.27 (m, 1H), 7.38 (dd, J=9.0, 4.9 Hz, 1H), 8.07 (s, 1H), 8.16 (s, 1H), 8.30 (s, 1H). MS (ES+): m/z 558.09/560.08 [MH$^+$]. HPLC: $t_R$=2.60 min (ZQ3, polar_5 min).

Example 173

2-(3-Aminoprop-1-ynyl)-7-[(R)-1-(2,6-dichloro-3-fluorophenyl)ethoxy]-3-(1-piperidin-4-yl-1H-pyrazol-4-yl)-furo[3,2-c]pyridin-6-ylamine

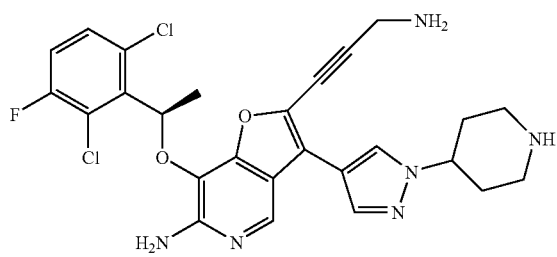

Prepared according to the procedure described above. $^1$H NMR (400 MHz, CD$_3$OD): δ=1.89 (d, J=6.9 Hz, 3H), 1.99-2.23 (m, 4H), 2.76-2.91 (m, 2H), 3.15-3.26 (m, 2H), 3.78 (s, 2H), 4.33-4.49 (m, 1H), 6.36-6.54 (m, 1H), 7.13-7.45 (m, 2H), 7.99-8.33 (m, 3H). MS (ES+): m/z 543.01/545.01 [MH$^+$]. HPLC: $t_R$=2.27 min (ZQ3, polar_5 min).

Example 174

2-(3-Aminobut-1-ynyl)-7-[(R)-1-(2,6-dichloro-3-fluorophenyl)ethoxy]-3-(1-piperidin-4-yl-1H-pyrazol-4-yl)-furo[3,2-c]pyridin-6-ylamine

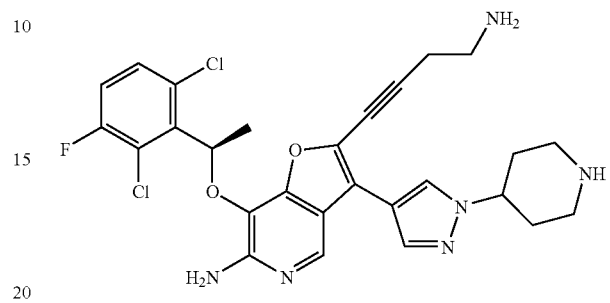

Prepared according to the procedure described above. $^1$H NMR (400 MHz, CD$_3$OD): δ=1.90 (d, J=6.7 Hz, 3H), 2.27-2.38 (m, 4H), 2.99-3.08 (m, 2H), 3.13-3.26 (m, 4H), 3.51-3.62 (m, 2H), 4.58-4.74 (m, 1H), 6.36-6.51 (m, 1H), 7.16-7.29 (m, 1H), 7.34-7.45 (m, 1H), 8.09 (s, 1H), 8.17 (s, 1H), 8.29 (s, 1H). MS (ES+): m/z 557.08/559.08 [MH$^+$]. HPLC: $t_R$=2.53 min (ZQ3, polar_5 min).

Example 175

6-Amino-7-[(R)-1-(2,6-dichloro-3-fluorophenyl)ethoxy]furo[3,2-c]pyridine-3-carboxylic acid methyl ester

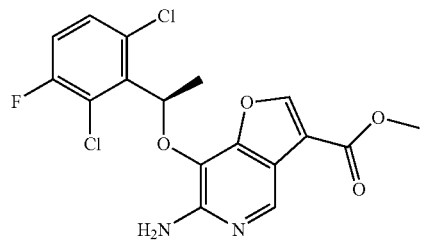

A mixture of 3-bromo-7-[(R)-1-(2,6-dichloro-3-fluorophenyl)ethoxy]furo[3,2-c]pyridin-6-ylamine (500 mg, 1.19 mmol), DIPEA (2.07 mL, 11.9 mmol), Pd(PPh$_3$)$_4$ (100 mg, 0.1 mmol) in MeOH (20 mL) was heated at 68° C. under carbon monooxide for 2 days. The mixture was concentrated under reduced pressure, and the residue was purified by silica gel chromatography (Hex:EtOAc=80:20→60:40) to give the title compound as a white solid. LC-MS (ES+): 398.90/400.91 [MH$^+$]. $^1$H NMR (CDCl$_3$, 400 MHz): δ 1.89 (d, J=6.6 Hz, 3H), 3.94 (s, 3H), 5.17 (br s, 2H), 6.53 (q, J=6.6 Hz, 1H), 7.07 (dd, J=8.8, 8.1 Hz, 1H), 7.29 (dd, J=8.8, 4.8 Hz, 1H), 8.04 (s, 1H), 8.41 (s, 1H).

Example 176

6-Amino-7-[(R)-1-(2,6-dichloro-3-fluorophenyl) ethoxy]furo[3,2-c]pyridine-3-carboxylic acid

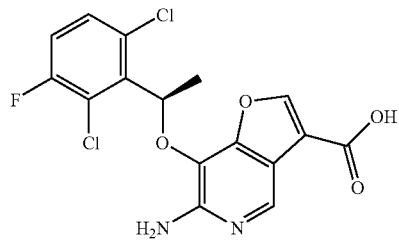

A suspension of 6-amino-7-[(R)-1-(2,6-dichloro-3-fluorophenyl)ethoxy]furo[3,2-c]pyridine-3-carboxylic acid methyl ester (140 mg, 0.35 mmol) in 1N aq. HCl (5 mL) was heated at 100° C. for 7 h. The mixture was cooled to rt, and the off-white solid was collected by filtration to give the title compound. LC-MS (ES+): 384.96/386.96 [MH$^+$]. $^1$H NMR (CD$_3$OD, 400 MHz): δ 1.95 (d, J=6.6 Hz, 3H), 6.70 (q, J=6.6 Hz, 1H), 7.26 (m, 1H), 7.44 (dd, J=9.1, 4.8 Hz, 1H), 8.20 (s, 1H), 8.43 (s, 1H).

Example 177

6-Amino-7-[(R)-1-(2,6-dichloro-3-fluorophenyl) ethoxy]furo[3,2-c]pyridine-3-carboxylic acid dimethylamide

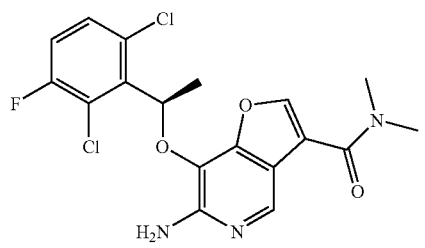

General Procedure X: To a solution of 6-amino-7-[(R)-1-(2,6-dichloro-3-fluorophenyl)-ethoxy]furo[3,2-c]pyridine-3-carboxylic acid (10.0 mg, 0.026 mmol) in DMF (0.5 mL) was added DIPEA (0.1 mL, 0.6 mmol), dimethylamine/MeOH (2M solution, 0.5 mL) and TBTU (17 mg, 0.052 mmol). The resulting mixture was stirred at rt for 1 h. The mixture was diluted with EtOAc (30 mL), washed with water (2×10 mL), sat. aq. NaHCO$_3$ (2×10 mL), brine (10 mL), and dried over anhydrous sodium sulfate. The crude material was purified by silica gel chromatography (100% EtOAc 5% MeOH/EtOAc) to give the title compound as a white solid. LC-MS (ES+): 411.97/413.99 [MH$^+$]. $^1$H NMR (CDCl$_3$, 400 MHz): δ 1.87 (d, J=6.6 Hz, 3H), 3.15 (s, 6H), 4.87 (br s, 2H), 6.52 (q, J=6.6 Hz, 1H), 7.06 (m, 1H), 7.29 (dd, J=8.8, 4.8 Hz, 1H), 7.62 (s, 1H), 8.19 (s, 1H).

Example 178

6-Amino-7-[(R)-1-(2,6-dichloro-3-fluorophenyl) ethoxy]furo[3,2-c]pyridine-3-carboxylic acid methylamide

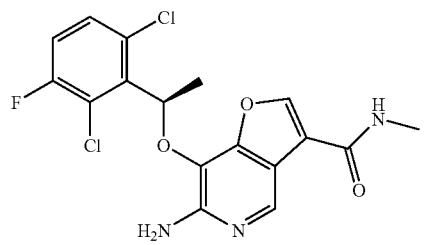

The title compound was prepared according to General Procedure X using MeNH$_2$.HCl. LC-MS (ES+): 397.95/399.93 [MH$^+$].

Example 179

6-Amino-7-[(R)-1-(2,6-dichloro-3-fluorophenyl) ethoxy]furo[3,2-c]pyridine-3-carboxylic acid ethylamide

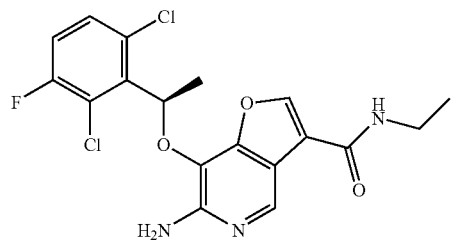

The title compound was prepared according to General Procedure X using EtNH$_2$.HCl. LC-MS (ES+): 411.97/413.96 [MH$^+$].

Example 180

6-Amino-7-[(R)-1-(2,6-dichloro-3-fluorophenyl) ethoxy]furo[3,2-c]pyridine-3-carboxamide

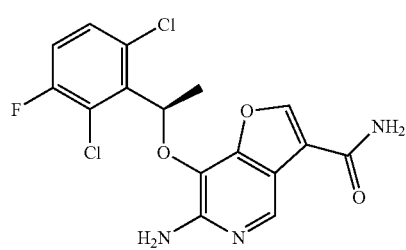

The title compound was prepared according to General Procedure X using conc. aq. ammonia. LC-MS (ES+): 384.00/386.01 [MH$^+$].

Example 181

4-({6-Amino-7-[(R)-1-(2,6-dichloro-3-fluorophenyl)ethoxy]furo[3,2-c]pyridine-3-carbonyl}-amino)-piperidine-1-carboxylic acid tert-butyl ester

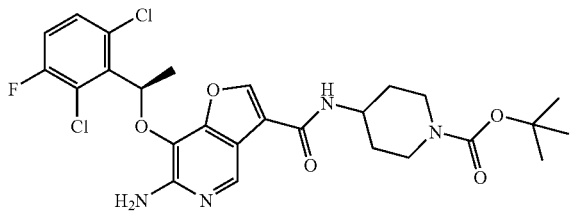

The title compound was prepared according to the above procedure using 4-amino-piperidine-1-carboxylic acid tert-butyl ester. LC-MS (ES+): 567.00/569.00 [MH+].

Example 182

6-Amino-7-[(R)-1-(2,6-dichloro-3-fluorophenyl)ethoxy]furo[3,2-c]pyridine-3-carboxylic acid piperidin-4-ylamide

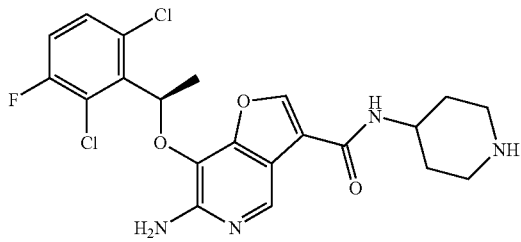

To a solution of 4-({6-amino-7-[(R)-1-(2,6-dichloro-3-fluorophenyl)ethoxy]furo[3,2-c]pyridine-3-carbonyl}-amino)-piperidine-1-carboxylic acid tert-butyl ester (6.0 mg, 0.01 mmol) in DCM (0.2 mL) was added 1M HCl in Et$_2$O (0.5 mL). The resulting mixture was stirred at rt overnight. LC-MS showed the reaction was complete and gave the desired product. Evaporation under reduced gave the title compound as a white solid. LC-MS (ES+): 467.00/469.04 [MH+].

Example 183

6-Amino-7-[(R)-1-(2,6-dichloro-3-fluorophenyl)ethoxy]furo[3,2-c]pyridine-3-carboxylic acid isopropylamide

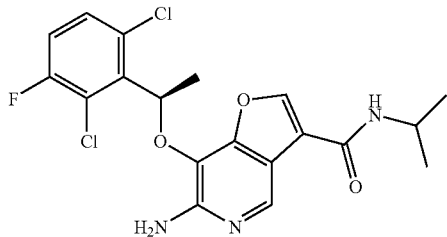

General procedure Y: To a mixture of 6-amino-7-[(R)-1-(2,6-dichloro-3-fluorophenyl)-ethoxy]furo[3,2-c]pyridine-3-carboxylic acid (6.00 mg, 0.016 mmol), TBTU (7.50 mg, 0.0234 mmol), DIPEA (30 μL, 0.2 mmol) and DMF (0.5 mL) was added 2-propanamine (5.0 mg, 0.08 mmol) at rt, and the solution was stirred for 20 min. The solution was used directly for HPLC purification. The fractions containing the pure product were concentrated in vacuo to afford the title compound as a white solid. $^1$H NMR (400 MHz, CD$_3$OD): δ=1.24 (d, J=6.6 Hz, 6H), 1.89 (d, J=6.8 Hz, 3H), 3.64-3.82 (m, 1H), 4.17 (dt, J=13.1, 6.6 Hz, 1H), 6.47 (q, J=6.8 Hz, 1H), 7.21 (t, J=8.6 Hz, 1H), 7.39 (dd, J=9.0, 4.9 Hz, 1H), 8.06 (s, 1H), 8.32 (s, 1H). MS (ES$^+$): m/z 426.02/428.03 (100/69) [MH$^+$]. HPLC: t$_R$=3.01 min (ZQ3, polar_5 min).

Example 184

6-Amino-7-[(R)-1-(2,6-dichloro-3-fluorophenyl)ethoxy]furo[3,2-c]pyridine-3-carboxylic acid tert-butylamide

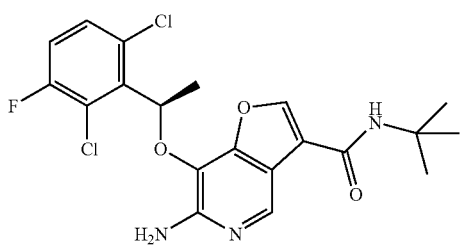

The title compound was prepared according to General procedure Y. $^1$H NMR (400 MHz, CD$_3$OD): δ=1.44 (s, 9H), 1.89 (d, J=6.8 Hz, 3H), 6.47 (q, J=6.7 Hz, 1H), 7.21 (t, J=8.6 Hz, 1H), 7.39 (dd, J=8.8, 4.8 Hz, 1H), 8.06 (s, 1H), 8.29 (s, 1H). MS (ES$^+$): m/z 440.01/442.00 (100/67) [MH$^+$]. HPLC: t$_R$=3.21 min (ZQ3, polar_5 min).

Example 185

6-Amino-7-[(R)-1-(2,6-dichloro-3-fluorophenyl)ethoxy]furo[3,2-c]pyridine-3-carboxylic acid (1-methylpiperidin-4-ylmethyl)amide

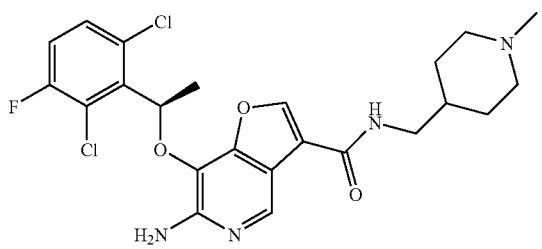

The title compound was prepared according to General procedure Y. $^1$H NMR (400 MHz, CD$_3$OD): δ=1.53 (q, J=13.6 Hz, 2H), 1.90 (d, J=6.6 Hz, 3H), 1.91-1.97 (m, 1H), 2.02 (d, J=14.7 Hz, 2H), 2.84 (s, 3H), 2.92-3.04 (m, 2H), 3.31-3.36 (m, 2H), 3.49 (d, J=11.9 Hz, 2H), 6.47 (q, J=6.7 Hz, 1H), 7.21 (t, J=8.6 Hz, 1H), 7.39 (dd, J=9.0, 4.9 Hz, 1H), 8.06 (s, 1H), 8.32 (s, 1H). MS (ES$^+$): m/z 494.98/497.00 (100/73) [MH$^+$]. HPLC: t$_R$=2.39 min (ZQ3, polar_5 min).

Example 186

6-Amino-7-[(R)-1-(2,6-dichloro-3-fluorophenyl)ethoxy]furo[3,2-c]pyridine-3-carboxylic acid (1-methylpiperidin-4-yl)amide

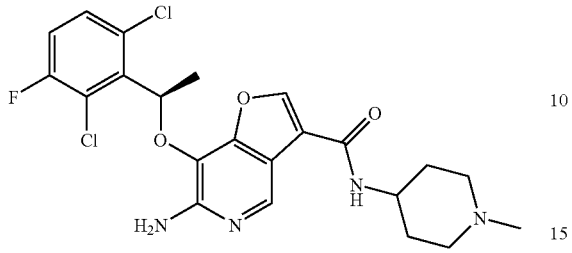

The title compound was prepared according to General procedure Y. $^1$H NMR (400 MHz, CD$_3$OD): δ=1.83-1.98 (m, 5H), 2.14-2.26 (m, 2H), 2.87 (s, 3H), 3.16 (t, J=11.4 Hz, 2H), 3.52 (d, J=12.4 Hz, 2H), 4.07-4.17 (m, 1H), 6.47 (q, J=6.7 Hz, 1H), 7.18-7.25 (m, 1H), 7.40 (dd, J=9.0, 4.9 Hz, 1H), 8.11 (s, 1H), 8.32 (s, 1H). MS (ES$^+$): m/z 480.98/483.00 (100/68) [MH$^+$]. HPLC: t$_R$=2.28 min (ZQ3, polar_5 min).

Example 187

6-Amino-7-[(R)-1-(2,6-dichloro-3-fluorophenyl)ethoxy]furo[3,2-c]pyridine-3-carboxylic acid (tetrahydropyran-4-ylmethyl)amide

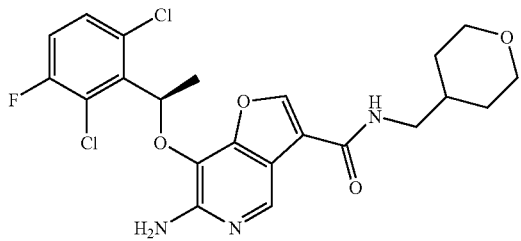

The title compound was prepared according to General procedure Y. $^1$H NMR (400 MHz, CD$_3$OD): δ=1.25-1.39 (m, 2H), 1.68 (dd, J=12.9, 1.8 Hz, 2H), 1.81-1.92 (m, 4H), 3.25 (d, J=7.1 Hz, 2H), 3.40 (td, J=11.7, 2.0 Hz, 2H), 3.95 (dd, J=11.0, 3.7 Hz, 2H), 6.47 (q, J=6.6 Hz, 1H), 7.17-7.24 (m, 1H), 7.39 (dd, J=9.0, 4.9 Hz, 1H), 8.05 (s, 1H), 8.32 (s, 1H). MS (ES$^+$): m/z 482.03/484.04 (100/71) [MH$^+$]. HPLC: t$_R$=2.89 min (ZQ3, polar_5 min).

Example 188

6-Amino-7-[(R)-1-(2,6-dichloro-3-fluorophenyl)ethoxy]furo[3,2-c]pyridine-3-carboxylic acid (tetrahydropyran-4-ylmethyl)amide

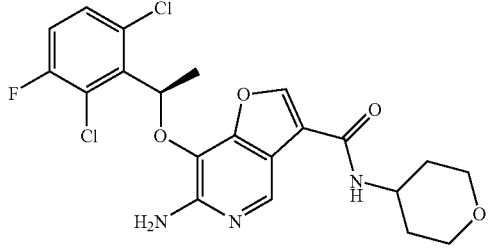

The title compound was prepared according to General procedure Y. $^1$H NMR (400 MHz, CD$_3$OD): δ=1.55-1.71 (m, 2H), 1.86-1.94 (m, 5H), 3.52 (td, J=11.7, 1.8 Hz, 2H), 3.98 (d, J=12.1 Hz, 2H), 4.04-4.13 (m, 1H), 6.47 (q, J=6.8 Hz, 1H), 7.18-7.24 (m, 1H), 7.39 (dd, J=9.0, 4.9 Hz, 1H), 8.08 (s, 1H), 8.33 (s, 1H). MS (ES$^+$): m/z 467.98/470.00 (100/71) [MH$^+$]. HPLC: t$_R$=2.72 min (ZQ3, polar_5 min).

Example 189

6-Amino-7-[(R)-1-(2,6-dichloro-3-fluorophenyl)ethoxy]furo[3,2-c]pyridine-3-carboxylic acid (3-dimethylaminopropyl)amide

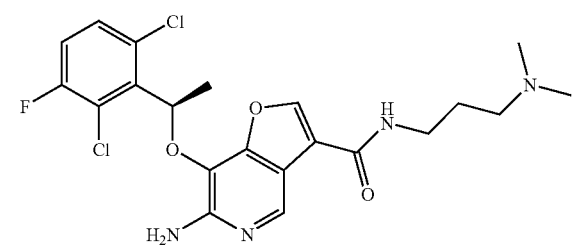

The title compound was prepared according to General procedure Y. $^1$H NMR (400 MHz, CD$_3$OD): δ=1.90 (d, J=6.8 Hz, 3H), 1.96-2.06 (m, 2H), 2.87 (s, 6H), 3.10-3.18 (m, 2H), 3.46 (t, J=6.4 Hz, 2H), 6.47 (q, J=6.7 Hz, 1H), 7.18-7.25 (m, 1H), 7.40 (dd, J=8.8, 4.8 Hz, 1H), 8.07 (s, 1H), 8.34 (s, 1H). MS (ES$^+$): m/z 468.95/470.98 (100/68) [MH$^+$]. HPLC: t$_R$=2.39 min (ZQ3, polar_5 min).

Example 190

6-Amino-7-[(R)-1-(2,6-dichloro-3-fluorophenyl)ethoxy]furo[3,2-c]pyridine-3-carboxylic acid (3-dimethylaminoethyl)amide

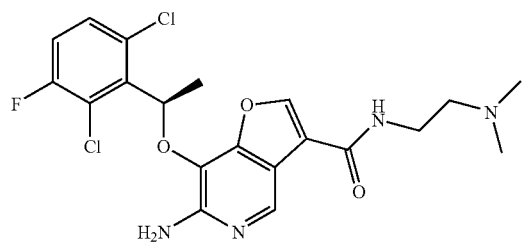

The title compound was prepared according to General procedure Y. $^1$H NMR (400 MHz, CD$_3$OD): δ=1.90 (d, J=6.8 Hz, 3H), 2.48 (s, 6H), 2.77 (t, J=6.4 Hz, 2H), 3.56 (t, J=6.4 Hz, 2H), 6.47 (q, J=6.9 Hz, 1H), 7.21 (t, J=8.7 Hz, 1H), 7.39 (dd, J=9.0, 4.9 Hz, 1H), 8.07 (s, 1H), 8.34 (s, 1H). MS (ES$^+$): m/z 454.95/456.96 (100/68) [MH$^+$]. HPLC: t$_R$=2.28 min (ZQ3, polar_5 min).

Example 191

6-Amino-7-[(R)-1-(2,6-dichloro-3-fluorophenyl)ethoxy]furo[3,2-c]pyridine-3-carboxylic acid (3-methoxypropyl)amide

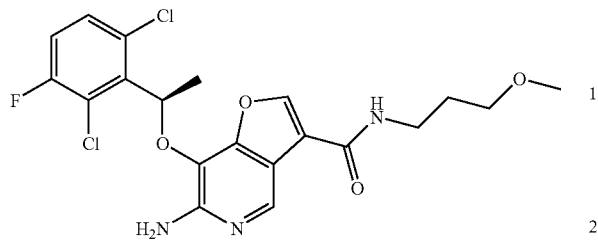

The title compound was prepared according to General procedure Y. $^1$H NMR (400 MHz, CD$_3$OD): δ=1.82-1.88 (m, 2H), 1.90 (d, J=6.8 Hz, 3H), 3.35 (s, 3H), 3.40-3.45 (m, 2H), 3.49 (t, J=6.2 Hz, 2H), 6.49 (q, J=6.6 Hz, 1H), 7.18-7.25 (m, 1H), 7.40 (dd, J=9.1, 4.8 Hz, 1H), 8.05 (s, 1H), 8.32 (s, 1H). MS (ES$^+$): m/z 456.01/458.02 (100/73) [MH$^+$]. HPLC: t$_R$=2.89 min (ZQ3, polar_5 min).

Example 192

6-Amino-7-[(R)-1-(2,6-dichloro-3-fluorophenyl)ethoxy]furo[3,2-c]pyridine-3-carboxylic acid (3-methoxyethyl)amide

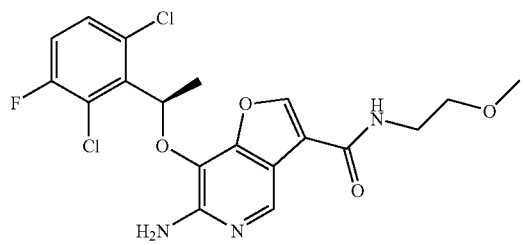

The title compound was prepared according to General procedure Y. $^1$H NMR (400 MHz, CD$_3$OD): δ=1.90 (d, J=6.8 Hz, 3H), 3.38 (s, 3H), 3.52-3.57 (m, 4H), 6.48 (q, J=6.7 Hz, 1H), 7.18-7.25 (m, 1H), 7.40 (dd, J=9.0, 4.9 Hz, 1H), 8.08 (s, 1H), 8.33 (s, 1H). MS (ES$^+$): m/z 441.98/441.99 (100/72) [MH$^+$]. HPLC: t$_R$=2.71 min (ZQ3, polar_5 min).

Example 193

6-Amino-7-[(R)-1-(2,6-dichloro-3-fluorophenyl)ethoxy]furo[3,2-c]pyridine-3-carboxylic acid (3-aminoethyl)amide

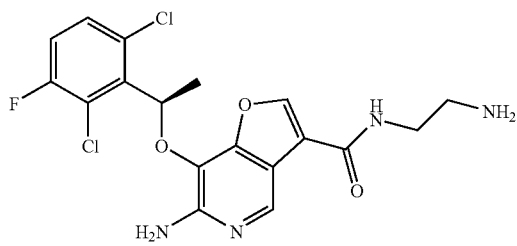

The title compound was prepared according to General procedure Y. $^1$H NMR (400 MHz, CD$_3$OD): δ=1.96 (d, J=6.8 Hz, 3H), 3.12-3.19 (m, 2H), 3.64 (td, J=5.9, 3.7 Hz, 2H), 6.69 (q, J=6.6 Hz, 1H), 7.23-7.29 (m, 1H), 7.44 (dd, J=8.8, 4.8 Hz, 1H), 8.32 (s, 1H), 8.36 (s, 1H). MS (ES$^+$): m/z 426.97/428.99 (100/69) [MH$^+$]. HPLC: t$_R$=2.34 min (ZQ3, polar_5 min).

Example 194

{6-Amino-7-[(R)-1-(2,6-dichloro-3-fluorophenyl)ethoxy]furo[3,2-c]pyridin-3-yl}-methanol

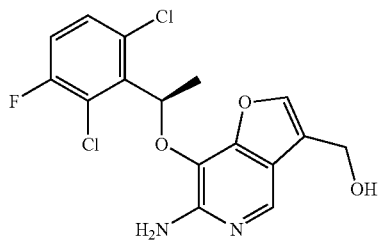

To a solution of 6-amino-7-[(R)-1-(2,6-dichloro-3-fluorophenyl)ethoxy]furo[3,2-c]pyridine-3-carboxylic acid methyl ester (140 mg, 0.35 mmol) in THF (5 mL) was added 0.7 mL of LiAlH$_4$ (1M solution in THF, 0.7 mmol) at 0° C. under nitrogen. The mixture was slowly warmed to rt. The reaction was quenched with EtOAc (25 mL), then water (1 mL). The organic phase was separated and washed with brine (10 mL), and dried over anhydrous sodium sulfate. The residue was purified by silica gel chromatography (Hex: EtOAc=50:50→100% EtOAc) to give the title compound as a white solid. LC-MS (ES+): 370.95/372.94 [MH$^+$]. $^1$H NMR (CDCl$_3$, 400 MHz): δ 1.66 (br s, 1H), 1.86 (d, J=6.6 Hz, 3H), 4.73 (br s, 2H), 4.79 (s, 2H), 6.53 (q, J=6.8 Hz, 1H), 7.04 (m, 1H), 7.27 (m, 1H), 7.37 (s, 1H), 8.10 (s, 1H).

Example 195

4-{6-Amino-7-[(R)-1-(2,6-dichloro-3-fluorophenyl)ethoxy]furo[3,2-c]pyridin-3-yl}-piperidine-1-carboxamide

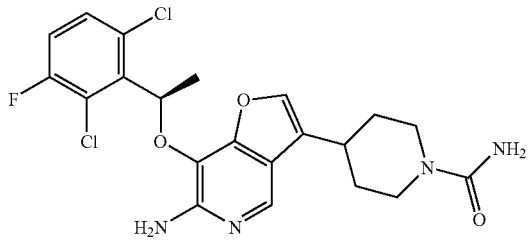

A mixture of 4-{6-amino-7-[(R)-1-(2,6-dichloro-3-fluorophenyl)ethoxy]furo[3,2-c]pyridine-3-yl}-3,6-dihydro-2H-pyridine-1-carboxamide (17.0 mg, 0.037 mmol), palladium 10% wt on activated carbon (10 mg), EtOAc (4 mL) and MeOH (0.4 mL) was flushed with nitrogen, then a hydrogen (0.5 L) balloon was added, and the mixture was stirred at rt for 3 h. The suspension was filtered through a syringe filter pad, and the filtrate was concentrated in vacuo. The material was redissolved in MeOH (0.5 mL) and purified via HPLC. The fractions containing the pure product were concentrated in vacuo to afford the title compound as a white solid. $^1$H NMR (400 MHz, CD$_3$OD): δ=1.55-1.69 (m, 2H), 1.87 (d, J=6.8 Hz, 3H), 1.98-2.06 (m, 2H), 2.89-3.03 (m, 3H), 4.11 (d, J=12.9 Hz, 2H), 6.53 (q, J=6.7 Hz, 1H), 7.18-7.25 (m, 1H), 7.37-7.43 (m, 2H), 8.02 (s, 1H). MS (ES$^+$): m/z 467.01/469.00 (100/69) [MH$^+$]. HPLC: t$_R$=2.58 min (ZQ3, polar_5 min).

Example 196

4-{6-Amino-7-[(R)-1-(2,6-dichloro-3-fluorophenyl)ethoxy]-furo[3,2-c]pyridin-3-yl}-N,N-cyano-N,N-dimethyl-3,6-dihydro-2H-pyridine-1-carboxamidine

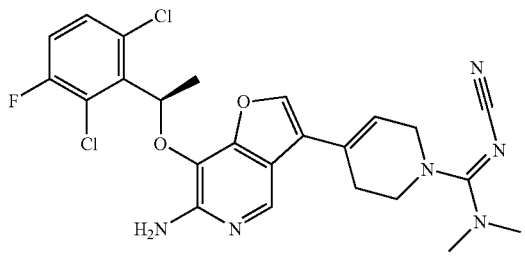

A mixture of 7-[(R)-1-(2,6-dichloro-3-fluorophenyl)ethoxy]-3-(1,2,3,6-tetrahydropyridin-4-yl)furo[3,2-c]pyridine-6-ylamine (10.0 mg, 0.0237 mmol), diphenyl cyanocarbonimidate (6.2 mg, 0.026 mmol) and TFE (1 mL) was stirred at rt for 30 min. The solvent was removed in vacuo, and the material was redissolved in DMSO (1 mL). 2M dimethylamine in MeOH (0.3 mL) was added, and the mixture was heated to 80° C. for 30 min. The solution was loaded into a SCX cartridge, washed with MeOH, and ejected with 2M NH$_3$ in MeOH. The product was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=1.88 (d, J=6.8 Hz, 3H), 2.65 (d, J=1.5 Hz, 2H), 3.04 (s, 6H), 3.67 (t, J=5.8 Hz, 2H), 4.12 (d, J=2.8 Hz, 2H), 6.26 (t, J=3.3 Hz, 1H), 6.51 (q, J=6.7 Hz, 1H), 7.21 (t, J=8.7 Hz, 1H), 7.39 (dd, J=9.0, 4.9 Hz, 1H), 7.67 (s, 1H), 8.20 (s, 1H). MS (ES$^+$): m/z 517.09/519.07 (100/72) [MH$^+$]. HPLC: t$_R$=3.02 min (ZQ3, polar_5 min).

Example 197

4-{6-Amino-7-[(R)-1-(2,6-dichloro-3-fluorophenyl)ethoxy]-furo[3,2-c]pyridin-3-yl}-N-cyano-3,6-dihydro-2H-pyridine-1-carboxamidine

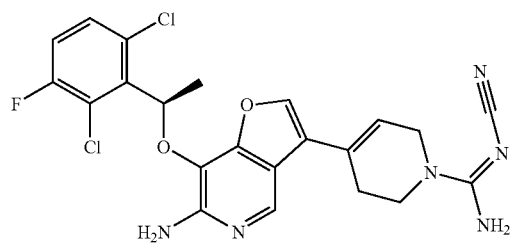

The title compound was prepared following the procedure for example 196, using 7M NH$_3$ in MeOH in place of dimethylamine. $^1$H NMR (400 MHz, CD$_3$OD): δ=1.88 (d, J=6.8 Hz, 3H), 2.49-2.56 (m, 2H), 3.74 (t, J=5.8 Hz, 2H), 4.17 (d, J=2.5 Hz, 2H), 6.24 (t, J=3.4 Hz, 1H), 6.49 (q, J=6.7 Hz, 1H), 7.16-7.24 (m, 1H), 7.39 (dd, J=9.0, 4.9 Hz, 1H), 7.66 (s, 1H), 8.18 (s, 1H). MS (ES$^+$): m/z 489.05/491.03 (100/67) [MH$^+$]. HPLC: t$_R$=2.92 min (ZQ3, polar_5 min).

Example 198

4-{6-Amino-7-[(R)-1-(2,6-dichloro-3-fluorophenyl)ethoxy]-furo[3,2-c]pyridin-3-yl}-N-cyano-N'-methyl-3,6-dihydro-2H-pyridine-1-carboxamidine

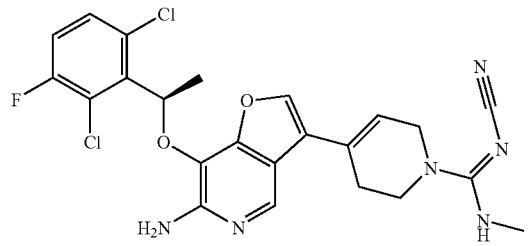

The title compound was prepared following the procedure for example 196, using 2M methylamine in MeOH in place of dimethylamine. $^1$H NMR (400 MHz, CD$_3$OD): δ=1.88 (d, J=6.8 Hz, 3H), 2.52-2.63 (m, 2H), 3.00 (s, 3H), 3.76 (t, J=5.8 Hz, 2H), 4.14 (d, J=2.8 Hz, 2H), 6.23 (t, J=3.3 Hz, 1H), 6.50 (q, J=6.7 Hz, 1H), 7.17-7.24 (m, 1H), 7.39 (dd, J=9.0, 4.9 Hz, 1H), 7.67 (s, 1H), 8.18 (s, 1H). MS (ES$^+$): m/z 503.02/505.01 (100/71) [MH$^+$]. HPLC: t$_R$=2.90 min (ZQ3, polar_5 min).

Example 199

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-acetic Acid

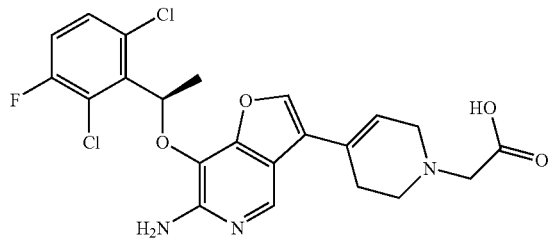

A mixture of 7-[(R)-1-(2,6-dichloro-3-fluorophenyl)ethoxy]-3-(1,2,3,6-tetrahydropyridin-4-yl)-furo[3,2-c]pyridine-6-ylamine (150.0 mg, 0.355 mmol), cesium carbonate (463 mg, 1.42 mmol) and DMF (4 mL) at rt was charged with chloroacetic acid methyl ester (37 μL, 0.43 mmol) and heated to 40° C. overnight. The solvent was removed in vacuo, and the material was dry-loaded onto silica gel for column chromatography, eluting with 2-5% MeOH/DCM. The fractions containing the pure ester were concentrated in vacuo and redissolved in EtOH (4 mL). The solution was charged with 2M aq. LiOH (0.9 mL) at rt, and stirred for 10 min. The solvents were removed in vacuo to afford the title compound as an orange solid. MS (ES+): m/z 497.97 (100) [MH+]. HPLC: $t_R$=2.36 min (ZQ3, polar__5 min).

Example 200

2-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-N,N-dimethylacetamide

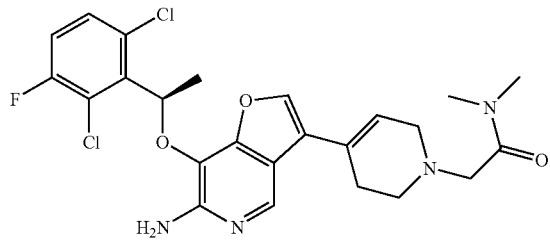

General Procedure U: A mixture of (4-{6-amino-7-[(R)-1-(2,6-dichloro-3-fluorophenyl)ethoxy]-furo[3,2-c]pyridin-3-yl}-3,6-dihydro-2H-pyridin-1-yl)-acetic acid (10.0 mg, 0.021 mmol), dimethylamine hydrochloride (8.49 mg, 0.104 mmol), TBTU (6.68 mg, 0.042 mmol), DIPEA (18.1 μL, 0.104 mmol) and DCM was stirred at rt for 30 min. The solution was transferred to a separatory funnel and extracted with DCM and water. The organic layer was loaded onto a prep TLC plate, eluting with 5% MeOH/DCM. The band containing the pure product was filtered off using 1:1 MeOH/DCM. The filtrate was concentrated in vacuo to afford the title compound as a white solid. ¹H NMR (400 MHz, CD₃OD): δ=1.86-1.90 (m, 3H), 2.54 (d, J=1.5 Hz, 2H), 2.81 (t, J=5.7 Hz, 2H), 2.95 (s, 3H), 3.11 (s, 3H), 3.29 (br. s., 2H), 3.38 (s, 2H), 6.25 (br. s., 1H), 6.50 (q, J=6.7 Hz, 1H), 7.17-7.25 (m, 1H), 7.40 (dd, J=8.8, 4.8 Hz, 1H), 7.61 (s, 1H), 8.18 (s, 1H). MS (ES+): m/z 506.96 (100) [MH+]. HPLC: $t_R$=2.45 min (ZQ3, polar__5 min).

Example 201

2-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-N-methylacetamide

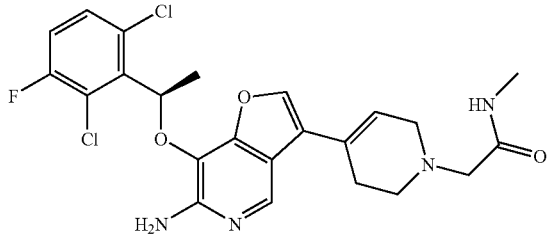

The title compound was prepared according to General procedure U. ¹H NMR (400 MHz, CD₃OD): δ=1.87 (d, J=6.8 Hz, 3H), 2.55 (br. s., 2H), 2.74-2.78 (m, 2H), 2.78 (s, 3H), 3.14 (s, 2H), 3.27 (d, J=2.3 Hz, 2H), 6.24 (br. s., 1H), 6.49 (q, J=6.8 Hz, 1H), 7.21 (t, J=8.6 Hz, 1H), 7.39 (dd, J=9.0, 4.9 Hz, 1H), 7.61 (s, 1H), 8.18 (s, 1H). MS (ES+): m/z 492.94 (100) [MH+]. HPLC: $t_R$=2.94 min (ZQ3, polar__5 min).

Example 202

2-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-acetamide

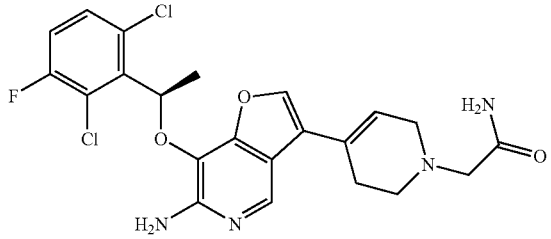

The title compound was prepared according to General procedure U. ¹H NMR (400 MHz, CD₃OD): δ=1.87 (d, J=6.6 Hz, 3H), 2.55 (d, J=1.5 Hz, 2H), 2.80 (t, J=5.7 Hz, 2H), 3.15 (s, 2H), 3.25-3.30 (m, 2H), 6.25 (t, J=3.5 Hz, 1H), 6.49 (q, J=6.8 Hz, 1H), 7.18-7.24 (m, 1H), 7.39 (dd, J=9.0, 4.9 Hz, 1H), 7.60 (s, 1H), 8.18 (s, 1H). MS (ES+): m/z 478.98 (100) [MH+]. HPLC: $t_R$=2.47 min (ZQ3, polar__5 min).

Example 203

2-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-1-(3-hydroxypyrrolidin-1-yl)ethanone

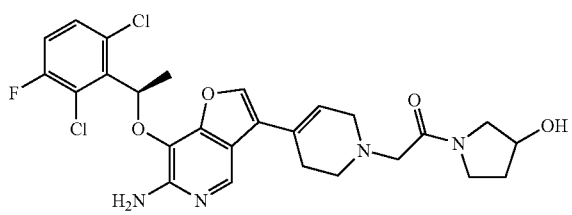

The title compound was prepared according to General procedure U. $^1$H NMR (400 MHz, CD$_3$OD): δ=1.52-1.74 (m, 1H), 1.87 (d, J=6.6 Hz, 3H), 1.93-2.18 (m, 2H), 2.54 (br. s., 2H), 2.84 (q, J=5.7 Hz, 2H), 3.35-3.45 (m, 1H), 3.47-3.71 (m, 5H), 4.22 (dd, J=5.8, 2.0 Hz, 1H), 4.38-4.48 (m, 1H), 6.25 (br. s., 1H), 6.49 (q, J=6.8 Hz, 1H), 7.21 (t, J=8.6 Hz, 1H), 7.40 (dd, J=9.0, 4.9 Hz, 1H), 7.61 (s, 1H), 8.18 (s, 1H). MS (ES$^+$): m/z 549.00 (100) [MH$^+$]. HPLC: $t_R$=2.16 min (ZQ2, polar_5 min).

Example 204

2-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-1-((2R*,6S*)-2,6-dimethylmorpholin-4-yl)ethanone

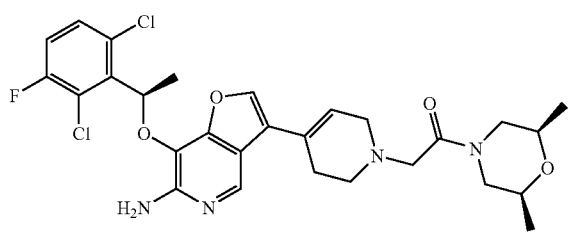

The title compound was prepared according to General procedure U. $^1$H NMR (400 MHz, CD$_3$OD): δ=1.19 (dd, J=6.1, 3.0 Hz, 6H), 1.89 (d, J=6.8 Hz, 3H), 2.43 (dd, J=13.0, 11.0 Hz, 1H), 2.73-2.88 (m, 3H), 3.34-3.40 (m, 2H), 3.48-3.72 (m, 3H), 3.83 (br. s., 2H), 3.95-4.05 (m, 1H), 4.12-4.22 (m, 1H), 4.36 (d, J=12.9 Hz, 1H), 6.28 (br. s., 1H), 6.50 (q, J=6.7 Hz, 1H), 7.22 (t, J=8.6 Hz, 1H), 7.40 (dd, J=9.0, 4.9 Hz, 1H), 7.74 (s, 1H), 8.21 (s, 1H). MS (ES$^+$): m/z 577.04 (100) [MH$^+$]. HPLC: $t_R$=2.36 min (ZQ2, polar_5 min).

Example 205

3-Amino-4-(4-{6-amino-7-[(R)-1-(2,6-dichloro-3-fluorophenyl)ethoxy]-furo[3,2-c]pyridin-3-yl}-3,6-dihydro-2H-pyridin-1-yl)-cyclobut-3-ene-1,2-dione

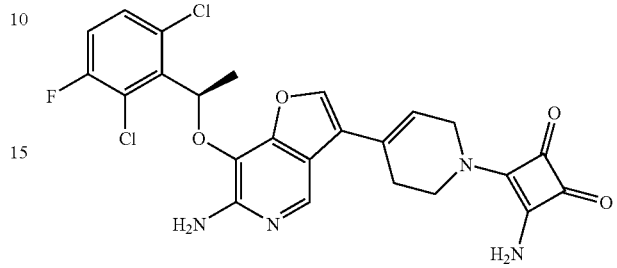

A mixture of 7-[(R)-1-(2,6-dichloro-3-fluorophenyl)ethoxy]-3-(1,2,3,6-tetrahydropyridin-4-yl)furo[3,2-c]pyridin-6-ylamine (10.0 mg, 0.0237 mmol), 3,4-diethoxy-3-cyclobutene-1,2-dione (40 mg, 0.2 mmol) and THF (2 mL) was heated to 40° C. overnight. The material was concentrated in vacuo and dry-loaded onto silica gel for column chromatography. The material was first eluted with 1:1 EtOAc/hexanes to wash away the cyclobutene starting material, then with 5% MeOH/DCM. The fractions containing the mono-ethyloxy-substituted intermediate product were concentrated in vacuo. The material was dissolved in 2M NH$_3$ in i-PrOH (2 mL) and heated to 50° C. in a sealed tube for 2 h. The solution was concentrated in vacuo and redissolved in DMF (0.5 mL) for HPLC purification. The fractions containing the pure product were concentrated in vacuo to afford the title compound as a white solid. $^1$H NMR (400 MHz, CD$_3$OD): δ=1.88 (d, J=6.8 Hz, 3H), 2.65 (br. s., 2H), 4.05 (br. s., 2H), 4.50 (br. s., 2H), 6.29 (br. s., 1H), 6.50 (q, J=6.7 Hz, 1H), 7.18-7.25 (m, 1H), 7.40 (dd, J=9.0, 4.9 Hz, 1H), 7.69 (s, 1H), 8.20 (s, 1H). MS (ES$^+$): m/z 517.01 (100) [MH$^+$]. HPLC: $t_R$=2.80 min (ZQ3, polar_5 min).

Example 206

5-{6-Amino-7-[(R)-1-(2,6-dichloro-3-fluorophenyl)ethoxy]-furo[3,2-c]pyridin-3-yl}-thiophene-2-carboxylic acid

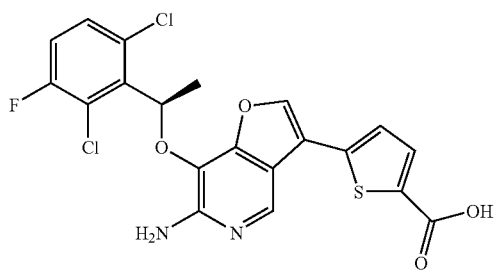

A mixture of 3-bromo-7-[(R)-1-(2,6-dichloro-3-fluorophenyl)ethoxy]furo[3,2-c]pyridine-6-ylamine (100.0 mg, 0.238 mmol), 5-(dihydroxyboryl)thiophene-2-carboxylic acid (205 mg, 1.19 mmol), Pd(PPh$_3$)$_4$ (10.0 mg, 0.01 mmol), potassium carbonate (98.7 mg, 0.714 mmol) and 4:1 dioxane:water (4 mL) was heated in a microwave reactor at 100° C. for 6 h. The material was dry-loaded onto silica gel for column chromatography. The crude product was eluted with 20% MeOH/DCM. The fractions containing the product were concentrated in vacuo to afford the title compound as a white solid. $^1$H NMR (400 MHz, CD$_3$OD): δ=1.90 (d, J=6.8 Hz, 3H), 6.54 (q, J=6.9 Hz, 1H), 7.22 (t, J=8.6 Hz, 1H), 7.31 (d, J=3.8 Hz, 1H), 7.41 (dd, J=9.0, 4.9 Hz, 1H), 7.53 (d, J=3.8 Hz, 1H), 7.92 (s, 1H), 8.27 (s, 1H).

Example 207

5-{6-Amino-7-[(R)-1-(2,6-dichloro-3-fluorophenyl)ethoxy]-furo[3,2-c]pyridin-3-yl}-thiophene-2-carboxylic acid ethyl amide

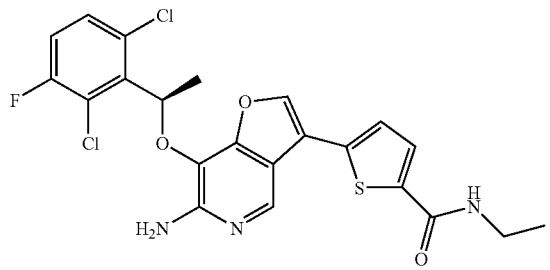

General procedure W: A mixture of 5-{6-amino-7-[(R)-1-(2,6-dichloro-3-fluorophenyl)-ethoxy]-furo[3,2-c]pyridine-3-yl}-thiophene-2-carboxylic acid (10.0 mg, 0.021 mmol), ethylamine (20 mg, 0.4 mmol), TBTU (13.7 mg, 0.43 mmol), DIPEA (0.04 mL, 0.2 mmol) and DCM (2 mL) was stirred at rt for 5 h. The solution was transferred to a separatory funnel, and extracted with DCM and water. The organic later was loaded onto a prep TCL plate, eluting with 3% (7N NH$_3$ in MeOH)/DCM. The band containing the pure product was collected and filtered off using 1:1 MeOH/DCM. The filtrate was concentrated in vacuo to afford the title compound as a white solid. $^1$H NMR (400 MHz, CD$_3$OD): δ=1.21-1.23 (m, 3H), 1.90 (d, J=6.6 Hz, 3H), 3.37-3.40 (m, 2H), 6.53 (q, J=6.7 Hz, 1H), 7.22 (t, J=8.7 Hz, 1H), 7.39-7.43 (m, 2H), 7.51 (s, 1H), 7.67 (d, J=3.8 Hz, 1H), 8.00 (s, 1H). MS (ES$^+$): m/z 493.95 (100) [MH$^+$]. HPLC: t$_R$=3.44 min (ZQ3, polar_5 min).

Example 208

5-{6-Amino-7-[(R)-1-(2,6-dichloro-3-fluorophenyl)ethoxy]-furo[3,2-c]pyridin-3-yl}-thiophene-2-carboxylic acid dimethyl amide

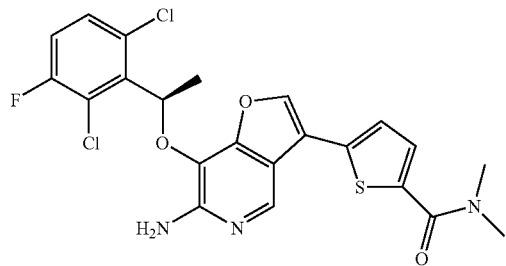

The title compound was prepared according to General procedure W. $^1$H NMR (400 MHz, CD$_3$OD): δ=1.90 (d, J=6.8 Hz, 3H), 3.24 (br. s., 6H), 6.53 (q, J=6.8 Hz, 1H), 7.22 (t, J=8.7 Hz, 1H), 7.38-7.43 (m, 2H), 7.50 (d, J=3.8 Hz, 1H), 7.99 (s, 1H), 8.24 (s, 1H). MS (ES$^+$): m/z 493.96 (100) [MH$^+$]. HPLC: t$_R$=3.45 min (ZQ3, polar_5 min).

Example 209

5-{6-Amino-7-[(R)-1-(2,6-dichloro-3-fluorophenyl)ethoxy]-furo[3,2-c]pyridin-3-yl}-thiophene-2-carboxamide

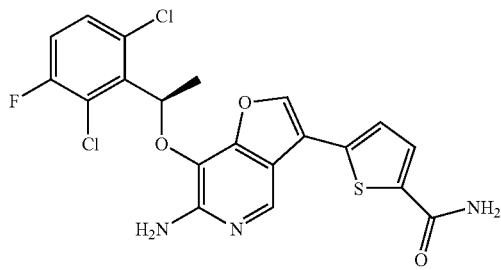

The title compound was prepared according to General procedure W. $^1$H NMR (400 MHz, CD$_3$OD): δ=1.90 (d, J=6.8 Hz, 3H), 6.54 (q, J=6.8 Hz, 1H), 7.23 (t, J=8.7 Hz, 1H), 7.38-7.44 (m, 2H), 7.72 (d, J=4.0 Hz, 1H), 8.01 (s, 1H), 8.26 (s, 1H). MS (ES$^+$): m/z 465.86 (100) [MH$^+$]. HPLC: t$_R$=3.14 min (ZQ3, polar_5 min).

Example 210

5-{6-Amino-7-[(R)-1-(2,6-dichloro-3-fluorophenyl)ethoxy]-furo[3,2-c]pyridin-3-yl}-thiophene-2-carbaldehyde

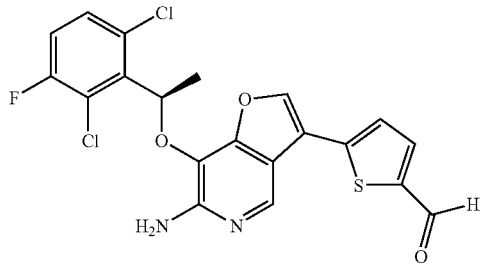

A mixture of 3-bromo-7-[(R)-1-(2,6-dichloro-3-fluorophenyl)-ethoxy]-furo[3,2-c]pyridine-6-ylamine (100.0 mg, 0.238 mmol), 5-formyl-2-thiopheneboronic acid (55.7 mg, 0.357 mmol), Pd(PPh$_3$)$_4$ (10.0 mg, 0.01 mmol), potassium carbonate (98.7 mg, 0.714 mmol) and 4:1 dioxane:water (10 mL) was heated to 90° C. overnight. The material was concentrated in vacuo, redissolved in DCM and transferred to a separatory funnel, extracting with sat. NaHCO$_3$. The organic layer was dry-loaded onto silica gel for column chromatography, eluting with 2% MeOH/DCM. The fractions containing the pure product were concentrated in vacuo to afford the title compound as a yellow solid. $^1$H NMR (400 MHz, CD$_3$OD): δ=1.90 (d, J=6.8 Hz, 3H), 6.53 (q, J=6.7 Hz, 1H), 7.20-7.25 (m, 1H), 7.41 (dd, J=8.8, 4.8 Hz, 1H), 7.59 (d, J=3.8 Hz, 1H), 7.94 (d, J=4.0 Hz, 1H), 8.13 (s, 1H), 8.28 (s, 1H), 9.89 (s, 1H). MS (ES$^+$): m/z 450.92 (100) [MH$^+$]. HPLC: t$_R$=3.75 min (ZQ3, polar_5 min).

Example 211

5-{6-Amino-7-[(R)-1-(2,6-dichloro-3-fluorophenyl)ethoxy]-furo[3,2-c]pyridin-3-yl}-thiophene-2-carbaldehyde

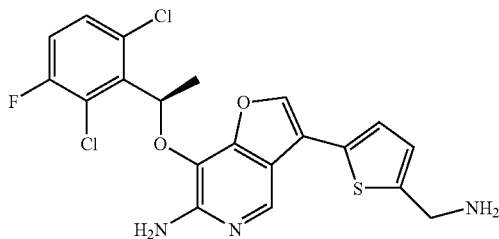

A mixture of 5-{6-Amino-7-[(R)-1-(2,6-dichloro-3-fluorophenyl)ethoxy]furo[3,2-c]pyridin-3-yl}-thiophene-2-carbaldehyde (10.0 mg, 0.022 mmol), hydroxylamine hydrochloride (1.85 mg, 0.0266 mmol), potassium acetate (2.61 mg, 0.0266 mmol) and EtOH (1 mL) was stirred at rt for 20 min. The solution was concentrated in vacuo, and extracted with DCM and water. The organic later was concentrated in vacuo. Zinc (14.5 mg, 0.222 mmol), 2M HCl in H$_2$O (0.5 mL) and THF (1 mL) were added, and the mixture was heated to 70° C. for 2 h. The solution was concentrated in vacuo, and extracted with DCM and sat. NaHCO$_3$. The organic layer was concentrated in vacuo and loaded onto a prep TLC plate, eluting with 6% (7N NH$_3$ in MeOH)/DCM. The band containing the pure product was filtered off using 1:1 MeOH/DCM. The filtrate was concentrated in vacuo to afford the title compound as a white solid. $^1$H NMR (400 MHz, CD$_3$OD): δ=1.88-1.92 (m, 3H), 2.03 (s, 2H), 6.54 (q, J=6.7 Hz, 1H), 7.01 (d, J=3.5 Hz, 1H), 7.20-7.27 (m, 2H), 7.41 (dd, J=9.0, 4.9 Hz, 1H), 7.85 (s, 1H), 8.22 (s, 1H). MS (ES$^+$): m/z 451.87 (100) [MH$^+$]. HPLC: t$_R$=2.62 min (ZQ3, polar_5 min).

Example 212

(5-{6-Amino-7-[(R)-1-(2,6-dichloro-3-fluorophenyl)ethoxy]-furo[3,2-c]pyridin-3-yl}-thiophen-2-yl)methanol

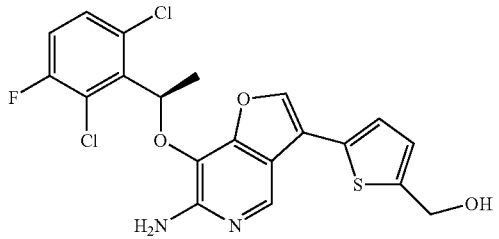

A solution of 5-{6-amino-7-[(R)-1-(2,6-dichloro-3-fluorophenyl)-ethoxy]-furo[3,2-c]pyridin-3-yl}-thiophene-2-carbaldehyde (6.0 mg, 0.013 mmol), sodium borohydride (2.5 mg, 0.067 mmol) and MeOH (1 mL) was stirred at 0° C. for 1 h. The material was concentrated in vacuo and redissolved in DMF (0.5 mL) for HPLC purification. The fractions containing the pure product were concentrated in vacuo to afford the title compound as a white solid. $^1$H NMR (400 MHz, CD$_3$OD): δ=1.90 (d, J=6.8 Hz, 3H), 4.76 (s, 2H), 6.54 (q, J=6.8 Hz, 1H), 7.01 (d, J=3.5 Hz, 1H), 7.19-7.27 (m, 2H), 7.41 (dd, J=9.0, 4.9 Hz, 1H), 7.86 (s, 1H), 8.22 (s, 1H). MS (ES$^+$): m/z 452.90 (100) [MH$^+$]. HPLC: t$_R$=3.27 min (ZQ3, polar_5 min).

Example 213

7-[(R)-1-(2,6-Dichloro-3-fluorophenyl)ethoxy]-3-(5-pyrrolidin-1-ylmethylthiophen-2-yl)-furo[3,2-c]pyridin-6-ylamine

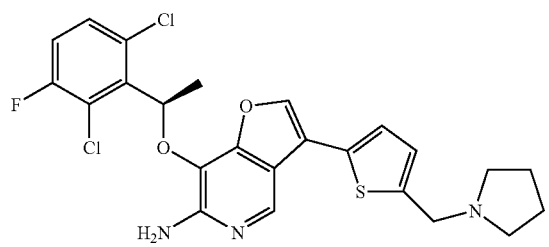

General procedure V: A mixture of 5-{6-amino-7-[(R)-1-(2,6-dichloro-3-fluorophenyl)-ethoxy]-furo[3,2-c]pyridin-3-yl}-thiophene-2-carbaldehyde (7.0 mg, 0.0155 mmol), pyrrolidine (20 mg, 0.3 mmol), sodium triacetoxyborohydride (6.57 mg, 0.031 mmol) and 1,2-dichloroethane (3 mL) was heated to 60° C. in a sealed tube overnight. The solution was concentrated in vacuo, redissolved in DMF (0.5 mL) and filtered through a syringe filter pad. The filtrate purified via HPLC. The fractions containing the pure product were concentrated in vacuo to afford the title compound as a white solid. $^1$H NMR (400 MHz, CD$_3$OD): δ=1.90 (d, J=6.8 Hz, 3H), 2.09 (ddd, J=6.8, 3.8, 3.5 Hz, 4H), 3.35 (t, J=6.9 Hz, 4H), 4.58 (s, 2H), 6.53 (q, J=6.8 Hz, 1H), 7.23 (t, J=8.7 Hz, 1H), 7.32 (d, J=3.5 Hz, 1H), 7.38-7.43 (m, 2H), 7.96 (s, 1H), 8.23 (s, 1H). MS (ES$^+$): m/z 505.91 (100) [MH$^+$]. HPLC: t$_R$=2.72 min (ZQ3, polar_5 min).

Example 214

7-[(R)-1-(2,6-Dichloro-3-fluorophenyl)ethoxy]-3-(5-dimethyl-aminomethylthiophen-2-yl)-furo[3,2-c]pyridin-6-ylamine

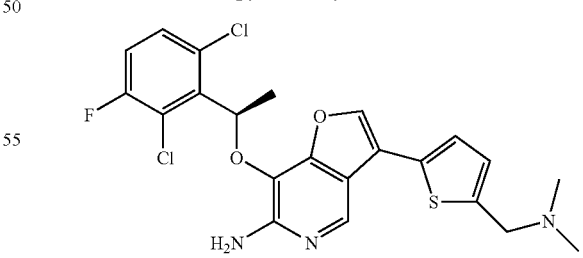

The title compound was prepared according to General procedure V. $^1$H NMR (400 MHz, CD$_3$OD): δ=1.91 (d, J=6.8 Hz, 3H), 2.82 (s, 6H), 4.44 (s, 2H), 6.54 (q, J=6.8 Hz, 1H), 7.24 (t, J=8.7 Hz, 1H), 7.31 (d, J=3.8 Hz, 1H), 7.39-7.44 (m, 2H), 7.96 (s, 1H), 8.24 (s, 1H). MS (ES$^+$): m/z 479.91 (100) [MH$^+$]. HPLC: t$_R$=2.68 min (ZQ3, polar_5 min).

Example 215

7-[(R)-1-(2,6-Dichloro-3-fluorophenyl)ethoxy]-3-(5-piperidin-1-ylmethylthiophen-2-yl)-furo[3,2-c]pyridin-6-ylamine

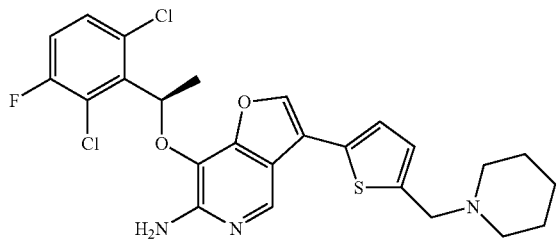

The title compound was prepared according to General procedure V. ¹H NMR (400 MHz, CD₃OD): δ=1.66 (br. s., 2H), 1.80-1.88 (m, 4H), 1.91 (d, J=6.8 Hz, 3H), 3.18 (br. s., 4H), 4.47 (s, 2H), 6.54 (q, J=6.8 Hz, 1H), 7.23 (t, J=8.6 Hz, 1H), 7.31 (d, J=3.5 Hz, 1H), 7.38-7.44 (m, 2H), 7.96 (s, 1H), 8.23 (s, 1H). MS (ES⁺): m/z 519.97 (100) [MH⁺]. HPLC: $t_R$=2.67 min (ZQ3, polar_5 min).

Example 216

1-(5-{6-Amino-7-[(R)-1-(2,6-dichloro-3-fluorophenyl)ethoxy]-furo[3,2-c]pyridin-3-yl}-thiophen-2-ylmethyl)piperidin-4-ol

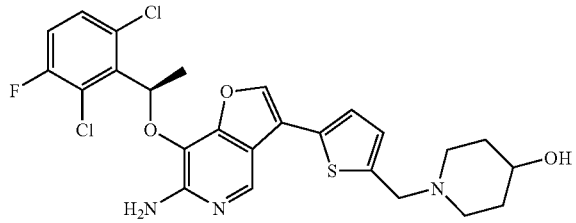

The title compound was prepared according to General procedure V. ¹H NMR (400 MHz, CD₃OD): δ=1.79 (br. s., 2H), 1.90 (d, J=6.6 Hz, 3H), 1.99 (dd, J=8.8, 4.8 Hz, 2H), 2.99 (br. s., 2H), 3.25-3.30 (m, 2H), 3.88 (br. s., 1H), 4.37 (s, 2H), 6.54 (q, J=6.8 Hz, 1H), 7.19-7.28 (m, 2H), 7.37-7.44 (m, 2H), 7.94 (s, 1H), 8.23 (s, 1H). MS (ES⁺): m/z 535.96 (100) [MH⁺]. HPLC: $t_R$=2.66 min (ZQ3, polar_5 min).

Example 217

7-[(R)-1-(2,6-Dichloro-3-fluorophenyl)ethoxy]-3-(5-piperazin-1-ylmethylthiophen-2-yl)-furo[3,2-c]pyridin-6-ylamine

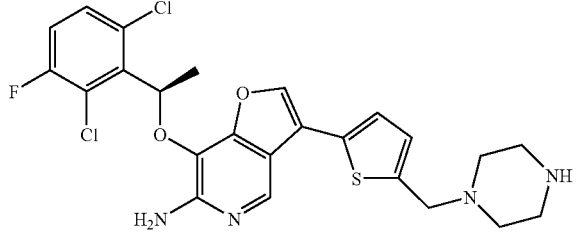

The title compound was prepared according to General procedure V. ¹H NMR (400 MHz, CD₃OD): δ=1.89 (d, J=6.8 Hz, 3H), 2.69-2.82 (m, 4H), 3.20-3.27 (m, 4H), 3.85 (s, 2H), 6.53 (q, J=6.8 Hz, 1H), 7.01 (d, J=3.5 Hz, 1H), 7.19-7.27 (m, 2H), 7.40 (dd, J=9.0, 4.9 Hz, 1H), 7.85 (s, 1H), 8.20 (s, 1H). MS (ES⁺): m/z 520.97 (100) [MH⁺]. HPLC: $t_R$=2.64 min (ZQ3, polar_5 min).

Example 218

7-[(R)-1-(2,6-Dichloro-3-fluorophenyl)ethoxy]-3-[5-(4-methylpiperazin-1-ylmethyl)-thiophen-2-yl]furo[3,2-c]pyridin-6-ylamine

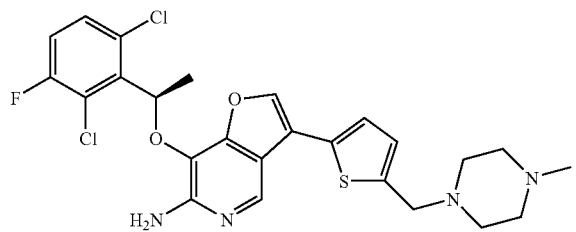

The title compound was prepared according to General procedure V. ¹H NMR (400 MHz, CD₃OD): δ=1.91 (d, J=6.6 Hz, 3H), 2.75 (br. s., 4H), 2.85 (s, 3H), 3.11-3.31 (m, 4H), 3.88 (s, 2H), 6.54 (q, J=6.8 Hz, 1H), 7.03 (d, J=3.8 Hz, 1H), 7.20-7.28 (m, 2H), 7.41 (dd, J=9.0, 4.9 Hz, 1H), 7.86 (s, 1H), 8.21 (s, 1H). MS (ES⁺): m/z 534.97 (100) [MH⁺]. HPLC: $t_R$=2.67 min (ZQ3, polar_5 min).

Example 219

7-[(R)-1-(2,6-Dichloro-3-fluorophenyl)ethoxy]-3-(5-thiomorpholin-4-ylmethylthiophen-2-yl)furo[3,2-c]pyridin-6-ylamine

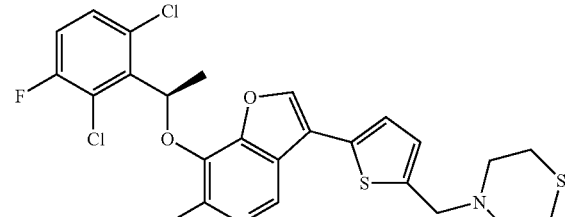

The title compound was prepared according to General procedure V. ¹H NMR (400 MHz, CD₃OD): δ=1.90 (d, J=6.8 Hz, 3H), 2.71-2.77 (m, 4H), 2.92-2.98 (m, 4H), 3.96 (s, 2H), 6.54 (q, J=6.8 Hz, 1H), 7.06 (d, J=3.8 Hz, 1H), 7.22 (t, J=8.7 Hz, 1H), 7.28 (d, J=3.5 Hz, 1H), 7.41 (dd, J=9.1, 4.8 Hz, 1H), 7.88 (s, 1H), 8.22 (s, 1H). MS (ES⁺): m/z 537.89 (100) [MH⁺]. HPLC: $t_R$=2.89 min (ZQ3, polar_5 min).

Example 220

3-(5-Azetidin-1-ylmethylthiophen-2-yl)-7-[(R)-1-(2,6-dichloro-3-fluorophenyl)ethoxy]furo[3,2-c]pyridin-6-ylamine

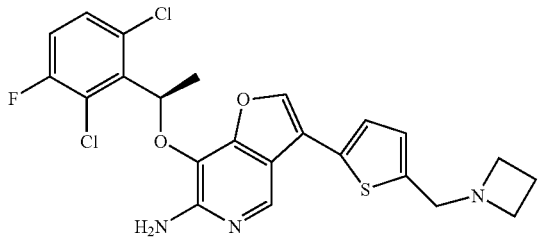

The title compound was prepared according to General procedure V. $^1$H NMR (400 MHz, CD$_3$OD): δ=1.91 (d, J=6.8 Hz, 3H), 2.50 (quin, J=8.1 Hz, 2H), 4.13 (t, J=8.1 Hz, 4H), 4.56 (s, 2H), 6.54 (q, J=6.8 Hz, 1H), 7.20-7.26 (m, 1H), 7.29 (d, J=3.8 Hz, 1H), 7.36-7.44 (m, 2H), 7.95 (s, 1H), 8.22 (s, 1H). MS (ES$^+$): m/z 491.94 (100) [MH$^+$]. HPLC: t$_R$=2.60 min (ZQ3, polar_5 min).

Example 221

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-((3R*,5S*)-3,4,5-trimethylpiperazin-1-yl)-methanone

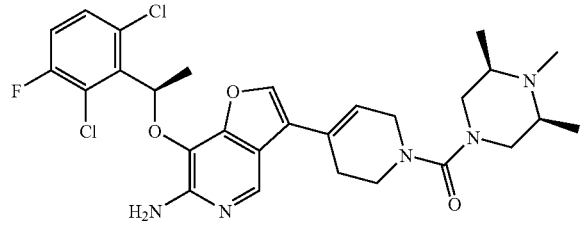

The title compound was prepared according to General Procedure D. $^1$H NMR (400 MHz, CD$_3$OD): δ=1.38 (d, J=6.3 Hz, 6H), 1.87 (d, J=6.8 Hz, 3H), 2.54 (d, J=1.3 Hz, 2H), 2.86 (s, 3H), 3.05 (dd, J=14.4, 11.4 Hz, 2H), 3.28 (d, J=3.0 Hz, 1H), 3.34 (d, J=6.1 Hz, 1H), 3.54 (t, J=5.8 Hz, 2H), 3.76 (d, J=15.4 Hz, 2H), 4.07 (d, J=2.5 Hz, 2H), 6.24 (br. s., 1H), 6.49 (q, J=6.8 Hz, 1H), 7.17-7.24 (m, 1H), 7.39 (dd, J=9.0, 4.9 Hz, 1H), 7.65 (s, 1H), 8.17 (s, 1H). MS (ES$^+$): m/z 576.04 (100) [MH$^+$]. HPLC: t$_R$=2.48 min (ZQ3, polar_5 min).

Example 222

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(5-ethyl-2,5-diazabicyclo[2.2.1]hept-2-yl)-methanone

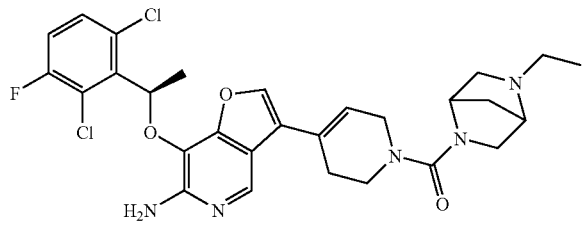

The title compound was prepared according to General Procedure D. $^1$H NMR (400 MHz, CD$_3$OD): δ=1.33 (t, J=7.2 Hz, 3H), 1.88 (d, J=6.6 Hz, 3H), 2.12-2.24 (m, 2H), 2.42-2.53 (m, 1H), 2.54-2.65 (m, 1H), 3.14-3.25 (m, 1H), 3.33-3.42 (m, 3H), 3.58 (d, J=11.4 Hz, 1H), 3.72-3.84 (m, 3H), 4.06 (br. s., 2H), 4.39 (s, 1H), 4.46 (s, 1H), 6.25 (br. s., 1H), 6.50 (q, J=6.8 Hz, 1H), 7.22 (t, J=8.6 Hz, 1H), 7.40 (dd, J=9.0, 4.9 Hz, 1H), 7.66 (s, 1H), 8.18 (s, 1H). MS (ES$^+$): m/z 574.02 (100) [MH$^+$]. HPLC: t$_R$=2.53 min (ZQ3, polar_5 min).

Example 223

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(2-oxa-5-azabicyclo[2.2.1]hept-5-yl)methanone

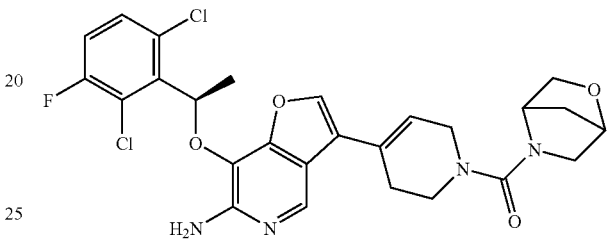

The title compound was prepared according to General Procedure D. $^1$H NMR (400 MHz, CD$_3$OD): δ=1.85 (s, 2H), 1.87 (d, J=6.8 Hz, 3H), 2.39-2.49 (m, 1H), 2.51-2.61 (m, 1H), 3.28 (s, 1H), 3.38 (ddd, J=13.1, 8.3, 4.5 Hz, 1H), 3.54 (dd, J=9.7, 1.6 Hz, 1H), 3.70 (ddd, J=13.3, 5.1, 4.9 Hz, 1H), 3.78 (dd, J=7.6, 1.8 Hz, 1H), 3.97-4.05 (m, 3H), 4.41 (d, J=1.5 Hz, 1H), 4.58 (s, 1H), 6.23 (br. s., 1H), 6.49 (q, J=6.8 Hz, 1H), 7.17-7.24 (m, 1H), 7.39 (dd, J=9.0, 4.9 Hz, 1H), 7.63 (s, 1H), 8.18 (s, 1H). MS (ES$^+$): m/z 547.01 (100) [MH$^+$]. HPLC: t$_R$=2.95 min (ZQ3, polar_5 min).

Example 224

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-((3R*,5S*)-3,5-dimethylpiperazin-1-yl)methanone

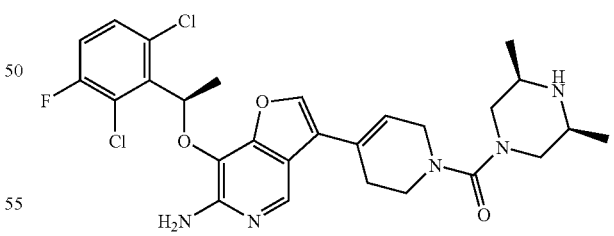

The title compound was prepared according to General Procedure E. $^1$H NMR (400 MHz, CD$_3$OD): δ=1.32 (d, J=6.6 Hz, 6H), 1.88 (d, J=6.8 Hz, 3H), 2.55 (br. s., 2H), 2.86 (dd, J=14.4, 11.4 Hz, 2H), 3.40 (ddd, J=11.2, 6.7, 3.3 Hz, 2H), 3.55 (t, J=5.7 Hz, 2H), 3.80 (dd, J=14.1, 2.3 Hz, 2H), 4.07 (d, J=2.5 Hz, 2H), 6.25 (br. s., 1H), 6.49 (q, J=6.7 Hz, 1H), 7.22 (t, J=8.6 Hz, 1H), 7.39 (dd, J=9.0, 4.9 Hz, 1H), 7.65 (s, 1H), 8.18 (s, 1H). MS (ES$^+$): m/z 562.05 (100) [MH$^+$]. HPLC: t$_R$=2.51 min (ZQ3, polar_5 min).

Example 225

(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-methylpiperazin-1-yl)-methanone

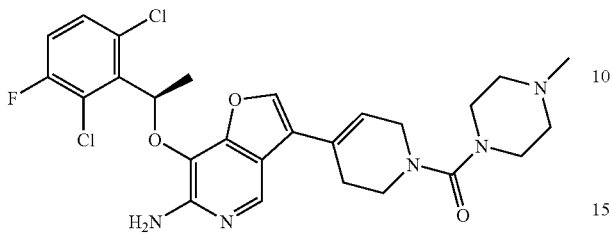

The title compound was prepared according to General Procedure E. ¹H NMR (400 MHz, CD₃OD): δ=1.88 (d, J=6.8 Hz, 3H), 2.55 (br. s., 2H), 2.76 (s, 3H), 3.10 (d, J=4.0 Hz, 4H), 3.48 (br. s, 4H), 3.54 (t, J=5.7 Hz, 2H), 4.06 (d, J=2.5 Hz, 2H), 6.25 (br. s., 1H), 6.50 (q, J=6.8 Hz, 1H), 7.22 (t, J=8.6 Hz, 1H), 7.40 (dd, J=9.0, 4.9 Hz, 1H), 7.65 (s, 1H), 8.18 (s, 1H). MS (ES⁺): m/z 548.04 (100) [MH⁺]. HPLC: $t_R$=2.37 min (ZQ2, polar_5 min).

Example 226

(R)-1-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-2-hydroxypropan-1-one

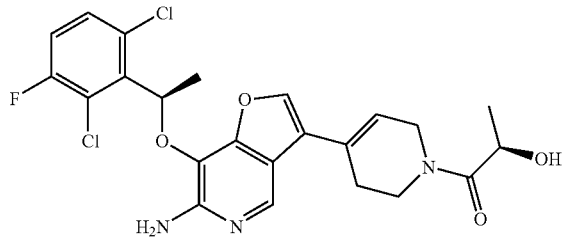

The title compound was prepared according to General Procedure B. ¹H NMR (400 MHz, CD₃OD): δ=1.35 (dd, J=14.7, 6.6 Hz, 3H), 1.88 (d, J=6.8 Hz, 3H), 2.50 (br. s., 1H), 2.57 (br. s., 1H), 3.67-3.85 (m, 2H), 4.17-4.30 (m, 2H), 4.63 (dq, J=13.3, 6.6 Hz, 1H), 6.27 (d, J=10.1 Hz, 1H), 6.50 (q, J=6.8 Hz, 1H), 7.22 (t, J=8.7 Hz, 1H), 7.40 (dd, J=9.0, 4.9 Hz, 1H), 7.67 (d, J=6.3 Hz, 1H), 8.20 (s, 1H). MS (ES⁺): m/z 494.04 (100) [MH⁺]. HPLC: $t_R$=2.79 min (ZQ3, polar_5 min).

Example 227

(S)-1-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-2-hydroxypropan-1-one

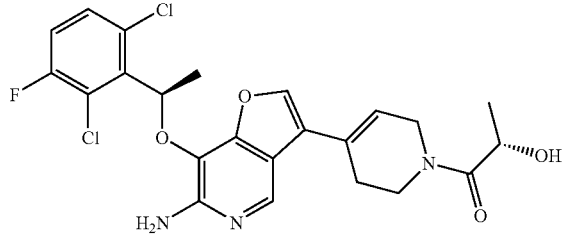

The title compound was prepared according to General Procedure B. ¹H NMR (400 MHz, CD₃OD): δ=1.35 (dd, J=13.4, 6.6 Hz, 3H), 1.88 (d, J=6.8 Hz, 3H), 2.50 (br. s., 1H), 2.57 (br. s., 1H), 3.69-3.94 (m, 2H), 4.25-4.35 (m, 2H), 4.56-4.69 (m, 1H), 6.28 (d, J=9.3 Hz, 1H), 6.50 (q, J=6.8 Hz, 1H), 7.22 (t, J=8.7 Hz, 1H), 7.40 (dd, J=8.8, 4.8 Hz, 1H), 7.67 (d, J=5.6 Hz, 1H), 8.22 (br. s., 1H). MS (ES⁺): m/z 493.90 (100) [MH⁺]. HPLC: $t_R$=2.88 min (ZQ3, polar_5 min).

Example 228

1-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-2-hydroxy-2-methylpropan-β-one

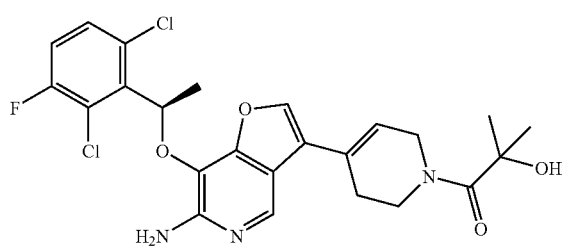

The title compound was prepared according to General Procedure B. ¹H NMR (400 MHz, CD₃OD): δ=1.45 (s, 6H), 1.88 (d, J=6.8 Hz, 3H), 2.54 (br. s., 2H), 3.84 (d, J=12.4 Hz, 2H), 4.73 (d, J=8.3 Hz, 2H), 6.28 (br. s., 1H), 6.51 (q, J=6.8 Hz, 1H), 7.21 (t, J=8.6 Hz, 1H), 7.39 (dd, J=8.8, 4.8 Hz, 1H), 7.67 (s, 1H), 8.12 (s, 1H). MS (ES⁺): m/z 508.02 (100) [MH⁺]. HPLC: $t_R$=2.94 min (ZQ3, polar_5 min).

Example 229

1-(4-{6-Amino-7-[(R)-1-(2,6-dichloro-3-fluorophenyl)ethoxy]-furo[3,2-c]pyridin-3-yl}-3,6-dihydro-2H-pyridin-1-yl)-2-hydroxypropan-1-one

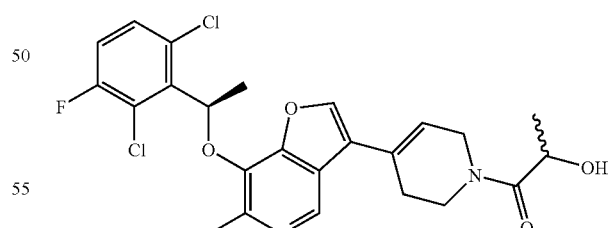

The title compound was prepared according to General Procedure B. ¹H NMR (400 MHz, CD₃OD): δ=1.35 (dd, J=13.9, 6.6 Hz, 3H), 1.89 (d, J=6.8 Hz, 3H), 2.51 (br. s., 1H), 2.57 (br. s., 1H), 3.67-3.85 (m, 2H), 4.28 (d, J=2.0 Hz, 2H), 4.58-4.70 (m, 1H), 6.30 (br. s., 1H), 6.51 (q, J=6.7 Hz, 1H), 7.22 (t, J=8.7 Hz, 1H), 7.40 (dd, J=9.0, 4.9 Hz, 1H), 7.67 (d, J=6.6 Hz, 1H), 8.21 (s, 1H). MS (ES⁺): m/z 493.97 (100) [MH⁺]. HPLC: $t_R$=2.84 min (ZQ3, polar_5 min).

Example 230

(4-{6-Amino-7-[(R)-1-(2,6-dichloro-3-fluorophenyl) ethoxy]-furo[3,2-c]pyridin-3-yl}-3,6-dihydro-2H-pyridin-1-yl)-(3H-[1,2,3]triazol-4-yl)-methanone

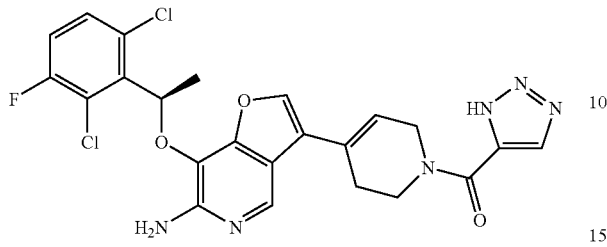

The title compound was prepared according to General Procedure B. $^1$H NMR (400 MHz, CD$_3$OD): δ=1.85-1.91 (m, 3H), 2.63 (br. s., 2H), 3.98 (br. s., 1H), 4.13 (d, J=16.7 Hz, 1H), 4.40 (br. s., 1H), 4.67 (br. s., 1H), 6.35 (br. s., 1H), 6.50 (q, J=6.8 Hz, 1H), 7.22 (t, J=8.6 Hz, 1H), 7.40 (dd, J=9.0, 4.9 Hz, 1H), 7.67 (s, 1H), 7.86 (s, 1H), 8.16-8.27 (m, 1H). MS (ES$^+$): m/z 517.03 (100) [MH$^+$]. HPLC: $t_R$=2.85 min (ZQ3, polar_5 min).

Example 231

(4-{6-Amino-7-[(R)-1-(2,6-dichloro-3-fluorophenyl) ethoxy]-furo[3,2-c]pyridin-3-yl}-3,6-dihydro-2H-pyridin-1-yl)-(2H-pyrazol-3-yl)-methanone

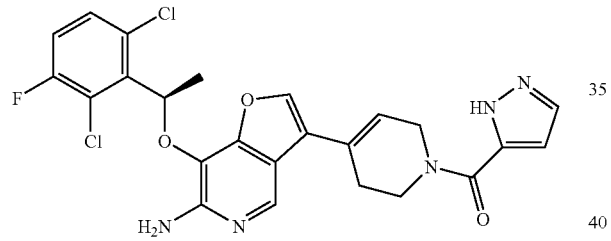

The title compound was prepared according to General Procedure B. $^1$H NMR (400 MHz, CD$_3$OD): δ=1.85-1.89 (m, 3H), 2.61 (br. s., 2H), 3.98 (br. s., 1H), 4.03-4.13 (m, 1H), 4.40 (br. s., 1H), 4.61 (br. s., 1H), 6.34 (br. s., 1H), 6.49 (q, J=6.8 Hz, 1H), 6.68 (s, 1H), 7.21 (t, J=8.6 Hz, 1H), 7.39 (dd, J=9.0, 4.9 Hz, 1H), 7.65 (br. s., 1H), 7.73 (br. s., 1H), 8.23 (s, 1H). MS (ES$^+$): m/z 516.03 (100) [MH$^+$]. HPLC: $t_R$=2.90 min (ZQ3, polar_5 min).

Example 232

(4-{6-Amino-7-[(R)-1-(2,6-dichloro-3-fluorophenyl) ethoxy]-furo[3,2-c]pyridin-3-yl}-3,6-dihydro-2H-pyridin-1-yl)-(1H-imidazol-2-yl)-methanone

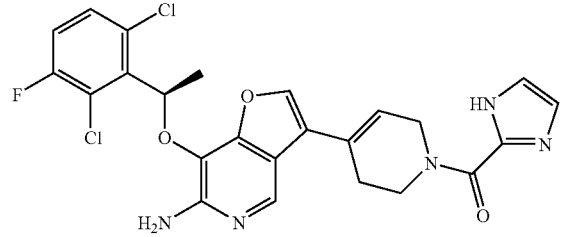

The title compound was prepared according to General Procedure B. $^1$H NMR (400 MHz, CD$_3$OD): δ=1.88 (d, J=6.8 Hz, 3H), 2.60 (br. s., 1H), 2.65 (br. s., 1H), 3.96 (br. s., 1H), 4.38 (br. s., 1H), 4.48 (br. s., 1H), 4.95 (br. s., 1H), 6.31 (d, J=18.9 Hz, 1H), 6.50 (q, J=6.7 Hz, 1H), 7.14-7.28 (m, 3H), 7.39 (dd, J=8.8, 4.8 Hz, 1H), 7.68 (s, 1H), 8.23 (br. s., 1H). MS (ES$^+$): m/z 515.99 (100) [MH$^+$]. HPLC: $t_R$=2.92 min (ZQ3, polar_5 min).

Example 233

(4-{6-Amino-7-[(R)-1-(2,6-dichloro-3-fluorophenyl) ethoxy]-furo[3,2-c]pyridin-3-yl}-3,6-dihydro-2H-pyridin-1-yl)-(3H-imidazol-4-yl)-methanone

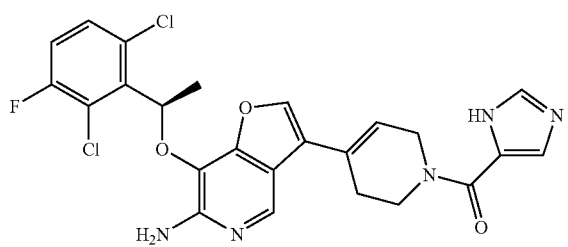

The title compound was prepared according to General Procedure B. $^1$H NMR (400 MHz, CD$_3$OD): δ=1.87 (d, J=6.8 Hz, 3H), 2.65 (s, 2H), 3.95 (br. s., 1H), 4.09 (br. s., 1H), 4.38 (br. s., 1H), 4.64 (br. s., 1H), 6.30 (br. s., 1H), 6.49 (q, J=6.8 Hz, 1H), 7.21 (t, J=8.6 Hz, 1H), 7.39 (dd, J=8.8, 4.8 Hz, 1H), 7.59 (d, J=1.0 Hz, 1H), 7.66 (s, 1H), 7.77 (d, J=1.0 Hz, 1H), 8.20 (br. s., 1H). MS (ES$^+$): m/z 515.95 (100) [MH$^+$]. HPLC: $t_R$=2.59 min (ZQ3, polar_5 min).

Example 234

(4-{6-Amino-7-[(R)-1-(2,6-dichloro-3-fluorophenyl) ethoxy]-furo[3,2-c]pyridin-3-yl}-3,6-dihydro-2H-pyridin-1-yl)-(1H-pyrrol-2-yl)-methanone

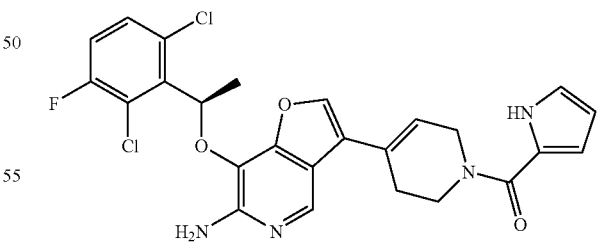

The title compound was prepared according to General Procedure B. $^1$H NMR (400 MHz, CD$_3$OD): δ=1.88 (d, J=6.8 Hz, 3H), 2.61 (br. s., 2H), 4.00 (br. s., 2H), 4.49 (br. s., 2H), 6.20-6.24 (m, 1H), 6.30 (br. s., 1H), 6.49 (q, J=6.8 Hz, 1H), 6.68 (dd, J=3.5, 1.3 Hz, 1H), 6.94 (dd, J=2.7, 1.4 Hz, 1H), 7.21 (t, J=8.6 Hz, 1H), 7.39 (dd, J=8.8, 4.8 Hz, 1H), 7.68 (s, 1H), 8.21 (s, 1H). MS (ES$^+$): m/z 514.98 (100) [MH$^+$]. HPLC: $t_R$=3.19 min (ZQ3, polar_5 min).

Example 235

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-((2S,4R)-4-fluoropyrrolidin-2-yl)-methanone

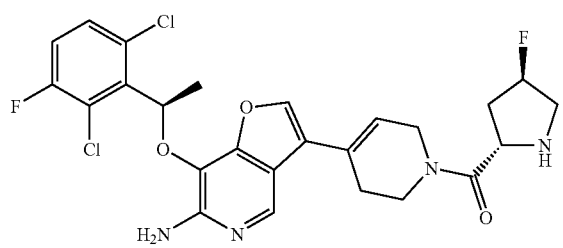

The title compound was prepared according to General Procedure B. $^1$H NMR (400 MHz, CD$_3$OD): δ=1.89 (d, J=6.8 Hz, 3H), 2.07-2.31 (m, 1H), 2.55 (br. s., 2H), 2.81-2.95 (m, 1H), 3.42-3.55 (m, 1H), 3.55-3.68 (m, 1H), 3.77 (t, J=5.8 Hz, 1H), 3.86-4.05 (m, 1H), 4.30 (d, J=2.0 Hz, 2H), 4.79-4.87 (m, 1H), 5.54 (br. s., 1H), 6.30 (d, J=3.8 Hz, 1H), 6.49 (q, J=6.8 Hz, 1H), 7.22 (t, J=8.6 Hz, 1H), 7.40 (dd, J=8.8, 4.8 Hz, 1H), 7.64-7.71 (m, 1H), 8.20 (d, J=2.3 Hz, 1H). MS (ES$^+$): m/z 537.02 (100) [MH$^+$]. HPLC: $t_R$=2.49 min (ZQ3, polar_5 min).

Example 236

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(1-methylpiperidin-2-yl)methanone

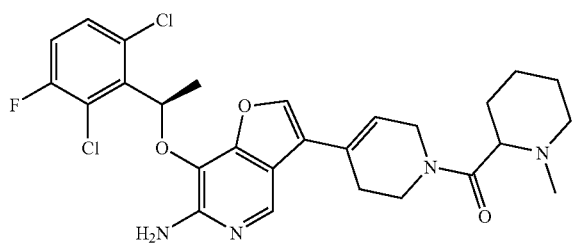

The title compound was prepared according to General Procedure B. $^1$H NMR (400 MHz, CD$_3$OD): δ=1.61-1.82 (m, 3H), 1.88 (d, J=6.8 Hz, 3H), 1.93 (br. s., 2H), 2.16 (d, J=2.8 Hz, 1H), 2.55 (br. s., 1H), 2.64 (d, J=12.9 Hz, 1H), 2.76-2.83 (m, 3H), 3.01-3.15 (m, 1H), 3.50 (br. s., 1H), 3.70-3.93 (m, 2H), 4.25 (br. s., 1H), 4.34 (br. s., 1H), 4.41 (br. s., 1H), 6.30 (d, J=10.6 Hz, 1H), 6.49 (q, J=6.7 Hz, 1H), 7.21 (t, J=8.6 Hz, 1H), 7.39 (dd, J=8.8, 4.8 Hz, 1H), 7.68 (d, J=9.3 Hz, 1H), 8.20 (d, J=1.8 Hz, 1H). MS (ES$^+$): m/z 547.05 (100) [MH$^+$]. HPLC: $t_R$=2.49 min (ZQ3, polar_5 min).

Example 237

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(S)-pyrrolidin-3-ylmethanone

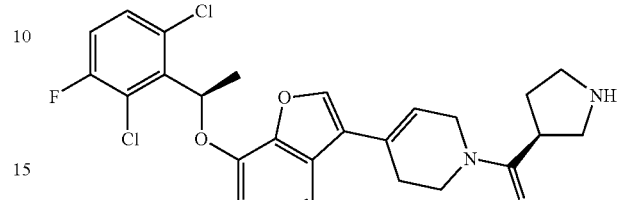

General Procedure N: A mixture of 7-[(R)-1-(2,6-dichloro-3-fluorophenyl)ethoxy]-3-(1,2,3,6-tetrahydropyridin-4-yl)-furo[3,2-c]pyridin-6-ylamine (8.0 mg, 0.019 mmol), (S)-pyrrolidine-1,3-dicarboxylic acid 1-tert-butyl ester (8.2 mg, 0.038 mmol), TBTU (9.12 mg, 0.0284 mmol), DIPEA (20 µL, 0.09 mmol) and DCM (1 mL) was stirred at rt for 30 min. The solution was transferred to a separatory funnel and extracted with DCM and water. The organic later was concentrated in vacuo, redissolved in dioxane and transferred to a sealed tube. 4M HCl in dioxane (0.1 mL) was added, and the mixture was heated to 50° C. for 2 h. The solution was concentrated in vacuo, dissolved in DMF (0.5 mL) and purified via HPLC. The fractions containing the pure product were concentrated in vacuo to afford the title compound as a yellow solid. $^1$H NMR (400 MHz, CD$_3$OD): δ=1.88 (d, J=6.6 Hz, 3H), 2.04-2.15 (m, 1H), 2.34-2.43 (m, 1H), 2.51 (d, J=1.3 Hz, 1H), 2.61 (d, J=2.5 Hz, 1H), 3.34-3.39 (m, 3H), 3.63-3.74 (m, 2H), 3.79-3.88 (m, 2H), 4.26 (br. s., 1H), 4.32 (br. s., 1H), 6.30 (br. s., 1H), 6.49 (q, J=6.8 Hz, 1H), 7.21 (t, J=8.6 Hz, 1H), 7.39 (dd, J=9.0, 4.9 Hz, 1H), 7.66 (d, J=9.9 Hz, 1H), 8.19 (s, 1H). MS (ES$^+$): m/z 519.01 (100) [MH$^+$]. HPLC: $t_R$=2.54 min (ZQ3, polar_5 min).

Example 238

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(S)-piperidin-2-ylmethanone

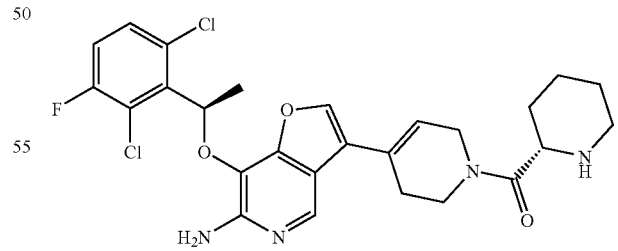

The title compound was prepared according to General Procedure N. $^1$H NMR (400 MHz, CD$_3$OD): δ=1.57-1.82 (m, 4H), 1.88 (d, J=6.6 Hz, 3H), 1.92 (d, J=6.8 Hz, 2H), 2.18 (dd, J=11.7, 10.7 Hz, 1H), 2.52 (br. s., 1H), 2.62 (br. s., 1H), 3.00-3.14 (m, 1H), 3.41 (dd, J=8.2, 3.7 Hz, 1H), 3.71-3.77 (m, 1H), 4.16-4.26 (m, 1H), 4.26-4.41 (m, 2H), 6.29 (d, J=8.8 Hz, 1H), 6.49 (q, J=6.7 Hz, 1H), 7.21 (t, J=8.6 Hz, 1H), 7.39 (dd, J=9.1, 4.8 Hz, 1H), 7.67 (d, J=7.6 Hz, 1H), 8.19 (s, 1H). MS (ES$^+$): m/z 532.99 (100) [MH$^+$]. HPLC: $t_R$=2.63 min (ZQ3, polar_5 min).

Example 239

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(R)-piperidin-2-ylmethanone

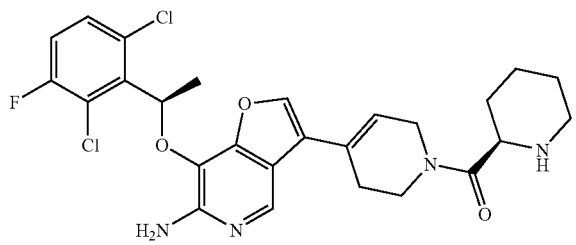

The title compound was prepared according to General Procedure N. $^1$H NMR (400 MHz, CD$_3$OD): δ=1.63 (br. s., 1H), 1.67-1.82 (m, 3H), 1.88 (d, J=6.6 Hz, 3H), 1.89-2.02 (m, 2H), 2.17 (t, J=12.4 Hz, 1H), 2.53 (br. s., 1H), 2.61 (d, J=1.8 Hz, 1H), 3.02-3.12 (m, 1H), 3.36-3.46 (m, 1H), 3.72-3.77 (m, 1H), 4.15-4.27 (m, 1H), 4.27-4.42 (m, 2H), 6.25-6.32 (m, 1H), 6.49 (q, J=6.8 Hz, 1H), 7.21 (t, J=8.7 Hz, 1H), 7.39 (dd, J=9.0, 4.9 Hz, 1H), 7.67 (d, J=8.6 Hz, 1H), 8.19 (s, 1H). MS (ES$^+$): m/z 532.99 (100) [MH$^+$]. HPLC: $t_R$=2.68 min (ZQ3, polar_5 min).

Example 240

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(S)-piperidin-3-ylmethanone

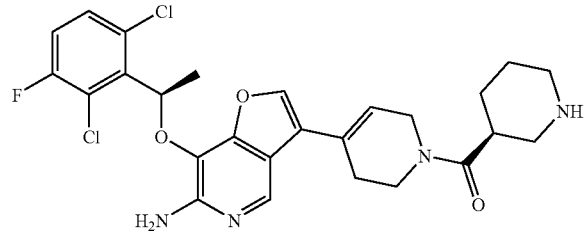

The title compound was prepared according to General Procedure N. $^1$H NMR (400 MHz, CD$_3$OD): δ=1.79-1.91 (m, 6H), 1.94-2.08 (m, 1H), 2.51 (br. s., 1H), 2.61 (br. s., 1H), 3.09-3.27 (m, 4H), 3.33-3.40 (m, 1H), 3.73-3.88 (m, 2H), 4.16-4.37 (m, 2H), 6.26-6.33 (m, 1H), 6.50 (q, J=6.7 Hz, 1H), 7.22 (t, J=8.6 Hz, 1H), 7.40 (dd, J=8.8, 4.8 Hz, 1H), 7.67 (d, J=8.8 Hz, 1H), 8.20 (s, 1H). MS (ES$^+$): m/z 532.99 (100) [MH$^+$]. HPLC: $t_R$=2.72 min (ZQ3, polar_5 min).

Example 241

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(R)-piperidin-3-ylmethanone

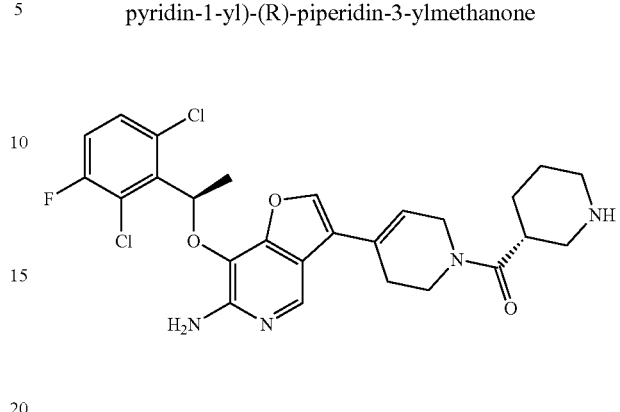

The title compound was prepared according to General Procedure N. $^1$H NMR (400 MHz, CD$_3$OD): δ=1.80-1.91 (m, 6H), 1.95-2.06 (m, 1H), 2.51 (br. s., 1H), 2.60 (br. s., 1H), 3.12-3.27 (m, 4H), 3.33-3.43 (m, 1H), 3.72-3.89 (m, 2H), 4.17-4.37 (m, 2H), 6.25-6.31 (m, 1H), 6.49 (q, J=6.8 Hz, 1H), 7.22 (t, J=8.6 Hz, 1H), 7.40 (dd, J=9.0, 4.9 Hz, 1H), 7.67 (d, J=8.1 Hz, 1H), 8.19 (s, 1H). MS (ES$^+$): m/z 532.99 (100) [MH$^+$]. HPLC: $t_R$=2.55 min (ZQ3, polar_5 min).

Example 242

(4-{6-Amino-7-[(R)-1-(2,6-dichloro-3-fluorophenyl)ethoxy]-furo[3,2-c]pyridin-3-yl}-3,6-dihydro-2H-pyridin-1-yl)-(R)-pyrrolidin-2-ylmethanone

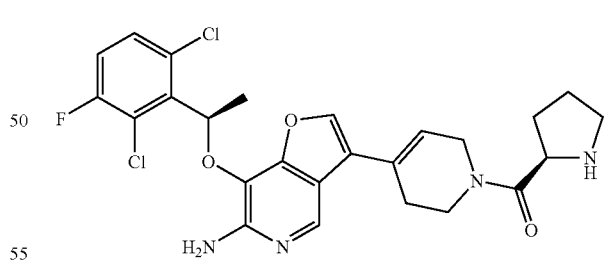

The title compound was prepared according to General Procedure N. $^1$H NMR (400 MHz, CD$_3$OD): δ=1.86-1.91 (m, 4H), 1.92-2.14 (m, 3H), 2.47-2.65 (m, 3H), 3.33-3.48 (m, 2H), 3.76 (t, J=5.9 Hz, 1H), 4.17-4.41 (m, 2H), 4.67-4.77 (m, 1H), 6.25-6.33 (m, 1H), 6.50 (q, J=6.8 Hz, 1H), 7.22 (t, J=8.6 Hz, 1H), 7.40 (dd, J=9.0, 4.9 Hz, 1H), 7.68 (d, J=9.3 Hz, 1H), 8.20 (d, J=1.8 Hz, 1H). MS (ES$^+$): m/z 518.98 (100) [MH$^+$]. HPLC: $t_R$=2.52 min (ZQ3, polar_5 min).

Example 243

N-(3-{6-Amino-7-[(R)-1-(2,6-dichloro-3-fluorophenyl)ethoxy]-furo[3,2-c]pyridin-3-yl}phenyl)benzenesulfonamide

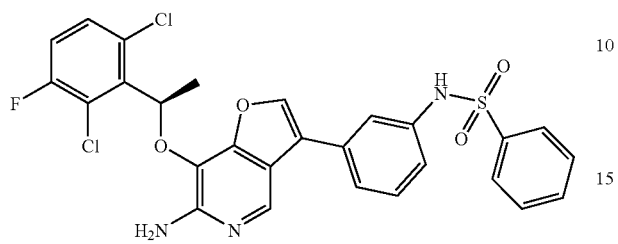

General Procedure O: A mixture of 3-(4,4,5,5-tetramethyl-1,3,2-dioxaborolan-2-yl)aniline (30.0 mg, 0.137 mmol), DCM (2 mL) and pyridine (0.04 mL) was charged with benzenesulfonyl chloride (36.3 mg, 0.205 mmol) at rt. The solution turned bright yellow. The mixture was heated to 25° C. overnight, and then concentrated in vacuo. The crude material was used directly for Suzuki coupling, mixed together with 3-bromo-7-[(R)-1-(2,6-dichloro-3-fluorophenyl)ethoxy]-furo[3,2-c]pyridine-6-ylamine (20.0 mg, 0.0476 mmol), Pd(PPh$_3$)$_4$ (5.5 mg, 0.0048 mmol), potassium carbonate (19.7 mg, 0.143 mmol) and 4:1 dioxane/H$_2$O (2 mL) and microwaved at 100° C. for 30 min. The solvents were removed in vacuo, and the material was redissolved in MeOH and passed through a PS-thiol cartridge to remove palladium. The crude mixture was concentrated in vacuo and redissolved in DMF (0.5 mL) for HPLC purification. The fractions containing the pure product were concentrated in vacuo to afford the title compound as a white solid. $^1$H NMR (400 MHz, CD$_3$OD): δ=1.87-1.92 (m, 3H), 6.55 (q, J=6.8 Hz, 1H), 7.10 (dt, J=7.3, 2.1 Hz, 1H), 7.20-7.26 (m, 1H), 7.28-7.35 (m, 2H), 7.38 (d, J=1.8 Hz, 1H), 7.42 (dd, J=9.0, 4.9 Hz, 1H), 7.48-7.52 (m, 2H), 7.55-7.58 (m, 1H), 7.78-7.80 (m, 2H), 7.81 (s, 1H), 8.06 (s, 1H). MS (ES$^+$): m/z 571.96 (100) [MH$^+$]. HPLC: t$_R$=3.69 min (ZQ3, polar_5 min).

Example 244

Propane-1-sulfonic acid (3-{6-amino-7-[(R)-1-(2,6-dichloro-3-fluorophenyl)ethoxy]-furo[3,2-c]pyridin-3-yl}phenyl)amide

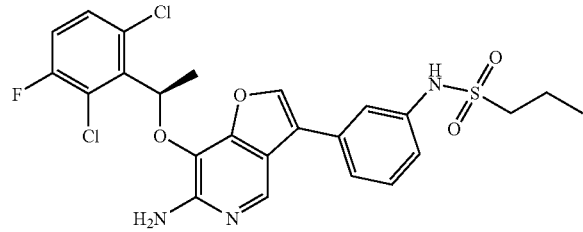

The title compound was prepared according to General Procedure O. $^1$H NMR (400 MHz, CD$_3$OD): δ=1.01 (t, J=7.6 Hz, 3H), 1.78-1.86 (m, 2H), 1.91 (d, J=6.6 Hz, 3H), 3.04-3.15 (m, 2H), 6.56 (d, J=6.8 Hz, 1H), 7.20-7.27 (m, 2H), 7.38-7.45 (m, 3H), 7.57 (s, 1H), 7.87 (s, 1H), 8.22 (s, 1H). MS (ES$^+$): m/z 538.01 (100) [MH$^+$]. HPLC: t$_R$=3.57 min (ZQ3, polar_5 min).

Example 245

Ethanesulfonic acid (3-{6-amino-7-[(R)-1-(2,6-dichloro-3-fluorophenyl)ethoxy]-furo[3,2-c]pyridin-3-yl}phenyl)amide

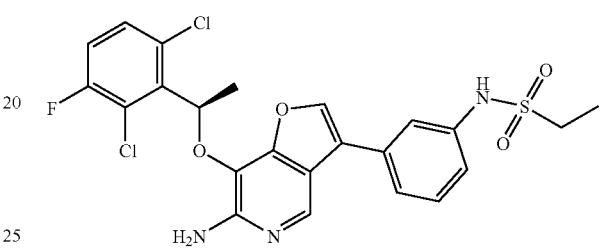

The title compound was prepared according to General Procedure O. $^1$H NMR (400 MHz, CD$_3$OD): δ=1.32 (t, J=7.3 Hz, 3H), 1.90 (d, J=6.8 Hz, 3H), 3.13 (q, J=7.3 Hz, 2H), 6.55 (q, J=6.8 Hz, 1H), 7.19-7.28 (m, 2H), 7.37-7.44 (m, 3H), 7.54-7.59 (m, 1H), 7.86 (s, 1H), 8.22 (s, 1H). MS (ES$^+$): m/z 524.01 (100) [MH$^+$]. HPLC: t$_R$=3.41 min (ZQ3, polar_5 min).

Example 246

Butane-1-sulfonic acid (3-{6-amino-7-[(R)-1-(2,6-dichloro-3-fluorophenyl)ethoxy]-furo[3,2-c]pyridin-3-yl}phenyl)amide

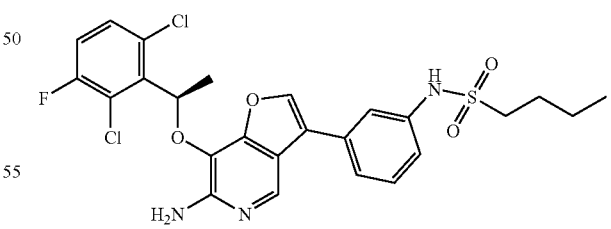

The title compound was prepared according to General Procedure O. $^1$H NMR (400 MHz, CD$_3$OD): δ=1.01 (t, J=7.6 Hz, 3H), 1.78-1.86 (m, 2H), 1.91 (d, J=6.6 Hz, 3H), 3.04-3.15 (m, 2H), 6.56 (d, J=6.8 Hz, 1H), 7.20-7.27 (m, 2H), 7.38-7.45 (m, 3H), 7.57 (s, 1H), 7.87 (s, 1H), 8.22 (s, 1H). MS (ES$^+$): m/z 538.01 (100) [MH$^+$]. HPLC: t$_R$=3.57 min (ZQ3, polar_5 min).

Example 247

Thiophene-2-sulfonic acid (3-{6-amino-7-[(R)-1-(2,6-dichloro-3-fluorophenyl)-ethoxy]-furo[3,2-c]pyridin-3-yl}phenyl)amide

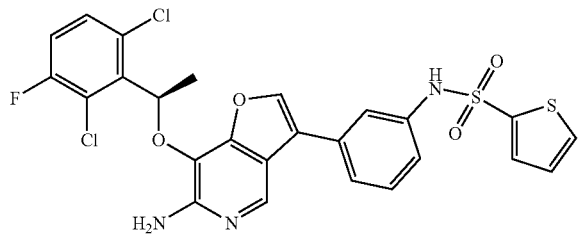

The title compound was prepared according to General Procedure O. ¹H NMR (400 MHz, CD₃OD): δ=1.89 (d, J=6.8 Hz, 3H), 6.54 (q, J=6.7 Hz, 1H), 7.06 (dd, J=4.8, 3.8 Hz, 1H), 7.14 (dt, J=7.3, 1.9 Hz, 1H), 7.20-7.25 (m, 1H), 7.32-7.45 (m, 4H), 7.52 (dd, J=3.8, 1.3 Hz, 1H), 7.71 (dd, J=5.1, 1.3 Hz, 1H), 7.80 (s, 1H), 8.11 (s, 1H). MS (ES⁺): m/z 577.92 (100) [MH⁺]. HPLC: $t_R$=3.65 min (ZQ3, polar_5 min).

Example 248

3,3,3-Trifluoropropane-1-sulfonic acid (3-{6-amino-7-[(R)-1-(2,6-dichloro-3-fluorophenyl)ethoxy]-furo[3,2-c]pyridin-3-yl}phenyl)amide

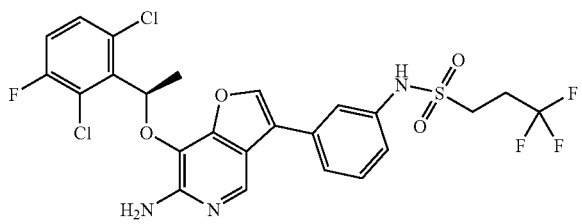

The title compound was prepared according to General Procedure O. ¹H NMR (400 MHz, CD₃OD): δ=1.91 (d, J=6.8 Hz, 3H), 2.65-2.76 (m, 2H), 3.33-3.39 (m, 2H), 6.56 (q, J=6.8 Hz, 1H), 7.20-7.28 (m, 2H), 7.39-7.47 (m, 3H), 7.57 (d, J=1.0 Hz, 1H), 7.88 (s, 1H), 8.22 (s, 1H). MS (ES⁺): m/z 591.99 (100) [MH⁺]. HPLC: $t_R$=3.69 min (ZQ3, polar_5 min).

Example 249

2-Dimethylaminoethanesulfonic Acid (3-{6-amino-7-[(R)-1-(2,6-dichloro-3-fluorophenyl)ethoxy]furo[3,2-c]pyridin-3-yl}phenyl)amide

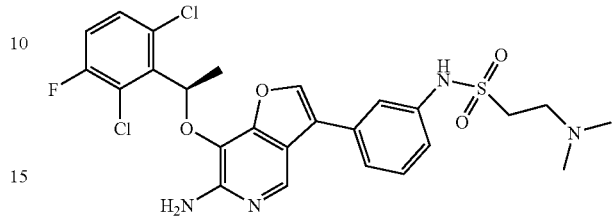

The title compound was prepared according to General Procedure O. ¹H NMR (400 MHz, CD₃OD): δ=1.90 (d, J=6.8 Hz, 3H), 2.20 (s, 6H), 2.77-2.82 (m, 2H), 3.30 (d, J=1.5 Hz, 2H), 6.55 (q, J=6.8 Hz, 1H), 7.19-7.27 (m, 2H), 7.38-7.44 (m, 3H), 7.58 (d, J=1.0 Hz, 1H), 7.87 (s, 1H), 8.23 (s, 1H). MS (ES⁺): m/z 567.04 (100) [MH⁺]. HPLC: $t_R$=2.54 min (ZQ3, polar_5 min).

Example 250

1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-2-(methylamino)ethanone

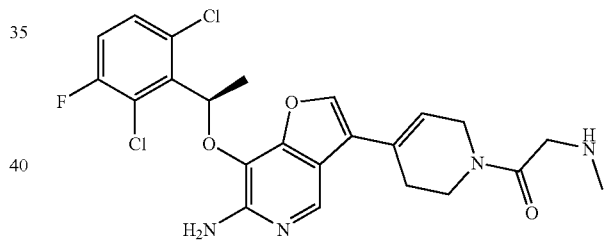

General Procedure P: A mixture of 7-[(R)-1-(2,6-dichloro-3-fluorophenyl)ethoxy]-3-(1,2,3,6-tetrahydropyridin-4-yl)-furo[3,2-c]pyridin-6-ylamine (10.0 mg, 0.0237 mmol), N-(tert-butoxycarbonyl)-N-methylglycine (9.0 mg, 0.047 mmol), TBTU (7.6 mg, 0.024 mmol), DIPEA (0.02 mL, 0.1 mmol) and DCM (1.0 mL) was stirred at rt for 30 min. The reaction mixture was diluted with DCM (20 mL) and then quenched with sat. aq. NaHCO₃ (20 mL). The organic layer was washed with brine (25 mL) and then concentrated under reduced pressure to yield a yellow oil. The yellow oil was dissolved in DCM (0.5 mL) and then treated with 1 M of HCl in Et₂O (1 mL). The resulting mixture was stirred for 30 min. The solvent was evaporated under reduced pressure. The resulting residue was dissolved in DMSO and submitted for Mass Directed Purification. The fractions containing the pure product were concentrated in vacuo to afford the title compound as a yellow oil. ¹H NMR (CD₃OD, 400 MHz): δ=1.89-1.94 (m, 3H), 2.47-2.60 (m, 2H), 2.74 (d, J=2.8 Hz, 3H), 3.63 (t, J=5.8 Hz, 1H), 3.83 (t, J=5.9 Hz, 1H), 4.08 (s, 1H), 4.14 (s, 2H), 4.27 (d, J=2.0 Hz, 1H), 6.24 (d, J=20.0 Hz, 1H), 6.66 (q, J=6.7 Hz, 1H), 7.23 (t, J=8.6 Hz, 1H), 7.41 (dd, J=9.0, 4.9 Hz, 1H), 7.90 (d, J=9.1 Hz, 1H), 8.25 (d, J=4.0 Hz, 1H). MS (ES⁺): m/z 493.02 [MH⁺].

Example 251

(2S)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]propan-1-one

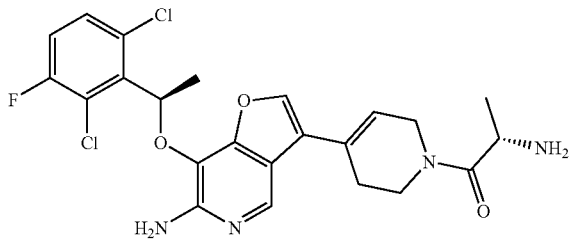

The title compound was prepared according to General Procedure P. ¹H NMR (CD₃OD, 400 MHz): δ=1.43-1.52 (m, 3H), 1.93 (d, J=6.6 Hz, 3H), 2.47-2.63 (m, 2H), 3.71-3.97 (m, 2H), 4.16-4.37 (m, 2H), 4.38-4.52 (m, 1H), 6.21-6.31 (m, 1H), 6.66 (q, J=6.7 Hz, 1H), 7.23 (t, J=8.6 Hz, 1H), 7.41 (dd, J=9.0, 4.9 Hz, 1H), 7.87-7.93 (m, 1H), 8.23-8.29 (m, 1H). MS (ES⁺): m/z 493.01 [MH⁺].

Example 252

(2R)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]propan-1-one

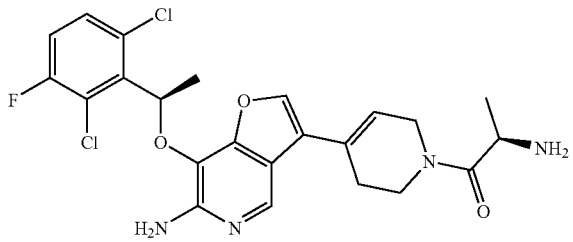

The title compound was prepared according to General Procedure P. ¹H NMR (CD₃OD, 400 MHz): δ=1.39-1.55 (m, 3H), 1.93 (d, J=6.8 Hz, 2H), 2.45-2.62 (m, 2H), 3.68-3.99 (m, 2H), 4.16-4.37 (m, 2H), 4.39-4.57 (m, 1H), 6.15-6.35 (m, 1H), 6.66 (qd, J=6.7, 2.7 Hz, 1H), 7.24 (t, J=8.6 Hz, 1H), 7.42 (dd, J=9.1, 4.8 Hz, 1H), 7.84-7.94 (m, 1H), 8.20-8.31 (m, 1H). MS (ES⁺): m/z 493.01 [MH⁺]

Example 253

2-Amino-1-[4-{6-amino-7-[(1R)-1-(2,6-dichloro-3-fluorophenyl)ethoxy]furo[3,2-c]pyridin-3-yl}-3,6-dihydropyridin-1(2H)-yl]ethanone

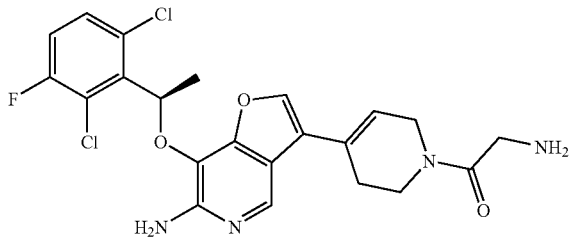

The title compound was prepared according to General Procedure P. ¹H NMR (CD₃OD, 400 MHz): δ=1.43-1.52 (m, 3H), 1.93 (d, J=6.6 Hz, 3H), 2.47-2.63 (m, 2H), 3.71-3.97 (m, 2H), 4.16-4.37 (m, 2H), 4.38-4.52 (m, 1H), 6.21-6.31 (m, 1H), 6.66 (q, J=6.7 Hz, 1H), 7.23 (t, J=8.6 Hz, 1H), 7.41 (dd, J=9.0, 4.9 Hz, 1H), 7.87-7.93 (m, 1H), 8.23-8.29 (m, 1H). MS (ES⁺): m/z 479.00 [MH⁺].

Example 254

(2S)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-3-hydroxypropan-1-one

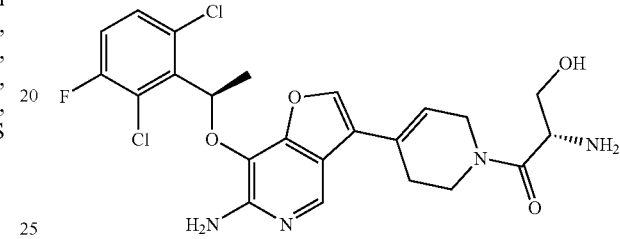

The title compound was prepared according to General Procedure P. ¹H NMR (CD₃OD, 400 MHz): δ=1.93 (d, J=6.6 Hz, 3H), 2.47-2.63 (m, 2H), 3.69-4.02 (m, 4H), 4.17-4.39 (m, 2H), 4.40-4.57 (m, 1H), 6.28 (br. s., 1H), 6.65 (q, J=6.7 Hz, 1H), 7.24 (t, J=8.6 Hz, 1H), 7.41 (dd, J=9.0, 4.9 Hz, 1H), 7.83-7.94 (m, 1H), 8.17-8.31 (m, 1H). MS (ES⁺): m/z 508.99 [MH⁺].

Example 255

(2R)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-3-hydroxypropan-1-one

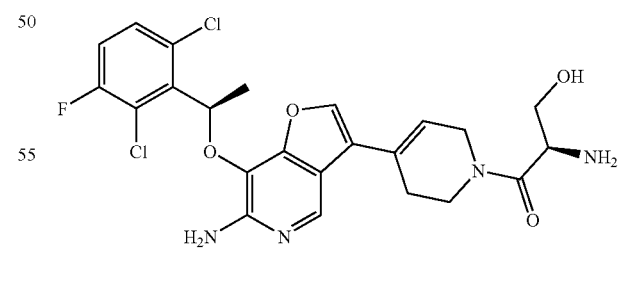

The title compound was prepared according to General Procedure P. ¹H NMR (CD₃OD, 400 MHz): δ=1.93 (d, J=6.8 Hz, 3H), 2.46-2.63 (m, 2H), 3.65-4.02 (m, 4H), 4.19-4.37 (m, 3H), 4.42-4.56 (m, 1H), 6.18-6.33 (m, 1H), 6.65 (q, J=6.6 Hz, 1H), 7.23 (t, J=8.7 Hz, 1H), 7.41 (dd, J=9.0, 4.9 Hz, 1H), 7.84-7.94 (m, 1H), 8.22-8.29 (m, 1H). MS (ES⁺): m/z 508.96 [MH⁺].

Example 256

(2S)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-3-phenylpropan-1-one

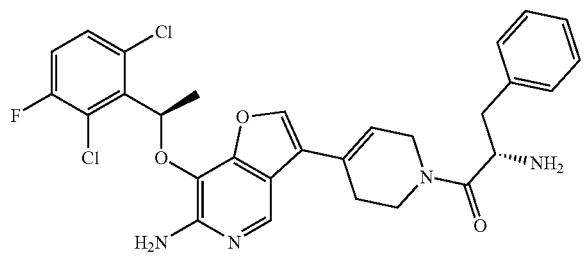

The title compound was prepared according to General Procedure P. MS (ES+): m/z 569.02 [MH+].

Example 257

(2R)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-3-phenylpropan-1-one

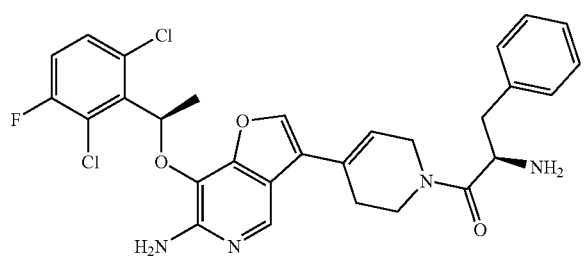

The title compound was prepared according to General Procedure P. MS (ES+): m/z 569.00 [MH+].

Example 258

(2S)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-4-methylpentan-1-one

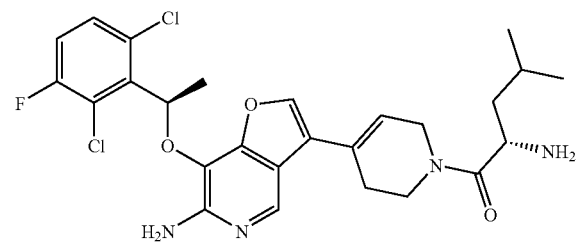

The title compound was prepared according to General Procedure P. ¹H NMR (CD₃OD, 400 MHz): δ=1.02 (d, J=6.8 Hz, 3H), 1.11 (dd, J=11.4, 7.1 Hz, 3H), 1.93 (d, J=6.8 Hz, 3H), 2.12-2.30 (m, 1H), 2.52 (d, J=4.8 Hz, 2H), 3.70-3.96 (m, 2H), 4.14-4.33 (m, 2H), 4.34-4.46 (m, 1H), 6.19-6.34 (m, 1H), 6.65 (m, 1H), 7.24 (t, J=8.6 Hz, 1H), 7.42 (dd, J=9.0, 4.9 Hz, 1H), 7.89 (d, J=7.1 Hz, 1H), 8.24 (d, J=14.4 Hz, 1H). MS (ES+): m/z 521.00 [MH+].

Example 259

(2R)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-4-methylpentan-1-one

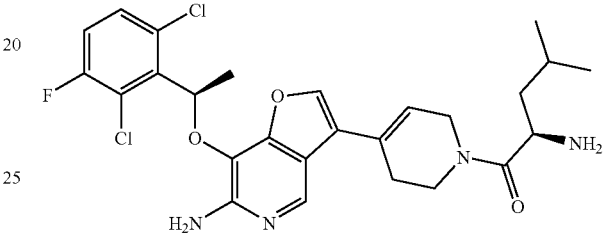

The title compound was prepared according to General Procedure P. ¹H NMR (CD₃OD, 400 MHz): δ=1.02 (dd, J=6.9, 4.7 Hz, 3H), 1.11 (dd, J=14.1, 7.1 Hz, 3H), 1.93 (d, J=6.8 Hz, 3H), 2.13-2.31 (m, 1H), 2.48-2.64 (m, 2H), 3.73-3.97 (m, 2H), 4.10-4.33 (m, 2H), 4.39 (d, J=5.1 Hz, 1H), 6.19-6.34 (m, 1H), 6.59-6.71 (m, 1H), 7.24 (t, J=8.6 Hz, 1H), 7.42 (dd, J=9.1, 4.8 Hz, 1H), 7.89 (d, J=7.1 Hz, 1H), 8.18-8.30 (m, 1H). MS (ES+): m/z 521.00 [MH+].

Example 260

2-Amino-1-[4-{6-amino-7-[(1R)-1-(2,6-dichloro-3-fluorophenyl)-ethoxy]furo[3,2-c]pyridin-3-yl}-3,6-dihydropyridin-1(2H)-yl]-3,3,3-trifluoropropan-1-one

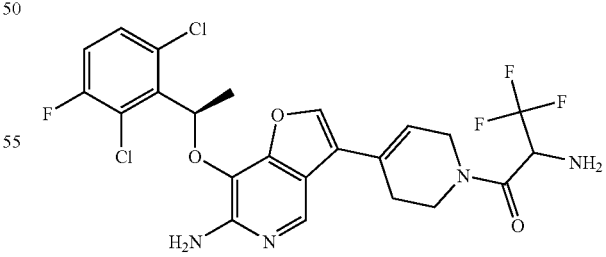

The title compound was prepared according to General Procedure P. ¹H NMR (CD₃OD, 400 MHz): δ=1.88 (d, J=6.8 Hz, 1H), 2.53 (br. s., 1H), 4.32 (d, J=5.6 Hz, 1H), 6.29 (br. s., 1H), 6.50 (dd, J=6.7, 2.1 Hz, 1H), 7.22 (t, J=8.6 Hz, 1H), 7.40 (dd, J=9.0, 4.9 Hz, 1H), 7.68 (d, J=6.8 Hz, 1H), 8.21 (br. s., 1H). MS (ES+): m/z 546.96 [MH+].

Example 261

(2S)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-2-phenylethanone

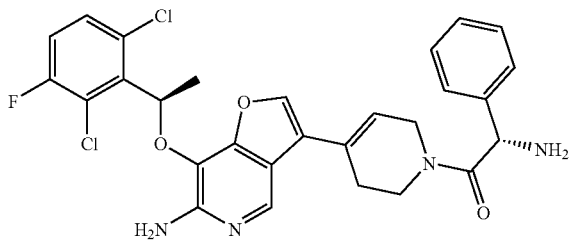

The title compound was prepared according to General Procedure P. ¹H NMR (CD₃OD, 400 MHz): δ=0.96-1.23 (m, 1H), 1.94 (dd, J=6.6, 3.3 Hz, 3H), 2.36-2.61 (m, 1H), 3.21 (s, 1H), 3.55 (d, J=1.8 Hz, 2H), 3.89 (br. s., 1H), 4.32 (br. s., 1H), 6.05-6.35 (m, 1H), 6.48-6.59 (m, 1H), 7.28 (t, J=8.6 Hz, 1H), 7.42-7.63 (m, 7H), 8.05-8.23 (m, 1H). MS (ES⁺): m/z 554.99 [MH⁺].

Example 262

(2R)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-2-phenylethanone

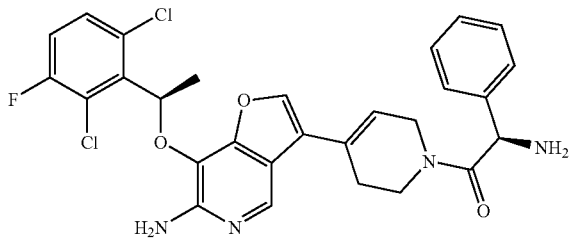

The title compound was prepared according to General Procedure P. ¹H NMR (CD₃OD, 400 MHz): δ=1.11-1.32 (m, 1H), 1.83-1.91 (m, 3H), 2.50 (br. s., 1H), 3.11-3.16 (m, 1H), 3.48 (d, J=1.5 Hz, 2H), 3.77 (br. s., 1H), 4.23 (br. s., 1H), 5.98-6.27 (m, 1H), 6.47 (br. s., 1H), 7.16-7.26 (m, 1H), 7.48 (br. s., 7H), 8.00-8.14 (m, 1H). MS (ES⁺): m/z 554.99 [MH⁺].

Example 263

(2S)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-3-(1H-imidazol-5-yl)propan-1-one

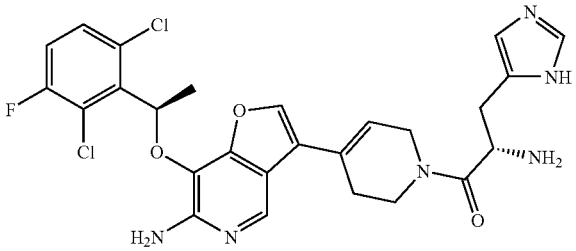

The title compound was prepared according to General Procedure P. ¹H NMR (CD₃OD, 400 MHz): δ=1.96 (d, J=6.8 Hz, 3H), 2.57 (br. s., 1H), 2.89 (s, 2H), 3.09-3.18 (m, 1H), 3.21 (dd, J=3.3, 1.8 Hz, 1H), 3.62-4.03 (m, 2H), 4.06-4.49 (m, 2H), 6.19-6.38 (m, 1H), 6.58 (d, J=6.8 Hz, 1H), 7.11 (d, J=13.4 Hz, 1H), 7.25-7.34 (m, 1H), 7.48 (dd, J=9.0, 4.7 Hz, 1H), 7.75 (d, J=11.4 Hz, 1H), 7.87 (d, J=20.0 Hz, 1H), 8.26 (d, J=3.8 Hz, 1H). MS (ES⁺): m/z 558.97 [MH⁺].

Example 264

(2R)-2-Amino-1-[4-{6-amino-7-[(1R)-1-(2,6-dichloro-3-fluoro-phenyl)ethoxy]furo[3,2-c]pyridin-3-yl}-3,6-dihydropyridin-1(2H)-yl]-3-(1H-imidazol-5-yl)propan-1-one

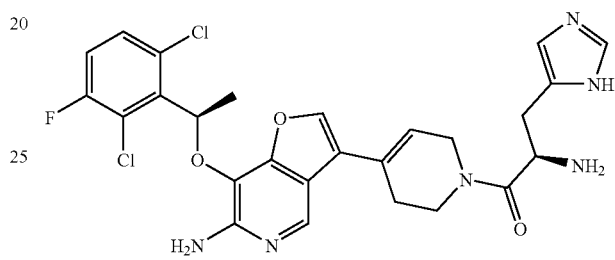

The title compound was prepared according to General Procedure P. ¹H NMR (CD₃OD, 400 MHz): δ=1.96 (d, J=6.8 Hz, 3H), 2.56 (br. s., 1H), 2.87-2.92 (m, 2H), 3.12 (br. s., 1H), 3.20-3.26 (m, 1H), 3.63-4.02 (m, 1H), 4.06-4.48 (m, 1H), 6.20-6.38 (m, 1H), 6.59 (d, J=6.8 Hz, 1H), 7.14 (d, J=13.9 Hz, 1H), 7.25-7.33 (m, 1H), 7.44-7.51 (m, 1H), 7.74-7.83 (m, 1H), 7.94 (d, J=17.4 Hz, 1H), 8.27 (s, 1H). MS (ES⁺): m/z 558.97 [MH⁺].

Example 265

(2S)-1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-2-hydroxy-2-phenylethanone

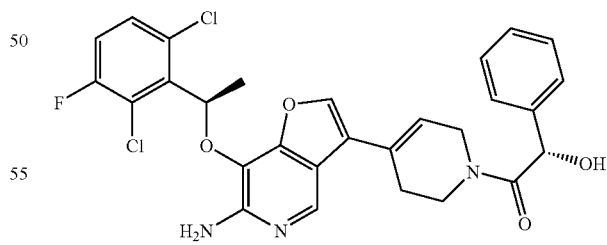

The title compound was prepared according to General Procedure P excluding HCl treatment. ¹H NMR (CD₃OD, 400 MHz): δ=1.90 (d, J=6.8 Hz, 3H), 2.25 (br. s., 1H), 2.52 (br. s., 1H), 2.91 (s, 1H), 3.04 (s, 1H), 3.55-3.74 (m, 1H), 3.75-3.87 (m, 1H), 3.87-4.04 (m, 1H), 4.17-4.32 (m, 1H), 6.05 (br. s., 1H), 6.28 (br. s., 1H), 6.51 (dq, J=6.4, 6.3 Hz, 1H), 7.19-7.31 (m, 1H), 7.31-7.56 (m, 6H), 8.02 (s, 1H), 8.17 (br. s., 1H), 8.32 (br. s., 1H). MS (ES⁺): m/z 556.00 [MH⁺].

Example 266

(2R)-1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-2-hydroxy-2-phenylethanone

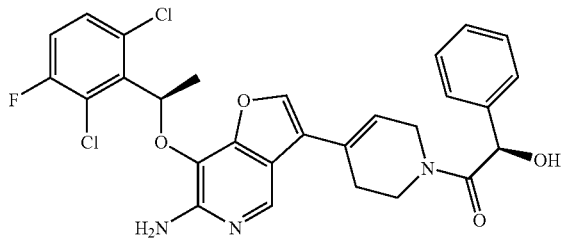

The title compound was prepared according to General Procedure P excluding HCl treatment. $^1$H NMR (CD$_3$OD, 400 MHz): δ=1.90 (d, J=6.8 Hz, 3H), 2.25 (br. s., 1H), 2.52 (br. s., 1H), 3.56-3.81 (m, 2H), 3.88-4.04 (m, 1H), 4.20 (br. s., 1H), 4.25 (br. s., 1H), 4.38-4.49 (m, 1H), 6.06 (br. s., 1H), 6.27 (br. s., 1H), 6.51 (q, J=6.7 Hz, 1H), 7.25 (t, J=8.6 Hz, 1H), 7.32-7.51 (m, 6H), 8.07 (br. s., 1H), 8.17 (br. s., 1H). MS (ES$^+$): m/z 555.94 [MH$^+$].

Example 267

(2S)-1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-2-hydroxy-3-methylbutan-1-one

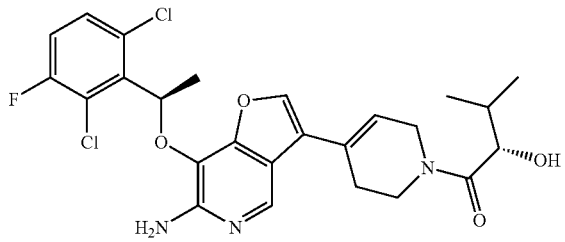

The title compound was prepared according to General Procedure P excluding HCl treatment. $^1$H NMR (CD$_3$OD, 400 MHz): δ=0.97 (br. s., 3H), 1.05 (br. s., 3H), 1.34 (br. s., 1H), 1.93 (d, J=4.8 Hz, 3H), 2.61 (br. s., 2H), 3.84 (br. s., 1H), 4.28-4.39 (m, 2H), 5.53 (br. s., 1H), 6.34 (br. s., 1H), 6.49-6.60 (m, 1H), 7.26 (br. s., 1H), 7.44 (br. s., 1H), 7.69 (br. s., 1H), 8.25 (br. s., 1H). MS (ES$^+$): m/z 522.01 [MH$^+$].

Example 268

(2R)-1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-2-hydroxy-3-methylbutan-1-one

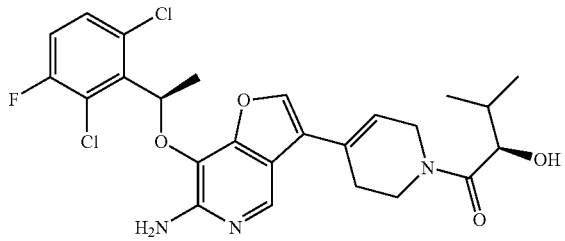

The title compound was prepared according to General Procedure P excluding HCl treatment. $^1$H NMR (CD$_3$OD, 400 MHz): δ=0.93-1.00 (m, 3H), 1.00-1.08 (m, 3H), 1.93 (d, J=6.8 Hz, 3H), 2.05 (s, 1H), 3.83 (br. s., 1H), 3.98 (s, 1H), 4.31 (br. s., 3H), 5.53 (s, 1H), 6.34 (br. s., 1H), 6.54 (d, J=6.8 Hz, 1H), 7.26 (t, J=8.6 Hz, 1H), 7.44 (dd, J=9.0, 4.9 Hz, 1H), 7.69 (s, 1H), 8.25 (s, 1H), 8.58 (s, 1H). MS (ES$^+$): m/z 522.01 [MH$^+$].

Example 269

(2S)-1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-3,3,3-trifluoro-2-hydroxypropan-1-one

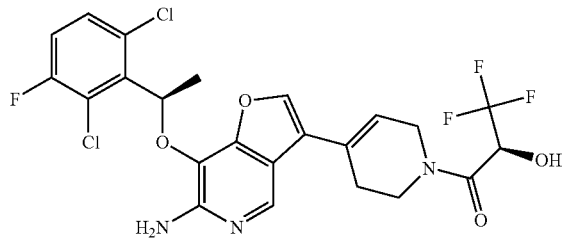

The title compound was prepared according to General Procedure P excluding HCl treatment. $^1$H NMR (CD$_3$OD, 400 MHz): δ=1.93 (d, J=6.8 Hz, 3H), 2.63 (br. s., 2H), 2.70 (s, 1H), 2.91 (s, 1H), 3.04 (s, 1H), 3.92 (br. s., 1H), 4.32 (br. s., 1H), 5.14 (br. s., 1H), 6.34 (br. s., 1H), 6.53 (s, 1H), 7.22-7.30 (m, 1H), 7.41-7.47 (m, 1H), 7.70 (s, 1H), 8.34 (br. s., 1H). MS (ES$^+$): m/z 547.91 [MH$^+$].

Example 270

1-[4-{6-Amino-7-[(1R)-1-(2,6-dichloro-3-fluorophenyl)ethoxy]furo[3,2-c]pyridin-3-yl}-3,6-dihydropyridin-1(2H)-yl]-3,3,3-trifluoro-2-hydroxypropan-1-one

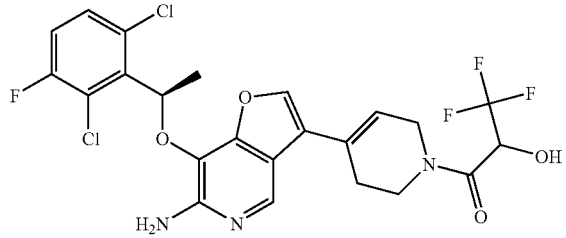

The title compound was prepared according to General Procedure P excluding HCl treatment. $^1$H NMR (CD$_3$OD, 400 MHz): δ=1.92 (d, J=6.8 Hz, 3H), 2.72-2.74 (m, 1H), 3.91 (s, 1H), 4.37 (br. s., 2H), 5.13 (dd, J=15.5, 6.7 Hz, 1H), 6.33 (br. s., 1H), 6.51-6.58 (m, 1H), 7.26 (t, J=8.6 Hz, 1H), 7.44 (dd, J=9.0, 4.9 Hz, 1H), 7.72 (d, J=6.8 Hz, 1H). MS (ES$^+$): m/z 547.98 [MH$^+$].

Example 271 tert-Butyl 4-(4-{6-Amino-7-[(1R)-1-(2,6-dichloro-3-fluorophenyl)-ethoxy]furo[3,2-c]pyridin-3-yl}-1H-pyrazol-1-yl)piperidine-1-carboxylate

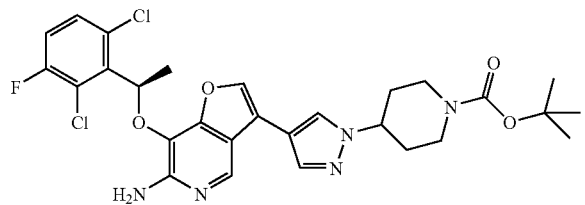

A suspension of 3-bromo-7-[(1R)-1-(2,6-dichloro-3-fluorophenyl)ethoxy]furo[3,2-c]pyridin-6-amine (202.8 mg, 0.4828 mmol, 1 eq), tert-butyl 4-[4-(4,4,5,5-tetramethyl-1,3,2-dioxaborolan-2-yl)-1H-pyrazol-1-yl]piperidine-1-carboxylate (218.3 mg, 0.5786 mmol, 1.2 eq), (1,1'-bis-(diphenylphosphino)-ferrocene) palladium dichloride (40.7 mg, 0.0556 mmol, 12 mol %), and $K_2CO_3$ (214.6 mg, 1.553 mmol, 3.2 eq) in a 4:1 mixture of dioxane (4 mL) to $H_2O$ (1 mL) was degassed and charged with nitrogen several times. The reaction sample was then irradiated under microwave heating [CEM, 100° C., 150 W, PowerMAX off, stirring] for 45 min. Additional tert-butyl 4-[4-(4,4,5,5-tetramethyl-1,3,2-dioxaborolan-2-yl)-1H-pyrazol-1-yl]piperidine-1-carboxylate (59.0 mg, 0.156 mmol, 0.3 eq) and (1,1'-bis-(diphenylphosphino)-ferrocene) palladium dichloride (12.5 mg, 0.0171 mmol, 4 mol %) were added and the reaction mixture was degassed and charged with nitrogen prior to microwave heating. After an additional 30 min of CEM microwave heating, the crude reaction mixture was diluted with EtOAc and washed with brine. An emulsion formed, which led to running the entire mixture through a small plug of Celite to remove unwanted particulate. The collected filtrate was washed again with brine (2×), dried over anhydrous $Na_2SO_4$, filtered, and concentrated in vacuo. The crude material was purified by column chromatography on silica gel [0.5"×10" glass column, eluting with Hex:EtOAc 1:1→1:2→1:3→0:1.] Fractions containing product were combined and concentrated in vacuo, giving the title material, as a yellow film. $^1H$ NMR (400 MHz, $CDCl_3$) δ=1.46 (s, 9H), 1.84 (d, J=6.8 Hz, 3H), 1.95 (qd, J=12.2, 4.4 Hz, 2H), 2.07-2.20 (m, 2H), 2.78-2.99 (m, 2H), 4.16-4.36 (m, 3H), 4.82 (s, 2H), 6.54 (q, J=6.7 Hz, 1H), 7.01 (dd, J=8.8, 8.1 Hz, 1H), 7.24 (dd, J=8.8, 4.8 Hz, 1H), 7.48 (s, 1H), 7.67 (s, 1H), 7.74 (s, 1H), 8.13 (s, 1H). MS (ES$^+$): m/z 590.14 (100) [MH$^+$]. HPLC: $t_R$=3.60 min (ZQ3, polar_5 min).

General procedure Q for N-alkylation/acylation, using isocyanate, chloroformate, and sulfonyl chloride species: To a solution of 7-[(1R)-1-(2,6-dichloro-3-fluorophenyl)ethoxy]-3-[1-(piperidin-4-yl)-1H-pyrazol-4-yl]furo[3,2-c]pyridin-6-amine dihydrochloride (10.6 mg, 0.0188 mmol, 1 eq) and DIPEA (26 µL, 0.15 mmol, 8 eq) in DMF (1 mL), one drop of the isocyanate, chloroformate, or sulfonyl chloride (approx. 0.0346 mmol, 1.8 eq) was added and the reaction was stirred at rt for 1 h. The DMF solution was syringe filtered and submitted directly to the analytical department for purification by MDPS. Fractions containing product were pooled together and all solvent was removed using the SpeedVac to give the title material.

Example 272

4-(4-{6-Amino-7-[(1R)-1-(2,6-dichloro-3-fluorophenyl)ethoxy]furo[3,2-c]pyridin-3-yl}-1H-pyrazol-1-yl)piperidine-1-carboxamide

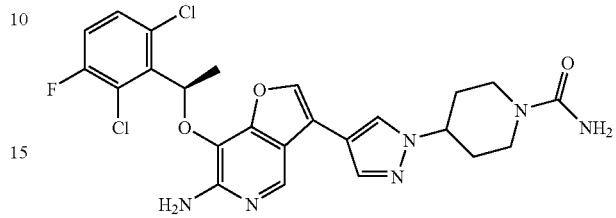

General Procedure Q was followed. $^1H$ NMR (400 MHz, DMSO-$d_6$): δ=1.74-1.83 (m, 2H), 1.86 (d, J=6.8 Hz, 3H), 1.98 (dd, J=12.4, 2.5 Hz, 2H), 2.84 (br t, J=11.9 Hz, 2H), 4.06 (br d, J=13.4 Hz, 2H), 4.37 (tt, J=11.5, 4.1 Hz, 1H), 6.03 (br s, 2H), 6.33 (q, J=6.7 Hz, 1H), 6.66 (br s, 2H), 7.46 (dd, J=8.6, 8.6 Hz, 1H), 7.53 (dd, J=9.1, 5.1 Hz, 1H), 7.90 (s, 1H), 8.13 (s, 1H), 8.34 (s, 1H), 8.44 (s, 1H). MS (ES$^+$): m/z 533.05/534.98 (100/99) [MH$^+$]. HPLC: $t_R$=2.79 min (ZQ3, polar_5 min).

Example 273

4-(4-{6-Amino-7-[(1R)-1-(2,6-dichloro-3-fluorophenyl)ethoxy]furo[3,2-c]pyridin-3-yl}-1H-pyrazol-1-yl)-N-ethylpiperidine-1-carboxamide

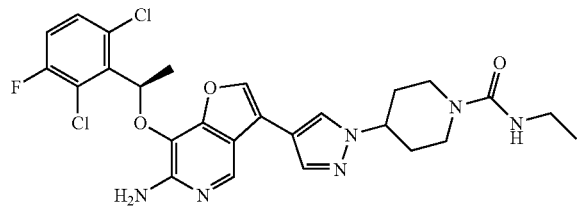

General procedure Q was followed, except the title material was isolated as a formate salt. $^1H$ NMR (400 MHz, DMSO-$d_6$): δ=1.02 (t, J=7.2 Hz, 3H), 1.74-1.89 (m, 2H), 1.84 (d, J=6.8 Hz, 3H), 1.98 (dd, J=12.1, 2.3 Hz, 2H), 2.76-2.87 (m, 2H), 3.06 (qd, J=7.1, 5.6 Hz, 2H), 4.07 (br d, J=13.4 Hz, 2H), 4.36 (dddd, J=11.4, 11.4, 4.0, 3.9 Hz, 1H), 5.59 (br s, 2H), 6.25 (q, J=6.7 Hz, 1H), 6.55 (t, J=5.3 Hz, 1H), 6.80 (br s, 1H), 7.44 (dd, J=8.6, 8.6 Hz, 1H), 7.51 (dd, J=9.1, 5.1 Hz, 1H), 7.86 (s, 1H), 7.94 (s, 1H), 8.30 (s, 1H), 8.34 (s, 2H). MS (ES$^+$): m/z 561.12/563.08 (100/90) [MH$^+$]. HPLC: $t_R$=2.97 min (ZQ3, polar_5 min)

Example 274

Methyl 4-(4-{6-Amino-7-[(1R)-1-(2,6-dichloro-3-fluorophenyl)ethoxy]furo[3,2-c]pyridin-3-yl}-1H-pyrazol-1-yl)piperidine-1-carboxylate

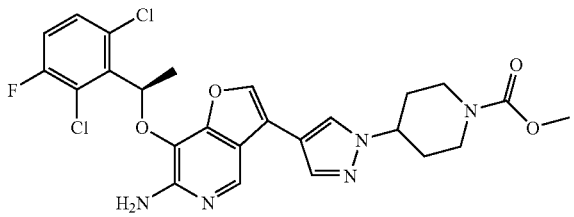

General procedure Q was followed, except the reaction was cooled to 0° C. prior to chloroformate addition and then quenched IMMEDIATELY after addition with a drop of water. The title material was collected as a formate salt. $^1$H NMR (400 MHz, DMSO-$d_6$): δ=1.74-1.93 (m, 2H), 1.84 (d, J=6.6 Hz, 3H), 1.98-2.07 (m, 2H), 3.00 (br s, 2H), 3.62 (s, 3H), 4.07 (br s, 2H), 4.42 (dddd, J=11.4, 11.4, 3.8 Hz, 3.8 Hz, 1H), 5.96 (br s, 1H), 6.28 (q, J=6.7 Hz, 1H), 6.54 (br s, 1H), 7.45 (dd, J=8.6, 8.6 Hz, 1H), 7.52 (dd, J=8.8, 5.1 Hz, 1H), 7.88 (s, 1H), 8.02 (br s, 1H), 8.32 (s, 1H), 8.38 (s, 1H). MS (ES$^+$): m/z 548.06/550.01 (100/94) [MH$^+$]. HPLC: $t_R$=3.18 min (ZQ3, polar_5 min).

Example 275

7-[(1R)-1-(2,6-Dichloro-3-fluorophenyl)ethoxy]-3-{1-[1-(methyl-sulfonyl)piperidin-4-yl]-1H-pyrazol-4-yl}furo[3,2-c]pyridin-6-amine

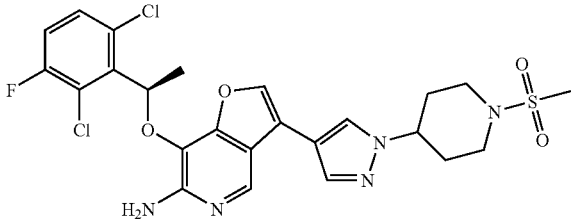

General procedure Q was followed, except the reaction was cooled to 0° C. prior to chloroformate addition and then quenched IMMEDIATELY after addition with a drop of water. The title material was collected as a formate salt. $^1$H NMR (400 MHz, DMSO-$d_6$): δ=1.84 (d, J=6.8 Hz, 3H), 2.05 (dddd, J=11.9, 11.9, 11.9, 4.0 Hz, 2H), 2.15 (dd, J=13.1, 3.3 Hz, 2H), 2.89-2.99 (m, 2H), 2.92 (s, 3H), 3.63-3.71 (m, 2H), 4.36 (dddd, J=11.1, 11.1, 4.2, 4.0 Hz, 1H), 5.61 (br s, 2H), 6.25 (q, J=6.8 Hz, 1H), 7.45 (dd, J=8.7, 8.7 Hz, 1H), 7.52 (dd, J=8.8, 5.1 Hz, 1H), 7.88 (s, 1H), 7.96 (s, 1H), 8.34 (s, 1H), 8.35 (s, 1H). MS (ES$^+$): m/z 568.03/569.97 (100/93) [MH$^+$]. HPLC: $t_R$=3.17 min (ZQ3, polar_5 min).

General Procedure R for the amide coupling of substituted piperidines: To a solution of 7-[(1R)-1-(2,6-dichloro-3-fluorophenyl)ethoxy]-3-[1-(piperidin-4-yl)-1H-pyrazol-4-yl]furo[3,2-c]pyridin-6-amine dihydrochloride (10.4 mg, 0.0185 mmol, 1 eq), TBTU (12.1 mg, 0.0377 mmol, 2 eq), and DIPEA (16 µL, 0.092 mmol, 5 eq) in DMF (1 mL), one drop of carboxylic acid (0.0369 mmol, 2 eq) was added and the reaction was stirred at rt for 20 min. The DMF solution was syringe filtered and submitted directly to the analytical department for purification by MDPS. Fractions containing product were pooled together and all solvent was evaporated using the SpeedVac to give the title material.

Example 276

1-[4-(4-{6-Amino-7-[(1R)-1-(2,6-dichloro-3-fluorophenyl)ethoxy]furo[3,2-c]pyridin-3-yl}-1H-pyrazol-1-yl)piperidin-1-yl]ethanone

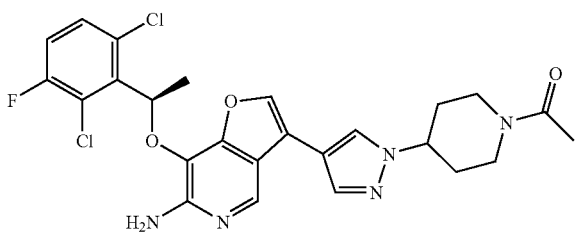

General Procedure R was followed. $^1$H NMR (400 MHz, DMSO-$d_6$): δ=1.78 (dddd, J=12.1, 12.1, 12.1, 4.3 Hz, 1H), 1.84 (d, J=6.8 Hz, 3H), 1.93 (dddd, J=12.1, 12.1, 12.1, 4.2 Hz, 1H), 1.99-2.11 (m, 2H), 2.05 (s, 3H), 2.72 (ddd, J=12.9, 9.6, 2.0 Hz, 1H), 3.21 (ddd, J=14.7, 12.1, 2.3 Hz, 1H), 3.87-3.98 (m, 1H), 4.39-4.51 (m, 2H), 5.71 (br s, 2H), 6.26 (q, J=6.7 Hz, 1H), 6.53 (br s, 1H, salt), 7.45 (dd, J=8.6, 8.6 Hz, 1H), 7.52 (dd, J=9.1, 5.1 Hz, 1H), 7.87 (s, 1H), 7.97 (s, 1H), 8.13 (br s, 1H, salt), 8.31 (s, 1H), 8.34 (s, 1H). MS (ES$^+$): m/z 532.08/534.02 (100/93) [MH$^+$]. HPLC: $t_R$=2.93 min (ZQ3, polar_5 min).

Example 277

4-(4-{6-Amino-7-[(1R)-1-(2,6-dichloro-3-fluorophenyl)ethoxy]furo[3,2-c]pyridin-3-yl}-1H-pyrazol-1-yl)piperidine-1-carbaldehyde

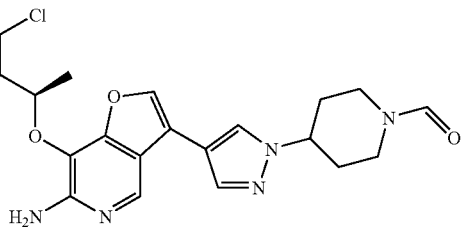

General Procedure R was followed. $^1$H NMR (400 MHz, DMSO-$d_6$): δ=1.74-1.95 (m, 2H), 1.84 (d, J=6.8 Hz, 3H), 2.01-2.16 (m, 2H), 2.80 (ddd, J=12.8, 12.8, 2.9 Hz, 1H), 3.22 (ddd, J=13.4, 13.4, 2.8 Hz, 1H), 3.82 (ddd, J=13.7, 1.7, 1.7 Hz, 1H), 4.27 (ddd, J=13.5, 2.0, 2.0 Hz, 1H), 4.50 (dddd, J=11.4, 11.4, 3.9, 3.8 Hz, 1H), 5.60 (br s, 2H), 6.25 (q, J=6.8 Hz, 1H), 7.45 (dd, J=8.8, 8.3 Hz, 1H), 7.52 (dd, J=9.1, 5.3 Hz, 1H), 7.87 (s, 1H), 7.95 (s, 1H), 8.05 (s, 1H), 8.25 (br s, 1H), 8.31 (s, 1H), 8.34 (s, 1H). MS (ES$^+$): m/z 518.05/520.03 (100/99) [MH$^+$]. HPLC: $t_R$=2.87 min (ZQ3, polar_5 min).

Example 278

7-[(1R)-1-(2,6-Dichloro-3-fluorophenyl)ethoxy]-3-[1-(1-ethylpiperidin-4-yl)-1H-pyrazol-4-yl]furo[3,2-c]pyridin-6-amine

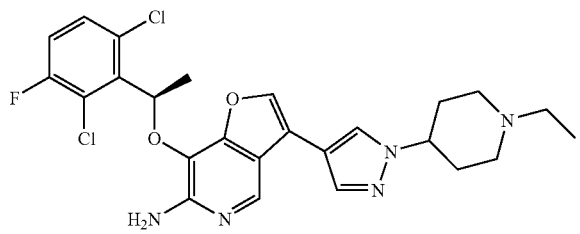

To a solution of 7-[(1R)-1-(2,6-dichloro-3-fluorophenyl)ethoxy]-3-[1-(piperidin-4-yl)-1H-pyrazol-4-yl]furo[3,2-c]pyridin-6-amine dihydrochloride (10.0 mg, 0.0178 mmol, 1 eq) and sodium triacetoxyborohydride (6.5 mg, 0.031 mmol, 1.7 eq) in DMF (1 mL), cooled to 0° C., acetaldehyde (1.99 µL, 0.0355 mmol, 2 eq) was added and stirred from 0° C. to rt. The DMF solution was syringe filtered and submitted directly to the analytical department for purification by MDPS. Fractions containing product were pooled together and all solvent was removed using the SpeedVac to give the title material, as a colorless trifluoroacetate salt. $^1$H NMR (400 MHz, CD$_3$OD) δ=1.39 (t, J=7.3 Hz, 3H), 1.95 (d, J=6.6 Hz, 3H), 2.30-2.45 (m, 4H), 3.18 (td, J=12.4, 4.4 Hz, 2H), 3.26 (q, J=7.4 Hz, 2H), 3.76 (br d, J=12.1 Hz, 2H), 4.60 (tt, J=10.5, 5.3 Hz, 1H), 6.71 (q, J=6.7 Hz, 1H), 7.25 (dd, J=8.6, 8.6 Hz, 1H), 7.43 (dd, J=9.0, 4.9 Hz, 1H), 7.92 (s, 1H), 8.02 (s, 1H), 8.17 (s, 1H), 8.24 (br s, 1H). MS (ES$^+$): m/z 518.05/520.03 (100/73) [MH$^+$]. HPLC: $t_R$=2.63 min (ZQ3, polar__5 min).

General Procedure S for Suzuki couplings: To a solution of 3-Bromo-7-[(R)-1-(2,6-dichloro-3-fluorophenyl)ethoxy]furo[3,2-c]pyridin-6-ylamine (10.0 mg, 0.0238 mmol, 1 eq.), boronic acid or ester (0.476 mmol, 2 eq.), potassium carbonate (9.9 mg, 0.0714, 3 eq.) in dioxane (0.9 mL) and water (0.3 mL) was added 1,1'-bis(diphenylphosphino)ferrocene] dichloropalladium(II), complex with dichloromethane (1:1) (1 mg, 0.001 mmol, 0.05 eq.). The mixture was evacuated by vacuum and filled with nitrogen 3 times and subjected to CEM microwave reactor for 100° C. in 30 min with stirring on and cooling off. The crude was passed through 500 mg Thiol-SPE to remove palladium. The clear solution was purified on the MDPS.

Example 279

7-[(R)-1-(2,6-Dichloro-3-fluorophenyl)ethoxy]-3-(1H-pyrrolo[2,3-b]pyridin-5-yl)furo[3,2-c]pyridin-6-ylamine

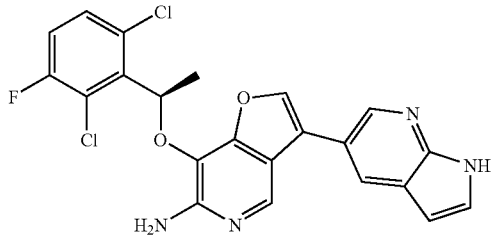

The title compound was prepared according to General Procedure S. MS (ES$^+$): m/z 457.05/459.05 (100/72) [MH$^+$]. HPLC: $t_R$=0.85 min (HPLC-ACQUITY, Analytical). $^1$H NMR (400 MHz, CD$_3$OD) δ 8.35 (d, J=2.0 Hz, 1H), 8.16 (d, J=2.0 Hz, 1H), 8.10 (s, 1H), 7.77 (s, 1H), 7.28-7.36 (m, 2H), 7.13 (t, J=8.6 Hz, 1H), 6.42-6.53 (m, 2H), 1.81 (d, J=6.8 Hz, 3H).

Example 280

5-{6-Amino-7-[(R)-1-(2,6-dichloro-3-fluorophenyl)ethoxy]furo[3,2-c]pyridin-3-yl}-N-tert-butylnicotinamide

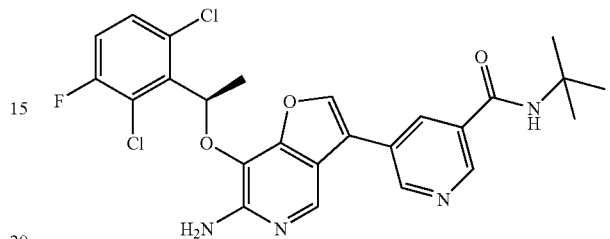

The title compound was prepared according to General Procedure S. MS (ES$^+$): m/z 517.09/519.08 (100/73) [MH$^+$]. HPLC: $t_R$=0.92 min (HPLC-ACQUITY, Analytical).

Example 281

1-[4-(5-{6-Amino-7-[(R)-1-(2,6-dichloro-3-fluorophenyl)ethoxy]furo[3,2-c]pyridin-3-yl}-pyridin-2-yl)-piperazin-1-yl]ethanone

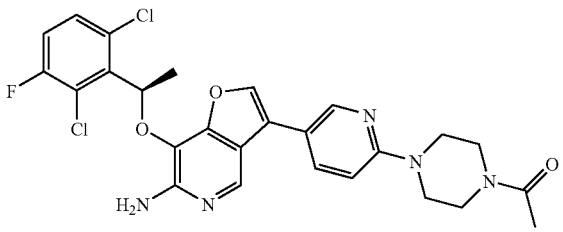

The title compound was prepared according to General Procedure S. MS (ES$^+$): m/z 544.09/546.06 (100/70) [MH$^+$]. HPLC: $t_R$=0.78 min (HPLC-ACQUITY, Analytical).

Example 282

(5-{6-Amino-7-[(R)-1-(2,6-dichloro-3-fluorophenyl)ethoxy]furo[3,2-c]pyridin-3-yl}pyridin-3-yl)morpholin-4-ylmethanone

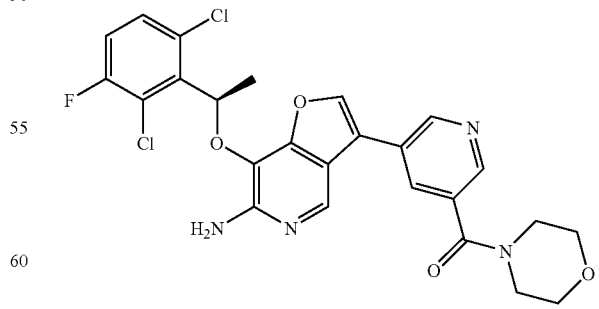

The title compound was prepared according to General Procedure S. MS (ES$^+$): m/z 531.07/533.04 (100/75) [MH$^+$]. HPLC: $t_R$=0.77 min (HPLC-ACQUITY, Analytical).

Example 283

7-[(R)-1-(2,6-Dichloro-3-fluorophenyl)ethoxy]-3-(2-morpholin-4-ylpyrimidin-5-yl)furo[3,2-c]pyridin-6-ylamine

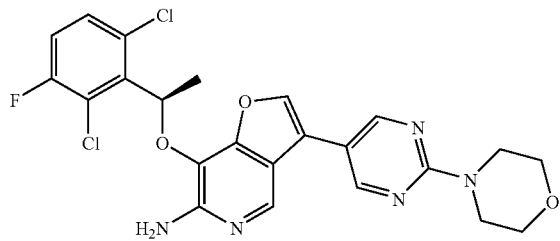

The title compound was prepared according to General Procedure S. MS (ES+): m/z 504.07/506.03 (100/75) [MH+]. HPLC: $t_R$=0.91 min (HPLC-ACQUITY, Analytical).

Example 284

1-(4-{6-Amino-7-[(R)-1-(2,6-dichloro-3-fluorophenyl)-ethoxy]furo[3,2-c]pyridin-3-yl}benzoyl)piperidin-4-one

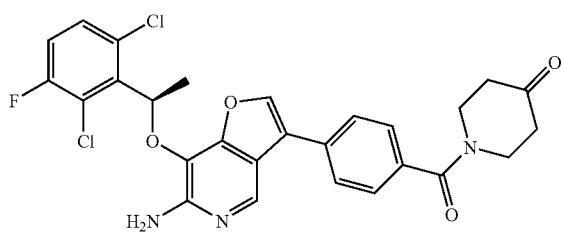

The title compound was prepared according to General Procedure S. MS (ES+): m/z 542.16/544.15 (100/72) [MH+]. HPLC: $t_R$=0.83 min (HPLC-ACQUITY, Analytical).

Example 285

4-{6-Amino-7-[(R)-1-(2,6-dichloro-3-fluorophenyl)ethoxy]furo[3,2-c]pyridin-3-yl}-N-(2-methoxyethyl)benzamide

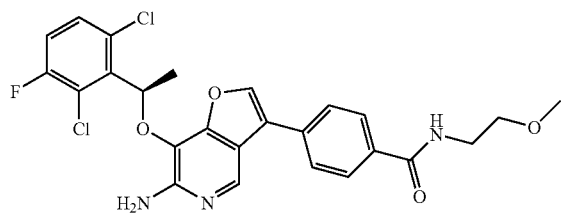

The title compound was prepared according to General Procedure S. MS (ES+): m/z 518.16/52.16 (100/78) [MH+]. HPLC: $t_R$=0.83 min (HPLC-ACQUITY, Analytical).

Example 286

4-{6-Amino-7-[(R)-1-(2,6-dichloro-3-fluorophenyl)ethoxy]furo[3,2-c]pyridin-3-yl}-N-(3-methoxypropyl)-benzamide

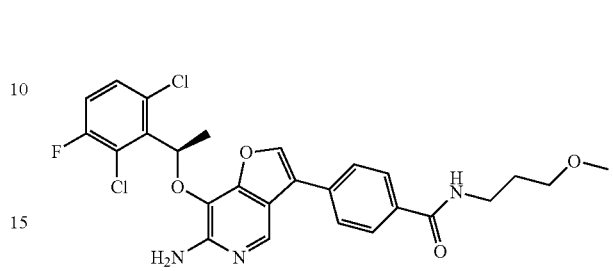

The title compound was prepared according to General Procedure S. MS (ES+): m/z 532.18/534.17 (100/80) [MH+]. HPLC: $t_R$=0.86 min (HPLC-ACQUITY, Analytical).

Example 287

4-{6-Amino-7-[(R)-1-(2,6-dichloro-3-fluorophenyl)ethoxy]furo[3,2-c]pyridin-3-yl}-N-(2-hydroxyethyl)benzamide

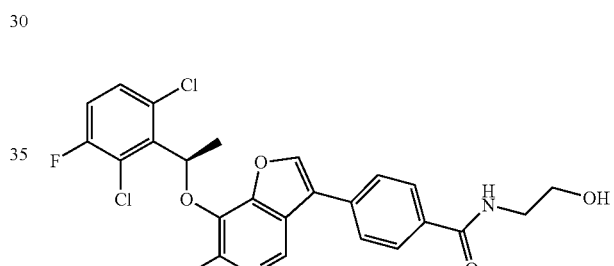

The title compound was prepared according to General Procedure S. MS (ES+): m/z 504.13/506.13 (100/68) [MH+]. HPLC: $t_R$=0.76 min (HPLC-ACQUITY, Analytical).

Example 288

4-{6-Amino-7-[(R)-1-(2,6-dichloro-3-fluorophenyl)ethoxy]furo[3,2-c]pyridin-3-yl}-N-(3-hydroxypropyl)benzamide

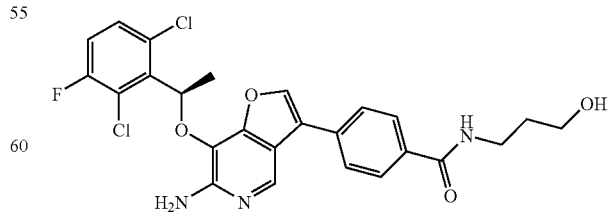

The title compound was prepared according to General Procedure S. MS (ES+): m/z 518.16/520.26 (100/82) [MH+]. HPLC: $t_R$=0.77 min (HPLC-ACQUITY, Analytical).

Example 289

4-{6-Amino-7-[(R)-1-(2,6-dichloro-3-fluorophenyl)ethoxy]furo[3,2-c]pyridin-3-yl}-N-methylbenzamide

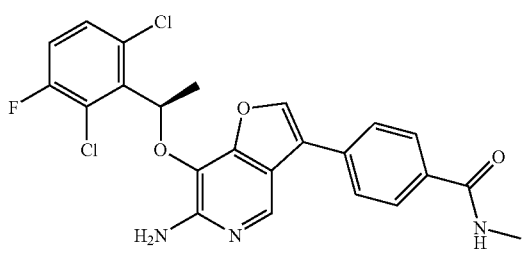

The title compound was prepared according to General Procedure S. MS (ES⁺): m/z 474.13/476.13 (100/84) [MH⁺]. HPLC: $t_R$=0.80 min (HPLC-ACQUITY, Analytical).

Example 290

(4-{6-Amino-7-[(R)-1-(2,6-dichloro-3-fluorophenyl)ethoxy]furo[3,2-c]pyridin-3-yl}phenyl)piperidin-1-ylmethanone

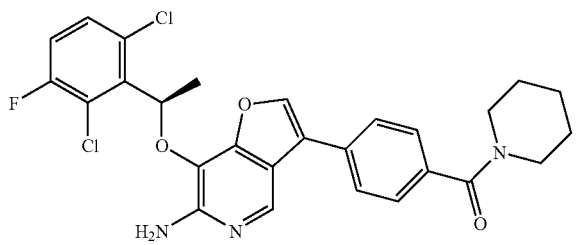

The title compound was prepared according to General Procedure S. MS (ES⁺): m/z 528.15/530.15 (100/82) [MH⁺]. HPLC: $t_R$=0.97 min (HPLC-ACQUITY, Analytical).

Example 291

7-[(R)-1-(2,6-Dichloro-3-fluorophenyl)ethoxy]-3-(5-morpholin-4-ylmethylthiophen-2-yl-furo[3,2-c]pyridin-6-ylamine

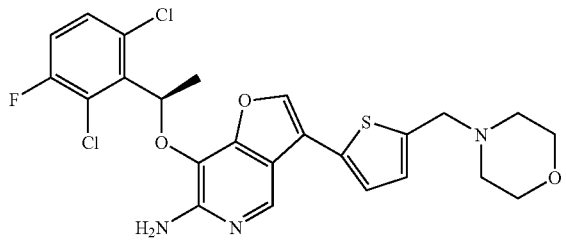

The title compound was prepared according to General Procedure S. MS (ES⁺): m/z 522.11/54.11 (100/78) [MH⁺]. HPLC: $t_R$=0.66 min (HPLC-ACQUITY, Analytical).

Example 292

5-{6-Amino-7-[(R)-1-(2,6-dichloro-3-fluorophenyl)ethoxy]furo[3,2-c]pyridin-3-yl}thiophene-3-carboxylic acid methyl ester

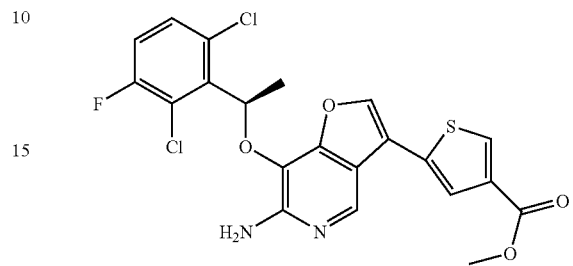

The title compound was prepared according to General Procedure S. MS (ES⁺): m/z 481.15/483.13 (100/78) [MH⁺]. HPLC: $t_R$=1.04 min (HPLC-ACQUITY, Analytical).

Example 293

(4-{6-Amino-7-[(R)-1-(2,6-dichloro-3-fluorophenyl)ethoxy]furo[3,2-c]pyridin-3-yl}phenyl)-(4-methyl-[1,4]diazepan-1-yl)methanone

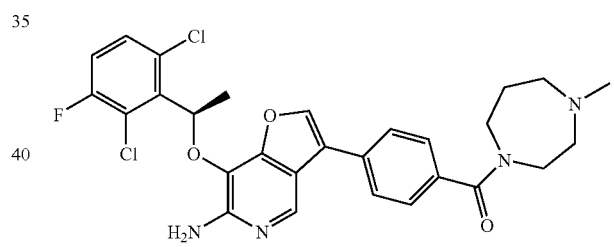

General Procedure T: 4-{6-Amino-7-[(R)-1-(2,6-dichloro-3-fluorophenyl)ethoxy]furo[3,2-c]pyridin-3-yl}-benzoic acid was prepared following General Procedure S. The crude material was not purified but used directly for the amide coupling step: 4-{6-amino-7-[(R)-1-(2,6-dichloro-3-fluorophenyl)ethoxy]furo[3,2-c]pyridin-3-yl}-benzoic acid (10 mg, 0.0217 mmol) was mixed with N-methylhomopiperazine (0.22 mmol, 10 eq.), TBTU (35 mg, 0.11 mmol, 5 eq.) and DMF (0.6 mL). The reaction mixture was stirred at room temperature overnight. The crude was passed through Thiol-SPE to remove palladium. The crude was passed through SCX-2 SPE and the basic compound was released by 2 M NH₃ in methanol. The resulting solution was purified using the MDPS. MS (ES⁺): m/z 557.18/559.17 (100/75) [MH⁺]. HPLC: $t_R$=0.64 min (HPLC-ACQUITY, Analytical). ¹H NMR (400 MHz, CD₃OD) δ 8.25 (s, 1H), 7.97 (s, 1H), 7.80 (d, J=8.3 Hz, 2H), 7.61 (d, J=8.1 Hz, 1H), 7.44 (dd, J=4.9, 9.0 Hz, 1H), 7.21-7.29 (m, 1H), 6.58 (q, J=6.7 Hz, 1H), 3.97 (br. s., 1H), 3.84 (br. s., 1H), 3.66 (br. s., 1H), 3.38 (br. s., 1H), 3.26 (br. s., 2H), 3.09-3.21 (m, 1H), 2.83-2.89 (m, 2H), 2.72 (br. s., 1H), 2.13 (br. s., 2H), 1.93 (d, J=6.8 Hz, 3H).

Example 294

(4-{6-Amino-7-[(R)-1-(2,6-dichloro-3-fluorophenyl)ethoxy]furo[3,2-c]pyridin-3-yl}phenyl)-((3S*,5R*)-3,5-dimethylpiperazin-1-yl)methanone

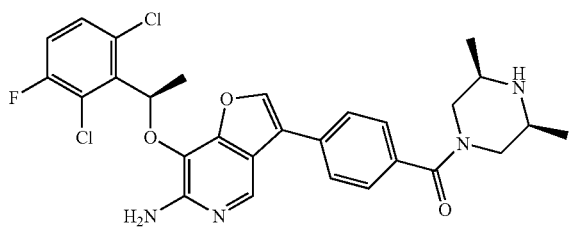

The title compound was prepared according to General Procedure T. MS (ES+): m/z 557.18/559.18 (100/80) [MH+]. HPLC: $t_R$=0.66 min (HPLC-ACQUITY, Analytical).

Example 295

(4-{6-Amino-7-[(R)-1-(2,6-dichloro-3-fluorophenyl)ethoxy]furo[3,2-c]pyridin-3-yl}phenyl)-((trans-2,5-dimethylpiperazin-1-yl)methanone

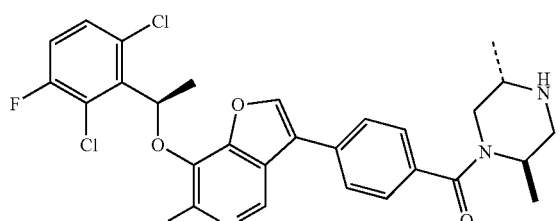

The title compound was prepared according to General Procedure T. MS (ES+): m/z 557.18/559.20 (100/78) [MH+]. HPLC: $t_R$=0.67 min (HPLC-ACQUITY, Analytical).

Example 296

(4-{6-Amino-7-[(R)-1-(2,6-dichloro-3-fluorophenyl)ethoxy]furo[3,2-c]pyridin-3-yl}phenyl)-(4-hydroxypiperidin-1-yl)methanone

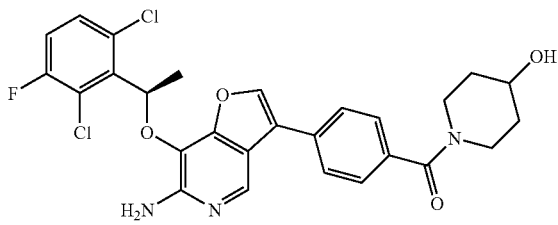

The title compound was prepared according to General Procedure T. MS (ES+): m/z 544.17/546.14 (100/86) [MH+]. HPLC: $t_R$=0.77 min (HPLC-ACQUITY, Analytical).

Example 297

(4-{6-Amino-7-[(R)-1-(2,6-dichloro-3-fluorophenyl)ethoxy]-furo[3,2-c]pyridin-3-yl}phenyl)-(2,6-cis-dimethylmorpholin-4-yl)methanone

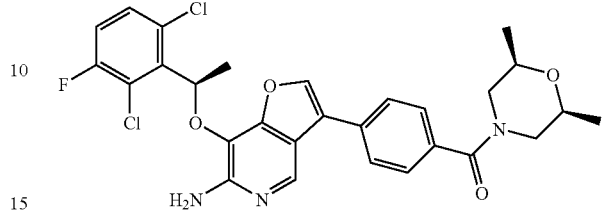

The title compound was prepared according to General Procedure T. MS (ES+): m/z 558.18/560.15 (100/79) [MH+]. HPLC: $t_R$=0.93 min (HPLC-ACQUITY, Analytical).

Example 298

4-{6-Amino-7-[(R)-1-(2,6-dichloro-3-fluorophenyl)ethoxy]furo[3,2-c]pyridin-3-yl}-N-(3-dimethylamino-2,2-dimethylpropyl)benzamide

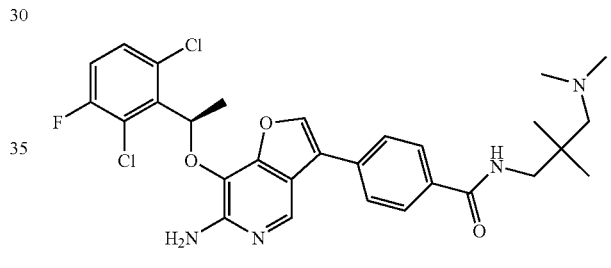

The title compound was prepared according to General Procedure T. MS (ES+): m/z 573.22/575.23 (100/75) [MH+]. HPLC: $t_R$=0.70 min (HPLC-ACQUITY, Analytical).

Example 299

(4-{6-Amino-7-[(R)-1-(2,6-dichloro-3-fluorophenyl)ethoxy]furo[3,2-c]pyridin-3-yl-phenyl)-(3-hydroxypyrrolidin-1-yl)methanone

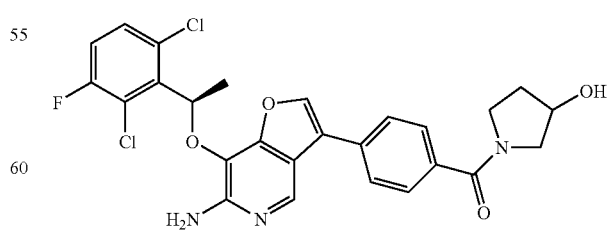

The title compound was prepared according to General Procedure T. MS (ES+): m/z 530.14/532.14 (100/78) [MH+]. HPLC: $t_R$=0.77 min (HPLC-ACQUITY, Analytical).

Example 300

2-[4-(4-{6-Amino-7-[(R)-1-(2,6-dichloro-3-fluorophenyl)ethoxy]furo[3,2-c]pyridin-3-yl}benzoyl)piperazin-1-yl]-N,N-dimethylacetamide

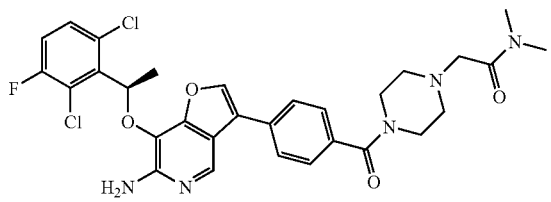

The title compound was prepared according to General Procedure T. MS (ES+): m/z 614.21/616.20 (100/82) [MH+]. HPLC: $t_R$=0.64 min (HPLC-ACQUITY, Analytical).

Example 301

(4-{6-Amino-7-[(R)-1-(2,6-dichloro-3-fluoro-phenyl)ethoxy]furo[3,2-c]pyridin-3-yl}phenyl)-{4-[2-(2-hydroxyethoxy)ethyl]piperazin-1-yl}methanone

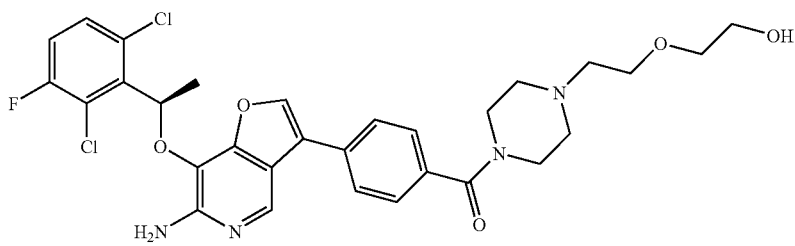

The title compound was prepared according to General Procedure T. MS (ES+): m/z 617.22/619.24 (100/80) [MH+]. HPLC: $t_R$=0.65 min (HPLC-ACQUITY, Analytical).

Example 302

4-{6-Amino-7-[(R)-1-(2,6-dichloro-3-fluorophenyl)ethoxy]furo[3,2-c]pyridin-3-yl}thiophene-2-carbaldehyde

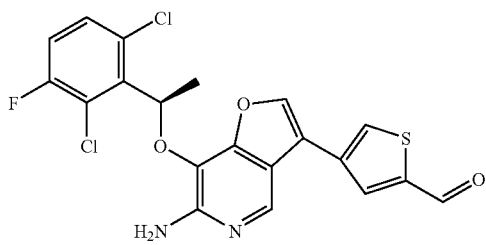

3-Bromo-7-[(R)-1-(2,6-dichloro-3-fluorophenyl)ethoxy]furo[3,2-c]pyridin-6-ylamine (150.0 mg, 0.357 mmol), 2-formylthiophene-4-boronic acid (111 mg, 0.714 mmol), potassium carbonate (148 mg, 1.07 mmol), 1,4-dioxane (4.2 mL, 54 mmol), H$_2$O (1.2 mL, 67 mmol) and (1,1'bis-(diphenylphosphino)ferrocene palladium dichloride (10 mg, 0.02 mmol) were mixed and heated at 80° C. overnight. The crude was worked up with DCM and H$_2$O. Product was purified by prep-TLC in DCM/methanol system. MS (ES+): m/z 451.01/453.04 (100/73) [MH+]. HPLC: $t_R$=0.93 min (HPLC-ACQUITY, Analytical). $^1$H NMR (400 MHz, DMSO-d$_6$): δ 9.99 (d, J=1.3 Hz, 1H), 8.49 (s, 1H), 8.42-8.47 (m, 2H), 8.26 (s, 1H), 7.49-7.56 (m, 1H), 7.42-7.49 (m, 1H), 6.26 (q, J=6.7 Hz, 1H), 5.71 (s, 2H), 1.85 (d, J=6.8 Hz, 3H).

Example 303

7-[(R)-1-(2,6-Dichloro-3-fluorophenyl)ethoxy]-3-(5-dimethyl-aminomethylthiophen-3-yl)furo[3,2-c]pyridin-6-ylamine

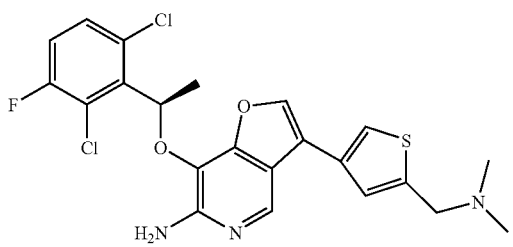

General Procedure U: 4-{6-Amino-7-[(R)-1-(2,6-dichloro-3-fluorophenyl)ethoxy]furo[3,2-c]pyridin-3-yl}thiophene-2-carbaldehyde (10.0 mg, 0.0222 mmol), amine (0.111 mmol; neat or as solution in THF or MeOH), sodium triacetoxyborohydride (23.5 mg, 0.111 mmol) and 1,2-dichloroethane (1.0 mL, 13 mmol) were mixed and stirred at 60° C. overnight. The crude was passed through SCX-2 SPE and the product was released by 2 M NH$_3$ in methanol and purified using the MDPS. The title compound was obtained using a 2M solution of dimethylamide in THF. MS (ES+): m/z 480.08/482.06 (100/80) [MH+]. HPLC: $t_R$=0.64 min (HPLC-ACQUITY, Analytical). $^1$H NMR (400 MHz, CD$_3$OD): δ 8.32 (s, 1H), 8.16 (s, 1H), 8.00 (d, J=1.5 Hz, 1H), 7.64 (d, J=1.3 Hz, 1H), 7.43 (dd, J=4.8, 8.8 Hz, 1H), 7.25 (t, J=8.6 Hz, 1H), 6.72 (q, J=6.7 Hz, 1H), 4.60 (s, 2H), 2.92 (s, 6H), 1.96 (d, J=6.6 Hz, 3H).

Example 304

7-[(R)-1-(2,6-Dichloro-3-fluorophenyl)ethoxy]-3-[5-(4-methyl-piperazin-1-ylmethyl)thiophen-3-yl]-furo[3,2-c]pyridin-6-ylamine

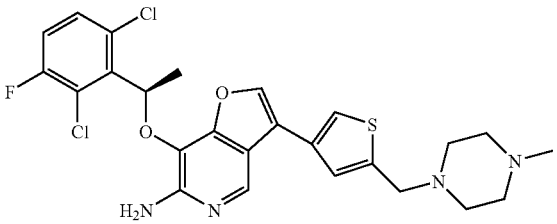

The title compound was prepared according to General Procedure U. MS (ES+): m/z 535.12/537.11 (100/78) [MH+]. HPLC: $t_R$=0.67 min (HPLC-ACQUITY, Analytical).

Example 305

7-[(R)-1-(2,6-Dichloro-3-fluorophenyl)ethoxy]-3-[5-(cis-3,5-dimethylpiperazin-1-ylmethyl)thiophen-3-yl]-furo[3,2-c]pyridin-6-ylamine

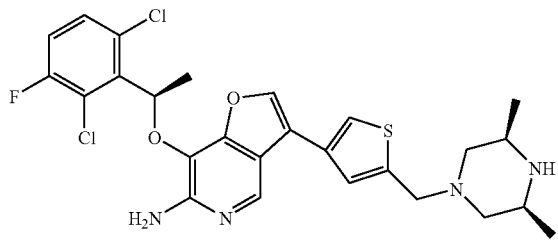

The title compound was prepared according to General Procedure U. MS (ES+): m/z 549.13/551.13 (100/80) [MH+]. HPLC: $t_R$=0.68 min (HPLC-ACQUITY, Analytical).

Example 306

1-(4-{6-Amino-7-[(R)-1-(2,6-dichloro-3-fluorophenyl)ethoxy]furo[3,2-c]pyridin-3-yl}thiophen-2-ylmethyl)piperidin-4-ol

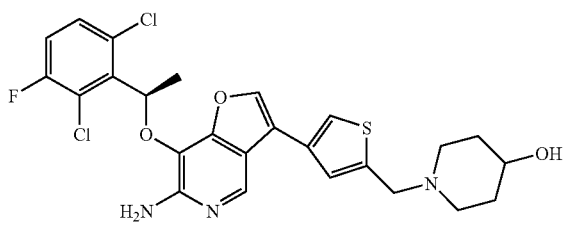

The title compound was prepared according to General Procedure U. MS (ES+): m/z 536.11/538.10 (100/80) [MH+]. HPLC: $t_R$=0.63 min (HPLC-ACQUITY, Analytical).

Example 307

1-(4-{6-Amino-7-[(R)-1-(2,6-dichloro-3-fluorophenyl)-ethoxy]furo[3,2-c]pyridin-3-yl}thiophen-2-ylmethyl)pyrrolidin-3-ol

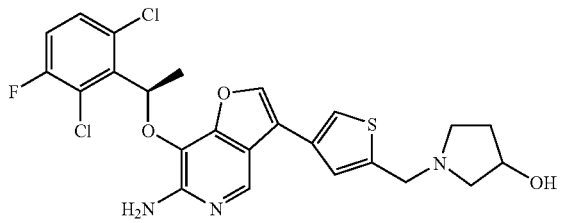

The title compound was prepared according to General Procedure U. MS (ES+): m/z 522.10/524.09 (100/80) [MH+]. HPLC: $t_R$=0.64 min (HPLC-ACQUITY, Analytical).

Example 308

7-[(R)-1-(2,6-Dichloro-3-fluorophenyl)ethoxy]-3-(5-pyrrolidin-1-ylmethylthiophen-3-yl)furo[3,2-c]pyridin-6-ylamine

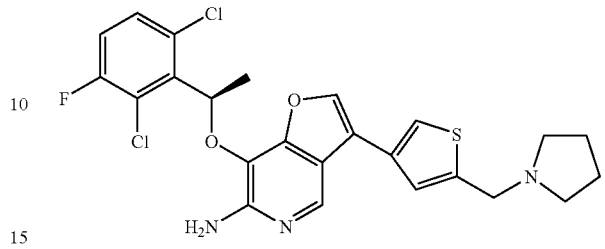

The title compound was prepared according to General Procedure U. MS (ES+): m/z 506.09/508.09 (100/81) [MH+]. HPLC: $t_R$=0.67 min (HPLC-ACQUITY, Analytical).

Example 309

3-(5-Azetidin-1-ylmethylthiophen-3-yl)-7-[(R)-1-(2,6-dichloro-3-fluorophenyl)ethoxy]furo[3,2-c]pyridin-6-ylamine

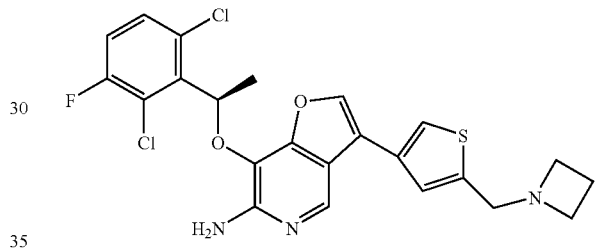

The title compound was prepared according to General Procedure U. MS (ES+): m/z 492.02/494.01 (100/80) [MH+]. HPLC: $t_R$=0.65 min (HPLC-ACQUITY, Analytical).

Example 310

3-(5-Aminomethylthiophen-3-yl)-7-[(R)-1-(2,6-dichloro-3-fluoro-phenyl)ethoxy]furo[3,2-c]pyridin-6-ylamine

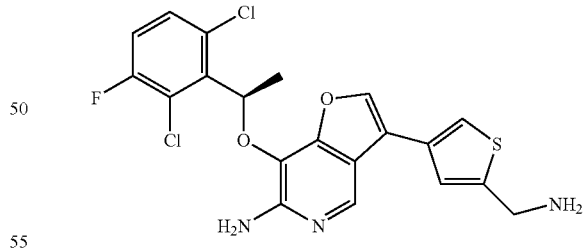

A mixture of 4-{6-amino-7-[(R)-1-(2,6-dichloro-3-fluorophenyl)ethoxy]furo[3,2-c]pyridin-3-yl}thiophene-2-carbaldehyde (10.0 mg, 0.0222 mmol), hydroxylamine hydrochloride (1.85 mg, 0.0266 mmol), potassium acetate, (2.61 mg, 0.0266 mmol) and ethanol (1.0 mL, 17 mmol) was stirred at room temperature for 20 minutes. The solution was concentrated in vacuo and extracted with DCM and sat. NaHCO₃. The organic layer was concentrated in vacuo. Zinc (14.5 mg, 0.222 mmol), 2 M of HCl in H₂O (0.5 mL) and THF (1.0 mL, 12 mmol) were added. The mixture was refluxed at 70° C. for 3 hours. The solution was concentrated in vacuo and extracted with DCM and sat. NaHCO$_3$. The organic layer was concentrated in vacuo and dissolved in DMSO. The sample was purified by the MDPS to afford the title compound as white solid. MS (ES$^+$): m/z 452.08/454.05 (100/75) [MH$^+$]. HPLC: t$_R$=0.62 min (HPLC-ACQUITY, Analytical). $^1$H NMR (400 MHz, CD$_3$OD): δ=1.91 (d, J=6.6 Hz, 3H), 4.33 (s, 2H), 6.55 (q, J=6.8 Hz, 1H), 7.23 (t, J=8.6 Hz, 1H), 7.41 (dd, J=9.0, 4.9 Hz, 1H), 7.51 (s, 1H), 7.77 (d, J=1.3 Hz, 1H), 7.89 (s, 1H), 8.24 (s, 1H).

Example 311

4-{6-Amino-7-[(R)-1-(2,6-dichloro-3-fluorophenyl)ethoxy]furo[3,2-c]pyridin-3-yl}thiophene-2-carboxylic acid

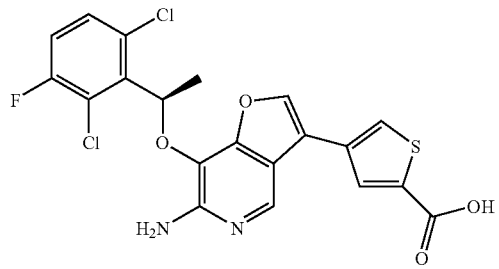

3-Bromo-7-[(R)-1-(2,6-dichloro-3-fluorophenyl)ethoxy]furo[3,2-c]pyridin-6-ylamine (180.0 mg, 0.4285 mmol), 2-carboxythiophene-4-boronic acid (147 mg, 0.857 mmol), potassium carbonate (178 mg, 1.28 mmol), 1,4-dioxane (4.2 mL, 54 mmol), H$_2$O (1.2 mL, 67 mmol) and [1,1'-bis(diphenylphosphino)ferrocene]dichloropalladium(II), complex with dichloromethane (1:1) (20 mg, 0.02 mmol) were mixed and heated in a microwave reactor at 90° C. for 20 minutes. The crude was passed through Thiol-SPE to remove palladium. MS (ES$^+$): m/z 467.02/469.02 (100/70) [MH$^+$]. HPLC: t$_R$=0.85 min (HPLC-ACQUITY, Analytical). $^1$H NMR (400 MHz, DMSO-d$_6$): δ=1.84 (d, J=6.8 Hz, 3H), 5.63 (s, 2H), 6.26 (q, J=6.8 Hz, 1H), 7.45 (t, J=8.7 Hz, 1H), 7.53 (dd, J=9.0, 4.9 Hz, 1H), 7.76 (br. s., 1H), 7.94 (br. s., 1H), 8.20 (s, 1H), 8.40 (s, 1H).

Example 312

4-{6-Amino-7-[(R)-1-(2,6-dichloro-3-fluorophenyl)ethoxy]furo[3,2-c]pyridin-3-yl}thiophene-2-carboxylic acid isopropylamide

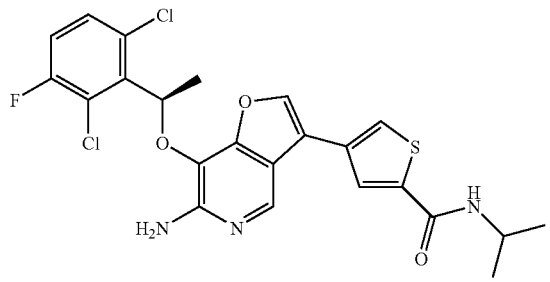

General Procedure Z: 4-{6-Amino-7-[(R)-1-(2,6-dichloro-3-fluorophenyl)ethoxy]furo[3,2-c]pyridin-3-yl}thiophene-2-carboxylic acid (10.0 mg, 0.0214 mmol), amine (0.214 mmol), DIPEA (18.6 μL, 0.107 mmol), TBTU (68.7 mg, 0.214 mmol) and DMF (0.7 mL, 9 mmol) were mixed and stirred at room temperature for 30 minutes. The crude material was purified by the MDPS. MS (ES$^+$): m/z 508.04/510.04 (100/83) [MH$^+$]. HPLC: t$_R$=0.93 min (HPLC-ACQUITY, Analytical). $^1$H NMR (400 MHz, DMSO-d$_6$): δ=1.18 (d, J=6.6 Hz, 6H), 1.86 (d, J=6.8 Hz, 3H), 4.06 (m, 1H), 5.68 (s, 2H), 6.26 (q, J=6.7 Hz, 1H), 7.45 (t, J=8.7 Hz, 1H), 7.52 (dd, J=8.8, 5.1 Hz, 1H), 8.07 (d, J=1.3 Hz, 1H), 8.12 (d, J=1.3 Hz, 1H), 8.33 (d, J=7.8 Hz, 1H), 8.45 (s, 1H).

Example 313

(4-{6-Amino-7-[(R)-1-(2,6-dichloro-3-fluorophenyl)ethoxy]-furo[3,2-c]pyridin-3-yl}-thiophen-2-yl)-(4-hydroxypiperidin-1-yl)methanone

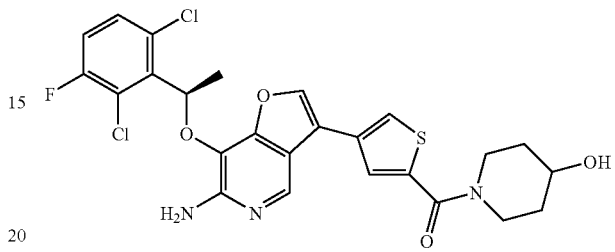

The title compound was prepared according to General Procedure Z. MS (ES$^+$): m/z 550.07/552.07 (100/80) [MH$^+$]. HPLC: t$_R$=0.78 min (HPLC-ACQUITY, Analytical).

Example 314

4-{6-Amino-7-[(R)-1-(2,6-dichloro-3-fluorophenyl)ethoxy]furo[3,2-c]pyridin-3-yl}-thiophene-2-carboxylic acid Ethylamide

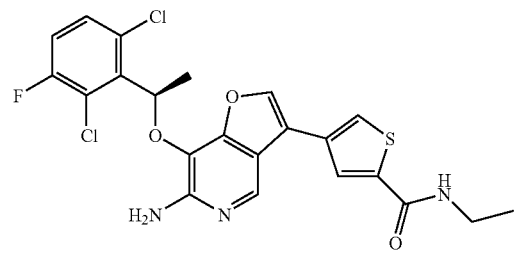

The title compound was prepared according to General Procedure Z. MS (ES$^+$): m/z 494.04/496.04 (100/72) [MH$^+$]. HPLC: t$_R$=0.88 min (HPLC-ACQUITY, Analytical).

Example 315

4-{6-Amino-7-[(R)-1-(2,6-dichloro-3-fluorophenyl)ethoxy]-furo[3,2-c]pyridin-3-yl}thiophene-2-carboxylic acid tert-butylamide

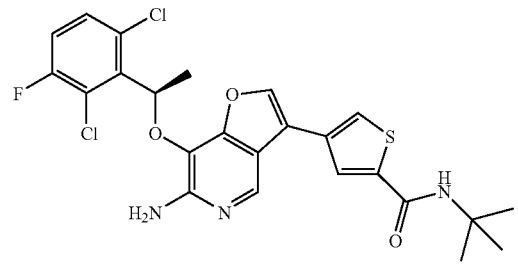

The title compound was prepared according to General Procedure Z. MS (ES$^+$): m/z 522.07/524.07 (100/75) [MH$^+$]. HPLC: t$_R$=1.02 min (HPLC-ACQUITY, Analytical).

Example 316

(4-{6-Amino-7-[(R)-1-(2,6-dichloro-3-fluorophenyl)ethoxy]furo[3,2-c]pyridin-3-yl}thiophen-2-yl)-(4-methylpiperazin-1-yl)methanone

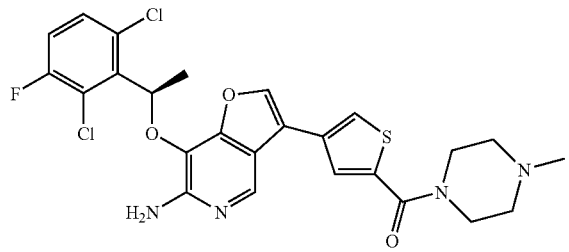

The title compound was prepared according to General Procedure Z. MS (ES⁺): m/z 549.09/551.06 (100/78) [MH⁺]. HPLC: $t_R$=0.64 min (HPLC-ACQUITY, Analytical).

Example 317

4-{6-Amino-7-[(R)-1-(2,6-dichloro-3-fluorophenyl)ethoxy]furo[3,2-c]pyridin-3-yl}thiophene-2-carboxylic acid Dimethylamide

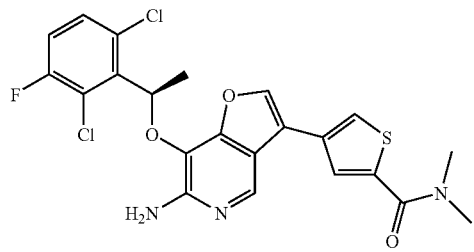

The title compound was prepared according to General Procedure Z. MS (ES⁺): m/z 494.06/496.04 (100/73) [MH⁺]. HPLC: $t_R$=0.86 min (HPLC-ACQUITY, Analytical).

Example 318

4-{6-Amino-7-[(R)-1-(2,6-dichloro-3-fluorophenyl)ethoxy]furo[3,2-c]pyridin-3-yl}thiophene-2-carboxamide

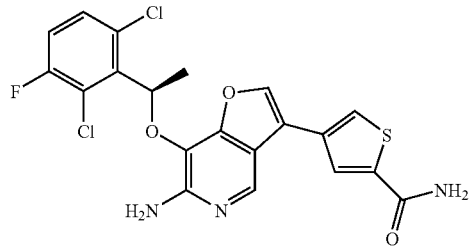

The title compound was prepared according to General Procedure Z. MS (ES⁺): m/z 466.04/468.02 (100/70) [MH⁺]. HPLC: $t_R$=0.79 min (HPLC-ACQUITY, Analytical).

Example 319

4-(5-{6-Amino-7-[(R)-1-(2,6-dichloro-3-fluorophenyl)ethoxy]furo[3,2-c]pyridin-3-yl}pyridin-2-yl)piperazine-1-carboxamide

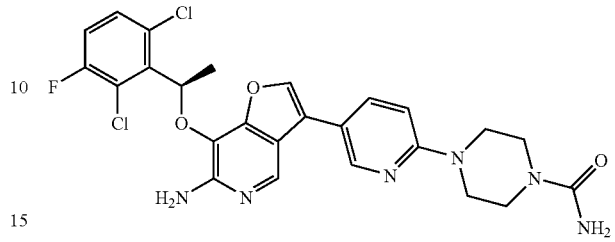

To a solution of 3-bromo-7-[(R)-1-(2,6-dichloro-3-fluorophenyl)ethoxy]furo[3,2-c]pyridin-6-ylamine (15.0 mg, 0.0357 mmol, 1 eq.), 1-[5-(4,4,5,5-tetramethyl[1,3,2]dioxaborolan-2-yl)pyridin-2-yl]piperazine (20.6 mg, 0.0714 mmol, 2 eq.), potassium carbonate (14.8 mg, 0.107, 3 eq.) in dioxane (0.9 mL) and water (0.3 mL) was added 1,1'-bis(diphenylphosphino)ferrocene]dichloropalladium(II), complex with dichloromethane (1:1) (1 mg, 0.002 mmol, 0.05 eq.). The mixture was evacuated by vacuum and filled with nitrogen 3 times and heated in a microwave reactor at 100° C. for 30 min. The crude mixture was dried in vacuo, and trimethylsilyl isocyanate (14.5 uL, 0.107 mmol), DIPEA (62.2 uL, 0.357 mmol), and DMF (0.2 mL, 2 mmol) were added. The resulting mixture was stirred at room temperature overnight. The crude solution was passed through Thiol-SPE to remove palladium. The solution was further passed through SCX-2 SPE and the product was released by 2M NH₃ in methanol. The solution was concentrated, dissolved in DMSO, and purified on the MDPS. MS (ES⁺): m/z 545.17/547.17 (100/76) [MH⁺]. HPLC: $t_R$=0.71 min (HPLC-ACQUITY, Analytical). ¹H NMR (400 MHz, DMSO-d₆): δ=1.83 (d, J=6.8 Hz, 3H), 3.49-3.57 (m, 8H), 5.63 (s, 2H), 6.07 (s, 2H), 6.27 (q, J=6.7 Hz, 1H), 6.96 (d, J=8.8 Hz, 1H), 7.46 (t, J=8.7 Hz, 1H), 7.53 (dd, J=9.0, 4.9 Hz, 1H), 7.87 (dd, J=8.7, 2.1 Hz, 1H), 8.04 (s, 1H), 8.28 (s, 1H), 8.48 (d, J=2.5 Hz, 1H).

Example 320

4-(4-{6-Amino-7-[(R)-1-(2,6-dichloro-3-fluorophenyl)ethoxy]furo[3,2-c]pyridin-3-yl}phenyl)piperazine-1-carboxamide

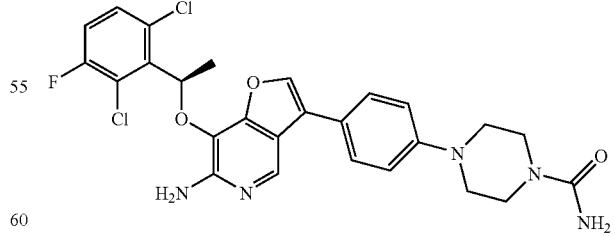

The title compound was prepared following the procedure for the previous example using 1-[4-(4,4,5,5-tetramethyl-[1,3,2]dioxaborolan-2-yl)phenyl]piperazine (2 eq.). MS (ES⁺): m/z 544.17/546.16 (100/71) [MH⁺]. HPLC: $t_R$=0.80 min (HPLC-ACQUITY, Analytical).

Example 321

(4-{6-Amino-7-[(R)-1-(2,6-dichloro-3-fluorophenyl)ethoxy]furo[3,2-c]pyridin-3-yl}-3,6-dihydro-2H-pyridin-1-yl)acetonitrile

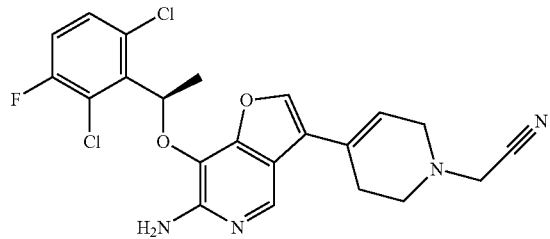

7-[(R)-1-(2,6-Dichloro-3-fluorophenyl)ethoxy]-3-(1,2,3,6-tetrahydropyridin-4-yl)furo[3,2-c]pyridin-6-ylamine (10.0 mg, 0.0237 mmol), DIPEA (16.5 μL, 0.0947 mmol) and DMF (1.00 mL, 12.9 mmol) were mixed. Bromoacetonitrile (1.7 μL, 0.026 mmol) was added at last at 0° C. The mixture was stirred at 0° C. for 2 hours. Crude was passed through SCX-2 SPE, and the product was released by 2 M NH$_3$ in methanol and purified on the MDPS. MS (ES$^+$): m/z 461.03/463.05 (100/81) [MH$^+$]. HPLC: t$_R$=0.83 min (HPLC-ACQUITY, Analytical). $^1$H NMR (400 MHz, DMSO-d$_6$): δ=1.82 (d, J=6.8 Hz, 3H), 2.46 (br. s., 2H), 2.65-2.74 (m, 2H), 3.19-3.22 (m, 2H), 3.85 (s, 2H), 5.60 (s, 2H), 6.21 (q, J=6.6 Hz, 1H), 6.31 (br. s., 1H), 7.45 (t, J=8.7 Hz, 1H), 7.52 (dd, J=9.0, 5.2 Hz, 1H), 7.78 (s, 1H), 8.30 (s, 1H).

Example 322

3-(1-Azetidin-3-yl-1,2,3,6-tetrahydropyridin-4-yl)-7-[(R)-1-(2,6-dichloro-3-fluorophenyl)ethoxy]furo[3,2-c]pyridin-6-ylamine

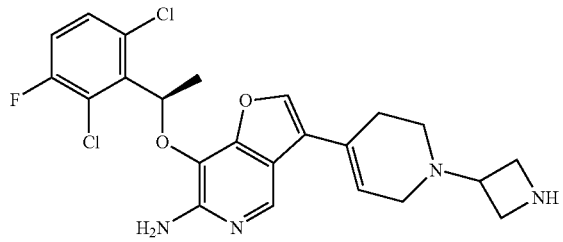

7-[(R)-1-(2,6-Dichloro-3-fluorophenyl)ethoxy]-3-(1,2,3,6-tetrahydropyridin-4-yl)furo[3,2-c]pyridin-6-ylamine (10.0 mg, 0.0237 mmol), tert-butyl 3-oxoazetidine-1-carboxylate (8.11 mg, 0.0474 mmol), sodium triacetoxyborohydride (25.1 mg, 0.118 mmol) and 1,2-dichloroethane (1.0 mL, 13 mmol) were mixed and stirred at 70° C. overnight. After extraction with DCM and water, the organic layer was dried and dissolved in DCM (1.0 mL, 16 mmol). TFA (1.0 mL, 13 mmol) was added at 0° C. The mixture was stirred at 0° C. for 1 hour. The crude was passed through SCX-2 SPE and product was released by 2 M NH$_3$ in methanol for purification by the MDPS. MS (ES$^+$): m/z 477.10/479.15 (100/80) [MH$^+$]. HPLC: t$_R$=0.57 min (HPLC-ACQUITY, Analytical). $^1$H NMR (400 MHz, CD$_3$OD): δ=1.88 (d, J=6.8 Hz, 3H), 2.54 (br. s., 2H), 2.64-2.68 (m, 2H), 3.11-3.18 (m, 2H), 3.53 (t, J=6.9 Hz, 1H), 3.94-4.08 (m, 4H), 6.27 (br. s., 1H), 6.50 (q, J=7.0 Hz, 1H), 7.22 (t, J=8.6 Hz, 1H), 7.40 (dd, J=9.0, 4.9 Hz, 1H), 7.63 (s, 1H), 8.18 (s, 1H).

Example 323

7-[(R)-1-(2,6-Dichloro-3-fluorophenyl)ethoxy]-3-[1-(1-methane-sulfonylazetidin-3-yl)-1,2,3,6-tetrahydropyridin-4-yl]furo[3,2-c]pyridin-6-ylamine

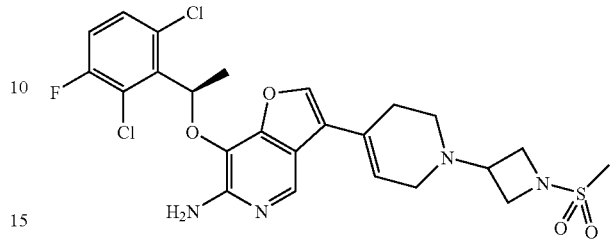

3-(1-Azetidin-3-yl-1,2,3,6-tetrahydropyridin-4-yl)-7-[(R)-1-(2,6-dichloro-3-fluoro-phenyl)ethoxy]furo[3,2-c]pyridin-6-ylamine (10.0 mg, 0.0209 mmol), DCM (0.13 mL) and DIPEA (7.3 μL, 0.042 mmol) were mixed and cooled at 0° C. Methanesulfonyl chloride (1.8 μL, 0.023 mmol) was added carefully at 0° C. The mixture was stirred at 0° C. for 30 minutes. The crude was passed through SCX-2 SPE and the product was released by 2 M NH$_3$ in methanol for MDP purification. MS (ES$^+$): m/z 555.05/557.04 (100/81) [MH$^+$]. HPLC: t$_R$=0.63 min (HPLC-ACQUITY, Analytical). $^1$H NMR (400 MHz, CD$_3$OD): δ=1.88 (d, J=6.8 Hz, 3H), 2.56 (br. s., 2H), 3.15-3.22 (m, 2H), 3.34-3.42 (m, 1H), 3.89 (dd, J=8.6, 5.3 Hz, 2H), 4.01-4.09 (m, 2H), 6.27 (br. s., 1H), 6.50 (q, J=6.7 Hz, 1H), 7.21 (t, J=8.6 Hz, 1H), 7.40 (dd, J=9.0, 4.9 Hz, 1H), 7.63 (s, 1H), 8.19 (s, 1H).

Example 324

3-(4-{6-Amino-7-[(R)-1-(2,6-dichloro-3-fluorophenyl)ethoxy]furo[3,2-c]pyridin-3-yl}-3,6-dihydro-2H-pyridin-1-yl)azetidine-1-carboxamide

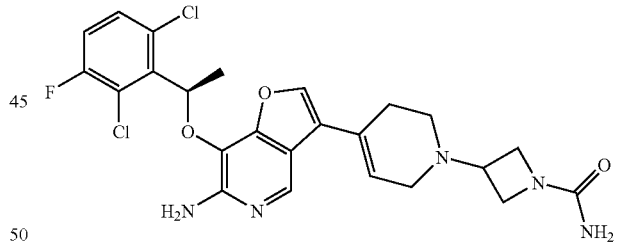

3-(1-Azetidin-3-yl-1,2,3,6-tetrahydropyridin-4-yl)-7-[(R)-1-(2,6-dichloro-3-fluoro-phenyl)ethoxy]furo[3,2-c]pyridin-6-ylamine (10.0 mg, 0.0209 mmol), trimethylsilyl isocyanate (4.25 μL, 0.0314 mmol), DMF (1.0 mL, 13 mmol) and DIPEA (7.30 μL, 0.0419 mmol) were mixed together and stirred at room temperature for 1 hour. The crude was passed through SCX-2 SPE and the product was release by 2 M NH$_3$ in methanol for MDP purification. MS (ES$^+$): m/z 555.05/557.04 (100/76) [MH$^+$]. HPLC: t$_R$=0.55 min (HPLC-ACQUITY, Analytical). $^1$H NMR (400 MHz, CD$_3$OD): δ=1.88 (d, J=6.8 Hz, 3H), 2.56 (br. s., 2H), 2.67-2.73 (m, 2H), 3.15-3.22 (m, 2H), 3.34-3.42 (m, 1H), 3.89 (dd, J=8.6, 5.3 Hz, 2H), 4.01-4.09 (m, 2H), 6.27 (br. s., 1H), 6.50 (q, J=6.7 Hz, 1H), 7.21 (t, J=8.6 Hz, 1H), 7.40 (dd, J=9.0, 4.9 Hz, 1H), 7.63 (s, 1H), 8.19 (s, 1H).

Example 325

5-{6-Amino-7-[(R)-1-(2,6-dichloro-3-fluorophenyl)ethoxy]furo[3,2-c]pyridin-3-yl}thiophene-3-carboxylic acid

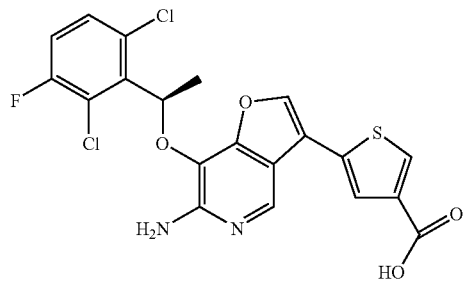

5-{6-Amino-7-[(R)-1-(2,6-dichloro-3-fluorophenyl)ethoxy]furo[3,2-c]pyridin-3-yl}thiophene-3-carboxylic acid methyl ester (100.0 mg, 0.2078 mmol) and 12 M of HCl in H$_2$O (10.0 mL) were mixed together and heated at 100° C. for 3 days. The solvent was evaporated in vacuo and the residue was purified using the MDPS. MS (ES$^+$): m/z 467.11/469.09 (100/72) [MH$^+$]. HPLC: t$_R$=0.90 min (HPLC-ACQUITY, Analytical). $^1$H NMR (400 MHz, CD$_3$OD): δ=1.91 (d, J=6.6 Hz, 3H), 6.55 (d, J=6.8 Hz, 1H), 7.23 (t, J=8.6 Hz, 1H), 7.41 (dd, J=9.0, 4.9 Hz, 1H), 7.73 (s, 1H), 7.91 (s, 1H), 7.98 (s, 1H), 8.28 (s, 1H).

The following seven compounds were prepared according to General Procedure Z, using 5-{6-amino-7-[(R)-1-(2,6-dichloro-3-fluorophenyl)ethoxy]furo[3,2-c]pyridin-3-yl}thiophene-3-carboxylic acid as starting material instead of the thiophene-2-carboxylic acid.

Example 326

5-{6-Amino-7-[(R)-1-(2,6-dichloro-3-fluorophenyl)ethoxy]furo[3,2-c]pyridin-3-yl}thiophene-3-carboxamide

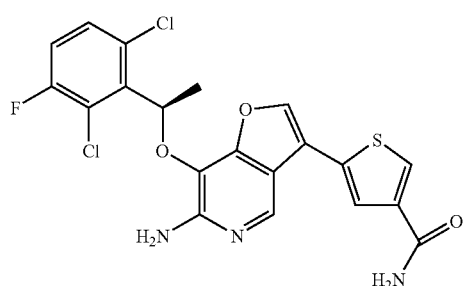

MS (ES$^+$): m/z 466.11/468.09 (100/64) [MH$^+$]. HPLC: t$_R$=0.82 min (HPLC-ACQUITY, Analytical). $^1$H NMR (400 MHz, CD$_3$OD): δ=1.91 (d, J=6.6 Hz, 3H), 6.54 (q, J=6.8 Hz, 1H), 7.18-7.27 (m, 1H), 7.41 (dd, J=8.8, 4.8 Hz, 1H), 7.78 (d, J=1.3 Hz, 1H), 7.94 (s, 1H), 8.09 (d, J=1.3 Hz, 1H), 8.29 (s, 1H).

Example 327

5-{6-Amino-7-[(R)-1-(2,6-dichloro-3-fluorophenyl)ethoxy]furo[3,2-c]pyridin-3-yl}thiophene-3-carboxylic acid methylamide

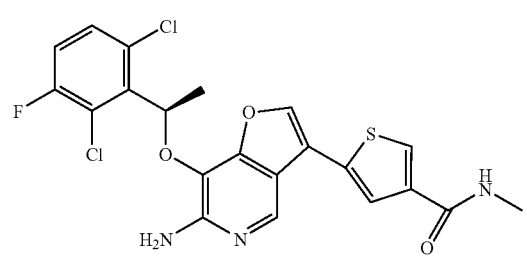

MS (ES$^+$): m/z 480.11/482.13 (100/72) [MH$^+$]. HPLC: t$_R$=0.86 min (HPLC-ACQUITY, Analytical).

Example 328

5-{6-Amino-7-[(R)-1-(2,6-dichloro-3-fluorophenyl)ethoxy]furo[3,2-c]pyridin-3-yl}thiophene-3-carboxylic acid Dimethylamide

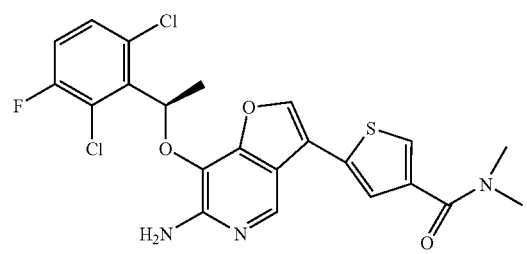

MS (ES$^+$): m/z 494.12/496.11 (100/70) [MH$^+$]. HPLC: t$_R$=0.90 min (HPLC-ACQUITY, Analytical).

Example 329

5-{6-Amino-7-[(R)-1-(2,6-dichloro-3-fluorophenyl)ethoxy]furo[3,2-c]pyridin-3-yl}-thiophene-3-carboxylic acid Ethylamide

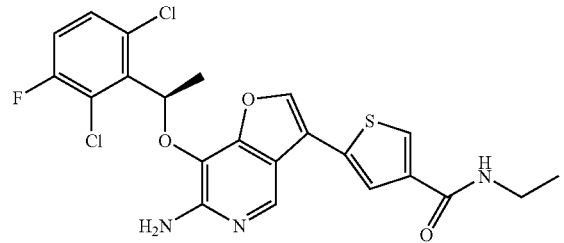

MS (ES$^+$): m/z 494.12/496.12 (100/72) [MH$^+$]. HPLC: t$_R$=0.91 min (HPLC-ACQUITY, Analytical).

Example 330

5-{6-Amino-7-[(R)-1-(2,6-dichloro-3-fluorophenyl)ethoxy]furo[3,2-c]pyridin-3-yl}thiophene-3-carboxylic acid Isopropylamide

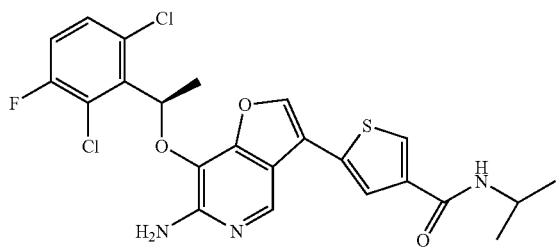

MS (ES⁺): m/z 508.13/510.10 (100/78) [MH⁺]. HPLC: $t_R$=0.96 min (HPLC-ACQUITY, Analytical).

Example 331

5-{6-Amino-7-[(R)-1-(2,6-dichloro-3-fluorophenyl)ethoxy]furo[3,2-c]pyridin-3-yl}thiophene-3-carboxylic acid tert-butylamide

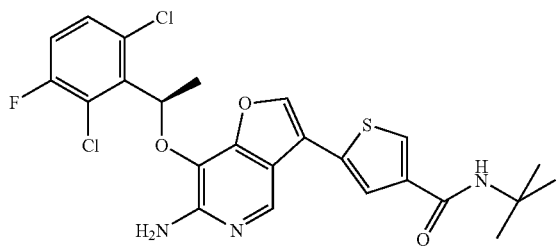

MS (ES⁺): m/z 522.42/524.18 (100/72) [MH⁺]. HPLC: $t_R$=1.04 min (HPLC-ACQUITY, Analytical).

Example 332

(5-{6-Amino-7-[(R)-1-(2,6-dichloro-3-fluorophenyl)ethoxy]furo[3,2-c]pyridin-3-yl}thiophen-3-yl)-(4-methylpiperazin-1-yl)methanone

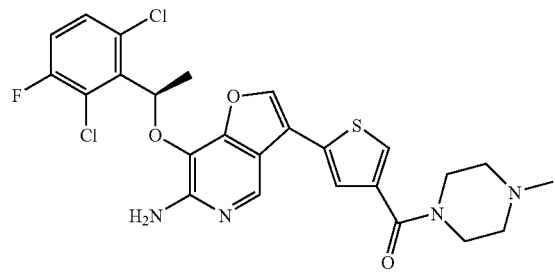

MS (ES⁺): m/z 549.04/551.16 (100/72) [MH⁺]. HPLC: $t_R$=0.66 min (HPLC-ACQUITY, Analytical).

Intermediate 10:
3-Bromo-6-nitrofuro[3,2-c]pyridin-7-ol

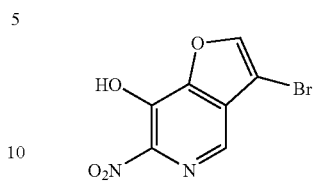

A solution of 3-Bromo-7-[1-(2,6-dichloro-3-fluorophenyl)ethoxy]-6-nitrofuro[3,2-c]pyridine (Intermediate 9a) (1.90 g, 0.00422 mol) in 48% aq. hydrogen bromide (100 mL, 2.0 mol) was stirred at 60° C. overnight. The reaction mixture was cooled down to rt. The reaction solution was diluted with H₂O (100 mL) and extracted with DCM (5×50 mL). The DCM solution was dried over Na₂SO₄ and concentrated under vacuum. The resulting solid was triturated with DCM/hexanes to give the title compound. MS (ES+): m/z 258.85/260.89 [MH⁺]. HPLC: $t_R$=2.81 min (ZQ3, polar_5 min). ¹H NMR (400 MHz, CD₃OD): δ=8.28 (s, 1H) 8.32 (s, 1H).

Example 333

7-[1-(2,6-Dichloro-3-fluorophenyl)ethoxy]-3-(1-piperidin-4-yl-1H-pyrazol-4-yl)-furo[3,2-c]pyridin-6-ylamine

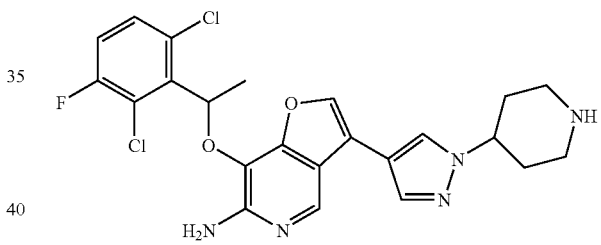

3-Bromo-7-[1-(2,6-dichloro-3-fluorophenyl)ethoxy]-6-nitrofuro[3,2-c]pyridine (Intermediate 9a) was reacted with iron/HCl as described in Example 2 to give 3-Bromo-7-[1-(2,6-dichloro-3-fluorophenyl)ethoxy]furo[3,2-c]pyridin-6-ylamine (=racemic Example 2).

To a stirred mixture of 4-[4-(4,4,5,5-tetramethyl-1,3,2-dioxaborolan-2-yl)-pyrazol-1-yl]-piperidine-1-carboxylic acid tert-butyl ester (26.94 mg, 0.071 mmol), 3-bromo-7-[1-(2,6-dichloro-3-fluorophenyl)ethoxy]furo[3,2-c]pyridin-6-ylamine (20.0 mg, 0.047 mmol), potassium carbonate (19.7 mg, 0.14 mmol) in DME (2.0 mL) and H₂O (0.40 mL) was added Pd(PPh₃)₄ (2.8 mg, 0.0024 mmol) under Nitrogen. The resulting mixture was refluxed at 100° C. for 30 min. LC-MS indicated completion of reaction. The solvent was then removed under reduced pressure and the resulting residue was purified by a flash chromatography (2% MeOH in DCM). MS (ES+): m/z 590.07, 592.08 (MH⁺). HPLC: $t_R$=3.48 min (ZQ3, polar_5 min). The product purified above was then dissolved in 2 mL dioxane, to this solution was added solution of 4 N HCl in dioxane (1 mL) at r.t., the resulting mixture was stirred at r.t. for 1.5 h. LC-MS indicated completion of reaction. The solvent was removed under reduced pressure to give the title compound as HCl salt. The ¹H NMR spectrum matches that of Example 5.

Example 334

7-[1-(2,6-Dichloro-3-fluorophenyl)ethoxy]-3-(1-piperidin-4-yl-1H-pyrazol-4-yl)-furo[3,2-c]pyridin-6-ylamine

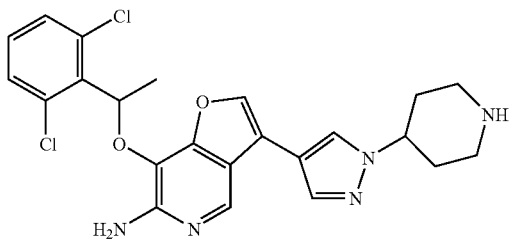

3-Bromo-6-nitrofuro[3,2-c]pyridin-7-ol (Intermediate 10) was reacted with racemic 1-(2,6-dichlorophenyl)ethanol following the procedure described for Intermediate 8. The resulting 3-Bromo-7-[1-(2,6-dichlorophenyl)ethoxy]-6-nitrofuro[3,2-c]pyridine was reacted with iron/HCl as described in Example 2 to give 3-Bromo-7-[1-(2,6-dichlorophenyl)ethoxy]furo[3,2-c]pyridin-6-ylamine. Suzuki coupling with 4-[4-(4,4,5,5-tetramethyl-1,3,2-dioxaborolan-2-yl)-pyrazol-1-yl]piperidine-1-carboxylic acid tert-butyl ester and Boc removal with HCl as described for Example 333 gave the title compound as HCl salt. $^1$H NMR (400 MHz, CD$_3$OD): δ=1.86 (d, J=6.8 Hz, 3H), 1.91-2.03 (m, 2H), 2.11 (dd, J=12.0, 2.2 Hz, 2H), 2.75 (td, J=12.8, 2.5 Hz, 2H), 3.13-3.23 (m, 2H), 4.26-4.39 (m, 1H), 6.59 (q, J=6.8 Hz, 1H), 7.23 (d, J=7.8 Hz, 1H), 7.31-7.39 (m, 2H), 7.77 (s, 1H), 7.82 (s, 1H), 8.07 (s, 1H), 8.13 (s, 1H). MS (ES+): m/z 472.00/474.00 [MH$^+$]. HPLC: $t_R$=2.38 min (ZQ3, polar__5 min).

Example 335

7-[(R)-1-(2-Chlorophenyl)ethoxy]-3-(1-piperidin-4-yl-1H-pyrazol-4-yl)-furo[3,2-c]pyridin-6-ylamine

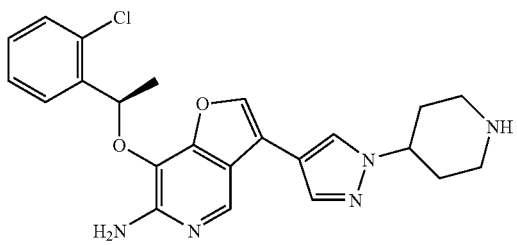

The title compound was prepared following the procedure for Example 334 using the appropriate alcohol. $^1$H NMR (400 MHz, CD$_3$OD): δ=1.66 (d, J=6.3 Hz, 3H), 1.88-2.13 (m, 4H), 2.73 (td, J=12.7, 2.4 Hz, 2H), 3.12-3.22 (m, 2H), 4.24-4.37 (m, 1H), 6.39 (q, J=6.4 Hz, 1H), 7.16-7.33 (m, 3H), 7.67-7.75 (m, 2H), 7.79 (s, 1H), 8.04 (s, 1H), 8.08 (s, 1H). MS (ES+): m/z 438.06/440.07 [MH$^+$]. HPLC: $t_R$=2.22 min (ZQ3, polar__5 min).

Example 336

7-[1-(2-Chloro-5-fluorophenyl)ethoxy]-3-(1-piperidin-4-yl-1H-pyrazol-4-yl)-furo[3,2-c]pyridin-6-ylamine

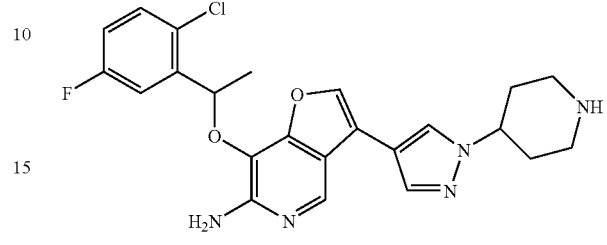

The title compound was prepared following the procedure for Example 334 using the appropriate alcohol. $^1$H NMR (400 MHz, CD$_3$OD): δ=1.66 (d, J=6.3 Hz, 3H), 1.87-2.15 (m, 4H), 2.74 (td, J=12.6, 2.3 Hz, 2H), 3.12-3.21 (m, 2H), 4.26-4.37 (m, 1H), 6.33 (q, J=6.2 Hz, 1H), 6.98 (td, J=8.3, 3.0 Hz, 1H), 7.33 (dd, J=8.8, 5.1 Hz, 1H), 7.51 (dd, J=9.6, 3.0 Hz, 1H), 7.73 (s, 1H), 7.80 (s, 1H), 8.05 (s, 1H), 8.11 (s, 1H). MS (ES$^+$): m/z 456.07/458.08 [MH$^+$]. HPLC: $t_R$=2.11 min (ZQ3, polar__5 min).

Example 337

7-[(R)-1-(3-fluorophenyl)ethoxy]-3-(1-piperidin-4-yl-1H-pyrazol-4-yl)-furo[3,2-c]pyridin-6-ylamine

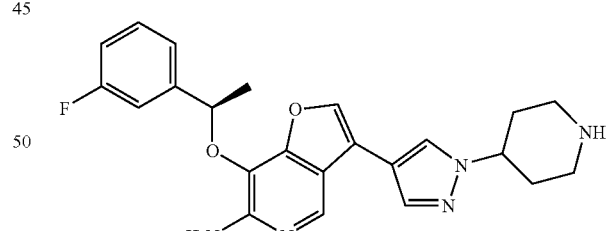

The title compound was prepared following the procedure for Example 334 using the appropriate alcohol. $^1$H NMR (400 MHz, CD$_3$OD): δ=1.67 (d, J=6.6 Hz, 3H), 1.86-2.14 (m, 4H), 2.73 (td, J=12.6, 2.3 Hz, 2H), 3.11-3.21 (m, 2H), 4.24-4.38 (m, 1H), 5.89 (q, J=6.3 Hz, 1H), 6.93 (td, J=8.3, 1.3 Hz, 1H), 7.18-7.30 (m, 3H), 7.76 (s, 1H), 7.79 (s, 1H), 8.04 (s, 1H), 8.08 (s, 1H). MS (ES+): m/z 422.11 [MH$^+$]. HPLC: $t_R$=2.18 min (ZQ3, polar__5 min).

Example 338

7-[(S)-1-(2,6-Dichloro-3-fluorophenyl)ethoxy]-3-(1-piperidin-4-yl-1H-pyrazol-4-yl)-furo[3,2-c]pyridin-6-ylamine

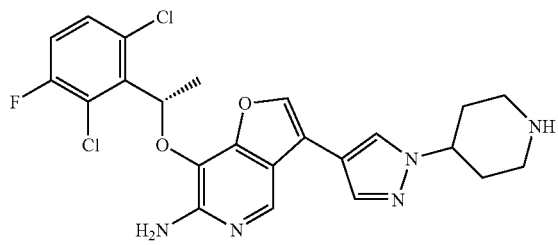

The title compound was prepared following the procedure for Example 334 using the appropriate alcohol. $^1$H NMR and LC/MS match those of Example 5.

Example 339

7-(2,6-Dichloro-3-fluorobenzyloxy)-3-(1-piperidin-4-yl-1H-pyrazol-4-yl)-furo[3,2-c]pyridin-6-ylamine

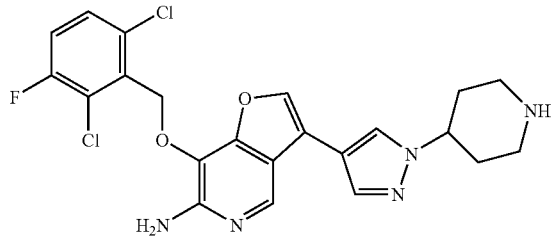

The title compound was prepared following the procedure for Example 334 using the appropriate alcohol. $^1$H-NMR (CD$_3$OD, 400 MHz): δ=2.28 (br. s., 4H), 3.13-3.19 (m, 2H), 3.47-3.50 (m, 2H), 4.57 (br. s., 1H), 5.73 (s, 2H), 7.29 (t, J=8.7 Hz, 1H), 7.41 (dd, J=9.0, 4.7 Hz, 1H), 7.87 (s, 1H), 8.04 (s, 1H), 8.23 (br. s., 1H), 8.32 (s, 1H). MS (ES+): m/z 476.01/478.03 [MH$^+$]. HPLC: $t_R$=2.30 min (polar_5 min, ZQ3).

Intermediate 11: 4-(4-{7-[1-(2,6-Dichloro-3-fluorophenyl)ethoxy]-6-nitrofuro[3,2-c]pyridin-3-yl}-pyrazol-1-yl)-piperidine-1-carboxylic acid tert-butyl ester

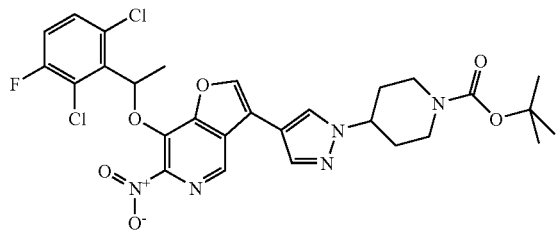

The title compound was prepared according to General Procedure A. $^1$H-NMR (CDCl$_3$, 400 MHz): δ=1.49 (s, 9H), 1.93 (d, J=6.8 Hz, 3H), 2.01 (dd, J=12.3, 4.2 Hz, 2H), 2.20 (dd, J=12.1, 2.3 Hz, 2H), 2.58 (s, 2H), 2.95 (br. s., 2H), 4.39 (t, J=3.9 Hz, 1H), 6.71 (q, J=6.7 Hz, 1H), 7.07 (d, J=8.1 Hz, 1H), 7.27 (dd, J=9.0, 4.9 Hz, 1H), 7.80 (d, J=4.6 Hz, 2H), 7.91 (s, 1H), 8.49 (s, 1H). MS (ES$^+$): m/z 620.00/621.97 [MH$^+$]. HPLC: $t_R$=4.25 min (polar_5 min, ZQ3).

Intermediate 12: 4-[4-(7-Hydroxy-6-nitrofuro[3,2-c]pyridin-3-yl)-pyrazol-1-yl]-piperidine-1-carboxylic acid tert-butyl ester

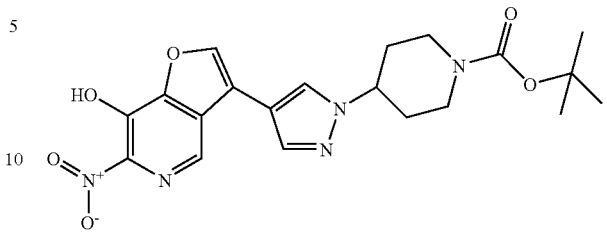

A solution of 4-(4-{7-[1-(2,6-Dichloro-3-fluorophenyl)ethoxy]-6-nitrofuro[3,2-c]pyridin-3-yl}-pyrazol-1-yl)-piperidine-1-carboxylic acid tert-butyl ester (Intermediate 11) (0.390 g, 0.628 mmol) in 48% HBr was stirred at 60° C. overnight. The solution was concentrated under reduced pressure. The resulting solid (crude 6-Nitro-3-(1-piperidin-4-yl-1H-pyrazol-4-yl)-furo[3,2-c]pyridin-7-ol) was used in the next step without purification.

A mixture of the crude 6-Nitro-3-(1-piperidin-4-yl-1H-pyrazol-4-yl)-furo[3,2-c]pyridin-7-ol (0.200 g, 0.607 mmol), Di-tert-butyldicarbonate (0.179 g, 0.820 mol) and DIPEA (0.212 g, 1.64 mmol) in DCM (5 mL) was stirred at 0° C. and then warmed up to rt for 2 h. The reaction mixture was diluted with DCM (10 mL) and then washed with water (3×15 mL) and brine (20 mL). The resulting DCM solution was dried over Na$_2$SO$_4$, concentrated under reduced pressure and then purified by silica gel (5% MeOH in DCM) to afford the title compound. $^1$H-NMR (CD$_3$OD, 400 MHz): δ=1.48 (s, 9H), 1.99 (dd, J=12.4, 4.3 Hz, 2H), 2.10-2.17 (m, 2H), 2.92-3.07 (m, 2H), 4.24 (d, J=13.9 Hz, 2H), 4.46 (s, 1H), 7.95 (s, 1H), 8.26 (s, 1H), 8.37 (s, 1H), 8.55 (s, 1H). MS (ES$^+$): m/z 430.04 [MH$^+$]. HPLC: $t_R$=3.39 min (polar_5 min, ZQ3).

Example 340

7-[1-(2,6-Dichlorophenyl)propoxy]-3-(1-piperidin-4-yl-1H-pyrazol-4-yl)furo[3,2-c]pyridin-6-ylamine

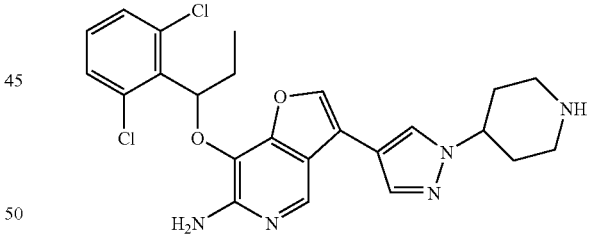

General procedure AA: To a mixture of 4-[4-(7-hydroxy-6-nitrofuro[3,2-c]pyridine-3-yl)-pyrazol-1-yl]-piperidine-1-carboxylic acid tert-butyl ester (20.0 mg, 0.047 mmol), 1-(2,6-dichlorophenyl)propan-1-ol (28.6 mg, 0.14 mmol), triphenylphosphine (24.4 mg, 0.093 mmol) and THF (2 mL) at rt was added diisopropyl azodicarboxylate (37.7 mg, 0.186 mmol) dropwise, and the solution was flushed with nitrogen and heated to 50° C. for 4 h. The solvents were removed in vacuo, and the material was redissolved in EtOH (3 mL). Iron powder (30 mg, 0.5 mmol) and 5 drops of conc. HCl were added, and the solution was refluxed for 30 min. The solution was directly passed through a SCX cartridge, washed with MeOH and ejected with 2M NH$_3$ in MeOH. The crude product was concentrated in vacuo, redissolved MeOH (1 mL) and purified via HPLC. The fractions containing the pure product were concentrated in vacuo to afford the title compound as a white solid. $^1$H NMR (400 MHz, CD$_3$OD): δ=1.06 (t, J=7.5 Hz, 3H), 1.93-2.05 (m, 2H), 2.09-2.17 (m, 2H), 2.33 (dt, J=13.7, 7.5 Hz, 1H), 2.48 (dd, J=14.3, 6.9 Hz, 1H), 2.78 (td, J=12.7, 2.7 Hz, 2H), 3.16-3.24 (m, 2H), 4.35 (tt, J=11.7, 4.1 Hz, 1H), 6.43 (t, J=7.5 Hz, 1H), 7.20-7.26 (m, 1H), 7.36 (d, J=8.1 Hz, 2H), 7.80 (s, 1H), 7.83 (s, 1H), 8.09 (s, 1H), 8.13 (s, 1H). MS (ES$^+$): m/z 498.06/500.05 (100/72) [MH$^+$]. HPLC: t$_R$=2.65 min (ZQ3, polar_5 min).

1-(2,6-Dichlorophenyl)propan-1-ol

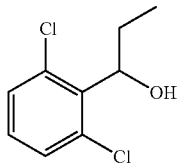

To a solution of 2,6-dichlorobenzaldehyde (880 mg, 5.03 mmol) in THF (10 mL) was added EtMgCl/THF (2.0 M, 3 mL, 6.0 mmol) at 0° C. under nitrogen, the resulting mixture was allowed to warm to rt and stirred at rt overnight. The mixture was quenched with sat. aq. NH$_4$Cl (5 mL) at 0° C., then diluted with Et$_2$O (50 mL), the organic phase was washed with brine (20 mL), and dried over anhydrous sodium sulfate. The residue was purified by silica gel chromatography (Hex:EtOAc=80:20) to give the title compound as a colorless oil. $^1$H NMR (CDCl$_3$): δ=1.00 (t, J=7.4 Hz, 3H), 1.95-2.11 (m, 2H), 2.82 (d, J=10.4 Hz, 1H, —OH), 5.34 (m, 1H), 7.13 (t, J=7.6 Hz, 1H), 7.29 (d, J=7.8 Hz, 2H.)

Example 341

7-[1-(2,6-Dichlorophenyl)but-3-ynyloxy]-3-(1-piperidin-4-yl-1H-pyrazol-4-yl)-furo[3,2-c]pyridin-6-ylamine

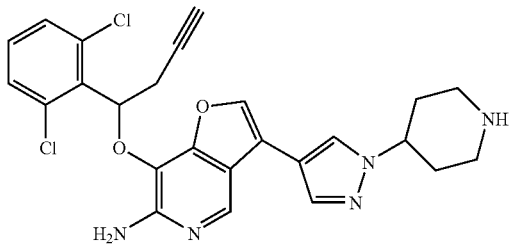

The title compound was prepared according to General Procedure AA. $^1$H NMR (400 MHz, CD$_3$OD): δ=2.25-2.38 (m, 5H), 3.16-3.25 (m, 2H), 3.32-3.41 (m, 2H), 3.53-3.62 (m, 2H), 4.59 (m, J=9.9, 9.9, 5.1, 4.9 Hz, 1H), 6.51 (t, J=7.6 Hz, 1H), 7.24-7.30 (m, 1H), 7.38 (d, J=7.8 Hz, 2H), 7.76 (s, 1H), 7.87 (s, 1H), 8.11 (s, 1H), 8.16 (s, 1H). MS (ES$^+$): m/z 495.97/497.99 (100/72) [MH$^+$]. HPLC: t$_R$=2.45 min (ZQ3, polar_5 min).

1-(2,6-Dichlorophenyl)but-3-yn-1-ol

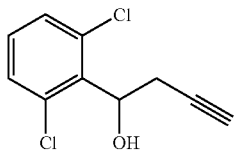

General Procedure BB: To a mixture of zinc (0.60 g, 9.2 mmol) in THF (1 mL) was added 1,2-Dibromoethane (0.03 mL, 0.3 mmol). The resulting mixture was stirred under reflux for 15 min and then cooled to rt. To the reaction mixture was added TMSCl (0.03 mL, 0.2 mmol) and THF (5 mL). A solution of propargyl bromide (0.750 mL, 8.42 mmol) and THF (3 mL) was then added dropwise to the reaction mixture over a 30 min period at −10° C. After 1 h, 2,6-Dichlorobenzaldehyde (1.46 g, 8.33 mmol) was added to the reaction mixture and allowed to warm to rt and stirred for 36 h. The reaction mixture was quenched with 1 M aqueous HCl (15 mL) and the organic layer was washed with brine (10 mL). The organic layer was dried over Na$_2$SO$_4$ and concentrated under reduced pressure to yield a dark yellow oil. The crude product was purified by silica gel chromatography using Hexane/EtOAc (80:20) as eluent to yield the desired product as a yellow oil. $^1$H NMR (CDCl$_3$, 400 MHz): δ=2.03-2.06 (m, 1H), 2.82-2.90 (m, 1H), 3.00-3.07 (m, 1H), 3.09 (d, J=9.1 Hz, 1H), 5.67 (td, J=8.8, 6.6 Hz, 1H), 7.14-7.21 (m, 1H), 7.32 (d, 2H).

Example 342

3-(1-Piperidin-4-yl-1H-pyrazol-4-yl)-7-(1-o-tolylethoxy)furo[3,2-c]pyridin-6-ylamine

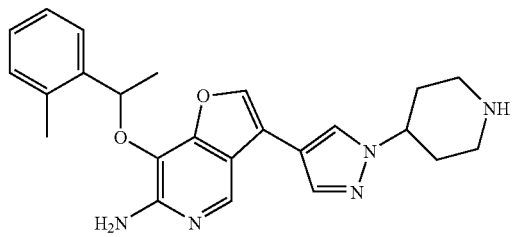

The title compound was prepared according to General Procedure AA. $^1$H NMR (400 MHz, CD$_3$OD): δ=1.66 (d, J=6.3 Hz, 3H), 1.91-2.03 (m, J=12.4, 12.3, 12.3, 4.0 Hz, 2H), 2.08-2.16 (m, 2H), 2.38 (s, 3H), 2.77 (td, J=12.6, 2.5 Hz, 2H), 3.16-3.23 (m, 2H), 4.28-4.41 (m, 1H), 6.26 (q, J=6.4 Hz, 1H), 7.06-7.18 (m, 3H), 7.57 (d, J=7.3 Hz, 1H), 7.77 (s, 1H), 7.80 (s, 1H), 8.07 (d, J=4.5 Hz, 2H). MS (ES$^+$): m/z 418.11 (100) [MH$^+$]. HPLC: t$_R$=2.36 min (ZQ3, polar_5 min).

Example 343

3-(1-Piperidin-4-yl-1H-pyrazol-4-yl)-7-(1-m-tolylethoxy)furo[3,2-c]pyridin-6-ylamine

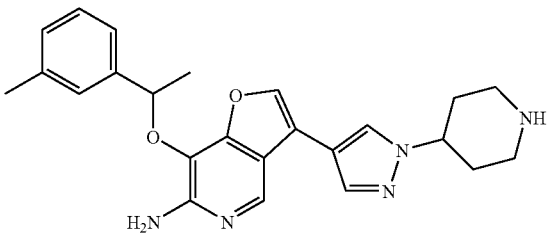

The title compound was prepared according to General Procedure AA. $^1$H NMR (400 MHz, CD$_3$OD): δ=1.68-1.74 (m, 3H), 1.94-2.08 (m, 2H), 2.15 (dd, J=12.5, 2.1 Hz, 2H), 2.30 (s, 3H), 2.81 (td, J=12.6, 2.5 Hz, 2H), 3.24 (d, J=12.9 Hz, 2H), 4.37 (tt, J=11.6, 3.9 Hz, 1H), 5.87 (q, J=6.3 Hz, 1H), 7.06 (d, J=7.6 Hz, 1H), 7.17 (t, J=7.6 Hz, 1H), 7.20-7.26 (m, 1H), 7.29 (s, 1H), 7.82 (s, 1H), 7.84 (s, 1H), 8.09 (s, 2H). MS (ES⁺): m/z 418.11 (100) [MH⁺]. HPLC: t_R=2.31 min (ZQ3, polar_5 min).

Example 344

3-(1-Piperidin-4-yl-1H-pyrazol-4-yl)-7-(1-p-tolylethoxy)furo[3,2-c]pyridin-6-ylamine

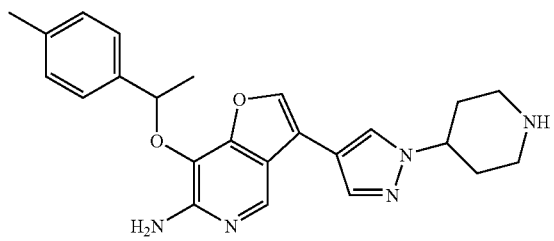

The title compound was prepared according to General Procedure AA. MS (ES⁺): m/z 418.12 (100) [MH⁺]. HPLC: t_R=2.41 min (ZQ3, polar_5 min).

Example 345

7-[1-(3-Methoxyphenyl)-ethoxy]-3-(1-piperidin-4-yl-1H-pyrazol-4-yl)furo[3,2-c]pyridin-6-ylamine

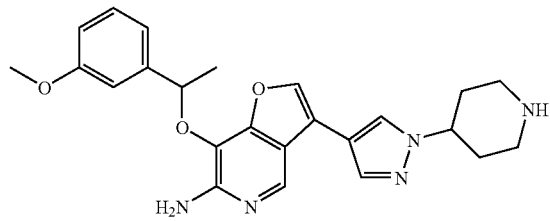

The title compound was prepared according to General Procedure AA. ¹H NMR (400 MHz, CD₃OD): δ=1.70 (d, J=6.3 Hz, 3H), 1.92-2.04 (m, 2H), 2.08-2.16 (m, 2H), 2.77 (td, J=12.7, 2.7 Hz, 2H), 3.20 (d, J=12.9 Hz, 2H), 3.75 (s, 3H), 4.29-4.39 (m, 1H), 5.88 (q, J=6.3 Hz, 1H), 6.77 (dd, J=8.3, 1.8 Hz, 1H), 6.98 (d, J=7.6 Hz, 1H), 7.02 (d, J=2.0 Hz, 1H), 7.16 (t, J=7.8 Hz, 1H), 7.80 (s, 1H), 7.81 (s, 1H), 8.07 (s, 1H), 8.07 (s, 1H). MS (ES⁺): m/z 434.07 (100) [MH⁺]. HPLC: t_R=2.25 min (ZQ3, polar_5 min).

Example 346

3-(1-Piperidin-4-yl-1H-pyrazol-4-yl)-7-[1-(2-trifluoromethyl-phenyl)ethoxy]furo[3,2-c]pyridin-6-ylamine

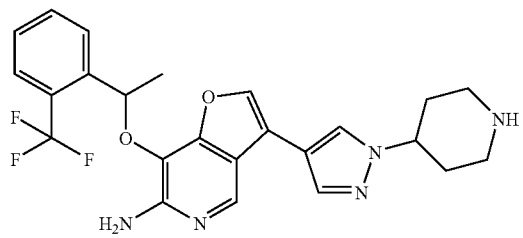

The title compound was prepared according to General Procedure AA. ¹H NMR (400 MHz, CD₃OD): δ=1.70 (d, J=6.3 Hz, 3H), 1.93-2.05 (m, 2H), 2.09-2.17 (m, 2H), 2.79 (td, J=12.7, 2.4 Hz, 2H), 3.22 (d, J=12.9 Hz, 2H), 4.30-4.41 (m, 1H), 6.26 (q, J=6.3 Hz, 1H), 7.44 (t, J=7.6 Hz, 1H), 7.62 (d, J=7.8 Hz, 1H), 7.68 (t, J=7.7 Hz, 1H), 7.76 (s, 1H), 7.82 (s, 1H), 8.08 (s, 1H), 8.11 (d, J=7.8 Hz, 1H), 8.13 (s, 1H). MS (ES⁺): m/z 472.07 (100) [MH⁺]. HPLC: t_R=2.45 min (ZQ3, polar_5 min).

Example 347

3-(1-Piperidin-4-yl-1H-pyrazol-4-yl)-7-[1-(3-trifluoromethyl-phenyl)ethoxy]furo[3,2-c]pyridin-6-ylamine

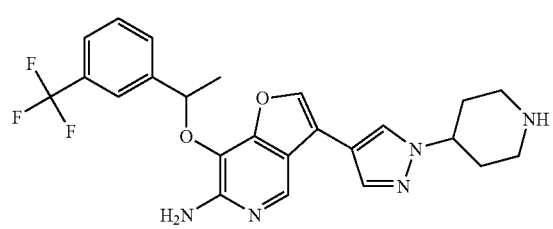

The title compound was prepared according to General Procedure AA. ¹H NMR (400 MHz, CD₃OD): δ=1.73 (d, J=6.3 Hz, 3H), 1.92-2.06 (m, 2H), 2.13 (dd, J=12.3, 2.1 Hz, 2H), 2.78 (td, J=12.6, 2.5 Hz, 2H), 3.17-3.25 (m, 2H), 4.28-4.40 (m, 1H), 5.97 (q, J=6.3 Hz, 1H), 7.45-7.50 (m, 1H), 7.51-7.57 (m, 1H), 7.72 (d, J=7.6 Hz, 1H), 7.78 (s, 1H), 7.79-7.83 (m, 2H), 8.07 (s, 1H), 8.10 (s, 1H). MS (ES⁺): m/z 472.09 (100) [MH⁺]. HPLC: t_R=2.44 min (ZQ3, polar_5 min).

Example 348

3-(1-Piperidin-4-yl-1H-pyrazol-4-yl)-7-[1-(4-trifluoromethyl-phenyl)ethoxy]furo[3,2-c]pyridin-6-ylamine

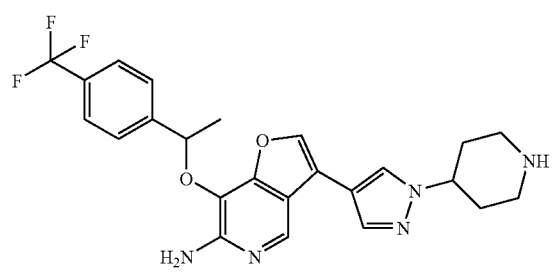

The title compound was prepared according to General Procedure AA. ¹H NMR (400 MHz, CD₃OD): δ=1.71 (d, J=6.3 Hz, 3H), 1.91-2.05 (m, 2H), 2.07-2.17 (m, 2H), 2.78 (td, J=12.6, 2.5 Hz, 2H), 3.21 (d, J=12.9 Hz, 2H), 4.35 (tt, J=11.6, 4.0 Hz, 1H), 5.97 (q, J=6.6 Hz, 1H), 7.59 (m, 2H), 7.67 (m, 2H), 7.78 (s, 1H), 7.81 (s, 1H), 8.06-8.09 (m, 1H), 8.11 (s, 1H). MS (ES⁺): m/z 472.10 (100) [MH⁺]. HPLC: t_R=2.42 min (ZQ3, polar_5 min).

Example 349

3-(1-Piperidin-4-yl-1H-pyrazol-4-yl)-7-[1-(2,3,6-trichlorophenyl)-ethoxy]furo[3,2-c]pyridin-6-ylamine

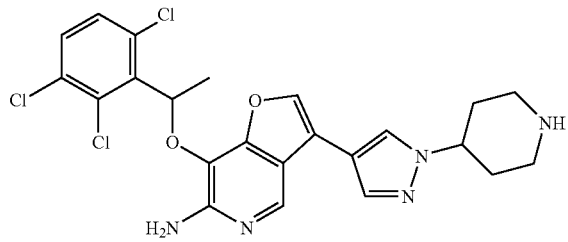

The title compound was prepared according to General Procedure AA. ¹H NMR (400 MHz, CD₃OD): δ=1.90 (d, J=6.8 Hz, 3H), 2.25-2.40 (m, 4H), 3.16-3.27 (m, 2H), 3.54-3.62 (m, 2H), 4.60 (dt, J=10.0, 5.0 Hz, 1H), 6.59 (q, J=6.7 Hz, 1H), 7.34-7.42 (m, 1H), 7.49 (d, J=8.6 Hz, 1H), 7.79 (s, 1H), 7.89 (s, 1H), 8.12 (s, 1H), 8.15 (s, 1H). MS (ES⁺): m/z 507.88 (100) [MH⁺]. HPLC: $t_R$=2.53 min (ZQ3, polar_5 min).

1-(2,3,6-Trichlorophenyl)ethanol

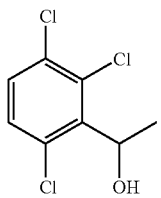

General Procedure CC: To a solution of 2,3,6-trichlorobenzaldehyde (1.00 g, 4.77 mmol) in THF (10 mL) was added MeMgBr/butyl ether (1M, 5.72 mL, 5.72 mmol) at 0° C. under nitrogen, the resulting mixture was allowed to warm to rt and stirred overnight. The mixture was quenched with sat. aq. NH₄Cl (15 mL) at 0° C., then diluted with Et₂O (15 mL), the organic phase was washed with brine (20 mL), and dried over anhydrous sodium sulfate. The solvent was evaporated under reduced pressure. The material was purified by silica gel chromatography using Hexane/EtOAc (80:20) as eluent to give the desired product as a colorless oil. ¹H NMR (CDCl₃, 400 MHz): δ=1.69 (d, J=6.8 Hz, 3H), 2.97 (br. s., 1H), 5.67 (q, J=6.8 Hz, 1H), 7.30 (d, J=3.0 Hz, 1H), 7.35-7.38 (m, 1H).

Example 350

7-[1-(2,6-Dichlorophenyl)propoxy]-3-(1-piperidin-4-yl-1H-pyrazol-4-yl)furo[3,2-c]pyridin-6-ylamine

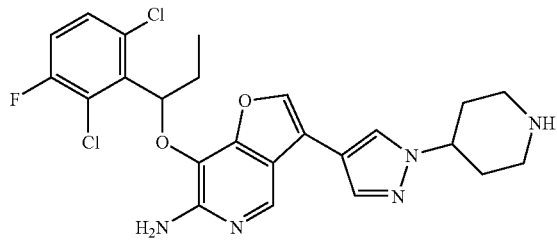

The title compound was prepared according to General Procedure AA. ¹H NMR (400 MHz, CD₃OD): δ=1.08 (t, J=7.6 Hz, 3H), 2.26-2.38 (m, 5H), 2.43-2.57 (m, 1H), 3.17-3.27 (m, 2H), 3.53-3.63 (m, 2H), 4.60 (dt, J=9.9, 4.9 Hz, 1H), 6.38 (t, J=7.5 Hz, 1H), 7.22 (t, J=8.7 Hz, 1H), 7.40 (dd, J=8.8, 4.8 Hz, 1H), 7.82 (s, 1H), 7.89 (s, 1H), 8.12 (s, 1H), 8.14 (s, 1H). MS (ES⁺): m/z 503.93/505.92 (100/73) [MH⁺]. HPLC: $t_R$=2.64 min (ZQ3, polar_5 min).

1-(2,6-Dichloro-3-fluorophenyl)propan-1-ol

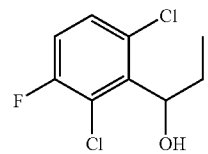

The title compound was prepared according to General Procedure CC. ¹H NMR (CDCl₃, 400 MHz): δ=1.01 (t, J=7.5 Hz, 3H), 1.92-2.16 (m, 2H), 2.79 (d, J=10.4 Hz, 1H), 5.30-5.37 (m, 1H), 7.02-7.07 (m, 1H), 7.27-7.30 (m, 1H).

Example 351

7-[1-(2-Chloro-3-fluorophenyl)ethoxy]-3-(1-piperidin-4-yl-1H-pyrazol-4-yl)-furo[3,2-c]pyridin-6-ylamine

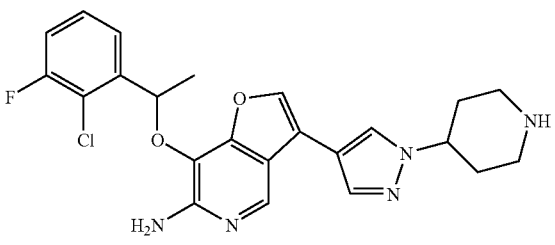

The title compound was prepared according to General Procedure AA. ¹H NMR (400 MHz, CD₃OD): δ=1.71 (d, J=6.3 Hz, 3H), 2.28-2.38 (m, 4H), 3.18-3.26 (m, 2H), 3.58 (ddd, J=12.9, 3.3, 3.2 Hz, 2H), 4.59 (tt, J=9.9, 5.0 Hz, 1H), 6.41 (q, J=6.3 Hz, 1H), 7.10-7.16 (m, 1H), 7.32 (td, J=8.1, 5.3 Hz, 1H), 7.55 (d, J=7.8 Hz, 1H), 7.75-7.78 (m, 1H), 7.86 (s, 1H), 8.07-8.11 (m, 2H). MS (ES⁺): m/z 455.99/457.97 (100/41) [MH⁺]. HPLC: $t_R$=2.46 min (ZQ3, polar_5 min).

Example 352

3-(1-Piperidin-4-yl-1H-pyrazol-4-yl)-7-[1-(3-trifluoromethoxy-phenyl)ethoxy]furo[3,2-c]pyridin-6-ylamine

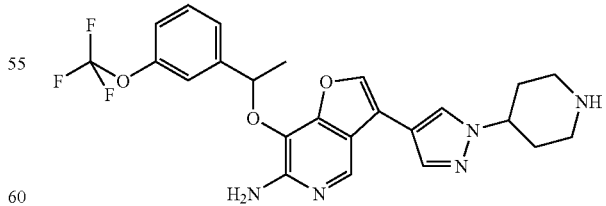

The title compound was prepared according to General Procedure AA. ¹H NMR (400 MHz, CD₃OD): δ=1.72 (d, J=6.6 Hz, 3H), 2.23-2.41 (m, 4H), 3.15-3.27 (m, 2H), 3.51-3.63 (m, 2H), 4.58 (dq, J=10.0, 4.9 Hz, 1H), 5.93 (q, J=6.6 Hz, 1H), 7.13 (dt, J=8.1, 1.1 Hz, 1H), 7.37 (t, J=8.0 Hz, 1H), 7.40

(s, 1H), 7.42-7.46 (m, 1H), 7.79 (s, 1H), 7.86 (s, 1H), 8.08 (s, 2H). MS (ES+): m/z 488.03 (100) [MH+]. HPLC: $t_R$=2.49 min (ZQ3, polar_5 min).

1-(3-Trifluoromethoxyphenyl)ethanol

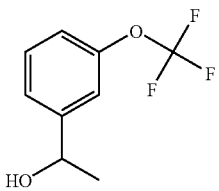

To a solution of 1-(3-Trifluoromethoxyphenyl)ethanone (1.00 g, 4.90 mmol) in THF (5 mL) at 0° C. was added 1M LiAlH₄ in THF (5.9 mL, 5.9 mmol), and the solution was allowed to warm to rt. A few drops of water were added to quench. The mixture was concentrated in vacuo, transferred to a separatory funnel, and extracted using DCM and sat. aq. Rochelle salt. The organic layer was concentrated in vacuo to afford the title compound as a clear oil.

Example 353

7-[1-(2,6-Dichloro-3-fluorophenyl)but-3-ynyloxy]-3-(1-piperidin-4-yl-1H-pyrazol-4-yl)furo[3,2-c]pyridin-6-ylamine

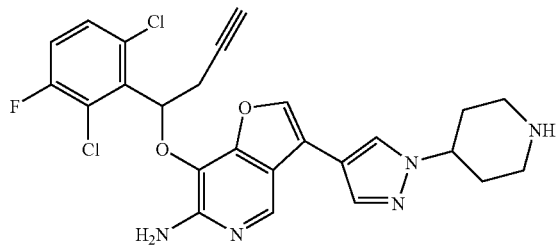

The title compound was prepared according to General Procedure AA. ¹H NMR (400 MHz, CD₃OD): δ=2.27-2.39 (m, 5H), 3.17-3.28 (m, 2H), 3.34-3.40 (m, 2H), 3.53-3.63 (m, 2H), 4.60 (dt, J=10.1, 5.1 Hz, 1H), 6.46 (t, J=7.7 Hz, 1H), 7.22-7.30 (m, 1H), 7.42 (dd, J=8.8, 4.8 Hz, 1H), 7.76 (s, 1H), 7.88 (s, 1H), 8.11 (s, 1H), 8.18 (s, 1H). MS (ES+): m/z 513.96/515.98 (100/71) [MH+]. HPLC: $t_R$=2.52 min (ZQ3, polar_5 min).

1-(2,6-Dichloro-3-fluorophenyl)but-3-yn-1-ol

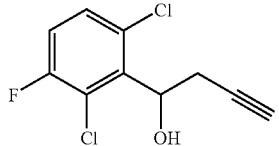

The title compound was prepared according to General Procedure BB. ¹H NMR (CDCl₃, 400 MHz): δ=2.04 (t, J=2.7 Hz, 1H), 2.84-2.92 (m, 1H), 2.99-3.08 (m, 2H), 5.66 (td, J=8.5, 6.8 Hz, 1H), 7.06-7.11 (m, 1H), 7.31 (dd, J=8.8, 4.8 Hz, 1H).

Example 354

3-(1-Piperidin-4-yl-1H-pyrazol-4-yl)-7-[1-(2-trifluoromethoxy-phenyl)ethoxy]furo[3,2-c]pyridin-6-ylamine

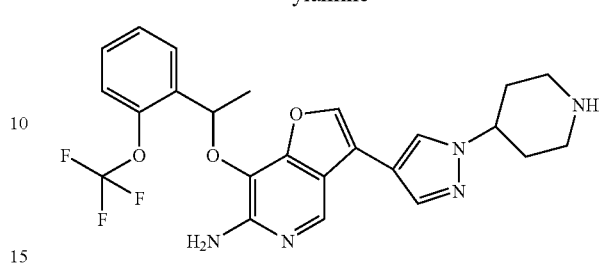

The title compound was prepared according to General Procedure AA. ¹H NMR (400 MHz, CD₃OD): δ=1.70 (d, J=6.6 Hz, 3H), 2.24-2.41 (m, 4H), 3.17-3.26 (m, 2H), 3.52-3.62 (m, 2H), 4.54-4.65 (m, 1H), 6.31 (q, J=6.6 Hz, 1H), 7.18-7.25 (m, 1H), 7.31-7.39 (m, 2H), 7.77 (s, 1H), 7.81-7.85 (m, 1H), 7.87 (s, 1H), 8.09 (d, J=2.8 Hz, 2H). MS (ES+): m/z 488.08 (100) [MH+]. HPLC: $t_R$=2.47 min (ZQ3, polar_5 min).

1-(2-Trifluoromethoxyphenyl)ethanol

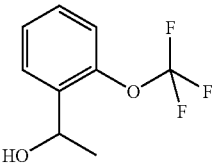

To a solution of 1-(2-Trifluoromethoxyphenyl)ethanone (1.00 g, 4.90 mmol) in THF (5 mL) at 0° C. was added 1M LiAlH₄ in THF (5.9 mL, 5.9 mmol), and the solution was allowed to warm to rt. A few drops of water were added to quench. The mixture was concentrated in vacuo, transferred to a separatory funnel, and extracted using DCM and sat. aq. Rochelle salt. The organic layer was concentrated in vacuo to afford the title compound as a clear oil.

Example 355

3-(1-Piperidin-4-yl-1H-pyrazol-4-yl)-7-[1-(4-trifluoromethoxy-phenyl)ethoxy]furo[3,2-c]pyridin-6-ylamine

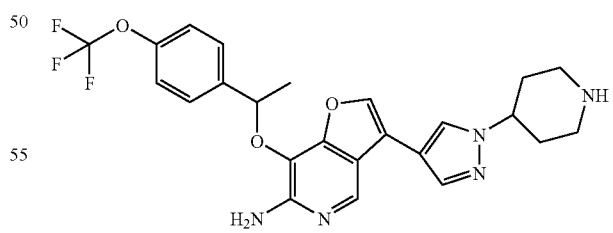

The title compound was prepared according to General Procedure AA. ¹H NMR (400 MHz, CD₃OD): δ=1.65-1.74 (m, 3H), 2.25-2.39 (m, 4H), 3.15-3.27 (m, 2H), 3.52-3.62 (m, 2H), 4.52-4.64 (m, J=9.9, 5.2, 5.0, 5.0 Hz, 1H), 5.92 (q, J=6.6 Hz, 1H), 7.18 (s, 1H), 7.20 (s, 1H), 7.55 (s, 1H), 7.56-7.59 (m, 1H), 7.80 (s, 1H), 7.87 (s, 1H), 8.09 (s, 2H). MS (ES+): m/z 488.06 (100) [MH+]. HPLC: $t_R$=2.44 min (ZQ3, polar_5 min).

1-(4-Trifluoromethoxyphenyl)ethanol

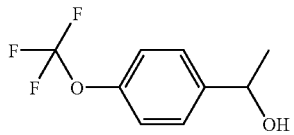

To a solution of 1-(4-Trifluoromethoxyphenyl)ethanone (1.00 g, 4.90 mmol) in THF (5 mL) at 0° C. was added IM LiAlH$_4$ in THF (5.9 mL, 5.9 mmol), and the solution was allowed to warm to rt. A few drops of water were added to quench. The mixture was concentrated in vacuo, transferred to a separatory funnel, and extracted using DCM and sat. aq. Rochelle salt. The organic layer was concentrated in vacuo to afford the title compound as a clear oil.

Example 356

7-[(E)-3-(2,6-Dichloro-3-fluorophenyl)allyloxy]-3-(1-piperidin-4-yl-1H-pyrazol-4-yl)furo[3,2-c]pyridin-6-ylamine

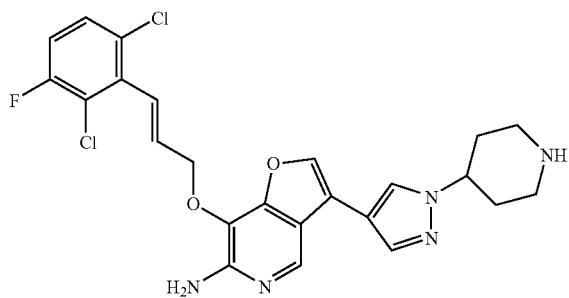

The title compound was prepared according to General Procedure AA, using 1-(2,6-dichloro-3-fluorophenyl)prop-2-en-1-ol. $^1$H NMR (400 MHz, CD$_3$OD): δ=2.29-2.41 (m, 4H), 3.19-3.28 (m, 2H), 3.55-3.62 (m, 2H), 4.57-4.65 (m, J=10.0, 5.3, 5.1 Hz, 1H), 5.17 (dd, J=5.9, 1.4 Hz, 2H), 6.35-6.50 (m, 1H), 6.65 (d, J=16.2 Hz, 1H), 7.14 (t, J=8.7 Hz, 1H), 7.36 (dd, J=9.0, 4.9 Hz, 1H), 7.87 (s, 1H), 7.91 (s, 1H), 8.14 (s, 1H), 8.17 (s, 1H). MS (ES$^+$): m/z 501.94/503.92 (100/75) [MH$^+$]. HPLC: t$_R$=2.63 min (ZQ3, polar_5 min).

1-(2,6-Dichloro-3-fluorophenyl)prop-2-en-1-ol (6233-34)

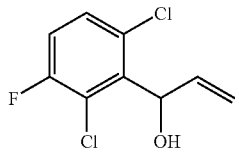

The title compound was prepared according to General Procedure CC. $^1$H NMR (CDCl$_3$, 400 MHz): δ=3.07 (d, J=8.3 Hz, 1H), 5.26-5.37 (m, 2H), 5.96-6.04 (m, 1H), 6.23 (ddd, J=17.3, 10.5, 5.1 Hz, 1H), 7.06-7.11 (m, 1H), 7.27-7.34 (m, 1H).

Example 357

7-[1-(2,6-Dichloro-3-fluorophenyl)butoxy]-3-(1-piperidin-4-yl-1H-pyrazol-4-yl)furo[3,2-c]pyridin-6-ylamine

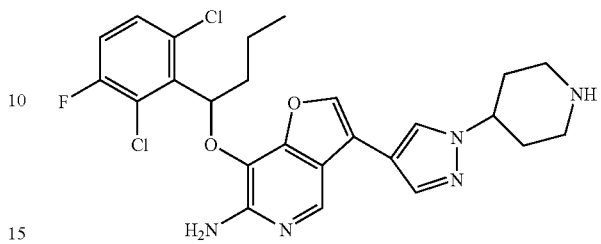

The title compound was prepared according to General Procedure AA. $^1$H NMR (400 MHz, CD$_3$OD): δ=1.03 (t, J=7.5 Hz, 3H), 1.36-1.49 (m, 1H), 1.56-1.69 (m, 1H), 2.15-2.38 (m, 5H), 2.42-2.53 (m, 1H), 3.17-3.26 (m, 2H), 3.57 (ddd, J=13.1, 3.3, 3.0 Hz, 2H), 4.59 (dt, J=10.0, 5.0 Hz, 1H), 6.45 (t, J=7.3 Hz, 1H), 7.17-7.23 (m, 1H), 7.38 (dd, J=9.0, 4.9 Hz, 1H), 7.80 (s, 1H), 7.87 (s, 1H), 8.10 (s, 1H), 8.11-8.13 (m, 1H). MS (ES$^+$): m/z 518.02/520.03 (100/71) [MH$^+$]. HPLC: t$_R$=2.64 min (ZQ2, polar_5 min).

1-(2,6-Dichloro-3-fluorophenyl)butan-1-ol

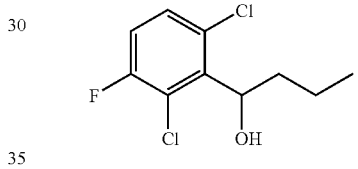

The title compound was prepared according to General Procedure CC. $^1$H NMR (CDCl$_3$, 400 MHz): δ=0.99 (t, J=7.3 Hz, 3H), 1.28-1.41 (m, 1H), 1.55-1.66 (m, 1H), 1.84-1.91 (m, 1H), 2.09 (dddd, J=18.6, 8.7, 5.1, 4.8 Hz, 1H), 2.75 (d, J=10.1 Hz, 1H), 5.42 (ddd, J=10.0, 8.7, 6.1 Hz, 1H), 7.03 (dd, J=9.0, 8.0 Hz, 1H), 7.27 (t, 1H).

Example 358

7-[1-(2,6-Dichloro-3-fluorophenyl)but-3-enyloxy]-3-(1-piperidin-4-yl-1H-pyrazol-4-yl)furo[3,2-c]pyridin-6-ylamine

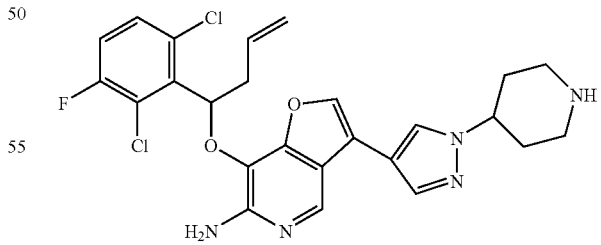

The title compound was prepared according to General Procedure AA. $^1$H NMR (400 MHz, CD$_3$OD): δ=2.25-2.41 (m, 4H), 3.10 (ddd, J=14.2, 7.6, 7.3 Hz, 1H), 3.17-3.27 (m, 3H), 3.58 (d, J=12.9 Hz, 2H), 4.60 (m, J=9.8, 9.8, 5.1, 4.9 Hz, 1H), 5.08 (d, J=10.1 Hz, 1H), 5.18 (d, J=17.2 Hz, 1H), 5.81-5.95 (m, 1H), 6.44 (t, J=7.5 Hz, 1H), 7.22 (t, J=8.6 Hz, 1H), 7.39 (dd, J=8.8, 4.8 Hz, 1H), 7.78 (s, 1H), 7.88 (s, 1H), 8.11

(s, 1H), 8.15 (s, 1H). MS (ES+): m/z 515.93/517.94 (100/74) [MH+]. HPLC: $t_R$=2.57 min (ZQ3, polar__5 min).

1-(2,6-Dichloro-3-fluorophenyl)but-3-en-1-ol

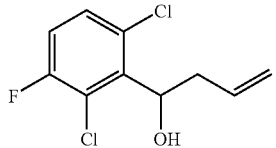

The title compound was prepared according to General Procedure CC. $^1$H NMR (CDCl$_3$, 400 MHz): δ=2.66-2.74 (m, 1H), 2.82 (d, J=9.3 Hz, 1H), 2.84-2.92 (m, 1H), 5.10-5.19 (m, 2H), 5.49 (td, J=9.0, 6.4 Hz, 1H), 5.84 (m, J=17.2, 10.1, 7.1, 7.1 Hz, 1H), 7.05 (dd, J=9.0, 8.0 Hz, 1H), 7.27-7.31 (m, 1H).

Example 359

7-[1-(2-Chloro-6-methoxyphenyl)ethoxy]-3-(1-piperidin-4-yl-1H-pyrazol-4-yl)furo[3,2-c]pyridin-6-ylamine

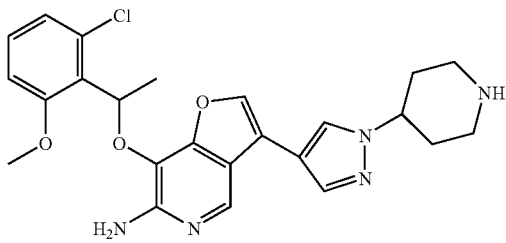

The title compound was prepared according to General Procedure AA. $^1$H NMR (400 MHz, CD$_3$OD): δ=1.81 (d, J=6.6 Hz, 3H), 2.01-2.11 (m, 2H), 2.14-2.21 (m, 2H), 2.86 (td, J=12.5, 2.5 Hz, 2H), 3.21-3.28 (m, 2H), 3.90 (s, 3H), 4.34-4.44 (m, 1H), 6.52 (q, J=6.6 Hz, 1H), 6.89 (dd, J=8.1, 1.0 Hz, 1H), 6.95 (d, J=8.3 Hz, 1H), 7.18 (t, J=8.2 Hz, 1H), 7.81 (s, 1H), 7.83 (s, 1H), 8.07 (s, 1H), 8.09 (s, 1H). MS (ES+): m/z 468.04/470.02 (100/39) [MH+]. HPLC: $t_R$=2.37 min (ZQ3, polar__5 min).

1-(2-Chloro-6-methoxyphenyl)ethanol

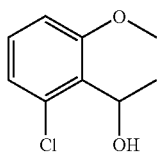

The title compound was prepared according to General Procedure CC. $^1$H NMR (CDCl$_3$, 400 MHz): δ=1.55 (d, J=6.8 Hz, 3H), 3.82 (d, J=11.6 Hz, 1H), 3.92 (s, 3H), 5.37 (m, J=11.6, 6.8, 6.7, 6.7 Hz, 1H), 6.84 (d, J=8.3 Hz, 1H), 6.99 (dd, J=8.1, 1.0 Hz, 1H), 7.12-7.17 (m, 1H).

Example 360

7-[1-(2,4-Dichloro-6-methoxyphenyl)ethoxy]-3-(1-piperidin-4-yl-1H-pyrazol-4-yl)furo[3,2-c]pyridin-6-ylamine

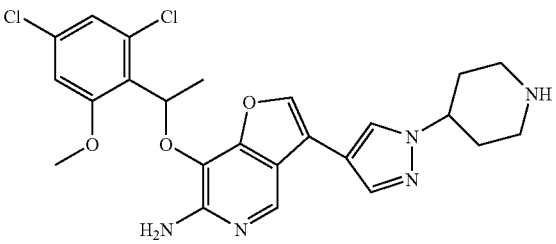

The title compound was prepared according to General Procedure AA. $^1$H NMR (400 MHz, CD$_3$OD): δ=1.81 (d, J=6.8 Hz, 3H), 2.23-2.39 (m, 4H), 3.17-3.27 (m, 2H), 3.52-3.62 (m, 2H), 3.92 (s, 3H), 4.60 (ddd, J=10.0, 5.2, 5.1 Hz, 1H), 6.45 (q, J=6.6 Hz, 1H), 6.95 (d, J=1.8 Hz, 1H), 7.01 (s, 1H), 7.79-7.84 (m, 1H), 7.88 (s, 1H), 8.10 (s, 2H). MS (ES+): m/z 502.02/504.04 (100/75) [MH+]. HPLC: $t_R$=2.59 min (ZQ3, polar__5 min).

1-(2,4-Dichloro-6-methoxyphenyl)ethanol

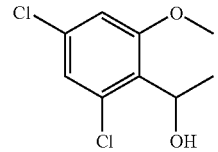

The title compound was prepared according to General Procedure CC. $^1$H NMR (CDCl$_3$, 400 MHz): δ=1.52 (d, 3H), 3.92 (s, 3H), 5.32 (dq, J=11.7, 6.7 Hz, 1H), 6.83 (d, J=1.8 Hz, 1H), 7.02 (d, J=2.0 Hz, 1H).

Example 361

7-[1-(2-Bromo-6-chlorophenyl)ethoxy]-3-(1-piperidin-4-yl-1H-pyrazol-4-yl)furo[3,2-c]pyridin-6-ylamine

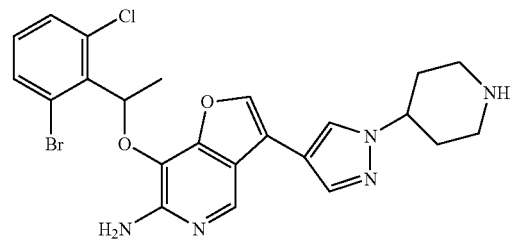

The title compound was prepared according to General Procedure AA. $^1$H NMR (400 MHz, CD$_3$OD): δ=1.86 (d, J=6.8 Hz, 3H), 1.94-2.05 (m, 2H), 2.08-2.16 (m, 2H), 2.78 (td, J=12.6, 2.5 Hz, 2H), 3.21 (d, J=12.9 Hz, 2H), 4.28-4.39 (m, 1H), 6.56 (q, J=6.7 Hz, 1H), 7.15 (t, J=8.1 Hz, 1H), 7.42 (d, J=8.1 Hz, 1H), 7.55 (d, J=8.1 Hz, 1H), 7.77 (s, 1H), 7.82 (s, 1H), 8.07 (s, 1H), 8.14 (s, 1H). MS (ES+): m/z 517.91/519.92 [MH+]. HPLC: $t_R$=2.49 min (ZQ3, polar__5 min).

1-(2-Bromo-6-chlorophenyl)ethanol

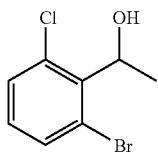

To a solution of LDA (6 mL, 12 mmol) in THF (10 mL) was added 3-chlorobromobenzene (1.91 g, 9.98 mmol) in THF (5 mL) at −78° C. under nitrogen, the resulting mixture was stirred at −78° C. for 1 h, then a solution of acetaldehyde (0.66 g, 15 mmol) in THF (5 mL) was added. The mixture was slowly warmed to rt. The mixture was quenched with water (10 mL), and diluted with EtOAc (50 mL). The organic phase was separated, washed with brine (10 mL), and dried over anhydrous sodium sulfate. The crude material was purified by silica gel chromatography (Hex:EtOAc=95:5→90:10) to give the title compound as a colorless oil. $^1$H NMR (CDCl$_3$): δ=1.64 (d, J=6.8 Hz, 3H), 2.98 (d, J=10.4 Hz, 1H, —OH), 5.58 (m, 1H), 7.04 (t, J=8.1 Hz, 1H), 7.31 (dd, J=8.1, 1.2 Hz, 1H), 7.49 (dd, J=8.1, 1.0 Hz, 1H).

Example 362

7-[1-(2,4-Dimethylpyridin-3-yl)ethoxy]-3-(1-piperidin-4-yl-1H-pyrazol-4-yl)furo[3,2-c]pyridin-6-ylamine

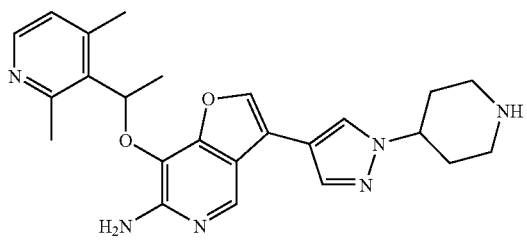

The title compound was prepared according to General Procedure AA. $^1$H NMR (400 MHz, CD$_3$OD): δ=1.80 (d, J=6.6 Hz, 3H), 2.24-2.40 (m, 4H), 2.56 (s, 3H), 2.71 (s, 3H), 3.16-3.26 (m, 2H), 3.50-3.63 (m, 2H), 4.59 (ddd, J=10.0, 5.2, 5.1 Hz, 1H), 6.11 (q, J=6.7 Hz, 1H), 7.07 (d, J=5.3 Hz, 1H), 7.71 (s, 1H), 7.85 (s, 1H), 8.08 (s, 1H), 8.11-8.16 (m, 2H). MS (ES$^+$): m/z 433.17 (100) [MH$^+$]. HPLC: t$_R$=1.74 min (ZQ3, polar_5 min).

1-(2,4-Dimethylpyridin-3-yl)ethanol

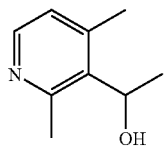

The title compound was prepared according to General Procedure CC. $^1$H NMR (CDCl$_3$, 400 MHz): δ=1.56 (s, 3H), 1.74 (br. s., 1H), 2.47 (s, 3H), 2.66 (s, 3H), 5.40 (q, J=6.7 Hz, 2H), 6.92 (d, J=4.8 Hz, 1H), 8.24 (d, J=5.1 Hz, 1H).

Example 363

7-[1-(2,6-Dichlorophenyl)-3-methylbut-3-enyloxy]-3-(1-piperidin-4-yl-1H-pyrazol-4-yl)furo[3,2-c]pyridin-6-ylamine

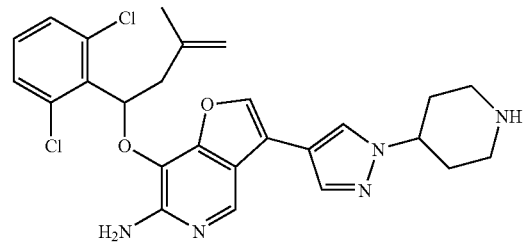

The title compound was prepared according to General Procedure AA. $^1$H NMR (400 MHz, CD$_3$OD): δ=1.85 (s, 3H), 2.24-2.39 (m, 4H), 3.02 (dd, J=13.8, 6.9 Hz, 1H), 3.15-3.27 (m, 3H), 3.53-3.61 (m, 2H), 4.60 (m, J=9.9, 9.9, 5.3, 5.1 Hz, 1H), 4.82 (br. s., 2H), 6.59 (t, J=7.2 Hz, 1H), 7.20-7.26 (m, 1H), 7.35 (br. s., 2H), 7.75-7.80 (m, 1H), 7.87 (s, 1H), 8.10 (s, 1H), 8.11-8.16 (m, 1H). MS (ES$^+$): m/z 512.03 (100) [MH$^+$]. HPLC: t$_R$=2.67 min (ZQ3, polar_5 min).

1-(2,6-Dichlorophenyl)-3-methylbut-3-en-1-ol

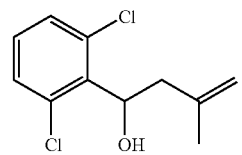

The title compound was prepared according to General Procedure CC. $^1$H NMR (CDCl$_3$, 400 MHz): δ=1.87 (s, 3H), 2.55 (dd, J=13.8, 5.2 Hz, 1H), 2.77 (d, J=9.3 Hz, 1H), 2.84 (ddd, J=13.9, 9.9, 0.8 Hz, 1H), 4.84 (d, J=1.0 Hz, 1H), 4.88-4.91 (m, 1H), 5.60 (td, J=9.5, 5.1 Hz, 1H), 7.14 (dd, J=8.6, 7.6 Hz, 1H), 7.30 (s, 1H), 7.32 (s, 1H).

Example 364

3-(1-Piperidin-4-yl-1H-pyrazol-4-yl)-7-[1-(2,4,6-trichlorophenyl)-ethoxy]furo[3,2-c]pyridin-6-ylamine

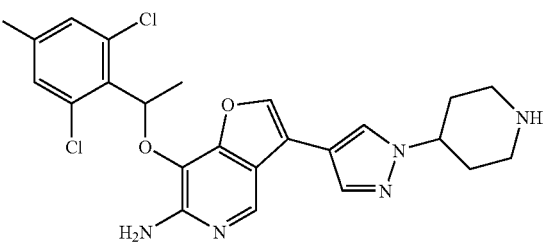

The title compound was prepared according to General Procedure AA. $^1$H NMR (400 MHz, CD$_3$OD): δ=1.87 (d, J=6.8 Hz, 3H), 2.26-2.40 (m, 4H), 3.17-3.26 (m, 2H), 3.58 (ddd, J=13.2, 3.3, 3.2 Hz, 2H), 4.59 (m, J=9.9, 9.9, 5.1, 4.9 Hz, 1H), 6.51 (q, J=6.7 Hz, 1H), 7.46 (s, 2H), 7.79 (s, 1H), 7.87 (s, 1H), 8.10 (s, 1H), 8.14 (s, 1H). MS (ES$^+$): m/z 505.97 (100) [MH$^+$]. HPLC: t$_R$=2.55 min (ZQ3, polar_5 min).

1-(2,4,6-Trichlorophenyl)ethanol

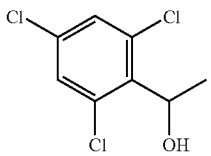

To a solution of LDA (3 mL, 6 mmol) in THF (5 mL) was added 1,3,5-trichlorobenzene (0.91 g, 5.0 mmol) in THF (3 mL) at −78° C. under nitrogen, the resulting mixture was stirred at −78° C. for 1 h, then a solution of acetaldehyde (0.33 g, 7.5 mmol) in THF (3 mL) was added. The mixture was slowly warmed to rt. The mixture was quenched with water (10 mL), and diluted with EtOAc (50 mL). The organic phase was separated, washed with brine (10 mL), and dried over anhydrous sodium sulfate. The crude material was purified by silica gel chromatography (Hex:EtOAc=95:5→90:10) to give the title compound as a colorless oil. $^1$H NMR (CDCl$_3$): δ 1.62 (d, J=6.8 Hz, 3H), 2.76 (d, J=9.9 Hz, 1H, —OH), 5.55 (m, 1H), 7.32 (s, 2H).

Example 365

7-[1-(2-Chloro-6-trifluoromethylphenyl)ethoxy]-3-(1-piperidin-4-yl-1H-pyrazol-4-yl)furo[3,2-c]pyridin-6-ylamine

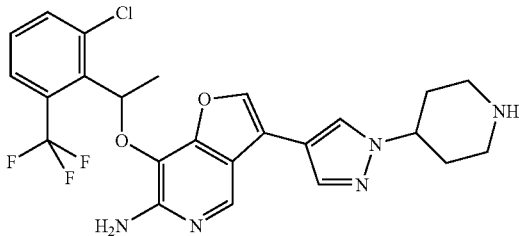

The title compound was prepared according to General Procedure AA. $^1$H NMR (400 MHz, CD$_3$OD): δ=1.91 (d, J=6.6 Hz, 3H), 2.28-2.41 (m, 4H), 3.17-3.28 (m, 2H), 3.52-3.64 (m, 2H), 4.60 (dq, J=9.8, 4.9 Hz, 1H), 6.22 (q, J=6.6 Hz, 1H), 7.50 (t, J=8.0 Hz, 1H), 7.67 (d, J=8.1 Hz, 1H), 7.77-7.82 (m, 2H), 7.89 (s, 1H), 8.12 (s, 1H), 8.18 (s, 1H). MS (ES$^+$): m/z 505.97/507.99 (100/41) [MH$^+$]. HPLC: t$_R$=2.50 min (ZQ3, polar_5 min).

1-[2-Chloro-6-(trifluoromethyl)phenyl]ethanol

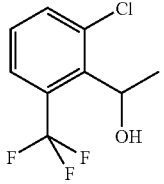

To a solution of 2-chloro-6-(trifluoromethyl)benzaldehyde (266.9 mg, 1.280 mmol, 1 eq) in anhydrous THF (5 mL) at 0° C. under nitrogen, a 3.0 M solution of methylmagnesium bromide in Et$_2$O (0.50 mL, 1.5 mmol, 1.2 eq) was added and the reaction was allowed to stir and warm to ambient temperature overnight. The reaction mixture was again cooled to 0° C. and saturated NH$_4$Cl was added. Diethyl ether was also added and the layers were separated. The combined organic layers were washed with brine, dried over anhydrous Na$_2$SO$_4$, filtered, and concentrated in vacuo. The colorless oil crude was purified by chromatography on silica gel [0.5"×10" glass column, eluting with 1:1 CH$_2$Cl$_2$:Heptane]. Fractions containing product were combined and concentrated in vacuo, affording the title material as a clear and colorless oil. $^1$H NMR (400 MHz, CDCl$_3$) δ=1.73 (d, J=6.8 Hz, 3H), 3.04 (br s, 1H), 5.43 (q, J=6.8 Hz, 1H), 7.33 (ddq, J=8.0, 8.0, 0.8 Hz, 1H), 7.59 (d, J=7.8 Hz, 1H), 7.63 (d, J=7.8 Hz, 1H). MS (ES$^+$): m/z 248.01/250.03 (100/37) [MNa$^+$]. HPLC: t$_R$=3.26 min (ZQ3, polar_5 min).

Example 366

7-[1-(2,6-Dichloro-3-fluorophenyl)-3-methylbutoxy]-3-(1-piperidin-4-yl-1H-pyrazol-4-yl)furo[3,2-c]pyridin-6-ylamine

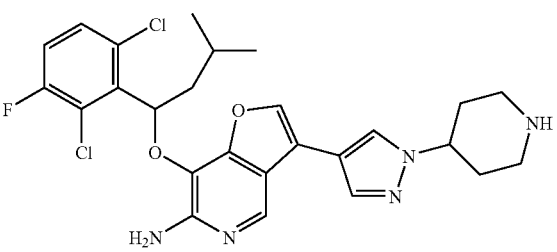

The title compound was prepared according to General Procedure AA. $^1$H NMR (400 MHz, CD$_3$OD): δ=1.07 (d, J=6.6 Hz, 3H), 1.05 (d, J=6.8 Hz, 3H), 1.90 (dt, J=13.4, 6.7 Hz, 1H), 1.95-2.03 (m, 1H), 2.28-2.40 (m, 4H), 2.51 (ddd, J=14.0, 8.3, 5.8 Hz, 1H), 3.16-3.27 (m, 2H), 3.53-3.61 (m, 2H), 4.60 (tt, J=10.0, 4.9 Hz, 1H), 6.55 (t, J=6.6 Hz, 1H), 7.20 (t, J=8.6 Hz, 1H), 7.37 (br. s., 1H), 7.82 (s, 1H), 7.88 (s, 1H), 8.11 (s, 1H), 8.12 (s, 1H). MS (ES$^+$): m/z 531.97/533.99 (100/74) [MH$^+$]. HPLC: t$_R$=2.66 min (ZQ3, polar_5 min).

1-(2,6-Dichloro-3-fluorophenyl)-3-methylbutan-1-ol

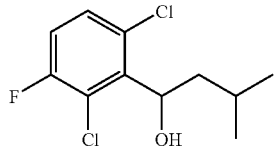

To a solution of 1-(2,6-dichloro-3-fluorophenyl)-3-methylbut-3-en-1-ol (0.95 mmol) in EtOAc (5.0 mL) was added palladium 10% wt on activated carbon (30 mg). The flask was evacuated and purged with hydrogen gas (3×) and allowed to stir under hydrogen for 2.5 h. The reaction mixture was filtered through a pad of celite. The filtrate was concentrated under reduced pressure to give a light yellow oil. The material was purified by silica gel chromatography using Hexane/EtOAc (80:20) as eluent to obtain the desired product as a colorless oil. $^1$H NMR (CDCl$_3$, 400 MHz): δ=1.02 (dd, J=6.6, 4.5 Hz, 6H), 1.58 (ddd, J=13.9, 8.8, 4.5 Hz, 1H), 2.05-2.13 (m, 1H), 2.71 (d, J=10.1 Hz, 1H), 5.49 (td, J=10.0, 4.8 Hz, 1H), 7.03 (dd, J=8.8, 7.8 Hz, 1H), 7.27-7.29 (m, 1H).

1-(2,6-Dichloro-3-fluorophenyl)-3-methylbut-3-en-1-ol

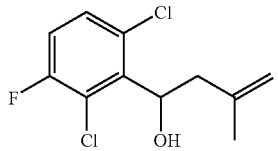

The title compound was prepared according to General Procedure CC. $^1$H NMR (CDCl$_3$, 400 MHz): δ=1.87 (s, 3H), 2.55 (dd, J=13.8, 5.2 Hz, 1H), 2.72 (d, J=8.8 Hz, 1H), 2.84 (ddd, J=13.9, 9.6, 0.8 Hz, 1H), 4.85 (d, J=1.0 Hz, 1H), 4.91 (t, J=1.5 Hz, 1H), 5.58 (td, J=9.2, 5.2 Hz, 1H), 7.04 (dd, J=8.8, 7.8 Hz, 1H), 7.27-7.30 (m, 1H).

Example 367

7-[(2-Chloro-3,6-difluorophenyl)cyclopropylmethoxy]-3-(1-piperidin-4-yl-1H-pyrazol-4-yl)furo[3,2-c]pyridin-6-ylamine

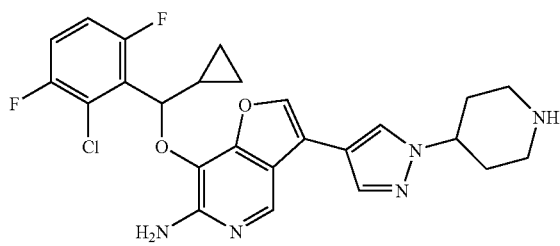

The title compound was prepared according to General Procedure AA. $^1$H NMR (400 MHz, CD$_3$OD): δ=0.38 (dd, J=9.7, 4.9 Hz, 1H), 0.51-0.66 (m, 2H), 0.72-0.81 (m, 1H), 1.86-2.00 (m, 1H), 2.26-2.39 (m, 4H), 3.24 (dd, J=12.0, 3.2 Hz, 2H), 3.53-3.63 (m, 2H), 4.53-4.65 (m, 1H), 5.38 (dd, J=9.6, 1.0 Hz, 1H), 7.07-7.28 (m, 2H), 7.82 (s, 1H), 7.89 (s, 1H), 8.11 (s, 1H), 8.16 (s, 1H). MS (ES$^+$): m/z 500.04/502.03 (100/41) [MH$^+$]. HPLC: t$_R$=2.46 min (ZQ3, polar_5 min).

(2-Chloro-3,6-difluorophenyl)(cyclopropyl)methanol

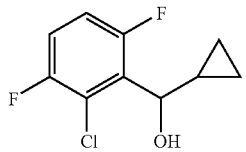

A 50 mL round-bottomed flask was charged with DCM (1 mL) at −30° C. under nitrogen with stirring. 1 M of diethyl zinc in hexane (1 mL) was added dropwise to the flask followed by the addition of diiodomethane (520 mg, 2.0 mmol). A solution of 1-(2-chloro-3,6-difluorophenyl)-prop-2-en-1-ol (50 mg, 0.2 mmol) in DCM was added to the reaction mixture at −20° C. with stirring. The reaction mixture was allowed to warm to rt and stirred for an additional 1 h. The reaction mixture was quenched with sat. aq. NH$_4$Cl solution (15 mL) and extracted with DCM (20 mL). The organic layer was washed with brine (15 mL), dried over anhydrous sodium sulfate, and filtered. The solvent was evaporated under reduced pressure to yield a yellow oil. The material was purified by silica gel chromatography using Hexane/EtOAc (80:20) as eluent to give the desired product as a colorless oil. $^1$H NMR (CDCl$_3$, 400 MHz): δ=0.39-0.48 (m, 1H), 0.48-0.60 (m, 2H), 0.67-0.76 (m, 1H), 1.55-1.63 (m, 1H), 2.48 (dd, J=8.1, 3.5 Hz, 1H), 4.46 (t, J=8.6 Hz, 1H), 6.97-7.10 (m, 2H).

1-(2-Chloro-3,6-difluorophenyl)prop-2-en-1-ol

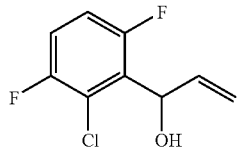

The title compound was prepared according to General Procedure CC. $^1$H NMR (CDCl$_3$, 400 MHz): δ=1.27 (t, J=7.2 Hz, 1H), 2.60 (dd, J=9.3, 4.3 Hz, 1H), 5.24-5.35 (m, 2H), 6.20 (dddd, J=17.2, 10.4, 5.4, 1.4 Hz, 1H), 7.00 (td, J=9.5, 4.2 Hz, 1H), 7.06-7.12 (m, 1H).

Example 368

7-[1-(2,6-Dichloro-3-fluorophenyl)-3-phenylpropoxy]-3-(1-piperidin-4-yl-1H-pyrazol-4-yl)furo[3,2-c]pyridin-6-ylamine

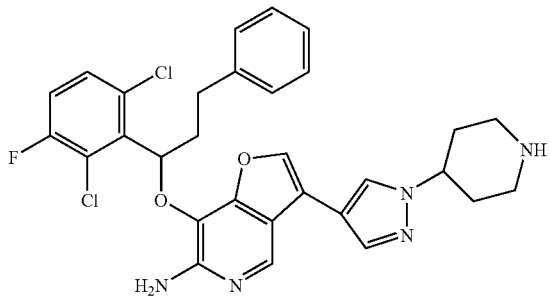

The title compound was prepared according to General Procedure AA. $^1$H NMR (400 MHz, CD$_3$OD): δ=2.26-2.40 (m, 4H), 2.47-2.56 (m, 1H), 2.71-2.90 (m, 2H), 2.92-3.01 (m, 1H), 3.18-3.26 (m, 2H), 3.58 (ddd, J=13.0, 3.4, 3.3 Hz, 2H), 4.59 (tt, J=9.9, 5.0 Hz, 1H), 6.42 (dd, J=7.8, 6.1 Hz, 1H), 7.11-7.25 (m, 6H), 7.35 (dd, J=9.0, 4.9 Hz, 1H), 7.73 (s, 1H), 7.87 (s, 1H), 8.10 (s, 1H), 8.13 (s, 1H). MS (ES$^+$): m/z 580.02/582.04 (100) [MH$^+$]. HPLC: t$_R$=2.79 min (ZQ3, polar_5 min).

1-(2,6-Dichloro-3-fluorophenyl)-3-phenylpropan-1-ol

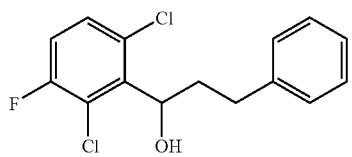

The title compound was prepared according to General Procedure CC. $^1$H NMR (CDCl$_3$, 400 MHz): δ=2.17 (dddd, J=13.8, 10.0, 7.0, 5.6 Hz, 1H), 2.45 (m, J=14.1, 9.3, 9.3, 4.9 Hz, 1H), 2.68 (ddd, J=14.0, 9.7, 6.9 Hz, 1H), 2.82 (d, J=10.1 Hz, 1H), 2.94 (ddd, J=14.1, 9.7, 4.9 Hz, 1H), 5.43 (td, J=9.6, 5.3 Hz, 1H), 7.00-7.06 (m, 1H), 7.17-7.26 (m, 4H), 7.28-7.32 (m, 2H).

Example 369

7-[1-(2-Chloronaphthalen-1-yl)ethoxy]-3-(1-piperidin-4-yl-1H-pyrazol-4-yl)furo[3,2-c]pyridin-6-ylamine

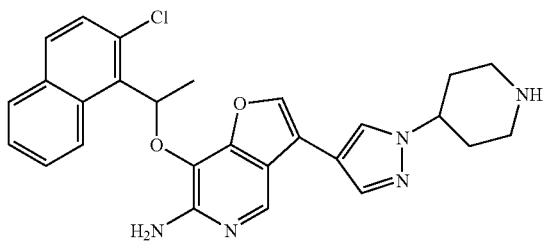

The title compound was prepared according to General Procedure AA. $^1$H NMR (400 MHz, CD$_3$OD): δ=2.03 (d, J=6.8 Hz, 3H), 2.27-2.37 (m, 4H), 3.17-3.26 (m, 2H), 3.57 (ddd, J=13.2, 3.3, 3.2 Hz, 2H), 4.58 (tt, J=9.9, 4.9 Hz, 1H), 6.78 (q, J=6.8 Hz, 1H), 7.40 (d, J=8.8 Hz, 1H), 7.49-7.56 (m, 1H), 7.64 (ddd, J=8.6, 6.9, 1.4 Hz, 1H), 7.75-7.80 (m, 2H), 7.85 (s, 1H), 7.88 (d, J=8.1 Hz, 1H), 8.08 (d, J=6.1 Hz, 2H), 8.90 (d, J=8.6 Hz, 1H). MS (ES$^+$): m/z 488.16/490.18 (100/39) [MH$^+$]. HPLC: $t_R$=2.44 min (ZQ2, polar_5 min).

1-(2-Chloronaphthalen-1-yl)-ethanol

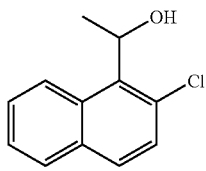

To an EtOH (70 ml) solution of 1-(2-Chloronaphthalen-1-yl)-ethanone (3.98 mmol; prepared according to *J. Org. Chem.* 1946, 11, 163-169) was added sodium borohydride (232 mg, 6.09 mmol). The mixture was stirred at rt under an atmosphere of nitrogen for one hour. After that time, the mixture was quenched with saturated NH$_4$Cl followed by water, extracted with EtOAc (3×50 ml). The extracts were washed with water (50 ml), brine (50 ml), and dried over MgSO$_4$. After concentration in vacuo, a beige oil was obtained. It was purified by chromatography on silica gel (25 g) eluting with an EtOAc/hexane gradient to give the title compound as a colorless oil. $^1$H NMR (400 MHz, CDCl$_3$): δ=1.44 (d, J=6.4 Hz, 3H), 2.33 (d, J=3.6 Hz, 1H), 5.97-6.06 (m, 1H), 7.39 (d, J=8.8 Hz, 1H), 7.45-7.58 (m, 2H), 7.67 (d, J=8.8 Hz, 1H), 7.81 (dd, J=1.6, 8.0 Hz, 1H), 8.75 (d, J=8.0 Hz, 1H). MS (ES$^+$): 189.19/191.20 [MH$^+$–H$_2$O]. HPLC: $t_R$=3.38 min (polar_5 min, ZQ3).

Example 370

7-[2-(4-Chlorophenyl)-1-methylethoxy]-3-(1-piperidin-4-yl-1H-pyrazol-4-yl)furo[3,2-c]pyridin-6-ylamine

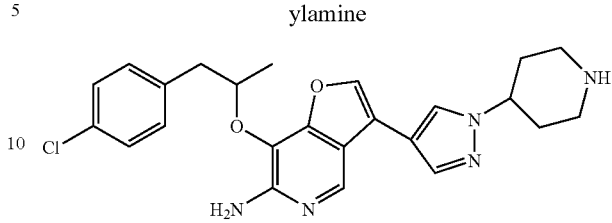

The title compound was prepared according to General Procedure AA. $^1$H NMR (400 MHz, CD$_3$OD): δ=1.35 (d, J=6.3 Hz, 3H), 2.25-2.43 (m, 4H), 2.95 (dd, J=13.8, 5.7 Hz, 1H), 3.09 (dd, J=13.9, 6.8 Hz, 1H), 3.18-3.29 (m, 2H), 3.59 (dt, J=13.1, 3.3 Hz, 2H), 4.61 (m, J=9.9, 9.9, 5.1, 4.9 Hz, 1H), 5.00-5.10 (m, 1H), 7.24 (m, 4H), 7.82 (s, 1H), 7.89 (s, 1H), 8.11 (d, J=2.3 Hz, 2H). MS (ES$^+$): m/z 452.08/454.10 (100/37) [MH$^+$]. HPLC: $t_R$=2.36 min (ZQ3, polar_5 min).

1-(4-Chlorophenyl)propan-2-ol

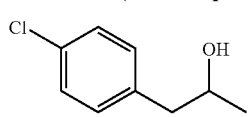

General Procedure FF: To a THF (5 mL) solution of 1.0 M of 4-chlorophenylmagnesium bromide in Et$_2$O (10.0 mL) was added a solution of propylene oxide (0.87 g, 15 mmol) in THF (5 mL) at −78° C. under nitrogen and stirred. The mixture was slowly warmed to rt. The mixture was quenched with sat. aq NH$_4$Cl (10 mL) and then extracted with EtOAc (50 mL). The organic phase was washed with brine (10 mL) and dried over anhydrous sodium sulfate. The crude material was purified by silica gel chromatography using Hexane/EtOAc (80:20) as eluent to give the desired product as a colorless oil. $^1$H NMR (CDCl$_3$, 400 MHz): δ=1.23-1.26 (m, 3H), 1.44 (d, J=3.8 Hz, 1H), 2.65-2.80 (m, 2H), 3.97-4.07 (m, 1H), 7.14-7.18 (m, 2H), 7.28-7.32 (m, 2H).

Example 371

7-[2-(2-Bromo-6-chlorophenyl)-1-methylethoxy]-3-(1-piperidin-4-yl-1H-pyrazol-4-yl)furo[3,2-c]pyridin-6-ylamine

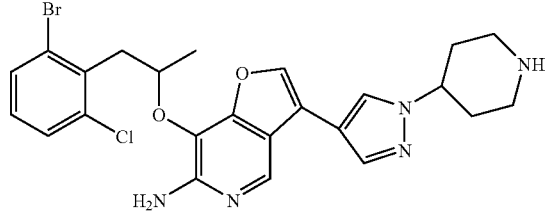

The title compound was prepared according to General Procedure AA. $^1$H NMR (400 MHz, CD$_3$OD): δ=1.44 (d, J=6.1 Hz, 3H), 2.27-2.40 (m, 4H), 3.17-3.27 (m, 2H), 3.38 (dd, J=13.6, 6.3 Hz, 1H), 3.50-3.63 (m, 3H), 4.61 (m, J=9.9, 9.9, 5.1, 4.9 Hz, 1H), 5.19-5.34 (m, 1H), 7.09 (t, J=8.1 Hz, 1H), 7.39 (dd, J=8.0, 1.1 Hz, 1H), 7.53 (dd, J=8.0, 1.1 Hz, 1H), 7.79 (s, 1H), 7.88 (s, 1H), 8.12 (d, J=6.3 Hz, 2H). MS (ES$^+$): m/z 529.99 (100) [MH$^+$]. HPLC: $t_R$=2.47 min (ZQ3, polar_5 min).

Example 304

7-[(R)-1-(2,6-Dichloro-3-fluorophenyl)ethoxy]-3-[5-(4-methyl-piperazin-1-ylmethyl)thiophen-3-yl]-furo[3,2-c]pyridin-6-ylamine

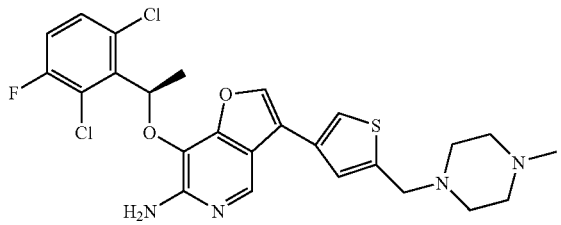

The title compound was prepared according to General Procedure U. MS (ES$^+$): m/z 535.12/537.11 (100/78) [MH$^+$]. HPLC: $t_R$=0.67 min (HPLC-ACQUITY, Analytical).

1-(2-Bromo-6-chlorophenyl)propan-2-ol

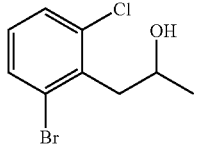

To a solution of LDA (6 mL, 12 mmol) in THF (10 mL) was added 3-chlorobromobenzene (1.91 g, 10.0 mmol) in THF (5 mL) at −78° C. under nitrogen, the resulting mixture was stirred at −78° C. for 1 h, then a solution of propylene oxide (1.7 g, 30 mmol) in THF (5 mL) was added. The mixture was slowly warmed to rt. The mixture was quenched with sat. aq NH$_4$Cl (10 mL), then extracted with EtOAc (50 mL). The organic phase was washed with brine (10 mL) and dried over anhydrous sodium sulfate. The crude material was purified by silica gel chromatography Hexane/EtOAc (80:20) to give the title compound as a yellow oil. $^1$H NMR (CDCl$_3$, 400 MHz): δ=1.34 (d, J=6.1 Hz, 3H), 1.49 (d, J=5.8 Hz, 1H), 3.11-3.26 (m, 2H), 4.20-4.31 (m, 1H), 7.03 (t, J=8.0 Hz, 1H), 7.36 (dd, J=8.0, 1.1 Hz, 1H), 7.50 (dd, J=8.0, 1.1 Hz, 1H).

Example 372

7-[1-(2,4-Dichloro-6-fluorophenyl)ethoxy]-3-(1-piperidin-4-yl-1H-pyrazol-4-yl)furo[3,2-c]pyridin-6-ylamine

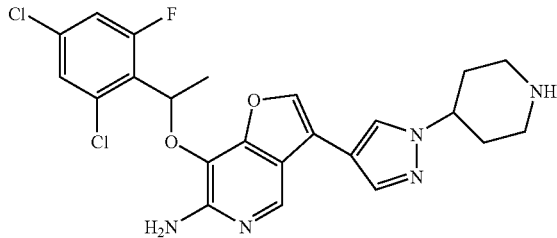

The title compound was prepared according to General Procedure AA. $^1$H NMR (400 MHz, CD$_3$OD): δ=1.83 (d, J=6.8 Hz, 3H), 2.26-2.40 (m, 4H), 3.16-3.27 (m, 2H), 3.58 (ddd, J=13.1, 3.4, 3.2 Hz, 2H), 4.59 (m, J=9.9, 9.9, 5.2, 4.9 Hz, 1H), 6.28-6.36 (m, 1H), 7.20-7.28 (m, 2H), 7.80 (s, 1H), 7.87 (s, 1H), 8.11 (s, 1H), 8.13-8.16 (m, 1H). MS (ES$^+$): m/z 490.01 (100) [MH$^+$]. HPLC: $t_R$=2.44 min (ZQ3, polar_5 min).

1-(2,4-Dichloro-6-fluorophenyl)ethanol

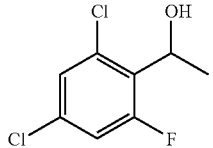

A solution of n-BuLi (4.8 mL, 12 mmol, 2.5 M solution in hexane) was added to THF (50 mL) at −78° C. under nitrogen, followed by the addition of 1.0 M KOtBu in THF (12 mL, 12 mmol). The mixture was stirred at −78° C. for 30 min, then 3,5-dichlorofluorobenzene (1.65 g, 10.0 mmol) in THF (5 mL) was added slowly, and the resulting mixture was stirred at this temperature for 30 min. Then a solution of acetaldehyde (0.88 g, 20 mmol) in THF (5 mL) was added. The mixture was slowly warmed to rt. The mixture was quenched with water (10 mL), and diluted with EtOAc (50 mL). The organic phase was separated, washed with brine (10 mL), and dried over anhydrous sodium sulfate. The crude material was purified by silica gel chromatography (Hex:EtOAc=95:5→90:10) to give the title compound as a colorless oil. $^1$H NMR (CDCl$_3$): δ=1.62 (d, J=6.8 Hz, 3H), 2.30 (br s, 1H, —OH), 5.35 (q, J=6.8 Hz, 1H), 7.05 (dd, J=10.6, 2.0 Hz, 1H), 7.20 (m, 1H).

Example 373

7-[(E)-3-(2,6-Dichloro-3-fluorophenyl)-1-methylallyloxy]-3-(1-piperidin-4-yl-1H-pyrazol-4-yl)furo[3,2-c]pyridin-6-ylamine

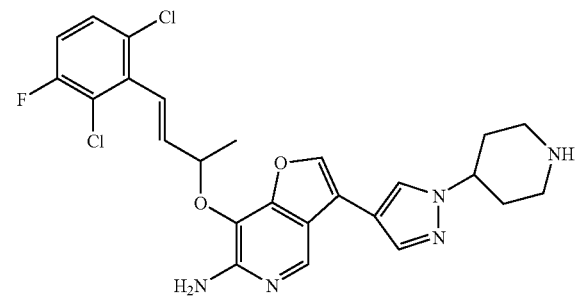

The title compound was prepared according to General Procedure AA, using (2E)-1-(2,6-dichloro-3-fluorophenyl)-but-2-en-1-ol. $^1$H NMR (400 MHz, CD$_3$OD): δ=1.69 (d, J=6.3 Hz, 3H), 2.28-2.44 (m, 4H), 3.20-3.29 (m, 2H), 3.61 (ddd, J=13.2, 3.5, 3.3 Hz, 2H), 4.63 (m, J=10.0, 10.0, 5.0, 4.8 Hz, 1H), 5.52 (qd, J=6.7, 6.6 Hz, 1H), 6.23 (dd, J=16.2, 7.8 Hz, 1H), 6.44 (d, J=16.2 Hz, 1H), 7.12 (t, J=8.7 Hz, 1H), 7.32 (dd, J=9.1, 4.8 Hz, 1H), 7.84-7.89 (m, 1H), 7.91 (s, 1H), 8.14 (s, 1H), 8.17 (s, 1H). MS (ES$^+$): m/z 516.07/518.09 (100/75) [MH$^+$]. HPLC: $t_R$=2.48 min (ZQ3, polar_5 min).

(2E)-1-(2,6-dichloro-3-fluorophenyl)but-2-en-1-ol

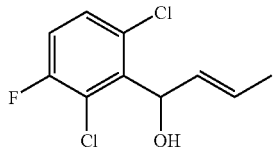

The title compound was prepared according to General Procedure CC. $^1$H NMR (CDCl$_3$, 400 MHz): δ=1.72-1.78 (m, 2H), 1.81 (dd, J=7.1, 1.8 Hz, 2H), 2.74 (br. s., 1H), 2.93 (br. s., 0H), 5.68-5.82 (m, 1H), 5.86-5.97 (m, 1H), 6.05 (m, J=10.5, 8.4, 1.8, 1.8, 1.8 Hz, 1H), 6.22 (d, J=8.6 Hz, 1H), 7.05 (dd, J=8.8, 8.1 Hz, 1H), 7.28-7.31 (m, 1H).

Example 374

7-[1-(2-Fluorophenyl)ethoxy]-3-(1-piperidin-4-yl-1H-pyrazol-4-yl)furo[3,2-c]pyridin-6-ylamine

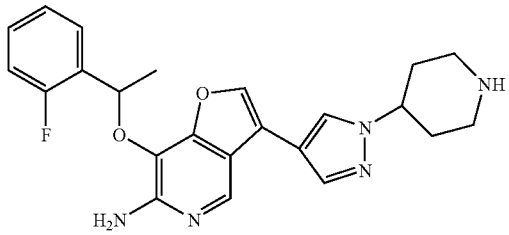

General procedure DD: To a mixture of 4-[4-(7-hydroxy-6-nitrofuro[3,2-c]pyridine-3-yl)-pyrazol-1-yl]-piperidine-1-carboxylic acid tert-butyl ester (20.0 mg, 0.047 mmol), 1-(2,6-dichlorophenyl)propan-1-ol (28.6 mg, 0.14 mmol), triphenylphosphine (24.4 mg, 0.093 mmol) and THF (2 mL) at rt was added diisopropyl azodicarboxylate (37.7 mg, 0.186 mmol) dropwise, and the solution was flushed with nitrogen and stirred at ambient temperature overnight. The solvents were removed in vacuo, and the material was redissolved in EtOH (3 mL). Iron powder (26 mg, 0.47 mmol) and 1 drop of conc. aq. (12M) HCl were added, and the solution was heated at 70° C. for 20 min. The iron powder was removed using the stir bar. 5 drops of aq. 12M HCl was added, and the solution was heated at 70° C. for 3 h. The solution was directly passed through a SCX-2 SPE cartridge, washed with MeOH and ejected with 2M NH$_3$ in MeOH. The crude product was concentrated in vacuo, redissolved MeOH (1 mL) and purified via MDP. MS (ES$^+$): m/z 422.24 (100) [MH$^+$]. HPLC: t$_R$=0.53 min (HPLC-ACQUITY, Analytical). $^1$H NMR (400 MHz, CD$_3$OD): δ=1.73 (d, J=6.6 Hz, 3H), 2.23-2.40 (m, 4H), 3.16-3.27 (m, 2H), 3.53-3.62 (m, 2H), 4.60 (tt, J=10.1, 5.0 Hz, 1H), 6.24 (q, J=6.4 Hz, 1H), 7.02 (td, J=9.5, 1.0 Hz, 1H), 7.09-7.17 (m, 1H), 7.22-7.30 (m, 1H), 7.61 (td, J=7.6, 1.8 Hz, 1H), 7.80 (s, 1H), 7.87 (s, 1H), 8.09 (d, J=1.3 Hz, 2H).

Example 375

7-[1-(2-Chloro-6-methylphenyl)ethoxy]-3-(1-piperidin-4-yl-1H-pyrazol-4-yl)furo[3,2-c]pyridin-6-ylamine

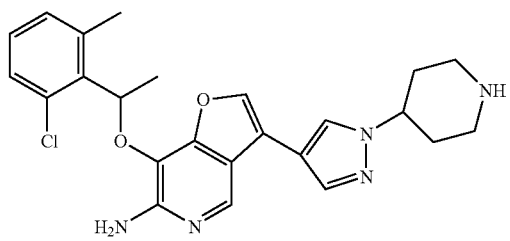

The title compound was prepared according to General Procedure DD. MS (ES$^+$): m/z 452.14/454.14 (100/38) [MH$^+$]. HPLC: t$_R$=0.58 min (HPLC-ACQUITY, Analytical).

Example 376

7-[1-(4-Fluorophenyl)ethoxy]-3-(1-piperidin-4-yl-1H-pyrazol-4-yl)furo[3,2-c]pyridin-6-ylamine

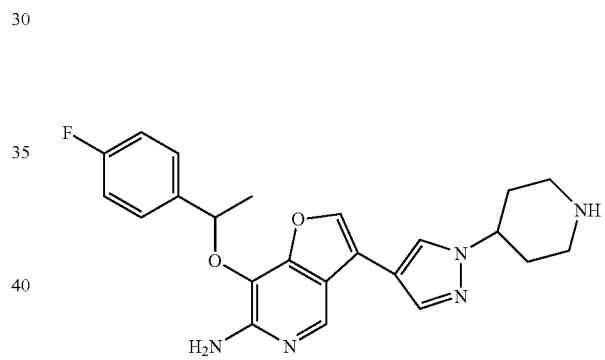

The title compound was prepared according to General Procedure DD. MS (ES$^+$): m/z 422.19 (100) [MH$^+$]. HPLC: t$_R$=0.52 min (HPLC-ACQUITY, Analytical).

Example 377

7-[1-(4-Chlorophenyl)ethoxy]-3-(1-piperidin-4-yl-1H-pyrazol-4-yl)furo[3,2-c]pyridin-6-ylamine

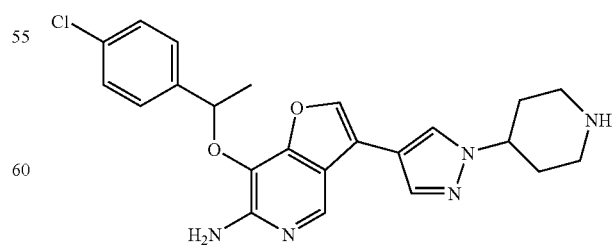

The title compound was prepared according to General Procedure DD. MS (ES$^+$): m/z 438.13/440.13 (100/32) [MH$^+$]. HPLC: t$_R$=0.55 min (HPLC-ACQUITY, Analytical).

Example 378

7-[1-(4-Chloro-2-fluorophenyl)ethoxy]-3-(1-piperidin-4-yl-1H-pyrazol-4-yl)furo[3,2-c]pyridin-6-ylamine

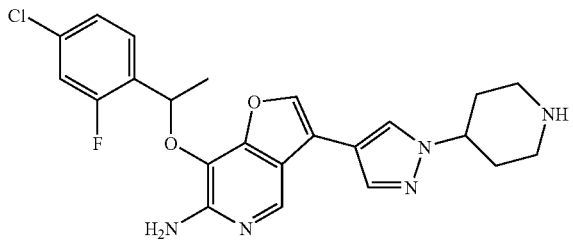

The title compound was prepared according to General Procedure DD. MS (ES+): m/z 456.11/458.12 (100/40) [MH+]. HPLC: $t_R$=0.57 min (HPLC-ACQUITY, Analytical).

Example 379

7-[1-(2-Chloro-3,6-difluorophenyl)ethoxy]-3-(1-piperidin-4-yl-1H-pyrazol-4-yl)furo[3,2-c]pyridin-6-ylamine

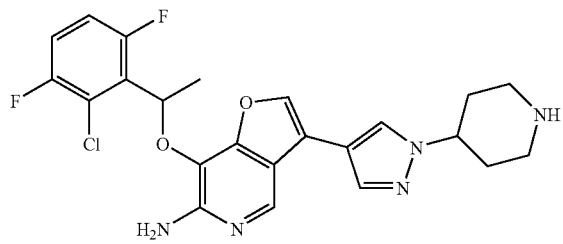

The title compound was prepared according to General Procedure DD. MS (ES+): m/z 474.13/476.13 (100/42) [MH+]. HPLC: $t_R$=0.56 min (HPLC-ACQUITY, Analytical).

1-(2-Chloro-3,6-difluorophenyl)ethanol

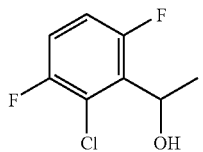

To a dry 18×250 mm test tube, 2-Chloro-3,6-difluorobenzaldehyde (1.00 g, 5.66 mmol) and THF (10.0 mL, 123 mmol) were added. The reaction tube was evacuated and filled with N₂ 3 times. Methylmagnesium bromide (0.810 g, 6.80 mmol) 1.0 M in butyl ether was added slowly at 0° C. The reaction mixture was stirred at room temperature overnight. 5 mL of sat. aq. NH₄Cl was added to quench the reaction at 0° C. Diethyl ether was added and aq. layer was extracted with ether 3 times. The combined organic layers were dried over Na₂SO₄ and the solvent was removed in vacuo. The material was not further purified and ready for the next step.

Example 380

7-[1-(3-Fluoro-2-methylphenyl)ethoxy]-3-(1-piperidin-4-yl-1H-pyrazol-4-yl)furo[3,2-c]pyridin-6-ylamine

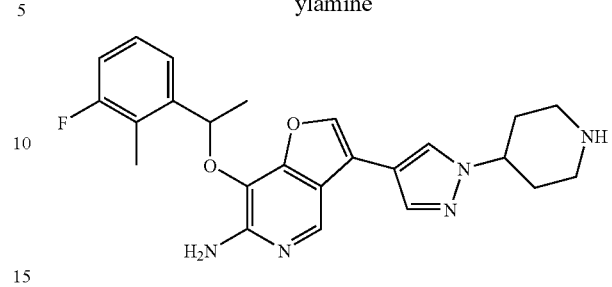

The title compound was prepared according to General Procedure DD. MS (ES+): m/z 436.22 (100) [MH+]. HPLC: $t_R$=0.55 min (HPLC-ACQUITY, Analytical).

Example 381

7-[1-(4-Chloro-3-fluorophenyl)ethoxy]-3-(1-piperidin-4-yl-1H-pyrazol-4-yl)furo[3,2-c]pyridin-6-ylamine

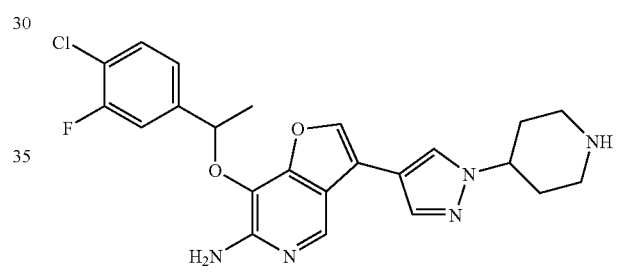

The title compound was prepared according to General Procedure DD. MS (ES+): m/z 456.16/458.16 (100/40) [MH+]. HPLC: $t_R$=0.56 min (HPLC-ACQUITY, Analytical).

Example 382

7-[1-(2,4-Dichlorophenyl)ethoxy]-3-(1-piperidin-4-yl-1H-pyrazol-4-yl)furo[3,2-c]pyridin-6-ylamine

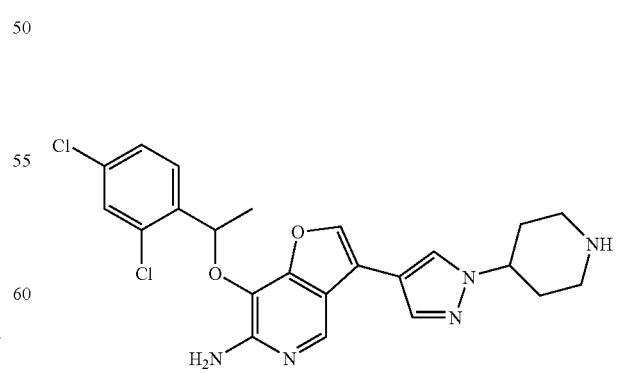

The title compound was prepared according to General Procedure DD. MS (ES+): m/z 472.13/474.12 (100/73) [MH+]. HPLC: $t_R$=0.66 min (HPLC-ACQUITY, Analytical).

Example 383

7-[1-(2,6-Difluorophenyl)ethoxy]-3-(1-piperidin-4-yl-1H-pyrazol-4-yl)furo[3,2-c]pyridin-6-ylamine

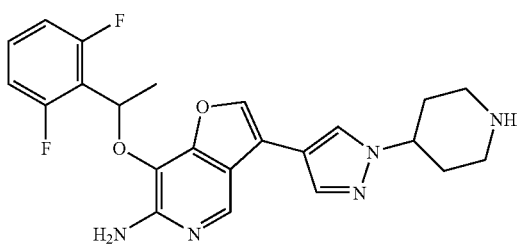

The title compound was prepared according to General Procedure DD. MS (ES$^+$): m/z 440.19 (100) [MH$^+$]. HPLC: t$_R$=0.53 min (HPLC-ACQUITY, Analytical).

Example 384

7-[1-(3,5-Difluorophenyl)ethoxy]-3-(1-piperidin-4-yl-1H-pyrazol-4-yl)furo[3,2-c]pyridin-6-ylamine

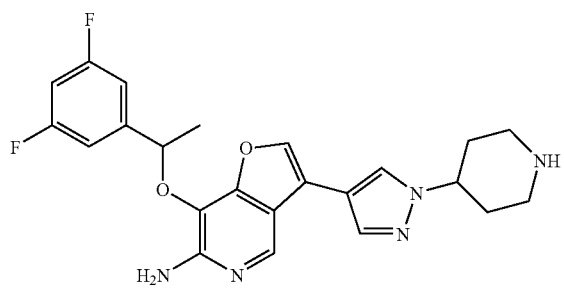

The title compound was prepared according to General Procedure DD. MS (ES$^+$): m/z 440.22 (100) [MH$^+$]. HPLC: t$_R$=0.53 min (HPLC-ACQUITY, Analytical).

Example 385

7-[1-(3-Chlorophenyl)ethoxy]-3-(1-piperidin-4-yl-1H-pyrazol-4-yl)furo[3,2-c]pyridin-6-ylamine

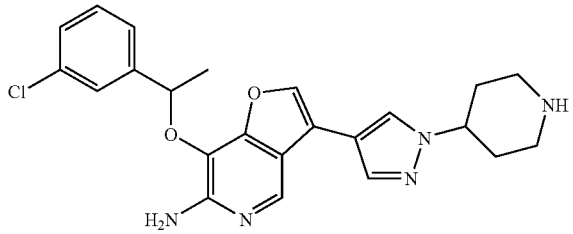

The title compound was prepared according to General Procedure DD. MS (ES$^+$): m/z 438.18/440.17 (100/45) [MH$^+$]. HPLC: t$_R$=0.54 min (HPLC-ACQUITY, Analytical).

Example 386

7-(1-Phenylethoxy)-3-(1-piperidin-4-yl-1H-pyrazol-4-yl)furo[3,2-c]pyridin-6-ylamine

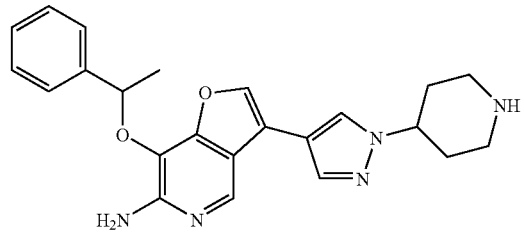

The title compound was prepared according to General Procedure DD. MS (ES$^+$): m/z 404.24 (100) [MH$^+$]. HPLC: t$_R$=0.50 min (HPLC-ACQUITY, Analytical).

Example 387

7-[1-(3-Bromophenyl)ethoxy]-3-(1-piperidin-4-yl-1H-pyrazol-4-yl)furo[3,2-c]pyridin-6-ylamine

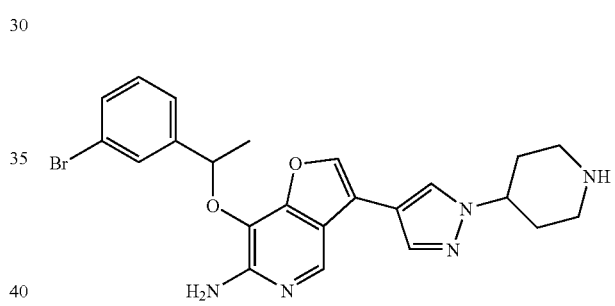

The title compound was prepared according to General Procedure DD. MS (ES$^+$): m/z 482.09/484.12 (100/96) [MH$^+$]. HPLC: t$_R$=0.58 min (HPLC-ACQUITY, Analytical).

Example 388

7-[1-(4-Bromophenyl)ethoxy]-3-(1-piperidin-4-yl-1H-pyrazol-4-yl)furo[3,2-c]pyridin-6-ylamine

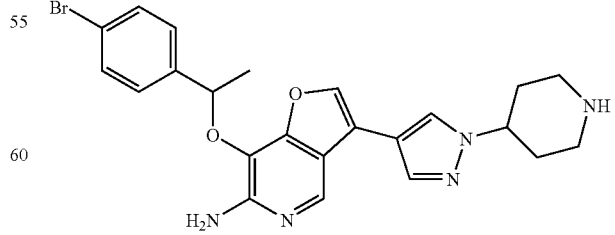

The title compound was prepared according to General Procedure DD. MS (ES$^+$): m/z 482.12/484.12 (98/100) [MH$^+$]. HPLC: t$_R$=0.57 min (HPLC-ACQUITY, Analytical).

Example 389

7-(8-Chloro-1,2,3,4-tetrahydronaphthalen-1-yloxy)-3-(1-piperidin-4-yl-1H-pyrazol-4-yl)furo[3,2-c]pyridin-6-ylamine

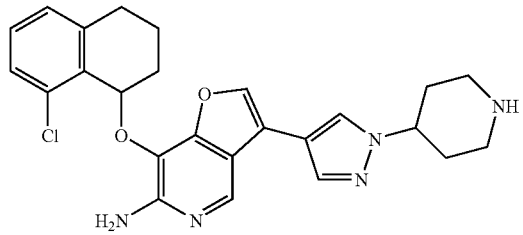

The title compound was prepared according to General Procedure DD. MS (ES+): m/z 464.14/466.17 (100/43) [MH+]. HPLC: $t_R$=0.61 min (HPLC-ACQUITY, Analytical).

8-Chloro-1,2,3,4-tetrahydronaphthalen-1-ol

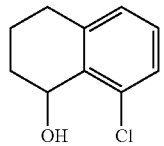

A solution of 8-chloro-3,4-dihydronaphthalen-1(2H)-one (1.26 mmol) in MeOH (4 mL) at 0° C. was quickly charged with a solution of sodium borohydride (3.23 mmol, 2.5 eq) in MeOH (2 mL). The reaction was stirred for 1.5 h from 0° C. to ambient temperature. The reaction was quenched with water and extracted with ether. All organic layers were combined and dried over anhydrous Na$_2$SO$_4$, filtered, and concentrated in vacuo. The crude was dissolved in minimal CH$_2$Cl$_2$ and was purified by two rounds of pTLC [Silicycle, 20×20 plate, 1000 μm, one development in neat CH$_2$Cl$_2$], giving the title material as an off-white solid. $^1$H NMR (400 MHz, CDCl$_3$) δ=1.72-1.85 (m, 2H), 1.92-2.05 (m, 1H), 2.16-2.24 (m, 1H), 2.38 (dd, J=3.8, 1.3 Hz, 1H), 2.71 (ddd, J=17.7, 12.1, 5.8 Hz, 1H), 2.82-2.92 (m, 1H), 5.09 (q, J=3.5 Hz, 1H), 7.06 (d, J=7.6 Hz, 1H), 7.15 (dd, J=7.7, 7.7 Hz, 1H), 7.24 (d, J=7.8 Hz, 1H). MS (ES+): m/z 164.98/166.98 (100/53) [MH+–H$_2$O]. HPLC: $t_R$=3.14 min (ZQ3, polar_5 min).

Example 390

7-(5-Fluoro-1,2,3,4-tetrahydronaphthalen-1-yloxy)-3-(1-piperidin-4-yl-1H-pyrazol-4-yl)furo[3,2-c]pyridin-6-ylamine

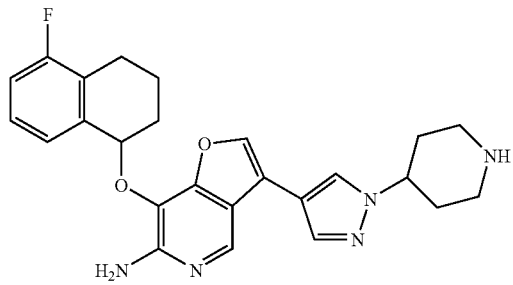

The title compound was prepared according to General Procedure DD. MS (ES+): m/z 448.20 (100) [MH+]. HPLC: $t_R$=0.58 min (HPLC-ACQUITY, Analytical).

5-Fluoro-1,2,3,4-tetrahydronaphthalen-1-ol

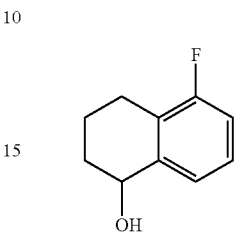

A solution of 5-fluoro-3,4-dihydronaphthalen-1(2H)-one (1.26 mmol) in MeOH (4 mL) at 0° C. was quickly charged with a solution of sodium borohydride (3.23 mmol, 2.5 eq) in MeOH (2 mL). The reaction was stirred for 1.5 h from 0° C. to ambient temperature. The reaction was quenched with water and extracted with ether. All organic layers were combined and dried over anhydrous Na$_2$SO$_4$, filtered, and concentrated in vacuo. The crude was dissolved in minimal CH$_2$Cl$_2$ and was purified by chromatography on silica gel [0.5"×10" glass column, eluting with neat CH$_2$Cl$_2$→5:1 CH$_2$Cl$_2$:EtOAc]. Fractions containing product were combined and concentrated in vacuo, giving the title material as a light yellow oil. $^1$H NMR (400 MHz, CDCl$_3$) δ=1.73 (d, J=6.8 Hz, 1H), 1.75-1.90 (m, 2H), 1.91-2.10 (m, 2H), 2.61-2.86 (m, 2H), 4.67-4.83 (m, 1H), 6.90 (ddd, J=8.5, 8.5, 2.8 Hz, 1H), 7.06 (dd, J=8.5, 5.7 Hz, 1H), 7.17 (dd, J=9.6, 2.8 Hz, 1H). MS (ES+): m/z 149.02 (100) [MH+–OH]. HPLC: $t_R$=2.96 min (ZQ3, polar_5 min).

Example 391

3-(1-Piperidin-4-yl-1H-pyrazol-4-yl)-7-((S)-2,2,2-trifluoro-1-phenylethoxy)furo[3,2-c]pyridin-6-ylamine

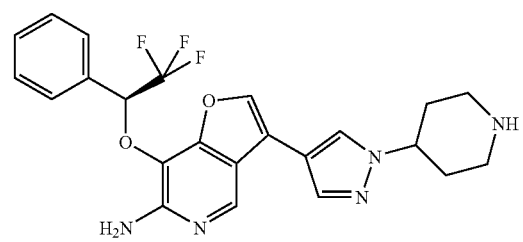

The title compound was prepared according to General Procedure DD. MS (ES+): m/z 458.17 (100) [MH+]. HPLC: $t_R$=0.60 min (HPLC-ACQUITY, Analytical).

Example 392

3-(1-Piperidin-4-yl-1H-pyrazol-4-yl)-7-((R)-2,2,2-trifluoro-1-phenylethoxy)furo[3,2-c]pyridin-6-ylamine

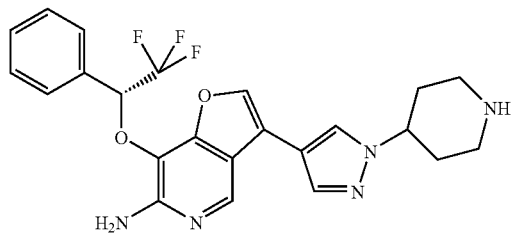

The title compound was prepared according to General Procedure DD. MS (ES$^+$): m/z 458.32 (100) [MH$^+$]. HPLC: $t_R$=0.58 min (HPLC-ACQUITY, Analytical).

Example 393

3-{1-[6-Amino-3-(1-piperidin-4-yl-1H-pyrazol-4-yl)furo[3,2-c]pyridin-7-yloxy]ethyl}benzonitrile

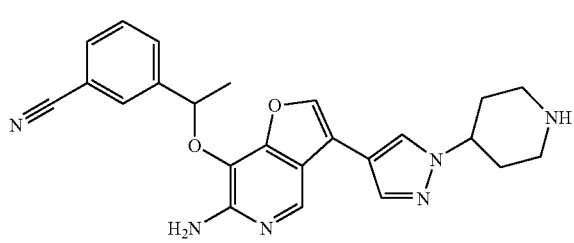

The title compound was prepared according to General Procedure DD. MS (ES$^+$): m/z 429.35 (100) [MH$^+$]. HPLC: $t_R$=0.41 min (HPLC-ACQUITY, Analytical).

Example 394

4-{1-[6-Amino-3-(1-piperidin-4-yl-1H-pyrazol-4-yl)furo[3,2-c]pyridin-7-yloxy]ethyl}benzonitrile

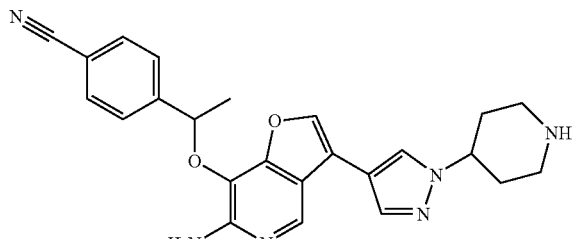

The title compound was prepared according to General Procedure DD. MS (ES$^+$): m/z 429.34 (100) [MH$^+$]. HPLC: $t_R$=0.42 min (HPLC-ACQUITY, Analytical).

Example 395

3-(1-Piperidin-4-yl-1H-pyrazol-4-yl)-7-((S)-1-pyridin-2-yl-ethoxy)furo[3,2-c]pyridin-6-ylamine

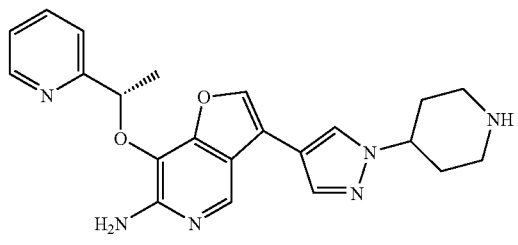

The title compound was prepared according to General Procedure DD. MS (ES$^+$): m/z 405.37 (100) [MH$^+$]. HPLC: $t_R$=0.34 min (HPLC-ACQUITY, Analytical).

Example 396

3-(1-Piperidin-4-yl-1H-pyrazol-4-yl)-7-((S)-1-pyridin-4-yl-ethoxy)furo[3,2-c]pyridin-6-ylamine

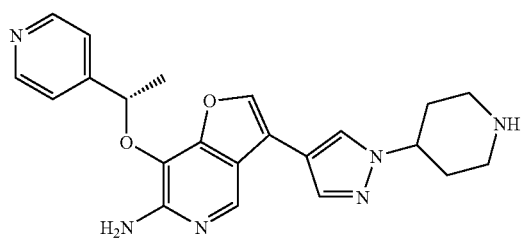

The title compound was prepared according to General Procedure DD. MS (ES$^+$): m/z 405.30 (100) [MH$^+$]. HPLC: $t_R$=0.26 min (HPLC-ACQUITY, Analytical).

Example 397

3-(1-Piperidin-4-yl-1H-pyrazol-4-yl)-7-((R)-1-pyridin-4-yl-ethoxy)furo[3,2-c]pyridin-6-ylamine

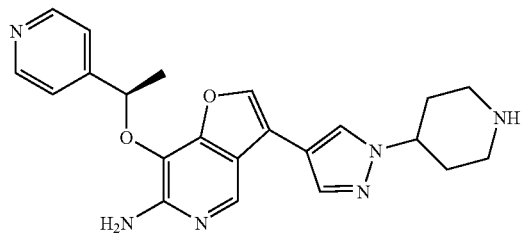

The title compound was prepared according to General Procedure DD. MS (ES$^+$): m/z 405.32 (100) [MH$^+$]. HPLC: $t_R$=0.26 min (HPLC-ACQUITY, Analytical).

Example 398

3-(1-Piperidin-4-yl-1H-pyrazol-4-yl)-7-(1-pyridin-3-ylethoxy)furo[3,2-c]pyridin-6-ylamine

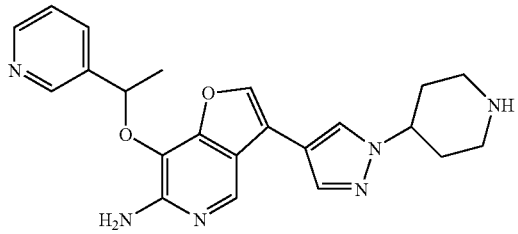

The title compound was prepared according to General Procedure DD. MS (ES+): m/z 405.33 (100) [MH+]. HPLC: $t_R$=0.28 min (HPLC-ACQUITY, Analytical).

Example 399

3-(1-Piperidin-4-yl-1H-pyrazol-4-yl)-7-((R)-1-pyridin-2-yl-ethoxy)furo[3,2-c]pyridin-6-ylamine

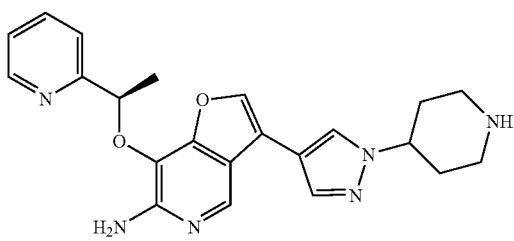

The title compound was prepared according to General Procedure DD. MS (ES+): m/z 405.31 (100) [MH+]. HPLC: $t_R$=0.35 min (HPLC-ACQUITY, Analytical).

Example 400

7-[1-(2-Bromophenyl)ethoxy]-3-(1-piperidin-4-yl-1H-pyrazol-4-yl)furo[3,2-c]pyridin-6-ylamine

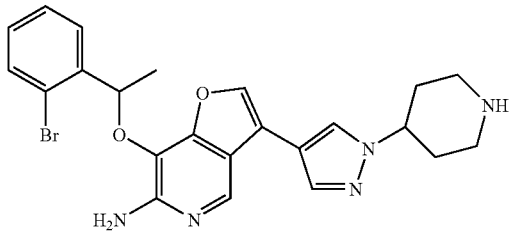

The title compound was prepared according to General Procedure DD. MS (ES+): m/z 482.22/484.27 (94/100) [MH+]. HPLC: $t_R$=0.55 min (HPLC-ACQUITY, Analytical).

Example 401

7-[1-(2-Chloro-6-fluorophenyl)ethoxy]-3-(1-piperidin-4-yl-1H-pyrazol-4-yl)furo[3,2-c]pyridin-6-ylamine

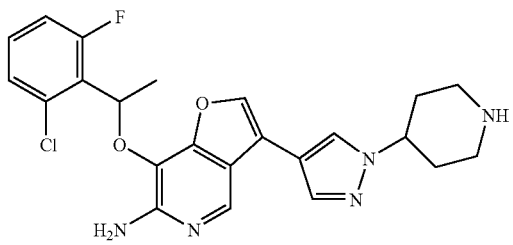

The title compound was prepared according to General Procedure DD. MS (ES+): m/z 456.23/458.25 (100/38) [MH+]. HPLC: $t_R$=0.54 min (HPLC-ACQUITY, Analytical).

Example 402

7-[1-(2,6-Dimethylphenyl)ethoxy]-3-(1-piperidin-4-yl-1H-pyrazol-4-yl)furo[3,2-c]pyridin-6-ylamine

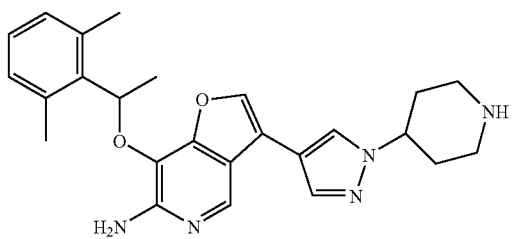

The title compound was prepared according to General Procedure DD. MS (ES+): m/z 432.32 (100) [MH+]. HPLC: $t_R$=0.55 min (HPLC-ACQUITY, Analytical).

1-(2,6-Dimethylphenyl)ethanol

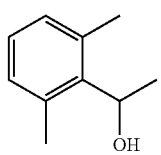

The title compound was prepared according to General Procedure CC. $^1$H NMR (CDCl$_3$, 400 MHz): δ=1.55 (d, J=6.8 Hz, 3H), 1.69 (d, J=2.5 Hz, 1H), 2.46 (s, 6H), 5.41 (qd, J=6.8, 2.7 Hz, 1H), 7.01 (s, 2H), 7.03-7.08 (m, 1H).

Example 403

7-[1-(1H-Benzimidazol-2-yl)ethoxy]-3-(1-piperidin-4-yl-1H-pyrazol-4-yl)furo[3,2-c]pyridin-6-ylamine

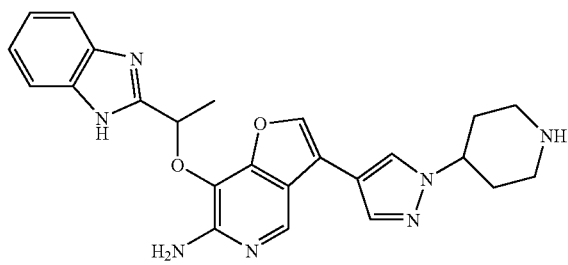

The title compound was prepared according to General Procedure DD. MS (ES$^+$): m/z 444.30 (100) [MH$^+$]. HPLC: t$_R$=0.33 min (HPLC-ACQUITY, Analytical).

Example 404

7-(1-Benzothiazol-2-ylethoxy)-3-(1-piperidin-4-yl-1H-pyrazol-4-yl)furo[3,2-c]pyridin-6-ylamine

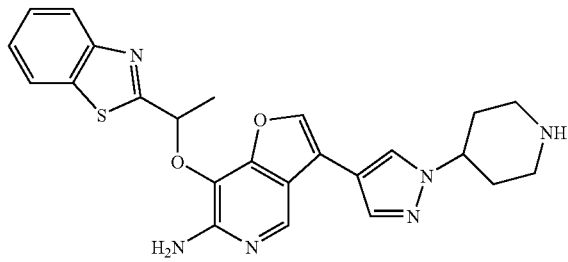

The title compound was prepared according to General Procedure DD. MS (ES$^+$): m/z 461.33 (100) [MH$^+$]. HPLC: t$_R$=0.47 min (HPLC-ACQUITY, Analytical).

Example 405

7-(1-Methyl-2-phenylethoxy)-3-(1-piperidin-4-yl-1H-pyrazol-4-yl)furo[3,2-c]pyridin-6-ylamine

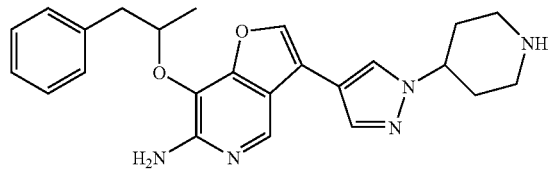

The title compound was prepared according to General Procedure DD. MS (ES$^+$): m/z 418.30 (100) [MH$^+$]. HPLC: t$_R$=0.49 min (HPLC-ACQUITY, Analytical).

Example 406

7-[2-(2-Methoxyphenyl)-1-methylethoxy]-3-(1-piperidin-4-yl-1H-pyrazol-4-yl)furo[3,2-c]pyridin-6-ylamine

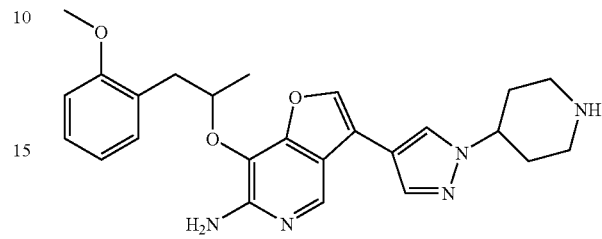

The title compound was prepared according to General Procedure DD. MS (ES$^+$): m/z 448.30 (100) [MH$^+$]. HPLC: t$_R$=0.48 min (HPLC-ACQUITY, Analytical).

Example 407

7-((1S,2S)-2-Phenylcyclopentyloxy)-3-(1-piperidin-4-yl-1H-pyrazol-4-ylfuro[3,2-c]pyridin-6-ylamine

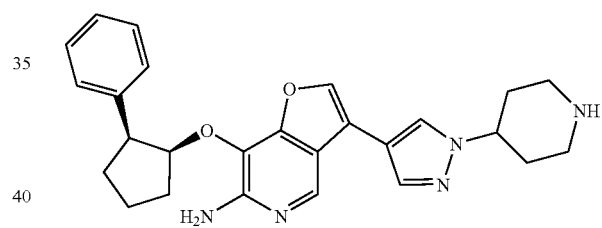

The title compound was prepared according to General Procedure DD. MS (ES$^+$): m/z 444.31 (100) [MH$^+$]. HPLC: t$_R$=0.52 min (HPLC-ACQUITY, Analytical).

Example 408

7-((1S,2S)-2-(3-Fluorophenyl)cyclopentyloxy)-3-(1-piperidin-4-yl-1H-pyrazol-4-ylfuro[3,2-c]pyridin-6-ylamine

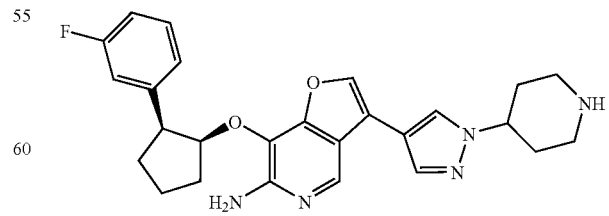

The title compound was prepared according to General Procedure DD. MS (ES$^+$): m/z 462.30 (100) [MH$^+$]. HPLC: t$_R$=0.55 min (HPLC-ACQUITY, Analytical).

Example 409

7-((1S,2S)-2-Phenylcyclohexyloxy)-3-(1-piperidin-4-yl-1H-pyrazol-4-yl)furo[3,2-c]pyridin-6-ylamine

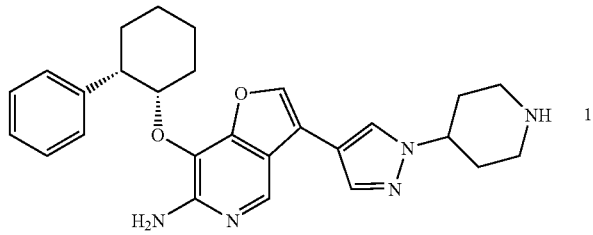

The title compound was prepared according to General Procedure DD. MS (ES+): m/z 458.33 (100) [MH+]. HPLC: $t_R$=0.59 min (HPLC-ACQUITY, Analytical).

Example 410

3-{1-[6-Amino-3-(1-piperidin-4-yl-1H-pyrazol-4-yl)furo[3,2-c]pyridin-7-yloxy]ethyl}benzoic acid methyl ester

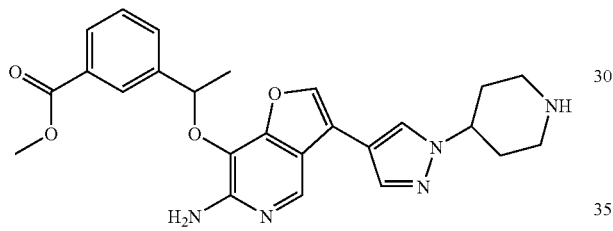

The title compound was prepared according to General Procedure DD. MS (ES+): m/z 462.37 (100) [MH+]. HPLC: $t_R$=0.44 min (HPLC-ACQUITY, Analytical).

3-(1-Hydroxyethyl)benzoic acid methyl ester

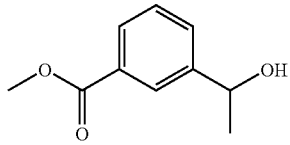

General Procedure EE: Into the EtOH (70 ml) solution of methyl-3-acetylbenzoate (771 mg, 3.98 mmol) was added sodium borohydride (232 mg, 6.09 mmol). The mixture was stirred at rt under an atmosphere of nitrogen for one hour. After that time, the mixture was quenched with saturated NH$_4$Cl followed by water, extracted with EtOAc (3×50 ml). The extracts were washed with water (50 ml), brine (50 ml), dried over MgSO$_4$. After concentrated in vacuo, a beige oil (6269-42, 700 mg) was obtained. It was purified by chromatography on silica gel (25 g) eluting with 20% (200 ml), 30% (200 ml) and 40% EtOAc/hexane (200 ml) to give the title compound as a colorless oil (504 mg, 67% yield). TLC: R$_f$=0.41 (eluting with 30% EtOAc/hexane). $^1$H NMR (400 MHz, CDCl$_3$): δ=1.52 (d, J=6.4 Hz, 3H), 1.89 (d, J=4.0 Hz, 1H), 3.92 (s, 3H), 4.93-5.01 (m, 1H), 7.43 (t, J=8.0 Hz, 1H), 7.59 (md, J=8.0 Hz, 1H), 7.95 (td, J=1.6 & 8.0 Hz, 1H), 8.03-8.05 (m, 1H). MS (ES+): m/z 181.19 [MH+]. HPLC: $t_R$=2.51 min (polar_5 min, ZQ3).

3-Acetylbenzoic acid methyl ester

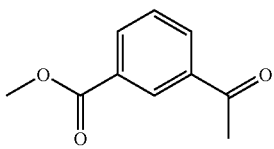

Sulfuric acid (23.4 µl, 0.430 mmol) was added into the MeOH (15 ml) solution of 3-acetylbenzoic acid (720 mg, 4.30 mmol). The mixture was stirred at 70° C. for 20 h. After that time, the mixture was cooled and was treated with saturated NaHCO$_3$ till pH>9, followed by adding water to dissolve the solid which was formed, extracted with EtOAc (2×50 ml). The extracts were washed with water (50 ml), brine (50 ml), dried over MgSO$_4$, filtered and concentrated in vacuo, giving the title compound as brown oil. $^1$H NMR (400 MHz, CDCl$_3$): δ=2.66 (s, 3H), 3.96 (s, 3H), 7.54-7.59 (m, 1H), 8.14-8.19 (m, 1H), 8.22-8.26 (m, 1H), 8.59-8.61 (m, 1H). MS (ES+): m/z 179.17 [MH+]. HPLC: $t_R$=2.82 min (polar_5 min, ZQ3).

Example 411

3-{1-[6-Amino-3-(1-piperidin-4-yl-1H-pyrazol-4-yl)furo[3,2-c]pyridin-7-yloxy]ethyl}benzamide

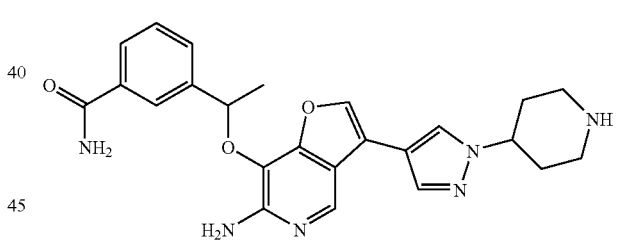

The title compound was prepared according to General Procedure DD. MS (ES+): m/z 447.36 (100) [MH+]. HPLC: $t_R$=0.36 min (HPLC-ACQUITY, Analytical).

3-(1-Hydroxyethyl)benzamide

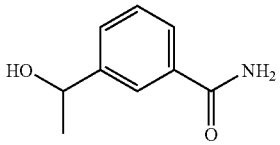

The title compound was prepared following General Procedure EE. $^1$H NMR (400 MHz, CD$_3$OD): δ=1.46 (d, J=6.8 Hz, 3H), 4.88 (q, J=6.4 Hz, 1H), 7.42 (t, J=8.0 Hz, 1H), 7.56 (md, J=8.0 Hz, 1H), 7.74 (td, J=1.6 & 8.0 Hz, 1H), 7.88 (t, J=1.6 Hz, 1H). MS (ES+): m/z 166.19 [MH+]. HPLC: $t_R$=1.71 min (polar_5 min, ZQ3).

261

3-Acetylbenzamide

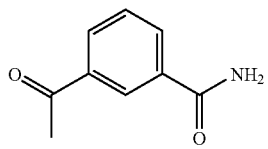

General Procedure FF: Into DMF (11 ml, 140 mmol) solution of 3-acetylbenzoic acid (706 mg, 4.30 mmol) which was cooled in ice/water bath was added triethylamine (602 µl, 4.30 mmol) followed by addition of ethyl chloroformate (424 µl, 4.30 mmol) dropwise in 5 min under an atmosphere of nitrogen. The mixture was stirred at 0° C. for 30 min and then at rt for 30 min. Ammonium hydroxide (28% aq. solution; 1.15 ml) was added, and the mixture was stirred at rt for 3 h. After that time, the mixture was poured into ice/water, extracted with EtOAc (3×50 ml). The extracts were washed with water (2×30 ml), brine (30 ml), dried over MgSO$_4$, filtered and concentrated in vacuo, giving the title compound as a white solid. $^1$H NMR (400 MHz, CDCl$_3$): δ=2.66 (s, 3H), 7.58 (dt, J=0.4 & 8.0 Hz, 1H), 8.05 (md, J=8.0 Hz, 1H), 8.12 (md, J=8.0 Hz, 1H), 8.38-8.41 (m, 1H). MS (ES$^+$): m/z 164.10 [MH$^+$]. HPLC: t$_R$=1.89 min (polar_5 min, ZQ3).

Example 412

3-{1-[6-Amino-3-(1-piperidin-4-yl-1H-pyrazol-4-yl)furo[3,2-c]pyridin-7-yloxy]ethyl}-N-methylbenzamide

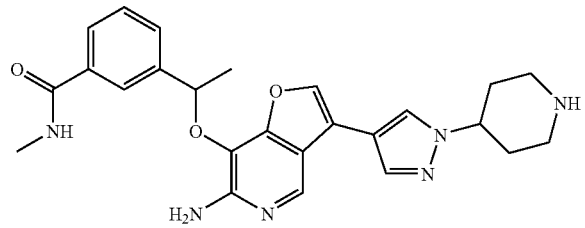

The title compound was prepared according to General Procedure DD. MS (ES$^+$): m/z 461.39 (100) [MH$^+$]. HPLC: t$_R$=0.37 min (HPLC-ACQUITY, Analytical).

3-(1-Hydroxyethyl)-N-methylbenzamide

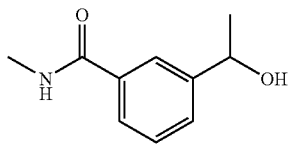

The title compound was prepared following General Procedure EE. $^1$H NMR (400 MHz, CD$_3$OD): 1.45 (d, J=6.4 Hz, 3H), 2.92 (s, 3H), 4.86 (q, J=6.4 Hz, 1H), 7.41 (t, J=8.0 Hz, 1H), 7.54 (md, J=8.0 Hz, 1H), 7.68 (td, J=1.6 & 7.6 Hz, 1H), 7.82 (t, J=2.0 Hz, 1H). MS (ES$^+$): m/z 180.18 [MH$^+$]. HPLC: t$_R$=1.83 min (polar_5 min, ZQ3).

262

3-Acetyl-N-methylbenzamide

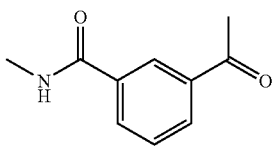

The title compound was prepared following General Procedure FF. $^1$H NMR (400 MHz, CDCl$_3$): δ=2.65 (s, 3H), 3.05 (d, J=4.8 Hz, 1H), 6.31 (brs, 1H), 7.55 (t, J=7.6 Hz, 1H), 8.01 (md, J=8.0 Hz, 1H), 8.08 (td, J=1.2 & 7.6 Hz, 1H), 8.33 (t, J=1.2 Hz, 1H). MS (ES$^+$): m/z 178.16 [MH$^+$]. HPLC: t$_R$=2.01 min (polar_5 min, ZQ3).

Example 413

7-[1-(3-Chloro-5-trifluoromethylpyridin-2-yl)ethoxy]-3-(1-piperidin-4-yl-1H-pyrazol-4-yl)furo[3,2-c]pyridin-6-ylamine

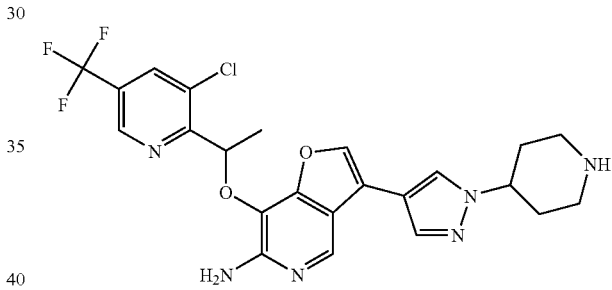

The title compound was prepared according to General Procedure DD. MS (ES$^+$): m/z 507.28/509.26 (100/46) [MH$^+$]. HPLC: t$_R$=0.54 min (HPLC-ACQUITY, Analytical).

Example 414

7-((S)-1-Methyl-2-phenylethoxy)-3-(1-piperidin-4-yl-1H-pyrazol-4-yl)furo[3,2-c]pyridin-6-ylamine

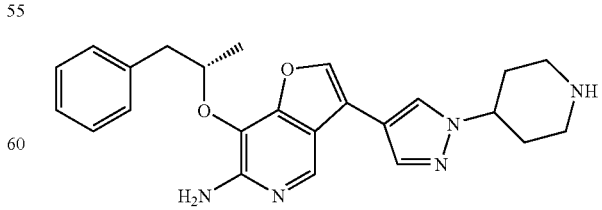

The title compound was prepared according to General Procedure DD. MS (ES$^+$): m/z 418.33 (100) [MH$^+$]. HPLC: t$_R$=0.48 min (HPLC-ACQUITY, Analytical).

Example 415

7-((R)-1-Methyl-2-phenylethoxy)-3-(1-piperidin-4-yl-1H-pyrazol-4-yl)furo[3,2-c]pyridin-6-ylamine

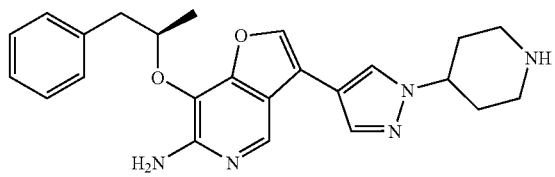

The title compound was prepared according to General Procedure DD. MS (ES+): m/z 418.34 (100) [MH+]. HPLC: $t_R$=0.48 min (HPLC-ACQUITY, Analytical).

Example 416

7-Phenethyloxy-3-(1-piperidin-4-yl-1H-pyrazol-4-yl)furo[3,2-c]pyridin-6-ylamine

The title compound was prepared according to General Procedure DD. MS (ES+): m/z 404.12 (100) [MH+]. HPLC: $t_R$=2.12 min (polar_5 min, ZQ3).

Example 417

7-[2-(2,6-Dichlorophenyl)-1-methylethoxy]-3-(1-piperidin-4-yl-1H-pyrazol-4-yl)furo[3,2-c]pyridin-6-ylamine

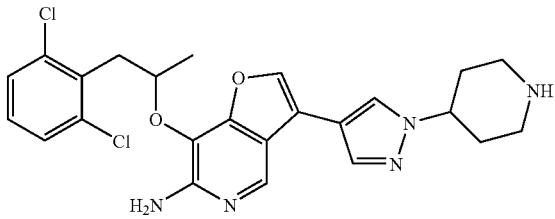

The title compound was prepared according to General Procedure DD. MS (ES+): m/z 486.03/487.96 (100/80) [MH+]. HPLC: $t_R$=2.34 min (polar_5 min, ZQ3).

1-(2,6-Dichlorophenyl)propan-2-ol

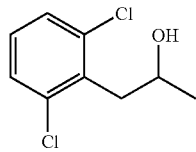

General Procedure GG: To a solution of 2,6-dichlorophenylacetone (500.00 mg, 2.46 mmol) in MeOH (5.0 mL) was added sodium borohydride (112 mg, 2.96 mmol) in small portions. The reaction mixture was allowed to stir overnight at rt. The reaction was monitored by TLC analysis on silica gel plates using Hexane/EtOAc (70:30) as eluent. The reaction mixture was quenched with aq. sat. NH4Cl (15 mL) and extracted with EtOAc (50 mL). The organic layer was washed with brine (20 mL), dried over Na2SO4, and filtered. The solvent was removed under reduced pressure to give a colorless oil. The crude material was purified by silica gel chromatography using Hexane/EtOAc (70:30) as eluent to obtain the desired product as a colorless oil. $^1$H NMR (CDCl3, 400 MHz): δ=1.33 (d, J=6.1 Hz, 3H), 1.49 (d, J=5.3 Hz, 1H), 3.08-3.22 (m, 2H), 4.18-4.29 (m, 1H), 7.09-7.14 (m, 1H), 7.31 (s, 1H), 7.33 (s, 1H).

Example 418

7-[2-(2,6-Difluorophenyl)-1-methylethoxy]-3-(1-piperidin-4-yl-1H-pyrazol-4-yl)furo[3,2-c]pyridin-6-ylamine

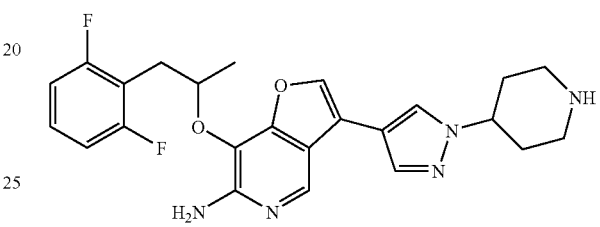

The title compound was prepared according to General Procedure DD. MS (ES+): m/z 454.12 (100) [MH+]. HPLC: $t_R$=2.22 min (polar_5 min, ZQ3).

1-(2,6-Difluorophenyl)propan-2-ol

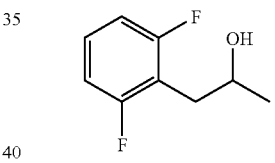

The title compound was prepared according to General Procedure GG. $^1$H NMR (CDCl3, 400 MHz): δ=1.27 (d, J=6.1 Hz, 3H), 1.47 (d, J=5.1 Hz, 1H), 2.81-2.92 (m, 2H), 4.05-4.17 (m, 1H), 6.84-6.92 (m, 2H), 7.19 (tt, J=8.3, 6.6 Hz, 1H).

Example 419

7-[2-(2-Chloro-6-fluorophenyl)-1-methylethoxy]-3-(1-piperidin-4-yl-1H-pyrazol-4-yl)furo[3,2-c]pyridin-6-ylamine

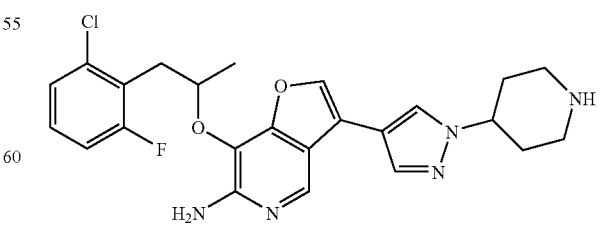

The title compound was prepared according to General Procedure DD. MS (ES+): m/z 470.08/472.03 (100/40) [MH+]. HPLC: $t_R$=2.29 min (polar_5 min, ZQ3).

1-(2-Chloro-6-fluorophenyl)propan-2-ol

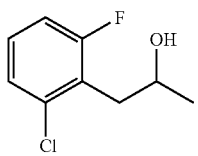

The title compound was prepared according to General Procedure GG. $^1$H NMR (CDCl$_3$, 400 MHz): δ=1.29 (d, J=5.6 Hz, 3H), 1.47 (d, J=5.3 Hz, 1H), 2.92-3.05 (m, 2H), 4.10-4.20 (m, 1H), 6.96-7.02 (m, 1H), 7.12-7.22 (m, 2H).

Example 420

4-{1-[6-Amino-3-(1-piperidin-4-yl-1H-pyrazol-4-yl) furo[3,2-c]pyridin-7-yloxy]ethyl}benzamide

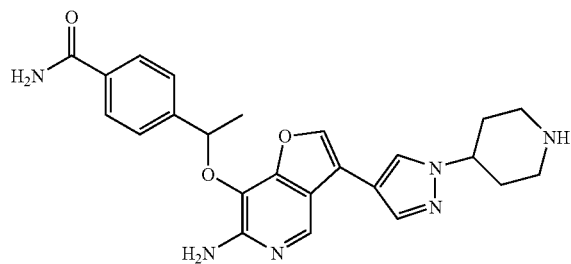

The title compound was prepared according to General Procedure DD. MS (ES$^+$): m/z 447.10 (100) [MH$^+$]. HPLC: t$_R$=1.84 min (polar__5 min, ZQ3).

4-(1-Hydroxyethyl)benzamide

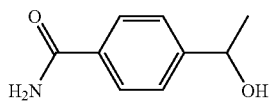

The title compound was prepared following General Procedure EE. $^1$H NMR (400 MHz, CD$_3$OD): δ=1.46 (d, J=6.8 Hz, 3H), 4.88 (q, J=6.4 Hz, 1H), 7.42 (t, J=8.0 Hz, 1H), 7.56 (md, J=8.0 Hz, 1H), 7.74 (td, J=1.6 & 8.0 Hz, 1H), 7.88 (t, J=1.6 Hz, 1H). MS (ES$^+$): m/z 166.19 [MH$^+$]. HPLC: t$_R$=1.71 min (polar__5 min, ZQ3).

4-Acetylbenzamide

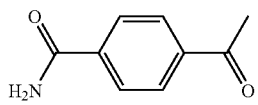

The title compound was prepared following General Procedure FF. $^1$H NMR (400 MHz, DMSO-d$_6$): δ=2.62 (s, 3H), 7.53 (brs, 1H), 7.96-8.03 (m, 2H), 8.12 (brs, 1H). MS (ES$^+$): m/z 164.17 [MH$^+$]. HPLC: t$_R$=1.87 min (polar__5 min, ZQ3).

Example 421

4-{1-[6-Amino-3-(1-piperidin-4-yl-1H-pyrazol-4-yl) furo[3,2-c]pyridin-7-yloxy]ethyl}-N-methylbenzamide

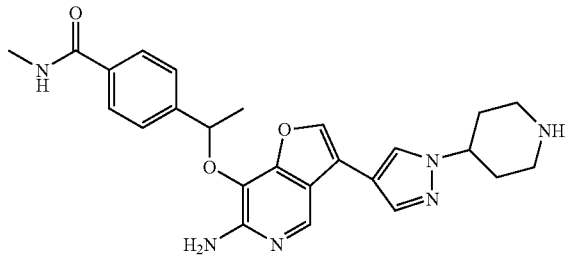

The title compound was prepared according to General Procedure DD. MS (ES$^+$): m/z 461.12 (100) [MH$^+$]. HPLC: t$_R$=1.83 min (polar__5 min, ZQ3).

4-(1-Hydroxyethyl)-N-methylbenzamide

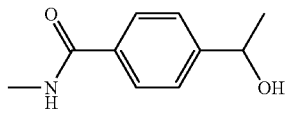

The title compound was prepared following General Procedure EE. $^1$H NMR (400 MHz, CD$_3$OD): δ=1.42-1.46 (m, 3H), 2.91 (s, 3H), 4.87 (q, J=6.4 Hz, 1H), 7.44-7.46 (m, 2H), 7.77 (td, J=2.0 & 8.4 Hz, 2H). MS (ES$^+$): m/z 180.18 [MH$^+$]. HPLC: t$_R$=1.78 min (polar__5 min, ZQ3).

4-Acetyl-N-methylbenzamide

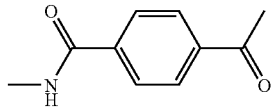

The title compound was prepared following General Procedure FF. $^1$H NMR (400 MHz, CD$_3$OD): δ=2.63 (s, 3H), 2.93 (s, 3H), 7.89-7.92 (m, 2H), 8.04-8.07 (m, 2H). MS (ES$^+$): m/z 178.16 [MH$^+$]. HPLC: t$_R$=1.99 min (polar__5 min, ZQ3).

Example 422

4-{1-[6-Amino-3-(1-piperidin-4-yl-1H-pyrazol-4-yl) furo[3,2-c]pyridin-7-yloxy]ethyl}benzoic acid methyl ester

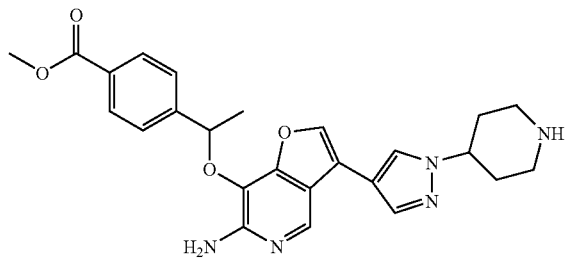

The title compound was prepared according to General Procedure DD. MS (ES$^+$): m/z 462.12 (100) [MH$^+$]. HPLC: t$_R$=2.11 min (polar__5 min, ZQ3).

4-(1-Hydroxyethyl)benzoic acid methyl ester

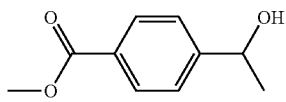

The title compound was prepared according to General Procedure EE, using commercially available methyl 4-acetylbenzoate. $^1$H NMR (400 MHz, CDCl$_3$): δ=1.51 (d, J=6.4 Hz, 3H), 1.84 (brs, 1H), 3.92 (s, 3H), 4.97 (quartet, J=6.4 Hz, 1H), 7.41-7.47 (m, 2H), 8.00-8.04 (m, 2H). MS (ES$^+$): 181.19 [MH$^+$]. HPLC: t$_R$=2.51 min (polar_5 min, ZQ3).

Example 423

7-[2-(2-Fluorophenyl)-1-methylethoxy]-3-(1-piperidin-4-yl-1H-pyrazol-4-yl)furo[3,2-c]pyridin-6-ylamine

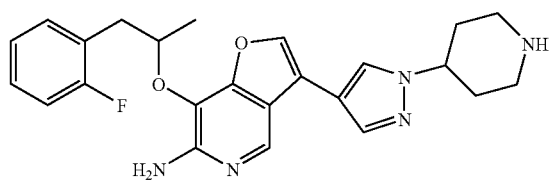

The title compound was prepared according to General Procedure DD. MS (ES$^+$): m/z 436.12 (100) [MH$^+$]. HPLC: t$_R$=2.25 min (polar_5 min, ZQ3).

1-(2-Fluorophenyl)propan-2-ol

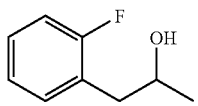

The title compound was prepared according to General Procedure GG. $^1$H NMR (CDCl$_3$, 400 MHz): δ=1.26 (d, J=5.8 Hz, 3H), 1.47 (d, J=4.0 Hz, 1H), 2.73-2.90 (m, 2H), 4.04-4.16 (m, 1H), 7.01-7.13 (m, 2H), 7.19-7.26 (m, 2H).

Example 424

7-[2-(3-Fluorophenyl)-1-methylethoxy]-3-(1-piperidin-4-yl-1H-pyrazol-4-yl)furo[3,2-c]pyridin-6-ylamine

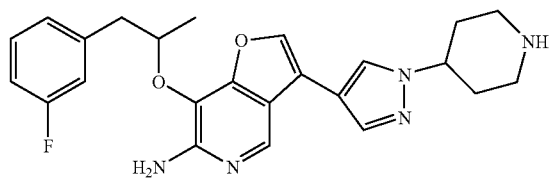

The title compound was prepared according to General Procedure DD. MS (ES$^+$): m/z 436.12 (100) [MH$^+$]. HPLC: t$_R$=2.20 min (polar_5 min, ZQ3).

1-(3-Fluorophenyl)propan-2-ol

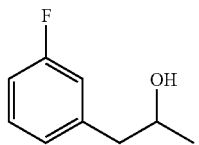

The title compound was prepared according to General Procedure GG. $^1$H NMR (CDCl$_3$, 400 MHz): δ=1.26 (d, J=6.1 Hz, 3H), 1.47 (d, J=3.8 Hz, 1H), 2.68-2.83 (m, 2H), 3.99-4.10 (m, 1H), 6.91-6.98 (m, 2H), 7.00 (d, J=7.8 Hz, 1H), 7.27-7.32 (m, 1H).

Example 425

7-[2-(4-Fluorophenyl)-1-methylethoxy]-3-(1-piperidin-4-yl-1H-pyrazol-4-yl)furo[3,2-c]pyridin-6-ylamine

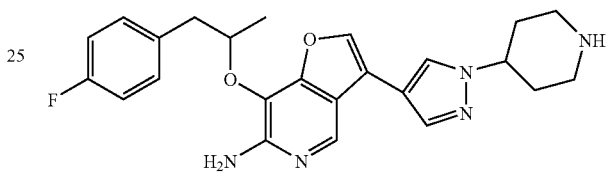

The title compound was prepared according to General Procedure DD. MS (ES$^+$): m/z 436.12 (100) [MH$^+$]. HPLC: t$_R$=2.22 min (polar_5 min, ZQ3).

1-(4-Fluorophenyl)propan-2-ol

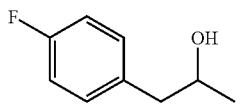

The title compound was prepared according to General Procedure GG. $^1$H NMR (CDCl$_3$, 400 MHz): δ=1.25 (d, J=6.1 Hz, 3H), 1.44 (d, J=3.8 Hz, 1H), 2.64-2.80 (m, 2H), 3.96-4.06 (m, 1H), 6.98-7.04 (m, 2H), 7.15-7.21 (m, 2H).

Example 426

7-[2-(2-Chlorophenyl)-1-methylethoxy]-3-(1-piperidin-4-yl-1H-pyrazol-4-yl)furo[3,2-c]pyridin-6-ylamine

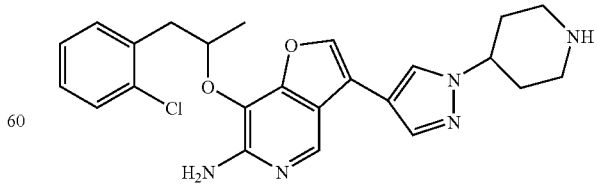

The title compound was prepared according to General Procedure DD. MS (ES$^+$): m/z 452.15/454.17 (100/38) [MH$^+$]. HPLC: t$_R$=2.15 min (polar_5 min, ZQ3).

269

1-(2-Chlorophenyl)propan-2-ol

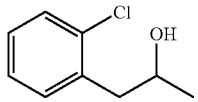

The title compound was prepared according to General Procedure GG. $^1$H NMR (CDCl$_3$, 400 MHz): δ=1.29 (d, J=6.1 Hz, 3H), 1.47 (d, J=3.8 Hz, 1H), 2.81-2.88 (m, 1H), 2.95-3.01 (m, 1H), 4.10-4.20 (m, 1H), 7.16-7.25 (m, 2H), 7.29 (d, J=2.0 Hz, 1H), 7.36-7.40 (m, 1H).

Example 427

7-[2-(3-Chlorophenyl)-1-methylethoxy]-3-(1-piperidin-4-yl-1H-pyrazol-4-yl)furo[3,2-c]pyridin-6-ylamine

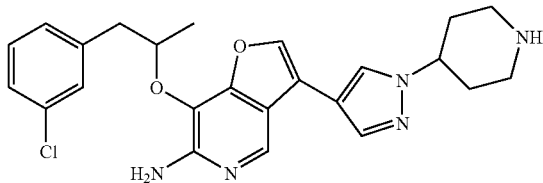

The title compound was prepared according to General Procedure DD. MS (ES$^+$): m/z 452.15/454.17 (100/38) [MH$^+$]. HPLC: t$_R$=2.34 min (polar_5 min, ZQ3).

1-(3-Chlorophenyl)propan-2-ol

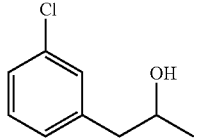

The title compound was prepared according to General Procedure GG. $^1$H NMR (CDCl$_3$, 400 MHz): δ=1.26 (d, J=6.3 Hz, 3H), 1.45 (d, J=4.0 Hz, 1H), 2.66-2.81 (m, 2H), 3.99-4.09 (m, 1H), 7.09-7.13 (m, 1H), 7.21-7.26 (m, 3H).

Example 428

7-[2-(3,4-Dichlorophenyl)-1-methylethoxy]-3-(1-piperidin-4-yl-1H-pyrazol-4-yl)furo[3,2-c]pyridin-6-ylamine

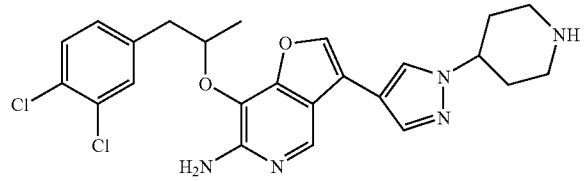

The title compound was prepared according to General Procedure DD. MS (ES$^+$): m/z 486.13/488.11 (100/80) [MH$^+$]. HPLC: t$_R$=2.33 min (polar_5 min, ZQ3).

270

1-(3,4-Dichlorophenyl)propan-2-ol

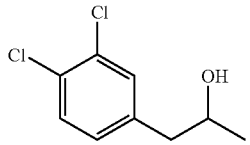

The title compound was prepared according to General Procedure GG. $^1$H NMR (CDCl$_3$, 400 MHz): δ=1.26 (d, J=6.1 Hz, 3H), 1.43 (d, J=4.0 Hz, 1H), 2.63-2.78 (m, 2H), 3.98-4.08 (m, 1H), 7.07 (dd, J=8.1, 2.0 Hz, 1H), 7.34 (d, J=2.0 Hz, 1H), 7.38 (d, J=8.3 Hz, 1H).

Example 429

7-[2-(2,4-Dichlorophenyl)-1-methylethoxy]-3-(1-piperidin-4-yl-1H-pyrazol-4-yl)furo[3,2-c]pyridin-6-ylamine

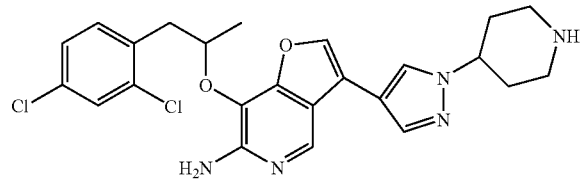

The title compound was prepared according to General Procedure DD. MS (ES$^+$): m/z 486.00/487.97 (100/80) [MH$^+$]. HPLC: t$_R$=2.40 min (polar_5 min, ZQ3).

1-(2,4-Dichlorophenyl)propan-2-ol

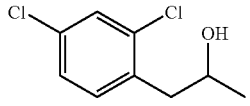

The title compound was prepared according to General Procedure GG. $^1$H NMR (CDCl$_3$, 400 MHz): δ=1.28 (d, J=6.1 Hz, 3H), 1.42 (d, J=4.3 Hz, 1H), 2.78-2.97 (m, 2H), 4.08-4.14 (m, 1H), 7.18-7.24 (m, 2H), 7.40 (d, J=1.5 Hz, 1H).

Example 430

7-[1-Methyl-2-(3-trifluoromethylphenyl)ethoxy]-3-(1-piperidin-4-yl-1H-pyrazol-4-yl)furo[3,2-c]pyridin-6-ylamine

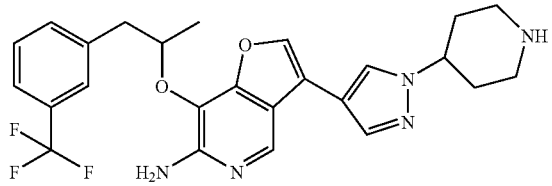

The title compound was prepared according to General Procedure DD. MS (ES$^+$): m/z 486.11 (100) [MH$^+$]. HPLC: t$_R$=2.33 min (polar_5 min, ZQ3).

1-[3-(Trifluoromethyl)phenyl]propan-2-ol

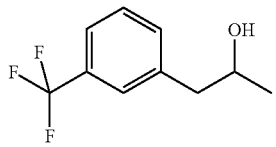

The title compound was prepared according to General Procedure GG. ¹H NMR (CDCl₃, 400 MHz): δ=1.27 (d, J=6.3 Hz, 3H), 1.43 (d, J=4.3 Hz, 1H), 2.75-2.89 (m, 2H), 4.02-4.10 (m, 1H), 7.39-7.54 (m, 4H).

Example 431

7-[2-(4-Methoxyphenyl)-1-methylethoxy]-3-(1-piperidin-4-yl-1H-pyrazol-4-yl)furo[3,2-c]pyridin-6-ylamine

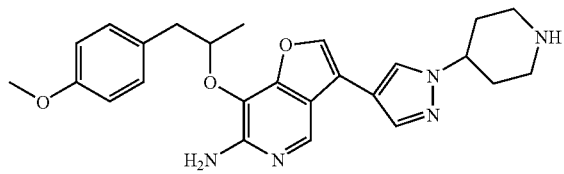

The title compound was prepared according to General Procedure DD. MS (ES⁺): m/z 448.38 (100) [MH⁺]. HPLC: $t_R$=0.52 min (HPLC-ACQUITY, Analytical).

1-(4-Methoxyphenyl)propan-2-ol

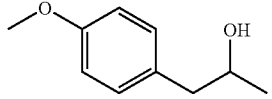

The title compound was prepared according to General Procedure GG. ¹H NMR (CDCl₃, 400 MHz): δ=1.25 (d, J=6.3 Hz, 3H), 1.48 (d, J=3.3 Hz, 1H), 2.59-2.78 (m, 2H), 3.81 (s, 3H), 3.95-4.04 (m, 1H), 6.85-6.90 (m, 2H), 7.12-7.17 (m, 2H).

Example 432

7-(1-Naphthalen-2-ylethoxy)-3-(1-piperidin-4-yl-1H-pyrazol-4-yl)furo[3,2-c]pyridin-6-ylamine

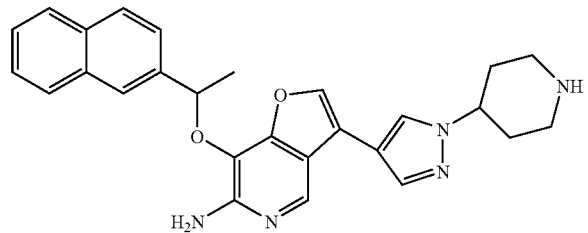

The title compound was prepared according to General Procedure DD. MS (ES⁺): m/z 454.13 (100) [MH⁺]. HPLC: $t_R$=2.57 min (polar_5 min, ZQ2).

Example 433

{2-[6-Amino-3-(1-piperidin-4-yl-1H-pyrazol-4-yl)furo[3,2-c]pyridin-7-yloxymethyl]phenyl}acetonitrile

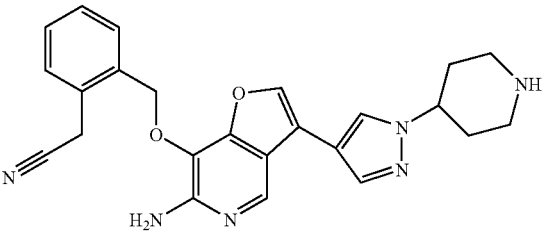

The title compound was prepared according to General Procedure DD. MS (ES⁺): m/z 429.35 (100) [MH⁺]. HPLC: $t_R$=0.45 min (HPLC-ACQUITY, Analytical).

(2-Hydroxymethylphenyl)acetonitrile

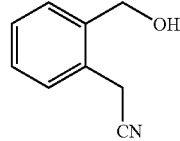

To a suspension of sodium borohydride (454 mg, 12.0 mmol) in THF (20 mL) was slowly added a solution of 2-cyanomethylbenzoic acid (1.61 g, 10.0 mmol) in THF (20 mL), then a solution of iodine (1.30 g, 5.0 mmol) in THF (20 mL) was slowly added at rt. The resulting mixture was stirred at rt for 1 h. The reaction was quenched with 3 N HCl (10 mL), then extracted with Et₂O (3×20 mL). The combined organic phases were washed with brine (20 mL), and dried over anhydrous sodium sulfate. The residue was purified by silica gel chromatography (Hex:EtOAc=80:20→60:40) to give the title compound as a yellow oil. ¹H NMR (CD₃OD): δ=3.98 (s, 2H), 4.27 (s, 2H), 7.33 (m, 2H), 7.41 (m, 2H).

2-Cyanomethylbenzoic Acid

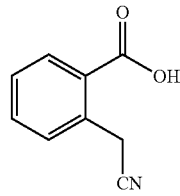

A mixture of methyl 2-cyanomethylbenzoate (10.5 g, 60.0 mmol) in aq. NaOH (66 mL, 66 mmol, 1N solution) was heated at 40° C. for 5 h and it became a clear solution. The mixture was cooled to 0° C. and acidified to pH 1 using 6N aq. HCl. The resulting white solid was collected by filtration. ¹H NMR (CD₃OD): δ=4.27 (s, 2H), 7.46 (td, J=7.8, 1.0 Hz, 1H), 7.54-7.60 (m, 2H), 8.09 (dd, J=7.8, 1.3 Hz, 1H).

Example 434

7-[1-(3-Bromo-5-fluorophenyl)ethoxy]-3-(1-piperidin-4-yl-1H-pyrazol-4-yl)furo[3,2-c]pyridin-6-ylamine

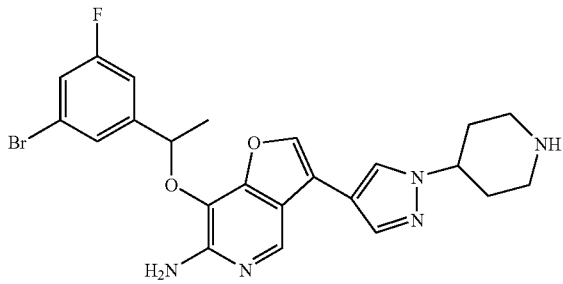

The title compound was prepared according to General Procedure DD. MS (ES+): m/z 500.15/502.15 (100/92) [MH+]. HPLC: $t_R$=0.60 min (HPLC-ACQUITY, Analytical).

1-(3-Bromo-5-fluorophenyl)ethanol

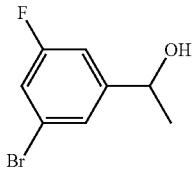

Into the THF (8 ml) solution of 3-bromo-5-fluorobenzaldehyde (374 mg, 1.84 mmol) which was cooled in ice/water bath was added methylmagnesium bromide in Et$_2$O (3.0 M, 0.92 ml) dropwise under an atmosphere of nitrogen. The combined mixture was stirred at 0° C. for 1 h and then at rt for 1 h. After that time, the mixture was quenched with saturated NH$_4$Cl (10 ml) followed by water (10 ml), extracted with EtOAc (2×25 ml). The extracts were washed with water (2×15 ml), brine (15 ml), dried over MgSO$_4$, filtered and concentrated in vacuo to give a beige oil. It was purified by chromatography on silica gel (15 g) eluting with 10% (100 ml), 15% (100 ml), 20% (100 ml) and 25% (100 ml) EtOAc/hexane to give the title compound. $^1$H NMR (400 MHz, CDCl$_3$): δ=1.47 (d, J=6.4 Hz, 3H), 1.87 (d, J=3.6 Hz, 1H), 4.83-4.90 (m, 1H), 7.02-7.06 (m, 1H), 7.14 (td, J=2.0 & 8.0 Hz, 1H), 7.31 (t, J=1.6 Hz, 1H). MS (ES+): m/z 201.22/203.18 [MH+–H$_2$O]. HPLC: $t_R$=3.07 min (polar_5 min, ZQ3).

3-Bromo-5-fluorobenzaldehyde

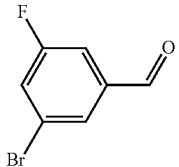

(3-Bromo-5-fluorophenyl)methanol (378 mg, 1.86 mmol) was dissolved in DCM (10 ml), into which was added pyridinium chlorochromate (880 mg, 4.00 mmol). The mixture was stirred at rt under an atmosphere of nitrogen for 16 h. After that time, the reaction mixture was passed through a silica gel plug, eluting with DCM (250 ml) to give the title compound as a brown solid. $^1$H NMR (400 MHz, CDCl$_3$): δ=7.50-7.54 (m, 2H), 7.81-7.83 (m, 1H), 9.33 (d, J=2.0 Hz, 1H). HPLC: $t_R$=3.27 min (polar_5 min, ZQ3).

(3-Bromo-5-fluorophenyl)methanol

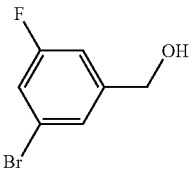

BH$_3$.THF in THF (1.00 M, 4.44 ml) was added dropwise into the THF (10 ml) solution of 3-bromo-5-fluorobenzoic acid (447 mg, 2.00 mmol) at rt under an atmosphere of nitrogen. The combined solution was stirred at rt for 24 h. After that time, the mixture was diluted with EtOAc (50 ml) and treated with saturated Na$_2$CO$_3$ (30 ml). The aqueous layer was extracted with EtOAc (2×25 ml). The extracts were washed with water (3×30 ml), brine (30 ml), dried over MgSO$_4$, filtered and concentrated in vacuo to give the title compounds as colorless oil. $^1$H NMR (400 MHz, CDCl$_3$): δ=1.83 (brs, 1H), 4.71 (s, 2H), 7.03-7.08 (m, 1H), 7.16-7.20 (m, 1H), 7.32-7.34 (m, 1H). HPLC: $t_R$=2.87 min (polar_5 min, ZQ3).

Example 435

7-[1-Methyl-2-(2-trifluoromethylphenyl)ethoxy]-3-(1-piperidin-4-yl-1H-pyrazol-4-yl)furo[3,2-c]pyridin-6-ylamine

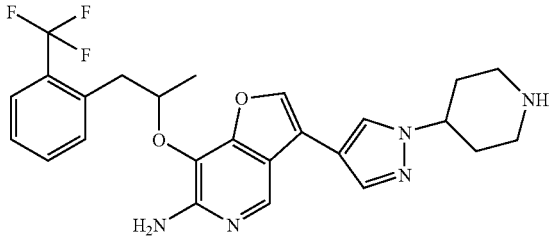

The title compound was prepared according to General Procedure DD. MS (ES+): m/z 486.27 (100) [MH+]. HPLC: $t_R$=0.60 min (HPLC-ACQUITY, Analytical).

1-[2-(Trifluoromethyl)phenyl]propan-2-ol

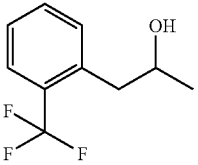

General Procedure HH: To a solution of 1-iodo-2-(trifluoromethyl)benzene (1.5 g, 5.5 mmol) in THF (10.0 mL) was added 2.5 M of n-BuLi in hexane (2.2 mL) at −78° C. and stirred for 10 min. Propylene oxide (370 mg, 6.4 mmol) was added to the reaction mixture at −78° C. and slowly warmed to rt. The reaction mixture was stirred for an additional 30 min. The reaction mixture was quenched with sat. aq. NH$_4$Cl and extracted with EtOAc. The organic layer was washed with brine, dried over anhydrous Na$_2$SO$_4$, and the solvent was removed under reduced pressure to give a yellow oil. The material was purified by silica gel chromatography using Hexane/EtOAc (80:20) as eluent to yield the desired product as a colorless oil. $^1$H NMR (CDCl$_3$, 400 MHz): δ=1.30 (d, J=6.1 Hz, 3H), 1.46 (d, J=4.3 Hz, 1H), 2.82-3.06 (m, 2H), 4.03-4.12 (m, 1H), 7.32-7.38 (m, 1H), 7.41-7.45 (m, 1H), 7.48-7.53 (m, 1H), 7.67 (d, J=8.1 Hz, 1H).

Example 436

7-[2-(2-Bromophenyl)-1-methylethoxy]-3-(1-piperidin-4-yl-1H-pyrazol-4-yl)furo[3,2-c]pyridin-6-ylamine

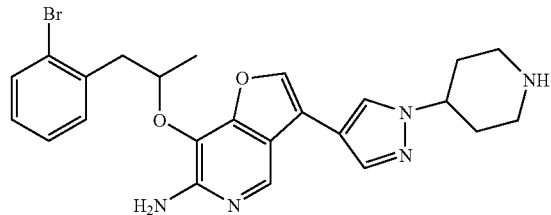

The title compound was prepared according to General Procedure DD. MS (ES+): m/z 496.18/498.19 (95/100) [MH+]. HPLC: $t_R$=0.57 min (HPLC-ACQUITY, Analytical).

1-(2-Bromophenyl)propan-2-ol

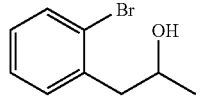

General Procedure II: To a solution of 1-bromo-2-iodobenzene (1.00 g, 3.53 mmol) in THF (10.0 mL) was added 2.0 M of isopropylmagnesium chloride in THF (1.8 mL) at −35° C. and stirred for 1 h. The reaction mixture was cooled to −78° C. and propylene oxide (250 mg, 4.2 mmol) was added. The reaction mixture was allowed to warm to rt and stirred overnight. The reaction mixture was quenched with sat. aq. NH4Cl (10 mL) and extracted with EtOAc (20 mL). The organic layer was washed with brine (10 mL), dried over Na2SO4 and the solvent was removed under reduced pressure to yield a colorless oil. The material was purified by silica gel chromatography using Hexane/EtOAc (80:20) as eluent to yield the desired product as a colorless oil. $^1$H NMR (CDCl3, 400 MHz): δ=1.30 (d, J=6.1 Hz, 3H), 1.47 (d, J=4.0 Hz, 1H), 2.82-3.01 (m, 2H), 4.10-4.21 (m, 1H), 7.08-7.14 (m, 1H), 7.26-7.27 (m, 1H), 7.28 (s, 1H), 7.57 (d, J=7.8 Hz, 1H).

Example 437

7-[2-(3-Methoxyphenyl)-1-methylethoxy]-3-(1-piperidin-4-yl-1H-pyrazol-4-yl)furo[3,2-c]pyridin-6-ylamine

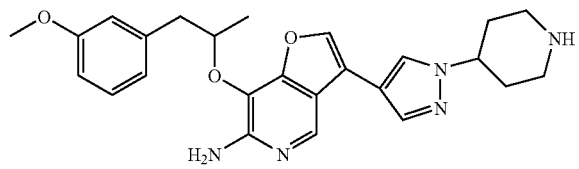

The title compound was prepared according to General Procedure DD. MS (ES+): m/z 448.31 (100) [MH+]. HPLC: $t_R$=0.50 min (HPLC-ACQUITY, Analytical).

1-(3-Methoxyphenyl)propan-2-ol

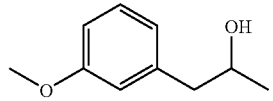

The title compound was prepared according to General Procedure FF. $^1$H NMR (CDCl3, 400 MHz): δ=1.27 (d, J=6.1 Hz, 3H), 1.52 (d, J=3.8 Hz, 1H), 2.64-2.83 (m, 2H), 3.82 (s, 3H), 3.99-4.10 (m, 1H), 6.76-6.85 (m, 3H), 7.25 (t, J=7.7 Hz, 1H).

Example 438

7-[1-Methyl-2-(4-trifluoromethylphenyl)ethoxy]-3-(1-piperidin-4-yl-1H-pyrazol-4-yl)furo[3,2-c]pyridin-6-ylamine

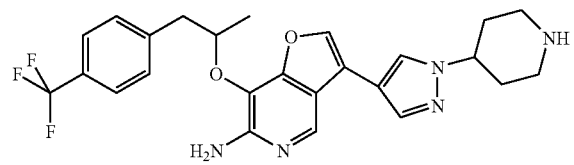

The title compound was prepared according to General Procedure DD. MS (ES+): m/z 486.27 (100) [MH+]. HPLC: $t_R$=0.60 min (HPLC-ACQUITY, Analytical).

1-[4-(Trifluoromethyl)phenyl]propan-2-ol

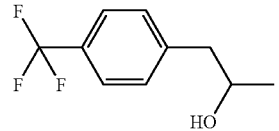

The title compound was prepared according to General Procedure HH. $^1$H NMR (CDCl3, 400 MHz): δ=1.27 (d, J=6.1 Hz, 3H), 1.43 (d, J=4.0 Hz, 1H), 2.75-2.89 (m, 2H), 4.03-4.12 (m, 1H), 7.35 (d, J=8.1 Hz, 2H), 7.58 (d, J=8.1 Hz, 2H).

Example 439

7-[2-(3-Bromophenyl)-1-methylethoxy]-3-(1-piperidin-4-yl-1H-pyrazol-4-yl)furo[3,2-c]pyridin-6-ylamine

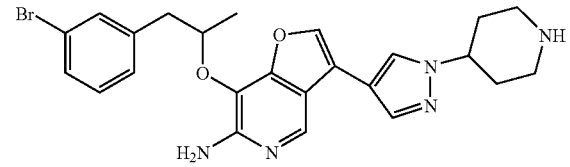

The title compound was prepared according to General Procedure DD. MS (ES+): m/z 496.19/498.18 (100/96) [MH+]. HPLC: $t_R$=0.58 min (HPLC-ACQUITY, Analytical).

1-(3-Bromophenyl)propan-2-ol

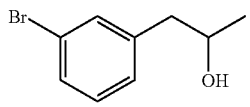

The title compound was prepared according to General Procedure II. ¹H NMR (CDCl₃, 400 MHz): δ=1.26 (d, J=6.3 Hz, 3H), 1.45 (d, J=4.0 Hz, 1H), 2.65-2.80 (m, 2H), 4.04 (dddd, J=6.0, 4.5, 1.5, 1.3 Hz, 1H), 7.13-7.22 (m, 2H), 7.36-7.41 (m, 2H).

Example 440

7-[2-(2-Chloro-6-trifluoromethylphenyl)-1-methyl-ethoxy]-3-(1-piperidin-4-yl-1H-pyrazol-4-yl)furo[3,2-c]pyridin-6-ylamine

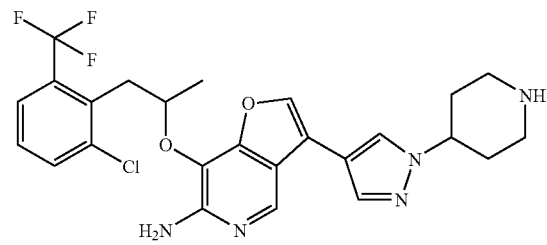

The title compound was prepared according to General Procedure DD. MS (ES⁺): m/z 520.22/522.24 (100/40) [MH⁺]. HPLC: $t_R$=0.67 min (HPLC-ACQUITY, Analytical).

1-[2-Chloro-6-(trifluoromethyl)phenyl]propan-2-ol

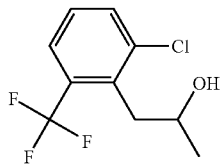

To a solution of 1-chloro-3-(trifluoromethyl)benzene (1.0 g, 5.5 mmol) in THF (10.0 mL) was added 2.5 M of n-BuLi in hexane (2.2 mL) at −78° C. and stirred for 1 h. Propylene oxide (370 mg, 6.4 mmol) was added to the reaction mixture at −78° C. and slowly warmed to rt. The reaction mixture was stirred for an additional 30 min. The reaction mixture was quenched with sat. aq. NH₄Cl and extracted with EtOAc. The organic layer was washed with brine, dried over anhydrous Na₂SO₄, and the solvent was removed under reduced pressure to give a yellow oil. The material was purified by silica gel chromatography using Hexane/EtOAc (80:20) as eluent to yield the desired product as a yellow oil. ¹H NMR (CDCl₃, 400 MHz): δ=1.33 (d, J=6.1 Hz, 3H), 1.40 (d, J=6.3 Hz, 1H), 3.08-3.22 (m, 2H), 4.21-4.33 (m, 1H), 7.29-7.34 (m, 1H), 7.58-7.64 (m, 2H).

Example 441

7-[2-(2-Fluoro-6-trifluoromethylphenyl)-1-methyl-ethoxy]-3-(1-piperidin-4-yl-1H-pyrazol-4-yl)furo[3,2-c]pyridin-6-ylamine

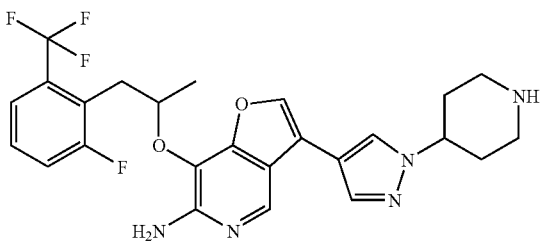

The title compound was prepared according to General Procedure DD. MS (ES⁺): m/z 504.27 (100) [MH⁺]. HPLC: $t_R$=0.63 min (HPLC-ACQUITY, Analytical).

1-[2-Fluoro-6-(trifluoromethyl)phenyl]propan-2-ol

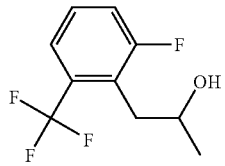

A solution of 2.5 M of n-BuLi in hexane (4.4 mL) was added to THF (10.0 mL) at −78° C. under nitrogen, followed by the addition of 1.0 M of KOtBu in THF (11 mL). The mixture was stirred at −78° C. for 30 min, then 1-fluoro-3-(trifluoromethyl)benzene (1.5 g, 9.1 mmol) in THF (5 mL) was added slowly, and the resulting mixture was stirred at this temperature for 30 min. Then a solution of propylene oxide (640 mg, 11 mmol) in THF (5 mL) was added at −78° C. The mixture was allowed to slowly warmed to rt and stirred overnight. The mixture was quenched with water (10 mL), and then extracted with EtOAc (50 mL). The organic phase was washed with brine (10 mL), and dried over anhydrous sodium sulfate. The solvent was removed under reduced pressure to yield a brown oil. The crude material was purified by silica gel chromatography using Hexane/EtOAc (80:20) as eluent to give the desired product as a yellow solid. ¹H NMR (CD₃OD, 400 MHz): δ=1.22 (d, J=6.3 Hz, 3H), 2.90-2.97 (m, 1H), 3.06-3.13 (m, 1H), 4.05-4.13 (m, 1H), 7.37-7.44 (m, 1H), 7.47 (td, J=7.9, 5.7 Hz, 1H), 7.54-7.59 (m, 1H). ¹H NMR (CDCl₃, 400 MHz): δ=1.30 (d, J=6.1 Hz, 3H), 1.41 (d, J=6.1 Hz, 1H), 2.93-3.07 (m, 1H), 4.08-4.17 (m, 1H), 7.23-7.27 (m, 1H), 7.29 (s, 1H), 7.30-7.37 (m, 1H), 7.48 (d, J=7.8 Hz, 1H).

Example 442

7-[1-(4-Bromo-2,6-dichlorophenyl)ethoxy]-3-(1-piperidin-4-yl-1H-pyrazol-4-yl)furo[3,2-c]pyridin-6-ylamine

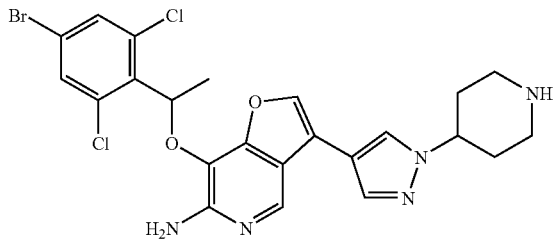

The title compound was prepared according to General Procedure DD. MS (ES$^+$): m/z 550.05/552.10/554.05 [MH$^+$]. HPLC: $t_R$=0.70 min (HPLC-ACQUITY, Analytical).

1-(4-Bromo-2,6-dichlorophenyl)ethanol

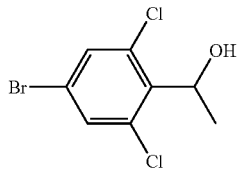

The title compound was prepared from 4-bromo-2,6-dichlorobenzaldehyde (prepared according to WO 2008/021851) by reaction with methylmagnesium bromide following the procedure for 1-(3-bromo-5-fluorophenyl)ethanol as described.

Example 443

7-[1-(6-Bromo-2-chloro-3-fluorophenyl)ethoxy]-3-(1-piperidin-4-yl-1H-pyrazol-4-yl)furo[3,2-c]pyridin-6-ylamine

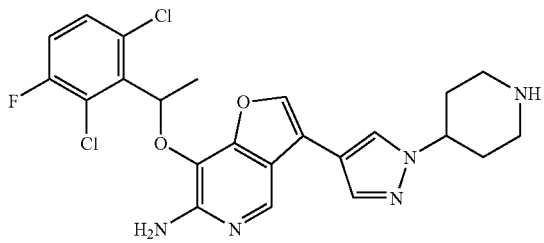

The title compound was prepared according to General Procedure DD. MS (ES$^+$): m/z 534.09/536.11 [MH$^+$]. HPLC: $t_R$=0.64 min (HPLC-ACQUITY, Analytical).

1-(6-Bromo-2-chloro-3-fluorophenyl)ethanol

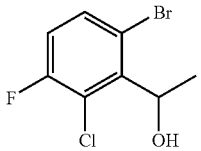

To a solution of 1.5 M of lithium diisopropylamide in cyclohexane (4.0 mL, 1.2 eq) in THF (5 mL), cooled to −78° C., 4-bromo-2-chloro-1-fluorobenzene (4.77 mmol, 1 eq) in THF (2 mL) was added dropwise under nitrogen and the resulting mixture was stirred at −78° C. for 1 h. A solution of acetaldehyde (354.5 mg, 8.047 mmol, 1.7 eq) in THF (1.5 mL) was then added dropwise at −78° C., after which the reaction was slowly warmed to rt (over 1.5 h). The mixture was quenched with water and diluted with EtOAc. The organic layer was separated, washed with brine, dried over anhydrous Na$_2$SO$_4$, filtered, and concentrated in vacuo. The crude material was adsorbed onto Hydromatrix and purified by silica gel chromatography (0.5"×10" glass column, eluting with EtOAc:Heptane 5:95→10:90→1:1). Fractions containing product were combined and concentrated in vacuo and was shown to contain a mixture of two regioisomers. The crude mixture was dissolved in MeOH (2 mL) and DMF (2 mL), syringe filtered, and purified by MDPS (separated by UV retention times, using formic acid conditions). The desired regioisomer fractions were pooled and evaporated using the SpeedVac to yield the desired title material. $^1$H NMR (400 MHz, CDCl$_3$) δ=1.65 (d, J=6.8 Hz, 3H), 2.66 (br s, 1H), 5.57 (q, J=6.8 Hz, 1H), 6.97 (dd, J=8.8, 8.1 Hz, 1H), 7.47 (dd, J=8.8, 5.1 Hz, 1H). MS (ES$^+$): m/z 278.02/280.13 [MNa$^+$]. HPLC: $t_R$=3.28 min (ZQ3, polar_5 min).

General Procedure JJ: To a solution of 4-[4-(7-Hydroxy-6-nitrofuro[3,2-c]pyridin-3-yl)-pyrazol-1-yl]piperidine-1-carboxylic acid tert-butyl ester (Intermediate 12) (15.0 mg, 0.0349 mmol), 1-(3-Bromophenyl)ethanol or 1-(3-Bromo-5-fluorophenyl)ethanol (0.105 mmol), and PPh$_3$ (18.3 mg, 0.0699 mmol) in THF (1.0 mL, 12 mmol) under nitrogen was added dropwise diisopropyl azodicarboxylate (12.7 mg, 0.0629 mmol), and the mixture was stirred at room temperature for 2 h. THF was evaporated by a stream of nitrogen, and ethanol (1.0 mL, 17 mmol) and iron (19.5 mg, 0.349 mmol) were added. 1 drop of 12M aq. HCl was added and the mixture was stirred at 70° C. for 30 minutes. The iron powder was taken out with the stirring bar. The mixture was passed through SCX-2 SPE and released by 2M NH$_3$ in methanol. The solution containing released intermediate was dried in vacuo and boronic acid or ester (0.476 mmol), potassium carbonate (9.9 mg, 0.0714), dioxane (0.9 mL), water (0.3 mL) and 1,1'-bis(diphenylphosphino)ferrocene]dichloropalladium(II), complex with dichloromethane (1:1) (1 mg, 0.001 mmol, 0.05 eq.) were added. The mixture was heated at 100° C. for 30 minutes in a microwave reactor. The crude was passed through a thiol-SPE cartridge to remove palladium and extracted with DCM and brine. The DCM layer was dried in vacuo and 1.0M HCl in ether was added to remove Boc group in 2 hours at room temperature. The crude was passed through a SCX-2 SPE cartridge, washed with methanol and released by 2 M NH$_3$ in methanol. The solution was dried and dissolved in DMSO for MDP purification to give the final compounds.

Example 444

7-(1-Biphenyl-3-ylethoxy)-3-(1-piperidin-4-yl-1H-pyrazol-4-yl)furo[3,2-c]pyridin-6-ylamine

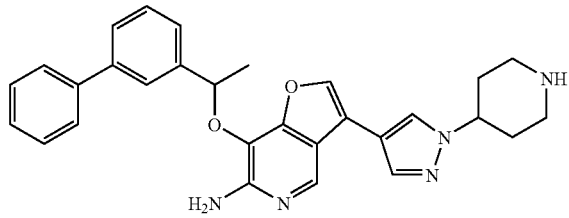

The title compound was prepared according to General Procedure JJ. MS (ES$^+$): m/z 480.34 (100) [MH$^+$]. HPLC: $t_R$=0.64 min (HPLC-ACQUITY, Analytical). $^1$H NMR (400 MHz, CD$_3$OD) δ=1.77 (d, J=6.3 Hz, 3H), 2.80 (td, J=12.6, 2.1 Hz, 2H), 3.23 (d, J=12.9 Hz, 2H), 4.31-4.40 (m, 1H), 5.98 (q, J=6.4 Hz, 1H), 7.28-7.36 (m, 2H), 7.39 (t, J=7.6 Hz, 3H), 7.46 (dd, J=7.6, 1.5 Hz, 1H), 7.52-7.57 (m, 2H), 7.69 (s, 1H), 7.80 (d, J=3.5 Hz, 2H), 8.06 (d, J=8.6 Hz, 2H).

Example 445

3-(1-Piperidin-4-yl-1H-pyrazol-4-yl)-7-{1-[3-(1H-pyrrol-2-yl)phenyl]ethoxyfuro[3,2-c]pyridin-6-ylamine

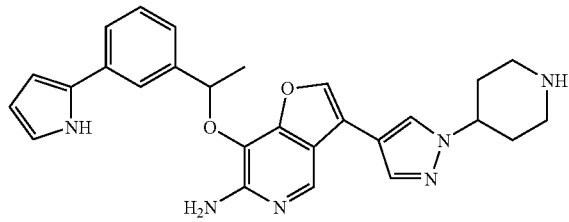

The title compound was prepared according to General Procedure JJ. MS (ES$^+$): m/z 469.38 (100) [MH$^+$]. HPLC: $t_R$=0.43 min (HPLC-ACQUITY, Analytical).

Example 446

3-(1-Piperidin-4-yl-1H-pyrazol-4-yl)-7-{1-[3-(2H-pyrazol-2-yl)phenyl]ethoxyfuro[3,2-c]pyridin-6-ylamine

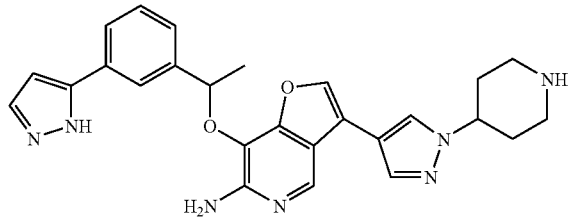

The title compound was prepared according to General Procedure JJ. MS (ES$^+$): m/z 470.36 (100) [MH$^+$]. HPLC: $t_R$=0.35 min (HPLC-ACQUITY, Analytical).

Example 447

3-(1-Piperidin-4-yl-1H-pyrazol-4-yl)-7-{1-[3-(1H-pyrazol-4-yl)phenyl]ethoxyfuro[3,2-c]pyridin-6-ylamine

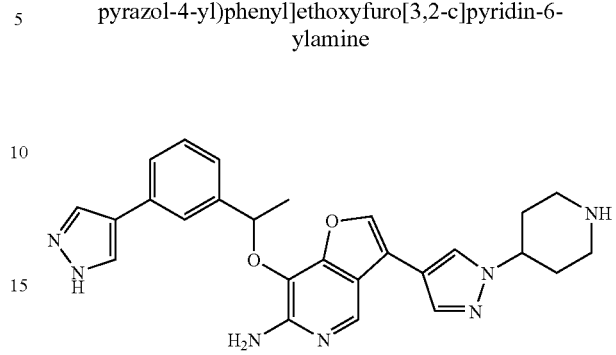

The title compound was prepared according to General Procedure JJ. MS (ES$^+$): m/z 470.33 (100) [MH$^+$]. HPLC: $t_R$=0.48 min (HPLC-ACQUITY, Analytical).

Example 448

7-{1-[3-(1-Methyl-1H-pyrazol-4-yl)phenyl]ethoxy}-3-(1-piperidin-4-yl-1H-pyrazol-4-yl)furo[3,2-c]pyridin-6-ylamine

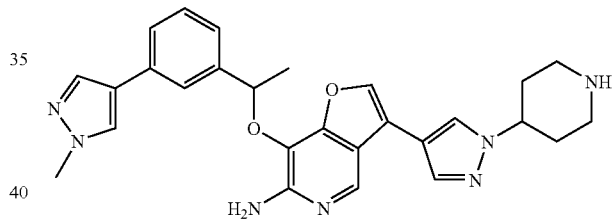

The title compound was prepared according to General Procedure JJ. MS (ES$^+$): m/z 484.11 (100) [MH$^+$]. HPLC: $t_R$=0.51 min (HPLC-ACQUITY, Analytical).

Example 449

7-[1-(5-Fluorobiphenyl-3-yl)ethoxy]-3-(1-piperidin-4-yl-1H-pyrazol-4-yl)furo[3,2-c]pyridin-6-ylamine

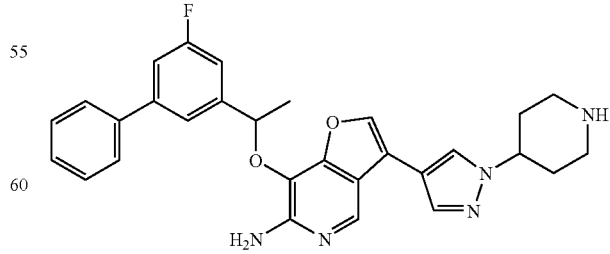

The title compound was prepared according to General Procedure JJ. MS (ES$^+$): m/z 498.34 (100) [MH$^+$]. HPLC: $t_R$=0.67 min (HPLC-ACQUITY, Analytical).

Example 450

7-{1-[3-Fluoro-5-(2H-pyrazol-3-yl)phenyl]ethoxy}-3-(1-piperidin-4-yl-1H-pyrazol-4-yl)furo[3,2-c]pyridin-6-ylamine

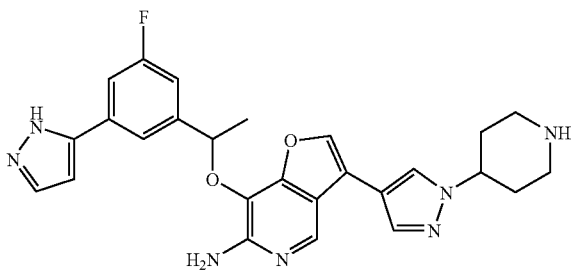

The title compound was prepared according to General Procedure JJ. MS (ES⁺): m/z 488.33 (100) [MH⁺]. HPLC: $t_R$=0.50 min (HPLC-ACQUITY, Analytical).

Example 451

7-{1-[3-Fluoro-5-(1H-pyrazol-4-yl)phenyl]ethoxy}-3-(1-piperidin-4-yl-1H-pyrazol-4-yl)furo[3,2-c]pyridin-6-ylamine

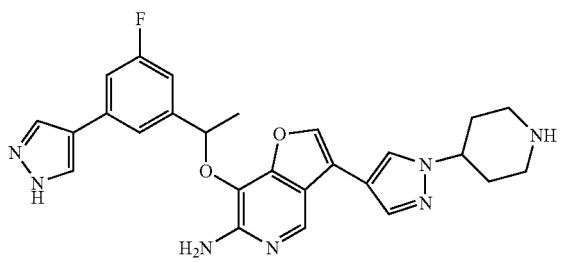

The title compound was prepared according to General Procedure JJ. MS (ES⁺): m/z 488.31 (100) [MH⁺]. HPLC: $t_R$=0.50 min (HPLC-ACQUITY, Analytical).

Example 452

7-{1-[3-Fluoro-5-(1-methyl-1H-pyrazol-4-yl)phenyl]ethoxy}-3-(1-piperidin-4-yl-1H-pyrazol-4-yl)furo[3,2-c]pyridin-6-ylamine

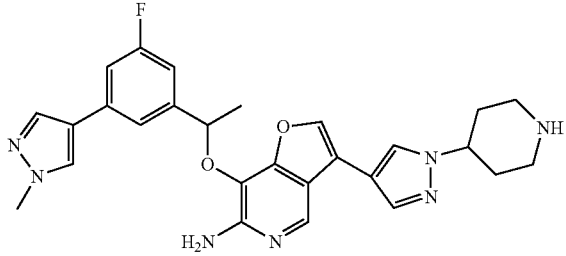

The title compound was prepared according to General Procedure JJ. MS (ES⁺): m/z 502.33 (100) [MH⁺]. HPLC: $t_R$=0.52 min (HPLC-ACQUITY, Analytical).

Example 453

3-Bromo-7-(1-methyl-2-phenylethoxy)furo[3,2-c]pyridin-6-ylamine

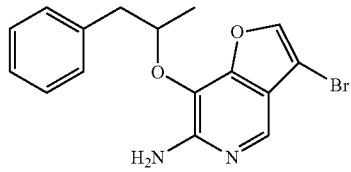

3-Bromo-6-nitrofuro[3,2-c]pyridin-7-ol (Intermediate 10) was reacted with racemic 1-phenylpropan-2-ol following the procedure described for Intermediate 8. The resulting intermediate was reacted with iron/HCl as described in Example 2 to give the title compound. MS (ES⁺): m/z 347.22/349.23 (100/99) [MH⁺]. HPLC: $t_R$=0.81 min (HPLC-ACQUITY, Analytical). ¹H NMR (400 MHz, CD₃OD): δ=1.32 (d, J=6.1 Hz, 3H), 2.93 (dd, J=13.5, 6.2 Hz, 1H), 3.10 (dd, J=13.6, 6.6 Hz, 1H), 4.98 (m, 1H), 7.13-7.21 (m, 1H), 7.25 (d, J=4.3 Hz, 4H), 7.70 (s, 1H), 7.82 (s, 1H).

Example 454

7-[(R)-1-(2,6-Dichloro-3-fluorophenyl)ethoxy]-3-(1-methyl-1H-imidazol-4-yl)-furo[3,2-c]pyridin-6-ylamine

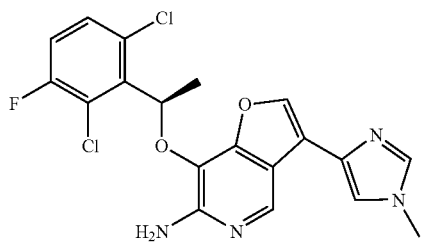

The title compound was prepared following the procedure for Example 135, using 1-methyl-4-(tributylstannanyl)-1H-imidazole prepared according to WO 2007/062288. MS (ES⁺): m/z 420.89/422.89/424.91 (100/70/12) [MH⁺]. HPLC: $t_R$=2.44 min (polar_5 min, ZQ3).

Intermediate 13: tert-Butyl 4-(7-(1-(2,6-dichloro-3-fluorophenyl)ethoxy)-6-nitrofuro[3,2-c]pyridin-3-yl)-5,6-dihydropyridine-1-(2H)-carboxylate

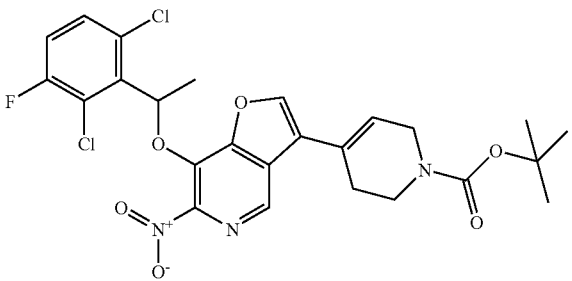

A mixture of 7-(1-(2,6-Dichloro-3-fluorophenyl)ethoxy)-3-bromo-6-nitrofuro[3,2-c]pyridine (12.6 g, 28.1 mmol), tert-butyl 5,6-dihydro-4-(4,4,5,5-tetramethyl-1,3,2-dioxaborolan-2-yl)pyridine-1(2H)-carboxylate (9.56 g, 30.9 mmol) and dioxane/water (4:1, 120 mL/30 mL) in a 500-mL round-bottom flask was stirred and degassed with nitrogen for 15 min. To the solution, Pd(PPh$_3$)$_2$Cl$_2$ (400 mg, 0.57 mmol) was added followed by potassium carbonate (5.82 g, 42.19 mmol) was added and degassed with nitrogen for another 5 min. The mixture was heated at 90-95° C. for 2.5 h. TLC (5% methanol in dichloromethane) indicated completion of the reaction. The mixture was cooled to RT, and solvent was removed on rotary evaporator. To the residue, water (60 mL) and dichloromethane (150 mL) were added. The organic layer was separated and the aqueous layer was extracted with dichloromethane (2×60 mL). All organic layers were combined and washed with brine solution (60 mL), dried over anhydrous sodium sulfate, filtered and concentrated under reduced pressure. The residue was purified by column chromatography on silica gel eluting with 1:1 ethyl acetate and dichloromethane to give the title compound. $^1$H NMR (CDCl$_3$, 300 MHz): δ=1.45 (s, 9H), 1.95 (d, J=6.6 Hz, 3H), 2.45 (brs, 2H), 3.62 (t, J=6.0 Hz, 2H), 4.18 (t, J=3.0 Hz, 2H), 6.25 (brs, 1H), 6.63 (t, J=6.0 Hz, 1H), 7.05 (m, 1H), 7.21 (m, 1H), 7.69 (s, 1H), 8.60 (s, 1H).

Intermediate 14: tert-Butyl 5,6-dihydro-4-(7-hydroxy-6-nitrofuro[3,2-c]pyridin-3-yl)pyridine-1(2H) carboxylate

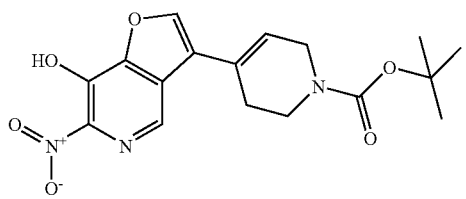

A mixture of tert-Butyl 4-(7-(1-(2,6-dichloro-3-fluorophenyl)ethoxy)-6-nitrofuro[3,2-c]pyridin-3-yl)-5,6-dihydropyridine-1-(2H)-carboxylate (Intermediate 13, 12.5 g, 22.7 mmol) and 48% aqueous hydrobromic acid solution was placed in a three necked RB flask (500 mL). The resultant mixture was heated at 55-60° C. for 24 h. At this point the TLC (5% MeOH in DCM) indicated that the reaction was complete. The reaction mixture was cooled to RT and evaporated to dryness under reduced pressure. The residue was washed several times with dichloromethane (until TLC indicated the absence of 1-(2,6-dichloro-3-fluorophenyl)ethanol in the DCM washings) and dried on rotary evaporator. The residue {3-(1,2,3,6-Tetrahydropyridin-4-yl)-6-nitrofuro[3,2-c]pyridine-7-ol hydrobromide salt} was used as such in the next step.

A solution of 3-(1,2,3,6-tetrahydrophyridin-4-yl)-6-nitrofuro[3,2-c]pyridine-7-ol hydrobromide salt (9.55 g, 19.9 mmol) in water (160 mL) was placed in a two necked RB flask (1 L). An aqueous sodium carbonate solution (7.25 g, 68.4 mmol) was added until the pH of the suspension reached ≈9-10. The suspension was cooled to 5-10° C., a solution of (Boc)$_2$O (14.84 g, 68.06 mmol) in dioxane (150 mL) was added slowly through a dropping funnel, and the reaction mixture was stirred overnight at RT. Aliquot portion was drawn and acidified with an aqueous NaHSO$_4$ solution and the TLC (30% ethyl acetate in hexane) indicated that the reaction was complete. The reaction mixture was concentrated to dryness under reduced pressure at 40-50° C. To the residue, water was added and carefully neutralized with an aqueous 20% NaHSO$_4$ solution to pH≈7.5-8.5. The precipitate was collected and redissolved in DCM and water, stirred for 15-20 min. The organic layer was separated and was evaporated. The residue was dissolved in water, the pH was adjusted to ≈2 by adding dilute aq. HCl, and the precipitate was filtered off and dried in vacuo to give the title compound as yellow solid. $^1$H NMR (CDCl$_3$, 300 MHz): δ=1.45 (s, 9H), 2.53 (br s, 2H), 3.70 (q, J=5.7 Hz, 2H), 4.16 (d, J=2.7 Hz, 2H), 6.29 (br s, 1H), 7.89 (s, 1H), 8.61 (s, 1H).

Example 455

4-{6-Amino-7-[1-(2,6-dichloro-3-fluorophenyl)ethoxy]furo[3,2-c]pyridin-3-yl}-3,6-dihydro-2H-pyridine-1-carboxamide

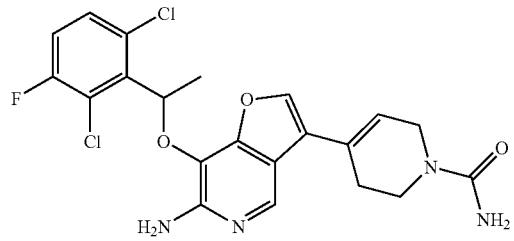

To a solution of tert-butyl 4-(7-hydroxy-6-nitrofuro[3,2-c]pyridin-3-yl)-3,6-dihydro-2H-pyridine-1-carboxylate (Intermediate 14) (20.0 mg, 0.0553 mmol), 1-(2,6-dichloro-3-fluorophenyl)ethanol (34.7 mg, 0.166 mmol), and PPh$_3$ (43.6 mg, 0.166 mmol) in THF (1.0 mL, 12 mmol) under nitrogen was added dropwise diisopropyl azodicarboxylate (22.4 mg, 0.111 mmol), and the mixture was heated at 40° C. overnight. THF was evaporated, and iron powder (30.9 mg, 0.553 mmol), ethanol (1.5 mL, 26 mmol) and 1 drop of aq. 12 M HCl were added. The mixture was stirred at 70° C. for 20 minutes. Iron was taken out by stirring bar. 5 drops of aq. 12 M HCl were added, and the mixture was stirred at 70° C. for 2 h, passed through SCX-2 SPE cartridge and eluted by 2 M NH$_3$ in methanol. This material was completely dried in vacuo overnight. Trimethylsilyl isocyanate (11.2 μL, 0.0830 mmol), DMF (1.0 mL, 13 mmol) and DIPEA (19.3 μL, 0.111 mmol) were added, and the mixture was stirred at room temperature for 1 h. The reaction mixture was filtered and purified using the MDPS to give the title compound. MS (ES$^+$): m/z 465.16/467.18 [MH$^+$]. HPLC: t$_R$=0.72 min (HPLC-ACQUITY, Analytical). $^1$H NMR (400 MHz, CD$_3$OD): δ=1.88 (d, J=6.8 Hz, 3H), 2.45-2.56 (m, 2H), 3.64 (t, J=5.8 Hz, 2H), 4.10 (d, J=2.5 Hz, 2H), 6.26 (br. s., 1H), 6.50 (q, J=6.8 Hz, 1H), 7.22 (t, J=8.7 Hz, 1H), 7.40 (dd, J=9.0, 4.9 Hz, 1H), 7.66 (s, 1H), 8.19 (br. s., 1H).

Example 456

4-{6-Amino-7-[(S)-1-(2,6-dichloro-3-fluorophenyl)ethoxy]furo[3,2-c]pyridin-3-yl}-3,6-dihydro-2H-pyridine-1-carboxamide

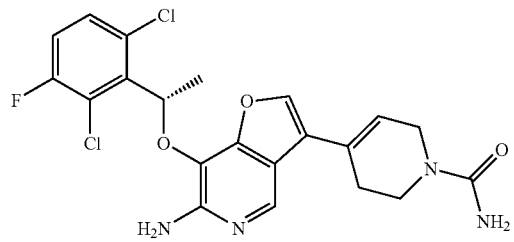

The title compound was prepared following the procedure for Example 455, using (S)-1-(2,6-dichloro-3-fluorophenyl)ethanol. $^1$H NMR spectrum and LC/MS match those of Example 455.

Example 457

4-{6-Amino-7-[1-(6-bromo-2-chloro-3-fluorophenyl)ethoxy]furo[3,2-c]pyridin-3-yl}-3,6-dihydro-2H-pyridine-1-carboxamide

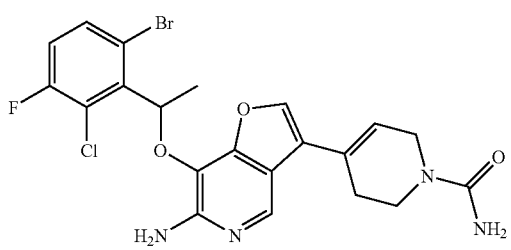

The title compound was prepared following the procedure for Example 455, using 1-(6-bromo-2-chloro-3-fluorophenyl)ethanol. MS (ES+): m/z 509.11/511.12 [MH+]. HPLC: $t_R$=0.74 min (HPLC-ACQUITY, Analytical).

Example 458

4-{6-Amino-7-[1-(2-bromo-6-chloro-3-fluorophenyl)ethoxy]furo[3,2-c]pyridin-3-yl}-3,6-dihydro-2H-pyridine-1-carboxamide

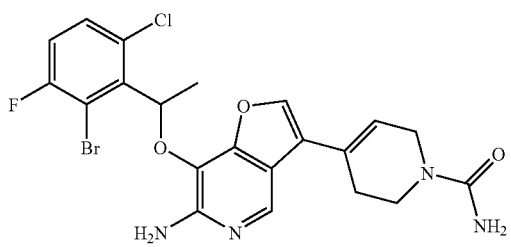

The title compound was prepared following the procedure for Example 455, using 1-(2-bromo-6-chloro-3-fluorophenyl)ethanol. MS (ES+): m/z 509.17/511.15/513.16 [MH+]. HPLC: $t_R$=0.73 min (HPLC-ACQUITY, Analytical).

1-(2-Bromo-6-chloro-3-fluorophenyl)ethanol

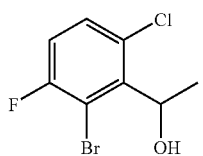

Starting from 2-bromo-4-chloro-1-fluorobenzene, the procedure for 1-(6-bromo-2-chloro-3-fluorophenyl)ethanol was followed, except column chromatography required a less polar solvent system for product elution (CH$_2$Cl$_2$:Heptane 3:1→1:0→neat EtOAc). Additionally, preparative TLC purification was also required to obtain pure product. $^1$H NMR (400 MHz, CDCl$_3$) δ=1.65 (d, J=6.8 Hz, 3H), 2.98 (br s, 1H), 5.59 (q, J=6.8 Hz, 1H), 7.01 (dd, J=8.7, 7.5 Hz, 1H), 7.32 (dd, J=8.7, 4.9 Hz, 1H). MS (ES+): m/z 275.99/277.96 [MNa+]. HPLC: $t_R$=3.23 min (ZQ3, polar_5 min).

Example 459

4-(6-Amino-7-{[1-(2,6-dichloro-3-fluorophenyl)but-3-yn-1-yl]oxy}furo[3,2-c]pyridin-3-yl)-3,6-dihydropyridine-1(2H)-carboxamide

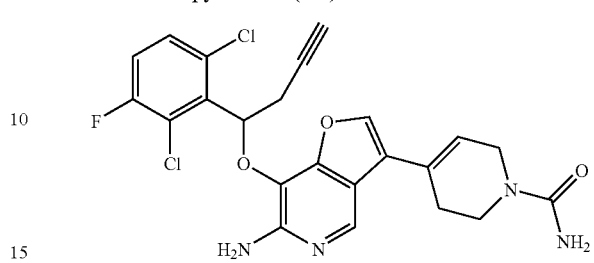

The title compound was prepared following the procedure for Example 455, using 1-(2,6-dichloro-3-fluorophenyl)but-3-yn-1-ol. MS (ES+): m/z 489.20/491.18 [MH+]. HPLC: $t_R$=0.73 min (HPLC-ACQUITY, Analytical).

Example 460

4-{6-Amino-7-[1-(2-chloro-3-fluoro-6-methoxyphenyl)ethoxy]furo[3,2-c]pyridin-3-yl}-3,6-dihydro-2H-pyridine-1-carboxamide

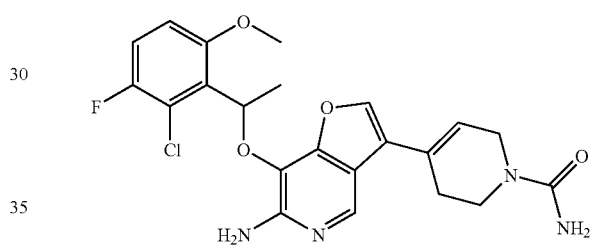

The title compound was prepared following the procedure for Example 455, using 1-(2-chloro-3-fluoro-6-methoxyphenyl)ethanol. MS (ES+): m/z 509.17/511.15 [MH+].

Example 461

1-(4-Fluorophenyl)-2-oxo-1,2-dihydropyridine-3-carboxylic acid [4-(6-aminofuro[3,2-c]pyridin-7-yloxymethyl)phenyl]amide

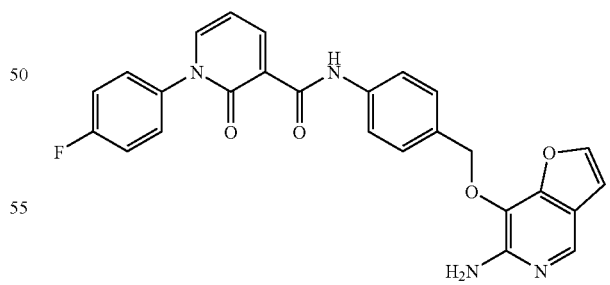

The mixture of 1-(4-fluorophenyl)-2-oxo-1,2-dihydropyridine-3-carboxylic acid [4-(6-nitrofuro[3,2-c]pyridin-7-yloxymethyl)phenyl]amide (13.8 mg, 0.0248 mmol), iron powder (62 mg, 1.1 mmol), EtOH (1.5 ml), 1,2-Dichloroethane (1.5 ml), and saturated NH$_4$Cl (0.3 ml) was heated at 75° C. for 30 min. After that time, the solvent was removed, and it was then dissolved in DMSO for Gilson HPLC purification. It gave the title compound as a light-yellow solid. $^1$H NMR (400 MHz, CDCl$_3$): δ=4.55 (brs, 2H), 5.35 (s, 2H), 6.60 (dd, J=6.8 & 7.2 Hz, 1H), 6.68 (d, J=2.4 Hz, 1H), 7.24-7.29 (m, 2H), 7.38-7.43 (m, 4H), 7.43 (d, J=2.4 Hz, 1H), 7.60 (dd, J=2.0 & 6.8 Hz, 1H), 7.73 (dd, J=2.0 & 6.4 Hz, 2H), 8.07 (s, 1H), 8.75 (dd, J=2.0 & 6.8 Hz, 1H), 11.85 (brs, 1H). MS (ES$^+$): m/z 471.05 [MH$^+$]. HPLC: t$_R$=2.60 min (polar_5 min, ZQ3).

1-(4-Fluorophenyl)-2-oxo-1,2-dihydropyridine-3-carboxylic acid [4-(6-nitrofuro[3,2-c]pyridin-7-yloxymethyl)phenyl]amide

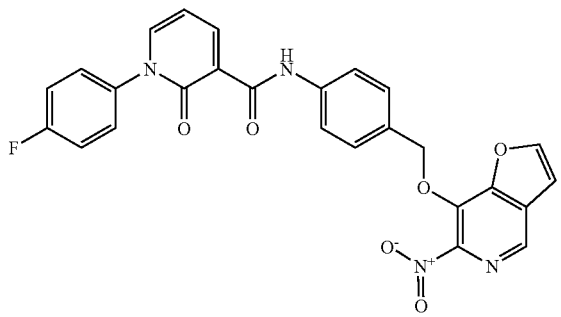

Into a DMF (1.5 ml) suspension of NaH (11.0 mg, 60% suspension in oil, 0.275 mmol), which was cooled at 0° C. under an atmosphere of nitrogen, was added the DMF (1.5 ml) solution of 6-nitrofuro[3,2-c]pyridin-7-ol (Intermediate 7) (45.1 mg, 0.248 mmol) dropwise. The mixture was stirred at 0° C. for 5 min and was then raised to rt and stirred at rt for 30 min. Then this reaction mixture was added dropwise into the DMF (4 ml) suspension of 1-(4-fluorophenyl)-2-oxo-1,2-dihydropyridine-3-carboxylic acid (4-bromomethylphenyl)-amide (0.248 mmol) at rt under an atmosphere of nitrogen. The combined mixture was stirred at rt for 1 h. After that time, the reaction mixture was poured into water. The solid was filtered off and washed with water to give a beige solid. It was triturated with EtOAc (4 ml). The solid was filtered off and the mother liquor was purified by TLC eluting with 2.5% MeOH/DCM 2 times to give the title compound as a yellow solid. $^1$H NMR (400 MHz, CDCl$_3$): δ=5.58 (s, 2H), 6.59 (dd, J=6.8 & 7.2 Hz, 1H), 6.96 (d, J=2.4 Hz, 1H), 7.23-7.29 (m, 2H), 7.38-7.45 (m, 4H), 7.60 (dd, J=2.0 & 4.8 Hz, 1H), 7.73 (dd, J=2.4 & 6.8 Hz, 2H), 7.88 (d, J=2.0, 1H), 8.44 (s, 1H), 8.73 (dd, J=2.4 & 6.8 Hz, 1H), 11.84 (brs, 1H). MS (ES$^+$): m/z 500.99 [MH$^+$]. HPLC: t$_R$=3.58 min (polar_5 min, ZQ3).

1-(4-Fluorophenyl)-2-oxo-1,2-dihydropyridine-3-carboxylic acid (4-bromo-methylphenyl)amide

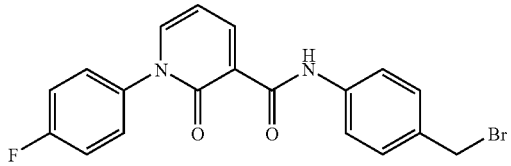

The mixture of 1-(4-fluorophenyl)-2-oxo-1,2-dihydropyridine-3-carboxylic acid p-tolylamide (183 mg, 0.482 mmol), NBS (108 mg, 0.603 mmol) and 2,2'-Azo-bis-isobutyronitrile (8.08 mg, 0.0482 mmol) in carbon tetrachloride (5 ml, 50 mmol) was heated at 80° C. under an atmosphere of nitrogen for 24 h. After that time, the mixture was filtered to give the title compound as a beige solid that was used for further reaction without purification. MS (ES$^+$): m/z 400.92/402.96 [MH$^+$]. HPLC: t$_R$=3.66 min (polar_5 min, ZQ3).

1-(4-Fluorophenyl)-2-oxo-1,2-dihydropyridine-3-carboxylic acid p-tolylamide

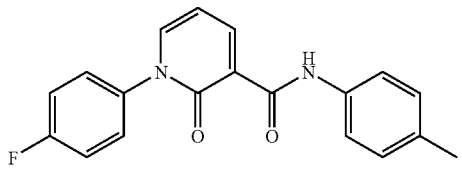

TBTU (276 mg, 0.851 mmol) was added to the mixture of 1-(4-fluorophenyl)-2-oxo-1,2-dihydropyridine-3-carboxylic acid (147 mg, 0.567 mmol), p-toluidine (73.7 mg, 0.681 mmol), and triethylamine (120 µl, 0.851 mmol) in DMF (3 ml) at rt. The combined mixture was stirred at rt for 16 h. After that time, the solvent was removed to give a black solid (500 mg). It was purified by chromatography on silica gel (15 g) eluting with 40% (100 ml), 50% (100 ml), 60% (100 ml) and 70% (100 ml) EtOAc/hexane to give the title compound as a light-brown solid. $^1$H NMR (400 MHz, CDCl$_3$): δ=2.31 (s, 3H), 6.58 (dd, J=6.8 & 7.2 Hz, 1H), 7.13 (d, J=8.4 Hz, 2H), 7.23-7.29 (m, 2H), 7.38-7.42 (m, 2H), 7.56-7.63 (m, 3H), 8.74 (dd, J=2.0 & 6.8 Hz, 1H), 11.69 (brs, 1H). MS (ES$^+$): m/z 323.09 [MH$^+$]. HPLC: t$_R$=3.69 min (polar_5 min, ZQ3).

Example 462

5-{4-[6-Amino-3-(1-piperidin-4-yl-1H-pyrazol-4-yl)-furo[3,2-c]pyridin-7-yloxymethyl]-phenyl}-2-benzyl-3-methyl-3H-pyrimidin-4-one

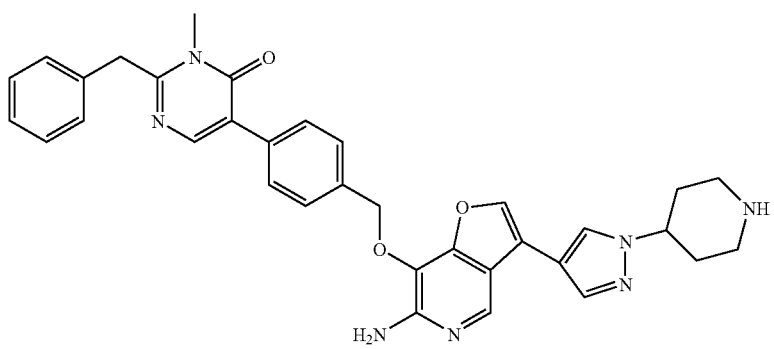

The title compound was prepared according to General Procedure AA. $^1$H NMR (400 MHz, CD$_3$OD): δ=2.25-2.40 (m, 4H), 3.17-3.27 (m, 2H), 3.55-3.62 (m, 2H), 3.65 (s, 3H), 4.18 (s, 2H), 4.61 (td, J=9.5, 4.0 Hz, 1H), 5.48 (s, 2H), 7.27-7.39 (m, 5H), 7.54 (d, J=8.1 Hz, 2H), 7.66 (d, J=8.1 Hz, 2H), 7.86 (s, 1H), 7.89 (d, J=1.8 Hz, 2H), 8.12 (d, J=4.3 Hz, 2H). MS (ES$^+$): m/z 588.17 (100) [MH$^+$]. HPLC: $t_R$=2.15 min (ZQ3, polar_5 min).

Example 463

5-{4-[6-Amino-3-(1-piperidin-4-yl-1H-pyrazol-4-yl)-furo[3,2-c]pyridin-7-yloxymethyl]-3-fluorophenyl}-2-benzyl-3-methyl-3H-pyrimidin-4-one

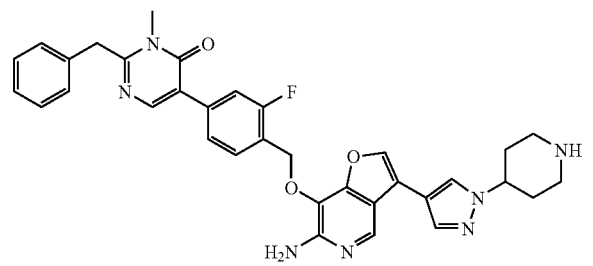

The title compound was prepared according to General Procedure AA. $^1$H NMR (400 MHz, CD$_3$OD): δ=2.26-2.39 (m, 4H), 3.16-3.25 (m, 2H), 3.53-3.61 (m, 2H), 3.65 (s, 3H), 4.17 (s, 2H), 4.60 (dt, J=9.9, 4.9 Hz, 1H), 5.50 (s, 2H), 7.26-7.37 (m, 5H), 7.45-7.49 (m, 1H), 7.51-7.59 (m, 2H), 7.85 (s, 1H), 7.88 (s, 1H), 7.97 (s, 1H), 8.11 (s, 1H), 8.14 (s, 1H). MS (ES$^+$): m/z 606.13 (100) [MH$^+$]. HPLC: $t_R$=2.19 min (ZQ3, polar_5 min).

General Procedure KK: To a mixture of 3-Bromo-6-nitro-furo[3,2-c]pyridin-7-ol or 6-nitrofuro[3,2-c]pyridin-7-ol (0.056 mmol), alcohol (0.11 mmol), PPh$_3$ (43.7 mg, 0.166 mmol) and THF (1.0 mL, 12 mmol) under nitrogen was added dropwise diisopropyl azodicarboxylate (22.4 mg, 0.111 mmol), and the mixture was stirred at room temperature overnight. THF was evaporated. Iron powder (4.31 mg, 0.0772 mmol), ethanol (1.0 mL, 17 mmol) and 1 drop of 12 M of aq. HCl in H$_2$O (20 μL) were added. The mixture was stirred at 70° C. for 30 minutes. The mixture was passed through SCX-2 SPE, washed with methanol and released by 2 M NH$_3$ in methanol. The solvent was dried and dissolved in DMSO for MDP purification.

Example 464

3-Bromo-7-(1-methyl-2-phenylethoxy)furo[3,2-c]pyridin-6-ylamine

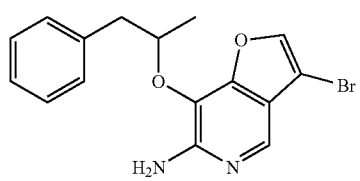

The title compound was prepared according to General Procedure KK. MS (ES$^+$): m/z 347.22/349.23 (100/99) [MH$^+$]. HPLC: $t_R$=0.81 min (HPLC-ACQUITY, Analytical). $^1$H NMR (400 MHz, CD$_3$OD): δ=1.32 (d, J=6.1 Hz, 3H), 2.93 (dd, J=13.5, 6.2 Hz, 1H), 3.10 (dd, J=13.6, 6.6 Hz, 1H), 4.98 (m, 1H), 7.13-7.21 (m, 1H), 7.25 (d, J=4.3 Hz, 4H), 7.70 (s, 1H), 7.82 (s, 1H).

Example 465

5-[4-(6-Amino-3-bromofuro[3,2-c]pyridin-7-yloxymethyl)phenyl]-2-benzyl-3-methyl-3H-pyrimidin-4-one

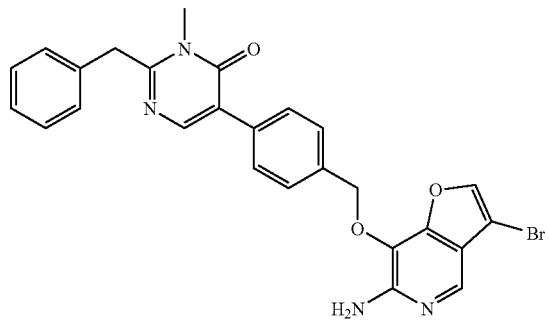

The title compound was prepared according to General Procedure KK. MS (ES$^+$): m/z 517.17/519.18 (92/100) [MH$^+$]. HPLC: $t_R$=0.69 min (HPLC-ACQUITY, Analytical).

Example 466

5-[4-(6-Amino-3-bromofuro[3,2-c]pyridin-7-yloxymethyl)-3-fluorophenyl]-2-benzyl-3-methyl-3H-pyrimidin-4-one

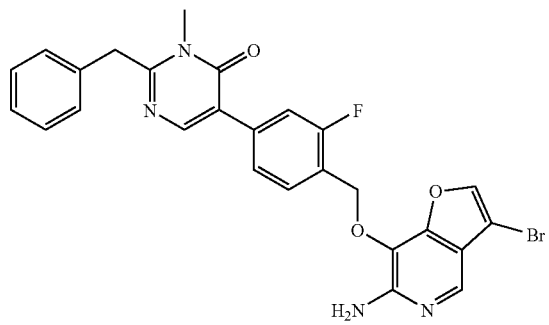

The title compound was prepared according to General Procedure KK. MS (ES$^+$): m/z 535.15/537.13 (95/100) [MH$^+$]. HPLC: $t_R$=0.74 min (HPLC-ACQUITY, Analytical).

Example 467

5-[4-(6-Aminofuro[3,2-c]pyridin-7-yloxymethyl)phenyl]-2-benzyl-3-methyl-3H-pyrimidin-4-one

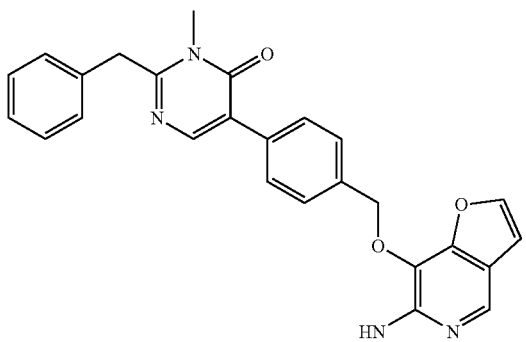

The title compound was prepared according to General Procedure KK. MS (ES⁺): m/z 439.36 (100) [MH⁺]. HPLC: $t_R$=0.53 min (HPLC-ACQUITY, Analytical). ¹H NMR (400 MHz, CD₃OD) δ=3.65 (s, 3H), 4.18 (s, 2H), 5.47 (s, 2H), 6.79 (d, J=2.0 Hz, 1H), 7.33 (m, 5H), 7.53 (d, J=8.1 Hz, 2H), 7.61-7.70 (m, 3H), 7.89 (s, 1H), 7.95 (s, 1H).

Example 468

5-[4-(6-Aminofuro[3,2-c]pyridin-7-yloxymethyl)-3-fluorophenyl]-2-benzyl-3-methyl-3H-pyrimidin-4-one

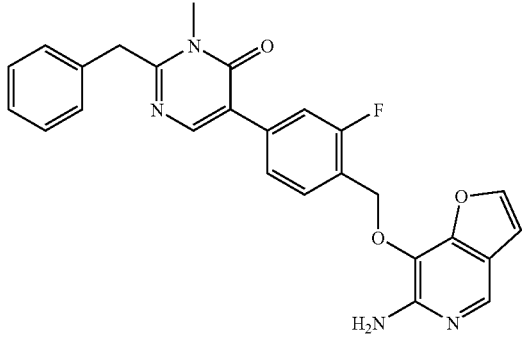

The title compound was prepared according to General Procedure KK. MS (ES⁺): m/z 457.33 (100) [MH⁺]. HPLC: $t_R$=0.55 min (HPLC-ACQUITY, Analytical).

Example 469

7-{(1R)-1-[6-(1-methyl-1H-pyrazol-4-yl)[1,2,4]triazolo[4,3-b]pyridazin-3-yl]ethoxy}-3-[1-(piperidin-4-yl)-1H-pyrazol-4-yl]furo[3,2-c]pyridin-6-amine

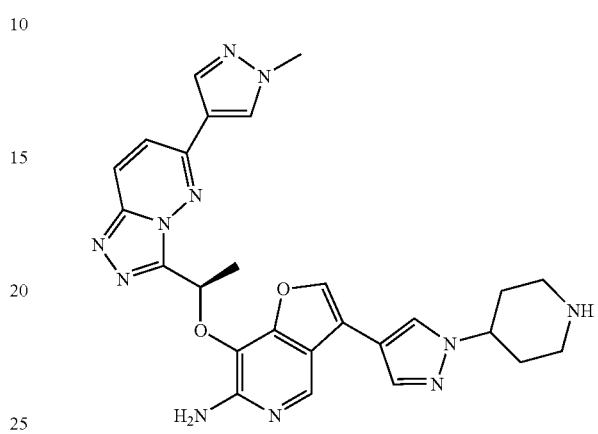

The title compound was prepared according to General Procedure AA. ¹H NMR (400 MHz, CD₃OD): δ=2.16 (d, J=6.6 Hz, 3H), 2.27-2.42 (m, 4H), 3.20-3.26 (m, 2H), 3.59 (d, J=13.4 Hz, 2H), 3.85 (s, 3H), 4.57-4.60 (m, 1H), 6.34 (q, J=6.7 Hz, 1H), 7.62 (d, J=9.9 Hz, 1H), 7.81 (s, 1H), 7.83 (s, 2H), 8.04 (d, J=5.3 Hz, 2H), 8.08 (s, 1H), 8.14 (d, J=9.6 Hz, 1H). MS (ES⁺): m/z 526.17 (100) [MH⁺]. HPLC: $t_R$=1.96 min (ZQ3, polar_5 min).

(S)-1-[6-(1-Methyl-1H-pyrazol-4-yl)-[1,2,4]triazolo[4,3-b]pyridazin-3-yl]ethanol

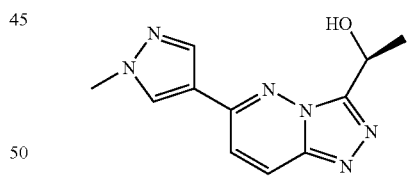

A mixture of (S)-1-(6-chloro[1,2,4]triazolo[4,3-b]pyridazin-3-yl)ethanol (30.0 mg, 0.151 mmol), 1-methyl-4-(4,4,5,5-tetramethyl-1,3,2-dioxaborolan-2-yl)-1H-pyrazole (62.8 mg, 0.302 mmol), Pd(PPh₃)₄ (20 mg, 0.02 mmol), potassium carbonate (62.6 mg, 0.453 mmol) and 4:1 dioxane:water (5 mL) was heated to 85° C. for 1 h. The organic solvent was removed in vacuo, and the material was transferred to a separatory funnel and extracted with DCM. The organic layer was dry-loaded onto silica gel, and the material was purified via column chromatography, eluting with 10% MeOH/DCM. The fractions containing the pure product were concentrated in vacuo to afford the title compound as a white solid. MS (ES⁺): m/z 245.08 (100) [MH⁺]. HPLC: $t_R$=2.00 min (ZQ3, polar_5 min).

(S)-1-(6-Chloro[1,2,4]triazolo[4,3-b]pyridazin-3-yl)ethanol

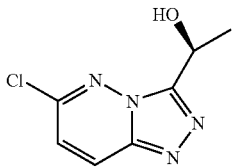

A mixture of 3-chloro-6-hydrazinopyridazine (1.44 g, 9.96 mmol), (S)-2-hydroxypropanoic acid (1.06 g, 10 mmol, i.e. L-lactic acid, 85% in water) and p-TsOH.H$_2$O (2.37 g, 12.4 mmol) in toluene was refluxed overnight. Some oil formed at the bottom of the flask. LC-MS of this oil showed the desired product was formed. Toluene was poured off, and the oil residue was suspended in water (10 mL), then basified with 3 N aq. NaOH to pH=10. This aqueous solution was extracted with EtOAc (3×30 mL), and the combined organic phases were washed with brine (20 mL), and dried over anhydrous sodium sulfate. Evaporation under reduced pressure afforded the title compound as an off-white solid. MS (ES+): 199/201 (3/1) [MH$^+$]. $^1$H NMR (400 MHz, CDCl$_3$): δ=1.88 (d, J=6.8 Hz, 3H), 2.94 (d, J=6.6 Hz, 1H, —OH), 5.51 (m, 1H), 7.15 (d, J=9.6 Hz, 1H), 8.11 (d, J=9.6 Hz, 1H).

Example 470

7-{(1R)-1-[6-(1-methyl-1H-pyrazol-4-yl) [1,2,4]triazolo[4,3-b]pyridazin-3-yl]ethoxy}furo[3,2-c]pyridin-6-amine

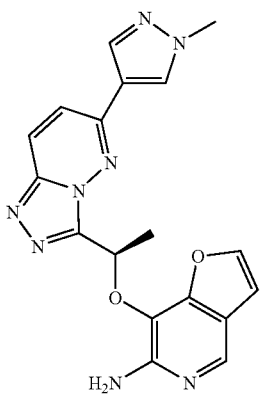

A mixture of 7-[(R)-1-(6-chloro-[1,2,4]triazolo[4,3-b]pyridazin-3-yl)-ethoxy]furo[3,2-c]pyridine-6-ylamine (15.0 mg, 0.045 mmol), 1-methyl-4-(4,4,5,5-tetramethyl-1,3,2-dioxaborolan-2-yl)-1H-pyrazole (18.9 mg, 0.091 mmol), Pd(PPh$_3$)$_4$ (5 mg, 0.004 mmol), potassium carbonate (18.8 mg, 0.136 mmol) and 4:1 dioxane:water (2 mL) was heated in a microwave reactor at 100° C. for 30 min. The solution was loaded into a SCX cartridge, washed with MeOH and ejected with 2M NH$_3$ in MeOH. The filtrate was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=2.13 (d, J=6.6 Hz, 3H), 3.96 (s, 3H), 6.33 (q, J=6.6 Hz, 1H), 6.76 (d, J=2.3 Hz, 1H), 7.56 (d, J=2.3 Hz, 1H), 7.63 (d, J=9.9 Hz, 1H), 7.85 (s, 1H), 7.93 (s, 1H), 8.08 (s, 1H), 8.13 (d, J=9.6 Hz, 1H). MS (ES$^+$): m/z 377.11 (100) [MH$^+$]. HPLC: t$_R$=1.95 min (ZQ3, polar_5 min).

7-[(1R)-1-(6-chloro[1,2,4]triazolo[4,3-b]pyridazin-3-yl)ethoxy]furo[3,2-c]pyridin-6-amine

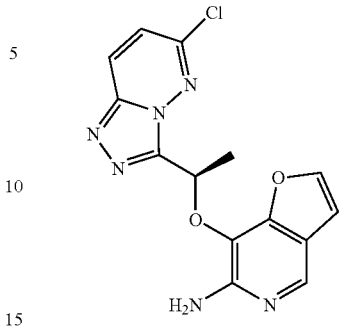

To a mixture of 6-nitrofuro[3,2-c]pyridin-7-ol (50.0 mg, 0.278 mmol), (S)-1-(6-chloro-[1,2,4]triazolo[4,3-b]pyridazin-3-yl)-ethanol (110 mg, 0.555 mmol), triphenylphosphine (191 mg, 1.11 mmol) and THF (10 mL) under nitrogen at rt was added diisopropyl azodicarboxylate (0.219 mL, 1.11 mmol) dropwise. The solution was heated to 40° C. for 2 h. The solvent was removed in vacuo, and EtOH (20 mL), iron powder (200 mg, 3 mmol) and conc. HCl (8 drops) were added. The mixture was heated to 75° C. for 1 h. The material was loaded into a SCX cartridge, washed with MeOH and ejected with 2M NH$_3$ in MeOH. The filtrate was concentrated in vacuo to afford the title compound as a dark orange solid, and was used in the next step without further purification. MS (ES$^+$): m/z 331.02 (100) [MH$^+$]. HPLC: t$_R$=1.92 min (ZQ3, polar_5 min).

Example 471

7-[(1R)-1-(6-phenyl[1,2,4]triazolo[4,3-b]pyridazin-3-yl)ethoxy]furo[3,2-c]pyridin-6-amine

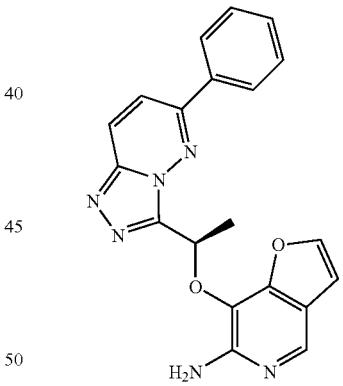

A mixture of 7-(6-chloro[1,2,4]triazolo[4,3-b]pyridazin-3-ylmethoxy)furo[3,2-c]pyridine-6-ylamine (15.0 mg, 0.047 mmol), phenylboronic acid (11.5 mg, 0.095 mmol), Pd(PPh$_3$)$_4$ (5 mg, 0.004 mmol), potassium carbonate (19.6 mg, 0.142 mmol) and 4:1 dioxane:water (2 mL) was heated in a microwave reactor at 100° C. for 30 min. The solution was loaded into a SCX cartridge, washed with MeOH and ejected with 2M NH$_3$ in MeOH. The filtrate was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=5.94 (s, 2H), 6.78 (d, J=2.3 Hz, 1H), 7.52-7.60 (m, 4H), 7.94-8.00 (m, 4H), 8.32 (d, J=9.6 Hz, 1H). MS (ES$^+$): m/z 359.04 (100) [MH$^+$]. HPLC: t$_R$=2.21 min (ZQ3, polar_5 min).

Example 472

7-{[6-(1-methyl-1H-pyrazol-4-yl) [1,2,4]triazolo[4,3-b]pyridazin-3-yl]methoxy}furo[3,2-c]pyridin-6-amine

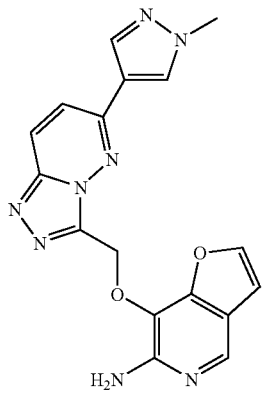

A mixture of 7-[(6-chloro[1,2,4]triazolo[4,3-b]pyridazin-3-yl)methoxy]furo[3,2-c]pyridin-6-amine (15.0 mg, 0.047 mmol), 1-methyl-4-(4,4,5,5-tetramethyl-1,3,2-dioxaborolan-2-yl)-1H-pyrazole (19.7 mg, 0.095 mmol), Pd(PPh$_3$)$_4$ (5 mg, 0.004 mmol), potassium carbonate (19.6 mg, 0.142 mmol) and 4:1 dioxane:water (2 mL) was microwaved at 100° C. for 30 min. The solution was loaded into a SCX cartridge, washed with MeOH and ejected with 2M NH$_3$ in MeOH. The filtrate was concentrated in vacuo, redissolved in MeOH (0.5 mL) and purified via HPLC. The fractions containing the pure product were concentrated in vacuo to afford the title compound as a white solid. MS (ES$^+$): m/z 363.06 (100) [MH$^+$]. HPLC: t$_R$=1.89 min (ZQ3, polar__5 min).

7-[(6-Chloro[1,2,4]triazolo[4,3-b]pyridazin-3-yl)methoxy]furo[3,2-c]pyridin-6-amine

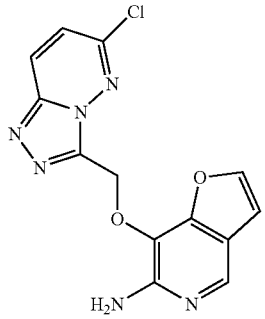

To a mixture of 6-nitrofuro[3,2-c]pyridin-7-ol (50.0 mg, 0.278 mmol), (6-chloro[1,2,4]triazolo[4,3-b]pyridazin-3-yl)methanol (102 mg, 0.555 mmol), triphenylphosphine (191 mg, 1.11 mmol) and THF (10 mL) under nitrogen at rt was added diisopropyl azodicarboxylate (0.219 mL, 1.11 mmol) dropwise. The solution was heated to 40° C. for 2 h. The solvent was removed in vacuo, and EtOH (20 mL), iron powder (200 mg, 3 mmol) and conc. HCl (8 drops) were added. The mixture was heated to 75° C. for 1 h. The material was loaded into a SCX cartridge, washed with MeOH and ejected with 2M NH$_3$ in MeOH. The filtrate was concentrated in vacuo to afford the title compound as a dark orange solid, and was used in the next step without further purification. MS (ES$^+$): m/z 317.02 (100) [MH$^+$]. HPLC: t$_R$=1.83 min (ZQ3, polar__5 min).

(6-Chloro[1,2,4]triazolo[4,3-b]pyridazin-3-yl)methanol

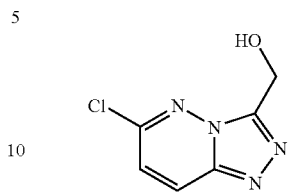

A mixture of 3-chloro-6-hydrazinopyridazine (1.44 g, 9.96 mmol), glycolic acid (0.76 g, 10 mmol) and p-TsOH.H$_2$O (2.37 g, 12.4 mmol) in toluene was refluxed overnight. Some oil formed at the bottom of the flask. LC-MS of this oil showed the desired product was formed. Toluene was decanted off, and the oil residue was suspended in water (10 mL), then basified with 3N aq. NaOH to pH=10, the resulting off-white solid was collected, and dried to give the title compound. LC-MS (ES+): 185/187 (3/1) [MH$^+$]. $^1$H NMR (CDCl$_3$): δ=2.96 (br s, 1H, —OH), 5.25 (s, 2H), 7.17 (d, J=9.6 Hz, 1H), 8.11 (d, J=9.6 Hz, 1H).

Example 473

7-[(6-phenyl[1,2,4]triazolo[4,3-b]pyridazin-3-yl)methoxy]furo[3,2-c]pyridin-6-amine

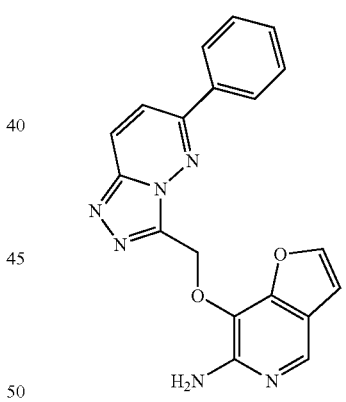

A mixture of 7-(6-chloro[1,2,4]triazolo[4,3-b]pyridazin-3-ylmethoxy]furo[3,2-c]pyridine-6-ylamine (15.0 mg, 0.047 mmol), phenylboronic acid (11.5 mg, 0.095 mmol), Pd(PPh$_3$)$_4$ (5 mg, 0.004 mmol), potassium carbonate (19.6 mg, 0.142 mmol) and 4:1 dioxane:water (2 mL) was heated in a microwave reactor at 100° C. for 30 min. The solution was loaded into a SCX cartridge, washed with MeOH and ejected with 2M NH$_3$ in MeOH. The filtrate was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=5.94 (s, 2H), 6.78 (d, J=2.3 Hz, 1H), 7.52-7.60 (m, 4H), 7.94-8.00 (m, 4H), 8.32 (d, J=9.6 Hz, 1H). MS (ES$^+$): m/z 359.04 (100) [MH$^+$]. HPLC: t$_R$=2.21 min (ZQ3, polar__5 min).

Example 474

7-{(1S)-1-[6-(1-methyl-1H-pyrazol-4-yl) [1,2,4]triazolo[4,3-b]pyridazin-3-yl]ethoxy}furo[3,2-c]pyridin-6-amine

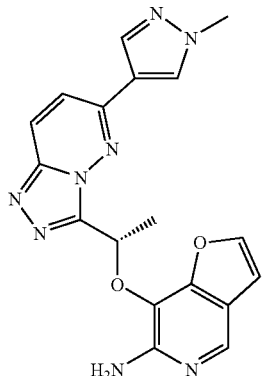

A mixture of 7-[(S)-1-(6-chloro[1,2,4]triazolo[4,3-b]pyridazin-3-yl)ethoxy]furo[3,2-c]pyridine-6-ylamine (15.0 mg, 0.045 mmol), 1-methyl-4-(4,4,5,5-tetramethyl-1,3,2-dioxaborolan-2-yl)-1H-pyrazole (18.9 mg, 0.091 mmol), Pd(PPh$_3$)$_4$ (5 mg, 0.004 mmol), potassium carbonate (18.8 mg, 0.136 mmol) and 4:1 dioxane:water (2 mL) was heated in a microwave reactor at 100° C. for 30 min. The solution was loaded into a SCX cartridge, washed with MeOH and ejected with 2M NH$_3$ in MeOH. The filtrate was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=2.07 (d, J=6.6 Hz, 3H), 3.98 (s, 3H), 6.47 (q, J=6.6 Hz, 1H), 6.81 (d, J=1.8 Hz, 1H), 7.49 (d, J=9.9 Hz, 1H), 7.63 (d, J=2.0 Hz, 1H), 7.88 (s, 1H), 7.97 (s, 1H), 8.02 (s, 1H), 8.10 (d, J=9.6 Hz, 1H). MS (ES$^+$): m/z 377.04 (100) [MH$^+$]. HPLC: t$_R$=1.95 min (ZQ3, polar__5 min).

7-[(1S)-1-(6-chloro[1,2,4]triazolo[4,3-b]pyridazin-3-yl)ethoxy]furo[3,2-c]pyridin-6-amine

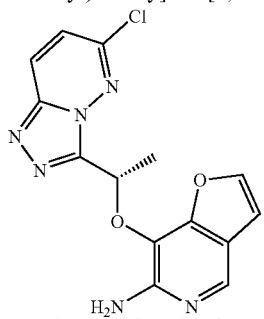

To a mixture of 6-nitrofuro[3,2-c]pyridin-7-ol (50.0 mg, 0.278 mmol), (R)-1-(6-chloro-[1,2,4]triazolo[4,3-b]pyridazin-3-yl)ethanol (110 mg, 0.555 mmol), triphenylphosphine (191 mg, 1.11 mmol) and THF (10 mL) under nitrogen at rt was added diisopropyl azodicarboxylate (0.219 mL, 1.11 mmol) dropwise. The solution was heated to 40° C. for 2 h. The solvent was removed in vacuo, and EtOH (20 mL), iron powder (200 mg, 3 mmol) and conc. HCl (8 drops) were added. The mixture was heated to 75° C. for 1 h. The material was loaded into a SCX cartridge, washed with MeOH and ejected with 2M NH$_3$ in MeOH. The filtrate was concentrated in vacuo to afford the title compound as a dark orange solid, and was used in the next step without further purification. MS (ES$^+$): m/z 331.04 (100) [MH$^+$]. HPLC: t$_R$=1.93 min (ZQ3, polar__5 min).

(R)-1-(6-Chloro[1,2,4]triazolo[4,3-b]pyridazin-3-yl)ethanol

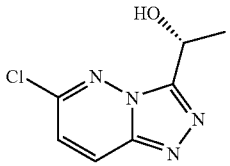

A mixture of 3-chloro-6-hydrazinopyridazine (1.44 g, 9.96 mmol), (R)-2-hydroxypropanoic acid (0.90 g, 10 mmol, i.e. D-lactic acid) and p-TsOH.H$_2$O (2.37 g, 12.4 mmol) in toluene was refluxed overnight. Some oil was formed at the bottom of the flask. LC-MS of this oil showed the desired product was formed. Toluene was poured off, and the oil residue was suspended in water (10 mL), then basified with 3 N aq. NaOH to pH=10. This aqueous solution was extracted with EtOAc (3×30 mL), and the combined organic phases were washed with brine (20 mL), and dried over anhydrous sodium sulfate. Evaporation under reduced pressure afforded the title compound as an off-white solid. MS (ES+): 199/201 (3/1) [MH$^+$]. $^1$H NMR (400 MHz, CDCl$_3$): δ=1.88 (d, J=6.8 Hz, 3H), 2.97 (d, J=6.8 Hz, 1H, —OH), 5.51 (m, 1H), 7.15 (d, J=9.6 Hz, 1H), 8.11 (d, J=9.6 Hz, 1H).

Example 475

7-[(1S)-1-(6-phenyl[1,2,4]triazolo[4,3-b]pyridazin-3-yl)ethoxy]furo[3,2-c]pyridin-6-amine

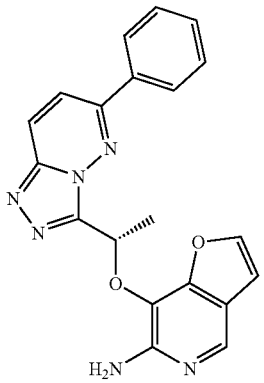

A mixture of 7-[(S)-1-(6-chloro[1,2,4]triazolo[4,3-b]pyridazin-3-yl)ethoxy]furo[3,2-c]pyridine-6-ylamine (15.0 mg, 0.045 mmol), phenylboronic acid (11.1 mg, 0.091 mmol), Pd(PPh$_3$)$_4$ (5 mg, 0.004 mmol), potassium carbonate (18.8 mg, 0.136 mmol) and 4:1 dioxane:water (2 mL) was heated in a microwave reactor at 100° C. for 30 min. The solution was loaded into a SCX cartridge, washed with MeOH and ejected with 2M NH$_3$ in MeOH. The filtrate was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=2.10 (d, J=6.8 Hz, 3H), 6.55 (q, J=6.6 Hz, 1H), 6.77 (d, J=2.5 Hz, 1H), 7.48-7.56 (m, 3H), 7.59 (d, J=2.3 Hz, 1H), 7.76 (d, J=9.6 Hz, 1H), 7.80-7.85 (m, 2H), 8.05 (s, 1H), 8.21 (d, J=9.6 Hz, 1H). MS (ES$^+$): m/z 373.09 (100) [MH$^+$]. HPLC: t$_R$=2.28 min (ZQ3, polar__5 min).

Example 476

7-[(1R)-1-(6-phenyl[1,2,4]triazolo[4,3-b]pyridazin-3-yl)ethoxy]-3-[1-(piperidin-4-yl)-1H-pyrazol-4-yl]furo[3,2-c]pyridin-6-amine

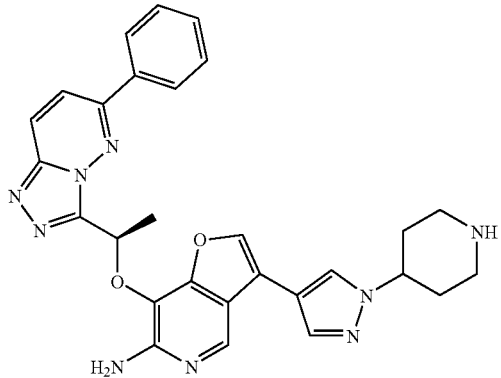

The title compound was prepared according to General Procedure AA. $^1$H NMR (400 MHz, CD$_3$OD): δ=2.18 (d, J=6.6 Hz, 3H), 2.26-2.40 (m, 4H), 3.18-3.27 (m, 2H), 3.59 (dt, J=13.1, 3.4 Hz, 2H), 4.59 (tt, J=10.0, 4.9 Hz, 1H), 6.42 (q, J=6.7 Hz, 1H), 7.39-7.50 (m, 3H), 7.77-7.80 (m, 3H), 7.82 (s, 1H), 7.88 (d, J=9.9 Hz, 1H), 8.02 (s, 1H), 8.05 (s, 1H), 8.26 (d, J=9.6 Hz, 1H), 8.39 (br s, 2H). MS (ES$^+$): m/z 522.13 (37) [MH$^+$]. HPLC: t$_R$=2.11 min (ZQ3, polar_5 min).

Example 477

7-[(6-phenyl[1,2,4]triazolo[4,3-b]pyridazin-3-yl)methoxy]-3-[1-(piperidin-4-yl)-1H-pyrazol-4-yl]furo[3,2-c]pyridin-6-amine

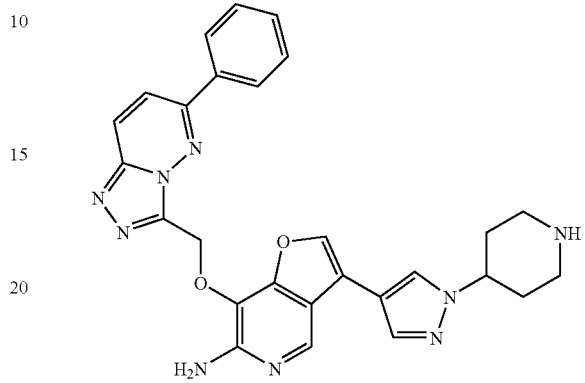

The title compound was prepared according to General Procedure AA. $^1$H NMR (400 MHz, CD$_3$OD): δ=2.24-2.42 (m, 4H), 3.23 (br t, J=10.5 Hz, 2H), 3.59 (br d, J=12.6 Hz, 2H), 4.53-4.65 (m, 1H), 5.91 (s, 2H), 7.36-7.55 (m, 3H), 7.73-7.78 (m, 1H), 7.83 (s, 1H), 7.91 (d, J=7.1 Hz, 2H), 7.94 (d, J=9.9 Hz, 1H), 8.05 (s, 1H), 8.13 (s, 1H), 8.30 (d, J=9.9 Hz, 1H), 8.57 (br s, 2H). MS (ES$^+$): m/z 508.11 (62) [MH$^+$]. HPLC: t$_R$=2.05 min (ZQ3, polar_5 min).

(1S)-1-(6-phenyl[1,2,4]triazolo[4,3-b]pyridazin-3-yl)ethanol

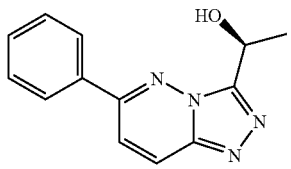

A suspension of (1S)-1-(6-chloro[1,2,4]triazolo[4,3-b]pyridazin-3-yl)ethanol (0.289 mmol, 1 eq), phenylboronic acid (0.650 mmol, 2.3 eq), Pd(PPh$_3$)$_4$ (45.9 mg, 0.0397 mmol, 14 mol %), and K$_2$CO$_3$ (132.0 mg, 0.9551 mmol, 3.3 eq) in a 4:1 ratio of dioxane (4 mL) to H$_2$O (1 mL) was evacuated and charged with nitrogen several times. The reaction sample was then heated conventionally at 85° C. for 1 h. CH$_2$Cl$_2$ and H$_2$O were added and a standard aqueous workup was performed. The crude material was purified by pTLC [Silicycle, 1000 μM, 20×20 plate], which required two developments in a 3% MeOH in EtOAc solvent system. $^1$H NMR (400 MHz, CDCl$_3$): δ=1.93 (d, J=6.6 Hz, 3H), 3.00 (br s, 1H), 5.64 (q, J=6.6 Hz, 1H), 7.53-7.61 (m, 3H), 7.66 (d, J=9.9 Hz, 1H), 7.95-8.01 (m, 2H), 8.25 (d, J=9.9 Hz, 1H). MS (ES$^+$): m/z 241.08 (100) [MH$^+$]. HPLC: t$_R$=2.51 min (ZQ3, polar_5 min).

(6-phenyl[1,2,4]triazolo[4,3-b]pyridazin-3-yl)methanol

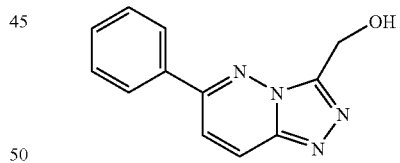

A suspension of (6-chloro[1,2,4]triazolo[4,3-b]pyridazin-3-yl)methanol (0.289 mmol, 1 eq), phenylboronic acid (0.665 mmol, 2.3 eq), Pd(PPh$_3$)$_4$ (45.9 mg, 0.0405 mmol, 14 mol %), and K$_2$CO$_3$ (132 mg, 0.955 mmol, 3.3 eq) in a 4:1 ratio of dioxane (4 mL) to H$_2$O (1 mL) was evacuated and charged with nitrogen several times. The reaction sample was then heated conventionally at 85° C. for 1 h. CH$_2$Cl$_2$ and H$_2$O were added and a standard aqueous workup was performed. The crude material was purified by pTLC [Silicycle, 1000 μM, 20×20 plate], which required two developments in a 3% MeOH in EtOAc solvent system. $^1$H NMR (400 MHz, CDCl$_3$): δ=1.69 (br s, 1H), 5.35 (s, 2H), 7.56-7.60 (m, 3H), 7.64 (d, J=9.6 Hz, 1H), 7.97-8.02 (m, 2H), 8.22 (d, J=9.6 Hz, 1H). MS (ES$^+$): m/z 227.08 (100) [MH$^+$]. HPLC: t$_R$=2.42 min (ZQ3, polar_5 min).

Example 478

7-[(1S)-1-(6-phenyl[1,2,4]triazolo[4,3-b]pyridazin-3-yl)ethoxy]-3-[1-(piperidin-4-yl)-1H-pyrazol-4-yl]furo[3,2-c]pyridin-6-amine

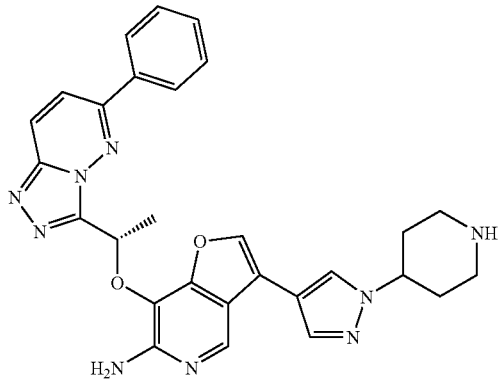

A suspension of 7-[(S)-1-(6-Chloro[1,2,4]triazolo[4,3-b]pyridazin-3-yl)ethoxy]-3-(1-piperidin-4-yl-1H-pyrazol-4-yl)furo[3,2-c]pyridin-6-ylamine (0.289 mmol, 1 eq), phenylboronic acid (0.507 mmol, 2.7 eq), Pd(PPh$_3$)$_4$ (83.6 mg, 0.0723 mmol, 25 mol %), and K$_2$CO$_3$ (200.4 mg, 1.45 mmol, 5.0 eq) in a 4:1 ratio of dioxane (4 mL) to H$_2$O (1 mL) was evacuated and charged with nitrogen several times. The reaction sample was then heated in a microwave reactor at 100° C. for 0.5 h. CH$_2$Cl$_2$ and H$_2$O were added and a standard aqueous workup was performed. The crude material was purified by chromatography on an SCX column and HPLC giving the title compound as a diformate salt. $^1$H NMR (400 MHz, CD$_3$OD): δ=2.18 (d, J=6.8 Hz, 3H), 2.24-2.40 (m, 4H), 3.18-3.27 (m, 2H), 3.59 (dt, J=12.8, 3.3 Hz, 2H), 4.59 (dddd, J=10.0, 5.1, 4.9 Hz, 1H), 6.42 (q, J=6.7 Hz, 1H), 7.38-7.50 (m, 3H), 7.73-7.83 (m, 4H), 7.88 (d, J=9.9 Hz, 1H), 8.01 (s, 1H), 8.05 (s, 1H), 8.25 (d, J=9.9 Hz, 1H), 8.35 (br s, 2H). MS (ES$^+$): m/z 522.20 (20) [MH$^+$]. HPLC: t$_R$=2.12 min (ZQ3, polar_5 min).

7-[(S)-1-(6-Chloro[1,2,4]triazolo[4,3-b]pyridazin-3-yl)ethoxy]-3-(1-piperidin-4-yl-1H-pyrazol-4-yl)furo[3,2-c]pyridin-6-ylamine

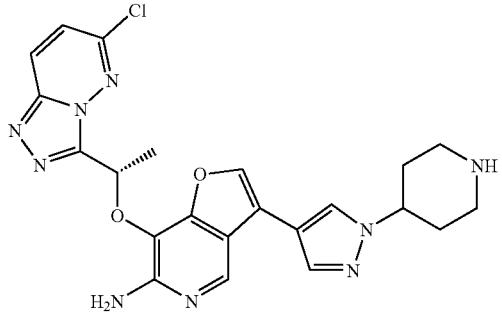

To a mixture of 4-[4-(7-hydroxy-6-nitrofuro[3,2-c]pyridin-3-yl)pyrazol-1-yl]piperidine-1-carboxylic acid tert-butyl ester (50.0 mg, 0.116 mmol), (R)-1-(6-chloro[1,2,4]triazolo[4,3-b]pyridazin-3-yl)ethanol (46.2 mg, 0.233 mmol), triphenylphosphine (122 mg, 0.466 mmol) and THF (5 mL) under nitrogen at rt was added diisopropyl azodicarboxylate (0.09 mL, 0.466 mmol) dropwise. The solution was heated to 40° C. overnight. The solvent was removed in vacuo, and EtOH (8 mL), iron powder (60 mg, 1 mmol) and conc. HCl (8 drops) were added. The mixture was heated to 75° C. for 2 h. The material was loaded into a SCX cartridge, washed with MeOH and ejected with 2M NH$_3$ in MeOH. The filtrate was concentrated in vacuo to afford the title compound as a dark orange solid, and was used in the next step without further purification.

Example 479

7-{(1S)-1-[6-(1-methyl-1H-pyrazol-4-yl) [1,2,4]triazolo[4,3-b]pyridazin-3-yl]ethoxy}-3-[1-(piperidin-4-yl)-1H-pyrazol-4-yl]furo[3,2-c]pyridin-6-amine

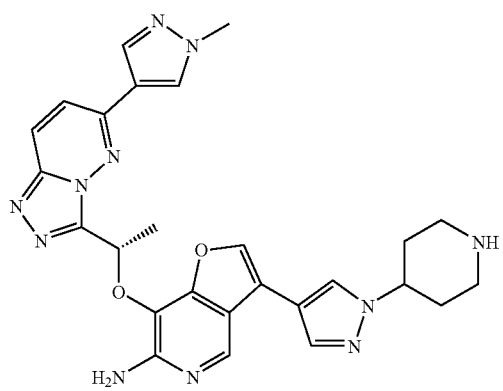

A suspension of 7-[(S)-1-(6-Chloro[1,2,4]triazolo[4,3-b]pyridazin-3-yl)ethoxy]-3-(1-piperidin-4-yl-1H-pyrazol-4-yl)furo[3,2-c]pyridin-6-ylamine (0.289 mmol, 1 eq), 1-methyl-4-(4,4,5,5-tetramethyl-1,3,2-dioxaborolan-2-yl)-1H-pyrazole (0.507 mmol, 2.7 eq), Pd(PPh$_3$)$_4$ (66.8 mg, 0.0578 mmol, 20 mol %), and K$_2$CO$_3$ (200 mg, 1.45 mmol, 5.0 eq) in a 4:1 ratio of dioxane (4 mL) to H$_2$O (1 mL) was evacuated and charged with nitrogen several times. The reaction sample was then heated in a microwave reactor at 100° C. for 0.5 h. CH$_2$Cl$_2$ and H$_2$O were added and a standard aqueous workup was performed. The crude material was purified by chromatography on an SCX column and HPLC giving the title compound as a diformate salt. $^1$H NMR (400 MHz, CD$_3$OD): δ=2.15 (d, J=6.8 Hz, 3H), 2.25-2.40 (m, 4H), 3.18-3.28 (ddd, J=12.9, 11.6, 3.8 Hz, 2H), 3.59 (dt, J=13.3, 3.3 Hz, 2H), 3.85 (s, 3H), 4.60 (dddd, J=10.0, 4.9, 4.8 Hz, 1H), 6.34 (q, J=6.6 Hz, 1H), 7.62 (d, J=9.6 Hz, 1H), 7.81 (s, 1H), 7.84 (s, 2H), 8.03 (s, 1H), 8.04 (s, 1H), 8.08 (s, 1H), 8.13 (d, J=9.6 Hz, 1H), 8.34 (br s, 4H). MS (ES$^+$): m/z 526.17 (20) [MH$^+$]. HPLC: t$_R$=1.94 min (ZQ3, polar_5 min).

Compositions

In some embodiments, the invention includes pharmaceutical compositions comprising a compound of the invention or a pharmaceutically acceptable salt thereof, formulated with or without one or more pharmaceutically acceptable carriers.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Biological Activity

It has been found that compounds of this invention, and pharmaceutically acceptable compositions thereof, are effective as inhibitors of kinases. In particular, the compounds are effective as inhibitors of at least one of Axl, Abl, Aurora-A, Aurora-B, Blk, c-Raf, cSRC, EphA2, Src, PRK2, FGFR3, Flt3, Lck, Mek1, PDK-1, GSK3β, EGFR, p70S6K, BMX, SGK, CaMKII, Tie-2, IGF-1R, Ron, Met, KDR, PAK1, PAK2, or TAK1.

Compounds of Formula I inhibit the activity of tyrosine kinase enzymes in animals, including humans, and they are useful in the treatment and/or prevention of various diseases and conditions. In particular, compounds disclosed herein are inhibitors of such kinases, in particular, but not limited to the above and can be used in the treatment of proliferative diseases, such as, but not limited to, cancer. Compounds disclosed herein are also useful in the treatment and/or prevention of various diseases and conditions in which EMT is involved, for example, the treatment of conditions characterized by a disregulation of EMT. The present invention is also directed to a pharmaceutical composition comprising a therapeutically effective amount of a compound of Formula I, or a pharmaceutically acceptable salt thereof, and a pharmaceutically acceptable carrier. The present invention is further directed to a method of treating a patient having a condition which is mediated by protein kinase activity by administering to the patient a therapeutically effective amount of the above-mentioned pharmaceutical composition.

The compounds of Formula I inhibit the activity of tyrosine kinase enzymes in animals, including humans, and they are useful in the treatment and/or prevention of various diseases and conditions. In particular, compounds disclosed herein are inhibitors of kinases, in particular, but not limited to, those noted above, and can be used in the treatment of proliferative diseases, such as, but not limited to, cancer. Since MET and RON kinases have been shown to play a role in the EMT process, the compounds of Formula I are useful in the treatment and/or prevention of various diseases and conditions in which EMT is involved, for example, the treatment of conditions characterized by a disregulation of EMT.

In some embodiments, the compound or salt of Formula I exhibits inhibition of c-Met in a cellular assay with an $IC_{50}$ of about 50 nM or less, about 200 nM or less, or about 500 nM or less.

In some embodiments, the compound or salt of Formula I exhibits inhibition of Ron in a cellular assay with an $IC_{50}$ of about 200 nM or less, about 500 nM or less, or about 1 µM or less.

In some embodiments, the compound or salt of Formula I exhibits inhibition of c-Met in a cellular assay selected from above and inhibition of Ron in a cellular assay with an $IC_{50}$ selected from above.

In some embodiments, the compound or salt of Formula I exhibits inhibition of c-Met in a cellular assay with an $IC_{50}$ of about 200 nM or less and inhibition of Ron in a cellular assay with an $IC_{50}$ of about 500 nM or less, and which is about 10-fold or more selective for c-Met over KDR.

The efficacy of the Examples of the invention, compounds of Formula (I), as inhibitors of tyrosine kinase enzymes were demonstrated and confirmed by a number of pharmacological in vitro assays. The following assays and their respective methods can be carried out with the compounds according to the invention. Activity possessed by compounds of Formula I may be demonstrated in vivo.

Someone skilled in the art will appreciate that a variety of assay formats may be used to determine the activity of the compounds of this invention. For example, AlphaScreen (Amplified Luminescent Proximity Homogeneous Assay) technology was used with the kinases described below. Assay ATP concentrations for individual kinases are included in the text.

KDR (human)—100 µM ATP: 9 µL of the reaction mix containing ATP at the desired concentration, biotinylated poly(Glu,Tyr) (84 ng/mL) and 0.334 mM vanadate in assay buffer (50 mM HEPES (pH=7.4), 12.5 mM $MgCl_2$ and 1% glycerol) are added to a well of a 384 well plate along with 1 µl of compound (or vehicle control, usually DMSO). DMSO concentration is controlled at a concentration of 1%. KDR is diluted to the optimized concentration (optimized on a lot-by-lot basis) in an enzyme diluent buffer (50 mM HEPES pH=7.4, 12.5 mM $MgCl_2$ and 1% glycerol, 0.03% Brij35 and 0.3 mM EGTA). 5 µL of this solution are then added to the well, and the complete reaction mixture is incubated for 60 min at RT. In subdued light, 5 µL of PT66 donor and acceptor beads (diluted 1:200 from manufacturers provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

IGF-1R (human)—100 µM ATP: To a well of a 384 well plate are added 9 µL of the reaction mix containing ATP at the desired concentration, biotinylated poly(Glu,Tyr) (84 ng/mL) and 0.334 mM vanadate in assay buffer (50 mM HEPES (pH=7.4), 12.5 mM $MgCl_2$ and 1% glycerol) along with 1 µL of compound (or vehicle control, usually DMSO). DMSO concentration is controlled at a concentration of 1%. IGF-1R is diluted to the optimized concentration (optimized on a lot-by-lot basis) in an enzyme diluent buffer (50 mM HEPES pH=7.4, 12.5 mM $MgCl_2$ and 1% glycerol, 0.03% Brij35, 0.3 mM EGTA, 6 mM DTT, and 0.003% BSA). 5 µL of this solution are then added to the well, and the complete reaction mixture is incubated for 60 min at RT. In subdued light, 5 µL of PT66 donor and acceptor beads (diluted 1:200 from manufacturer's provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

RON (human)—$K_m$ of ATP: RON assay is performed in a 384 well assay containing 200 ng/µL biotinylated poly(Glu,Tyr), 0.334 mM vanadate, desired concentration of ATP optimized for the enzyme in assay buffer (50 mM HEPES (pH=7.4), 12.5 mM $MgCl_2$ and 1% glycerol). Desired compound is added in a final concentration of 1% DMSO with control being vehicle of DMSO alone. RON is diluted to the optimized (on a lot-by-lot basis) concentration in an enzyme diluent buffer (50 mM HEPES pH=7.4, 12.5 mM $MgCl_2$ and 1% glycerol, 0.03% Brij35, 0.3 mM EGTA, 1 mM DTT, and 0.003% BSA). Enzyme is added to initiate the reaction and incubated for 30 min at RT. In subdued light, appropriate amount of PT66 donor and acceptor beads (diluted 1:260 from manufacturer's provision in a 25 mM Tris HCl (pH=7.5), 200 mM NaCl, 100 mM EDTA, 0.3% BSA buffer) are added to the wells. The plates, incubated for 1 h, are read on an AlphaQuest plate reader.

MET (human)—Km of ATP: MET assay is performed in a 384 well assay containing 200 ng/µL biotinylated poly(Glu,Tyr), 0.334 mM vanadate, desired concentration of ATP optimized for the enzyme in assay buffer (50 mM HEPES (pH=7.4), 5 mM $MgCl_2$, 5 mM $MnCl_2$, and 1% glycerol). Desired compound is added in a final concentration of 1% DMSO with control being vehicle of DMSO alone. MET is diluted to the optimized concentration (optimized on a lot-by-lot basis) in an enzyme diluent buffer (50 mM Tris pH=7.4, 1% glycerol, 0.03% Brij35, 0.24 mM EGTA, 1 mM DTT, and 0.003% BSA). Enzyme is added to initiate the reaction and incubated for 60 min at RT. In subdued light, appropriate amount of PT66 donor and acceptor beads (diluted 1:260 from manufacturer's provision in a 25 mM Tris HCl (pH=7.5), 400 mM NaCl, 100 mM EDTA, 0.3% BSA buffer) are added to the wells. The plates, incubated for 1 h, are read on an AlphaQuest plate reader The activities of compounds of the present invention against the kinases for which assays are not described above were determined at Invitrogen using the SelectScreen™ Kinase Profiling Service.

Activities of exemplary compounds of the present invention are shown in TABLE 1. The Example # of Table I corresponds to the compound example number under the above working examples section. Biochemical activities of exemplary compounds of the present invention determined using the assays described herein are shown in TABLE 1: A, $IC_{50} \leq 0.5$ µM; B, $0.5$ µM $< IC_{50} \leq 5$ µM; C, $5$ µM $< IC_{50} \leq 20$ µM; D, $IC_{50} > 20$ µM; NT, not tested.

TABLE 1

| Example# | RON biochemical $IC_{50}$ | Met biochemical $IC_{50}$ |
|---|---|---|
| 2 | C | B |
| 3 | B | B |
| 4 | B | B |
| 5 | A | A |
| 6 | B | A |
| 8 | B | A |
| 9 | A | A |
| 10 | A | A |
| 11 | B | B |
| 12 | B | A |
| 13 | A | A |
| 14 | B | A |
| 15 | B | B |
| 16 | B | B |
| 17 | A | A |
| 18 | A | A |
| 19 | B | B |
| 20 | A | A |
| 21 | A | A |
| 22 | A | A |
| 23 | B | B |
| 24 | A | A |
| 25 | B | A |
| 26 | B | B |
| 27 | A | A |
| 28 | B | B |
| 29 | A | A |
| 30 | B | B |
| 31 | B | B |
| 32 | B | B |
| 33 | A | A |
| 34 | A | A |
| 35 | B | A |
| 36 | A | A |
| 37 | A | A |
| 38 | A | A |
| 39 | B | A |
| 40 | A | A |
| 41 | A | A |
| 42 | A | A |
| 43 | A | A |
| 44 | A | A |
| 45 | A | A |
| 46 | B | A |
| 47 | B | B |
| 48 | B | A |
| 49 | B | B |
| 50 | B | B |
| 51 | B | B |
| 52 | B | B |
| 53 | B | B |
| 54 | B | B |
| 55 | B | A |
| 56 | B | B |
| 57 | B | B |
| 58 | B | B |
| 59 | B | B |
| 60 | C | B |
| 61 | B | B |
| 62 | B | B |
| 63 | B | B |
| 64 | B | B |
| 65 | B | B |
| 66 | B | B |
| 67 | B | A |
| 68 | B | B |
| 69 | B | B |
| 70 | B | B |
| 71 | A | A |
| 72 | B | A |
| 73 | B | B |
| 74 | A | A |
| 75 | B | A |
| 76 | B | A |
| 77 | B | B |
| 78 | B | B |

TABLE 1-continued

| Example# | RON biochemical IC$_{50}$ | Met biochemical IC$_{50}$ |
|---|---|---|
| 79 | B | A |
| 80 | B | B |
| 81 | B | B |
| 82 | B | A |
| 83 | B | B |
| 84 | B | A |
| 85 | B | B |
| 86 | A | A |
| 87 | B | B |
| 88 | A | A |
| 89 | A | A |
| 90 | B | A |
| 91 | A | A |
| 92 | C | B |
| 93 | C | B |
| 94 | B | A |
| 95 | A | A |
| 96 | B | A |
| 97 | B | B |
| 98 | B | A |
| 99 | A | A |
| 100 | B | B |
| 101 | B | A |
| 102 | B | A |
| 103 | B | A |
| 104 | B | A |
| 105 | B | A |
| 106 | A | A |
| 107 | B | B |
| 108 | B | B |
| 109 | B | B |
| 110 | B | B |
| 111 | B | B |
| 112 | B | B |
| 113 | B | B |
| 114 | B | B |
| 115 | B | B |
| 116 | C | B |
| 117 | B | B |
| 118 | B | A |
| 119 | C | B |
| 120 | B | B |
| 121 | B | B |
| 122 | A | A |
| 123 | B | B |
| 124 | B | B |
| 125 | C | B |
| 126 | B | B |
| 127 | B | A |
| 128 | B | B |
| 129 | B | B |
| 130 | A | A |
| 131 | B | A |
| 132 | A | A |
| 133 | B | B |
| 134 | B | B |
| 135 | B | B |
| 136 | B | B |
| 137 | B | B |
| 138 | B | A |
| 139 | B | A |
| 140 | B | A |
| 141 | B | B |
| 142 | B | A |
| 143 | B | A |
| 144 | NT | NT |
| 145 | A | B |
| 146 | B | A |
| 147 | NT | NT |
| 148 | B | A |
| 149 | B | A |
| 150 | B | B |
| 151 | B | A |
| 152 | B | B |
| 153 | B | A |
| 154 | A | A |
| 155 | A | A |
| 156 | A | A |
| 157 | A | A |
| 158 | A | A |
| 159 | A | A |
| 160 | A | A |
| 161 | A | A |
| 162 | A | A |
| 163 | A | A |
| 164 | A | A |
| 165 | NT | NT |
| 166 | NT | NT |
| 167 | B | A |
| 168 | B | A |
| 169 | B | B |
| 170 | B | B |
| 171 | A | A |
| 172 | A | A |
| 173 | A | A |
| 174 | A | A |
| 175 | C | B |
| 176 | C | B |
| 177 | C | B |
| 178 | B | B |
| 179 | C | A |
| 180 | C | B |
| 181 | C | B |
| 182 | B | A |
| 183 | B | B |
| 184 | C | B |
| 185 | B | A |
| 186 | B | A |
| 187 | B | B |
| 188 | B | A |
| 189 | B | A |
| 190 | B | A |
| 191 | B | B |
| 192 | B | A |
| 193 | B | A |
| 194 | B | B |
| 195 | B | B |
| 196 | B | B |
| 197 | B | B |
| 198 | B | B |
| 199 | NT | NT |
| 200 | B | A |
| 201 | B | A |
| 202 | B | A |
| 203 | B | A |
| 204 | B | A |
| 205 | B | A |
| 206 | B | A |
| 207 | B | B |
| 208 | B | B |
| 209 | B | B |
| 210 | B | B |
| 211 | B | A |
| 212 | B | B |
| 213 | A | A |
| 214 | A | A |
| 215 | A | A |
| 216 | A | A |
| 217 | A | A |
| 218 | A | A |
| 219 | B | B |
| 220 | A | A |
| 221 | A | A |
| 222 | A | A |
| 223 | B | B |
| 224 | A | A |
| 225 | A | A |
| 226 | A | A |
| 227 | B | A |
| 228 | B | B |
| 229 | A | A |
| 230 | B | B |

TABLE 1-continued

| Example# | RON biochemical IC$_{50}$ | Met biochemical IC$_{50}$ |
|---|---|---|
| 231 | B | B |
| 232 | B | B |
| 233 | B | B |
| 234 | B | B |
| 235 | A | A |
| 236 | A | A |
| 237 | A | A |
| 238 | A | A |
| 239 | A | A |
| 240 | A | A |
| 241 | A | A |
| 242 | A | A |
| 243 | C | B |
| 244 | B | B |
| 245 | B | B |
| 246 | C | B |
| 247 | C | B |
| 248 | C | B |
| 249 | B | B |
| 250 | A | A |
| 251 | A | A |
| 252 | A | A |
| 253 | A | A |
| 254 | A | A |
| 255 | A | A |
| 256 | B | A |
| 257 | B | A |
| 258 | NT | NT |
| 259 | NT | NT |
| 260 | B | B |
| 261 | B | A |
| 262 | A | A |
| 263 | A | A |
| 264 | C | A |
| 265 | A | B |
| 266 | B | B |
| 267 | A | B |
| 268 | B | B |
| 269 | B | B |
| 270 | B | A |
| 271 | NT | NT |
| 272 | B | B |
| 273 | B | B |
| 274 | B | B |
| 275 | B | B |
| 276 | B | B |
| 277 | B | B |
| 278 | B | A |
| 279 | NT | NT |
| 280 | C | B |
| 281 | B | A |
| 282 | C | B |
| 283 | B | B |
| 284 | B | B |
| 285 | B | B |
| 286 | B | B |
| 287 | B | B |
| 288 | B | B |
| 289 | B | B |
| 290 | B | B |
| 291 | B | B |
| 292 | B | B |
| 293 | A | A |
| 294 | A | A |
| 295 | B | B |
| 296 | B | B |
| 297 | B | B |
| 298 | B | A |
| 299 | B | B |
| 300 | B | B |
| 301 | B | B |
| 302 | B | B |
| 303 | A | A |
| 304 | A | A |
| 305 | A | A |
| 306 | A | A |
| 307 | A | A |
| 308 | A | A |
| 309 | A | A |
| 310 | A | A |
| 311 | B | A |
| 312 | B | A |
| 313 | B | B |
| 314 | B | B |
| 315 | B | A |
| 316 | A | A |
| 317 | B | B |
| 318 | B | B |
| 319 | B | B |
| 320 | B | B |
| 321 | B | A |
| 322 | A | A |
| 323 | B | B |
| 324 | A | A |
| 325 | C | C |
| 326 | C | B |
| 327 | C | B |
| 328 | B | B |
| 329 | C | B |
| 330 | C | C |
| 331 | C | B |
| 332 | C | B |
| 333 | A | A |
| 334 | A | A |
| 335 | B | A |
| 336 | B | A |
| 337 | B | A |
| 338 | B | B |
| 339 | B | A |
| 340 | B | A |
| 341 | A | A |
| 342 | B | A |
| 343 | B | B |
| 344 | B | B |
| 345 | B | B |
| 346 | B | B |
| 347 | B | A |
| 348 | B | A |
| 349 | A | A |
| 350 | A | A |
| 351 | B | A |
| 352 | B | B |
| 353 | B | A |
| 354 | B | B |
| 355 | B | B |
| 356 | A | A |
| 357 | A | A |
| 358 | A | A |
| 359 | A | A |
| 360 | B | A |
| 361 | A | A |
| 362 | B | A |
| 363 | B | B |
| 364 | A | A |
| 365 | B | A |
| 366 | B | B |
| 367 | A | A |
| 368 | B | B |
| 369 | B | B |
| 370 | B | A |
| 371 | B | A |
| 372 | B | A |
| 373 | B | A |
| 374 | B | B |
| 375 | B | A |
| 376 | B | B |
| 377 | B | B |
| 378 | B | A |
| 379 | A | A |
| 380 | B | A |
| 381 | A | A |
| 382 | B | A |

TABLE 1-continued

| Example# | RON biochemical IC$_{50}$ | Met biochemical IC$_{50}$ |
|---|---|---|
| 383 | B | A |
| 384 | B | B |
| 385 | B | A |
| 386 | B | B |
| 387 | B | A |
| 388 | B | A |
| 389 | B | B |
| 390 | A | A |
| 391 | B | A |
| 392 | B | A |
| 393 | B | A |
| 394 | B | A |
| 395 | B | B |
| 396 | B | A |
| 397 | B | B |
| 398 | B | B |
| 399 | B | B |
| 400 | B | A |
| 401 | B | A |
| 402 | B | B |
| 403 | B | B |
| 404 | B | B |
| 405 | A | A |
| 406 | A | A |
| 407 | B | A |
| 408 | B | B |
| 409 | B | B |
| 410 | B | B |
| 411 | B | B |
| 412 | B | B |
| 413 | B | B |
| 414 | B | A |
| 415 | B | B |
| 416 | B | B |
| 417 | B | B |
| 418 | B | A |
| 419 | B | B |
| 420 | C | B |
| 421 | C | B |
| 422 | B | B |
| 423 | B | A |
| 424 | B | A |
| 425 | B | A |
| 426 | B | A |
| 427 | A | A |
| 428 | A | B |
| 429 | NT | NT |
| 430 | NT | NT |
| 431 | B | B |
| 432 | B | B |
| 433 | B | B |
| 434 | A | A |
| 435 | B | A |
| 436 | A | A |
| 437 | A | A |
| 438 | NT | NT |
| 439 | A | A |
| 440 | B | A |
| 441 | B | A |
| 442 | A | A |
| 443 | A | A |
| 444 | B | B |
| 445 | B | B |
| 446 | A | B |
| 447 | B | B |
| 448 | B | B |
| 449 | B | B |
| 450 | B | A |
| 451 | B | A |
| 452 | B | A |
| 453 | NT | NT |
| 454 | NT | NT |
| 455 | B | A |
| 456 | B | A |
| 457 | B | A |
| 458 | NT | NT |
| 459 | B | A |
| 460 | NT | NT |
| 461 | D | B |
| 462 | A | A |
| 463 | A | A |
| 464 | NT | NT |
| 465 | C | B |
| 466 | B | B |
| 467 | C | D |
| 468 | C | C |
| 469 | C | A |
| 470 | D | B |
| 471 | D | C |
| 472 | C | B |
| 473 | D | B |
| 474 | D | B |
| 475 | D | C |
| 476 | B | A |
| 478 | D | B |
| 479 | C | B |

USES

The present invention is also directed to a method of treating a patient having a condition which is mediated by protein kinase activity by administering to the patient a therapeutically effective amount of the above-mentioned pharmaceutical composition.

The present invention is also directed to a method of treating a patient having condition mediated at least in part by MET and/or RON and that is susceptible to treatment with a compound that is a MET, RON, or dual inhibitor. In some embodiments, the compounds is selective over KDR by 4, 6, 8, 10, 12-fold or more.

The compounds of Formula I of the present invention are useful in the treatment of a variety of cancers, including, but not limited to, solid tumor, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

Thus, in some embodiments, there is provided a method of treating a condition mediated by protein kinase activity comprising administering to a patient in need thereof a therapeutically effective amount of a compound or salt of a compound of Formula I.

In some embodiments, the protein kinase is one or more of Axl, Abl, ALK, Aurora-A, Aurora-B, Blk, c-Raf, cSRC, EphA2, Src, PRK2, FGFR3, Flt3, Lck, Mek1, PDK-1, GSK3β, EGFR, p70S6K, BMX, SGK, CaMKII, Tie-2, IGF-1R, Ron, Met, KDR, PAK1, PAK2, or TAK1.

In some embodiments, the condition is a hyperproliferative disorder. In some embodiments, the condition is cancer.

In some embodiments, the condition is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, or malignant ascites.

In some embodiments, the condition is lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, or a glioblastoma.

In some embodiments, the condition is GBM, NSCLC, or gastric cancer.

In some embodiments, there is provided a method of treating a condition characterized by a disregulation of Epithelial-Mesenchymal Transition (EMT) comprising administering to a patient in need thereof a therapeutically effective amount of a compound or salt of Formula I.

In some embodiments, the method inhibits EMT in cancer cells.

In some embodiments, the condition is a cancer mediated at least in part by c-Met.

In some embodiments, the condition is a cancer selected from bladder, colorectal, non-small cell lung, breast, or pancreatic, ovarian, gastric, head and neck, prostate, hepatocellular, renal, glioma, or sarcoma.

In some embodiments, the compound or salt thereof is a dual RON and c-Met inhibitor.

In some embodiments, the method further comprises administering a therapeutically effective amount of at least one additional anti-cancer agent sequentially and/or in combination.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

GENERAL DEFINITIONS

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

As used herein, for example, "$C_{0-12}$alkyl" is used to mean an alkyl having 0-12 carbons—that is, 0, 1, 2, 3, 4, 5, 6, 7, 8, 9, 10, 11, or 12 carbons in a straight or branched configuration. $C_0$alkyl means a single covalent chemical bond.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" refers to fluoro, chloro, bromo, or iodo.

Unless otherwise specified, the term "cycloalkyl" refers to a 3-12 carbon mono-cyclic, bicyclic, or polycyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like. Cycloalkyl can be bicycloalkyl, polycycloalkyl or spiroalkyl.

The term "bicycloalkyl" and "polycycloalkyl" refer to a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" refers to a structure consisting of two cycloalkyl moieties that have exactly one atom in common. Examples include, but are not limited to, spiro[4.5]decyl, spiro[2.3]hexyl, and the like.

The term "heterobicycloalkyl" refers to a bicycloalkyl structure in which at least one carbon atom is replaced with a heteroatom independently selected from oxygen, nitrogen, and sulfur.

The term "heterospiroalkyl" refers to a spiroalkyl structure in which at least one carbon atom is replaced with a heteroatom independently selected from oxygen, nitrogen, and sulfur.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, and the like.

Unless otherwise specified, the term "cycloalkenyl" refers to a cyclic aliphatic 3 to 12 ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example ethynyl, propargyl, and the like.

The term "aryl" refers to an all-carbon monocyclic, bicyclic, or polycyclic groups of 6 to 12 carbon atoms having a completely conjugated pi-electron system, which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The terms "heteroaryl" refer to a substituted or unsubstituted monocyclic, bicyclic, or polycyclic group of 5 to 12 ring atoms containing one or more ring heteroatoms selected from N, O, and S, the remaining ring atoms being C, and, in addition, having a completely conjugated pi-electron system. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

The term "heterocycloalkyl" refers to a substituted or unsubstituted monocyclic, bicyclic, or polycyclic ring group having in the ring(s) of 3 to 12 ring atoms, in which one or more ring atoms are heteroatoms selected from N, O, and S, the remaining ring atoms being C. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-aza-bicyclo[2.2.1]heptane, 2-oxa-bicyclo[2.2.2]octane, and the like, are such heterocycloalkyls.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

One in the art understands that an "oxo" requires a second bond from the atom to which the oxo is attached. Accordingly, it is understood that oxo cannot be substituted onto an aryl or heteroaryl ring.

The invention claimed is:

1. A compound or a pharmaceutically acceptable salt thereof, of Formula I:

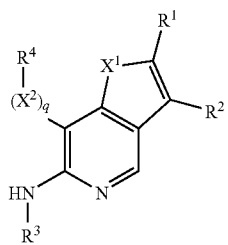

I wherein:
$X^1$ is O;
$(X^2)_q$ is O;

$R^1$ is H, halo, —CN, —CF$_3$, —NO$_2$, C$_{0-12}$alkyl, C$_{2-12}$alkenyl, C$_{2-12}$alkynyl, C$_{3-12}$cycloalkylC$_{0-12}$alkyl, C$_{3-12}$heterocycloalkylC$_{0-12}$alkyl, arylC$_{0-12}$alkyl or heteroarylC$_{0-12}$alkyl, any of which is optionally substituted with one or more independent G$^1$ substituents;

$R^2$ is H, halo, —CN, —CF$_3$—NO$_2$, C$_{0-12}$alkyl, C$_{2-12}$alkenyl, C$_{2-12}$alkynyl, C$_{3-12}$cycloalkylC$_{0-12}$alkyl, C$_{3-12}$heterocycloalkylC$_{0-12}$alkyl, arylC$_{0-12}$alkyl or heteroarylC$_{0-12}$alkyl, any of which is optionally substituted with one or more independent G$^2$ substituents;

or R$^2$ is tetrahydropyridinyl, which is a structure of Formula II:

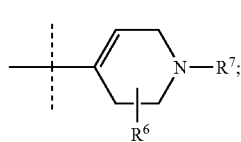

II $R^3$ is H or C$_{1-12}$alkyl;

$R^4$ is H, C$_{1-12}$alkyl, C$_{3-12}$cycloalkylC$_{0-12}$alkyl, C$_{3-12}$heterocycloalkylC$_{0-12}$alkyl, arylC$_{0-12}$alkyl, arylC$_{3-12}$cycloalkyl, arylC$_{3-12}$heterocycloalkyl, heteroarylC$_{0-12}$alkyl, heteroarylC$_{3-12}$cycloalkyl or heteroarylC$_{3-12}$heterocycloalkyl, any of which is optionally substituted with one or more independent G$^3$ substituents;

or R$^4$ is —(CR$^{10}$R$^{11}$)$_n$A$^1$;

A$^1$ is aryl or heteroaryl optionally substituted by one or more independent G$^4$;

$R^5$ is H, C$_{1-12}$alkyl, C$_{3-12}$cycloalkylC$_{0-12}$alkyl, C$_{3-12}$heterocycloalkylC$_{0-12}$alkyl, arylC$_{0-12}$alkyl, heteroaryl C$_{0-12}$ alkyl, C$_{1-12}$alkyl—O—C$_{2-12}$alkyl, C$_{1-12}$alkyl—S(O)$_m$—C$_{2-12}$alkyl, (C$_{0-12}$alkyl)(C$_{0-12}$alkyl)N—C$_{2-12}$alkyl, C$_{2-12}$alkenylC$_{1-12}$alkyl or C$_{2-12}$alkynylC$_{1-12}$alkyl, any of which is optionally substituted with one or more independent G$^5$ substituents;

$R^{10}$ and $R^{11}$ are each independently H, C$_{1-12}$alkyl, C$_{1-12}$alkyl-O—C$_{1-12}$alkyl, (C$_{1-12}$alkyl)(C$_{0-12}$alkyl)N—C$_{1-12}$alkyl, C$_{1-12}$alkyl-S(O)$_m$—C$_{1-12}$alkyl, C$_{3-12}$cycloalkylC$_{0-12}$alkyl, C$_{3-12}$cycloalkenylC$_{1-12}$alkyl or C$_{3-12}$heterocycloalkylC$_{0-10}$alkyl, any of which is optionally substituted by one or more independent G$^6$ substituents; or R$^{10}$ and R$^{11}$ are taken together with the carbon atom to which they are attached to form a 3-12 membered saturated or unsaturated ring, wherein said ring is optionally substituted by one or more independent G$^7$ substituents and said ring optionally includes one or more heteroatoms selected from O, N, or S(O)$_m$;

$R^6$ is selected from H, C$_{1-12}$alkyl, C$_{1-12}$alkyl-O—C$_{1-12}$alkyl, (C$_{1-12}$alkyl)(C$_{0-12}$alkyl)N—C$_{1-12}$alkyl or C$_{1-12}$alkyl-S(O)$_m$—C$_{1-12}$alkyl, any of which is optionally substituted by one or more independent G$^8$ substituents;

$R^7$ is H, C$_{1-12}$alkyl, R$^8$O—C$_{2-12}$alkyl, R$^8$R$^9$N—C$_{2-12}$alkyl, R$^8$S(O)$_m$—C$_{2-12}$alkyl, C$_{3-12}$cycloalkylC$_{0-12}$alkyl, C$_{3-12}$cycloalkenylC$_{1-12}$alkyl, C$_{3-12}$heterocycloalkylC$_{0-12}$alkyl, arylC$_{0-12}$alkyl, heteroarylC$_{0-12}$alkyl, C$_{1-12}$alkylC$_{3-12}$cycloalkyl, C$_{3-12}$cycloalkylC$_{3-12}$cycloalkyl, C$_{3-12}$cycloalkenylC$_{3-12}$cycloalkyl, C$_{3-12}$heterocycloalkylC$_{3-12}$cycloalkyl, arylC$_{3-12}$cycloalkyl, heteroarylC$_{3-12}$cycloalkyl, C$_{1-12}$alkylC$_{3-12}$ heterocycloalkyl, C$_{3-12}$cycloalkylC$_{3-12}$heterocycloalkyl, C$_{3-12}$cycloalkenylC$_{3-12}$heterocycloalkyl, C$_{3-12}$heterocycloalkylC$_{3-12}$heterocycloalkyl, arylC$_{3-12}$heterocycloalkyl, heteroarylC$_{3-12}$heterocycloalkyl, —C(O)R$^a$, R⁸O—C₀₋₁₂alkylC(O)—, R⁸R⁹N—C₀₋₁₂alkylC(O)—, R⁸S(O)ₘC₀₋₁₂alkylC(O)—, —CO₂R⁸, —C(O)NR⁸R⁹, —S(O)ₘR⁸, —SO₂NR⁸R⁹ or —C(S)OR⁸, any of which is optionally substituted with one or more independent G⁹ substituents;

G¹, G², G³, G⁴, G⁵, G⁶, G⁷, G⁸, and G⁹ are each independently selected from H, halo, —CN, —CF₃, —OCF₃, —NO₂, C₁₋₁₂alkyl, C₂₋₁₂ alkenyl, C₂₋₁₂ alkynyl, C₃₋₁₂cycloalkylC₀₋₁₂alkyl, C₃₋₁₂heterocycloalkylC₀₋₁₂alkyl, arylC₀₋₁₂alkyl, heteroarylC₀₋₁₂alkyl, —OR¹², —S(O)ₘR¹², —NR¹²R¹³, —SO₂NR¹²R¹³, —C(O)Rᵇ, —C(O)NR¹²R¹³, —C(O)—C(O)NR¹²R¹³, —C(O)OR¹², —C(O)—C(O)OR¹², —OC(O)Rᵇ, —NR¹²C(O)Rᵇ, —NR¹²S(O)₂R¹³, —(CR¹⁴R¹⁵)ₙC(O)Rᵇ, —(CR¹⁴R¹⁵)ₙC(O)OR¹², —(CR¹⁴R¹⁵)ₙC(O)NR¹²R¹³, —(CR¹⁴R¹⁵)ₙS(O)₂NR¹²R¹³, —(CR¹⁴R¹⁵)ₙNR¹²R¹³, —(CR¹⁴R¹⁵)ₙOR¹², —(CR¹⁴R¹⁵)ₙS(O)ₘR¹², —NR¹⁶C(O)NR¹²R¹³, —NR¹⁶S(O)₂NR¹²R¹³ or —NR¹⁶S(O)NR¹²R¹³, any of which is optionally substituted with one or more independent Q¹ substituents;

Q¹ is selected from H, halo, —CN, —NO₂, oxo, —CF₃, —OCF₃, C₁₋₁₂alkyl, arylC₀₋₁₂alkyl, heteroarylC₀₋₁₂alkyl, C₃₋₁₂cycloalkylC₀₋₁₂alkyl, C₃₋₁₂heterocycloalkylC₀₋₁₂alkyl, arylC₃₋₁₂cycloalkyl, heteroaryl C₃₋₁₂ cycloalkyl, C₃₋₁₂heterocycloalkylC₃₋₁₂cycloalkyl, C₃₋₁₂cycloalkylC₃₋₁₂cycloalkyl, C₁₋₁₂alkylC₃₋₁₂heterocycloalkyl, C₃₋₁₂heterocycloalkylC₃₋₁₂heterocycloalkyl, arylC₃₋₁₂heterocycloalkyl, heteroarylC₃₋₁₂heterocycloalkyl, —C(O)—C(O)NR¹⁷R¹⁸, —C(O)—C(O)OR¹⁷, —OC(O)Rᶜ, —NR¹⁷C(O)Rᶜ, —NR¹⁷S(O)₂R¹⁸, —(CR¹⁹R²⁰)ₙC(O)Rᶜ, —(CR¹⁹R²⁰)ₙC(O)OR¹⁷, —(CR¹⁹R²⁰)ₙC(O)NR¹⁷R¹⁸, —(CR¹⁹R²⁰)ₙS(O)₂NR¹⁷R¹⁸, —(CR¹⁹R²⁰)ₙNR¹⁷R¹⁸, —(CR¹⁹R²⁰)ₙOR¹⁷, —(CR¹⁹R²⁰)ₙS(O)ₘR¹⁷, —NR²¹C(O)NR¹⁷R¹⁸, —NR²¹S(O)₂NR¹⁷R¹⁸ or —NR²¹S(O)NR¹⁷R¹⁸, any of which is optionally substituted with one or more independent Q² substituents;

Q² is selected from H, halo, —CN, —OH, —NH₂, —NO₂, oxo, —CF₃, —OCF₃, —CO₂H, —S(O)ₘH, C₁₋₁₂alkyl, arylC₀₋₁₂alkyl, heteroarylC₀₋₁₂alkyl, C₃₋₁₂cycloalkylC₀₋₁₂alkyl, C₃₋₁₂heterocycloalkylC₀₋₁₂alkyl, arylC₃₋₁₂cycloalkyl, heteroarylC₃₋₁₂cycloalkyl, C₃₋₁₂heterocycloalkylC₃₋₁₂cycloalkyl, C₃₋₁₂cycloalkylC₃₋₁₂cycloalkyl, C₁₋₁₂alkylC₃₋₁₂heterocycloalkyl, C₃₋₁₂heterocycloalkylC₃₋₁₂heterocycloalkyl, arylC₃₋₁₂heterocycloalkyl or heteroarylC₃₋₁₂heterocycloalkyl, any of which is optionally substituted with one or more independent halo, —CN, —OH, —NH₂ or C₁₋₁₀alkyl which may be partially or fully halogenated, or —O—C₁₋₁₀alkyl which may be partially or fully halogenated;

R⁸, R⁹, R¹², R¹³, R¹⁴, R¹⁵, R¹⁶, R¹⁷, R¹⁸, R¹⁹, R²⁰, R²¹, Rᵃ, Rᵇ, and Rᶜ are each independently selected from H, C₁₋₁₂alkyl, arylC₀₋₁₂alkyl, heteroarylC₀₋₁₂alkyl, C₃₋₁₂cycloalkylC₀₋₁₂alkyl, C₃₋₁₂heterocycloalkylC₀₋₁₂alkyl, arylC₃₋₁₂cycloalkyl, heteroarylC₃₋₁₂cycloalkyl, C₃₋₁₂heterocycloalkylC₃₋₁₂cycloalkyl, C₃₋₁₂cycloalkylc₃₋₁₂cycloalkyl, C₁₋₁₂alkylC₃₋₁₂heterocycloalkyl, C₃₋₁₂heterocycloalkylC₃₋₁₂heterocycloalkyl, arylC₃₋₁₂heterocycloalkyl, or heteroarylC₃₋₁₂heterocycloalkyl substituents;

—NR⁸R⁹, —NR¹²R¹³ and —NR¹⁷R¹⁸ is each independently linear structure; or R⁸ and R⁹, or R¹² and R¹³, or R¹⁷ and R¹⁸, respectively, is taken together with the nitrogen atom to which they are attached to form a 3-12 membered saturated or unsaturated ring, wherein said ring optionally includes one or more heteroatoms selected from O, N, or S(O)ₘ;

—CR¹⁴R¹⁵ or —CR¹⁹R²⁰ is each independently linear structure; or R¹⁴ and R¹⁵, or R¹⁹ and R²⁰, respectively, is taken together with the carbon atom to which they are attached to form a 3-12 membered saturated or unsaturated ring, wherein said ring optionally includes one or more heteroatoms selected from O, N, or S(O)ₘ;

each n is independently 0-7; each m is independently 0-2.

2. The compound or salt of claim 1 wherein R⁴ is —(CR¹⁰R¹¹)ₙA¹.

3. The compound or salt of claim 1 wherein the compound of Formula I has the Formula Ia:

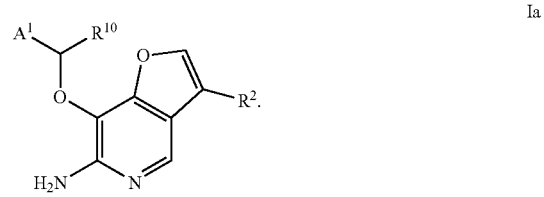

Ia

4. The compound or salt of claim 1 wherein the compound of Formula I has the Formula Ib:

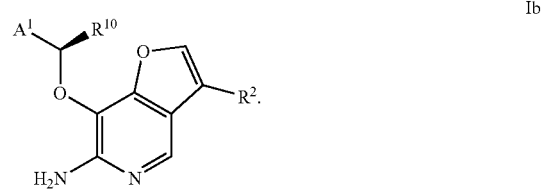

Ib

5. The compound or salt of claim 4 wherein A¹ is aryl which is optionally further substituted by one or more independent G⁴ substituents.

6. The compound or salt of claim 5 wherein R² is arylC₀₋₁₂alkyl or heteroarylC₀₋₁₂alkyl, any of which is optionally substituted with one or more independent G² substituents.

7. The compound or salt of claim 5 wherein R² is a structure of Formula II

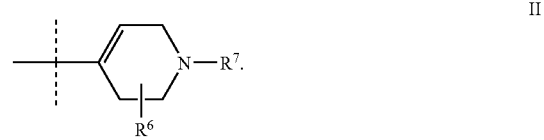

II

8. The compound or salt of claim 1, having the Formula:

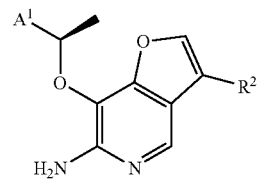

wherein:

R² is

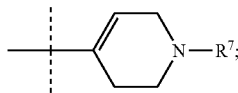

R⁷ is $C_{0-6}$alkyl, —C(O)Rᵃ, or —C(O)NR⁸R⁹, any of which is optionally substituted with 1-2 independent G⁹ substituents;

G⁹ is selected from $C_{0-6}$alkyl, $C_{2-6}$alkenyl, $C_{2-6}$alkynyl, —OR¹², —S(O)$_m$R¹², —NR¹²R¹³, —SO₂NR¹²R¹³, —C(O)Rᵇ, —C(O)(CR¹⁴R¹⁵)$_n$NR¹²R¹³, —C(O)—C(O)NR¹²R¹³, —C(O)OR¹², —C(O)—C(O)OR¹², —OC(O)Rᵇ, —NR¹²C(O)Rᵇ, —NR¹²S(O)₂R¹³, —(CR¹⁴R¹⁵)$_n$C(O)Rᵇ, —(CR¹⁴R¹⁵)$_n$C(O)OR¹², —(CR¹⁴R¹⁵)$_n$C(O)NR¹²R¹³, —(CR¹⁴R¹⁵)$_n$S(O)₂NR¹²R¹³, —(CR¹⁴R¹⁵)$_n$NR¹²R¹³, —(CR¹⁴R¹⁵)$_n$OR¹², —(CR¹⁴R¹⁵)$_n$S(O)$_m$R¹², —NR¹⁶C(O)NR¹²R¹³, —NR¹⁶S(O)₂NR¹²R¹³, or —NR¹⁶S(O)NR¹²R¹³, any of which is optionally substituted by 1-2 Q¹;

each Q¹ is independently selected from $C_{0-6}$alkyl, aryl$C_{0-6}$alkyl, heteroaryl$C_{0-6}$alkyl, $C_{3-6}$cycloalkyl$C_{0-6}$alkyl, $C_{3-6}$heterocycloalkyl$C_{0-6}$alkyl, or —(CR¹⁴R¹⁵)$_n$NR¹²R¹³;

R⁸, R⁹, and Rᵃ are each independently selected from H, $C_{1-12}$alkyl, aryl$C_{0-12}$alkyl, heteroaryl$C_{0-12}$alkyl, $C_{3-12}$cycloalkyl$C_{0-12}$alkyl, $C_{3-12}$heterocycloalkyl$C_{0-12}$alkyl, aryl$C_{3-12}$cycloalkyl, heteroaryl$C_{3-12}$cycloalkyl, $C_{3-12}$heterocycloalkyl$C_{3-12}$cycloalkyl, $C_{3-12}$cycloalkyl$C_{3-12}$cycloalkyl, $C_{1-12}$alkyl$C_{3-12}$heterocycloalkyl, $C_{3-12}$heterocycloalkyl$C_{3-12}$heterocycloalkyl, aryl$C_{3-12}$heterocycloalkyl, or heteroaryl$C_{3-12}$heterocycloalkyl substituents;

—NR⁸R⁹ is linear structure or R⁸ and R⁹ is taken together with the nitrogen atom to which they are attached to form a 3-12 membered saturated or unsaturated ring, wherein said ring optionally includes one or more heteroatoms selected from O, N, or S(O)$_m$;

each R¹², R¹³, R¹⁴, R¹⁵, R¹⁶, and Rᵇ is independently $C_{0-6}$alkyl; —NR¹²R¹³ is independently linear structure; or R¹² and R¹³ can be taken together with the nitrogen atom to which they are attached to form a 3-6 membered saturated or unsaturated ring, wherein said ring optionally includes one or more heteroatoms selected from O, N, or S(O)$_m$; —CR¹⁴R¹⁵ is linear structure; or R¹⁴ and R¹⁵ can be taken together with the carbon atom to which they are attached to form a 3-6 membered saturated or unsaturated ring, wherein said ring optionally includes one or more heteroatoms selected from O, N, or S(O)$_m$;

each n is independently 0-6; each m is independently 0-2; and

A¹ is phenyl which is optionally substituted with 3-4 ortho or meta substituents each independently selected from Br, Cl, F, or methoxy.

9. The compound or salt of claim 1, having the Formula:

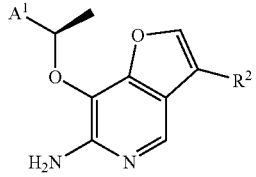

wherein:

R² is phenyl or pyridyl each optionally substituted by G²;

G² is selected from $C_{0-6}$alkyl, $C_{2-6}$alkenyl, $C_{2-6}$alkynyl, —OR¹², —S(O)$_m$R¹², —NR¹²R¹³, —SO₂NR¹²R¹³, —C(O)Rᵇ, —C(O)(CR¹⁴R¹⁵)$_n$NR¹²R¹³, —C(O)—C(O)NR¹²R¹³, —C(O)OR¹², —C(O)—C(O)OR¹², —OC(O)Rᵇ, —NR¹²C(O)Rᵇ, —NR¹²S(O)₂R¹³, —(CR¹⁴R¹⁵)$_n$C(O)Rᵇ, —(CR¹⁴R¹⁵)$_n$C(O)OR¹², —(CR¹⁴R¹⁵)$_n$C(O)NR¹²R¹³, —(CR¹⁴R¹⁵)$_n$S(O)₂NR¹²R¹³, —(CR¹⁴R¹⁵)$_n$NR¹²R¹³, —(CR¹⁴R¹⁵)$_n$OR¹², —(CR¹⁴R¹⁵)$_n$S(O)$_m$R¹², —NR¹⁶C(O)NR¹²R¹³, —NR¹⁶S(O)²NR¹²R¹³, or —NR¹⁶S(O)NR¹²R¹³, any of which is optionally substituted by 1-2 Q¹;

each Q¹ is independently selected from $C_{0-6}$alkyl, aryl$C_{0-6}$alkyl, heteroaryl$C_{0-6}$alkyl, $C_{3-6}$cycloalkyl$C_{0-6}$alkyl, $C_{3-6}$heterocycloalkyl$C_{0-6}$alkyl, or —(CR¹⁴R¹⁵)$_n$NR¹²R¹³;

each R¹², R¹³, R¹⁴, R¹⁵, R¹⁶, and Rᵇ is independently $C_{0-6}$alkyl; —NR¹²R¹³ is independently linear structure; or R¹² and R¹³ can be taken together with the nitrogen atom to which they are attached to form a 3-6 membered saturated or unsaturated ring, wherein said ring optionally includes one or more heteroatoms selected from O, N, or S(O)$_m$; —CR¹⁴R¹⁵ is linear structure; or R¹⁴ and R¹⁵ can be taken together with the carbon atom to which they are attached to form a 3-6 membered saturated or unsaturated ring, wherein said ring optionally includes one or more heteroatoms selected from O, N, or S(O)$_m$;

each n is independently 0-6; each m is independently 0-2; and

A¹ is phenyl which is optionally substituted with 3-4 ortho or meta substituents each independently selected from Br, Cl, F, or methoxy.

10. The compound or salt of claim 1, having the Formula:

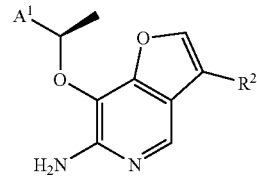

wherein:

R² is pyrazolyl, imidazolyl, or thiazolyl, each optionally substituted by G²;

G² is selected from $C_{0-6}$alkyl, $C_{2-6}$alkenyl, $C_{2-6}$alkynyl, —OR¹², —S(O)$_m$R¹², —NR¹²R¹³, —SO₂NR¹²R¹³, —C(O)Rᵇ, —C(O)(CR¹⁴R¹⁵)$_n$NR¹²R¹³, —C(O)—C(O)NR¹²R¹³, —C(O)OR¹², —C(O)—C(O)OR¹², —OC(O)Rᵇ, —NR¹²C(O)Rᵇ, —NR¹²S(O)₂R¹³, —(CR¹⁴R¹⁵)$_n$C(O)Rᵇ, —(CR¹⁴R¹⁵)$_n$C(O)OR¹², —(CR¹⁴R¹⁵)$_n$C(O)NR¹²R¹³, —(CR¹⁴R¹⁵)$_n$S(O)₂NR¹²R¹³, —(CR¹⁴R¹⁵)$_n$NR¹²R¹³, —(CR¹⁴R¹⁵)$_n$OR¹², —(CR¹⁴R¹⁵)$_n$S(O)$_m$R¹², —NR¹⁶C(O)NR¹²R¹³, —NR¹⁶S(O)₂NR¹²R¹³, or —NR¹⁶S(O)NR¹²R¹³, any of which is optionally substituted by 1-2 Q¹;

each Q¹ is independently selected from $C_{0-6}$alkyl, aryl$C_{0-6}$alkyl, heteroaryl$C_{0-6}$alkyl, $C_{3-6}$cycloalkyl$C_{0-6}$alkyl, $C_{3-6}$heterocycloalkyl$C_{0-6}$alkyl, or —(CR¹⁴R¹⁵)$_n$NR¹²R¹³;

each R¹², R¹³, R¹⁴, R¹⁵, R¹⁶, and Rᵇ is independently $C_{0-6}$alkyl; —NR¹²R¹³ is independently linear structure; or R¹² and R¹³ can be taken together with the nitrogen atom to which they are attached to form a 3-6 membered saturated or unsaturated ring, wherein said ring optionally includes one or more heteroatoms selected from O, N, or $S(O)_m$; —$CR^{14}R^{15}$ is linear structure; or $R^{14}$ and $R^{15}$ can be taken together with the carbon atom to which they are attached to form a 3-6 membered saturated or unsaturated ring, wherein said ring optionally includes one or more heteroatoms selected from O, N, or $S(O)_m$;
each n is independently 0-6; each m is independently 0-2; and $A^1$ is phenyl which is optionally substituted with 3-4 ortho or meta substituents each independently selected from Br, Cl, F, or methoxy.

11. The compound or salt of claim 1, which exhibits inhibition of c-Met in a cellular assay with an $IC_{50}$ of about 200 nM or less.

12. The compound or salt of claim 1, which is selected from:

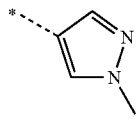

| R | Name |
|---|---|
| 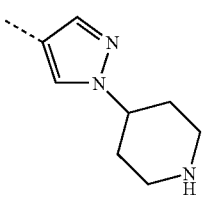 | 7-[(R)-1-(2,6-Dichloro-3-fluorophenyl)-ethoxy]-3-(1-methyl-1H-pyrazol-4-yl)-furo[3,2-c]pyridin-6-ylamine |
| 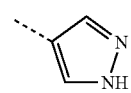 | 7-[(R)-1-(2,6-Dichloro-3-fluorophenyl)ethoxy]-3-(1-piperidin-4-yl-1H-pyrazol-4-yl)-furo[3,2-c]pyridin-6-ylamine |
| 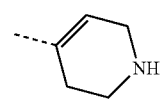 | 7-[(R)-1-(2,6-Dichloro-3-fluorophenyl)ethoxy]-3-(1H-pyrazol-4-yl)-furo[3,2-c]pyridin-6-ylamine |
| 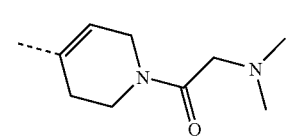 | 7-[(R)-1-(2,6-Dichloro-3-fluorophenyl)-ethoxy]-3-(1,2,3,6-tetrahydropyridin-4-yl)-furo[3,2-c]pyridin-6-ylamine |
| 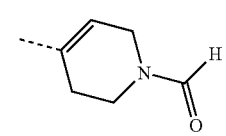 | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2-dimethylaminoethanone |
| 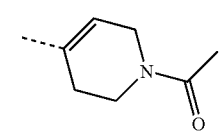 | 4-{6-Amino-7-[(R)-1-(2,6-dichloro-3-fluorophenyl)-ethoxy]-furo[3,2-c]pyridin-3-yl}-3,6-dihydro-2H-pyridine-1-carbaldehyde |
| 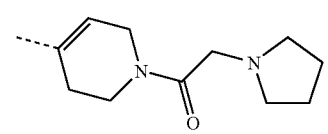 | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-ethanone |
|  | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-2-pyrrolidin-1-ylethanone |

-continued

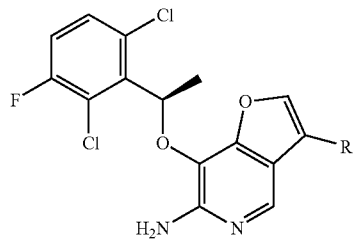

| R | Name |
|---|---|
| ![R group structure] | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(1-methylpiperidin-4-yl)-methanone |
| ![R group structure] | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-((S)-1-methylpyrrolidin-2-yl)-methanone |
| ![R group structure] | 1-(4-{6-Amino-7-[(R)-1-(2,6-dichloro-3-fluorophenyl)-ethoxy]-furo[3,2-c]pyridin-3-yl}-3,6-dihydro-2H-pyridin-1-yl)-4-dimethylaminobutan-1-one |
| ![R group structure] | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperidin-4-ylmethanone |
| ![R group structure] | (4-{6-Amino-7-[(R)-1-(2,6-dichloro-3-fluorophenyl)ethoxy]furo[3,2-c]pyridin-3-yl}-3,6-dihydro-2H-pyridin-1-yl)-(S)-pyrrolidin-2-ylmethanone |
| ![R group structure] | (1-Aminocyclopropyl)-(4-{6-amino-7-[(R)-1-(2,6-dichloro-3-fluorophenyl)-ethoxy]-furo[3,2-c]pyridin-3-yl}-3,6-dihydro-2H-pyridin-1-yl)-methanone |
| ![R group structure] | 2-Amino-1-(4-{6-amino-7-[(R)-1-(2,6-dichloro-3-fluorophenyl)-ethoxy]-furo[3,2-c]pyridin-3-yl}-3,6-dihydro-2H-pyridin-1-yl)-2-methylpropan-1-one |
| ![R group structure] | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-ethylpiperazin-1-yl)-methanone |

-continued

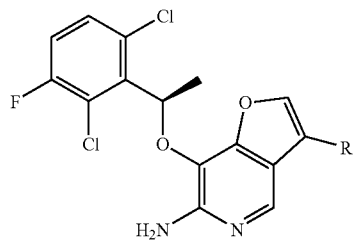

| R | Name |
|---|---|
| ![structure] piperidine-piperazine-tBu | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-(4-tert-butylpiperazin-1-yl)-methanone |
| ![structure] piperidine-piperazine-H | (4-{6-Amino-7-[(R)-1-(2,6-dichloro-3-fluorophenyl)-ethoxy]-furo[3,2-c]pyridin-3-yl}-3,6-dihydro-2H-pyridin-1-yl)-piperazin-1-ylmethanone |
| ![structure] carboxamide | 4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid amide |
| ![structure] N-methylcarboxamide | 4-{6-Amino-7-[(R)-1-(2,6-dichloro-3-fluorophenyl)-ethoxy]-furo[3,2-c]pyridin-3-yl}-3,6-dihydro-2H-pyridine-1-carboxylic acid methylamide |
| ![structure] N-methyl tetrahydropyridine | 7-[(R)-1-(2,6-Dichloro-3-fluorophenyl)-ethoxy]-3-(1-methyl-1,2,3,6-tetrahydropyridin-4-yl)-furo[3,2-c]pyridin-6-ylamine |
| ![structure] N-ethyl tetrahydropyridine | 7-[(R)-1-(2,6-Dichloro-3-fluorophenyl)-ethoxy]-3-(1-ethyl-1,2,3,6-tetrahydropyridin-4-yl)-furo[3,2-c]pyridin-6-ylamine |
| ![structure] N-aminoethyl tetrahydropyridine | 3-[1-(2-Aminoethyl)-1,2,3,6-tetrahydropyridin-4-yl]-7-[(R)-1-(2,6-dichloro-3-fluorophenyl)-ethoxy]-furo[3,2-c]pyridin-6-ylamine |

-continued

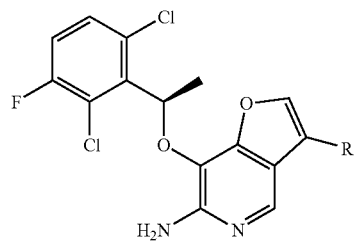

| R | Name |
|---|---|
| ![structure] methanesulfonyl tetrahydropyridine | 7-[(R)-1-(2,6-Dichloro-3-fluorophenyl)-ethoxy]-3-(1-methanesulfonyl-1,2,3,6-tetrahydropyridin-4-yl)-furo[3,2-c]pyridin-6-ylamine |
| ![structure] benzamide with dimethylaminoethyl | 4-{6-Amino-7-[(R)-1-(2,6-dichloro-3-fluorophenyl)ethoxy]-furo[3,2-c]pyridin-3-yl}-N-(2-dimethylaminoethyl)benzamide |
| ![structure] N,N-dimethylbenzamide | 4-{6-Amino-7-[(R)-1-(2,6-dichloro-3-fluorophenyl)ethoxy]-furo[3,2-c]pyridin-3-yl}-N,N-dimethylbenzamide |
| ![structure] methylpiperazinyl methanone | (4-{6-Amino-7-[(R)-1-(2,6-dichloro-3-fluorophenyl)ethoxy]-furo[3,2-c]pyridin-3-yl}phenyl)-(4-methylpiperazin-1-yl)methanone |
| ![structure] methanesulfonamide | N-(3-{6-Amino-7-[(R)-1-(2,6-dichloro-3-fluorophenyl)ethoxy]-furo[3,2-c]pyridin-3-yl}phenyl)methanesulfonamide |
| ![structure] phenyl-methylpiperazine | 7-[(R)-1-(2,6-Dichloro-3-fluorophenyl)ethoxy]-3-[4-(4-methylpiperazin-1-yl)-phenyl]furo[3,2-c]pyridin-6-ylamine |
| ![structure] pyridinyl-methylpiperazine | 7-[(R)-1-(2,6-Dichloro-3-fluorophenyl)ethoxy]-3-[6-(4-methylpiperazin-1-yl)pyridin-3-yl]furo[3,2-c]pyridin-6-ylamine |

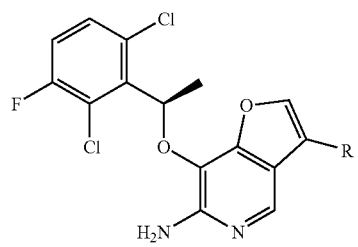

| R | Name |
|---|---|
| (HO-CH2CH2-N-piperazine-N-C(O)-phenyl-3-yl) | (3-{6-Amino-7-[(R)-1-(2,6-dichloro-3-fluorophenyl)ethoxy]-furo[3,2-c]pyridin-3-yl}phenyl)-[4-(2-hydroxyethyl)piperazin-1-yl]methanone |
| (4-yl phenyl-C(O)-N-piperazine-N-CH2CH2-OH) | (4-{6-Amino-7-[(R)-1-(2,6-dichloro-3-fluorophenyl)ethoxy]-furo[3,2-c]pyridin-3-yl}phenyl)-[4-(2-hydroxyethyl)piperazin-1-yl]methanone |
| (4-yl phenyl-C(O)-N-piperazine-NH) | (4-{6-Amino-7-[(R)-1-(2,6-dichloro-3-fluorophenyl)ethoxy]furo[3,2-c]pyridin-3-yl}phenyl)piperazin-1-ylmethanone |
| (5-yl pyridin-2-yl-piperazine-NH) | 7-[(R)-(2,6-Dichloro-3-fluorophenyl)ethoxy]-3-(6-piperazin-1-yl-pyridin-3-yl)furo[3,2-c]pyridin-6-ylamine, or |
| (4-yl pyridin-2-yl-piperazine-NH) | 7-[(R)-(2,6-Dichloro-3-fluorophenyl)ethoxy]-3-(2-piperazin-1-yl-pyridin-4-yl)furo[3,2-c]pyridin-6-ylamine. |

13. The compound or salt of claim 1, which is selected from:

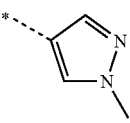

| R | Name |
|---|------|
| 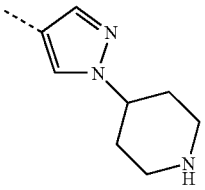 | 7-[(R)-1-(2-Chloro-3,6-difluorophenyl)-ethoxy]-3-(1-methyl-1H-pyrazol-4-yl)-furo[3,2-c]pyridin-6-ylamine |
| 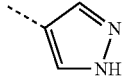 | 7-[(R)-1-(2-Chloro-3,6-difluorophenyl)ethoxy]-3-(1-piperidin-4-yl-1H-pyrazol-4-yl)-furo[3,2-c]pyridin-6-ylamine |
| 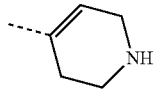 | 7-[(R)-1-(2-Chloro-3,6-difluorophenyl)ethoxy]-3-(1H-pyrazol-4-yl)-furo[3,2-c]pyridin-6-ylamine |
| 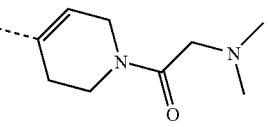 | 7-[(R)-1-(2-Chloro-3,6-difluorophenyl)-ethoxy]-3-(1,2,3,6-tetrahydropyridin-4-yl)-furo[3,2-c]pyridin-6-ylamine |
| 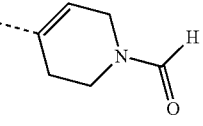 | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-2-dimethylaminoethanone |
| 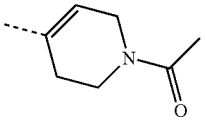 | 4-{6-Amino-7-[(R)-1-(2-chloro-3,6-difluorophenyl)-ethoxy]-furo[3,2-c]pyridin-3-yl}-3,6-dihydro-2H-pyridine-1-carbaldehyde |
| 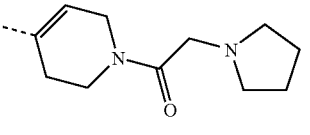 | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-ethanone |
| 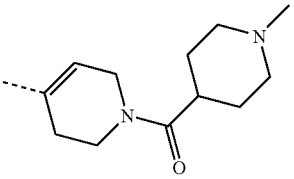 | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-2-pyrrolidin-1-ylethanone |
| | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-(1-methylpiperidin-4-yl)-methanone |

-continued

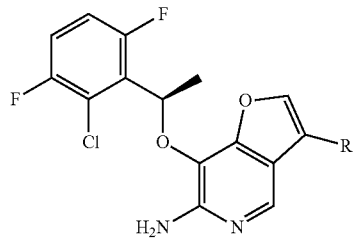

| R | Name |
|---|---|
| ![pyridinyl-methylpyrrolidinyl] | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-((S)-1-methylpyrrolidin-2-yl)-methanone |
| ![pyridinyl-dimethylaminobutanone] | 1-(4-{6-Amino-7-[(R)-1-(2-chloro-3,6-difluorophenyl)-ethoxy]-furo[3,2-c]pyridin-3-yl}-3,6-dihydro-2H-pyridin-1-yl)-4-dimethylaminobutan-1-one |
| ![pyridinyl-piperidinylmethanone] | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-piperidin-4-ylmethanone |
| ![pyridinyl-pyrrolidinylmethanone] | (4-{6-Amino-7-[(R)-1-(2-chloro-3,6-difluorophenyl)ethoxy]furo[3,2-c]pyridin-3-yl}-3,6-dihydro-2H-pyridin-1-yl)-(S)-pyrrolidin-2-ylmethanone |
| ![pyridinyl-aminocyclopropyl] | (1-Aminocyclopropyl)-(4-{6-amino-7-[(R)-1-(2-chloro-3,6-difluorophenyl)-ethoxy]-furo[3,2-c]pyridin-3-yl}-3,6-dihydro-2H-pyridin-1-yl)-methanone |
| ![pyridinyl-aminomethylpropanone] | 2-Amino-1-(4-{6-amino-7-[(R)-1-(2-chloro-3,6-difluorophenyl)-ethoxy]-furo[3,2-c]pyridin-3-yl}-3,6-dihydro-2H-pyridin-1-yl)-2-methylpropan-1-one |
| ![pyridinyl-ethylpiperazinyl] | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-(4-ethylpiperazin-1-yl)-methanone |
| ![pyridinyl-tertbutylpiperazinyl] | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-(4-tert-butylpiperazin-1-yl)-methanone |

-continued

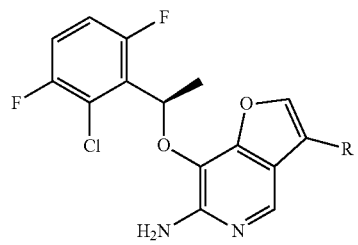

| R | Name |
|---|---|
| (piperazine-carbonyl-cyclohexenyl) | (4-{6-Amino-7-[(R)-1-(2-chloro-3,6-difluorophenyl)-ethoxy]-furo[3,2-c]pyridin-3-yl}-3,6-dihydro-2H-pyridin-1-yl)-piperazin-1-ylmethanone |
| (carboxamide-cyclohexenyl) | 4-{6-Amino-7-[(R)-1-(2-chloro-3,6-difluorophenyl)-ethoxy]-furo[3,2-c]pyridin-3-yl}-3,6-dihydro-2H-pyridine-1-carboxylic acid amide |
| (N-methylcarboxamide-cyclohexenyl) | 4-{6-Amino-7-[(R)-1-(2-chloro-3,6-difluorophenyl)-ethoxy]-furo[3,2-c]pyridin-3-yl}-3,6-dihydro-2H-pyridine-1-carboxylic acid methylamide |
| (1-methyl-tetrahydropyridin-4-yl) | 7-[(R)-1-(2-chloro-3,6-difluorophenyl)-ethoxy]-3-(1-methyl-1,2,3,6-tetrahydropyridin-4-yl)-furo[3,2-c]pyridin-6-ylamine |
| (1-ethyl-tetrahydropyridin-4-yl) | 7-[(R)-1-(2-chloro-3,6-difluorophenyl)-ethoxy]-3-(1-ethyl-1,2,3,6-tetrahydropyridin-4-yl)-furo[3,2-c]pyridin-6-ylamine |
| (1-(2-aminoethyl)-tetrahydropyridin-4-yl) | 3-[1-(2-Aminoethyl)-1,2,3,6-tetrahydropyridin-4-yl]-7-[(R)-1-(2-chloro-3,6-difluorophenyl)-ethoxy]-furo[3,2-c]pyridin-6-ylamine |
| (1-methanesulfonyl-tetrahydropyridin-4-yl) | 7-[(R)-1-(2-chloro-3,6-difluorophenyl)-ethoxy]-3-(1-methanesulfonyl-1,2,3,6-tetrahydropyridin-4-yl)-furo[3,2-c]pyridin-6-ylamine |
| (N-(2-dimethylaminoethyl)benzamide) | 4-{6-Amino-7-[(R)-1-(2-chloro-3,6-difluorophenyl)ethoxy]-furo[3,2-c]pyridin-3-yl}-N-(2-dimethylaminoethyl)benzamide |
| (N,N-dimethylbenzamide) | 4-{6-Amino-7-[(R)-1-(2-chloro-3,6-difluorophenyl)ethoxy]-furo[3,2-c]pyridin-3-yl}-N,N-dimethylbenzamide |

-continued

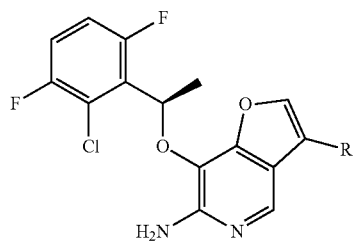

| R | Name |
|---|---|
| ![piperazine-methylpiperazinyl-methanone] | (4-{6-Amino-7-[(R)-1-(2-chloro-3,6-difluorophenyl)ethoxy]-furo[3,2-c]pyridin-3-yl}phenyl)-(4-methylpiperazin-1-yl)methanone |
| ![methanesulfonamide] | N-(3-{6-Amino-7-[(R)-1-(2-chloro-3,6-difluorophenyl)ethoxy]-furo[3,2-c]pyridin-3-yl}phenyl)methanesulfonamide |
| ![phenyl-methylpiperazine] | 7-[(R)-1-(2-Chloro-3,6-difluorophenyl)ethoxy]-3-[4-(4-methylpiperazin-1-yl)-phenyl]furo[3,2-c]pyridin-6-ylamine |
| ![pyridyl-methylpiperazine] | 7-[(R)-1-(2-Chloro-3,6-difluorophenyl)ethoxy]-3-[6-(4-methylpiperazin-1-yl)pyridin-3-yl]furo[3,2-c]pyridin-6-ylamine |
| ![hydroxyethylpiperazinyl-methanone meta] | (3-{6-Amino-7-[(R)-1-(2-chloro-3,6-difluorophenyl)ethoxy]-furo[3,2-c]pyridin-3-yl}phenyl)-[4-(2-hydroxyethyl)piperazin-1-yl]methanone |
| ![hydroxyethylpiperazinyl-methanone para] | (4-{6-Amino-7-[(R)-1-(2-chloro-3,6-difluorophenyl)ethoxy]-furo[3,2-c]pyridin-3-yl}phenyl)-[4-(2-hydroxyethyl)piperazin-1-yl]methanone |

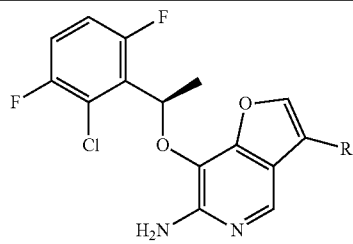

| R | Name |
|---|---|
| ![piperazinyl-phenyl-carbonyl] | (4-{6-Amino-7-[(R)-1-(2-chloro-3,6-difluorophenyl)ethoxy]furo[3,2-c]pyridin-3-yl}phenyl)piperazin-1-ylmethanone |
| ![6-piperazinyl-pyridin-3-yl] | 7-[(R)-(2-Chloro-3,6-difluorophenyl)ethoxy]-3-(6-piperazin-1-yl-pyridin-3-yl)furo[3,2-c]pyridin-6-ylamine, or |
| ![2-piperazinyl-pyridin-4-yl] | 7-[(R)-(2-Chloro-3,6-difluorophenyl)ethoxy]-3-(2-piperazin-1-yl-pyridin-4-yl)furo[3,2-c]pyridin-6-ylamine. |

14. The compound or salt of claim 1, which is selected from:

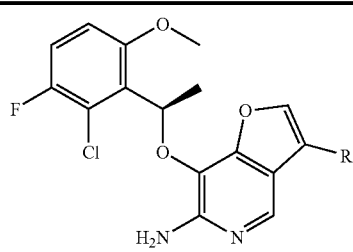

| R | Name |
|---|---|
| ![1-methylpyrazol-4-yl] | 7-[(R)-1-(2-Chloro-3-fluoro-6-methoxyphenyl)-ethoxy]-3-(1-methyl-1H-pyrazol-4-yl)-furo[3,2-c]pyridin-6-ylamine |
| ![1-piperidinyl-pyrazol-4-yl] | 7-[(R)-1-(2-Chloro-3-fluoro-6-methoxyphenyl)ethoxy]-3-(1-piperidin-4-yl-1H-pyrazol-4-yl)-furo[3,2-c]pyridin-6-ylamine |

-continued

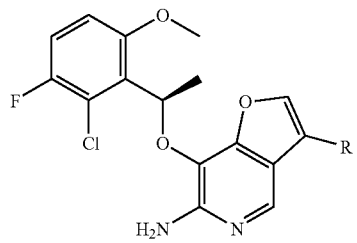

| R | Name |
|---|---|
| pyrazol-4-yl (NH) | 7-[(R)-1-(2-Chloro-3-fluoro-6-methoxyphenyl)ethoxy]-3-(1H-pyrazol-4-yl)-furo[3,2-c]pyridin-6-ylamine |
| 1,2,3,6-tetrahydropyridin-4-yl | 7-[(R)-1-(2-Chloro-3-fluoro-6-methoxyphenyl)-ethoxy]-3-(1,2,3,6-tetrahydropyridin-4-yl)-furo[3,2-c]pyridin-6-ylamine |
| tetrahydropyridine-N-C(O)CH₂N(CH₃)₂ | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-2-dimethylaminoethanone |
| tetrahydropyridine-N-CHO | 4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-carbaldehyde |
| tetrahydropyridine-N-C(O)CH₃ | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-ethanone |
| tetrahydropyridine-N-C(O)CH₂-pyrrolidine | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-2-pyrrolidin-1-ylethanone |
| tetrahydropyridine-N-C(O)-(1-methylpiperidin-4-yl) | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-(1-methylpiperidin-4-yl)-methanone |
| tetrahydropyridine-N-C(O)-(1-methylpyrrolidin-2-yl) | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-((S)-1-methylpyrrolidin-2-yl)-methanone |
| tetrahydropyridine-N-C(O)(CH₂)₃N(CH₃)₂ | 1-(4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-4-dimethylaminobutan-1-one |

-continued

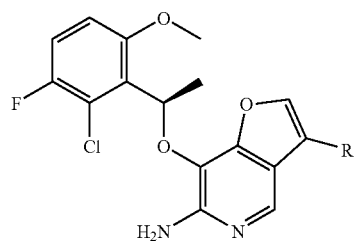

| R | Name |
|---|---|
| ![piperidine-carbonyl-tetrahydropyridine] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-piperidin-4-ylmethanone |
| ![pyrrolidine-carbonyl-tetrahydropyridine] | (4-{6-Amino-7-[(R)-1-(2-chloro-3-fluoro-6-methoxyphenyl)ethoxy]furo[3,2-c]pyridin-3-yl}-3,6-dihydro-2H-pyridin-1-yl)-(S)-pyrrolidin-2-ylmethanone |
| ![aminocyclopropyl-carbonyl-tetrahydropyridine] | (1-Aminocyclopropyl)-(4-{6-amino-7-[(R)-1-(2-chloro-3-fluoro-6-methoxyphenyl)-ethoxy]-furo[3,2-c]pyridin-3-yl}-3,6-dihydro-2H-pyridin-1-yl)-methanone |
| ![aminomethylpropanone-tetrahydropyridine] | 2-Amino-1-(4-{6-amino-7-[(R)-1-(2-chloro-3-fluoro-6-methoxyphenyl)-ethoxy-furo[3,2-c]pyridin-3-yl}-3,6-dihydro-2H-pyridin-1-yl)-2-methylpropan-1-one |
| ![ethylpiperazine-carbonyl-tetrahydropyridine] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-(4-ethylpiperazin-1-yl)-methanone |
| ![tertbutylpiperazine-carbonyl-tetrahydropyridine] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-(4-tert-butylpiperazin-1-yl)-methanone |
| ![piperazine-carbonyl-tetrahydropyridine] | (4-{6-Amino-7-[(R)-1-(2-chloro-3-fluoro-6-methoxyphenyl)-ethoxy]-furo[3,2-c]pyridin-3-yl}-3,6-dihydro-2H-pyridin-1-yl)-piperazin-1-ylmethanone |

-continued

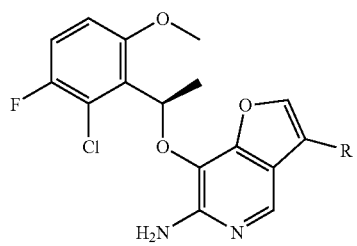

| R | Name |
|---|---|
| ![piperidine-carboxamide] | 4-{6-Amino-7-[(R)-1-(2-chloro-3-fluoro-6-methoxyphenyl)-ethoxy]-furo[3,2-c]pyridin-3-yl}-3,6-dihydro-2H-pyridine-1-carboxylic acid amide |
| ![piperidine-N-methylcarboxamide] | 4-{6-Amino-7-[(R)-1-(2-chloro-3-fluoro-6-methoxyphenyl)-ethoxy]-furo[3,2-c]pyridin-3-yl}-3,6-dihydro-2H-pyridine-1-carboxylic acid methylamide |
| ![N-methyl-tetrahydropyridine] | 7-[(R)-1-(2-chloro-3-fluoro-6-methoxyphenyl)-ethoxy]-3-(1-methyl-1,2,3,6-tetrahydropyridin-4-yl)-furo[3,2-c]pyridin-6-ylamine |
| ![N-ethyl-tetrahydropyridine] | 7-[(R)-1-(2-chloro-3-fluoro-6-methoxyphenyl)-ethoxy]-3-(1-ethyl-1,2,3,6-tetrahydropyridin-4-yl)-furo[3,2-c]pyridin-6-ylamine |
| ![N-aminoethyl-tetrahydropyridine] | 3-[1-(2-Aminoethyl)-1,2,3,6-tetrahydropyridin-4-yl]-7-[(R)-1-(2-chloro-3-fluoro-6-methoxyphenyl)-ethoxy]-furo[3,2-c]pyridin-6-ylamine |
| ![N-mesyl-tetrahydropyridine] | 7-[(R)-1-(2-chloro-3-fluoro-6-methoxyphenyl)-ethoxy]-3-(1-methanesulfonyl-1,2,3,6-tetrahydropyridin-4-yl)-furo[3,2-c]pyridin-6-ylamine |
| ![benzamide-dimethylaminoethyl] | 4-{6-Amino-7-[(R)-1-(2-chloro-3-fluoro-6-methoxyphenyl)ethoxy]-furo[3,2-c]pyridin-3-yl}-N-(2-dimethylaminoethyl)benzamide |
| ![N,N-dimethylbenzamide] | 4-{6-Amino-7-[(R)-1-(2-chloro-3-fluoro-6-methoxyphenyl)ethoxy]-furo[3,2-c]pyridin-3-yl}-N,N-dimethylbenzamide |
| ![methylpiperazine-benzoyl] | (4-{6-Amino-7-[(R)-1-(2-chloro-3-fluoro-6-methoxyphenyl)ethoxy]-furo[3,2-c]pyridin-3-yl}phenyl)-(4-methylpiperazin-1-yl)methanone |

-continued

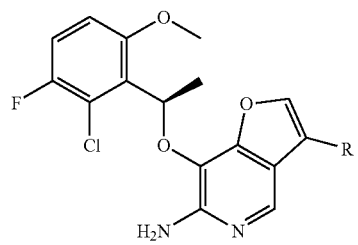

| R | Name |
|---|---|
| (3-substituted phenyl methanesulfonamide) | N-(3-{6-Amino-7-[(R)-1-(2-chloro-3-fluoro-6-methoxyphenyl)ethoxy]-furo[3,2-c]pyridin-3-yl}phenyl)methanesulfonamide |
| (4-(4-methylpiperazin-1-yl)phenyl) | 7-[(R)-1-(2-Chloro-3-fluoro-6-methoxyphenyl)ethoxy]-3-[4-(4-methylpiperazin-1-yl)-phenyl]furo[3,2-c]pyridin-6-ylamine |
| (6-(4-methylpiperazin-1-yl)pyridin-3-yl) | 7-[(R)-1-(2-Chloro-3-fluoro-6-methoxyphenyl)ethoxy]-3-[6-(4-methylpiperazin-1-yl)pyridin-3-yl]furo[3,2-c]pyridin-6-ylamine |
| (3-{[4-(2-hydroxyethyl)piperazin-1-yl]carbonyl}phenyl) | (3-{6-Amino-7-[(R)-1-(2-chloro-3-fluoro-6-methoxyphenyl)ethoxy]-furo[3,2-c]pyridin-3-yl}phenyl)-[4-(2-hydroxyethyl)piperazin-1-yl]methanone |
| (4-{[4-(2-hydroxyethyl)piperazin-1-yl]carbonyl}phenyl) | (4-{6-Amino-7-[(R)-1-(2-chloro-3-fluoro-6-methoxyphenyl)ethoxy]-furo[3,2-c]pyridin-3-yl}phenyl)-[4-(2-hydroxyethyl)piperazin-1-yl]methanone |
| (4-(piperazin-1-ylcarbonyl)phenyl) | (4-{6-Amino-7-[(R)-1-(2-chloro-3-fluoro-6-methoxyphenyl)ethoxy]furo[3,2-c]pyridin-3-yl}phenyl)piperazin-1-ylmethanone |

-continued

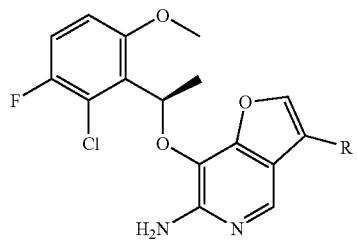

| R | Name |
|---|---|
| ![pyridine-piperazine] | 7-[(R)-( 2-chloro-3-fluoro-6-methoxyphenyl)ethoxy]-3-(6-piperazin-1-yl-pyridin-3-yl)furo[3,2-c]pyridin-6-ylamine, or |
| ![pyridine-piperazine] | 7-[(R)-( 2-chloro-3-fluoro-6-methoxyphenyl)ethoxy]-3-(2-piperazin-1-yl-pyridin-4-yl)furo[3,2-c]pyridin-6-ylamine. |

15. The compound or salt of claim 1, which is selected from:

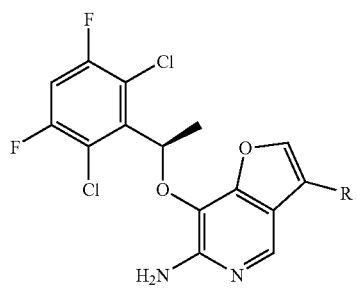

| R | Name |
|---|---|
| ![1-methylpyrazole] | 7-[(R)-1-(2,6-Dichloro-3,5-difluorophenyl)-ethoxy]-3-(1-methyl-1H-pyrazol-4-yl)-furo[3,2-c]pyridin-6-ylamine |
| ![1-piperidinylpyrazole] | 7-[(R)-1-(2,6-Dichloro-3,5-difluorophenyl)ethoxy]-3-(1-piperidin-4-yl-1H-pyrazol-4-yl)-furo[3,2-c]pyridin-6-ylamine |
| ![pyrazole] | 7-[(R)-1-(2,6-Dichloro-3,5-difluorophenyl)ethoxy]-3-(1H-pyrazol-4-yl)-furo[3,2-c]pyridin-6-ylamine |

-continued

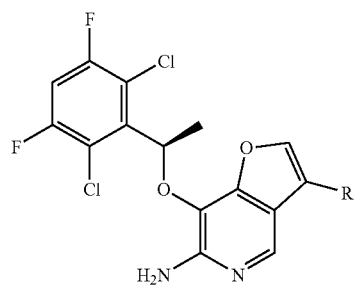

| R | Name |
|---|------|
| (tetrahydropyridin-4-yl, NH) | 7-[(R)-1-(2,6-Dichloro-3,5-difluorophenyl)-ethoxy]-3-(1,2,3,6-tetrahydropyridin-4-yl)-furo[3,2-c]pyridin-6-ylamine |
| (dihydropyridinyl-N-C(O)CH2-N(CH3)2) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-2-dimethylaminoethanone |
| (dihydropyridinyl-N-CHO) | 4-{6-Amino-7-[(R)-1-(2,6-dichloro-3,5-difluorophenyl)-ethoxy]-furo[3,2-c]pyridin-3-yl}-3,6-dihydro-2H-pyridine-1-carbaldehyde |
| (dihydropyridinyl-N-C(O)CH3) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-ethanone |
| (dihydropyridinyl-N-C(O)CH2-pyrrolidinyl) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-2-pyrrolidin-1-ylethanone |
| (dihydropyridinyl-N-C(O)-(1-methylpiperidin-4-yl)) | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-(1-methylpiperidin-4-yl)-methanone |
| (dihydropyridinyl-N-C(O)-((S)-1-methylpyrrolidin-2-yl)) | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-((S)-1-methylpyrrolidin-2-yl)-methanone |
| (dihydropyridinyl-N-C(O)CH2CH2CH2-N(CH3)2) | 1-(4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-4-dimethylaminobutan-1-one |

-continued

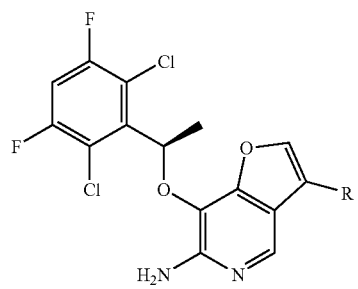

| R | Name |
|---|---|
| ![piperidine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-piperidin-4-ylmethanone |
| ![pyrrolidine-carbonyl-tetrahydropyridine] | (4-{6-Amino-7-[(R)-1-(2,6-dichloro-3,5-difluorophenyl)ethoxy]furo[3,2-c]pyridin-3-yl}-3,6-dihydro-2H-pyridin-1-yl)-(S)-pyrrolidin-2-ylmethanone |
| ![aminocyclopropyl-carbonyl-tetrahydropyridine] | (1-Aminocyclopropyl)-(4-{6-amino-7-[(R)-1-(2,6-dichloro-3,5-difluorophenyl)-ethoxy]-furo[3,2-c]pyridin-3-yl}-3,6-dihydro-2H-pyridin-1-yl)-methanone |
| ![amino-methylpropanone-tetrahydropyridine] | 2-Amino-1-(4-{6-amino-7-[(R)-1-(2,6-dichloro-3,5-difluorophenyl)-ethoxy]-furo[3,2-c]pyridin-3-yl}-3,6-dihydro-2H-pyridin-1-yl)-2-methylpropan-1-one |
| ![ethylpiperazine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-(4-ethylpiperazin-1-yl)-methanone |
| ![tertbutylpiperazine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-(4-tert-butylpiperazin-1-yl)-methanone |
| ![piperazine-carbonyl-tetrahydropyridine] | (4-{6-Amino-7-[(R)-1-(2,6-dichloro-3,5-difluorophenyl)-ethoxy]-furo[3,2-c]pyridin-3-yl}-3,6-dihydro-2H-pyridin-1-yl)-piperazin-1-ylmethanone |

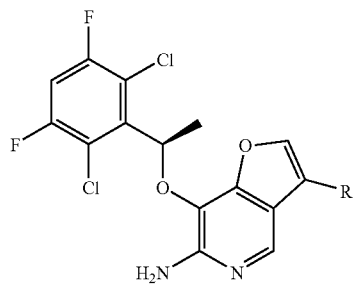

| R | Name |
|---|---|
| [piperidine-CONH2] | 4-{6-Amino-7-[(R)-1-(2,6-dichloro-3,5-difluorophenyl)-ethoxy]-furo[3,2-c]pyridin-3-yl}-3,6-dihydro-2H-pyridine-1-carboxylic acid amide |
| [piperidine-CONHMe] | 4-{6-Amino-7-[(R)-1-(2,6-dichloro-3,5-difluorophenyl)-ethoxy]-furo[3,2-c]pyridin-3-yl}-3,6-dihydro-2H-pyridine-1-carboxylic acid methylamide |
| [N-methyl tetrahydropyridine] | 7-[(R)-1-(2,6-Dichloro-3,5-difluorophenyl)-ethoxy]-3-(1-methyl-1,2,3,6-tetrahydropyridin-4-yl)-furo[3,2-c]pyridin-6-ylamine |
| [N-ethyl tetrahydropyridine] | 7-[(R)-1-(2,6-Dichloro-3,5-difluorophenyl)-ethoxy]-3-(1-ethyl-1,2,3,6-tetrahydropyridin-4-yl)-furo[3,2-c]pyridin-6-ylamine |
| [N-(2-aminoethyl) tetrahydropyridine] | 3-[1-(2-Aminoethyl)-1,2,3,6-tetrahydropyridin-4-yl]-7-[(R)-1-(2,6-dichloro-3,5-difluorophenyl)-ethoxy]-furo[3,2-c]pyridin-6-ylamine |
| [N-methanesulfonyl tetrahydropyridine] | 7-[(R)-1-(2,6-Dichloro-3,5-difluorophenyl)-ethoxy]-3-(1-methanesulfonyl-1,2,3,6-tetrahydropyridin-4-yl)-furo[3,2-c]pyridin-6-ylamine |
| [phenyl-CONH-CH2CH2-NMe2] | 4-{6-Amino-7-[(R)-1-(2,6-dichloro-3,5-difluorophenyl)ethoxy]-furo[3,2-c]pyridin-3-yl}-N-(2-dimethylaminoethyl)benzamide |
| [phenyl-CON(Me)2] | 4-{6-Amino-7-[(R)-1-(2,6-dichloro-3,5-difluorophenyl)ethoxy]-furo[3,2-c]pyridin-3-yl}-N,N-dimethylbenzamide |
| [phenyl-CO-(4-methylpiperazine)] | (4-{6-Amino-7-[(R)-1-(2,6-dichloro-3,5-difluorophenyl)ethoxy]-furo[3,2-c]pyridin-3-yl}phenyl)-(4-methylpiperazin-1-yl)methanone |

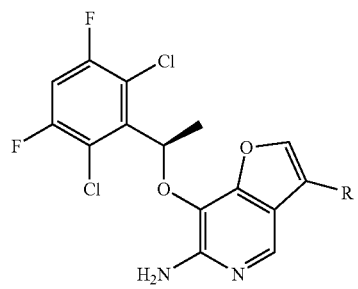

| R | Name |
|---|---|
| (m-phenyl-NHSO2CH3) | N-(3-{6-Amino-7-[(R)-1-(2,6-dichloro-3,5-difluorophenyl)ethoxy]-furo[3,2-c]pyridin-3-yl}phenyl)methanesulfonamide |
| (p-phenyl-4-methylpiperazin-1-yl) | 7-[(R)-1-(2,6-Dichloro-3,5-difluorophenyl)ethoxy]-3-[4-(4-methylpiperazin-1-yl)-phenyl]furo[3,2-c]pyridin-6-ylamine |
| (pyridin-3-yl-6-(4-methylpiperazin-1-yl)) | 7-[(R)-1-(2,6-Dichloro-3,5-difluorophenyl)ethoxy]-3-[6-(4-methylpiperazin-1-yl)pyridin-3-yl]furo[3,2-c]pyridin-6-ylamine |
| (m-phenyl-C(O)-piperazin-N-CH2CH2OH) | (3-{6-Amino-7-[(R)-1-(2,6-dichloro-3,5-difluorophenyl)ethoxy]-furo[3,2-c]pyridin-3-yl}phenyl)-[4-(2-hydroxyethyl)piperazin-1-yl]methanone |
| (p-phenyl-C(O)-piperazin-N-CH2CH2OH) | (4-{6-Amino-7-[(R)-1-(2,6-dichloro-3,5-difluorophenyl)ethoxy]-furo[3,2-c]pyridin-3-yl}phenyl)-[4-(2-hydroxyethyl)piperazin-1-yl]methanone |
| (p-phenyl-C(O)-piperazin-NH) | (4-{6-Amino-7-[(R)-1-(2,6-dichloro-3,5-difluorophenyl)ethoxy]furo[3,2-c]pyridin-3-yl}phenyl)piperazin-1-ylmethanone |

-continued

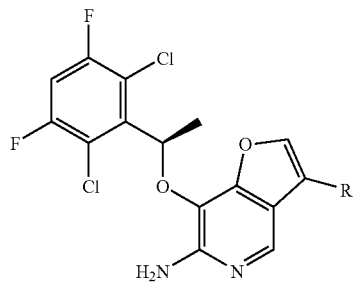

| R | Name |
|---|---|
| 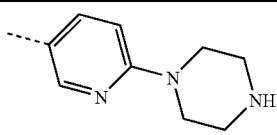 | 7-[(R)-(2,6-Dichloro-3,5-difluorophenyl)ethoxy]-3-(6-piperazin-1-yl-pyridin-3-yl)furo[3,2-c]pyridin-6-ylamine, or |
| 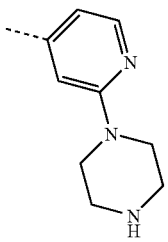 | 7-[(R)-(2,6-Dichloro-3,5-difluorophenyl)ethoxy]-3-(2-piperazin-1-yl-pyridin-4-yl)furo[3,2-c]pyridin-6-ylamine. |

16. A pharmaceutical composition comprising the compound or salt of claim 1 formulated with or without one or more pharmaceutically acceptable carriers.

17. The compound or salt of claim 1, which is 4-{6-amino-7-[(R)-1-(2-chloro-3,6-difluorophenyl)-ethoxy]-furo[3,2-c]pyridin-3-yl}-3,6-dihydro-2H-pyridine-1-carbaldehyde.

18. The compound or salt of claim 1, which is (4-{6-amino-7-[(R)-1-(2,6-dichloro-3-fluorophenyl)ethoxy]-furo [3,2-c]pyridin-3-yl}-3,6-dihydro-2H-pyridin-1-yl)-(1-methylpiperidin-2-yl)methanone.

19. The compound or salt of claim 1, which is (4-{6-amino-7-[(R)-1-(2,6-dichloro-3-fluorophenyl)ethoxy]-furo[3,2-c]pyridin-3-yl}-3,6-dihydro-2H-pyridin-1-yl)-(S)-pyrrolidin-3-ylmethanone.

* * * * *